United States Patent
Moore et al.

(10) Patent No.: US 11,884,746 B2
(45) Date of Patent: Jan. 30, 2024

(54) MATRIPTASE AND U-PLASMINOGEN ACTIVATOR SUBSTRATES AND OTHER CLEAVABLE MOIETIES AND METHODS OF USE THEREOF

(71) Applicant: CytomX Therapeutics, Inc., South San Francisco, CA (US)

(72) Inventors: Stephen James Moore, Danville, CA (US); Margaret Thy Luu Nguyen, San Francisco, CA (US); Daniel Robert Hostetter, Palo Alto, CA (US); Olga Vasiljeva, Cupertino, CA (US)

(73) Assignee: CytomX Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 17/240,278

(22) Filed: Apr. 26, 2021

(65) Prior Publication Data
US 2022/0411470 A1    Dec. 29, 2022

Related U.S. Application Data

(60) Division of application No. 16/160,846, filed on Oct. 15, 2018, now Pat. No. 11,028,126, which is a continuation of application No. 15/390,975, filed on Dec. 27, 2016, now Pat. No. 10,138,272, which is a division of application No. 14/610,468, filed on Jan. 30, 2015, now Pat. No. 9,562,073.

(60) Provisional application No. 61/971,009, filed on Mar. 27, 2014, provisional application No. 61/934,619, filed on Jan. 31, 2014.

(51) Int. Cl.
| | |
|---|---|
| C07K 7/06 | (2006.01) |
| A61K 47/65 | (2017.01) |
| A61K 47/68 | (2017.01) |
| C07K 7/08 | (2006.01) |
| C07K 16/00 | (2006.01) |
| A61K 49/00 | (2006.01) |
| C07K 16/28 | (2006.01) |
| A61K 39/00 | (2006.01) |

(52) U.S. Cl.
CPC ............... *C07K 7/06* (2013.01); *A61K 47/65* (2017.08); *A61K 47/6803* (2017.08); *A61K 47/6835* (2017.08); *A61K 47/6889* (2017.08); *A61K 49/0056* (2013.01); *C07K 7/08* (2013.01); *C07K 16/00* (2013.01); *C07K 16/2809* (2013.01); *C07K 16/2863* (2013.01); *A61K 2039/505* (2013.01); *C07K 2317/54* (2013.01); *C07K 2317/55* (2013.01); *C07K 2317/569* (2013.01); *C07K 2317/622* (2013.01); *C07K 2317/92* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Bostwell et al. |
| 4,485,045 | A | 11/1984 | Regen |
| 4,544,545 | A | 10/1985 | Ryan et al. |
| 5,013,556 | A | 5/1991 | Woodle et al. |
| 5,030,719 | A | 7/1991 | Umemoto et al. |
| 6,551,795 | B1 | 4/2003 | Rubenfield et al. |
| 6,558,728 | B1 | 5/2003 | Poulsen et al. |
| 7,276,497 | B2 | 10/2007 | Chari et al. |
| 7,439,319 | B2 | 10/2008 | Smith et al. |
| 7,442,159 | B1 | 10/2008 | Riechmann et al. |
| 7,465,790 | B2 | 12/2008 | Waldmann et al. |
| 7,666,817 | B2 | 2/2010 | Daugherty et al. |
| 7,935,785 | B2 | 5/2011 | Smith et al. |
| 8,513,390 | B2 | 8/2013 | Stagliano et al. |
| 8,518,404 | B2 | 8/2013 | Daugherty et al. |
| 8,524,220 | B1 | 9/2013 | Bermudes |
| 8,529,898 | B2 | 9/2013 | Daugherty et al. |
| 8,541,203 | B2 | 9/2013 | Daugherty et al. |
| 8,563,269 | B2 | 10/2013 | Stagliano et al. |
| 8,809,504 | B2 | 8/2014 | Lauermann |
| 9,120,853 | B2 | 9/2015 | Lowman et al. |
| 9,127,053 | B2 | 9/2015 | West et al. |

(Continued)

FOREIGN PATENT DOCUMENTS

| | | | |
|---|---|---|---|
| EP | 1 523 503 B1 | 4/2009 | |
| EP | 1 324 771 B1 | 6/2011 | |

(Continued)

OTHER PUBLICATIONS

Liu et al. ('Targeting of tumor cells by cell surface urokinase plasminogen activator-dependent anthrax toxin' JBC v276(21) May 25, 2001 pp. 17976-17984) (Year: 2001).*

(Continued)

*Primary Examiner* — Ronald T Niebauer
(74) *Attorney, Agent, or Firm* — Rothwell, Figg, Ernst & Manbeck, P.C.

(57) ABSTRACT

The invention relates generally to polypeptides that include a cleavable moiety that is a substrate for at least one protease selected from matriptase and u-plasminogen activator (uPA), to activatable antibodies and other larger molecules that include the cleavable moiety that is a substrate for at least one protease selected from matriptase and u-plasminogen activator, and to methods of making and using these polypeptides that include a cleavable moiety that is a substrate for at least one protease selected from matriptase and u-plasminogen activator in a variety of therapeutic, diagnostic and prophylactic indications.

6 Claims, 4 Drawing Sheets

Specification includes a Sequence Listing.

(56) References Cited

U.S. PATENT DOCUMENTS

| | | | |
|---|---|---|---|
| 9,169,321 B2 | 10/2015 | Daugherty et al. | |
| 9,453,078 B2 | 9/2016 | Stagliano et al. | |
| 9,562,073 B2 * | 2/2017 | Moore | C07K 16/2809 |
| 10,059,762 B2 | 8/2018 | Stagliano et al. | |
| 10,077,300 B2 | 9/2018 | Daugherty et al. | |
| 10,118,961 B2 | 11/2018 | Stagliano et al. | |
| 10,138,272 B2 * | 11/2018 | Moore | A61P 35/00 |
| 10,179,817 B2 * | 1/2019 | Sagert | A61K 49/0032 |
| 10,233,244 B2 * | 3/2019 | Sagert | A61P 35/02 |
| 10,336,824 B2 | 7/2019 | West et al. | |
| 10,513,558 B2 * | 12/2019 | Tipton | C07K 16/3038 |
| 10,669,337 B2 * | 6/2020 | Irving | A61K 47/6849 |
| 10,669,339 B2 | 6/2020 | West et al. | |
| 10,745,481 B2 * | 8/2020 | West | C07K 16/2803 |
| 10,875,913 B2 | 12/2020 | Stagliano et al. | |
| 11,028,126 B2 * | 6/2021 | Moore | A61K 47/6803 |
| 11,267,896 B2 * | 3/2022 | Sagert | A61K 49/0032 |
| 2003/0219402 A1 | 11/2003 | Rutter | |
| 2004/0109855 A1 | 6/2004 | Waldmann et al. | |
| 2004/0123343 A1 | 6/2004 | La Rosa et al. | |
| 2005/0208602 A1 | 9/2005 | Rosen et al. | |
| 2007/0218074 A1 | 9/2007 | Man | |
| 2009/0304719 A1 | 12/2009 | Daugherty et al. | |
| 2010/0041588 A1 | 2/2010 | Keay et al. | |
| 2010/0189651 A1 | 7/2010 | Stagliano et al. | |
| 2011/0214205 A1 | 9/2011 | Dietrich et al. | |
| 2011/0287517 A1 | 11/2011 | Steward et al. | |
| 2012/0149061 A1 | 6/2012 | Stagliano et al. | |
| 2012/0207756 A1 | 8/2012 | Stagliano et al. | |
| 2012/0237512 A1 | 9/2012 | Daugherty et al. | |
| 2012/0237977 A1 | 9/2012 | Daugherty et al. | |
| 2012/0244154 A1 | 9/2012 | Daugherty et al. | |
| 2012/0321626 A1 | 12/2012 | Zhou et al. | |
| 2013/0078201 A1 | 3/2013 | Daly et al. | |
| 2013/0150558 A1 | 6/2013 | Williams et al. | |
| 2013/0309230 A1 | 11/2013 | Stagliano et al. | |
| 2014/0010810 A1 | 1/2014 | West et al. | |
| 2014/0023664 A1 | 1/2014 | Lowman et al. | |
| 2014/0024810 A1 | 1/2014 | Stagliano et al. | |
| 2014/0045195 A1 | 2/2014 | Daugherty et al. | |
| 2014/0363430 A1 | 12/2014 | West et al. | |
| 2015/0087810 A1 | 3/2015 | Moore et al. | |
| 2016/0122425 A1 | 5/2016 | Daugherty et al. | |
| 2016/0194399 A1 | 7/2016 | Irving et al. | |
| 2016/0228546 A1 | 8/2016 | Stagliano et al. | |
| 2016/0289324 A1 | 10/2016 | Moore et al. | |
| 2016/0355587 A1 | 12/2016 | West et al. | |
| 2017/0044259 A1 | 2/2017 | Tipton et al. | |
| 2017/0081397 A1 | 3/2017 | Stagliano et al. | |
| 2018/0303952 A1 | 10/2018 | Sagert et al. | |
| 2019/0016814 A1 | 1/2019 | Humphrey et al. | |
| 2019/0119370 A1 | 4/2019 | Stagliano et al. | |
| 2019/0211089 A1 | 7/2019 | Daugherty et al. | |
| 2019/0241652 A9 | 8/2019 | Moore et al. | |
| 2019/0284283 A1 | 9/2019 | Moore et al. | |
| 2019/0359714 A1 | 11/2019 | Tipton et al. | |
| 2019/0382493 A1 | 12/2019 | West et al. | |
| 2020/0339694 A1 | 10/2020 | West et al. | |
| 2021/0284721 A1 | 9/2021 | Stagliano et al. | |

FOREIGN PATENT DOCUMENTS

| | | |
|---|---|---|
| JP | 2012514982 A | 7/2012 |
| JP | 6835586 B2 | 2/2021 |
| WO | WO 1994/11026 A2 | 5/1994 |
| WO | WO 1999/15563 A1 | 4/1999 |
| WO | WO 2001/57182 A2 | 8/2001 |
| WO | WO 2001/91798 A2 | 12/2001 |
| WO | WO 2002/12475 A2 | 2/2002 |
| WO | WO 2002/30460 A2 | 4/2002 |
| WO | WO 2002/038796 | 5/2002 |
| WO | WO 2002/38796 A2 | 5/2002 |
| WO | WO 2003/038083 A1 | 5/2003 |
| WO | WO 2004/009638 A1 | 1/2004 |
| WO | WO 2006/110599 A2 | 10/2006 |
| WO | WO 2007/105027 A1 | 9/2007 |
| WO | WO 2008/052187 A2 | 5/2008 |
| WO | WO 2009/025846 A2 | 2/2009 |
| WO | WO 2010/046628 | 4/2010 |
| WO | WO 2010/046628 A1 | 4/2010 |
| WO | 2010081173 A2 | 7/2010 |
| WO | WO 2010/081173 A2 | 7/2010 |
| WO | WO 2010/096838 A2 | 8/2010 |
| WO | WO 2010/129609 A2 | 11/2010 |
| WO | WO 2011/028698 A2 | 3/2011 |
| WO | WO 2012/156919 * | 11/2012 |
| WO | WO 2013/163631 A2 | 10/2013 |
| WO | WO 2013/192546 A2 | 12/2013 |
| WO | WO 2013/192550 A2 | 12/2013 |
| WO | WO 2014/026136 A2 | 2/2014 |
| WO | WO 2014/052462 A2 | 4/2014 |
| WO | WO 2014/107599 A2 | 7/2014 |
| WO | WO 2014/176284 A1 | 10/2014 |
| WO | WO 2014/193973 | 12/2014 |
| WO | WO 2014/193973 A2 | 12/2014 |
| WO | WO 2015/048329 | 4/2015 |
| WO | 2015116933 A2 | 8/2015 |
| WO | WO 2016/014974 A2 | 1/2016 |
| WO | WO 2020/118109 | 6/2020 |

OTHER PUBLICATIONS

Japanese Office Action issued in Japanese Application No. 2021-016630 dated Sep. 20, 2022, 7 pages.

Bendig, Mary M., "Humanization of Rodent Monoclonal Antibodies by CDR Grafting", Methods: A Companion to Methods in Enzymology (1995); 8:83-93.

Colman, Peter M. "Effects of amino acid sequence changes on antibody-antigen interactions", Res. Immunol. (1994) 145(1): 33-36.

Murphy et al., "Enhancing recombinant antibody performance by optimally engineering its format", J. Immunol. Methods (2018) 463:127-133.

Rudikoff et al., "Single Amino Acid Substitution altering antigen-binding specificity", Proc. Natl. Acad. Sci. USA (1982) 79(6):1979-1983.

ADC Review, "Maytansine" [online]. Retrieved from: http://adcreview.com/adc-university/adcs-101/cytotoxic-agents/maytansine/, on Mar. 17, 2016, 4 pages.

BLAST search of LSGRSANP (retrieved from https://blast.ncbi.nlm.nih.gov/Blast.cgi on May 23, 2018, 7 pages) (2018).

BLAST search SEQ ID No. 362 from U.S. Pat. No. 9,562,073 (retrieved from http://blast.ncbi.nlm.nih.gov/Blast.cgi on Mar. 17, 2016, 8 pages).

BLAST search of SEQ ID No. 363 from U.S. Pat. No. 9,562,073 (retrieved from http://blast.ncbi.nlm.nih.gov/Blast.cgi on Mar. 17, 2016, 7 pages).

BLAST search of SEQ ID No. 364 from U.S. Pat. No. 9,562,073 (retrieved from http://blast.ncbi.nlm.nih.gov/Blast.cgi on Mar. 17, 2016, 8 pages).

Casadaban et al., "Analysis of gene control signals by DNA fusion and cloning in *Escherichia coli*" J Mol Biol, 138(2):179-207 (1980).

Donaldson, J.M. et al., "Design and development of masked therapeutic antibodies to limit off-target effects: application to anti-EGFR antibodies", Cancer Biology & Therapy, vol. 8, No. 22, 2009, p. 2147-2152.

Genbank Accession No. ADA97619, "Sequence 28102 from patent US6551795", Rubenfield, 2009, 1 page.

Genbank Accession No. AEL07912.1, "conserved hypothetical protein [Xanthumonas campestris pv.raphani 756C]" [retrieved on Dec. 28, 2017]. Retrieved from internet: https://www.ncbi.nlm.nih.gov/protein/AEL07912, 1 page.

Genbank Accession No. AF099373, "protein ITFG3 [Callorhinchus milii]" 2013, 1 page.

Genbank Accession No. YP 005352726.1, "petG gene product (chloroplast) [Ginko biloba] [online]. [retrieved on Dec. 28, 2017]. Retrieved from the Internet: <https://www.ncbi.nlm.nih.gov/protein/YP_005352726.1>, 1 page.

(56) References Cited

OTHER PUBLICATIONS

GENESEQ Accession No. AAB46481, "B. brevis tyrocidin synthetase activating domain 9" [online] First entry Apr. 9, 2001, revised Sep. 11, 2003, 2 pages.

GENPEPT Accession No. P0C9K2, "RecName: Full=Protein MGF 110-14L; Flags: Precursor" May 5, 2009; Database DDBJ/EMBL/Genbank [online]. Retrieved from the Internet: <https://www.ncbi.nlm.nih.gov/protein/229544532?sat=12&satkey=1040226>; retrieved on Sep. 28, 2018, 3 pages.

GENPEPT Accession No. YP_008873205 "Hypothetical protein [Pseudomonas phage PPpW-3]" Kawato et al.; submitted Dec. 9, 2013, 1 page.

Gerspach et al. "Restoration of membrane TNF-like activity by cell surface targeting and matrix metalloproteinase-mediated processing of a TNF prodrug" Cell Death and Differentiation, 2006. 13:273-284.

Gerspach et al., "Target-selective activation of TNF prodrug by urokinase-type plasminogen activator (uPA) mediated proteolytic processing at the cell surface" Cancer Immunol Immunother, vol. 55: 1590-1600 (2006).

Harris J.et al. "Rapid and general profiling of protease specificity by using combinatorial fluorogenic substrate libraries", PNAS Jul. 5, 2000, vol. 97, No. 14, pp. 7754-7759.

Henikoff, S et al. (1992) "Amino acid substitution matrices from protein blocks" Proc Natl Acad Sci U S A, 89:10915-10919.

Irving, B.A. (Feb. 2015) "Probodies Empower a New Generation of Antibody Immunotherapies," CytomX Therapeutics Inc. presentation at Keystone Symposia™ on Molecular and Cellular Biology, Feb. 8-13, 2015; 25 pages.

Jabaiah, A. and P.S. Daugherty, "Directed evolution of protease beacons that enable sensitive detection of endogenous MT1-MMP activity in tumor cell lines" Chem Biol, Mar. 25, 2011;18(3):392-401.

Jeong K. et al. "Recombinant antibodies: Engineering and production in yeast and bacterial hosts", Biotechnology Journal (2011), vol. 6, p. 16-27.

Ke, S-H. et al. "Distinguishing the specificities of closely related proteases" J Biol Chem, Jun. 26, 1997; vol. 272, No. 26, pp. 16603-16609.

Ke, S-H. et al., "Optimal subsite occupancy and design of 3 selective inhibitor of urokinase", J Biol Chem, Aug. 15, 1997; vol. 272, No. 33, pp. 20456-20462.

Kridel, S.J. et al. "Substrate hydrolysis by matrix metalloproteinase-9" J Biol Chem, Jun. 8, 2011; vol. 276, No. 23, pp. 20572-20578. Epub Mar. 14, 2001.

Liu, S. et al. "Intermolecular complementation achieves high-specificity tumor targeting by anthrax toxin", Nature Biotechnology, vol. 23, No. 6, p. 725-730 (2005).

Lopez-Otin, C. et al. "Protease degradomics: a new challenge for proteomics", Nature Reviews: Molecular Cell Biology, vol. 3, p. 509-519., (2002).

"Maytansinoid DM4" [online]. Retrieved from: https://pubchem.ncbi.nlm.nih.gov/compound/46926355#section=Top on Mar. 17, 2016; 9 pages.

Nangia-Makker P., et al. (Dec. 15, 2007) "Galectin-3 cleavage: a novel surrogate marker for matrix metalloproteinase activity in growing breast cancers" Cancer Res, 67(24):11760-11768. NIH Public Access Author Manuscript; available in PMC Apr. 2, 2013 [online]. Retrieved from the Internet: https://www.ncbi.nlm.nih.gov/pmc/articles/PMC3613979; 17 pages.

Paul, *Fundamental Immunology, 3rd Edition*. Lippincott Williams & Wilkins, 1993; pp. 292-295.

Portolano et al. "Lack of Promiscuity in Autoantigen-Specific H and L Chain Combinations as Revealed by Human H and L Chain Roulette", *Journal of Immunology*, vol. 150, No. 3, p. 880-887, (1993).

Prudova, A. et al. (May 2010) "Multiplex N-terminome analysis of MMP-2 and MMP-9 substrate degradomes by iTRAQ-TAILS quantitative proteomics" *Mol Cell Proteomics*. 9(5):894-911. doi: 10.1074/mcp.M000050-MCP201. Epub Mar. 20, 2010.

Ratnikov et al., "Basis for substrate recognition and distinction by matrix metalloproteinases" *Proc. Natl. Acad. Sci.*, vol. 111(4): E4148-55 (2014).

Rothberg, J.M. et al., "An integrated semiconductor device enabling non-optical genome sequencing" Nature. Jul. 20, 2011;475(7356):348-352.

Takeuchi, T. et al., "Cellular Localization of Membrane-type Saline Protease 1 and Identification of Protease-activated Receptor-2 and Single-chain Urokinase-type Plasminogen Activator as Substrates", *J Biol Chem*, (2000), vol. 275, No. 34, pp. 26333-26342.

Turk, B.E. et al. "Determination of protease cleavage site motifs using mixture-based oriented peptide libraries" Nat Biotechnol, Jul. 2001; 19(7):661-667.

UNIPROT Accession No. B8J087, "Uncharacterized protein" Mar. 3, 2009, 2 pages.

UNIPROT Accession No. Q9ZZR8, "Cytochrome b" May 1, 1999, 2 pages.

Venkatesh, B. et al. (2014) "Elephant shark genome provides unique insights into gnathostome evolution", Nature, vol. 505, No. 7482, pp. 174-179.

Villacres, E. et al. (1993) "Cloning, Chromosomal Mapping, and Expression of Human Fetal Brain Type I Adenylyl Cyclase" Genomics, vol. 16, No. 2, 1993, p. 473-478.

Waterhouse, A.M. et al. (2009) "Jalview Version 2—a multiple sequence alignment editor and analysis workbench" Bioinformatics, 25(9):1189-1191.

Wikipedia.com, "Derivative (chemistry)", accessed Sep. 11, 2017 [online]. Downloaded from: https://en.wikipedia.org/w/index.php?title=Derivative_(chemistry)&oldid=779855519, 1 page.

Zhao T. et al. (May 21, 2010) "A novel strategy to tag matrix metalloproteinasespositive cells for in vivo imaging of invasive and metastatic activity of tumor cells" *J Control Release*, 144:(1):109-114. doi: 10.1016/j.jconrel.2010.01.023. Epub Jan. 21, 2010; abstract.

EMBL Database (Jan. 2, 2014) "*Callorhinchus milii* (elephant shark) protein ITFG3" ID AFO99373, 2 pages.

LeBeau et al. (Jan. 2, 2013) "Imaging a functional tumorigenic biomarker in the transformed epithelium", Proc. Natl. Assoc. Sci. USA, 110(1):93-98.

List et al. (2005) "Deregulated matriptase causes ras-independent multistage carcinogenesis and promotes ras-mediated malignant transformation", Genes & Develop. 19:1934-1950.

Tateno, H. et al. (Jul. 24, 1998) "Isolation and Characterization of Rhamnose-binding Lectins from Eggs of Steelhead Trout (*Oncorhynchus mykiss*) Homologous to Low Density Lipoprotein Receptor Superfamily" J Biol Chem, vol. 273, No. 30, pp. 19190-19197.

Vasiljeva et al. (2019) "The Multifaceted Roles of Tumor-Associated Proteases and Harnessing Their Activity for Prodrug Activation", Biol. Chem. [online]. Retrieved from: https://doi.org/10.1515/hsz-2018-0451 (Received Dec. 1, 2018; Accepted Mar. 18, 2019).

Kopylov, A. et al. (2007) "Methods of quantitative proteomics" *Biomed Chem*, 53(6):613-643. Russian; English abstract on p. 643.

Non-Final Office Action dated Dec. 8, 2022 in U.S. Appl. No. 16/179,670, 12 pages.

Examination Report dated Feb. 24, 2023 in EP 19828467.1, 12 pages.

Russian Office Action dated Dec. 21, 2022 in RU Application No. 2020106752, 20 pages.

Japanese Office Action dated Jun. 21, 2022 in JP 2021-080015, 10 pages.

Japanese Office Action dated Jan. 7, 2020 in JP 2017-556794, 7 pages.

De Groot, N., "AsnC family protein from Sedimentitalea nanhaiensis", XP093016536, Retrieved from the Internet on Jan. 23, 2023: https://rest.uniprot.org/unisave/AOA1I7CZR5?format=txt&versions=3.

Khantasup et al., "Design and Generation of Humanized Single-chain Fv Derived from Mouse Hybridoma for Potential Targeting Application", Monoclon. Antib. Immunodiagn. Immunother. (2015) 34(6):404-417.

Kopylov et al., "Methods of quantitative proteomics", Biomed Khim. (2007) 53(6):613-643.

(56) References Cited

OTHER PUBLICATIONS

LeBeau et al., "Imaging a functional tumorigenic biomarker in the transformed epithelium", Proc. Natl. Assoc. Sci USA (2013) 110(1):93-98.
List et al., "Deregulated matriptase causes ras-independent multi-stage carcinogenesis and promotes ras-mediated malignant transformation", Genes & Develop. (2005) 19:1934-1950.
Tateno et al. (Jul. 24, 1998) "Isolation and Characterization of Rhamnose-binding Lectins from Eggs of Steelhead Trout (*Oncorhynchus mykiss*) Homologous to Low Density Lipoprotein Receptor Superfamily", J. Biol. Chem. (1998) 273(30): 19190-19197.
Uniprot Accession No. M3HF54 (Yu J. et al., Genome sequence of Candida maltosa Xu316, a potential industrial strain for xylitol and ethanol production, 1 page (Downloaded from https://rest.uniprot.org/unisave/M3HF547format=txt&versions=2). 2013.
Vasiljeva et al., "The Multifaceted Roles of Tumor-Associated Proteases and Harnessing Their Activity for Prodrug Activation", Biol. Chem. (2019) https://doi.org/10.1515/hsz-2018-0451.
Yarmolinskaya et al., "Matrix Metalloproteinases and Inhibitors: Classification, Mechanism of Action", J. Obstetrics and Women's Diseases (2012) 61(1):113-125.

\* cited by examiner

SEQUENCE LISTING

```
<160> NUMBER OF SEQ ID NOS: 696

<210> SEQ ID NO 1
<211> LENGTH: 5
<212> TYPE: PRT
<213> ORGANISM: Artificial Sequence
<220> FEATURE:
<223> OTHER INFORMATION: Matriptase Cleavable Core CM Consensus
      Sequence 1
<220> FEATURE:
<221> NAME/KEY: misc_feature
<222> LOCATION: (1)..(1)
<223> OTHER INFORMATION: Xaa may be Ala, Gly, His, Lys, Leu, Asn, Pro,
      Arg, Ser or Val
<220> FEATURE:
<221> NAME/KEY: misc_feature
<222> LOCATION: (2)..(2)
<223> OTHER INFORMATION: Xaa may be Ala, His, Leu, Met, Pro, Gln, Arg,
      Ser or Val
<220> FEATURE:
<221> NAME/KEY: misc_feature
<222> LOCATION: (3)..(3)
<223> OTHER INFORMATION: Xaa may be Ala, Glu, Phe, Gly, Ile, Leu, Pro,
      Arg, Ser, Thr or Val
<220> FEATURE:
<221> NAME/KEY: misc_feature
<222> LOCATION: (4)..(4)
<223> OTHER INFORMATION: Xaa may be Ala, Ile, Lys, Asn, Arg, Thr or Trp
<220> FEATURE:
<221> NAME/KEY: misc_feature
<222> LOCATION: (5)..(5)
<223> OTHER INFORMATION: Xaa may be Ala, Gly, Ile, Leu, Met, Gln, Arg,
      Ser or Val

<400> SEQUENCE: 1

Xaa Xaa Xaa Xaa Xaa
1               5

<210> SEQ ID NO 2
<211> LENGTH: 5
<212> TYPE: PRT
<213> ORGANISM: Artificial Sequence
<220> FEATURE:
<223> OTHER INFORMATION: Matriptase Cleavable Core Subgenus of Core CM
      Consensus 1
<220> FEATURE:
<221> NAME/KEY: misc_feature
<222> LOCATION: (1)..(1)
<223> OTHER INFORMATION: Xaa may be Ala, Gly, Pro, Arg, Ser or Val
<220> FEATURE:
<221> NAME/KEY: misc_feature
<222> LOCATION: (2)..(2)
<223> OTHER INFORMATION: Xaa may be Ala, Leu, Met, Pro, Ser or Val
<220> FEATURE:
<221> NAME/KEY: misc_feature
<222> LOCATION: (3)..(3)
<223> OTHER INFORMATION: Xaa may be Gly, Leu or Pro
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ala, Gly, Arg, Ser or Val
```

```
<400> SEQUENCE: 2

Xaa Xaa Xaa Xaa Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: Matriptase Cleavable Core Subgenus of Core CM
      Consensus 1
<220> FEATURE:
<221> NAME/KEY: misc_feature
<222> LOCATION: (1)..(1)
<223> OTHER INFORMATION: Xaa may be Ala, Pro, Arg, Ser or Val
<220> FEATURE:
<221> NAME/KEY: misc_feature
<222> LOCATION: (2)..(2)
<223> OTHER INFORMATION: Xaa may be Ala, Leu, Met, Ser or Val
<220> FEATURE:
<221> NAME/KEY: misc_feature
<222> LOCATION: (3)..(3)
<223> OTHER INFORMATION: Xaa may be Pro
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ala, Gly, Ser or Val

<400> SEQUENCE: 3

Xaa Xaa Xaa Xaa Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: Matriptase Cleavable Core Subgenus of Core CM
      Consensus 1
<220> FEATURE:
<221> NAME/KEY: misc_feature
<222> LOCATION: (1)..(1)
<223> OTHER INFORMATION: Xaa may be Ala, Pro or Arg
<220> FEATURE:
<221> NAME/KEY: misc_feature
<222> LOCATION: (2)..(2)
<223> OTHER INFORMATION: Xaa may be Ala, Ser or Val
<220> FEATURE:
<221> NAME/KEY: misc_feature
<222> LOCATION: (3)..(3)
<223> OTHER INFORMATION: Xaa may be Pro
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser or Val

<400> SEQUENCE: 4

Xaa Xaa Xaa Xaa Xaa
1               5

<210> SEQ ID NO 5
<211> LENGTH: 5
<212> TYPE: PRT
<213> ORGANISM: Artificial Sequence
```

```
<220> FEATURE:
<223> OTHER INFORMATION: Matriptase Cleavable Core Subgenus of Core CM
      Consensus 1
<220> FEATURE:
<221> NAME/KEY: misc_feature
<222> LOCATION: (1)..(1)
<223> OTHER INFORMATION: Xaa may be Ala, Pro or Arg
<220> FEATURE:
<221> NAME/KEY: misc_feature
<222> LOCATION: (2)..(2)
<223> OTHER INFORMATION: Xaa may be Ala or Ser
<220> FEATURE:
<221> NAME/KEY: misc_feature
<222> LOCATION: (3)..(3)
<223> OTHER INFORMATION: Xaa may be Pro
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser

<400> SEQUENCE: 5

Xaa Xaa Xaa Xaa Xaa
1               5

<210> SEQ ID NO 6
<211> LENGTH: 5
<212> TYPE: PRT
<213> ORGANISM: Artificial Sequence
<220> FEATURE:
<223> OTHER INFORMATION: Matriptase Cleavable Core CM Consensus
      Sequence 2
<220> FEATURE:
<221> NAME/KEY: misc_feature
<222> LOCATION: (1)..(1)
<223> OTHER INFORMATION: Xaa may be Ala, Leu, Pro, Arg, Ser, Thr or Val
<220> FEATURE:
<221> NAME/KEY: misc_feature
<222> LOCATION: (2)..(2)
<223> OTHER INFORMATION: Xaa may be Lys or Arg
<220> FEATURE:
<221> NAME/KEY: misc_feature
<222> LOCATION: (3)..(3)
<223> OTHER INFORMATION: Xaa may be Asp or Arg
<220> FEATURE:
<221> NAME/KEY: misc_feature
<222> LOCATION: (4)..(4)
<223> OTHER INFORMATION: Xaa may be Ala, Gly, Leu, Met, Ser, Thr, Val
      or Trp
<220> FEATURE:
<221> NAME/KEY: misc_feature
<222> LOCATION: (5)..(5)
<223> OTHER INFORMATION: Xaa may be Phe, Gly, Met, Pro or Val

<400> SEQUENCE: 6

Xaa Xaa Xaa Xaa Xaa
1               5

<210> SEQ ID NO 7
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 2
<220> FEATURE:
<221> NAME/KEY: misc_feature
<222> LOCATION: (1)..(1)
<223> OTHER INFORMATION: Xaa may be Ala, Arg, Ser or Thr
<220> FEATURE:
<221> NAME/KEY: misc_feature
<222> LOCATION: (2)..(2)
```

```
<223> OTHER INFORMATION: Xaa may be Lys or Arg
<220> FEATURE:
<221> NAME/KEY: misc_feature
<222> LOCATION: (3)..(3)
<223> OTHER INFORMATION: Xaa may be Asp or Arg
<220> FEATURE:
<221> NAME/KEY: misc_feature
<222> LOCATION: (4)..(4)
<223> OTHER INFORMATION: Xaa may be Leu or Val
<220> FEATURE:
<221> NAME/KEY: misc_feature
<222> LOCATION: (5)..(5)
<223> OTHER INFORMATION: Xaa may be Phe or Pro

<400> SEQUENCE: 7

Xaa Xaa Xaa Xaa Xaa
1               5

<210> SEQ ID NO 8
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 2
<220> FEATURE:
<221> NAME/KEY: misc_feature
<222> LOCATION: (1)..(1)
<223> OTHER INFORMATION: Xaa may be Ala, Ser or Thr
<220> FEATURE:
<221> NAME/KEY: misc_feature
<222> LOCATION: (2)..(2)
<223> OTHER INFORMATION: Xaa may be Lys or Arg
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Leu or Val
<220> FEATURE:
<221> NAME/KEY: misc_feature
<222> LOCATION: (5)..(5)
<223> OTHER INFORMATION: Xaa may be Phe or Pro

<400> SEQUENCE: 8

Xaa Xaa Xaa Xaa Xaa
1               5

<210> SEQ ID NO 9
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 2
<220> FEATURE:
<221> NAME/KEY: misc_feature
<222> LOCATION: (1)..(1)
<223> OTHER INFORMATION: Xaa may be Ser or Thr
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Leu or Val
<220> FEATURE:
<221> NAME/KEY: misc_feature
```

```
<222> LOCATION: (5)..(5)
<223> OTHER INFORMATION: Xaa may be Pro

<400> SEQUENCE: 9

Xaa Xaa Xaa Xaa Xaa
1               5

<210> SEQ ID NO 10
<211> LENGTH: 5
<212> TYPE: PRT
<213> ORGANISM: Artificial Sequence
<220> FEATURE:
<223> OTHER INFORMATION: Matriptase Cleavable Core CM Consensus
      Sequence 3
<220> FEATURE:
<221> NAME/KEY: misc_feature
<222> LOCATION: (1)..(1)
<223> OTHER INFORMATION: Xaa may be Glu, Gly, Pro, Arg, Ser, Val or Trp
<220> FEATURE:
<221> NAME/KEY: misc_feature
<222> LOCATION: (2)..(2)
<223> OTHER INFORMATION: Xaa may be Ala, Gly, Leu, Met, Pro, Ser or Val
<220> FEATURE:
<221> NAME/KEY: misc_feature
<222> LOCATION: (3)..(3)
<223> OTHER INFORMATION: Xaa may be Ala, Ile, Leu or Arg
<220> FEATURE:
<221> NAME/KEY: misc_feature
<222> LOCATION: (4)..(4)
<223> OTHER INFORMATION: Xaa may be Ala, Gly, Ile or Pro
<220> FEATURE:
<221> NAME/KEY: misc_feature
<222> LOCATION: (5)..(5)
<223> OTHER INFORMATION: Xaa may be Gly or Arg

<400> SEQUENCE: 10

Xaa Xaa Xaa Xaa Xaa
1               5

<210> SEQ ID NO 11
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 3
<220> FEATURE:
<221> NAME/KEY: misc_feature
<222> LOCATION: (1)..(1)
<223> OTHER INFORMATION: Xaa may be Gly, Pro, Arg, Ser or Val
<220> FEATURE:
<221> NAME/KEY: misc_feature
<222> LOCATION: (2)..(2)
<223> OTHER INFORMATION: Xaa may be Pro or Val
<220> FEATURE:
<221> NAME/KEY: misc_feature
<222> LOCATION: (3)..(3)
<223> OTHER INFORMATION: Xaa may be Leu or Arg
<220> FEATURE:
<221> NAME/KEY: misc_feature
<222> LOCATION: (4)..(4)
<223> OTHER INFORMATION: Xaa may be Gly
<220> FEATURE:
<221> NAME/KEY: misc_feature
<222> LOCATION: (5)..(5)
<223> OTHER INFORMATION: Xaa may be Gly or Arg

<400> SEQUENCE: 11

Xaa Xaa Xaa Xaa Xaa
1               5

<210> SEQ ID NO 12
<211> LENGTH: 5
```

```
<212> TYPE: PRT
<213> ORGANISM: Artificial Sequence
<220> FEATURE:
<223> OTHER INFORMATION: Matriptase Cleavable Subgenus of Core CM
      Consensus 3
<220> FEATURE:
<221> NAME/KEY: misc_feature
<222> LOCATION: (1)..(1)
<223> OTHER INFORMATION: Xaa may be Pro or Arg
<220> FEATURE:
<221> NAME/KEY: misc_feature
<222> LOCATION: (2)..(2)
<223> OTHER INFORMATION: Xaa may be Pro
<220> FEATURE:
<221> NAME/KEY: misc_feature
<222> LOCATION: (3)..(3)
<223> OTHER INFORMATION: Xaa may be Leu
<220> FEATURE:
<221> NAME/KEY: misc_feature
<222> LOCATION: (4)..(4)
<223> OTHER INFORMATION: Xaa may be Gly
<220> FEATURE:
<221> NAME/KEY: misc_feature
<222> LOCATION: (5)..(5)
<223> OTHER INFORMATION: Xaa may be Arg

<400> SEQUENCE: 12

Xaa Xaa Xaa Xaa Xaa
1               5

<210> SEQ ID NO 13
<211> LENGTH: 5
<212> TYPE: PRT
<213> ORGANISM: Artificial Sequence
<220> FEATURE:
<223> OTHER INFORMATION: Matriptase Cleavable Core CM Consensus
      Sequence 4
<220> FEATURE:
<221> NAME/KEY: misc_feature
<222> LOCATION: (1)..(1)
<223> OTHER INFORMATION: Xaa may be Ala, Gly, His, Leu, Arg or Ser
<220> FEATURE:
<221> NAME/KEY: misc_feature
<222> LOCATION: (2)..(2)
<223> OTHER INFORMATION: Xaa may be Asp, His, Asn, Arg, Ser, Thr or Trp
<220> FEATURE:
<221> NAME/KEY: misc_feature
<222> LOCATION: (3)..(3)
<223> OTHER INFORMATION: Xaa may be Ala, Asn, Pro, Arg, Ser, Thr or Val
<220> FEATURE:
<221> NAME/KEY: misc_feature
<222> LOCATION: (4)..(4)
<223> OTHER INFORMATION: Xaa may be Phe, Gly, Leu, Met, Pro, Gln, Arg,
      Ser or Tyr
<220> FEATURE:
<221> NAME/KEY: misc_feature
<222> LOCATION: (5)..(5)
<223> OTHER INFORMATION: Xaa may be Ile, Gly, Leu, Pro, Ser, Val or Trp

<400> SEQUENCE: 13

Xaa Xaa Xaa Xaa Xaa
1               5

<210> SEQ ID NO 14
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 4
<220> FEATURE:
<221> NAME/KEY: misc_feature
<222> LOCATION: (1)..(1)
<223> OTHER INFORMATION: Xaa may be Ala, Gly, His, Leu, Arg or Ser
<220> FEATURE:
```

```
<221> NAME/KEY: misc_feature
<222> LOCATION: (2)..(2)
<223> OTHER INFORMATION: Xaa may be Asp, His, Arg or Thr
<220> FEATURE:
<221> NAME/KEY: misc_feature
<222> LOCATION: (3)..(3)
<223> OTHER INFORMATION: Xaa may be Ala, Pro, Arg, Ser, Thr or Val
<220> FEATURE:
<221> NAME/KEY: misc_feature
<222> LOCATION: (4)..(4)
<223> OTHER INFORMATION: Xaa may be Phe, Gly, Leu, Met, Pro or Ser
<220> FEATURE:
<221> NAME/KEY: misc_feature
<222> LOCATION: (5)..(5)
<223> OTHER INFORMATION: Xaa may be Gly, Leu, Pro, Ser, Val or Trp

<400> SEQUENCE: 14

Xaa Xaa Xaa Xaa Xaa
1               5

<210> SEQ ID NO 15
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 4
<220> FEATURE:
<221> NAME/KEY: misc_feature
<222> LOCATION: (1)..(1)
<223> OTHER INFORMATION: Xaa may be Gly, Leu or Ser
<220> FEATURE:
<221> NAME/KEY: misc_feature
<222> LOCATION: (2)..(2)
<223> OTHER INFORMATION: Xaa may be Arg or Thr
<220> FEATURE:
<221> NAME/KEY: misc_feature
<222> LOCATION: (3)..(3)
<223> OTHER INFORMATION: Xaa may be Ala, Pro or Ser
<220> FEATURE:
<221> NAME/KEY: misc_feature
<222> LOCATION: (4)..(4)
<223> OTHER INFORMATION: Xaa may be Phe, Gly, Met or Ser
<220> FEATURE:
<221> NAME/KEY: misc_feature
<222> LOCATION: (5)..(5)
<223> OTHER INFORMATION: Xaa may be Gly, Pro, Ser, Val or Trp

<400> SEQUENCE: 15

Xaa Xaa Xaa Xaa Xaa
1               5

<210> SEQ ID NO 16
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 4
<220> FEATURE:
<221> NAME/KEY: misc_feature
<222> LOCATION: (1)..(1)
<223> OTHER INFORMATION: Xaa may be Gly, Leu or Ser
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ala or Ser
<220> FEATURE:
<221> NAME/KEY: misc_feature
<222> LOCATION: (4)..(4)
<223> OTHER INFORMATION: Xaa may be Gly or Met
```

```
<220> FEATURE:
<221> NAME/KEY: misc_feature
<222> LOCATION: (5)..(5)
<223> OTHER INFORMATION: Xaa may be Gly, Pro, Ser or Trp

<400> SEQUENCE: 16

Xaa Xaa Xaa Xaa Xaa
1               5

<210> SEQ ID NO 17
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 4
<220> FEATURE:
<221> NAME/KEY: misc_feature
<222> LOCATION: (1)..(1)
<223> OTHER INFORMATION: Xaa may be Leu
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ala or Ser
<220> FEATURE:
<221> NAME/KEY: misc_feature
<222> LOCATION: (4)..(4)
<223> OTHER INFORMATION: Xaa may be Gly
<220> FEATURE:
<221> NAME/KEY: misc_feature
<222> LOCATION: (5)..(5)
<223> OTHER INFORMATION: Xaa may be Trp

<400> SEQUENCE: 17

Xaa Xaa Xaa Xaa Xaa
1               5

<210> SEQ ID NO 18
<211> LENGTH: 5
<212> TYPE: PRT
<213> ORGANISM: Artificial Sequence
<220> FEATURE:
<223> OTHER INFORMATION: Matriptase Cleavable Core CM Consensus
      Sequence 5
<220> FEATURE:
<221> NAME/KEY: misc_feature
<222> LOCATION: (1)..(1)
<223> OTHER INFORMATION: Xaa may be Gly, Lys, Leu, Ser, Val or Trp
<220> FEATURE:
<221> NAME/KEY: misc_feature
<222> LOCATION: (2)..(2)
<223> OTHER INFORMATION: Xaa may be Gly, Ile, Pro, Gln, Arg or Ser
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Gly, Lys, Arg, Ser or Val
<220> FEATURE:
<221> NAME/KEY: misc_feature
<222> LOCATION: (5)..(5)
<223> OTHER INFORMATION: Xaa may be Ala, Cys, Gly, Leu, Met, Pro, Ser,
      Val or Tyr

<400> SEQUENCE: 18

Xaa Xaa Xaa Xaa Xaa
1               5
```

```
<210> SEQ ID NO 19
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 5
<220> FEATURE:
<221> NAME/KEY: misc_feature
<222> LOCATION: (1)..(1)
<223> OTHER INFORMATION: Xaa may be Gly, Leu, Ser, Val or Trp
<220> FEATURE:
<221> NAME/KEY: misc_feature
<222> LOCATION: (2)..(2)
<223> OTHER INFORMATION: Xaa may be Gly, Gln, Arg or Ser
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Gly, Ser or Val
<220> FEATURE:
<221> NAME/KEY: misc_feature
<222> LOCATION: (5)..(5)
<223> OTHER INFORMATION: Xaa may be Ala, Gly, Leu, Ser, Val

<400> SEQUENCE: 19

Xaa Xaa Xaa Xaa Xaa
1               5

<210> SEQ ID NO 20
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 5
<220> FEATURE:
<221> NAME/KEY: misc_feature
<222> LOCATION: (1)..(1)
<223> OTHER INFORMATION: Xaa may be Val
<220> FEATURE:
<221> NAME/KEY: misc_feature
<222> LOCATION: (2)..(2)
<223> OTHER INFORMATION: Xaa may be Ser
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ser
<220> FEATURE:
<221> NAME/KEY: misc_feature
<222> LOCATION: (5)..(5)
<223> OTHER INFORMATION: Xaa may be Ala Val

<400> SEQUENCE: 20

Xaa Xaa Xaa Xaa Xaa
1               5

<210> SEQ ID NO 21
<211> LENGTH: 5
<212> TYPE: PRT
<213> ORGANISM: Artificial Sequence
<220> FEATURE:
<223> OTHER INFORMATION: Matriptase Cleavable Core CM Consensus
      Sequence 6
<220> FEATURE:
<221> NAME/KEY: misc_feature
<222> LOCATION: (1)..(1)
```

```
<223> OTHER INFORMATION: Xaa may be Ala, Glu, Gly, Ile, Leu, Met, Arg
      or Ser
<220> FEATURE:
<221> NAME/KEY: misc_feature
<222> LOCATION: (2)..(2)
<223> OTHER INFORMATION: Xaa may be Ala, Gly, Lys, Leu, Asn, Arg, Ser
      or Val
<220> FEATURE:
<221> NAME/KEY: misc_feature
<222> LOCATION: (3)..(3)
<223> OTHER INFORMATION: Xaa may be Phe, His, Leu, Arg or Tyr
<220> FEATURE:
<221> NAME/KEY: misc_feature
<222> LOCATION: (4)..(4)
<223> OTHER INFORMATION: Xaa may be Ala, Phe, Gly, His, Pro or Ser
<220> FEATURE:
<221> NAME/KEY: misc_feature
<222> LOCATION: (5)..(5)
<223> OTHER INFORMATION: Xaa may be Phe, Gly, Met, Asn, Pro, Arg, Ser
      or Val

<400> SEQUENCE: 21

Xaa Xaa Xaa Xaa Xaa
1               5

<210> SEQ ID NO 22
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 6
<220> FEATURE:
<221> NAME/KEY: misc_feature
<222> LOCATION: (1)..(1)
<223> OTHER INFORMATION: Xaa may be Ala, Glu, Gly, Leu, Met, Arg or Ser
<220> FEATURE:
<221> NAME/KEY: misc_feature
<222> LOCATION: (2)..(2)
<223> OTHER INFORMATION: Xaa may be Gly, Lys, Leu, Asn, Arg, Ser or Val
<220> FEATURE:
<221> NAME/KEY: misc_feature
<222> LOCATION: (3)..(3)
<223> OTHER INFORMATION: Xaa may be Arg or Tyr
<220> FEATURE:
<221> NAME/KEY: misc_feature
<222> LOCATION: (4)..(4)
<223> OTHER INFORMATION: Xaa may be Ala, Phe, Gly, Pro or Ser
<220> FEATURE:
<221> NAME/KEY: misc_feature
<222> LOCATION: (5)..(5)
<223> OTHER INFORMATION: Xaa may be Phe, Gly, Met, Pro, Arg, Ser or Val

<400> SEQUENCE: 22

Xaa Xaa Xaa Xaa Xaa
1               5

<210> SEQ ID NO 23
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 6
<220> FEATURE:
<221> NAME/KEY: misc_feature
<222> LOCATION: (1)..(1)
<223> OTHER INFORMATION: Xaa may be Ala, Glu, Gly, Met or Ser
<220> FEATURE:
<221> NAME/KEY: misc_feature
<222> LOCATION: (2)..(2)
<223> OTHER INFORMATION: Xaa may be Gly, Leu, Ser or Val
<220> FEATURE:
<221> NAME/KEY: misc_feature
<222> LOCATION: (3)..(3)
```

```
<223> OTHER INFORMATION: Xaa may be Arg or Tyr
<220> FEATURE:
<221> NAME/KEY: misc_feature
<222> LOCATION: (4)..(4)
<223> OTHER INFORMATION: Xaa may be Ala, Gly, Pro or Ser
<220> FEATURE:
<221> NAME/KEY: misc_feature
<222> LOCATION: (5)..(5)
<223> OTHER INFORMATION: Xaa may be Phe, Gly, Met, Pro, Arg, Ser or Val

<400> SEQUENCE: 23

Xaa Xaa Xaa Xaa Xaa
1               5

<210> SEQ ID NO 24
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 6
<220> FEATURE:
<221> NAME/KEY: misc_feature
<222> LOCATION: (1)..(1)
<223> OTHER INFORMATION: Xaa may be Ala, Gly or Ser
<220> FEATURE:
<221> NAME/KEY: misc_feature
<222> LOCATION: (2)..(2)
<223> OTHER INFORMATION: Xaa may be Leu, Ser or Val
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala
<220> FEATURE:
<221> NAME/KEY: misc_feature
<222> LOCATION: (5)..(5)
<223> OTHER INFORMATION: Xaa may be Met or Pro

<400> SEQUENCE: 24

Xaa Xaa Xaa Xaa Xaa
1               5

<210> SEQ ID NO 25
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 6
<220> FEATURE:
<221> NAME/KEY: misc_feature
<222> LOCATION: (1)..(1)
<223> OTHER INFORMATION: Xaa may be Ala
<220> FEATURE:
<221> NAME/KEY: misc_feature
<222> LOCATION: (2)..(2)
<223> OTHER INFORMATION: Xaa may be Leu, Ser or Val
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala
<220> FEATURE:
<221> NAME/KEY: misc_feature
<222> LOCATION: (5)..(5)
<223> OTHER INFORMATION: Xaa may be Met or Pro

<400> SEQUENCE: 25
```

```
Xaa Xaa Xaa Xaa Xaa
1               5

<210> SEQ ID NO 26
<211> LENGTH: 5
<212> TYPE: PRT
<213> ORGANISM: Artificial Sequence
<220> FEATURE:
<223> OTHER INFORMATION: Matriptase Cleavable Core CM Consensus
      Sequence 7
<220> FEATURE:
<221> NAME/KEY: misc_feature
<222> LOCATION: (1)..(1)
<223> OTHER INFORMATION: Xaa may be Ala, Glu, Lys, Leu, Pro, Ser, Thr,
      Val, Trp or Tyr
<220> FEATURE:
<221> NAME/KEY: misc_feature
<222> LOCATION: (2)..(2)
<223> OTHER INFORMATION: Xaa may be Ala, Ile, Leu, Pro, Arg, Ser, Val
      or Tyr
<220> FEATURE:
<221> NAME/KEY: misc_feature
<222> LOCATION: (3)..(3)
<223> OTHER INFORMATION: Xaa may be Glu, Gly, His, Leu, Pro or Val
<220> FEATURE:
<221> NAME/KEY: misc_feature
<222> LOCATION: (4)..(4)
<223> OTHER INFORMATION: Xaa may be Gly, Lys, Leu or Arg
<220> FEATURE:
<221> NAME/KEY: misc_feature
<222> LOCATION: (5)..(5)
<223> OTHER INFORMATION: Xaa may be Gln or Arg

<400> SEQUENCE: 26

Xaa Xaa Xaa Xaa Xaa
1               5

<210> SEQ ID NO 27
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 7
<220> FEATURE:
<221> NAME/KEY: misc_feature
<222> LOCATION: (1)..(1)
<223> OTHER INFORMATION: Xaa may be Glu, Pro, Ser, Val or Trp
<220> FEATURE:
<221> NAME/KEY: misc_feature
<222> LOCATION: (2)..(2)
<223> OTHER INFORMATION: Xaa may be Ala, Pro, Arg, Ser, Val or Tyr
<220> FEATURE:
<221> NAME/KEY: misc_feature
<222> LOCATION: (3)..(3)
<223> OTHER INFORMATION: Xaa may be Glu, Gly, His, Leu, Pro or Val
<220> FEATURE:
<221> NAME/KEY: misc_feature
<222> LOCATION: (4)..(4)
<223> OTHER INFORMATION: Xaa may be Gly, Lys, Leu or Arg
<220> FEATURE:
<221> NAME/KEY: misc_feature
<222> LOCATION: (5)..(5)
<223> OTHER INFORMATION: Xaa may be Gln or Arg

<400> SEQUENCE: 27

Xaa Xaa Xaa Xaa Xaa
1               5

<210> SEQ ID NO 28
<211> LENGTH: 5
<212> TYPE: PRT
<213> ORGANISM: Artificial Sequence
```

```
<220> FEATURE:
<223> OTHER INFORMATION: Matriptase Cleavable Subgenus of Core CM
      Consensus 7
<220> FEATURE:
<221> NAME/KEY: misc_feature
<222> LOCATION: (1)..(1)
<223> OTHER INFORMATION: Xaa may be Pro or Val
<220> FEATURE:
<221> NAME/KEY: misc_feature
<222> LOCATION: (2)..(2)
<223> OTHER INFORMATION: Xaa may be Ala, Pro or Arg
<220> FEATURE:
<221> NAME/KEY: misc_feature
<222> LOCATION: (3)..(3)
<223> OTHER INFORMATION: Xaa may be Glu, Gly, Pro or Val
<220> FEATURE:
<221> NAME/KEY: misc_feature
<222> LOCATION: (4)..(4)
<223> OTHER INFORMATION: Xaa may be Gly or Arg
<220> FEATURE:
<221> NAME/KEY: misc_feature
<222> LOCATION: (5)..(5)
<223> OTHER INFORMATION: Xaa may be Arg

<400> SEQUENCE: 28

Xaa Xaa Xaa Xaa Xaa
1               5

<210> SEQ ID NO 29
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 7
<220> FEATURE:
<221> NAME/KEY: misc_feature
<222> LOCATION: (1)..(1)
<223> OTHER INFORMATION: Xaa may be Pro or Val
<220> FEATURE:
<221> NAME/KEY: misc_feature
<222> LOCATION: (2)..(2)
<223> OTHER INFORMATION: Xaa may be Ala or Arg
<220> FEATURE:
<221> NAME/KEY: misc_feature
<222> LOCATION: (3)..(3)
<223> OTHER INFORMATION: Xaa may be Gly or Val
<220> FEATURE:
<221> NAME/KEY: misc_feature
<222> LOCATION: (4)..(4)
<223> OTHER INFORMATION: Xaa may be Gly or Arg
<220> FEATURE:
<221> NAME/KEY: misc_feature
<222> LOCATION: (5)..(5)
<223> OTHER INFORMATION: Xaa may be Arg

<400> SEQUENCE: 29

Xaa Xaa Xaa Xaa Xaa
1               5

<210> SEQ ID NO 30
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 7
<220> FEATURE:
<221> NAME/KEY: misc_feature
<222> LOCATION: (1)..(1)
<223> OTHER INFORMATION: Xaa may be Pro or Val
<220> FEATURE:
<221> NAME/KEY: misc_feature
<222> LOCATION: (2)..(2)
<223> OTHER INFORMATION: Xaa may be Ala
```

```
<220> FEATURE:
<221> NAME/KEY: misc_feature
<222> LOCATION: (3)..(3)
<223> OTHER INFORMATION: Xaa may be Gly or Val
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Arg

<400> SEQUENCE: 30

Xaa Xaa Xaa Xaa Xaa
1               5

<210> SEQ ID NO 31
<211> LENGTH: 5
<212> TYPE: PRT
<213> ORGANISM: Artificial Sequence
<220> FEATURE:
<223> OTHER INFORMATION: Matriptase Cleavable Core CM Consensus
      Sequence 8
<220> FEATURE:
<221> NAME/KEY: misc_feature
<222> LOCATION: (1)..(1)
<223> OTHER INFORMATION: Xaa may be Ala, Gly, Ile, Lys, Pro, Ser or Thr
<220> FEATURE:
<221> NAME/KEY: misc_feature
<222> LOCATION: (2)..(2)
<223> OTHER INFORMATION: Xaa may be Arg or Thr
<220> FEATURE:
<221> NAME/KEY: misc_feature
<222> LOCATION: (3)..(3)
<223> OTHER INFORMATION: Xaa may be His, Met or Ser
<220> FEATURE:
<221> NAME/KEY: misc_feature
<222> LOCATION: (4)..(4)
<223> OTHER INFORMATION: Xaa may be Phe, Met or Arg
<220> FEATURE:
<221> NAME/KEY: misc_feature
<222> LOCATION: (5)..(5)
<223> OTHER INFORMATION: Xaa may be Ala, Gly, Ile, Leu, Pro, Gln, Arg,
      Ser, Val or Trp

<400> SEQUENCE: 31

Xaa Xaa Xaa Xaa Xaa
1               5

<210> SEQ ID NO 32
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 8
<220> FEATURE:
<221> NAME/KEY: misc_feature
<222> LOCATION: (1)..(1)
<223> OTHER INFORMATION: Xaa may be Ala, Gly, Ile, Lys, Ser or Thr
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Phe, Met or Arg
<220> FEATURE:
<221> NAME/KEY: misc_feature
```

```
<222> LOCATION: (5)..(5)
<223> OTHER INFORMATION: Xaa may be Ala, Ile, Leu, Arg or Trp

<400> SEQUENCE: 32

Xaa Xaa Xaa Xaa Xaa
1               5

<210> SEQ ID NO 33
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 8
<220> FEATURE:
<221> NAME/KEY: misc_feature
<222> LOCATION: (1)..(1)
<223> OTHER INFORMATION: Xaa may be Gly or Lys
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Met
<220> FEATURE:
<221> NAME/KEY: misc_feature
<222> LOCATION: (5)..(5)
<223> OTHER INFORMATION: Xaa may be Ala, Leu, Arg or Trp

<400> SEQUENCE: 33

Xaa Xaa Xaa Xaa Xaa
1               5

<210> SEQ ID NO 34
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 8
<220> FEATURE:
<221> NAME/KEY: misc_feature
<222> LOCATION: (1)..(1)
<223> OTHER INFORMATION: Xaa may be Gly
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Met
<220> FEATURE:
<221> NAME/KEY: misc_feature
<222> LOCATION: (5)..(5)
<223> OTHER INFORMATION: Xaa may be Ala or Leu

<400> SEQUENCE: 34

Xaa Xaa Xaa Xaa Xaa
1               5

<210> SEQ ID NO 35
<211> LENGTH: 5
```

```
<212> TYPE: PRT
<213> ORGANISM: Artificial Sequence
<220> FEATURE:
<223> OTHER INFORMATION: Matriptase Cleavable Core CM Consensus
      Sequence 9
<220> FEATURE:
<221> NAME/KEY: misc_feature
<222> LOCATION: (1)..(1)
<223> OTHER INFORMATION: Xaa may be Ile, Leu or Ser
<220> FEATURE:
<221> NAME/KEY: misc_feature
<222> LOCATION: (2)..(2)
<223> OTHER INFORMATION: Xaa may be Ala, Gly, Lys, Pro, Arg or Val
<220> FEATURE:
<221> NAME/KEY: misc_feature
<222> LOCATION: (3)..(3)
<223> OTHER INFORMATION: Xaa may be Leu, Arg or Ser
<220> FEATURE:
<221> NAME/KEY: misc_feature
<222> LOCATION: (4)..(4)
<223> OTHER INFORMATION: Xaa may be Ala, Lys, Met, Pro, Arg, Ser or Thr
<220> FEATURE:
<221> NAME/KEY: misc_feature
<222> LOCATION: (5)..(5)
<223> OTHER INFORMATION: Xaa may be Phe, Gly, His, Ile, Lys, Leu, Met,
      Pro, Arg, Ser or Val

<400> SEQUENCE: 35

Xaa Xaa Xaa Xaa Xaa
1               5

<210> SEQ ID NO 36
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 9
<220> FEATURE:
<221> NAME/KEY: misc_feature
<222> LOCATION: (1)..(1)
<223> OTHER INFORMATION: Xaa may be Ile or Leu
<220> FEATURE:
<221> NAME/KEY: misc_feature
<222> LOCATION: (2)..(2)
<223> OTHER INFORMATION: Xaa may be Ala, Gly, Pro or Val
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala, Met, Pro, Arg, Ser or Thr
<220> FEATURE:
<221> NAME/KEY: misc_feature
<222> LOCATION: (5)..(5)
<223> OTHER INFORMATION: Xaa may be Gly, Lys, Leu, Arg, Ser or Val

<400> SEQUENCE: 36

Xaa Xaa Xaa Xaa Xaa
1               5

<210> SEQ ID NO 37
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 9
<220> FEATURE:
<221> NAME/KEY: misc_feature
<222> LOCATION: (1)..(1)
<223> OTHER INFORMATION: Xaa may be Leu
<220> FEATURE:
```

<221> NAME/KEY: misc_feature
<222> LOCATION: (2)..(2)
<223> OTHER INFORMATION: Xaa may be Ala, Gly, Pro or Val
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala, Met, Pro, Arg or Ser
<220> FEATURE:
<221> NAME/KEY: misc_feature
<222> LOCATION: (5)..(5)
<223> OTHER INFORMATION: Xaa may be Gly, Lys, Leu, Ser or Val

<400> SEQUENCE: 37

Xaa Xaa Xaa Xaa Xaa
1               5

<210> SEQ ID NO 38
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 9
<220> FEATURE:
<221> NAME/KEY: misc_feature
<222> LOCATION: (1)..(1)
<223> OTHER INFORMATION: Xaa may be Leu
<220> FEATURE:
<221> NAME/KEY: misc_feature
<222> LOCATION: (2)..(2)
<223> OTHER INFORMATION: Xaa may be Ala, Gly or Pro
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala or Ser
<220> FEATURE:
<221> NAME/KEY: misc_feature
<222> LOCATION: (5)..(5)
<223> OTHER INFORMATION: Xaa may be Gly or Leu

<400> SEQUENCE: 38

Xaa Xaa Xaa Xaa Xaa
1               5

<210> SEQ ID NO 39
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 9
<220> FEATURE:
<221> NAME/KEY: misc_feature
<222> LOCATION: (1)..(1)
<223> OTHER INFORMATION: Xaa may be Leu
<220> FEATURE:
<221> NAME/KEY: misc_feature
<222> LOCATION: (2)..(2)
<223> OTHER INFORMATION: Xaa may be Ala or Pro
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala

```
<220> FEATURE:
<221> NAME/KEY: misc_feature
<222> LOCATION: (5)..(5)
<223> OTHER INFORMATION: Xaa may be Gly or Leu

<400> SEQUENCE: 39

Xaa Xaa Xaa Xaa Xaa
1               5

<210> SEQ ID NO 40
<211> LENGTH: 5
<212> TYPE: PRT
<213> ORGANISM: Artificial Sequence
<220> FEATURE:
<223> OTHER INFORMATION: Matriptase Cleavable Core CM Consensus
      Sequence 10
<220> FEATURE:
<221> NAME/KEY: misc_feature
<222> LOCATION: (1)..(1)
<223> OTHER INFORMATION: Xaa may be Glu, Leu, Gln, Ser, Thr or Val
<220> FEATURE:
<221> NAME/KEY: misc_feature
<222> LOCATION: (2)..(2)
<223> OTHER INFORMATION: Xaa may be Leu, Arg or Ser
<220> FEATURE:
<221> NAME/KEY: misc_feature
<222> LOCATION: (3)..(3)
<223> OTHER INFORMATION: Xaa may be His, Lys or Arg
<220> FEATURE:
<221> NAME/KEY: misc_feature
<222> LOCATION: (4)..(4)
<223> OTHER INFORMATION: Xaa may be Ala, Met, Arg or Ser
<220> FEATURE:
<221> NAME/KEY: misc_feature
<222> LOCATION: (5)..(5)
<223> OTHER INFORMATION: Xaa may be Gly, Leu, Met, Arg, Ser or Trp

<400> SEQUENCE: 40

Xaa Xaa Xaa Xaa Xaa
1               5

<210> SEQ ID NO 41
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 10
<220> FEATURE:
<221> NAME/KEY: misc_feature
<222> LOCATION: (1)..(1)
<223> OTHER INFORMATION: Xaa may be Glu, Leu, Thr or Val
<220> FEATURE:
<221> NAME/KEY: misc_feature
<222> LOCATION: (2)..(2)
<223> OTHER INFORMATION: Xaa may be Arg or Ser
<220> FEATURE:
<221> NAME/KEY: misc_feature
<222> LOCATION: (3)..(3)
<223> OTHER INFORMATION: Xaa may be Lys or Arg
<220> FEATURE:
<221> NAME/KEY: misc_feature
<222> LOCATION: (4)..(4)
<223> OTHER INFORMATION: Xaa may be Met, Arg or Ser
<220> FEATURE:
<221> NAME/KEY: misc_feature
<222> LOCATION: (5)..(5)
<223> OTHER INFORMATION: Xaa may be Gly, Leu, Met, Ser or Trp

<400> SEQUENCE: 41

Xaa Xaa Xaa Xaa Xaa
1               5
```

-continued

```
<210> SEQ ID NO 42
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 10
<220> FEATURE:
<221> NAME/KEY: misc_feature
<222> LOCATION: (1)..(1)
<223> OTHER INFORMATION: Xaa may be Glu, Thr or Val
<220> FEATURE:
<221> NAME/KEY: misc_feature
<222> LOCATION: (2)..(2)
<223> OTHER INFORMATION: Xaa may be Arg or Ser
<220> FEATURE:
<221> NAME/KEY: misc_feature
<222> LOCATION: (3)..(3)
<223> OTHER INFORMATION: Xaa may be Lys or Arg
<220> FEATURE:
<221> NAME/KEY: misc_feature
<222> LOCATION: (4)..(4)
<223> OTHER INFORMATION: Xaa may be Met or Arg
<220> FEATURE:
<221> NAME/KEY: misc_feature
<222> LOCATION: (5)..(5)
<223> OTHER INFORMATION: Xaa may be Gly, Leu, Met, Ser or Trp

<400> SEQUENCE: 42

Xaa Xaa Xaa Xaa Xaa
1               5

<210> SEQ ID NO 43
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 10
<220> FEATURE:
<221> NAME/KEY: misc_feature
<222> LOCATION: (1)..(1)
<223> OTHER INFORMATION: Xaa may be Glu or Val
<220> FEATURE:
<221> NAME/KEY: misc_feature
<222> LOCATION: (2)..(2)
<223> OTHER INFORMATION: Xaa may be Ser
<220> FEATURE:
<221> NAME/KEY: misc_feature
<222> LOCATION: (3)..(3)
<223> OTHER INFORMATION: Xaa may be Lys or Arg
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Leu, Ser or Trp

<400> SEQUENCE: 43

Xaa Xaa Xaa Xaa Xaa
1               5

<210> SEQ ID NO 44
<211> LENGTH: 5
<212> TYPE: PRT
<213> ORGANISM: Artificial Sequence
<220> FEATURE:
<223> OTHER INFORMATION: Matriptase Cleavable Subgenus of Core CM
      Consensus 10
<220> FEATURE:
<221> NAME/KEY: misc_feature
<222> LOCATION: (1)..(1)
<223> OTHER INFORMATION: Xaa may be Glu
```

```
<220> FEATURE:
<221> NAME/KEY: misc_feature
<222> LOCATION: (2)..(2)
<223> OTHER INFORMATION: Xaa may be Ser
<220> FEATURE:
<221> NAME/KEY: misc_feature
<222> LOCATION: (3)..(3)
<223> OTHER INFORMATION: Xaa may be Lys or Arg
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Leu or Trp

<400> SEQUENCE: 44

Xaa Xaa Xaa Xaa Xaa
1               5

<210> SEQ ID NO 45
<211> LENGTH: 6
<212> TYPE: PRT
<213> ORGANISM: Artificial Sequence
<220> FEATURE:
<223> OTHER INFORMATION: Matriptase Cleavable Expanded Core CM
      Consensus Sequence 1
<220> FEATURE:
<221> NAME/KEY: misc_feature
<222> LOCATION: (1)..(1)
<223> OTHER INFORMATION: Xaa may be Ala, Gly, His, Lys, Leu, Asn, Pro,
      Arg, Ser or Val
<220> FEATURE:
<221> NAME/KEY: misc_feature
<222> LOCATION: (2)..(2)
<223> OTHER INFORMATION: Xaa may be Ala, His, Leu, Met, Pro, Gln, Arg,
      Ser or Val
<220> FEATURE:
<221> NAME/KEY: misc_feature
<222> LOCATION: (3)..(3)
<223> OTHER INFORMATION: Xaa may be Ala, Glu, Phe, Gly, Ile, Leu, Pro,
      Arg, Ser, Thr or Val
<220> FEATURE:
<221> NAME/KEY: misc_feature
<222> LOCATION: (4)..(4)
<223> OTHER INFORMATION: Xaa may be Ala, Ile, Lys, Asn, Arg, Thr or Trp
<220> FEATURE:
<221> NAME/KEY: misc_feature
<222> LOCATION: (5)..(5)
<223> OTHER INFORMATION: Xaa may be Ala, Gly, Ile, Leu, Met, Gln, Arg,
      Ser or Val
<220> FEATURE:
<221> NAME/KEY: misc_feature
<222> LOCATION: (6)..(6)
<223> OTHER INFORMATION: Xaa may be Phe, Gly, His, Leu, Met, Arg, Ser
      or Trp

<400> SEQUENCE: 45

Xaa Xaa Xaa Xaa Xaa Xaa
1               5

<210> SEQ ID NO 46
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 1
<220> FEATURE:
<221> NAME/KEY: misc_feature
<222> LOCATION: (1)..(1)
<223> OTHER INFORMATION: Xaa may be Ala, Gly, Pro, Arg, Ser or Val
<220> FEATURE:
<221> NAME/KEY: misc_feature
```

```
<222> LOCATION: (2)..(2)
<223> OTHER INFORMATION: Xaa may be Ala, Leu, Met, Pro, Ser or Val
<220> FEATURE:
<221> NAME/KEY: misc_feature
<222> LOCATION: (3)..(3)
<223> OTHER INFORMATION: Xaa may be Gly, Leu or Pro
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ala, Gly, Arg, Ser or Val
<220> FEATURE:
<221> NAME/KEY: misc_feature
<222> LOCATION: (6)..(6)
<223> OTHER INFORMATION: Xaa may be Phe, Gly, His, Leu, Met, Ser or Trp

<400> SEQUENCE: 46

Xaa Xaa Xaa Xaa Xaa Xaa
1               5

<210> SEQ ID NO 47
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 1
<220> FEATURE:
<221> NAME/KEY: misc_feature
<222> LOCATION: (1)..(1)
<223> OTHER INFORMATION: Xaa may be Ala, Pro, Arg, Ser or Val
<220> FEATURE:
<221> NAME/KEY: misc_feature
<222> LOCATION: (2)..(2)
<223> OTHER INFORMATION: Xaa may be Ala, Leu, Met, Ser or Val
<220> FEATURE:
<221> NAME/KEY: misc_feature
<222> LOCATION: (3)..(3)
<223> OTHER INFORMATION: Xaa may be Pro
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ala, Gly, Ser or Val
<220> FEATURE:
<221> NAME/KEY: misc_feature
<222> LOCATION: (6)..(6)
<223> OTHER INFORMATION: Xaa may be Phe, Gly, His, Met, Ser or Trp

<400> SEQUENCE: 47

Xaa Xaa Xaa Xaa Xaa Xaa
1               5

<210> SEQ ID NO 48
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 1
<220> FEATURE:
<221> NAME/KEY: misc_feature
<222> LOCATION: (1)..(1)
<223> OTHER INFORMATION: Xaa may be Ala, Pro or Arg
<220> FEATURE:
<221> NAME/KEY: misc_feature
<222> LOCATION: (2)..(2)
<223> OTHER INFORMATION: Xaa may be Ala, Ser or Val
<220> FEATURE:
```

```
<221> NAME/KEY: misc_feature
<222> LOCATION: (3)..(3)
<223> OTHER INFORMATION: Xaa may be Pro
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser or Val
<220> FEATURE:
<221> NAME/KEY: misc_feature
<222> LOCATION: (6)..(6)
<223> OTHER INFORMATION: Xaa may be Phe, Gly, His, Met or Ser

<400> SEQUENCE: 48

Xaa Xaa Xaa Xaa Xaa Xaa
1               5

<210> SEQ ID NO 49
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 1
<220> FEATURE:
<221> NAME/KEY: misc_feature
<222> LOCATION: (1)..(1)
<223> OTHER INFORMATION: Xaa may be Ala, Pro or Arg
<220> FEATURE:
<221> NAME/KEY: misc_feature
<222> LOCATION: (2)..(2)
<223> OTHER INFORMATION: Xaa may be Ala or Ser
<220> FEATURE:
<221> NAME/KEY: misc_feature
<222> LOCATION: (3)..(3)
<223> OTHER INFORMATION: Xaa may be Pro
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Phe, Gly, His or Ser

<400> SEQUENCE: 49

Xaa Xaa Xaa Xaa Xaa Xaa
1               5

<210> SEQ ID NO 50
<211> LENGTH: 6
<212> TYPE: PRT
<213> ORGANISM: Artificial Sequence
<220> FEATURE:
<223> OTHER INFORMATION: Matriptase Cleavable Expanded Core CM
      Consensus Sequence 2A
<220> FEATURE:
<221> NAME/KEY: misc_feature
<222> LOCATION: (1)..(1)
<223> OTHER INFORMATION: Xaa may be Ala, Glu, Gly, Leu, Pro, Gln, Ser,
      Thr or Val
<220> FEATURE:
<221> NAME/KEY: misc_feature
<222> LOCATION: (2)..(2)
<223> OTHER INFORMATION: Xaa may be Ala, Leu, Pro, Arg, Ser, Thr or Val
<220> FEATURE:
<221> NAME/KEY: misc_feature
<222> LOCATION: (3)..(3)
```

-continued

```
<223> OTHER INFORMATION: Xaa may be Lys or Arg
<220> FEATURE:
<221> NAME/KEY: misc_feature
<222> LOCATION: (4)..(4)
<223> OTHER INFORMATION: Xaa may be Asp or Arg
<220> FEATURE:
<221> NAME/KEY: misc_feature
<222> LOCATION: (5)..(5)
<223> OTHER INFORMATION: Xaa may be Ala, Gly, Leu, Met, Ser, Thr, Val
      or Trp
<220> FEATURE:
<221> NAME/KEY: misc_feature
<222> LOCATION: (6)..(6)
<223> OTHER INFORMATION: Xaa may be Phe, Gly, Met, Pro or Val

<400> SEQUENCE: 50

Xaa Xaa Xaa Xaa Xaa Xaa
1               5

<210> SEQ ID NO 51
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 2A
<220> FEATURE:
<221> NAME/KEY: misc_feature
<222> LOCATION: (1)..(1)
<223> OTHER INFORMATION: Xaa may be Glu, Gly, Leu, Pro, Gln or Ser
<220> FEATURE:
<221> NAME/KEY: misc_feature
<222> LOCATION: (2)..(2)
<223> OTHER INFORMATION: Xaa may be Ala, Arg, Ser or Thr
<220> FEATURE:
<221> NAME/KEY: misc_feature
<222> LOCATION: (3)..(3)
<223> OTHER INFORMATION: Xaa may be Lys or Arg
<220> FEATURE:
<221> NAME/KEY: misc_feature
<222> LOCATION: (4)..(4)
<223> OTHER INFORMATION: Xaa may be Asp or Arg
<220> FEATURE:
<221> NAME/KEY: misc_feature
<222> LOCATION: (5)..(5)
<223> OTHER INFORMATION: Xaa may be Leu or Val
<220> FEATURE:
<221> NAME/KEY: misc_feature
<222> LOCATION: (6)..(6)
<223> OTHER INFORMATION: Xaa may be Phe or Pro

<400> SEQUENCE: 51

Xaa Xaa Xaa Xaa Xaa Xaa
1               5

<210> SEQ ID NO 52
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 2A
<220> FEATURE:
<221> NAME/KEY: misc_feature
<222> LOCATION: (1)..(1)
<223> OTHER INFORMATION: Xaa may be Glu, Leu, Pro or Gln
<220> FEATURE:
<221> NAME/KEY: misc_feature
<222> LOCATION: (2)..(2)
<223> OTHER INFORMATION: Xaa may be Ala, Ser or Thr
<220> FEATURE:
<221> NAME/KEY: misc_feature
<222> LOCATION: (3)..(3)
<223> OTHER INFORMATION: Xaa may be Lys or Arg
<220> FEATURE:
```

```
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Leu or Val
<220> FEATURE:
<221> NAME/KEY: misc_feature
<222> LOCATION: (6)..(6)
<223> OTHER INFORMATION: Xaa may be Phe or Pro

<400> SEQUENCE: 52

Xaa Xaa Xaa Xaa Xaa Xaa
1               5

<210> SEQ ID NO 53
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 2A
<220> FEATURE:
<221> NAME/KEY: misc_feature
<222> LOCATION: (1)..(1)
<223> OTHER INFORMATION: Xaa may be Glu, Pro or Gln
<220> FEATURE:
<221> NAME/KEY: misc_feature
<222> LOCATION: (2)..(2)
<223> OTHER INFORMATION: Xaa may be Ser or Thr
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Leu or Val
<220> FEATURE:
<221> NAME/KEY: misc_feature
<222> LOCATION: (6)..(6)
<223> OTHER INFORMATION: Xaa may be Pro

<400> SEQUENCE: 53

Xaa Xaa Xaa Xaa Xaa Xaa
1               5

<210> SEQ ID NO 54
<211> LENGTH: 6
<212> TYPE: PRT
<213> ORGANISM: Artificial Sequence
<220> FEATURE:
<223> OTHER INFORMATION: Matriptase Cleavable Expanded Core CM
      Consensus Sequence 2B
<220> FEATURE:
<221> NAME/KEY: misc_feature
<222> LOCATION: (1)..(1)
<223> OTHER INFORMATION: Xaa may be Ala, Leu, Pro, Arg, Ser, Thr or Val
<220> FEATURE:
<221> NAME/KEY: misc_feature
<222> LOCATION: (2)..(2)
<223> OTHER INFORMATION: Xaa may be Lys or Arg
<220> FEATURE:
<221> NAME/KEY: misc_feature
<222> LOCATION: (3)..(3)
<223> OTHER INFORMATION: Xaa may be Asp or Arg
<220> FEATURE:
<221> NAME/KEY: misc_feature
<222> LOCATION: (4)..(4)
<223> OTHER INFORMATION: Xaa may be Ala, Gly, Leu, Met, Ser, Thr, Val
```

```
    or Trp
<220> FEATURE:
<221> NAME/KEY: misc_feature
<222> LOCATION: (5)..(5)
<223> OTHER INFORMATION: Xaa may be Phe, Gly, Met, Pro or Val
<220> FEATURE:
<221> NAME/KEY: misc_feature
<222> LOCATION: (6)..(6)
<223> OTHER INFORMATION: Xaa may be Gly, Leu, Met, Asn, Pro, Ser, Val
      or Tyr

<400> SEQUENCE: 54

Xaa Xaa Xaa Xaa Xaa Xaa
1               5

<210> SEQ ID NO 55
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 2B
<220> FEATURE:
<221> NAME/KEY: misc_feature
<222> LOCATION: (1)..(1)
<223> OTHER INFORMATION: Xaa may be Ala, Arg, Ser or Thr
<220> FEATURE:
<221> NAME/KEY: misc_feature
<222> LOCATION: (2)..(2)
<223> OTHER INFORMATION: Xaa may be Lys or Arg
<220> FEATURE:
<221> NAME/KEY: misc_feature
<222> LOCATION: (3)..(3)
<223> OTHER INFORMATION: Xaa may be Asp or Arg
<220> FEATURE:
<221> NAME/KEY: misc_feature
<222> LOCATION: (4)..(4)
<223> OTHER INFORMATION: Xaa may be Leu or Val
<220> FEATURE:
<221> NAME/KEY: misc_feature
<222> LOCATION: (5)..(5)
<223> OTHER INFORMATION: Xaa may be Phe or Pro
<220> FEATURE:
<221> NAME/KEY: misc_feature
<222> LOCATION: (6)..(6)
<223> OTHER INFORMATION: Xaa may be Gly, Leu, Ser or Val

<400> SEQUENCE: 55

Xaa Xaa Xaa Xaa Xaa Xaa
1               5

<210> SEQ ID NO 56
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 2B
<220> FEATURE:
<221> NAME/KEY: misc_feature
<222> LOCATION: (1)..(1)
<223> OTHER INFORMATION: Xaa may be Ala, Ser or Thr
<220> FEATURE:
<221> NAME/KEY: misc_feature
<222> LOCATION: (2)..(2)
<223> OTHER INFORMATION: Xaa may be Lys or Arg
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Leu or Val
<220> FEATURE:
```

```
<221> NAME/KEY: misc_feature
<222> LOCATION: (5)..(5)
<223> OTHER INFORMATION: Xaa may be Phe or Pro
<220> FEATURE:
<221> NAME/KEY: misc_feature
<222> LOCATION: (6)..(6)
<223> OTHER INFORMATION: Xaa may be Gly, Leu, Ser or Val

<400> SEQUENCE: 56

Xaa Xaa Xaa Xaa Xaa Xaa
1               5

<210> SEQ ID NO 57
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 2B
<220> FEATURE:
<221> NAME/KEY: misc_feature
<222> LOCATION: (1)..(1)
<223> OTHER INFORMATION: Xaa may be Ser or Thr
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Leu or Val
<220> FEATURE:
<221> NAME/KEY: misc_feature
<222> LOCATION: (5)..(5)
<223> OTHER INFORMATION: Xaa may be Pro
<220> FEATURE:
<221> NAME/KEY: misc_feature
<222> LOCATION: (6)..(6)
<223> OTHER INFORMATION: Xaa may be Leu or Val

<400> SEQUENCE: 57

Xaa Xaa Xaa Xaa Xaa Xaa
1               5

<210> SEQ ID NO 58
<211> LENGTH: 7
<212> TYPE: PRT
<213> ORGANISM: Artificial Sequence
<220> FEATURE:
<223> OTHER INFORMATION: Matriptase Cleavable Expanded Core CM
      Consensus Sequence 2C
<220> FEATURE:
<221> NAME/KEY: misc_feature
<222> LOCATION: (1)..(1)
<223> OTHER INFORMATION: Xaa may be Ala, Glu, Gly, Leu, Pro, Gln, Ser,
      Thr or Val
<220> FEATURE:
<221> NAME/KEY: misc_feature
<222> LOCATION: (2)..(2)
<223> OTHER INFORMATION: Xaa may be Ala, Leu, Pro, Arg, Ser, Thr or Val
<220> FEATURE:
<221> NAME/KEY: misc_feature
<222> LOCATION: (3)..(3)
<223> OTHER INFORMATION: Xaa may be Lys or Arg
<220> FEATURE:
<221> NAME/KEY: misc_feature
<222> LOCATION: (4)..(4)
<223> OTHER INFORMATION: Xaa may be Asp or Arg
<220> FEATURE:
<221> NAME/KEY: misc_feature
<222> LOCATION: (5)..(5)
```

```
<223> OTHER INFORMATION: Xaa may be Ala, Gly, Leu, Met, Ser, Thr, Val
      or Trp
<220> FEATURE:
<221> NAME/KEY: misc_feature
<222> LOCATION: (6)..(6)
<223> OTHER INFORMATION: Xaa may be Phe, Gly, Met, Pro or Val
<220> FEATURE:
<221> NAME/KEY: misc_feature
<222> LOCATION: (7)..(7)
<223> OTHER INFORMATION: Xaa may be Gly, Leu, Met, Asn, Pro, Ser, Val
      or Tyr

<400> SEQUENCE: 58

Xaa Xaa Xaa Xaa Xaa Xaa Xaa
1               5

<210> SEQ ID NO 59
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 2C
<220> FEATURE:
<221> NAME/KEY: misc_feature
<222> LOCATION: (1)..(1)
<223> OTHER INFORMATION: Xaa may be Glu, Gly, Leu, Pro, Gln or Ser
<220> FEATURE:
<221> NAME/KEY: misc_feature
<222> LOCATION: (2)..(2)
<223> OTHER INFORMATION: Xaa may be Ala, Arg, Ser or Thr
<220> FEATURE:
<221> NAME/KEY: misc_feature
<222> LOCATION: (3)..(3)
<223> OTHER INFORMATION: Xaa may be Lys or Arg
<220> FEATURE:
<221> NAME/KEY: misc_feature
<222> LOCATION: (4)..(4)
<223> OTHER INFORMATION: Xaa may be Asp or Arg
<220> FEATURE:
<221> NAME/KEY: misc_feature
<222> LOCATION: (5)..(5)
<223> OTHER INFORMATION: Xaa may be Leu or Val
<220> FEATURE:
<221> NAME/KEY: misc_feature
<222> LOCATION: (6)..(6)
<223> OTHER INFORMATION: Xaa may be Phe or Pro
<220> FEATURE:
<221> NAME/KEY: misc_feature
<222> LOCATION: (7)..(7)
<223> OTHER INFORMATION: Xaa may be Gly, Leu, Ser or Val

<400> SEQUENCE: 59

Xaa Xaa Xaa Xaa Xaa Xaa Xaa
1               5

<210> SEQ ID NO 60
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 2C
<220> FEATURE:
<221> NAME/KEY: misc_feature
<222> LOCATION: (1)..(1)
<223> OTHER INFORMATION: Xaa may be Glu, Leu, Pro or Gln
<220> FEATURE:
<221> NAME/KEY: misc_feature
<222> LOCATION: (2)..(2)
<223> OTHER INFORMATION: Xaa may be Ala, Ser or Thr
<220> FEATURE:
<221> NAME/KEY: misc_feature
<222> LOCATION: (3)..(3)
<223> OTHER INFORMATION: Xaa may be Lys or Arg
```

```
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Leu or Val
<220> FEATURE:
<221> NAME/KEY: misc_feature
<222> LOCATION: (6)..(6)
<223> OTHER INFORMATION: Xaa may be Phe or Pro
<220> FEATURE:
<221> NAME/KEY: misc_feature
<222> LOCATION: (7)..(7)
<223> OTHER INFORMATION: Xaa may be Gly, Leu, Ser or Val

<400> SEQUENCE: 60

Xaa Xaa Xaa Xaa Xaa Xaa Xaa
1               5

<210> SEQ ID NO 61
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 2C
<220> FEATURE:
<221> NAME/KEY: misc_feature
<222> LOCATION: (1)..(1)
<223> OTHER INFORMATION: Xaa may be Glu, Pro or Gln
<220> FEATURE:
<221> NAME/KEY: misc_feature
<222> LOCATION: (2)..(2)
<223> OTHER INFORMATION: Xaa may be Ser or Thr
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Leu or Val
<220> FEATURE:
<221> NAME/KEY: misc_feature
<222> LOCATION: (6)..(6)
<223> OTHER INFORMATION: Xaa may be Pro
<220> FEATURE:
<221> NAME/KEY: misc_feature
<222> LOCATION: (7)..(7)
<223> OTHER INFORMATION: Xaa may be Leu or Val

<400> SEQUENCE: 61

Xaa Xaa Xaa Xaa Xaa Xaa Xaa
1               5

<210> SEQ ID NO 62
<211> LENGTH: 6
<212> TYPE: PRT
<213> ORGANISM: Artificial Sequence
<220> FEATURE:
<223> OTHER INFORMATION: Matriptase Cleavable Expanded Core CM
      Consensus Sequence 3A
<220> FEATURE:
<221> NAME/KEY: misc_feature
<222> LOCATION: (1)..(1)
<223> OTHER INFORMATION: Xaa may be Asp, Gly, Lys, Ser, Thr or Val
<220> FEATURE:
<221> NAME/KEY: misc_feature
<222> LOCATION: (2)..(2)
```

-continued

```
<223> OTHER INFORMATION: Xaa may be Glu, Gly, Pro, Arg, Ser, Val or Trp
<220> FEATURE:
<221> NAME/KEY: misc_feature
<222> LOCATION: (3)..(3)
<223> OTHER INFORMATION: Xaa may be Ala, Gly, Leu, Met, Pro, Ser or Val
<220> FEATURE:
<221> NAME/KEY: misc_feature
<222> LOCATION: (4)..(4)
<223> OTHER INFORMATION: Xaa may be Ala, Ile, Leu or Arg
<220> FEATURE:
<221> NAME/KEY: misc_feature
<222> LOCATION: (5)..(5)
<223> OTHER INFORMATION: Xaa may be Ala, Gly, Ile or Pro
<220> FEATURE:
<221> NAME/KEY: misc_feature
<222> LOCATION: (6)..(6)
<223> OTHER INFORMATION: Xaa may be Gly or Arg

<400> SEQUENCE: 62

Xaa Xaa Xaa Xaa Xaa Xaa
1               5

<210> SEQ ID NO 63
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 3A
<220> FEATURE:
<221> NAME/KEY: misc_feature
<222> LOCATION: (1)..(1)
<223> OTHER INFORMATION: Xaa may be Gly, Lys or Ser
<220> FEATURE:
<221> NAME/KEY: misc_feature
<222> LOCATION: (2)..(2)
<223> OTHER INFORMATION: Xaa may be Gly, Pro, Arg, Ser or Val
<220> FEATURE:
<221> NAME/KEY: misc_feature
<222> LOCATION: (3)..(3)
<223> OTHER INFORMATION: Xaa may be Pro or Val
<220> FEATURE:
<221> NAME/KEY: misc_feature
<222> LOCATION: (4)..(4)
<223> OTHER INFORMATION: Xaa may be Leu or Arg
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Gly or Arg

<400> SEQUENCE: 63

Xaa Xaa Xaa Xaa Xaa Xaa
1               5

<210> SEQ ID NO 64
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 3A
<220> FEATURE:
<221> NAME/KEY: misc_feature
<222> LOCATION: (1)..(1)
<223> OTHER INFORMATION: Xaa may be Gly or Ser
<220> FEATURE:
<221> NAME/KEY: misc_feature
<222> LOCATION: (2)..(2)
<223> OTHER INFORMATION: Xaa may be Pro or Arg
<220> FEATURE:
<221> NAME/KEY: misc_feature
```

-continued

```
<222> LOCATION: (3)..(3)
<223> OTHER INFORMATION: Xaa may be Pro
<220> FEATURE:
<221> NAME/KEY: misc_feature
<222> LOCATION: (4)..(4)
<223> OTHER INFORMATION: Xaa may be Leu
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg

<400> SEQUENCE: 64

Xaa Xaa Xaa Xaa Xaa Xaa
1               5

<210> SEQ ID NO 65
<211> LENGTH: 7
<212> TYPE: PRT
<213> ORGANISM: Artificial Sequence
<220> FEATURE:
<223> OTHER INFORMATION: Matriptase Cleavable Expanded Core CM
      Consensus Sequence 3B
<220> FEATURE:
<221> NAME/KEY: misc_feature
<222> LOCATION: (1)..(1)
<223> OTHER INFORMATION: Xaa may be Cys, Gly, Ile, Leu or Ser
<220> FEATURE:
<221> NAME/KEY: misc_feature
<222> LOCATION: (2)..(2)
<223> OTHER INFORMATION: Xaa may be Asp, Gly, Lys, Ser, Thr or Val
<220> FEATURE:
<221> NAME/KEY: misc_feature
<222> LOCATION: (3)..(3)
<223> OTHER INFORMATION: Xaa may be Glu, Gly, Pro, Arg, Ser, Val or Trp
<220> FEATURE:
<221> NAME/KEY: misc_feature
<222> LOCATION: (4)..(4)
<223> OTHER INFORMATION: Xaa may be Ala, Gly, Leu, Met, Pro, Ser or Val
<220> FEATURE:
<221> NAME/KEY: misc_feature
<222> LOCATION: (5)..(5)
<223> OTHER INFORMATION: Xaa may be Ala, Ile, Leu or Arg
<220> FEATURE:
<221> NAME/KEY: misc_feature
<222> LOCATION: (6)..(6)
<223> OTHER INFORMATION: Xaa may be Ala, Gly, Ile or Pro
<220> FEATURE:
<221> NAME/KEY: misc_feature
<222> LOCATION: (7)..(7)
<223> OTHER INFORMATION: Xaa may be Gly or Arg

<400> SEQUENCE: 65

Xaa Xaa Xaa Xaa Xaa Xaa Xaa
1               5

<210> SEQ ID NO 66
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 3B
<220> FEATURE:
<221> NAME/KEY: misc_feature
<222> LOCATION: (1)..(1)
<223> OTHER INFORMATION: Xaa may be Cys, Gly or Ser
<220> FEATURE:
<221> NAME/KEY: misc_feature
<222> LOCATION: (2)..(2)
<223> OTHER INFORMATION: Xaa may be Gly, Lys or Ser
<220> FEATURE:
```

```
<221> NAME/KEY: misc_feature
<222> LOCATION: (3)..(3)
<223> OTHER INFORMATION: Xaa may be Gly, Pro, Arg, Ser or Val
<220> FEATURE:
<221> NAME/KEY: misc_feature
<222> LOCATION: (4)..(4)
<223> OTHER INFORMATION: Xaa may be Pro or Val
<220> FEATURE:
<221> NAME/KEY: misc_feature
<222> LOCATION: (5)..(5)
<223> OTHER INFORMATION: Xaa may be Leu or Arg
<220> FEATURE:
<221> NAME/KEY: misc_feature
<222> LOCATION: (6)..(6)
<223> OTHER INFORMATION: Xaa may be Gly
<220> FEATURE:
<221> NAME/KEY: misc_feature
<222> LOCATION: (7)..(7)
<223> OTHER INFORMATION: Xaa may be Gly or Arg

<400> SEQUENCE: 66

Xaa Xaa Xaa Xaa Xaa Xaa Xaa
1               5

<210> SEQ ID NO 67
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 3B
<220> FEATURE:
<221> NAME/KEY: misc_feature
<222> LOCATION: (1)..(1)
<223> OTHER INFORMATION: Xaa may be Cys, Gly or Ser
<220> FEATURE:
<221> NAME/KEY: misc_feature
<222> LOCATION: (2)..(2)
<223> OTHER INFORMATION: Xaa may be Gly or Ser
<220> FEATURE:
<221> NAME/KEY: misc_feature
<222> LOCATION: (3)..(3)
<223> OTHER INFORMATION: Xaa may be Pro or Arg
<220> FEATURE:
<221> NAME/KEY: misc_feature
<222> LOCATION: (4)..(4)
<223> OTHER INFORMATION: Xaa may be Pro
<220> FEATURE:
<221> NAME/KEY: misc_feature
<222> LOCATION: (5)..(5)
<223> OTHER INFORMATION: Xaa may be Leu
<220> FEATURE:
<221> NAME/KEY: misc_feature
<222> LOCATION: (6)..(6)
<223> OTHER INFORMATION: Xaa may be Gly
<220> FEATURE:
<221> NAME/KEY: misc_feature
<222> LOCATION: (7)..(7)
<223> OTHER INFORMATION: Xaa may be Arg

<400> SEQUENCE: 67

Xaa Xaa Xaa Xaa Xaa Xaa Xaa
1               5

<210> SEQ ID NO 68
<211> LENGTH: 8
<212> TYPE: PRT
<213> ORGANISM: Artificial Sequence
<220> FEATURE:
<223> OTHER INFORMATION: Matriptase Cleavable Expanded Core CM
      Consensus Sequence 3C
<220> FEATURE:
<221> NAME/KEY: misc_feature
<222> LOCATION: (1)..(1)
<223> OTHER INFORMATION: Xaa may be Gly or Ser
```

```
<220> FEATURE:
<221> NAME/KEY: misc_feature
<222> LOCATION: (2)..(2)
<223> OTHER INFORMATION: Xaa may be Cys, Gly, Ile, Leu or Ser
<220> FEATURE:
<221> NAME/KEY: misc_feature
<222> LOCATION: (3)..(3)
<223> OTHER INFORMATION: Xaa may be Asp, Gly, Lys, Ser, Thr or Val
<220> FEATURE:
<221> NAME/KEY: misc_feature
<222> LOCATION: (4)..(4)
<223> OTHER INFORMATION: Xaa may be Glu, Gly, Pro, Arg, Ser, Val or Trp
<220> FEATURE:
<221> NAME/KEY: misc_feature
<222> LOCATION: (5)..(5)
<223> OTHER INFORMATION: Xaa may be Ala, Gly, Leu, Met, Pro, Ser or Val
<220> FEATURE:
<221> NAME/KEY: misc_feature
<222> LOCATION: (6)..(6)
<223> OTHER INFORMATION: Xaa may be Ala, Ile, Leu or Arg
<220> FEATURE:
<221> NAME/KEY: misc_feature
<222> LOCATION: (7)..(7)
<223> OTHER INFORMATION: Xaa may be Ala, Gly, Ile or Pro
<220> FEATURE:
<221> NAME/KEY: misc_feature
<222> LOCATION: (8)..(8)
<223> OTHER INFORMATION: Xaa may be Gly or Arg

<400> SEQUENCE: 68

Xaa Xaa Xaa Xaa Xaa Xaa Xaa Xaa
1               5

<210> SEQ ID NO 69
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 3C
<220> FEATURE:
<221> NAME/KEY: misc_feature
<222> LOCATION: (1)..(1)
<223> OTHER INFORMATION: Xaa may be Gly or Ser
<220> FEATURE:
<221> NAME/KEY: misc_feature
<222> LOCATION: (2)..(2)
<223> OTHER INFORMATION: Xaa may be Cys, Gly or Ser
<220> FEATURE:
<221> NAME/KEY: misc_feature
<222> LOCATION: (3)..(3)
<223> OTHER INFORMATION: Xaa may be Gly, Lys or Ser
<220> FEATURE:
<221> NAME/KEY: misc_feature
<222> LOCATION: (4)..(4)
<223> OTHER INFORMATION: Xaa may be Gly, Pro, Arg, Ser or Val
<220> FEATURE:
<221> NAME/KEY: misc_feature
<222> LOCATION: (5)..(5)
<223> OTHER INFORMATION: Xaa may be Pro or Val
<220> FEATURE:
<221> NAME/KEY: misc_feature
<222> LOCATION: (6)..(6)
<223> OTHER INFORMATION: Xaa may be Leu or Arg
<220> FEATURE:
<221> NAME/KEY: misc_feature
<222> LOCATION: (7)..(7)
<223> OTHER INFORMATION: Xaa may be Gly
<220> FEATURE:
<221> NAME/KEY: misc_feature
<222> LOCATION: (8)..(8)
<223> OTHER INFORMATION: Xaa may be Gly or Arg

<400> SEQUENCE: 69

Xaa Xaa Xaa Xaa Xaa Xaa Xaa Xaa
1               5
```

```
<210> SEQ ID NO 70
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 3C
<220> FEATURE:
<221> NAME/KEY: misc_feature
<222> LOCATION: (1)..(1)
<223> OTHER INFORMATION: Xaa may be Gly or Ser
<220> FEATURE:
<221> NAME/KEY: misc_feature
<222> LOCATION: (2)..(2)
<223> OTHER INFORMATION: Xaa may be Cys, Gly or Ser
<220> FEATURE:
<221> NAME/KEY: misc_feature
<222> LOCATION: (3)..(3)
<223> OTHER INFORMATION: Xaa may be Gly or Ser
<220> FEATURE:
<221> NAME/KEY: misc_feature
<222> LOCATION: (4)..(4)
<223> OTHER INFORMATION: Xaa may be Pro or Arg
<220> FEATURE:
<221> NAME/KEY: misc_feature
<222> LOCATION: (5)..(5)
<223> OTHER INFORMATION: Xaa may be Pro
<220> FEATURE:
<221> NAME/KEY: misc_feature
<222> LOCATION: (6)..(6)
<223> OTHER INFORMATION: Xaa may be Leu
<220> FEATURE:
<221> NAME/KEY: misc_feature
<222> LOCATION: (7)..(7)
<223> OTHER INFORMATION: Xaa may be Gly
<220> FEATURE:
<221> NAME/KEY: misc_feature
<222> LOCATION: (8)..(8)
<223> OTHER INFORMATION: Xaa may be Arg

<400> SEQUENCE: 70

Xaa Xaa Xaa Xaa Xaa Xaa Xaa Xaa
1               5

<210> SEQ ID NO 71
<211> LENGTH: 6
<212> TYPE: PRT
<213> ORGANISM: Artificial Sequence
<220> FEATURE:
<223> OTHER INFORMATION: Matriptase Cleavable Expanded Core CM
      Consensus Sequence 4A
<220> FEATURE:
<221> NAME/KEY: misc_feature
<222> LOCATION: (1)..(1)
<223> OTHER INFORMATION: Xaa may be Gly, Met, Arg or Ser
<220> FEATURE:
<221> NAME/KEY: misc_feature
<222> LOCATION: (2)..(2)
<223> OTHER INFORMATION: Xaa may be Ala, Gly, His, Leu, Arg or Ser
<220> FEATURE:
<221> NAME/KEY: misc_feature
<222> LOCATION: (3)..(3)
<223> OTHER INFORMATION: Xaa may be Asp, His, Asn, Arg, Ser, Thr or Trp
<220> FEATURE:
<221> NAME/KEY: misc_feature
<222> LOCATION: (4)..(4)
<223> OTHER INFORMATION: Xaa may be Ala, Asn, Pro, Arg, Ser, Thr or Val
<220> FEATURE:
<221> NAME/KEY: misc_feature
<222> LOCATION: (5)..(5)
<223> OTHER INFORMATION: Xaa may be Phe, Gly, Leu, Met, Pro, Gln, Arg,
      Ser or Tyr
<220> FEATURE:
<221> NAME/KEY: misc_feature
<222> LOCATION: (6)..(6)
```

<223> OTHER INFORMATION: Xaa may be Ile, Gly, Leu, Pro, Ser, Val or Trp

<400> SEQUENCE: 71

Xaa Xaa Xaa Xaa Xaa Xaa
1               5

<210> SEQ ID NO 72
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 4A
<220> FEATURE:
<221> NAME/KEY: misc_feature
<222> LOCATION: (1)..(1)
<223> OTHER INFORMATION: Xaa may be Gly, Met, Arg or Ser
<220> FEATURE:
<221> NAME/KEY: misc_feature
<222> LOCATION: (2)..(2)
<223> OTHER INFORMATION: Xaa may be Ala, Gly, His, Leu, Arg or Ser
<220> FEATURE:
<221> NAME/KEY: misc_feature
<222> LOCATION: (3)..(3)
<223> OTHER INFORMATION: Xaa may be Asp, His, Arg or Thr
<220> FEATURE:
<221> NAME/KEY: misc_feature
<222> LOCATION: (4)..(4)
<223> OTHER INFORMATION: Xaa may be Ala, Pro, Arg, Ser, Thr or Val
<220> FEATURE:
<221> NAME/KEY: misc_feature
<222> LOCATION: (5)..(5)
<223> OTHER INFORMATION: Xaa may be Phe, Gly, Leu, Met, Pro or Ser
<220> FEATURE:
<221> NAME/KEY: misc_feature
<222> LOCATION: (6)..(6)
<223> OTHER INFORMATION: Xaa may be Gly, Leu, Pro, Ser, Val or Trp

<400> SEQUENCE: 72

Xaa Xaa Xaa Xaa Xaa Xaa
1               5

<210> SEQ ID NO 73
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 4A
<220> FEATURE:
<221> NAME/KEY: misc_feature
<222> LOCATION: (1)..(1)
<223> OTHER INFORMATION: Xaa may be Gly, Met, Arg or Ser
<220> FEATURE:
<221> NAME/KEY: misc_feature
<222> LOCATION: (2)..(2)
<223> OTHER INFORMATION: Xaa may be Gly, Leu or Ser
<220> FEATURE:
<221> NAME/KEY: misc_feature
<222> LOCATION: (3)..(3)
<223> OTHER INFORMATION: Xaa may be Arg or Thr
<220> FEATURE:
<221> NAME/KEY: misc_feature
<222> LOCATION: (4)..(4)
<223> OTHER INFORMATION: Xaa may be Ala, Pro or Ser
<220> FEATURE:
<221> NAME/KEY: misc_feature
<222> LOCATION: (5)..(5)
<223> OTHER INFORMATION: Xaa may be Phe, Gly, Met or Ser
<220> FEATURE:
<221> NAME/KEY: misc_feature
<222> LOCATION: (6)..(6)
<223> OTHER INFORMATION: Xaa may be Gly, Pro, Ser, Val or Trp

<400> SEQUENCE: 73

```
Xaa Xaa Xaa Xaa Xaa Xaa
1               5

<210> SEQ ID NO 74
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 4A
<220> FEATURE:
<221> NAME/KEY: misc_feature
<222> LOCATION: (1)..(1)
<223> OTHER INFORMATION: Xaa may be Gly, Met, Arg or Ser
<220> FEATURE:
<221> NAME/KEY: misc_feature
<222> LOCATION: (2)..(2)
<223> OTHER INFORMATION: Xaa may be Gly, Leu or Ser
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala or Ser
<220> FEATURE:
<221> NAME/KEY: misc_feature
<222> LOCATION: (5)..(5)
<223> OTHER INFORMATION: Xaa may be Gly or Met
<220> FEATURE:
<221> NAME/KEY: misc_feature
<222> LOCATION: (6)..(6)
<223> OTHER INFORMATION: Xaa may be Gly, Pro, Ser or Trp

<400> SEQUENCE: 74

Xaa Xaa Xaa Xaa Xaa Xaa
1               5

<210> SEQ ID NO 75
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 4A
<220> FEATURE:
<221> NAME/KEY: misc_feature
<222> LOCATION: (1)..(1)
<223> OTHER INFORMATION: Xaa may be Met
<220> FEATURE:
<221> NAME/KEY: misc_feature
<222> LOCATION: (2)..(2)
<223> OTHER INFORMATION: Xaa may be Leu
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala or Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Trp

<400> SEQUENCE: 75

Xaa Xaa Xaa Xaa Xaa Xaa
1               5
```

```
<210> SEQ ID NO 76
<211> LENGTH: 7
<212> TYPE: PRT
<213> ORGANISM: Artificial Sequence
<220> FEATURE:
<223> OTHER INFORMATION: Matriptase Cleavable Expanded Core CM
      Consensus Sequence 4B
<220> FEATURE:
<221> NAME/KEY: misc_feature
<222> LOCATION: (1)..(1)
<223> OTHER INFORMATION: Xaa may be Gly, Met, Arg or Ser
<220> FEATURE:
<221> NAME/KEY: misc_feature
<222> LOCATION: (2)..(2)
<223> OTHER INFORMATION: Xaa may be Ala, Gly, His, Leu, Arg or Ser
<220> FEATURE:
<221> NAME/KEY: misc_feature
<222> LOCATION: (3)..(3)
<223> OTHER INFORMATION: Xaa may be Asp, His, Asn, Arg, Ser, Thr or Trp
<220> FEATURE:
<221> NAME/KEY: misc_feature
<222> LOCATION: (4)..(4)
<223> OTHER INFORMATION: Xaa may be Ala, Asn, Pro, Arg, Ser, Thr or Val
<220> FEATURE:
<221> NAME/KEY: misc_feature
<222> LOCATION: (5)..(5)
<223> OTHER INFORMATION: Xaa may be Phe, Gly, Leu, Met, Pro, Gln, Arg,
      Ser or Tyr
<220> FEATURE:
<221> NAME/KEY: misc_feature
<222> LOCATION: (6)..(6)
<223> OTHER INFORMATION: Xaa may be Ile, Gly, Leu, Pro, Ser, Val or Trp
<220> FEATURE:
<221> NAME/KEY: misc_feature
<222> LOCATION: (7)..(7)
<223> OTHER INFORMATION: Xaa may be Gly, Pro, Arg or Ser

<400> SEQUENCE: 76

Xaa Xaa Xaa Xaa Xaa Xaa Xaa
1               5

<210> SEQ ID NO 77
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 4B
<220> FEATURE:
<221> NAME/KEY: misc_feature
<222> LOCATION: (1)..(1)
<223> OTHER INFORMATION: Xaa may be Gly, Met, Arg or Ser
<220> FEATURE:
<221> NAME/KEY: misc_feature
<222> LOCATION: (2)..(2)
<223> OTHER INFORMATION: Xaa may be Ala, Gly, His, Leu, Arg or Ser
<220> FEATURE:
<221> NAME/KEY: misc_feature
<222> LOCATION: (3)..(3)
<223> OTHER INFORMATION: Xaa may be Asp, His, Arg or Thr
<220> FEATURE:
<221> NAME/KEY: misc_feature
<222> LOCATION: (4)..(4)
<223> OTHER INFORMATION: Xaa may be Ala, Pro, Arg, Ser, Thr or Val
<220> FEATURE:
<221> NAME/KEY: misc_feature
<222> LOCATION: (5)..(5)
<223> OTHER INFORMATION: Xaa may be Phe, Gly, Leu, Met, Pro or Ser
<220> FEATURE:
<221> NAME/KEY: misc_feature
<222> LOCATION: (6)..(6)
<223> OTHER INFORMATION: Xaa may be Gly, Leu, Pro, Ser, Val or Trp
<220> FEATURE:
<221> NAME/KEY: misc_feature
<222> LOCATION: (7)..(7)
```

```
<223> OTHER INFORMATION: Xaa may be Gly, Pro, Arg or Ser

<400> SEQUENCE: 77

Xaa Xaa Xaa Xaa Xaa Xaa Xaa
1               5

<210> SEQ ID NO 78
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 4B
<220> FEATURE:
<221> NAME/KEY: misc_feature
<222> LOCATION: (1)..(1)
<223> OTHER INFORMATION: Xaa may be Gly, Met, Arg or Ser
<220> FEATURE:
<221> NAME/KEY: misc_feature
<222> LOCATION: (2)..(2)
<223> OTHER INFORMATION: Xaa may be Gly, Leu or Ser
<220> FEATURE:
<221> NAME/KEY: misc_feature
<222> LOCATION: (3)..(3)
<223> OTHER INFORMATION: Xaa may be Arg or Thr
<220> FEATURE:
<221> NAME/KEY: misc_feature
<222> LOCATION: (4)..(4)
<223> OTHER INFORMATION: Xaa may be Ala, Pro or Ser
<220> FEATURE:
<221> NAME/KEY: misc_feature
<222> LOCATION: (5)..(5)
<223> OTHER INFORMATION: Xaa may be Phe, Gly, Met or Ser
<220> FEATURE:
<221> NAME/KEY: misc_feature
<222> LOCATION: (6)..(6)
<223> OTHER INFORMATION: Xaa may be Gly, Pro, Ser, Val or Trp
<220> FEATURE:
<221> NAME/KEY: misc_feature
<222> LOCATION: (7)..(7)
<223> OTHER INFORMATION: Xaa may be Gly, Arg or Ser

<400> SEQUENCE: 78

Xaa Xaa Xaa Xaa Xaa Xaa Xaa
1               5

<210> SEQ ID NO 79
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 4B
<220> FEATURE:
<221> NAME/KEY: misc_feature
<222> LOCATION: (1)..(1)
<223> OTHER INFORMATION: Xaa may be Gly, Met, Arg or Ser
<220> FEATURE:
<221> NAME/KEY: misc_feature
<222> LOCATION: (2)..(2)
<223> OTHER INFORMATION: Xaa may be Gly, Leu or Ser
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala or Ser
<220> FEATURE:
<221> NAME/KEY: misc_feature
<222> LOCATION: (5)..(5)
<223> OTHER INFORMATION: Xaa may be Gly or Met
<220> FEATURE:
<221> NAME/KEY: misc_feature
```

-continued

```
<222> LOCATION: (6)..(6)
<223> OTHER INFORMATION: Xaa may be Gly, Pro, Ser or Trp
<220> FEATURE:
<221> NAME/KEY: misc_feature
<222> LOCATION: (7)..(7)
<223> OTHER INFORMATION: Xaa may be Gly, Arg or Ser

<400> SEQUENCE: 79

Xaa Xaa Xaa Xaa Xaa Xaa Xaa
1               5

<210> SEQ ID NO 80
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 4B
<220> FEATURE:
<221> NAME/KEY: misc_feature
<222> LOCATION: (1)..(1)
<223> OTHER INFORMATION: Xaa may be Met
<220> FEATURE:
<221> NAME/KEY: misc_feature
<222> LOCATION: (2)..(2)
<223> OTHER INFORMATION: Xaa may be Leu
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala or Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Trp
<220> FEATURE:
<221> NAME/KEY: misc_feature
<222> LOCATION: (7)..(7)
<223> OTHER INFORMATION: Xaa may be Arg

<400> SEQUENCE: 80

Xaa Xaa Xaa Xaa Xaa Xaa Xaa
1               5

<210> SEQ ID NO 81
<211> LENGTH: 8
<212> TYPE: PRT
<213> ORGANISM: Artificial Sequence
<220> FEATURE:
<223> OTHER INFORMATION: Matriptase Cleavable Expanded Core CM
      Consensus Sequence 4C
<220> FEATURE:
<221> NAME/KEY: misc_feature
<222> LOCATION: (1)..(1)
<223> OTHER INFORMATION: Xaa may be Gly, Met, Arg or Ser
<220> FEATURE:
<221> NAME/KEY: misc_feature
<222> LOCATION: (2)..(2)
<223> OTHER INFORMATION: Xaa may be Ala, Gly, His, Leu, Arg or Ser
<220> FEATURE:
<221> NAME/KEY: misc_feature
<222> LOCATION: (3)..(3)
<223> OTHER INFORMATION: Xaa may be Asp, His, Asn, Arg, Ser, Thr or Trp
<220> FEATURE:
<221> NAME/KEY: misc_feature
<222> LOCATION: (4)..(4)
<223> OTHER INFORMATION: Xaa may be Ala, Asn, Pro, Arg, Ser, Thr or Val
<220> FEATURE:
```

```
<221> NAME/KEY: misc_feature
<222> LOCATION: (5)..(5)
<223> OTHER INFORMATION: Xaa may be Phe, Gly, Leu, Met, Pro, Gln, Arg,
      Ser or Tyr
<220> FEATURE:
<221> NAME/KEY: misc_feature
<222> LOCATION: (6)..(6)
<223> OTHER INFORMATION: Xaa may be Ile, Gly, Leu, Pro, Ser, Val or Trp
<220> FEATURE:
<221> NAME/KEY: misc_feature
<222> LOCATION: (7)..(7)
<223> OTHER INFORMATION: Xaa may be Gly, Pro, Arg or Ser
<220> FEATURE:
<221> NAME/KEY: misc_feature
<222> LOCATION: (8)..(8)
<223> OTHER INFORMATION: Xaa may be Gly, Leu, Arg, Ser or Val

<400> SEQUENCE: 81

Xaa Xaa Xaa Xaa Xaa Xaa Xaa Xaa
1               5

<210> SEQ ID NO 82
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 4C
<220> FEATURE:
<221> NAME/KEY: misc_feature
<222> LOCATION: (1)..(1)
<223> OTHER INFORMATION: Xaa may be Gly, Met, Arg or Ser
<220> FEATURE:
<221> NAME/KEY: misc_feature
<222> LOCATION: (2)..(2)
<223> OTHER INFORMATION: Xaa may be Ala, Gly, His, Leu, Arg or Ser
<220> FEATURE:
<221> NAME/KEY: misc_feature
<222> LOCATION: (3)..(3)
<223> OTHER INFORMATION: Xaa may be Asp, His, Arg or Thr
<220> FEATURE:
<221> NAME/KEY: misc_feature
<222> LOCATION: (4)..(4)
<223> OTHER INFORMATION: Xaa may be Ala, Pro, Arg, Ser, Thr or Val
<220> FEATURE:
<221> NAME/KEY: misc_feature
<222> LOCATION: (5)..(5)
<223> OTHER INFORMATION: Xaa may be Phe, Gly, Leu, Met, Pro or Ser
<220> FEATURE:
<221> NAME/KEY: misc_feature
<222> LOCATION: (6)..(6)
<223> OTHER INFORMATION: Xaa may be Gly, Leu, Pro, Ser, Val or Trp
<220> FEATURE:
<221> NAME/KEY: misc_feature
<222> LOCATION: (7)..(7)
<223> OTHER INFORMATION: Xaa may be Gly, Pro, Arg or Ser
<220> FEATURE:
<221> NAME/KEY: misc_feature
<222> LOCATION: (8)..(8)
<223> OTHER INFORMATION: Xaa may be Gly, Leu, Arg, Ser or Val

<400> SEQUENCE: 82

Xaa Xaa Xaa Xaa Xaa Xaa Xaa Xaa
1               5

<210> SEQ ID NO 83
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 4C
<220> FEATURE:
<221> NAME/KEY: misc_feature
<222> LOCATION: (1)..(1)
```

<223> OTHER INFORMATION: Xaa may be Gly, Met, Arg or Ser
<220> FEATURE:
<221> NAME/KEY: misc_feature
<222> LOCATION: (2)..(2)
<223> OTHER INFORMATION: Xaa may be Gly, Leu or Ser
<220> FEATURE:
<221> NAME/KEY: misc_feature
<222> LOCATION: (3)..(3)
<223> OTHER INFORMATION: Xaa may be Arg or Thr
<220> FEATURE:
<221> NAME/KEY: misc_feature
<222> LOCATION: (4)..(4)
<223> OTHER INFORMATION: Xaa may be Ala, Pro or Ser
<220> FEATURE:
<221> NAME/KEY: misc_feature
<222> LOCATION: (5)..(5)
<223> OTHER INFORMATION: Xaa may be Phe, Gly, Met or Ser
<220> FEATURE:
<221> NAME/KEY: misc_feature
<222> LOCATION: (6)..(6)
<223> OTHER INFORMATION: Xaa may be Gly, Pro, Ser, Val or Trp
<220> FEATURE:
<221> NAME/KEY: misc_feature
<222> LOCATION: (7)..(7)
<223> OTHER INFORMATION: Xaa may be Gly, Arg or Ser
<220> FEATURE:
<221> NAME/KEY: misc_feature
<222> LOCATION: (8)..(8)
<223> OTHER INFORMATION: Xaa may be Gly, Leu, Ser or Val

<400> SEQUENCE: 83

Xaa Xaa Xaa Xaa Xaa Xaa Xaa Xaa
1               5

<210> SEQ ID NO 84
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 4C
<220> FEATURE:
<221> NAME/KEY: misc_feature
<222> LOCATION: (1)..(1)
<223> OTHER INFORMATION: Xaa may be Gly, Met, Arg or Ser
<220> FEATURE:
<221> NAME/KEY: misc_feature
<222> LOCATION: (2)..(2)
<223> OTHER INFORMATION: Xaa may be Gly, Leu or Ser
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala or Ser
<220> FEATURE:
<221> NAME/KEY: misc_feature
<222> LOCATION: (5)..(5)
<223> OTHER INFORMATION: Xaa may be Gly or Met
<220> FEATURE:
<221> NAME/KEY: misc_feature
<222> LOCATION: (6)..(6)
<223> OTHER INFORMATION: Xaa may be Gly, Pro, Ser or Trp
<220> FEATURE:
<221> NAME/KEY: misc_feature
<222> LOCATION: (7)..(7)
<223> OTHER INFORMATION: Xaa may be Gly, Arg or Ser
<220> FEATURE:
<221> NAME/KEY: misc_feature
<222> LOCATION: (8)..(8)
<223> OTHER INFORMATION: Xaa may be Gly, Leu, Ser or Val

<400> SEQUENCE: 84

Xaa Xaa Xaa Xaa Xaa Xaa Xaa Xaa

```
<210> SEQ ID NO 85
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 4C
<220> FEATURE:
<221> NAME/KEY: misc_feature
<222> LOCATION: (1)..(1)
<223> OTHER INFORMATION: Xaa may be Met
<220> FEATURE:
<221> NAME/KEY: misc_feature
<222> LOCATION: (2)..(2)
<223> OTHER INFORMATION: Xaa may be Leu
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala or Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Trp
<220> FEATURE:
<221> NAME/KEY: misc_feature
<222> LOCATION: (7)..(7)
<223> OTHER INFORMATION: Xaa may be Arg
<220> FEATURE:
<221> NAME/KEY: misc_feature
<222> LOCATION: (8)..(8)
<223> OTHER INFORMATION: Xaa may be Gly, Leu or Ser

<400> SEQUENCE: 85

Xaa Xaa Xaa Xaa Xaa Xaa Xaa Xaa
1               5

<210> SEQ ID NO 86
<211> LENGTH: 6
<212> TYPE: PRT
<213> ORGANISM: Artificial Sequence
<220> FEATURE:
<223> OTHER INFORMATION: Matriptase Cleavable Expanded Core CM
      Consensus Sequence 5A
<220> FEATURE:
<221> NAME/KEY: misc_feature
<222> LOCATION: (1)..(1)
<223> OTHER INFORMATION: Xaa may be Ala, Glu, Gly, His, Ile, Leu, Asn,
      Pro, Ser or Val
<220> FEATURE:
<221> NAME/KEY: misc_feature
<222> LOCATION: (2)..(2)
<223> OTHER INFORMATION: Xaa may be Gly, Lys, Leu, Ser, Val or Trp
<220> FEATURE:
<221> NAME/KEY: misc_feature
<222> LOCATION: (3)..(3)
<223> OTHER INFORMATION: Xaa may be Gly, Ile, Pro, Gln, Arg or Ser
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Gly, Lys, Arg, Ser or Val
<220> FEATURE:
<221> NAME/KEY: misc_feature
```

-continued

```
<222> LOCATION: (6)..(6)
<223> OTHER INFORMATION: Xaa may be Ala, Cys, Gly, Leu, Met, Pro, Ser,
      Val or Tyr

<400> SEQUENCE: 86

Xaa Xaa Xaa Xaa Xaa Xaa
1               5

<210> SEQ ID NO 87
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 5A
<220> FEATURE:
<221> NAME/KEY: misc_feature
<222> LOCATION: (1)..(1)
<223> OTHER INFORMATION: Xaa may be Gly, Ile, Ser or Val
<220> FEATURE:
<221> NAME/KEY: misc_feature
<222> LOCATION: (2)..(2)
<223> OTHER INFORMATION: Xaa may be Gly, Leu, Ser, Val or Trp
<220> FEATURE:
<221> NAME/KEY: misc_feature
<222> LOCATION: (3)..(3)
<223> OTHER INFORMATION: Xaa may be Gly, Gln, Arg or Ser
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Gly, Ser or Val
<220> FEATURE:
<221> NAME/KEY: misc_feature
<222> LOCATION: (6)..(6)
<223> OTHER INFORMATION: Xaa may be Ala, Gly, Leu, Ser or Val

<400> SEQUENCE: 87

Xaa Xaa Xaa Xaa Xaa Xaa
1               5

<210> SEQ ID NO 88
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 5A
<220> FEATURE:
<221> NAME/KEY: misc_feature
<222> LOCATION: (1)..(1)
<223> OTHER INFORMATION: Xaa may be Gly, Ile, Ser or Val
<220> FEATURE:
<221> NAME/KEY: misc_feature
<222> LOCATION: (2)..(2)
<223> OTHER INFORMATION: Xaa may be Val
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Ala or Val
```

<400> SEQUENCE: 88

Xaa Xaa Xaa Xaa Xaa Xaa
1               5

<210> SEQ ID NO 89
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 5A
<220> FEATURE:
<221> NAME/KEY: misc_feature
<222> LOCATION: (1)..(1)
<223> OTHER INFORMATION: Xaa may be Ile
<220> FEATURE:
<221> NAME/KEY: misc_feature
<222> LOCATION: (2)..(2)
<223> OTHER INFORMATION: Xaa may be Val
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Ala or Val

<400> SEQUENCE: 89

Xaa Xaa Xaa Xaa Xaa Xaa
1               5

<210> SEQ ID NO 90
<211> LENGTH: 7
<212> TYPE: PRT
<213> ORGANISM: Artificial Sequence
<220> FEATURE:
<223> OTHER INFORMATION: Matriptase Cleavable Expanded Core CM
      Consensus Sequence 5B
<220> FEATURE:
<221> NAME/KEY: misc_feature
<222> LOCATION: (1)..(1)
<223> OTHER INFORMATION: Xaa may be Ala, Gly, Lys, Met, Pro, Gln, Ser,
      Val or Tyr
<220> FEATURE:
<221> NAME/KEY: misc_feature
<222> LOCATION: (2)..(2)
<223> OTHER INFORMATION: Xaa may be Ala, Glu, Gly, His, Ile, Leu, Asn,
      Pro, Ser or Val
<220> FEATURE:
<221> NAME/KEY: misc_feature
<222> LOCATION: (3)..(3)
<223> OTHER INFORMATION: Xaa may be Gly, Lys, Leu, Ser, Val or Trp
<220> FEATURE:
<221> NAME/KEY: misc_feature
<222> LOCATION: (4)..(4)
<223> OTHER INFORMATION: Xaa may be Gly, Ile, Pro, Gln, Arg or Ser
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Gly, Lys, Arg, Ser or Val
<220> FEATURE:

```
<221> NAME/KEY: misc_feature
<222> LOCATION: (7)..(7)
<223> OTHER INFORMATION: Xaa may be Ala, Cys, Gly, Leu, Met, Pro, Ser,
      Val or Tyr

<400> SEQUENCE: 90

Xaa Xaa Xaa Xaa Xaa Xaa Xaa
1               5

<210> SEQ ID NO 91
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 5B
<220> FEATURE:
<221> NAME/KEY: misc_feature
<222> LOCATION: (1)..(1)
<223> OTHER INFORMATION: Xaa may be Ala, Gly, Lys, Ser, Val or Tyr
<220> FEATURE:
<221> NAME/KEY: misc_feature
<222> LOCATION: (2)..(2)
<223> OTHER INFORMATION: Xaa may be Gly, Ile, Ser or Val
<220> FEATURE:
<221> NAME/KEY: misc_feature
<222> LOCATION: (3)..(3)
<223> OTHER INFORMATION: Xaa may be Gly, Leu, Ser, Val or Trp
<220> FEATURE:
<221> NAME/KEY: misc_feature
<222> LOCATION: (4)..(4)
<223> OTHER INFORMATION: Xaa may be Gly, Gln, Arg or Ser
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Gly, Ser or Val
<220> FEATURE:
<221> NAME/KEY: misc_feature
<222> LOCATION: (7)..(7)
<223> OTHER INFORMATION: Xaa may be Ala, Gly, Leu, Ser or Val

<400> SEQUENCE: 91

Xaa Xaa Xaa Xaa Xaa Xaa Xaa
1               5

<210> SEQ ID NO 92
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 5B
<220> FEATURE:
<221> NAME/KEY: misc_feature
<222> LOCATION: (1)..(1)
<223> OTHER INFORMATION: Xaa may be Gly, Ser, Val or Tyr
<220> FEATURE:
<221> NAME/KEY: misc_feature
<222> LOCATION: (2)..(2)
<223> OTHER INFORMATION: Xaa may be Gly, Ile, Ser or Val
<220> FEATURE:
<221> NAME/KEY: misc_feature
<222> LOCATION: (3)..(3)
<223> OTHER INFORMATION: Xaa may be Val
<220> FEATURE:
<221> NAME/KEY: misc_feature
<222> LOCATION: (4)..(4)
<223> OTHER INFORMATION: Xaa may be Ser
<220> FEATURE:
<221> NAME/KEY: misc_feature
<222> LOCATION: (5)..(5)
```

```
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Ser
<220> FEATURE:
<221> NAME/KEY: misc_feature
<222> LOCATION: (7)..(7)
<223> OTHER INFORMATION: Xaa may be Ala or Val

<400> SEQUENCE: 92

Xaa Xaa Xaa Xaa Xaa Xaa Xaa
1               5

<210> SEQ ID NO 93
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 5B
<220> FEATURE:
<221> NAME/KEY: misc_feature
<222> LOCATION: (1)..(1)
<223> OTHER INFORMATION: Xaa may be Tyr
<220> FEATURE:
<221> NAME/KEY: misc_feature
<222> LOCATION: (2)..(2)
<223> OTHER INFORMATION: Xaa may be Ile
<220> FEATURE:
<221> NAME/KEY: misc_feature
<222> LOCATION: (3)..(3)
<223> OTHER INFORMATION: Xaa may be Val
<220> FEATURE:
<221> NAME/KEY: misc_feature
<222> LOCATION: (4)..(4)
<223> OTHER INFORMATION: Xaa may be Ser
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Ser
<220> FEATURE:
<221> NAME/KEY: misc_feature
<222> LOCATION: (7)..(7)
<223> OTHER INFORMATION: Xaa may be Ala or Val

<400> SEQUENCE: 93

Xaa Xaa Xaa Xaa Xaa Xaa Xaa
1               5

<210> SEQ ID NO 94
<211> LENGTH: 8
<212> TYPE: PRT
<213> ORGANISM: Artificial Sequence
<220> FEATURE:
<223> OTHER INFORMATION: Matriptase Cleavable Expanded Core CM
      Consensus Sequence 5C
<220> FEATURE:
<221> NAME/KEY: misc_feature
<222> LOCATION: (1)..(1)
<223> OTHER INFORMATION: Xaa may be Gly, Lys, Pro, Gln, Ser or Thr
<220> FEATURE:
<221> NAME/KEY: misc_feature
<222> LOCATION: (2)..(2)
<223> OTHER INFORMATION: Xaa may be Ala, Gly, Lys, Met, Pro, Gln, Ser,
      Val or Tyr
<220> FEATURE:
<221> NAME/KEY: misc_feature
<222> LOCATION: (3)..(3)
<223> OTHER INFORMATION: Xaa may be Ala, Glu, Gly, His, Ile, Leu, Asn,
      Pro, Ser or Val
```

```
<220> FEATURE:
<221> NAME/KEY: misc_feature
<222> LOCATION: (4)..(4)
<223> OTHER INFORMATION: Xaa may be Gly, Lys, Leu, Ser, Val or Trp
<220> FEATURE:
<221> NAME/KEY: misc_feature
<222> LOCATION: (5)..(5)
<223> OTHER INFORMATION: Xaa may be Gly, Ile, Pro, Gln, Arg or Ser
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Gly, Lys, Arg, Ser or Val
<220> FEATURE:
<221> NAME/KEY: misc_feature
<222> LOCATION: (8)..(8)
<223> OTHER INFORMATION: Xaa may be Ala, Cys, Gly, Leu, Met, Pro, Ser,
      Val or Tyr

<400> SEQUENCE: 94

Xaa Xaa Xaa Xaa Xaa Xaa Xaa Xaa
1               5

<210> SEQ ID NO 95
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 5C
<220> FEATURE:
<221> NAME/KEY: misc_feature
<222> LOCATION: (1)..(1)
<223> OTHER INFORMATION: Xaa may be Gly, Pro, Gln, Ser or Thr
<220> FEATURE:
<221> NAME/KEY: misc_feature
<222> LOCATION: (2)..(2)
<223> OTHER INFORMATION: Xaa may be Ala, Gly, Lys, Ser, Val or Tyr
<220> FEATURE:
<221> NAME/KEY: misc_feature
<222> LOCATION: (3)..(3)
<223> OTHER INFORMATION: Xaa may be Gly, Ile, Ser or Val
<220> FEATURE:
<221> NAME/KEY: misc_feature
<222> LOCATION: (4)..(4)
<223> OTHER INFORMATION: Xaa may be Gly, Leu, Ser, Val or Trp
<220> FEATURE:
<221> NAME/KEY: misc_feature
<222> LOCATION: (5)..(5)
<223> OTHER INFORMATION: Xaa may be Gly, Gln, Arg or Ser
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Gly, Ser or Val
<220> FEATURE:
<221> NAME/KEY: misc_feature
<222> LOCATION: (8)..(8)
<223> OTHER INFORMATION: Xaa may be Ala, Gly, Leu, Ser or Val

<400> SEQUENCE: 95

Xaa Xaa Xaa Xaa Xaa Xaa Xaa Xaa
1               5

<210> SEQ ID NO 96
<211> LENGTH: 8
<212> TYPE: PRT
<213> ORGANISM: Artificial Sequence
<220> FEATURE:
```

```
<223> OTHER INFORMATION: Matriptase Cleavable Subgenus of Expanded Core
      CM Consensus 5C
<220> FEATURE:
<221> NAME/KEY: misc_feature
<222> LOCATION: (1)..(1)
<223> OTHER INFORMATION: Xaa may be Gly, Gln or Ser
<220> FEATURE:
<221> NAME/KEY: misc_feature
<222> LOCATION: (2)..(2)
<223> OTHER INFORMATION: Xaa may be Gly, Ser, Val or Tyr
<220> FEATURE:
<221> NAME/KEY: misc_feature
<222> LOCATION: (3)..(3)
<223> OTHER INFORMATION: Xaa may be Gly, Ile, Ser or Val
<220> FEATURE:
<221> NAME/KEY: misc_feature
<222> LOCATION: (4)..(4)
<223> OTHER INFORMATION: Xaa may be Val
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
<222> LOCATION: (8)..(8)
<223> OTHER INFORMATION: Xaa may be Ala or Val

<400> SEQUENCE: 96

Xaa Xaa Xaa Xaa Xaa Xaa Xaa Xaa
1               5

<210> SEQ ID NO 97
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 5C
<220> FEATURE:
<221> NAME/KEY: misc_feature
<222> LOCATION: (1)..(1)
<223> OTHER INFORMATION: Xaa may be Gly, Gln or Ser
<220> FEATURE:
<221> NAME/KEY: misc_feature
<222> LOCATION: (2)..(2)
<223> OTHER INFORMATION: Xaa may be Tyr
<220> FEATURE:
<221> NAME/KEY: misc_feature
<222> LOCATION: (3)..(3)
<223> OTHER INFORMATION: Xaa may be Ile
<220> FEATURE:
<221> NAME/KEY: misc_feature
<222> LOCATION: (4)..(4)
<223> OTHER INFORMATION: Xaa may be Val
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
<222> LOCATION: (8)..(8)
```

<223> OTHER INFORMATION: Xaa may be Ala or Val

<400> SEQUENCE: 97

Xaa Xaa Xaa Xaa Xaa Xaa Xaa Xaa
1               5

<210> SEQ ID NO 98
<211> LENGTH: 6
<212> TYPE: PRT
<213> ORGANISM: Artificial Sequence
<220> FEATURE:
<223> OTHER INFORMATION: Matriptase Cleavable Expanded Core CM
      Consensus Sequence 6
<220> FEATURE:
<221> NAME/KEY: misc_feature
<222> LOCATION: (1)..(1)
<223> OTHER INFORMATION: Xaa may be Gly, Lys, Pro, Arg, Ser or Thr
<220> FEATURE:
<221> NAME/KEY: misc_feature
<222> LOCATION: (2)..(2)
<223> OTHER INFORMATION: Xaa may be Ala, Glu, Gly, Ile, Leu, Met, Arg
      or Ser
<220> FEATURE:
<221> NAME/KEY: misc_feature
<222> LOCATION: (3)..(3)
<223> OTHER INFORMATION: Xaa may be Ala, Gly, Lys, Leu, Asn, Arg, Ser
      or Val
<220> FEATURE:
<221> NAME/KEY: misc_feature
<222> LOCATION: (4)..(4)
<223> OTHER INFORMATION: Xaa may be Phe, His, Leu, Arg or Tyr
<220> FEATURE:
<221> NAME/KEY: misc_feature
<222> LOCATION: (5)..(5)
<223> OTHER INFORMATION: Xaa may be Ala, Phe, Gly, His, Pro or Ser
<220> FEATURE:
<221> NAME/KEY: misc_feature
<222> LOCATION: (6)..(6)
<223> OTHER INFORMATION: Xaa may be Phe, Gly, Met, Asn, Pro, Arg, Ser
      or Val

<400> SEQUENCE: 98

Xaa Xaa Xaa Xaa Xaa Xaa
1               5

<210> SEQ ID NO 99
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 6
<220> FEATURE:
<221> NAME/KEY: misc_feature
<222> LOCATION: (1)..(1)
<223> OTHER INFORMATION: Xaa may be Gly, Lys, Arg, Ser or Thr
<220> FEATURE:
<221> NAME/KEY: misc_feature
<222> LOCATION: (2)..(2)
<223> OTHER INFORMATION: Xaa may be Ala, Glu, Gly, Leu, Met, Arg or Ser
<220> FEATURE:
<221> NAME/KEY: misc_feature
<222> LOCATION: (3)..(3)
<223> OTHER INFORMATION: Xaa may be Gly, Lys, Leu, Asn, Arg, Ser or Val
<220> FEATURE:
<221> NAME/KEY: misc_feature
<222> LOCATION: (4)..(4)
<223> OTHER INFORMATION: Xaa may be Arg or Tyr
<220> FEATURE:
<221> NAME/KEY: misc_feature
<222> LOCATION: (5)..(5)
<223> OTHER INFORMATION: Xaa may be Ala, Phe, Gly, Pro or Ser
<220> FEATURE:
<221> NAME/KEY: misc_feature
<222> LOCATION: (6)..(6)

<223> OTHER INFORMATION: Xaa may be Phe, Gly, Met, Pro, Arg, Ser or Val

<400> SEQUENCE: 99

Xaa Xaa Xaa Xaa Xaa Xaa
1               5

<210> SEQ ID NO 100
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 6
<220> FEATURE:
<221> NAME/KEY: misc_feature
<222> LOCATION: (1)..(1)
<223> OTHER INFORMATION: Xaa may be Gly, Arg, Ser or Thr
<220> FEATURE:
<221> NAME/KEY: misc_feature
<222> LOCATION: (2)..(2)
<223> OTHER INFORMATION: Xaa may be Ala, Glu, Gly, Met or Ser
<220> FEATURE:
<221> NAME/KEY: misc_feature
<222> LOCATION: (3)..(3)
<223> OTHER INFORMATION: Xaa may be Gly, Leu, Ser or Val
<220> FEATURE:
<221> NAME/KEY: misc_feature
<222> LOCATION: (4)..(4)
<223> OTHER INFORMATION: Xaa may be Arg or Tyr
<220> FEATURE:
<221> NAME/KEY: misc_feature
<222> LOCATION: (5)..(5)
<223> OTHER INFORMATION: Xaa may be Ala, Gly, Pro or Ser
<220> FEATURE:
<221> NAME/KEY: misc_feature
<222> LOCATION: (6)..(6)
<223> OTHER INFORMATION: Xaa may be Phe, Gly, Met, Pro, Arg, Ser or Val

<400> SEQUENCE: 100

Xaa Xaa Xaa Xaa Xaa Xaa
1               5

<210> SEQ ID NO 101
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 6
<220> FEATURE:
<221> NAME/KEY: misc_feature
<222> LOCATION: (1)..(1)
<223> OTHER INFORMATION: Xaa may be Gly, Arg or Ser
<220> FEATURE:
<221> NAME/KEY: misc_feature
<222> LOCATION: (2)..(2)
<223> OTHER INFORMATION: Xaa may be Ala, Gly or Ser
<220> FEATURE:
<221> NAME/KEY: misc_feature
<222> LOCATION: (3)..(3)
<223> OTHER INFORMATION: Xaa may be Leu, Ser or Val
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ala
<220> FEATURE:
<221> NAME/KEY: misc_feature
<222> LOCATION: (6)..(6)
<223> OTHER INFORMATION: Xaa may be Met or Pro

<400> SEQUENCE: 101

Xaa Xaa Xaa Xaa Xaa Xaa
1               5

<210> SEQ ID NO 102
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 6
<220> FEATURE:
<221> NAME/KEY: misc_feature
<222> LOCATION: (1)..(1)
<223> OTHER INFORMATION: Xaa may be Gly, Arg or Ser
<220> FEATURE:
<221> NAME/KEY: misc_feature
<222> LOCATION: (2)..(2)
<223> OTHER INFORMATION: Xaa may be Ala
<220> FEATURE:
<221> NAME/KEY: misc_feature
<222> LOCATION: (3)..(3)
<223> OTHER INFORMATION: Xaa may be Leu, Ser or Val
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ala
<220> FEATURE:
<221> NAME/KEY: misc_feature
<222> LOCATION: (6)..(6)
<223> OTHER INFORMATION: Xaa may be Met or Pro

<400> SEQUENCE: 102

Xaa Xaa Xaa Xaa Xaa Xaa
1               5

<210> SEQ ID NO 103
<211> LENGTH: 6
<212> TYPE: PRT
<213> ORGANISM: Artificial Sequence
<220> FEATURE:
<223> OTHER INFORMATION: Matriptase Cleavable Expanded Core CM
      Consensus Sequence 7A
<220> FEATURE:
<221> NAME/KEY: misc_feature
<222> LOCATION: (1)..(1)
<223> OTHER INFORMATION: Xaa may be Ala, Glu, Lys, Leu, Pro, Ser, Thr,
      Val, Trp or Tyr
<220> FEATURE:
<221> NAME/KEY: misc_feature
<222> LOCATION: (2)..(2)
<223> OTHER INFORMATION: Xaa may be Ala, Ile, Leu, Pro, Arg, Ser, Val
      or Tyr
<220> FEATURE:
<221> NAME/KEY: misc_feature
<222> LOCATION: (3)..(3)
<223> OTHER INFORMATION: Xaa may be Glu, Gly, His, Leu, Pro or Val
<220> FEATURE:
<221> NAME/KEY: misc_feature
<222> LOCATION: (4)..(4)
<223> OTHER INFORMATION: Xaa may be Gly, Lys, Leu or Arg
<220> FEATURE:
<221> NAME/KEY: misc_feature
<222> LOCATION: (5)..(5)
<223> OTHER INFORMATION: Xaa may be Gln or Arg
<220> FEATURE:
<221> NAME/KEY: misc_feature
<222> LOCATION: (6)..(6)
<223> OTHER INFORMATION: Xaa may be Ala, Gly, His, Met, Arg or Ser

<400> SEQUENCE: 103

```
Xaa Xaa Xaa Xaa Xaa Xaa
1               5

<210> SEQ ID NO 104
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 7A
<220> FEATURE:
<221> NAME/KEY: misc_feature
<222> LOCATION: (1)..(1)
<223> OTHER INFORMATION: Xaa may be Glu, Pro, Ser, Val or Trp
<220> FEATURE:
<221> NAME/KEY: misc_feature
<222> LOCATION: (2)..(2)
<223> OTHER INFORMATION: Xaa may be Ala, Pro, Arg, Ser, Val or Tyr
<220> FEATURE:
<221> NAME/KEY: misc_feature
<222> LOCATION: (3)..(3)
<223> OTHER INFORMATION: Xaa may be Glu, Gly, His, Leu, Pro or Val
<220> FEATURE:
<221> NAME/KEY: misc_feature
<222> LOCATION: (4)..(4)
<223> OTHER INFORMATION: Xaa may be Gly, Lys, Leu or Arg
<220> FEATURE:
<221> NAME/KEY: misc_feature
<222> LOCATION: (5)..(5)
<223> OTHER INFORMATION: Xaa may be Gln or Arg
<220> FEATURE:
<221> NAME/KEY: misc_feature
<222> LOCATION: (6)..(6)
<223> OTHER INFORMATION: Xaa may be Ala, Gly, His, Met, Arg or Ser

<400> SEQUENCE: 104

Xaa Xaa Xaa Xaa Xaa Xaa
1               5

<210> SEQ ID NO 105
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 7A
<220> FEATURE:
<221> NAME/KEY: misc_feature
<222> LOCATION: (1)..(1)
<223> OTHER INFORMATION: Xaa may be Pro or Val
<220> FEATURE:
<221> NAME/KEY: misc_feature
<222> LOCATION: (2)..(2)
<223> OTHER INFORMATION: Xaa may be Ala, Pro or Arg
<220> FEATURE:
<221> NAME/KEY: misc_feature
<222> LOCATION: (3)..(3)
<223> OTHER INFORMATION: Xaa may be Glu, Gly, Pro or Val
<220> FEATURE:
<221> NAME/KEY: misc_feature
<222> LOCATION: (4)..(4)
<223> OTHER INFORMATION: Xaa may be Gly or Arg
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Gly, Met or Ser

<400> SEQUENCE: 105

Xaa Xaa Xaa Xaa Xaa Xaa
1               5
```

```
<210> SEQ ID NO 106
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 7A
<220> FEATURE:
<221> NAME/KEY: misc_feature
<222> LOCATION: (1)..(1)
<223> OTHER INFORMATION: Xaa may be Pro or Val
<220> FEATURE:
<221> NAME/KEY: misc_feature
<222> LOCATION: (2)..(2)
<223> OTHER INFORMATION: Xaa may be Ala or Arg
<220> FEATURE:
<221> NAME/KEY: misc_feature
<222> LOCATION: (3)..(3)
<223> OTHER INFORMATION: Xaa may be Gly or Val
<220> FEATURE:
<221> NAME/KEY: misc_feature
<222> LOCATION: (4)..(4)
<223> OTHER INFORMATION: Xaa may be Gly or Arg
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Met or Ser

<400> SEQUENCE: 106

Xaa Xaa Xaa Xaa Xaa Xaa
1               5

<210> SEQ ID NO 107
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 7A
<220> FEATURE:
<221> NAME/KEY: misc_feature
<222> LOCATION: (1)..(1)
<223> OTHER INFORMATION: Xaa may be Pro or Val
<220> FEATURE:
<221> NAME/KEY: misc_feature
<222> LOCATION: (2)..(2)
<223> OTHER INFORMATION: Xaa may be Ala
<220> FEATURE:
<221> NAME/KEY: misc_feature
<222> LOCATION: (3)..(3)
<223> OTHER INFORMATION: Xaa may be Gly or Val
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Met or Ser

<400> SEQUENCE: 107

Xaa Xaa Xaa Xaa Xaa Xaa
1               5

<210> SEQ ID NO 108
<211> LENGTH: 7
```

```
<212> TYPE: PRT
<213> ORGANISM: Artificial Sequence
<220> FEATURE:
<223> OTHER INFORMATION: Matriptase Cleavable Expanded Core CM
      Consensus Sequence 7B
<220> FEATURE:
<221> NAME/KEY: misc_feature
<222> LOCATION: (1)..(1)
<223> OTHER INFORMATION: Xaa may be Glu, Gly, Lys, Pro, Gln, Ser, Thr
      or Val
<220> FEATURE:
<221> NAME/KEY: misc_feature
<222> LOCATION: (2)..(2)
<223> OTHER INFORMATION: Xaa may be Ala, Glu, Lys, Leu, Pro, Ser, Thr,
      Val, Trp or Tyr
<220> FEATURE:
<221> NAME/KEY: misc_feature
<222> LOCATION: (3)..(3)
<223> OTHER INFORMATION: Xaa may be Ala, Ile, Leu, Pro, Arg, Ser, Val
      or Tyr
<220> FEATURE:
<221> NAME/KEY: misc_feature
<222> LOCATION: (4)..(4)
<223> OTHER INFORMATION: Xaa may be Glu, Gly, His, Leu, Pro or Val
<220> FEATURE:
<221> NAME/KEY: misc_feature
<222> LOCATION: (5)..(5)
<223> OTHER INFORMATION: Xaa may be Gly, Lys, Leu or Arg
<220> FEATURE:
<221> NAME/KEY: misc_feature
<222> LOCATION: (6)..(6)
<223> OTHER INFORMATION: Xaa may be Gln or Arg
<220> FEATURE:
<221> NAME/KEY: misc_feature
<222> LOCATION: (7)..(7)
<223> OTHER INFORMATION: Xaa may be Ala, Gly, His, Met, Arg or Ser

<400> SEQUENCE: 108

Xaa Xaa Xaa Xaa Xaa Xaa Xaa
1               5

<210> SEQ ID NO 109
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 7B
<220> FEATURE:
<221> NAME/KEY: misc_feature
<222> LOCATION: (1)..(1)
<223> OTHER INFORMATION: Xaa may be Gly, Lys, Pro, Gln, Ser or Val
<220> FEATURE:
<221> NAME/KEY: misc_feature
<222> LOCATION: (2)..(2)
<223> OTHER INFORMATION: Xaa may be Glu, Pro, Ser, Val or Trp
<220> FEATURE:
<221> NAME/KEY: misc_feature
<222> LOCATION: (3)..(3)
<223> OTHER INFORMATION: Xaa may be Ala, Pro, Arg, Ser, Val or Tyr
<220> FEATURE:
<221> NAME/KEY: misc_feature
<222> LOCATION: (4)..(4)
<223> OTHER INFORMATION: Xaa may be Glu, Gly, His, Leu, Pro or Val
<220> FEATURE:
<221> NAME/KEY: misc_feature
<222> LOCATION: (5)..(5)
<223> OTHER INFORMATION: Xaa may be Gly, Lys, Leu or Arg
<220> FEATURE:
<221> NAME/KEY: misc_feature
<222> LOCATION: (6)..(6)
<223> OTHER INFORMATION: Xaa may be Gln or Arg
<220> FEATURE:
<221> NAME/KEY: misc_feature
<222> LOCATION: (7)..(7)
<223> OTHER INFORMATION: Xaa may be Ala, Gly, His, Met, Arg or Ser
```

-continued

```
<400> SEQUENCE: 109

Xaa Xaa Xaa Xaa Xaa Xaa Xaa
1               5

<210> SEQ ID NO 110
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 7B
<220> FEATURE:
<221> NAME/KEY: misc_feature
<222> LOCATION: (1)..(1)
<223> OTHER INFORMATION: Xaa may be Gly, Pro, Ser or Val
<220> FEATURE:
<221> NAME/KEY: misc_feature
<222> LOCATION: (2)..(2)
<223> OTHER INFORMATION: Xaa may be Pro or Val
<220> FEATURE:
<221> NAME/KEY: misc_feature
<222> LOCATION: (3)..(3)
<223> OTHER INFORMATION: Xaa may be Ala, Pro or Arg
<220> FEATURE:
<221> NAME/KEY: misc_feature
<222> LOCATION: (4)..(4)
<223> OTHER INFORMATION: Xaa may be Glu, Gly, Pro or Val
<220> FEATURE:
<221> NAME/KEY: misc_feature
<222> LOCATION: (5)..(5)
<223> OTHER INFORMATION: Xaa may be Gly or Arg
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Gly, Met or Ser

<400> SEQUENCE: 110

Xaa Xaa Xaa Xaa Xaa Xaa Xaa
1               5

<210> SEQ ID NO 111
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 7B
<220> FEATURE:
<221> NAME/KEY: misc_feature
<222> LOCATION: (1)..(1)
<223> OTHER INFORMATION: Xaa may be Gly, Pro, Ser or Val
<220> FEATURE:
<221> NAME/KEY: misc_feature
<222> LOCATION: (2)..(2)
<223> OTHER INFORMATION: Xaa may be Pro or Val
<220> FEATURE:
<221> NAME/KEY: misc_feature
<222> LOCATION: (3)..(3)
<223> OTHER INFORMATION: Xaa may be Ala or Arg
<220> FEATURE:
<221> NAME/KEY: misc_feature
<222> LOCATION: (4)..(4)
<223> OTHER INFORMATION: Xaa may be Gly or Val
<220> FEATURE:
<221> NAME/KEY: misc_feature
<222> LOCATION: (5)..(5)
<223> OTHER INFORMATION: Xaa may be Gly or Arg
<220> FEATURE:
<221> NAME/KEY: misc_feature
<222> LOCATION: (6)..(6)
<223> OTHER INFORMATION: Xaa may be Arg
```

```
<220> FEATURE:
<221> NAME/KEY: misc_feature
<222> LOCATION: (7)..(7)
<223> OTHER INFORMATION: Xaa may be Met or Ser

<400> SEQUENCE: 111

Xaa Xaa Xaa Xaa Xaa Xaa Xaa
1               5

<210> SEQ ID NO 112
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 7B
<220> FEATURE:
<221> NAME/KEY: misc_feature
<222> LOCATION: (1)..(1)
<223> OTHER INFORMATION: Xaa may be Gly, Ser or Val
<220> FEATURE:
<221> NAME/KEY: misc_feature
<222> LOCATION: (2)..(2)
<223> OTHER INFORMATION: Xaa may be Pro or Val
<220> FEATURE:
<221> NAME/KEY: misc_feature
<222> LOCATION: (3)..(3)
<223> OTHER INFORMATION: Xaa may be Ala
<220> FEATURE:
<221> NAME/KEY: misc_feature
<222> LOCATION: (4)..(4)
<223> OTHER INFORMATION: Xaa may be Gly or Val
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Met or Ser

<400> SEQUENCE: 112

Xaa Xaa Xaa Xaa Xaa Xaa Xaa
1               5

<210> SEQ ID NO 113
<211> LENGTH: 8
<212> TYPE: PRT
<213> ORGANISM: Artificial Sequence
<220> FEATURE:
<223> OTHER INFORMATION: Matriptase Cleavable Expanded Core CM
      Consensus Sequence 7C
<220> FEATURE:
<221> NAME/KEY: misc_feature
<222> LOCATION: (1)..(1)
<223> OTHER INFORMATION: Xaa may be Glu, Gly, Lys, Pro, Gln, Ser, Thr
      or Val
<220> FEATURE:
<221> NAME/KEY: misc_feature
<222> LOCATION: (2)..(2)
<223> OTHER INFORMATION: Xaa may be Ala, Glu, Lys, Leu, Pro, Ser, Thr,
      Val, Trp or Tyr
<220> FEATURE:
<221> NAME/KEY: misc_feature
<222> LOCATION: (3)..(3)
<223> OTHER INFORMATION: Xaa may be Ala, Ile, Leu, Pro, Arg, Ser, Val
      or Tyr
<220> FEATURE:
<221> NAME/KEY: misc_feature
<222> LOCATION: (4)..(4)
<223> OTHER INFORMATION: Xaa may be Glu, Gly, His, Leu, Pro or Val
```

```
<220> FEATURE:
<221> NAME/KEY: misc_feature
<222> LOCATION: (5)..(5)
<223> OTHER INFORMATION: Xaa may be Gly, Lys, Leu or Arg
<220> FEATURE:
<221> NAME/KEY: misc_feature
<222> LOCATION: (6)..(6)
<223> OTHER INFORMATION: Xaa may be Gln or Arg
<220> FEATURE:
<221> NAME/KEY: misc_feature
<222> LOCATION: (7)..(7)
<223> OTHER INFORMATION: Xaa may be Ala, Gly, His, Met, Arg or Ser
<220> FEATURE:
<221> NAME/KEY: misc_feature
<222> LOCATION: (8)..(8)
<223> OTHER INFORMATION: Xaa may be Phe, Gly, Leu, Met, Pro, Ser or Trp

<400> SEQUENCE: 113

Xaa Xaa Xaa Xaa Xaa Xaa Xaa Xaa
1               5

<210> SEQ ID NO 114
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 7C
<220> FEATURE:
<221> NAME/KEY: misc_feature
<222> LOCATION: (1)..(1)
<223> OTHER INFORMATION: Xaa may be Gly, Lys, Pro, Gln, Ser or Val
<220> FEATURE:
<221> NAME/KEY: misc_feature
<222> LOCATION: (2)..(2)
<223> OTHER INFORMATION: Xaa may be Glu, Pro, Ser, Val or Trp
<220> FEATURE:
<221> NAME/KEY: misc_feature
<222> LOCATION: (3)..(3)
<223> OTHER INFORMATION: Xaa may be Ala, Pro, Arg, Ser, Val or Tyr
<220> FEATURE:
<221> NAME/KEY: misc_feature
<222> LOCATION: (4)..(4)
<223> OTHER INFORMATION: Xaa may be Glu, Gly, His, Leu, Pro or Val
<220> FEATURE:
<221> NAME/KEY: misc_feature
<222> LOCATION: (5)..(5)
<223> OTHER INFORMATION: Xaa may be Gly, Lys, Leu or Arg
<220> FEATURE:
<221> NAME/KEY: misc_feature
<222> LOCATION: (6)..(6)
<223> OTHER INFORMATION: Xaa may be Gln or Arg
<220> FEATURE:
<221> NAME/KEY: misc_feature
<222> LOCATION: (7)..(7)
<223> OTHER INFORMATION: Xaa may be Ala, Gly, His, Met, Arg or Ser
<220> FEATURE:
<221> NAME/KEY: misc_feature
<222> LOCATION: (8)..(8)
<223> OTHER INFORMATION: Xaa may be Gly, Leu, Met, Pro, Ser or Trp

<400> SEQUENCE: 114

Xaa Xaa Xaa Xaa Xaa Xaa Xaa Xaa
1               5

<210> SEQ ID NO 115
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 7C
<220> FEATURE:
<221> NAME/KEY: misc_feature
<222> LOCATION: (1)..(1)
```

<223> OTHER INFORMATION: Xaa may be Gly, Pro, Ser or Val
<220> FEATURE:
<221> NAME/KEY: misc_feature
<222> LOCATION: (2)..(2)
<223> OTHER INFORMATION: Xaa may be Pro or Val
<220> FEATURE:
<221> NAME/KEY: misc_feature
<222> LOCATION: (3)..(3)
<223> OTHER INFORMATION: Xaa may be Ala, Pro or Arg
<220> FEATURE:
<221> NAME/KEY: misc_feature
<222> LOCATION: (4)..(4)
<223> OTHER INFORMATION: Xaa may be Glu, Gly, Pro or Val
<220> FEATURE:
<221> NAME/KEY: misc_feature
<222> LOCATION: (5)..(5)
<223> OTHER INFORMATION: Xaa may be Gly or Arg
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Gly, Met or Ser
<220> FEATURE:
<221> NAME/KEY: misc_feature
<222> LOCATION: (8)..(8)
<223> OTHER INFORMATION: Xaa may be Gly, Leu, Met, Pro, Ser or Trp

<400> SEQUENCE: 115

Xaa Xaa Xaa Xaa Xaa Xaa Xaa Xaa
1               5

<210> SEQ ID NO 116
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 7C
<220> FEATURE:
<221> NAME/KEY: misc_feature
<222> LOCATION: (1)..(1)
<223> OTHER INFORMATION: Xaa may be Gly, Pro, Ser or Val
<220> FEATURE:
<221> NAME/KEY: misc_feature
<222> LOCATION: (2)..(2)
<223> OTHER INFORMATION: Xaa may be Pro or Val
<220> FEATURE:
<221> NAME/KEY: misc_feature
<222> LOCATION: (3)..(3)
<223> OTHER INFORMATION: Xaa may be Ala or Arg
<220> FEATURE:
<221> NAME/KEY: misc_feature
<222> LOCATION: (4)..(4)
<223> OTHER INFORMATION: Xaa may be Gly or Val
<220> FEATURE:
<221> NAME/KEY: misc_feature
<222> LOCATION: (5)..(5)
<223> OTHER INFORMATION: Xaa may be Gly or Arg
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Met or Ser
<220> FEATURE:
<221> NAME/KEY: misc_feature
<222> LOCATION: (8)..(8)
<223> OTHER INFORMATION: Xaa may be Gly, Leu, Pro, Ser or Trp

<400> SEQUENCE: 116

Xaa Xaa Xaa Xaa Xaa Xaa Xaa Xaa

```
1               5
```

<210> SEQ ID NO 117
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 7C
<220> FEATURE:
<221> NAME/KEY: misc_feature
<222> LOCATION: (1)..(1)
<223> OTHER INFORMATION: Xaa may be Gly, Ser or Val
<220> FEATURE:
<221> NAME/KEY: misc_feature
<222> LOCATION: (2)..(2)
<223> OTHER INFORMATION: Xaa may be Pro or Val
<220> FEATURE:
<221> NAME/KEY: misc_feature
<222> LOCATION: (3)..(3)
<223> OTHER INFORMATION: Xaa may be Ala
<220> FEATURE:
<221> NAME/KEY: misc_feature
<222> LOCATION: (4)..(4)
<223> OTHER INFORMATION: Xaa may be Gly or Val
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Met or Ser
<220> FEATURE:
<221> NAME/KEY: misc_feature
<222> LOCATION: (8)..(8)
<223> OTHER INFORMATION: Xaa may be Gly, Leu or Ser

<400> SEQUENCE: 117

```
Xaa Xaa Xaa Xaa Xaa Xaa Xaa Xaa
1               5
```

<210> SEQ ID NO 118
<211> LENGTH: 6
<212> TYPE: PRT
<213> ORGANISM: Artificial Sequence
<220> FEATURE:
<223> OTHER INFORMATION: Matriptase Cleavable Expanded Core CM
      Consensus Sequence 8A
<220> FEATURE:
<221> NAME/KEY: misc_feature
<222> LOCATION: (1)..(1)
<223> OTHER INFORMATION: Xaa may be Ala, Gly, Ile, Lys, Pro, Ser or Thr
<220> FEATURE:
<221> NAME/KEY: misc_feature
<222> LOCATION: (2)..(2)
<223> OTHER INFORMATION: Xaa may be Arg or Thr
<220> FEATURE:
<221> NAME/KEY: misc_feature
<222> LOCATION: (3)..(3)
<223> OTHER INFORMATION: Xaa may be His, Met or Ser
<220> FEATURE:
<221> NAME/KEY: misc_feature
<222> LOCATION: (4)..(4)
<223> OTHER INFORMATION: Xaa may be Phe, Met or Arg
<220> FEATURE:
<221> NAME/KEY: misc_feature
<222> LOCATION: (5)..(5)
<223> OTHER INFORMATION: Xaa may be Ala, Gly, Ile, Leu, Pro, Gln, Arg,
      Ser, Val or Trp
<220> FEATURE:
<221> NAME/KEY: misc_feature

```
<222> LOCATION: (6)..(6)
<223> OTHER INFORMATION: Xaa may be Ala, Gly, Leu, Met, Pro, Gln, Arg,
      Ser, Thr, Val or Trp

<400> SEQUENCE: 118

Xaa Xaa Xaa Xaa Xaa Xaa
1               5

<210> SEQ ID NO 119
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 8A
<220> FEATURE:
<221> NAME/KEY: misc_feature
<222> LOCATION: (1)..(1)
<223> OTHER INFORMATION: Xaa may be Ala, Gly, Ile, Lys, Ser or Thr
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Phe, Met or Arg
<220> FEATURE:
<221> NAME/KEY: misc_feature
<222> LOCATION: (5)..(5)
<223> OTHER INFORMATION: Xaa may be Ala, Ile, Leu, Arg or Trp
<220> FEATURE:
<221> NAME/KEY: misc_feature
<222> LOCATION: (6)..(6)
<223> OTHER INFORMATION: Xaa may be Gly, Leu, Met, Pro, Gln, Arg, Ser
      or Val

<400> SEQUENCE: 119

Xaa Xaa Xaa Xaa Xaa Xaa
1               5

<210> SEQ ID NO 120
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 8A
<220> FEATURE:
<221> NAME/KEY: misc_feature
<222> LOCATION: (1)..(1)
<223> OTHER INFORMATION: Xaa may be Gly or Lys
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Met
<220> FEATURE:
<221> NAME/KEY: misc_feature
<222> LOCATION: (5)..(5)
<223> OTHER INFORMATION: Xaa may be Ala, Leu, Arg or Trp
<220> FEATURE:
<221> NAME/KEY: misc_feature
<222> LOCATION: (6)..(6)
```

<223> OTHER INFORMATION: Xaa may be Gly, Leu, Met, Pro, Arg or Ser

<400> SEQUENCE: 120

Xaa Xaa Xaa Xaa Xaa Xaa
1               5

<210> SEQ ID NO 121
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 8A
<220> FEATURE:
<221> NAME/KEY: misc_feature
<222> LOCATION: (1)..(1)
<223> OTHER INFORMATION: Xaa may be Gly
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Met
<220> FEATURE:
<221> NAME/KEY: misc_feature
<222> LOCATION: (5)..(5)
<223> OTHER INFORMATION: Xaa may be Ala or Leu
<220> FEATURE:
<221> NAME/KEY: misc_feature
<222> LOCATION: (6)..(6)
<223> OTHER INFORMATION: Xaa may be Gly, Leu, Met, Arg or Ser

<400> SEQUENCE: 121

Xaa Xaa Xaa Xaa Xaa Xaa
1               5

<210> SEQ ID NO 122
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 8A
<220> FEATURE:
<221> NAME/KEY: misc_feature
<222> LOCATION: (1)..(1)
<223> OTHER INFORMATION: Xaa may be Gly
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Met
<220> FEATURE:
<221> NAME/KEY: misc_feature
<222> LOCATION: (5)..(5)
<223> OTHER INFORMATION: Xaa may be Ala or Leu
<220> FEATURE:
<221> NAME/KEY: misc_feature
<222> LOCATION: (6)..(6)
<223> OTHER INFORMATION: Xaa may be Leu or Met

<400> SEQUENCE: 122

Xaa Xaa Xaa Xaa Xaa Xaa
1               5

<210> SEQ ID NO 123
<211> LENGTH: 7
<212> TYPE: PRT
<213> ORGANISM: Artificial Sequence
<220> FEATURE:
<223> OTHER INFORMATION: Matriptase Cleavable Expanded Core CM
      Consensus Sequence 8B
<220> FEATURE:
<221> NAME/KEY: misc_feature
<222> LOCATION: (1)..(1)
<223> OTHER INFORMATION: Xaa may be Ala, Gly, Ile, Lys, Pro, Ser or Thr
<220> FEATURE:
<221> NAME/KEY: misc_feature
<222> LOCATION: (2)..(2)
<223> OTHER INFORMATION: Xaa may be Arg or Thr
<220> FEATURE:
<221> NAME/KEY: misc_feature
<222> LOCATION: (3)..(3)
<223> OTHER INFORMATION: Xaa may be His, Met or Ser
<220> FEATURE:
<221> NAME/KEY: misc_feature
<222> LOCATION: (4)..(4)
<223> OTHER INFORMATION: Xaa may be Phe, Met or Arg
<220> FEATURE:
<221> NAME/KEY: misc_feature
<222> LOCATION: (5)..(5)
<223> OTHER INFORMATION: Xaa may be Ala, Gly, Ile, Leu, Pro, Gln, Arg,
      Ser, Val or Trp
<220> FEATURE:
<221> NAME/KEY: misc_feature
<222> LOCATION: (6)..(6)
<223> OTHER INFORMATION: Xaa may be Ala, Gly, Leu, Met, Pro, Gln, Arg,
      Ser, Thr, Val or Trp
<220> FEATURE:
<221> NAME/KEY: misc_feature
<222> LOCATION: (7)..(7)
<223> OTHER INFORMATION: Xaa may be Ala, Gly, Lys, Met, Pro, Arg, Ser,
      Trp or Tyr

<400> SEQUENCE: 123

Xaa Xaa Xaa Xaa Xaa Xaa Xaa
1               5

<210> SEQ ID NO 124
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 8B
<220> FEATURE:
<221> NAME/KEY: misc_feature
<222> LOCATION: (1)..(1)
<223> OTHER INFORMATION: Xaa may be Ala, Gly, Ile, Lys, Ser or Thr
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Phe, Met or Arg
<220> FEATURE:
<221> NAME/KEY: misc_feature
<222> LOCATION: (5)..(5)
<223> OTHER INFORMATION: Xaa may be Ala, Ile, Leu, Arg or Trp
<220> FEATURE:
<221> NAME/KEY: misc_feature

```
<222> LOCATION: (6)..(6)
<223> OTHER INFORMATION: Xaa may be Gly, Leu, Met, Pro, Gln, Arg, Ser
      or Val
<220> FEATURE:
<221> NAME/KEY: misc_feature
<222> LOCATION: (7)..(7)
<223> OTHER INFORMATION: Xaa may be Ala, Gly, Pro, Arg, Ser, Trp or Tyr

<400> SEQUENCE: 124

Xaa Xaa Xaa Xaa Xaa Xaa Xaa
1               5

<210> SEQ ID NO 125
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 8B
<220> FEATURE:
<221> NAME/KEY: misc_feature
<222> LOCATION: (1)..(1)
<223> OTHER INFORMATION: Xaa may be Gly or Lys
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Met
<220> FEATURE:
<221> NAME/KEY: misc_feature
<222> LOCATION: (5)..(5)
<223> OTHER INFORMATION: Xaa may be Ala, Leu, Arg or Trp
<220> FEATURE:
<221> NAME/KEY: misc_feature
<222> LOCATION: (6)..(6)
<223> OTHER INFORMATION: Xaa may be Gly, Leu, Met, Pro, Arg or Ser
<220> FEATURE:
<221> NAME/KEY: misc_feature
<222> LOCATION: (7)..(7)
<223> OTHER INFORMATION: Xaa may be Ala, Gly, Pro, Arg, Ser or Trp

<400> SEQUENCE: 125

Xaa Xaa Xaa Xaa Xaa Xaa Xaa
1               5

<210> SEQ ID NO 126
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 8B
<220> FEATURE:
<221> NAME/KEY: misc_feature
<222> LOCATION: (1)..(1)
<223> OTHER INFORMATION: Xaa may be Gly
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Met
```

```
<220> FEATURE:
<221> NAME/KEY: misc_feature
<222> LOCATION: (5)..(5)
<223> OTHER INFORMATION: Xaa may be Ala or Leu
<220> FEATURE:
<221> NAME/KEY: misc_feature
<222> LOCATION: (6)..(6)
<223> OTHER INFORMATION: Xaa may be Gly, Leu, Met, Arg or Ser
<220> FEATURE:
<221> NAME/KEY: misc_feature
<222> LOCATION: (7)..(7)
<223> OTHER INFORMATION: Xaa may be Ala, Gly, Pro, Arg or Ser

<400> SEQUENCE: 126

Xaa Xaa Xaa Xaa Xaa Xaa Xaa
1               5

<210> SEQ ID NO 127
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 8B
<220> FEATURE:
<221> NAME/KEY: misc_feature
<222> LOCATION: (1)..(1)
<223> OTHER INFORMATION: Xaa may be Gly
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Met
<220> FEATURE:
<221> NAME/KEY: misc_feature
<222> LOCATION: (5)..(5)
<223> OTHER INFORMATION: Xaa may be Ala or Leu
<220> FEATURE:
<221> NAME/KEY: misc_feature
<222> LOCATION: (6)..(6)
<223> OTHER INFORMATION: Xaa may be Leu or Met
<220> FEATURE:
<221> NAME/KEY: misc_feature
<222> LOCATION: (7)..(7)
<223> OTHER INFORMATION: Xaa may be Gly, Pro or Ser

<400> SEQUENCE: 127

Xaa Xaa Xaa Xaa Xaa Xaa Xaa
1               5

<210> SEQ ID NO 128
<211> LENGTH: 8
<212> TYPE: PRT
<213> ORGANISM: Artificial Sequence
<220> FEATURE:
<223> OTHER INFORMATION: Matriptase Cleavable Expanded Core CM
      Consensus Sequence 8C
<220> FEATURE:
<221> NAME/KEY: misc_feature
<222> LOCATION: (1)..(1)
<223> OTHER INFORMATION: Xaa may be Ala, Gly, Ile, Lys, Pro, Ser or Thr
<220> FEATURE:
<221> NAME/KEY: misc_feature
<222> LOCATION: (2)..(2)
<223> OTHER INFORMATION: Xaa may be Arg or Thr
<220> FEATURE:
<221> NAME/KEY: misc_feature
<222> LOCATION: (3)..(3)
```

```
<223> OTHER INFORMATION: Xaa may be His, Met or Ser
<220> FEATURE:
<221> NAME/KEY: misc_feature
<222> LOCATION: (4)..(4)
<223> OTHER INFORMATION: Xaa may be Phe, Met or Arg
<220> FEATURE:
<221> NAME/KEY: misc_feature
<222> LOCATION: (5)..(5)
<223> OTHER INFORMATION: Xaa may be Ala, Gly, Ile, Leu, Pro, Gln, Arg,
      Ser, Val or Trp
<220> FEATURE:
<221> NAME/KEY: misc_feature
<222> LOCATION: (6)..(6)
<223> OTHER INFORMATION: Xaa may be Ala, Gly, Leu, Met, Pro, Gln, Arg,
      Ser, Thr, Val or Trp
<220> FEATURE:
<221> NAME/KEY: misc_feature
<222> LOCATION: (7)..(7)
<223> OTHER INFORMATION: Xaa may be Ala, Gly, Lys, Met, Pro, Arg, Ser,
      Trp or Tyr
<220> FEATURE:
<221> NAME/KEY: misc_feature
<222> LOCATION: (8)..(8)
<223> OTHER INFORMATION: Xaa may be Phe, Gly, Ile, Leu, Pro, Gln, Ser
      or Tyr

<400> SEQUENCE: 128

Xaa Xaa Xaa Xaa Xaa Xaa Xaa Xaa
1               5

<210> SEQ ID NO 129
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 8C
<220> FEATURE:
<221> NAME/KEY: misc_feature
<222> LOCATION: (1)..(1)
<223> OTHER INFORMATION: Xaa may be Ala, Gly, Ile, Lys, Ser or Thr
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Phe, Met or Arg
<220> FEATURE:
<221> NAME/KEY: misc_feature
<222> LOCATION: (5)..(5)
<223> OTHER INFORMATION: Xaa may be Ala, Ile, Leu, Arg or Trp
<220> FEATURE:
<221> NAME/KEY: misc_feature
<222> LOCATION: (6)..(6)
<223> OTHER INFORMATION: Xaa may be Gly, Leu, Met, Pro, Gln, Arg, Ser
      or Val
<220> FEATURE:
<221> NAME/KEY: misc_feature
<222> LOCATION: (7)..(7)
<223> OTHER INFORMATION: Xaa may be Ala, Gly, Pro, Arg, Ser, Trp or Tyr
<220> FEATURE:
<221> NAME/KEY: misc_feature
<222> LOCATION: (8)..(8)
<223> OTHER INFORMATION: Xaa may be Phe, Gly, Leu, Pro or Ser

<400> SEQUENCE: 129

Xaa Xaa Xaa Xaa Xaa Xaa Xaa Xaa
1               5
```

-continued

```
<210> SEQ ID NO 130
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 8C
<220> FEATURE:
<221> NAME/KEY: misc_feature
<222> LOCATION: (1)..(1)
<223> OTHER INFORMATION: Xaa may be Gly or Lys
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Met
<220> FEATURE:
<221> NAME/KEY: misc_feature
<222> LOCATION: (5)..(5)
<223> OTHER INFORMATION: Xaa may be Ala, Leu, Arg or Trp
<220> FEATURE:
<221> NAME/KEY: misc_feature
<222> LOCATION: (6)..(6)
<223> OTHER INFORMATION: Xaa may be Gly, Leu, Met, Pro, Arg or Ser
<220> FEATURE:
<221> NAME/KEY: misc_feature
<222> LOCATION: (7)..(7)
<223> OTHER INFORMATION: Xaa may be Ala, Gly, Pro, Arg, Ser or Trp
<220> FEATURE:
<221> NAME/KEY: misc_feature
<222> LOCATION: (8)..(8)
<223> OTHER INFORMATION: Xaa may be Phe, Gly, Leu, Pro or Ser

<400> SEQUENCE: 130

Xaa Xaa Xaa Xaa Xaa Xaa Xaa Xaa
1               5

<210> SEQ ID NO 131
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 8C
<220> FEATURE:
<221> NAME/KEY: misc_feature
<222> LOCATION: (1)..(1)
<223> OTHER INFORMATION: Xaa may be Gly
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Met
<220> FEATURE:
<221> NAME/KEY: misc_feature
<222> LOCATION: (5)..(5)
<223> OTHER INFORMATION: Xaa may be Ala or Leu
<220> FEATURE:
<221> NAME/KEY: misc_feature
<222> LOCATION: (6)..(6)
<223> OTHER INFORMATION: Xaa may be Gly, Leu, Met, Arg or Ser
<220> FEATURE:
<221> NAME/KEY: misc_feature
```

-continued

```
<222> LOCATION: (7)..(7)
<223> OTHER INFORMATION: Xaa may be Ala, Gly, Pro, Arg or Ser
<220> FEATURE:
<221> NAME/KEY: misc_feature
<222> LOCATION: (8)..(8)
<223> OTHER INFORMATION: Xaa may be Phe, Gly, Pro or Ser

<400> SEQUENCE: 131

Xaa Xaa Xaa Xaa Xaa Xaa Xaa Xaa
1               5

<210> SEQ ID NO 132
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 8C
<220> FEATURE:
<221> NAME/KEY: misc_feature
<222> LOCATION: (1)..(1)
<223> OTHER INFORMATION: Xaa may be Gly
<220> FEATURE:
<221> NAME/KEY: misc_feature
<222> LOCATION: (2)..(2)
<223> OTHER INFORMATION: Xaa may be Arg
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Met
<220> FEATURE:
<221> NAME/KEY: misc_feature
<222> LOCATION: (5)..(5)
<223> OTHER INFORMATION: Xaa may be Ala or Leu
<220> FEATURE:
<221> NAME/KEY: misc_feature
<222> LOCATION: (6)..(6)
<223> OTHER INFORMATION: Xaa may be Leu or Met
<220> FEATURE:
<221> NAME/KEY: misc_feature
<222> LOCATION: (7)..(7)
<223> OTHER INFORMATION: Xaa may be Gly, Pro or Ser
<220> FEATURE:
<221> NAME/KEY: misc_feature
<222> LOCATION: (8)..(8)
<223> OTHER INFORMATION: Xaa may be Gly, Pro or Ser

<400> SEQUENCE: 132

Xaa Xaa Xaa Xaa Xaa Xaa Xaa Xaa
1               5

<210> SEQ ID NO 133
<211> LENGTH: 6
<212> TYPE: PRT
<213> ORGANISM: Artificial Sequence
<220> FEATURE:
<223> OTHER INFORMATION: Matriptase Cleavable Expanded Core CM
      Consensus Sequence 9A
<220> FEATURE:
<221> NAME/KEY: misc_feature
<222> LOCATION: (1)..(1)
<223> OTHER INFORMATION: Xaa may be Ile, Leu or Ser
<220> FEATURE:
<221> NAME/KEY: misc_feature
<222> LOCATION: (2)..(2)
<223> OTHER INFORMATION: Xaa may be Ala, Gly, Lys, Pro, Arg or Val
<220> FEATURE:
<221> NAME/KEY: misc_feature
<222> LOCATION: (3)..(3)
<223> OTHER INFORMATION: Xaa may be Leu, Arg or Ser
<220> FEATURE:
```

```
<221> NAME/KEY: misc_feature
<222> LOCATION: (4)..(4)
<223> OTHER INFORMATION: Xaa may be Ala, Lys, Met, Pro, Arg, Ser or Thr
<220> FEATURE:
<221> NAME/KEY: misc_feature
<222> LOCATION: (5)..(5)
<223> OTHER INFORMATION: Xaa may be Phe, Gly, His, Ile, Lys, Leu, Met,
      Pro, Arg, Ser or Val
<220> FEATURE:
<221> NAME/KEY: misc_feature
<222> LOCATION: (6)..(6)
<223> OTHER INFORMATION: Xaa may be Phe, Gly, Ile, Leu, Met, Pro, Arg,
      Ser, Thr, Val, Trp or Tyr

<400> SEQUENCE: 133

Xaa Xaa Xaa Xaa Xaa Xaa
1               5

<210> SEQ ID NO 134
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 9A
<220> FEATURE:
<221> NAME/KEY: misc_feature
<222> LOCATION: (1)..(1)
<223> OTHER INFORMATION: Xaa may be Ile or Leu
<220> FEATURE:
<221> NAME/KEY: misc_feature
<222> LOCATION: (2)..(2)
<223> OTHER INFORMATION: Xaa may be Ala, Gly, Pro or Val
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala, Met, Pro, Arg, Ser or Thr
<220> FEATURE:
<221> NAME/KEY: misc_feature
<222> LOCATION: (5)..(5)
<223> OTHER INFORMATION: Xaa may be Gly, Lys, Leu, Arg, Ser or Val
<220> FEATURE:
<221> NAME/KEY: misc_feature
<222> LOCATION: (6)..(6)
<223> OTHER INFORMATION: Xaa may be Phe, Gly, Ile, Leu, Met, Ser or Val

<400> SEQUENCE: 134

Xaa Xaa Xaa Xaa Xaa Xaa
1               5

<210> SEQ ID NO 135
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 9A
<220> FEATURE:
<221> NAME/KEY: misc_feature
<222> LOCATION: (1)..(1)
<223> OTHER INFORMATION: Xaa may be Leu
<220> FEATURE:
<221> NAME/KEY: misc_feature
<222> LOCATION: (2)..(2)
<223> OTHER INFORMATION: Xaa may be Ala, Gly, Pro or Val
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
```

```
<222> LOCATION: (4)..(4)
<223> OTHER INFORMATION: Xaa may be Ala, Met, Pro, Arg or Ser
<220> FEATURE:
<221> NAME/KEY: misc_feature
<222> LOCATION: (5)..(5)
<223> OTHER INFORMATION: Xaa may be Gly, Lys, Leu, Ser or Val
<220> FEATURE:
<221> NAME/KEY: misc_feature
<222> LOCATION: (6)..(6)
<223> OTHER INFORMATION: Xaa may be Phe, Gly, Ile, Leu, Ser or Val

<400> SEQUENCE: 135

Xaa Xaa Xaa Xaa Xaa Xaa
1               5

<210> SEQ ID NO 136
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 9A
<220> FEATURE:
<221> NAME/KEY: misc_feature
<222> LOCATION: (1)..(1)
<223> OTHER INFORMATION: Xaa may be Leu
<220> FEATURE:
<221> NAME/KEY: misc_feature
<222> LOCATION: (2)..(2)
<223> OTHER INFORMATION: Xaa may be Ala, Gly or Pro
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala or Ser
<220> FEATURE:
<221> NAME/KEY: misc_feature
<222> LOCATION: (5)..(5)
<223> OTHER INFORMATION: Xaa may be Gly or Leu
<220> FEATURE:
<221> NAME/KEY: misc_feature
<222> LOCATION: (6)..(6)
<223> OTHER INFORMATION: Xaa may be Ile or Leu

<400> SEQUENCE: 136

Xaa Xaa Xaa Xaa Xaa Xaa
1               5

<210> SEQ ID NO 137
<211> LENGTH: 6
<212> TYPE: PRT
<213> ORGANISM: Artificial Sequence
<220> FEATURE:
<223> OTHER INFORMATION: Matriptase Cleavable Subgenus of Expanded Core
      CM Consensus 9A
<220> FEATURE:
<221> NAME/KEY: misc_feature
<222> LOCATION: (1)..(1)
<223> OTHER INFORMATION: Xaa may be Leu
<220> FEATURE:
<221> NAME/KEY: misc_feature
<222> LOCATION: (2)..(2)
<223> OTHER INFORMATION: Xaa may be Ala or Pro
<220> FEATURE:
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ala
<220> FEATURE:
```

```
<221> NAME/KEY: misc_feature
<222> LOCATION: (5)..(5)
<223> OTHER INFORMATION: Xaa may be Gly or Leu
<220> FEATURE:
<221> NAME/KEY: misc_feature
<222> LOCATION: (6)..(6)
<223> OTHER INFORMATION: Xaa may be Ile or Leu

<400> SEQUENCE: 137

Xaa Xaa Xaa Xaa Xaa Xaa
1               5

<210> SEQ ID NO 138
<211> LENGTH: 7
<212> TYPE: PRT
<213> ORGANISM: Artificial Sequence
<220> FEATURE:
<223> OTHER INFORMATION: Matriptase Cleavable Expanded Core CM
      Consensus Sequence 9B
<220> FEATURE:
<221> NAME/KEY: misc_feature
<222> LOCATION: (1)..(1)
<223> OTHER INFORMATION: Xaa may be Gly, Lys, Pro, Gln, Arg, Ser or Thr
<220> FEATURE:
<221> NAME/KEY: misc_feature
<222> LOCATION: (2)..(2)
<223> OTHER INFORMATION: Xaa may be Ile, Leu or Ser
<220> FEATURE:
<221> NAME/KEY: misc_feature
<222> LOCATION: (3)..(3)
<223> OTHER INFORMATION: Xaa may be Ala, Gly, Lys, Pro, Arg or Val
<220> FEATURE:
<221> NAME/KEY: misc_feature
<222> LOCATION: (4)..(4)
<223> OTHER INFORMATION: Xaa may be Leu, Arg or Ser
<220> FEATURE:
<221> NAME/KEY: misc_feature
<222> LOCATION: (5)..(5)
<223> OTHER INFORMATION: Xaa may be Ala, Lys, Met, Pro, Arg, Ser or Thr
<220> FEATURE:
<221> NAME/KEY: misc_feature
<222> LOCATION: (6)..(6)
<223> OTHER INFORMATION: Xaa may be Phe, Gly, His, Ile, Lys, Leu, Met,
      Pro, Arg, Ser or Val
<220> FEATURE:
<221> NAME/KEY: misc_feature
<222> LOCATION: (7)..(7)
<223> OTHER INFORMATION: Xaa may be Phe, Gly, Ile, Leu, Met, Pro, Arg,
      Ser, Thr, Val, Trp or Tyr

<400> SEQUENCE: 138

Xaa Xaa Xaa Xaa Xaa Xaa Xaa
1               5

<210> SEQ ID NO 139
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 9B
<220> FEATURE:
<221> NAME/KEY: misc_feature
<222> LOCATION: (1)..(1)
<223> OTHER INFORMATION: Xaa may be Gly, Pro, Arg, Ser or Thr
<220> FEATURE:
<221> NAME/KEY: misc_feature
<222> LOCATION: (2)..(2)
<223> OTHER INFORMATION: Xaa may be Ile or Leu
<220> FEATURE:
<221> NAME/KEY: misc_feature
<222> LOCATION: (3)..(3)
<223> OTHER INFORMATION: Xaa may be Ala, Gly, Pro or Val
<220> FEATURE:
<221> NAME/KEY: misc_feature
```

```
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ala, Met, Pro, Arg, Ser or Thr
<220> FEATURE:
<221> NAME/KEY: misc_feature
<222> LOCATION: (6)..(6)
<223> OTHER INFORMATION: Xaa may be Gly, Lys, Leu, Arg, Ser or Val
<220> FEATURE:
<221> NAME/KEY: misc_feature
<222> LOCATION: (7)..(7)
<223> OTHER INFORMATION: Xaa may be Phe, Gly, Ile, Leu, Met, Ser or Val

<400> SEQUENCE: 139

Xaa Xaa Xaa Xaa Xaa Xaa Xaa
1               5

<210> SEQ ID NO 140
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 9B
<220> FEATURE:
<221> NAME/KEY: misc_feature
<222> LOCATION: (1)..(1)
<223> OTHER INFORMATION: Xaa may be Gly, Pro, Arg or Ser
<220> FEATURE:
<221> NAME/KEY: misc_feature
<222> LOCATION: (2)..(2)
<223> OTHER INFORMATION: Xaa may be Leu
<220> FEATURE:
<221> NAME/KEY: misc_feature
<222> LOCATION: (3)..(3)
<223> OTHER INFORMATION: Xaa may be Ala, Gly, Pro or Val
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ala, Met, Pro, Arg or Ser
<220> FEATURE:
<221> NAME/KEY: misc_feature
<222> LOCATION: (6)..(6)
<223> OTHER INFORMATION: Xaa may be Gly, Lys, Leu, Ser or Val
<220> FEATURE:
<221> NAME/KEY: misc_feature
<222> LOCATION: (7)..(7)
<223> OTHER INFORMATION: Xaa may be Phe, Gly, Ile, Leu, Ser or Val

<400> SEQUENCE: 140

Xaa Xaa Xaa Xaa Xaa Xaa Xaa
1               5

<210> SEQ ID NO 141
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 9B
<220> FEATURE:
<221> NAME/KEY: misc_feature
<222> LOCATION: (1)..(1)
<223> OTHER INFORMATION: Xaa may be Pro
<220> FEATURE:
<221> NAME/KEY: misc_feature
<222> LOCATION: (2)..(2)
<223> OTHER INFORMATION: Xaa may be Leu
<220> FEATURE:
```

```
<221> NAME/KEY: misc_feature
<222> LOCATION: (3)..(3)
<223> OTHER INFORMATION: Xaa may be Ala, Gly or Pro
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ala or Ser
<220> FEATURE:
<221> NAME/KEY: misc_feature
<222> LOCATION: (6)..(6)
<223> OTHER INFORMATION: Xaa may be Gly or Leu
<220> FEATURE:
<221> NAME/KEY: misc_feature
<222> LOCATION: (7)..(7)
<223> OTHER INFORMATION: Xaa may be Ile or Leu

<400> SEQUENCE: 141

Xaa Xaa Xaa Xaa Xaa Xaa Xaa
1               5

<210> SEQ ID NO 142
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 9B
<220> FEATURE:
<221> NAME/KEY: misc_feature
<222> LOCATION: (1)..(1)
<223> OTHER INFORMATION: Xaa may be Pro
<220> FEATURE:
<221> NAME/KEY: misc_feature
<222> LOCATION: (2)..(2)
<223> OTHER INFORMATION: Xaa may be Leu
<220> FEATURE:
<221> NAME/KEY: misc_feature
<222> LOCATION: (3)..(3)
<223> OTHER INFORMATION: Xaa may be Ala or Pro
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ala
<220> FEATURE:
<221> NAME/KEY: misc_feature
<222> LOCATION: (6)..(6)
<223> OTHER INFORMATION: Xaa may be Gly or Leu
<220> FEATURE:
<221> NAME/KEY: misc_feature
<222> LOCATION: (7)..(7)
<223> OTHER INFORMATION: Xaa may be Ile or Leu

<400> SEQUENCE: 142

Xaa Xaa Xaa Xaa Xaa Xaa Xaa
1               5

<210> SEQ ID NO 143
<211> LENGTH: 8
<212> TYPE: PRT
<213> ORGANISM: Artificial Sequence
<220> FEATURE:
<223> OTHER INFORMATION: Matriptase Cleavable Expanded Core CM
      Consensus Sequence 9C
<220> FEATURE:
<221> NAME/KEY: misc_feature
<222> LOCATION: (1)..(1)
<223> OTHER INFORMATION: Xaa may be Ala, Gly, Ile, Lys, Pro, Arg, Ser
```

```
                                   or Val
<220> FEATURE:
<221> NAME/KEY: misc_feature
<222> LOCATION: (2)..(2)
<223> OTHER INFORMATION: Xaa may be Gly, Lys, Pro, Gln, Arg, Ser or Thr
<220> FEATURE:
<221> NAME/KEY: misc_feature
<222> LOCATION: (3)..(3)
<223> OTHER INFORMATION: Xaa may be Ile, Leu or Ser
<220> FEATURE:
<221> NAME/KEY: misc_feature
<222> LOCATION: (4)..(4)
<223> OTHER INFORMATION: Xaa may be Ala, Gly, Lys, Pro, Arg or Val
<220> FEATURE:
<221> NAME/KEY: misc_feature
<222> LOCATION: (5)..(5)
<223> OTHER INFORMATION: Xaa may be Leu, Arg or Ser
<220> FEATURE:
<221> NAME/KEY: misc_feature
<222> LOCATION: (6)..(6)
<223> OTHER INFORMATION: Xaa may be Ala, Lys, Met, Pro, Arg, Ser or Thr
<220> FEATURE:
<221> NAME/KEY: misc_feature
<222> LOCATION: (7)..(7)
<223> OTHER INFORMATION: Xaa may be Phe, Gly, His, Ile, Lys, Leu, Met,
      Pro, Arg, Ser or Val
<220> FEATURE:
<221> NAME/KEY: misc_feature
<222> LOCATION: (8)..(8)
<223> OTHER INFORMATION: Xaa may be Phe, Gly, Ile, Leu, Met, Pro, Arg,
      Ser, Thr, Val, Trp or Tyr

<400> SEQUENCE: 143

Xaa Xaa Xaa Xaa Xaa Xaa Xaa Xaa
1               5

<210> SEQ ID NO 144
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 9C
<220> FEATURE:
<221> NAME/KEY: misc_feature
<222> LOCATION: (1)..(1)
<223> OTHER INFORMATION: Xaa may be Gly, Lys, Pro, Arg, Ser or Val
<220> FEATURE:
<221> NAME/KEY: misc_feature
<222> LOCATION: (2)..(2)
<223> OTHER INFORMATION: Xaa may be Gly, Pro, Arg, Ser or Thr
<220> FEATURE:
<221> NAME/KEY: misc_feature
<222> LOCATION: (3)..(3)
<223> OTHER INFORMATION: Xaa may be Ile or Leu
<220> FEATURE:
<221> NAME/KEY: misc_feature
<222> LOCATION: (4)..(4)
<223> OTHER INFORMATION: Xaa may be Ala, Gly, Pro or Val
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Ala, Met, Pro, Arg, Ser or Thr
<220> FEATURE:
<221> NAME/KEY: misc_feature
<222> LOCATION: (7)..(7)
<223> OTHER INFORMATION: Xaa may be Gly, Lys, Leu, Arg, Ser or Val
<220> FEATURE:
<221> NAME/KEY: misc_feature
<222> LOCATION: (8)..(8)
<223> OTHER INFORMATION: Xaa may be Phe, Gly, Ile, Leu, Met, Ser or Val

<400> SEQUENCE: 144
```

Xaa Xaa Xaa Xaa Xaa Xaa Xaa Xaa
1               5

<210> SEQ ID NO 145
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 9C
<220> FEATURE:
<221> NAME/KEY: misc_feature
<222> LOCATION: (1)..(1)
<223> OTHER INFORMATION: Xaa may be Gly, Pro, Arg or Ser
<220> FEATURE:
<221> NAME/KEY: misc_feature
<222> LOCATION: (2)..(2)
<223> OTHER INFORMATION: Xaa may be Gly, Pro, Arg or Ser
<220> FEATURE:
<221> NAME/KEY: misc_feature
<222> LOCATION: (3)..(3)
<223> OTHER INFORMATION: Xaa may be Leu
<220> FEATURE:
<221> NAME/KEY: misc_feature
<222> LOCATION: (4)..(4)
<223> OTHER INFORMATION: Xaa may be Ala, Gly, Pro or Val
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Ala, Met, Pro, Arg or Ser
<220> FEATURE:
<221> NAME/KEY: misc_feature
<222> LOCATION: (7)..(7)
<223> OTHER INFORMATION: Xaa may be Gly, Lys, Leu, Ser or Val
<220> FEATURE:
<221> NAME/KEY: misc_feature
<222> LOCATION: (8)..(8)
<223> OTHER INFORMATION: Xaa may be Phe, Gly, Ile, Leu, Ser or Val

<400> SEQUENCE: 145

Xaa Xaa Xaa Xaa Xaa Xaa Xaa Xaa
1               5

<210> SEQ ID NO 146
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 9C
<220> FEATURE:
<221> NAME/KEY: misc_feature
<222> LOCATION: (1)..(1)
<223> OTHER INFORMATION: Xaa may be Gly, Pro, Arg or Ser
<220> FEATURE:
<221> NAME/KEY: misc_feature
<222> LOCATION: (2)..(2)
<223> OTHER INFORMATION: Xaa may be Pro
<220> FEATURE:
<221> NAME/KEY: misc_feature
<222> LOCATION: (3)..(3)
<223> OTHER INFORMATION: Xaa may be Leu
<220> FEATURE:
<221> NAME/KEY: misc_feature
<222> LOCATION: (4)..(4)
<223> OTHER INFORMATION: Xaa may be Ala, Gly or Pro
<220> FEATURE:
<221> NAME/KEY: misc_feature
<222> LOCATION: (5)..(5)
<223> OTHER INFORMATION: Xaa may be Arg
<220> FEATURE:

```
<221> NAME/KEY: misc_feature
<222> LOCATION: (6)..(6)
<223> OTHER INFORMATION: Xaa may be Ala or Ser
<220> FEATURE:
<221> NAME/KEY: misc_feature
<222> LOCATION: (7)..(7)
<223> OTHER INFORMATION: Xaa may be Gly or Leu
<220> FEATURE:
<221> NAME/KEY: misc_feature
<222> LOCATION: (8)..(8)
<223> OTHER INFORMATION: Xaa may be Ile or Leu

<400> SEQUENCE: 146

Xaa Xaa Xaa Xaa Xaa Xaa Xaa Xaa
1               5

<210> SEQ ID NO 147
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 9C
<220> FEATURE:
<221> NAME/KEY: misc_feature
<222> LOCATION: (1)..(1)
<223> OTHER INFORMATION: Xaa may be Arg
<220> FEATURE:
<221> NAME/KEY: misc_feature
<222> LOCATION: (2)..(2)
<223> OTHER INFORMATION: Xaa may be Pro
<220> FEATURE:
<221> NAME/KEY: misc_feature
<222> LOCATION: (3)..(3)
<223> OTHER INFORMATION: Xaa may be Leu
<220> FEATURE:
<221> NAME/KEY: misc_feature
<222> LOCATION: (4)..(4)
<223> OTHER INFORMATION: Xaa may be Ala or Pro
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Ala
<220> FEATURE:
<221> NAME/KEY: misc_feature
<222> LOCATION: (7)..(7)
<223> OTHER INFORMATION: Xaa may be Gly or Leu
<220> FEATURE:
<221> NAME/KEY: misc_feature
<222> LOCATION: (8)..(8)
<223> OTHER INFORMATION: Xaa may be Ile or Leu

<400> SEQUENCE: 147

Xaa Xaa Xaa Xaa Xaa Xaa Xaa Xaa
1               5

<210> SEQ ID NO 148
<211> LENGTH: 7
<212> TYPE: PRT
<213> ORGANISM: Artificial Sequence
<220> FEATURE:
<223> OTHER INFORMATION: Matriptase Cleavable Expanded Core CM
      Consensus Sequence 10A
<220> FEATURE:
<221> NAME/KEY: misc_feature
<222> LOCATION: (1)..(1)
<223> OTHER INFORMATION: Xaa may be Gly, His, Asn, Pro, Arg, Ser, Thr
      or Val
<220> FEATURE:
<221> NAME/KEY: misc_feature
<222> LOCATION: (2)..(2)
```

```
<223> OTHER INFORMATION: Xaa may be Glu, Leu, Gln, Ser, Thr or Val
<220> FEATURE:
<221> NAME/KEY: misc_feature
<222> LOCATION: (3)..(3)
<223> OTHER INFORMATION: Xaa may be Leu, Arg or Ser
<220> FEATURE:
<221> NAME/KEY: misc_feature
<222> LOCATION: (4)..(4)
<223> OTHER INFORMATION: Xaa may be His, Lys or Arg
<220> FEATURE:
<221> NAME/KEY: misc_feature
<222> LOCATION: (5)..(5)
<223> OTHER INFORMATION: Xaa may be Ala, Met, Arg or Ser
<220> FEATURE:
<221> NAME/KEY: misc_feature
<222> LOCATION: (6)..(6)
<223> OTHER INFORMATION: Xaa may be Gly, Leu, Met, Arg, Ser or Trp
<220> FEATURE:
<221> NAME/KEY: misc_feature
<222> LOCATION: (7)..(7)
<223> OTHER INFORMATION: Xaa may be Ala, Gly, Ile, Met, Asn, Pro, Ser,
      Val or Tyr

<400> SEQUENCE: 148

Xaa Xaa Xaa Xaa Xaa Xaa Xaa
1               5

<210> SEQ ID NO 149
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 10A
<220> FEATURE:
<221> NAME/KEY: misc_feature
<222> LOCATION: (1)..(1)
<223> OTHER INFORMATION: Xaa may be Gly, Asn, Pro, Ser, Thr or Val
<220> FEATURE:
<221> NAME/KEY: misc_feature
<222> LOCATION: (2)..(2)
<223> OTHER INFORMATION: Xaa may be Glu, Leu, Thr or Val
<220> FEATURE:
<221> NAME/KEY: misc_feature
<222> LOCATION: (3)..(3)
<223> OTHER INFORMATION: Xaa may be Arg or Ser
<220> FEATURE:
<221> NAME/KEY: misc_feature
<222> LOCATION: (4)..(4)
<223> OTHER INFORMATION: Xaa may be Lys or Arg
<220> FEATURE:
<221> NAME/KEY: misc_feature
<222> LOCATION: (5)..(5)
<223> OTHER INFORMATION: Xaa may be Met, Arg or Ser
<220> FEATURE:
<221> NAME/KEY: misc_feature
<222> LOCATION: (6)..(6)
<223> OTHER INFORMATION: Xaa may be Gly, Leu, Met, Ser or Trp
<220> FEATURE:
<221> NAME/KEY: misc_feature
<222> LOCATION: (7)..(7)
<223> OTHER INFORMATION: Xaa may be Ala, Gly, Ile, Met, Pro, Ser or Val

<400> SEQUENCE: 149

Xaa Xaa Xaa Xaa Xaa Xaa Xaa
1               5

<210> SEQ ID NO 150
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 10A
<220> FEATURE:
```

```
<221> NAME/KEY: misc_feature
<222> LOCATION: (1)..(1)
<223> OTHER INFORMATION: Xaa may be Gly, Asn, Pro, Ser or Val
<220> FEATURE:
<221> NAME/KEY: misc_feature
<222> LOCATION: (2)..(2)
<223> OTHER INFORMATION: Xaa may be Glu, Thr or Val
<220> FEATURE:
<221> NAME/KEY: misc_feature
<222> LOCATION: (3)..(3)
<223> OTHER INFORMATION: Xaa may be Arg or Ser
<220> FEATURE:
<221> NAME/KEY: misc_feature
<222> LOCATION: (4)..(4)
<223> OTHER INFORMATION: Xaa may be Lys or Arg
<220> FEATURE:
<221> NAME/KEY: misc_feature
<222> LOCATION: (5)..(5)
<223> OTHER INFORMATION: Xaa may be Met or Arg
<220> FEATURE:
<221> NAME/KEY: misc_feature
<222> LOCATION: (6)..(6)
<223> OTHER INFORMATION: Xaa may be Gly, Leu, Met, Ser or Trp
<220> FEATURE:
<221> NAME/KEY: misc_feature
<222> LOCATION: (7)..(7)
<223> OTHER INFORMATION: Xaa may be Ala, Gly, Ile, Met, Pro, Ser or Val

<400> SEQUENCE: 150

Xaa Xaa Xaa Xaa Xaa Xaa Xaa
1               5

<210> SEQ ID NO 151
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 10A
<220> FEATURE:
<221> NAME/KEY: misc_feature
<222> LOCATION: (1)..(1)
<223> OTHER INFORMATION: Xaa may be Gly, Pro, Ser or Val
<220> FEATURE:
<221> NAME/KEY: misc_feature
<222> LOCATION: (2)..(2)
<223> OTHER INFORMATION: Xaa may be Glu or Val
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Lys or Arg
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Leu, Ser or Trp
<220> FEATURE:
<221> NAME/KEY: misc_feature
<222> LOCATION: (7)..(7)
<223> OTHER INFORMATION: Xaa may be Gly, Ile, Met, Pro, Ser or Val

<400> SEQUENCE: 151

Xaa Xaa Xaa Xaa Xaa Xaa Xaa
1               5

<210> SEQ ID NO 152
<211> LENGTH: 7
<212> TYPE: PRT
```

```
<213> ORGANISM: Artificial Sequence
<220> FEATURE:
<223> OTHER INFORMATION: Matriptase Cleavable Subgenus of Expanded Core
      CM Consensus 10A
<220> FEATURE:
<221> NAME/KEY: misc_feature
<222> LOCATION: (1)..(1)
<223> OTHER INFORMATION: Xaa may be Gly, Pro or Ser
<220> FEATURE:
<221> NAME/KEY: misc_feature
<222> LOCATION: (2)..(2)
<223> OTHER INFORMATION: Xaa may be Glu
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Lys or Arg
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Leu or Trp
<220> FEATURE:
<221> NAME/KEY: misc_feature
<222> LOCATION: (7)..(7)
<223> OTHER INFORMATION: Xaa may be Met

<400> SEQUENCE: 152

Xaa Xaa Xaa Xaa Xaa Xaa Xaa
1               5

<210> SEQ ID NO 153
<211> LENGTH: 7
<212> TYPE: PRT
<213> ORGANISM: Artificial Sequence
<220> FEATURE:
<223> OTHER INFORMATION: Matriptase Cleavable Expanded Core CM
      Consensus Sequence 10B
<220> FEATURE:
<221> NAME/KEY: misc_feature
<222> LOCATION: (1)..(1)
<223> OTHER INFORMATION: Xaa may be Glu, Leu, Gln, Ser, Thr or Val
<220> FEATURE:
<221> NAME/KEY: misc_feature
<222> LOCATION: (2)..(2)
<223> OTHER INFORMATION: Xaa may be Leu, Arg or Ser
<220> FEATURE:
<221> NAME/KEY: misc_feature
<222> LOCATION: (3)..(3)
<223> OTHER INFORMATION: Xaa may be His, Lys or Arg
<220> FEATURE:
<221> NAME/KEY: misc_feature
<222> LOCATION: (4)..(4)
<223> OTHER INFORMATION: Xaa may be Ala, Met, Arg or Ser
<220> FEATURE:
<221> NAME/KEY: misc_feature
<222> LOCATION: (5)..(5)
<223> OTHER INFORMATION: Xaa may be Gly, Leu, Met, Arg, Ser or Trp
<220> FEATURE:
<221> NAME/KEY: misc_feature
<222> LOCATION: (6)..(6)
<223> OTHER INFORMATION: Xaa may be Ala, Gly, Ile, Met, Asn, Pro, Ser,
      Val or Tyr
<220> FEATURE:
<221> NAME/KEY: misc_feature
<222> LOCATION: (7)..(7)
<223> OTHER INFORMATION: Xaa may be Gly, Ile, Leu, Asn, Pro, Ser, Val
      or Trp

<400> SEQUENCE: 153
```

Xaa Xaa Xaa Xaa Xaa Xaa Xaa
1               5

<210> SEQ ID NO 154
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 10B
<220> FEATURE:
<221> NAME/KEY: misc_feature
<222> LOCATION: (1)..(1)
<223> OTHER INFORMATION: Xaa may be Glu, Leu, Thr or Val
<220> FEATURE:
<221> NAME/KEY: misc_feature
<222> LOCATION: (2)..(2)
<223> OTHER INFORMATION: Xaa may be Arg or Ser
<220> FEATURE:
<221> NAME/KEY: misc_feature
<222> LOCATION: (3)..(3)
<223> OTHER INFORMATION: Xaa may be Lys or Arg
<220> FEATURE:
<221> NAME/KEY: misc_feature
<222> LOCATION: (4)..(4)
<223> OTHER INFORMATION: Xaa may be Met, Arg or Ser
<220> FEATURE:
<221> NAME/KEY: misc_feature
<222> LOCATION: (5)..(5)
<223> OTHER INFORMATION: Xaa may be Gly, Leu, Met, Ser or Trp
<220> FEATURE:
<221> NAME/KEY: misc_feature
<222> LOCATION: (6)..(6)
<223> OTHER INFORMATION: Xaa may be Ala, Gly, Ile, Met, Pro, Ser or Val
<220> FEATURE:
<221> NAME/KEY: misc_feature
<222> LOCATION: (7)..(7)
<223> OTHER INFORMATION: Xaa may be Gly, Ile, Leu, Asn, Pro, Ser or Val

<400> SEQUENCE: 154

Xaa Xaa Xaa Xaa Xaa Xaa Xaa
1               5

<210> SEQ ID NO 155
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 10B
<220> FEATURE:
<221> NAME/KEY: misc_feature
<222> LOCATION: (1)..(1)
<223> OTHER INFORMATION: Xaa may be Glu, Thr or Val
<220> FEATURE:
<221> NAME/KEY: misc_feature
<222> LOCATION: (2)..(2)
<223> OTHER INFORMATION: Xaa may be Arg or Ser
<220> FEATURE:
<221> NAME/KEY: misc_feature
<222> LOCATION: (3)..(3)
<223> OTHER INFORMATION: Xaa may be Lys or Arg
<220> FEATURE:
<221> NAME/KEY: misc_feature
<222> LOCATION: (4)..(4)
<223> OTHER INFORMATION: Xaa may be Met or Arg
<220> FEATURE:
<221> NAME/KEY: misc_feature
<222> LOCATION: (5)..(5)
<223> OTHER INFORMATION: Xaa may be Gly, Leu, Met, Ser or Trp
<220> FEATURE:
<221> NAME/KEY: misc_feature
<222> LOCATION: (6)..(6)
<223> OTHER INFORMATION: Xaa may be Ala, Gly, Ile, Met, Pro, Ser or Val
<220> FEATURE:
<221> NAME/KEY: misc_feature

```
<222> LOCATION: (7)..(7)
<223> OTHER INFORMATION: Xaa may be Gly, Ile, Leu, Asn, Pro, Ser or Val

<400> SEQUENCE: 155

Xaa Xaa Xaa Xaa Xaa Xaa Xaa
1               5

<210> SEQ ID NO 156
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 10B
<220> FEATURE:
<221> NAME/KEY: misc_feature
<222> LOCATION: (1)..(1)
<223> OTHER INFORMATION: Xaa may be Glu or Val
<220> FEATURE:
<221> NAME/KEY: misc_feature
<222> LOCATION: (2)..(2)
<223> OTHER INFORMATION: Xaa may be Ser
<220> FEATURE:
<221> NAME/KEY: misc_feature
<222> LOCATION: (3)..(3)
<223> OTHER INFORMATION: Xaa may be Lys or Arg
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Leu, Ser or Trp
<220> FEATURE:
<221> NAME/KEY: misc_feature
<222> LOCATION: (6)..(6)
<223> OTHER INFORMATION: Xaa may be Gly, Ile, Met, Pro, Ser or Val
<220> FEATURE:
<221> NAME/KEY: misc_feature
<222> LOCATION: (7)..(7)
<223> OTHER INFORMATION: Xaa may be Gly, Leu, Asn, Pro, Ser or Val

<400> SEQUENCE: 156

Xaa Xaa Xaa Xaa Xaa Xaa Xaa
1               5

<210> SEQ ID NO 157
<211> LENGTH: 7
<212> TYPE: PRT
<213> ORGANISM: Artificial Sequence
<220> FEATURE:
<223> OTHER INFORMATION: Matriptase Cleavable Subgenus of Expanded Core
      CM Consensus 10B
<220> FEATURE:
<221> NAME/KEY: misc_feature
<222> LOCATION: (1)..(1)
<223> OTHER INFORMATION: Xaa may be Glu
<220> FEATURE:
<221> NAME/KEY: misc_feature
<222> LOCATION: (2)..(2)
<223> OTHER INFORMATION: Xaa may be Ser
<220> FEATURE:
<221> NAME/KEY: misc_feature
<222> LOCATION: (3)..(3)
<223> OTHER INFORMATION: Xaa may be Lys or Arg
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Leu or Trp
<220> FEATURE:
```

```
<221> NAME/KEY: misc_feature
<222> LOCATION: (6)..(6)
<223> OTHER INFORMATION: Xaa may be Met
<220> FEATURE:
<221> NAME/KEY: misc_feature
<222> LOCATION: (7)..(7)
<223> OTHER INFORMATION: Xaa may be Gly, Pro or Ser

<400> SEQUENCE: 157

Xaa Xaa Xaa Xaa Xaa Xaa Xaa
1               5

<210> SEQ ID NO 158
<211> LENGTH: 8
<212> TYPE: PRT
<213> ORGANISM: Artificial Sequence
<220> FEATURE:
<223> OTHER INFORMATION: Matriptase Cleavable Expanded Core CM
      Consensus Sequence 10C
<220> FEATURE:
<221> NAME/KEY: misc_feature
<222> LOCATION: (1)..(1)
<223> OTHER INFORMATION: Xaa may be Gly, His, Asn, Pro, Arg, Ser, Thr
      or Val
<220> FEATURE:
<221> NAME/KEY: misc_feature
<222> LOCATION: (2)..(2)
<223> OTHER INFORMATION: Xaa may be Glu, Leu, Gln, Ser, Thr or Val
<220> FEATURE:
<221> NAME/KEY: misc_feature
<222> LOCATION: (3)..(3)
<223> OTHER INFORMATION: Xaa may be Leu, Arg or Ser
<220> FEATURE:
<221> NAME/KEY: misc_feature
<222> LOCATION: (4)..(4)
<223> OTHER INFORMATION: Xaa may be His, Lys or Arg
<220> FEATURE:
<221> NAME/KEY: misc_feature
<222> LOCATION: (5)..(5)
<223> OTHER INFORMATION: Xaa may be Ala, Met, Arg or Ser
<220> FEATURE:
<221> NAME/KEY: misc_feature
<222> LOCATION: (6)..(6)
<223> OTHER INFORMATION: Xaa may be Gly, Leu, Met, Arg, Ser or Trp
<220> FEATURE:
<221> NAME/KEY: misc_feature
<222> LOCATION: (7)..(7)
<223> OTHER INFORMATION: Xaa may be Ala, Gly, Ile, Met, Asn, Pro, Ser,
      Val or Tyr
<220> FEATURE:
<221> NAME/KEY: misc_feature
<222> LOCATION: (8)..(8)
<223> OTHER INFORMATION: Xaa may be Gly, Ile, Leu, Asn, Pro, Ser, Val
      or Trp

<400> SEQUENCE: 158

Xaa Xaa Xaa Xaa Xaa Xaa Xaa Xaa
1               5

<210> SEQ ID NO 159
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 10C
<220> FEATURE:
<221> NAME/KEY: misc_feature
<222> LOCATION: (1)..(1)
<223> OTHER INFORMATION: Xaa may be Gly, Asn, Pro, Ser, Thr or Val
<220> FEATURE:
<221> NAME/KEY: misc_feature
<222> LOCATION: (2)..(2)
<223> OTHER INFORMATION: Xaa may be Glu, Leu, Thr or Val
<220> FEATURE:
```

```
<221> NAME/KEY: misc_feature
<222> LOCATION: (3)..(3)
<223> OTHER INFORMATION: Xaa may be Arg or Ser
<220> FEATURE:
<221> NAME/KEY: misc_feature
<222> LOCATION: (4)..(4)
<223> OTHER INFORMATION: Xaa may be Lys or Arg
<220> FEATURE:
<221> NAME/KEY: misc_feature
<222> LOCATION: (5)..(5)
<223> OTHER INFORMATION: Xaa may be Met, Arg or Ser
<220> FEATURE:
<221> NAME/KEY: misc_feature
<222> LOCATION: (6)..(6)
<223> OTHER INFORMATION: Xaa may be Gly, Leu, Met, Ser or Trp
<220> FEATURE:
<221> NAME/KEY: misc_feature
<222> LOCATION: (7)..(7)
<223> OTHER INFORMATION: Xaa may be Ala, Gly, Ile, Met, Pro, Ser or Val
<220> FEATURE:
<221> NAME/KEY: misc_feature
<222> LOCATION: (8)..(8)
<223> OTHER INFORMATION: Xaa may be Gly, Ile, Leu, Asn, Pro, Ser or Val

<400> SEQUENCE: 159

Xaa Xaa Xaa Xaa Xaa Xaa Xaa Xaa
1               5

<210> SEQ ID NO 160
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 10C
<220> FEATURE:
<221> NAME/KEY: misc_feature
<222> LOCATION: (1)..(1)
<223> OTHER INFORMATION: Xaa may be Gly, Asn, Pro, Ser or Val
<220> FEATURE:
<221> NAME/KEY: misc_feature
<222> LOCATION: (2)..(2)
<223> OTHER INFORMATION: Xaa may be Glu, Thr or Val
<220> FEATURE:
<221> NAME/KEY: misc_feature
<222> LOCATION: (3)..(3)
<223> OTHER INFORMATION: Xaa may be Arg or Ser
<220> FEATURE:
<221> NAME/KEY: misc_feature
<222> LOCATION: (4)..(4)
<223> OTHER INFORMATION: Xaa may be Lys or Arg
<220> FEATURE:
<221> NAME/KEY: misc_feature
<222> LOCATION: (5)..(5)
<223> OTHER INFORMATION: Xaa may be Met or Arg
<220> FEATURE:
<221> NAME/KEY: misc_feature
<222> LOCATION: (6)..(6)
<223> OTHER INFORMATION: Xaa may be Gly, Leu, Met, Ser or Trp
<220> FEATURE:
<221> NAME/KEY: misc_feature
<222> LOCATION: (7)..(7)
<223> OTHER INFORMATION: Xaa may be Ala, Gly, Ile, Met, Pro, Ser or Val
<220> FEATURE:
<221> NAME/KEY: misc_feature
<222> LOCATION: (8)..(8)
<223> OTHER INFORMATION: Xaa may be Gly, Ile, Leu, Asn, Pro, Ser or Val

<400> SEQUENCE: 160

Xaa Xaa Xaa Xaa Xaa Xaa Xaa Xaa
1               5

<210> SEQ ID NO 161
<211> LENGTH: 8
<212> TYPE: PRT
```

```
<213> ORGANISM: Artificial Sequence
<220> FEATURE:
<223> OTHER INFORMATION: Matriptase Cleavable Subgenus of Expanded Core
      CM Consensus 10C
<220> FEATURE:
<221> NAME/KEY: misc_feature
<222> LOCATION: (1)..(1)
<223> OTHER INFORMATION: Xaa may be Gly, Pro, Ser or Val
<220> FEATURE:
<221> NAME/KEY: misc_feature
<222> LOCATION: (2)..(2)
<223> OTHER INFORMATION: Xaa may be Glu or Val
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Lys or Arg
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Leu, Ser or Trp
<220> FEATURE:
<221> NAME/KEY: misc_feature
<222> LOCATION: (7)..(7)
<223> OTHER INFORMATION: Xaa may be Gly, Ile, Met, Pro, Ser or Val
<220> FEATURE:
<221> NAME/KEY: misc_feature
<222> LOCATION: (8)..(8)
<223> OTHER INFORMATION: Xaa may be Gly, Leu, Asn, Pro, Ser or Val

<400> SEQUENCE: 161

Xaa Xaa Xaa Xaa Xaa Xaa Xaa Xaa
1               5

<210> SEQ ID NO 162
<211> LENGTH: 8
<212> TYPE: PRT
<213> ORGANISM: Artificial Sequence
<220> FEATURE:
<223> OTHER INFORMATION: Matriptase Cleavable Subgenus of Expanded Core
      CM Consensus 10C
<220> FEATURE:
<221> NAME/KEY: misc_feature
<222> LOCATION: (1)..(1)
<223> OTHER INFORMATION: Xaa may be Gly, Pro or Ser
<220> FEATURE:
<221> NAME/KEY: misc_feature
<222> LOCATION: (2)..(2)
<223> OTHER INFORMATION: Xaa may be Glu
<220> FEATURE:
<221> NAME/KEY: misc_feature
<222> LOCATION: (3)..(3)
<223> OTHER INFORMATION: Xaa may be Ser
<220> FEATURE:
<221> NAME/KEY: misc_feature
<222> LOCATION: (4)..(4)
<223> OTHER INFORMATION: Xaa may be Lys or Arg
<220> FEATURE:
<221> NAME/KEY: misc_feature
<222> LOCATION: (5)..(5)
<223> OTHER INFORMATION: Xaa may be Arg
<220> FEATURE:
<221> NAME/KEY: misc_feature
<222> LOCATION: (6)..(6)
<223> OTHER INFORMATION: Xaa may be Leu or Trp
<220> FEATURE:
<221> NAME/KEY: misc_feature
<222> LOCATION: (7)..(7)
<223> OTHER INFORMATION: Xaa may be Met
<220> FEATURE:
```

<221> NAME/KEY: misc_feature
<222> LOCATION: (8)..(8)
<223> OTHER INFORMATION: Xaa may be Gly, Pro or Ser

<400> SEQUENCE: 162

Xaa Xaa Xaa Xaa Xaa Xaa Xaa Xaa
1               5

<210> SEQ ID NO 163
<211> LENGTH: 5
<212> TYPE: PRT
<213> ORGANISM: Artificial Sequence
<220> FEATURE:
<223> OTHER INFORMATION: Core CM consensus 1 sequence

<400> SEQUENCE: 163

Ala Ala Pro Arg Ser
1               5

<210> SEQ ID NO 164
<211> LENGTH: 6
<212> TYPE: PRT
<213> ORGANISM: Artificial Sequence
<220> FEATURE:
<223> OTHER INFORMATION: Expanded core CM consensus 1 sequence

<400> SEQUENCE: 164

Ala Ala Pro Arg Ser Phe
1               5

<210> SEQ ID NO 165
<211> LENGTH: 5
<212> TYPE: PRT
<213> ORGANISM: Artificial Sequence
<220> FEATURE:
<223> OTHER INFORMATION: Core CM consensus 2 sequence

<400> SEQUENCE: 165

Ser Arg Arg Val Pro
1               5

<210> SEQ ID NO 166
<211> LENGTH: 6
<212> TYPE: PRT
<213> ORGANISM: Artificial Sequence
<220> FEATURE:
<223> OTHER INFORMATION: Expanded core CM consensus 2 sequence

<400> SEQUENCE: 166

Gln Ser Arg Arg Val Pro
1               5

<210> SEQ ID NO 167
<211> LENGTH: 6
<212> TYPE: PRT
<213> ORGANISM: Artificial Sequence
<220> FEATURE:
<223> OTHER INFORMATION: Expanded core CM consensus 2 sequence

<400> SEQUENCE: 167

Gln Thr Arg Arg Val Pro
1               5

<210> SEQ ID NO 168
<211> LENGTH: 6
<212> TYPE: PRT
<213> ORGANISM: Artificial Sequence
<220> FEATURE:
<223> OTHER INFORMATION: Expanded core CM consensus 2 sequence

<400> SEQUENCE: 168

Ser Arg Arg Val Pro Leu
1               5

<210> SEQ ID NO 169
<211> LENGTH: 6
<212> TYPE: PRT
<213> ORGANISM: Artificial Sequence
<220> FEATURE:
<223> OTHER INFORMATION: Expanded core CM consensus 2 sequence

<400> SEQUENCE: 169

Ser Arg Arg Val Pro Val
1               5

<210> SEQ ID NO 170
<211> LENGTH: 7
<212> TYPE: PRT
<213> ORGANISM: Artificial Sequence
<220> FEATURE:
<223> OTHER INFORMATION: Expanded core CM consensus 2 sequence

<400> SEQUENCE: 170

Gln Ser Arg Arg Val Pro Leu
1               5

<210> SEQ ID NO 171
<211> LENGTH: 7
<212> TYPE: PRT
<213> ORGANISM: Artificial Sequence
<220> FEATURE:
<223> OTHER INFORMATION: Expanded core CM consensus 2 sequence

<400> SEQUENCE: 171

Gln Ser Arg Arg Val Pro Val
1               5

<210> SEQ ID NO 172
<211> LENGTH: 7
<212> TYPE: PRT
<213> ORGANISM: Artificial Sequence
<220> FEATURE:
<223> OTHER INFORMATION: Expanded core CM consensus 2 sequence

<400> SEQUENCE: 172

Gln Thr Arg Arg Val Pro Leu
1               5

<210> SEQ ID NO 173
<211> LENGTH: 7
<212> TYPE: PRT
<213> ORGANISM: Artificial Sequence
<220> FEATURE:
<223> OTHER INFORMATION: Expanded core CM consensus 2 sequence

<400> SEQUENCE: 173

Gln Thr Arg Arg Val Pro Val
1               5

<210> SEQ ID NO 174
<211> LENGTH: 5
<212> TYPE: PRT
<213> ORGANISM: Artificial Sequence
<220> FEATURE:

```
<223> OTHER INFORMATION: Core CM consensus 3 sequence

<400> SEQUENCE: 174

Pro Pro Leu Gly Arg
1               5

<210> SEQ ID NO 175
<211> LENGTH: 6
<212> TYPE: PRT
<213> ORGANISM: Artificial Sequence
<220> FEATURE:
<223> OTHER INFORMATION: Expanded core CM consensus 3 sequence

<400> SEQUENCE: 175

Gly Pro Pro Leu Gly Arg
1               5

<210> SEQ ID NO 176
<211> LENGTH: 6
<212> TYPE: PRT
<213> ORGANISM: Artificial Sequence
<220> FEATURE:
<223> OTHER INFORMATION: Expanded core CM consensus 3 sequence

<400> SEQUENCE: 176

Ser Pro Pro Leu Gly Arg
1               5

<210> SEQ ID NO 177
<211> LENGTH: 7
<212> TYPE: PRT
<213> ORGANISM: Artificial Sequence
<220> FEATURE:
<223> OTHER INFORMATION: Expanded core CM consensus 3 sequence

<400> SEQUENCE: 177

Cys Gly Pro Pro Leu Gly Arg
1               5

<210> SEQ ID NO 178
<211> LENGTH: 7
<212> TYPE: PRT
<213> ORGANISM: Artificial Sequence
<220> FEATURE:
<223> OTHER INFORMATION: Expanded core CM consensus 3 sequence

<400> SEQUENCE: 178

Cys Ser Pro Pro Leu Gly Arg
1               5

<210> SEQ ID NO 179
<211> LENGTH: 7
<212> TYPE: PRT
<213> ORGANISM: Artificial Sequence
<220> FEATURE:
<223> OTHER INFORMATION: Expanded core CM consensus 3 sequence

<400> SEQUENCE: 179

Gly Gly Pro Pro Leu Gly Arg
1               5

<210> SEQ ID NO 180
<211> LENGTH: 7
<212> TYPE: PRT
<213> ORGANISM: Artificial Sequence
<220> FEATURE:
<223> OTHER INFORMATION: Expanded core CM consensus 3 sequence
```

```
<400> SEQUENCE: 180

Gly Ser Pro Pro Leu Gly Arg
1               5

<210> SEQ ID NO 181
<211> LENGTH: 7
<212> TYPE: PRT
<213> ORGANISM: Artificial Sequence
<220> FEATURE:
<223> OTHER INFORMATION: Expanded core CM consensus 3 sequence

<400> SEQUENCE: 181

Ser Gly Pro Pro Leu Gly Arg
1               5

<210> SEQ ID NO 182
<211> LENGTH: 7
<212> TYPE: PRT
<213> ORGANISM: Artificial Sequence
<220> FEATURE:
<223> OTHER INFORMATION: Expanded core CM consensus 3 sequence

<400> SEQUENCE: 182

Ser Ser Pro Pro Leu Gly Arg
1               5

<210> SEQ ID NO 183
<211> LENGTH: 8
<212> TYPE: PRT
<213> ORGANISM: Artificial Sequence
<220> FEATURE:
<223> OTHER INFORMATION: Expanded core CM consensus 3 sequence

<400> SEQUENCE: 183

Gly Cys Gly Pro Pro Leu Gly Arg
1               5

<210> SEQ ID NO 184
<211> LENGTH: 8
<212> TYPE: PRT
<213> ORGANISM: Artificial Sequence
<220> FEATURE:
<223> OTHER INFORMATION: Expanded core CM consensus 3 sequence

<400> SEQUENCE: 184

Gly Cys Ser Pro Pro Leu Gly Arg
1               5

<210> SEQ ID NO 185
<211> LENGTH: 8
<212> TYPE: PRT
<213> ORGANISM: Artificial Sequence
<220> FEATURE:
<223> OTHER INFORMATION: Expanded core CM consensus 3 sequence

<400> SEQUENCE: 185

Gly Gly Gly Pro Pro Leu Gly Arg
1               5

<210> SEQ ID NO 186
<211> LENGTH: 8
<212> TYPE: PRT
<213> ORGANISM: Artificial Sequence
<220> FEATURE:
<223> OTHER INFORMATION: Expanded core CM consensus 3 sequence
```

```
<400> SEQUENCE: 186

Gly Gly Ser Pro Pro Leu Gly Arg
1               5

<210> SEQ ID NO 187
<211> LENGTH: 8
<212> TYPE: PRT
<213> ORGANISM: Artificial Sequence
<220> FEATURE:
<223> OTHER INFORMATION: Expanded core CM consensus 3 sequence

<400> SEQUENCE: 187

Gly Ser Gly Pro Pro Leu Gly Arg
1               5

<210> SEQ ID NO 188
<211> LENGTH: 8
<212> TYPE: PRT
<213> ORGANISM: Artificial Sequence
<220> FEATURE:
<223> OTHER INFORMATION: Expanded core CM consensus 3 sequence

<400> SEQUENCE: 188

Gly Ser Ser Pro Pro Leu Gly Arg
1               5

<210> SEQ ID NO 189
<211> LENGTH: 8
<212> TYPE: PRT
<213> ORGANISM: Artificial Sequence
<220> FEATURE:
<223> OTHER INFORMATION: Expanded core CM consensus 3 sequence

<400> SEQUENCE: 189

Ser Cys Gly Pro Pro Leu Gly Arg
1               5

<210> SEQ ID NO 190
<211> LENGTH: 8
<212> TYPE: PRT
<213> ORGANISM: Artificial Sequence
<220> FEATURE:
<223> OTHER INFORMATION: Expanded core CM consensus 3 sequence

<400> SEQUENCE: 190

Ser Cys Ser Pro Pro Leu Gly Arg
1               5

<210> SEQ ID NO 191
<211> LENGTH: 8
<212> TYPE: PRT
<213> ORGANISM: Artificial Sequence
<220> FEATURE:
<223> OTHER INFORMATION: Expanded core CM consensus 3 sequence

<400> SEQUENCE: 191

Ser Gly Gly Pro Pro Leu Gly Arg
1               5

<210> SEQ ID NO 192
<211> LENGTH: 8
<212> TYPE: PRT
<213> ORGANISM: Artificial Sequence
<220> FEATURE:
<223> OTHER INFORMATION: Expanded core CM consensus 3 sequence

<400> SEQUENCE: 192
```

```
Ser Gly Ser Pro Pro Leu Gly Arg
1               5

<210> SEQ ID NO 193
<211> LENGTH: 8
<212> TYPE: PRT
<213> ORGANISM: Artificial Sequence
<220> FEATURE:
<223> OTHER INFORMATION: Expanded core CM consensus 3 sequence

<400> SEQUENCE: 193

Ser Ser Gly Pro Pro Leu Gly Arg
1               5

<210> SEQ ID NO 194
<211> LENGTH: 8
<212> TYPE: PRT
<213> ORGANISM: Artificial Sequence
<220> FEATURE:
<223> OTHER INFORMATION: Expanded core CM consensus 3 sequence

<400> SEQUENCE: 194

Ser Ser Ser Pro Pro Leu Gly Arg
1               5

<210> SEQ ID NO 195
<211> LENGTH: 5
<212> TYPE: PRT
<213> ORGANISM: Artificial Sequence
<220> FEATURE:
<223> OTHER INFORMATION: Core CM consensus 4 sequence

<400> SEQUENCE: 195

Leu Arg Ser Gly Trp
1               5

<210> SEQ ID NO 196
<211> LENGTH: 6
<212> TYPE: PRT
<213> ORGANISM: Artificial Sequence
<220> FEATURE:
<223> OTHER INFORMATION: Expanded core CM consensus 4

<400> SEQUENCE: 196

Met Leu Arg Ser Gly Trp
1               5

<210> SEQ ID NO 197
<211> LENGTH: 7
<212> TYPE: PRT
<213> ORGANISM: Artificial Sequence
<220> FEATURE:
<223> OTHER INFORMATION: Expanded core CM consensus 4

<400> SEQUENCE: 197

Met Leu Arg Ser Gly Trp Arg
1               5

<210> SEQ ID NO 198
<211> LENGTH: 8
<212> TYPE: PRT
<213> ORGANISM: Artificial Sequence
<220> FEATURE:
<223> OTHER INFORMATION: Expanded core CM consensus 4

<400> SEQUENCE: 198
```

Met Leu Arg Ser Gly Trp Arg Gly
1               5

<210> SEQ ID NO 199
<211> LENGTH: 8
<212> TYPE: PRT
<213> ORGANISM: Artificial Sequence
<220> FEATURE:
<223> OTHER INFORMATION: Expanded core CM consensus 4

<400> SEQUENCE: 199

Met Leu Arg Ser Gly Trp Arg Leu
1               5

<210> SEQ ID NO 200
<211> LENGTH: 8
<212> TYPE: PRT
<213> ORGANISM: Artificial Sequence
<220> FEATURE:
<223> OTHER INFORMATION: Expanded core CM consensus 4

<400> SEQUENCE: 200

Met Leu Arg Ser Gly Trp Arg Ser
1               5

<210> SEQ ID NO 201
<211> LENGTH: 5
<212> TYPE: PRT
<213> ORGANISM: Artificial Sequence
<220> FEATURE:
<223> OTHER INFORMATION: Core CM consensus 5 sequence

<400> SEQUENCE: 201

Val Ser Arg Ser Ala
1               5

<210> SEQ ID NO 202
<211> LENGTH: 6
<212> TYPE: PRT
<213> ORGANISM: Artificial Sequence
<220> FEATURE:
<223> OTHER INFORMATION: Expanded core CM consensus 5 sequence

<400> SEQUENCE: 202

Ile Val Ser Arg Ser Ala
1               5

<210> SEQ ID NO 203
<211> LENGTH: 7
<212> TYPE: PRT
<213> ORGANISM: Artificial Sequence
<220> FEATURE:
<223> OTHER INFORMATION: Expanded core CM consensus 5 sequence

<400> SEQUENCE: 203

Tyr Ile Val Ser Arg Ser Ala
1               5

<210> SEQ ID NO 204
<211> LENGTH: 8
<212> TYPE: PRT
<213> ORGANISM: Artificial Sequence
<220> FEATURE:
<223> OTHER INFORMATION: Expanded core CM consensus 5 sequence

<400> SEQUENCE: 204

Gln Tyr Ile Val Ser Arg Ser Ala

```
1               5

<210> SEQ ID NO 205
<211> LENGTH: 5
<212> TYPE: PRT
<213> ORGANISM: Artificial Sequence
<220> FEATURE:
<223> OTHER INFORMATION: Core CM consensus 6 sequence

<400> SEQUENCE: 205

Ala Leu Arg Ala Pro
1               5

<210> SEQ ID NO 206
<211> LENGTH: 6
<212> TYPE: PRT
<213> ORGANISM: Artificial Sequence
<220> FEATURE:
<223> OTHER INFORMATION: Expanded core CM consensus 6 sequence

<400> SEQUENCE: 206

Arg Ala Leu Arg Ala Pro
1               5

<210> SEQ ID NO 207
<211> LENGTH: 5
<212> TYPE: PRT
<213> ORGANISM: Artificial Sequence
<220> FEATURE:
<223> OTHER INFORMATION: Core CM consensus 7 sequence

<400> SEQUENCE: 207

Pro Ala Gly Arg Arg
1               5

<210> SEQ ID NO 208
<211> LENGTH: 6
<212> TYPE: PRT
<213> ORGANISM: Artificial Sequence
<220> FEATURE:
<223> OTHER INFORMATION: Expanded core CM consensus 7 sequence

<400> SEQUENCE: 208

Pro Ala Gly Arg Arg Ser
1               5

<210> SEQ ID NO 209
<211> LENGTH: 7
<212> TYPE: PRT
<213> ORGANISM: Artificial Sequence
<220> FEATURE:
<223> OTHER INFORMATION: Expanded core CM consensus 7 sequence

<400> SEQUENCE: 209

Pro Ala Gly Arg Arg Ser Leu
1               5

<210> SEQ ID NO 210
<211> LENGTH: 7
<212> TYPE: PRT
<213> ORGANISM: Artificial Sequence
<220> FEATURE:
<223> OTHER INFORMATION: Expanded core CM consensus 7 sequence

<400> SEQUENCE: 210

Val Pro Ala Gly Arg Arg Ser
1               5
```

```
<210> SEQ ID NO 211
<211> LENGTH: 8
<212> TYPE: PRT
<213> ORGANISM: Artificial Sequence
<220> FEATURE:
<223> OTHER INFORMATION: Expanded core CM consensus 7 sequence

<400> SEQUENCE: 211

Val Pro Ala Gly Arg Arg Ser Leu
1               5

<210> SEQ ID NO 212
<211> LENGTH: 5
<212> TYPE: PRT
<213> ORGANISM: Artificial Sequence
<220> FEATURE:
<223> OTHER INFORMATION: Core CM consensus 8 sequence

<400> SEQUENCE: 212

Gly Arg Ser Met Leu
1               5

<210> SEQ ID NO 213
<211> LENGTH: 6
<212> TYPE: PRT
<213> ORGANISM: Artificial Sequence
<220> FEATURE:
<223> OTHER INFORMATION: Expanded core CM consensus 8 sequence

<400> SEQUENCE: 213

Gly Arg Ser Met Leu Leu
1               5

<210> SEQ ID NO 214
<211> LENGTH: 6
<212> TYPE: PRT
<213> ORGANISM: Artificial Sequence
<220> FEATURE:
<223> OTHER INFORMATION: Expanded core CM consensus 8 sequence

<400> SEQUENCE: 214

Gly Arg Ser Met Leu Met
1               5

<210> SEQ ID NO 215
<211> LENGTH: 7
<212> TYPE: PRT
<213> ORGANISM: Artificial Sequence
<220> FEATURE:
<223> OTHER INFORMATION: Expanded core CM consensus 8 sequence

<400> SEQUENCE: 215

Gly Arg Ser Met Leu Leu Gly
1               5

<210> SEQ ID NO 216
<211> LENGTH: 7
<212> TYPE: PRT
<213> ORGANISM: Artificial Sequence
<220> FEATURE:
<223> OTHER INFORMATION: Expanded core CM consensus 8 sequence

<400> SEQUENCE: 216

Gly Arg Ser Met Leu Leu Pro
1               5
```

```
<210> SEQ ID NO 217
<211> LENGTH: 7
<212> TYPE: PRT
<213> ORGANISM: Artificial Sequence
<220> FEATURE:
<223> OTHER INFORMATION: Expanded core CM consensus 8 sequence

<400> SEQUENCE: 217

Gly Arg Ser Met Leu Leu Ser
1               5

<210> SEQ ID NO 218
<211> LENGTH: 7
<212> TYPE: PRT
<213> ORGANISM: Artificial Sequence
<220> FEATURE:
<223> OTHER INFORMATION: Expanded core CM consensus 8 sequence

<400> SEQUENCE: 218

Gly Arg Ser Met Leu Met Gly
1               5

<210> SEQ ID NO 219
<211> LENGTH: 7
<212> TYPE: PRT
<213> ORGANISM: Artificial Sequence
<220> FEATURE:
<223> OTHER INFORMATION: Expanded core CM consensus 8 sequence

<400> SEQUENCE: 219

Gly Arg Ser Met Leu Met Pro
1               5

<210> SEQ ID NO 220
<211> LENGTH: 7
<212> TYPE: PRT
<213> ORGANISM: Artificial Sequence
<220> FEATURE:
<223> OTHER INFORMATION: Expanded core CM consensus 8 sequence

<400> SEQUENCE: 220

Gly Arg Ser Met Leu Met Ser
1               5

<210> SEQ ID NO 221
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 221

Gly Arg Ser Met Leu Leu Gly Gly
1               5

<210> SEQ ID NO 222
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 222

Gly Arg Ser Met Leu Leu Pro Gly
1               5
```

```
<210> SEQ ID NO 223
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 223

Gly Arg Ser Met Leu Leu Ser Gly
1               5

<210> SEQ ID NO 224
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 224

Gly Arg Ser Met Leu Met Gly Gly
1               5

<210> SEQ ID NO 225
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 225

Gly Arg Ser Met Leu Met Pro Gly
1               5

<210> SEQ ID NO 226
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 226

Gly Arg Ser Met Leu Met Ser Gly
1               5

<210> SEQ ID NO 227
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 227

Gly Arg Ser Met Leu Leu Gly Pro
1               5

<210> SEQ ID NO 228
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 228

Gly Arg Ser Met Leu Leu Pro Pro
1               5

<210> SEQ ID NO 229
```

```
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 229

Gly Arg Ser Met Leu Leu Ser Pro
1               5

<210> SEQ ID NO 230
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 230

Gly Arg Ser Met Leu Met Gly Pro
1               5

<210> SEQ ID NO 231
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 231

Gly Arg Ser Met Leu Met Pro Pro
1               5

<210> SEQ ID NO 232
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 232

Gly Arg Ser Met Leu Met Ser Pro
1               5

<210> SEQ ID NO 233
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 233

Gly Arg Ser Met Leu Leu Gly Ser
1               5

<210> SEQ ID NO 234
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 234

Gly Arg Ser Met Leu Leu Pro Ser
1               5

<210> SEQ ID NO 235
<211> LENGTH: 8
```

```
<212> TYPE: PRT
<213> ORGANISM: Artificial Sequence
<220> FEATURE:
<223> OTHER INFORMATION: Expanded core CM consensus 8 sequence

<400> SEQUENCE: 235

Gly Arg Ser Met Leu Leu Ser Ser
1               5

<210> SEQ ID NO 236
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 236

Gly Arg Ser Met Leu Met Gly Ser
1               5

<210> SEQ ID NO 237
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 237

Gly Arg Ser Met Leu Met Pro Ser
1               5

<210> SEQ ID NO 238
<211> LENGTH: 8
<212> TYPE: PRT
<213> ORGANISM: Artificial Sequence
<220> FEATURE:
<223> OTHER INFORMATION: Expanded core CM consensus 8 sequence

<400> SEQUENCE: 238

Gly Arg Ser Met Leu Met Ser Ser
1               5

<210> SEQ ID NO 239
<211> LENGTH: 5
<212> TYPE: PRT
<213> ORGANISM: Artificial Sequence
<220> FEATURE:
<223> OTHER INFORMATION: Core CM consensus 9 sequence

<400> SEQUENCE: 239

Leu Ala Arg Ala Gly
1               5

<210> SEQ ID NO 240
<211> LENGTH: 6
<212> TYPE: PRT
<213> ORGANISM: Artificial Sequence
<220> FEATURE:
<223> OTHER INFORMATION: Expanded core CM consensus 9 sequence

<400> SEQUENCE: 240

Leu Ala Arg Ala Gly Ile
1               5

<210> SEQ ID NO 241
<211> LENGTH: 6
<212> TYPE: PRT
```

```
<213> ORGANISM: Artificial Sequence
<220> FEATURE:
<223> OTHER INFORMATION: Expanded core CM consensus 9 sequence

<400> SEQUENCE: 241

Leu Ala Arg Ala Gly Leu
1               5

<210> SEQ ID NO 242
<211> LENGTH: 7
<212> TYPE: PRT
<213> ORGANISM: Artificial Sequence
<220> FEATURE:
<223> OTHER INFORMATION: Expanded core CM consensus 9 sequence

<400> SEQUENCE: 242

Pro Leu Ala Arg Ala Gly Ile
1               5

<210> SEQ ID NO 243
<211> LENGTH: 7
<212> TYPE: PRT
<213> ORGANISM: Artificial Sequence
<220> FEATURE:
<223> OTHER INFORMATION: Expanded core CM consensus 9 sequence

<400> SEQUENCE: 243

Pro Leu Ala Arg Ala Gly Leu
1               5

<210> SEQ ID NO 244
<211> LENGTH: 8
<212> TYPE: PRT
<213> ORGANISM: Artificial Sequence
<220> FEATURE:
<223> OTHER INFORMATION: Expanded core CM consensus 9 sequence

<400> SEQUENCE: 244

Arg Pro Leu Ala Arg Ala Gly Ile
1               5

<210> SEQ ID NO 245
<211> LENGTH: 8
<212> TYPE: PRT
<213> ORGANISM: Artificial Sequence
<220> FEATURE:
<223> OTHER INFORMATION: Expanded core CM consensus 9 sequence

<400> SEQUENCE: 245

Arg Pro Leu Ala Arg Ala Gly Leu
1               5

<210> SEQ ID NO 246
<211> LENGTH: 5
<212> TYPE: PRT
<213> ORGANISM: Artificial Sequence
<220> FEATURE:
<223> OTHER INFORMATION: Core CM consensus 10 sequence

<400> SEQUENCE: 246

Glu Ser Arg Arg Trp
1               5

<210> SEQ ID NO 247
<211> LENGTH: 6
<212> TYPE: PRT
<213> ORGANISM: Artificial Sequence
```

```
<220> FEATURE:
<223> OTHER INFORMATION: Expanded core CM consensus 10 sequence

<400> SEQUENCE: 247

Glu Ser Arg Arg Trp Met
1               5

<210> SEQ ID NO 248
<211> LENGTH: 7
<212> TYPE: PRT
<213> ORGANISM: Artificial Sequence
<220> FEATURE:
<223> OTHER INFORMATION: Expanded core CM consensus 10 sequence

<400> SEQUENCE: 248

Glu Ser Arg Arg Trp Met Pro
1               5

<210> SEQ ID NO 249
<211> LENGTH: 8
<212> TYPE: PRT
<213> ORGANISM: Artificial Sequence
<220> FEATURE:
<223> OTHER INFORMATION: Expanded core CM consensus 10 sequence

<400> SEQUENCE: 249

Pro Glu Ser Arg Arg Trp Met Pro
1               5

<210> SEQ ID NO 250
<211> LENGTH: 8
<212> TYPE: PRT
<213> ORGANISM: Artificial Sequence
<220> FEATURE:
<223> OTHER INFORMATION: Cleavable moiety

<400> SEQUENCE: 250

Ile Leu Pro Arg Ser Pro Ala Phe
1               5

<210> SEQ ID NO 251
<211> LENGTH: 8
<212> TYPE: PRT
<213> ORGANISM: Artificial Sequence
<220> FEATURE:
<223> OTHER INFORMATION: Cleavable moiety

<400> SEQUENCE: 251

Val Ala Gly Arg Ser Met Arg Pro
1               5

<210> SEQ ID NO 252
<211> LENGTH: 8
<212> TYPE: PRT
<213> ORGANISM: Artificial Sequence
<220> FEATURE:
<223> OTHER INFORMATION: Cleavable moiety

<400> SEQUENCE: 252

Val Val Pro Glu Gly Arg Arg Ser
1               5

<210> SEQ ID NO 253
<211> LENGTH: 8
<212> TYPE: PRT
<213> ORGANISM: Artificial Sequence
<220> FEATURE:
```

```
<223> OTHER INFORMATION: Cleavable moiety

<400> SEQUENCE: 253

Gln Gly Arg Ala Ile Thr Phe Ile
1               5

<210> SEQ ID NO 254
<211> LENGTH: 8
<212> TYPE: PRT
<213> ORGANISM: Artificial Sequence
<220> FEATURE:
<223> OTHER INFORMATION: Cleavable moiety

<400> SEQUENCE: 254

Val Leu Ser Lys Gln Met Ser Phe
1               5

<210> SEQ ID NO 255
<211> LENGTH: 8
<212> TYPE: PRT
<213> ORGANISM: Artificial Sequence
<220> FEATURE:
<223> OTHER INFORMATION: Cleavable moiety

<400> SEQUENCE: 255

Leu Lys Gly Arg Ser Tyr Tyr Tyr
1               5

<210> SEQ ID NO 256
<211> LENGTH: 8
<212> TYPE: PRT
<213> ORGANISM: Artificial Sequence
<220> FEATURE:
<223> OTHER INFORMATION: Cleavable moiety

<400> SEQUENCE: 256

Lys Arg Met Pro Val Gln Phe Leu
1               5

<210> SEQ ID NO 257
<211> LENGTH: 8
<212> TYPE: PRT
<213> ORGANISM: Artificial Sequence
<220> FEATURE:
<223> OTHER INFORMATION: Cleavable moiety

<400> SEQUENCE: 257

Pro Gln His Arg Ile Val Ser Phe
1               5

<210> SEQ ID NO 258
<211> LENGTH: 8
<212> TYPE: PRT
<213> ORGANISM: Artificial Sequence
<220> FEATURE:
<223> OTHER INFORMATION: Cleavable moiety

<400> SEQUENCE: 258

Tyr Lys Lys Phe Val Gly Ser Leu
1               5

<210> SEQ ID NO 259
<211> LENGTH: 8
<212> TYPE: PRT
<213> ORGANISM: Artificial Sequence
<220> FEATURE:
<223> OTHER INFORMATION: Cleavable moiety
```

```
<400> SEQUENCE: 259

His Met Met Gln Tyr Ala Arg His
1               5

<210> SEQ ID NO 260
<211> LENGTH: 8
<212> TYPE: PRT
<213> ORGANISM: Artificial Sequence
<220> FEATURE:
<223> OTHER INFORMATION: Cleavable moiety

<400> SEQUENCE: 260

Ile Pro Phe Ser Trp Ser Arg Phe
1               5

<210> SEQ ID NO 261
<211> LENGTH: 8
<212> TYPE: PRT
<213> ORGANISM: Artificial Sequence
<220> FEATURE:
<223> OTHER INFORMATION: Cleavable moiety

<400> SEQUENCE: 261

Leu Ser Gln Ala Arg Trp Arg Lys
1               5

<210> SEQ ID NO 262
<211> LENGTH: 8
<212> TYPE: PRT
<213> ORGANISM: Artificial Sequence
<220> FEATURE:
<223> OTHER INFORMATION: Cleavable moiety

<400> SEQUENCE: 262

Asp Ile Ser His Trp Arg Arg Ser
1               5

<210> SEQ ID NO 263
<211> LENGTH: 8
<212> TYPE: PRT
<213> ORGANISM: Artificial Sequence
<220> FEATURE:
<223> OTHER INFORMATION: Cleavable moiety

<400> SEQUENCE: 263

Arg Lys Thr Val Gln His Trp Trp
1               5

<210> SEQ ID NO 264
<211> LENGTH: 8
<212> TYPE: PRT
<213> ORGANISM: Artificial Sequence
<220> FEATURE:
<223> OTHER INFORMATION: Cleavable moiety

<400> SEQUENCE: 264

Arg Phe Tyr Arg Asn Gln Phe Phe
1               5

<210> SEQ ID NO 265
<211> LENGTH: 8
<212> TYPE: PRT
<213> ORGANISM: Artificial Sequence
<220> FEATURE:
<223> OTHER INFORMATION: Cleavable moiety
```

```
<400> SEQUENCE: 265

Arg Ser Leu Val Phe Ala Pro Ile
1               5

<210> SEQ ID NO 266
<211> LENGTH: 8
<212> TYPE: PRT
<213> ORGANISM: Artificial Sequence
<220> FEATURE:
<223> OTHER INFORMATION: Cleavable moiety

<400> SEQUENCE: 266

Arg Ser Pro Ser Arg Leu Lys Cys
1               5

<210> SEQ ID NO 267
<211> LENGTH: 8
<212> TYPE: PRT
<213> ORGANISM: Artificial Sequence
<220> FEATURE:
<223> OTHER INFORMATION: Cleavable moiety

<400> SEQUENCE: 267

Arg Lys Met Pro Asn Ile Thr Val
1               5

<210> SEQ ID NO 268
<211> LENGTH: 8
<212> TYPE: PRT
<213> ORGANISM: Artificial Sequence
<220> FEATURE:
<223> OTHER INFORMATION: uPA and/or Matriptase Cleavable Core CM
      Consensus Sequence 11
<220> FEATURE:
<221> NAME/KEY: misc_feature
<222> LOCATION: (1)..(1)
<223> OTHER INFORMATION: Xaa may be Asp, Ile, Leu, Arg, Ser or Val
<220> FEATURE:
<221> NAME/KEY: misc_feature
<222> LOCATION: (2)..(2)
<223> OTHER INFORMATION: Xaa may be Cys, Gly, His, Ile, Lys, Asn, Arg,
      Ser, Thr or Tyr
<220> FEATURE:
<221> NAME/KEY: misc_feature
<222> LOCATION: (3)..(3)
<223> OTHER INFORMATION: Xaa may be Asp, Gly or Ser
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Phe or Ser
<220> FEATURE:
<221> NAME/KEY: misc_feature
<222> LOCATION: (6)..(6)
<223> OTHER INFORMATION: Xaa may be Ala, Asp, Gly, His, Ile, Leu, Thr
      or Val
<220> FEATURE:
<221> NAME/KEY: misc_feature
<222> LOCATION: (7)..(7)
<223> OTHER INFORMATION: Xaa may be His, Ile, Asn, Arg, Ser or Thr
<220> FEATURE:
<221> NAME/KEY: misc_feature
<222> LOCATION: (8)..(8)
<223> OTHER INFORMATION: Xaa may be His, Leu, Met, Arg, Val or Tyr

<400> SEQUENCE: 268

Xaa Xaa Xaa Xaa Xaa Xaa Xaa Xaa
1               5
```

```
<210> SEQ ID NO 269
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 11
<220> FEATURE:
<221> NAME/KEY: misc_feature
<222> LOCATION: (1)..(1)
<223> OTHER INFORMATION: Xaa may be Asp, Leu, Ser or Val
<220> FEATURE:
<221> NAME/KEY: misc_feature
<222> LOCATION: (2)..(2)
<223> OTHER INFORMATION: Xaa may be Cys, Gly, Asn, Arg, Ser or Thr
<220> FEATURE:
<221> NAME/KEY: misc_feature
<222> LOCATION: (3)..(3)
<223> OTHER INFORMATION: Xaa may be Asp, Gly or Ser
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Phe or Ser
<220> FEATURE:
<221> NAME/KEY: misc_feature
<222> LOCATION: (6)..(6)
<223> OTHER INFORMATION: Xaa may be Ala, Gly, Ile, Leu, Thr or Val
<220> FEATURE:
<221> NAME/KEY: misc_feature
<222> LOCATION: (7)..(7)
<223> OTHER INFORMATION: Xaa may be His, Ile, Asn or Ser
<220> FEATURE:
<221> NAME/KEY: misc_feature
<222> LOCATION: (8)..(8)
<223> OTHER INFORMATION: Xaa may be His, Met, Arg or Tyr

<400> SEQUENCE: 269

Xaa Xaa Xaa Xaa Xaa Xaa Xaa Xaa
1               5

<210> SEQ ID NO 270
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 11
<220> FEATURE:
<221> NAME/KEY: misc_feature
<222> LOCATION: (1)..(1)
<223> OTHER INFORMATION: Xaa may be Leu or Val
<220> FEATURE:
<221> NAME/KEY: misc_feature
<222> LOCATION: (2)..(2)
<223> OTHER INFORMATION: Xaa may be Gly, His, Lys, Asn, Ser or Thr
<220> FEATURE:
<221> NAME/KEY: misc_feature
<222> LOCATION: (3)..(3)
<223> OTHER INFORMATION: Xaa may be Gly
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Ala or Asp
<220> FEATURE:
```

```
<221> NAME/KEY: misc_feature
<222> LOCATION: (7)..(7)
<223> OTHER INFORMATION: Xaa may be Asn or Arg
<220> FEATURE:
<221> NAME/KEY: misc_feature
<222> LOCATION: (8)..(8)
<223> OTHER INFORMATION: Xaa may be His or Tyr

<400> SEQUENCE: 270

Xaa Xaa Xaa Xaa Xaa Xaa Xaa Xaa
1               5

<210> SEQ ID NO 271
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 11
<220> FEATURE:
<221> NAME/KEY: misc_feature
<222> LOCATION: (1)..(1)
<223> OTHER INFORMATION: Xaa may be Leu or Val
<220> FEATURE:
<221> NAME/KEY: misc_feature
<222> LOCATION: (2)..(2)
<223> OTHER INFORMATION: Xaa may be Gly, His, Asn or Ser
<220> FEATURE:
<221> NAME/KEY: misc_feature
<222> LOCATION: (3)..(3)
<223> OTHER INFORMATION: Xaa may be Gly
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Ala or Asp
<220> FEATURE:
<221> NAME/KEY: misc_feature
<222> LOCATION: (7)..(7)
<223> OTHER INFORMATION: Xaa may be Asn
<220> FEATURE:
<221> NAME/KEY: misc_feature
<222> LOCATION: (8)..(8)
<223> OTHER INFORMATION: Xaa may be His

<400> SEQUENCE: 271

Xaa Xaa Xaa Xaa Xaa Xaa Xaa Xaa
1               5

<210> SEQ ID NO 272
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 11
<220> FEATURE:
<221> NAME/KEY: misc_feature
<222> LOCATION: (1)..(1)
<223> OTHER INFORMATION: Xaa may be Leu or Val
<220> FEATURE:
<221> NAME/KEY: misc_feature
<222> LOCATION: (2)..(2)
<223> OTHER INFORMATION: Xaa may be Ser
<220> FEATURE:
<221> NAME/KEY: misc_feature
<222> LOCATION: (3)..(3)
<223> OTHER INFORMATION: Xaa may be Gly
```

```
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Ala or Asp
<220> FEATURE:
<221> NAME/KEY: misc_feature
<222> LOCATION: (7)..(7)
<223> OTHER INFORMATION: Xaa may be Asn
<220> FEATURE:
<221> NAME/KEY: misc_feature
<222> LOCATION: (8)..(8)
<223> OTHER INFORMATION: Xaa may be His

<400> SEQUENCE: 272

Xaa Xaa Xaa Xaa Xaa Xaa Xaa Xaa
1               5

<210> SEQ ID NO 273
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 11
<220> FEATURE:
<221> NAME/KEY: misc_feature
<222> LOCATION: (1)..(1)
<223> OTHER INFORMATION: Xaa may be Leu or Val
<220> FEATURE:
<221> NAME/KEY: misc_feature
<222> LOCATION: (2)..(2)
<223> OTHER INFORMATION: Xaa may be Gly or Ser
<220> FEATURE:
<221> NAME/KEY: misc_feature
<222> LOCATION: (3)..(3)
<223> OTHER INFORMATION: Xaa may be Gly
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Ala
<220> FEATURE:
<221> NAME/KEY: misc_feature
<222> LOCATION: (7)..(7)
<223> OTHER INFORMATION: Xaa may be Asn
<220> FEATURE:
<221> NAME/KEY: misc_feature
<222> LOCATION: (8)..(8)
<223> OTHER INFORMATION: Xaa may be His

<400> SEQUENCE: 273

Xaa Xaa Xaa Xaa Xaa Xaa Xaa Xaa
1               5

<210> SEQ ID NO 274
<211> LENGTH: 8
<212> TYPE: PRT
<213> ORGANISM: Artificial Sequence
<220> FEATURE:
<223> OTHER INFORMATION: uPA and/or Matriptase Cleavable Core CM
```

```
        Consensus Sequence 12
<220> FEATURE:
<221> NAME/KEY: misc_feature
<222> LOCATION: (1)..(1)
<223> OTHER INFORMATION: Xaa may be Asp, Ile, Leu, Arg, Ser or Val
<220> FEATURE:
<221> NAME/KEY: misc_feature
<222> LOCATION: (2)..(2)
<223> OTHER INFORMATION: Xaa may be Cys, Gly, His, Ile, Lys, Asn, Arg,
      Ser, Thr or Tyr
<220> FEATURE:
<221> NAME/KEY: misc_feature
<222> LOCATION: (3)..(3)
<223> OTHER INFORMATION: Xaa may be Asp, Gly or Ser
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Phe or Ser
<220> FEATURE:
<221> NAME/KEY: misc_feature
<222> LOCATION: (6)..(6)
<223> OTHER INFORMATION: Xaa may be Ala, Asp, Gly, His, Ile, Leu, Thr
      or Val
<220> FEATURE:
<221> NAME/KEY: misc_feature
<222> LOCATION: (7)..(7)
<223> OTHER INFORMATION: Xaa may be His, Ile, Asn, Arg, Ser or Thr
<220> FEATURE:
<221> NAME/KEY: misc_feature
<222> LOCATION: (8)..(8)
<223> OTHER INFORMATION: Xaa may be His, Leu, Met, Arg, Val or Tyr

<400> SEQUENCE: 274

Xaa Xaa Xaa Xaa Xaa Xaa Xaa Xaa
1               5

<210> SEQ ID NO 275
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 12
<220> FEATURE:
<221> NAME/KEY: misc_feature
<222> LOCATION: (1)..(1)
<223> OTHER INFORMATION: Xaa may be Leu
<220> FEATURE:
<221> NAME/KEY: misc_feature
<222> LOCATION: (2)..(2)
<223> OTHER INFORMATION: Xaa may be Asn, Ser or Thr
<220> FEATURE:
<221> NAME/KEY: misc_feature
<222> LOCATION: (3)..(3)
<223> OTHER INFORMATION: Xaa may be Gly
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Ala, Asp or His
<220> FEATURE:
<221> NAME/KEY: misc_feature
<222> LOCATION: (7)..(7)
<223> OTHER INFORMATION: Xaa may be Asn or Arg
<220> FEATURE:
<221> NAME/KEY: misc_feature
```

```
<222> LOCATION: (8)..(8)
<223> OTHER INFORMATION: Xaa may be His, Leu, Val or Tyr

<400> SEQUENCE: 275

Xaa Xaa Xaa Xaa Xaa Xaa Xaa Xaa
1               5

<210> SEQ ID NO 276
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 12
<220> FEATURE:
<221> NAME/KEY: misc_feature
<222> LOCATION: (1)..(1)
<223> OTHER INFORMATION: Xaa may be Leu or Val
<220> FEATURE:
<221> NAME/KEY: misc_feature
<222> LOCATION: (2)..(2)
<223> OTHER INFORMATION: Xaa may be Gly, His, Lys, Asn, Ser or Thr
<220> FEATURE:
<221> NAME/KEY: misc_feature
<222> LOCATION: (3)..(3)
<223> OTHER INFORMATION: Xaa may be Gly
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Ala or Asp
<220> FEATURE:
<221> NAME/KEY: misc_feature
<222> LOCATION: (7)..(7)
<223> OTHER INFORMATION: Xaa may be Asn or Arg
<220> FEATURE:
<221> NAME/KEY: misc_feature
<222> LOCATION: (8)..(8)
<223> OTHER INFORMATION: Xaa may be His or Tyr

<400> SEQUENCE: 276

Xaa Xaa Xaa Xaa Xaa Xaa Xaa Xaa
1               5

<210> SEQ ID NO 277
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 12
<220> FEATURE:
<221> NAME/KEY: misc_feature
<222> LOCATION: (1)..(1)
<223> OTHER INFORMATION: Xaa may be Leu or Val
<220> FEATURE:
<221> NAME/KEY: misc_feature
<222> LOCATION: (2)..(2)
<223> OTHER INFORMATION: Xaa may be Gly, His, Asn or Ser
<220> FEATURE:
<221> NAME/KEY: misc_feature
<222> LOCATION: (3)..(3)
<223> OTHER INFORMATION: Xaa may be Gly
<220> FEATURE:
<221> NAME/KEY: misc_feature
<222> LOCATION: (4)..(4)
<223> OTHER INFORMATION: Xaa may be Arg
<220> FEATURE:
```

```
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Ala or Asp
<220> FEATURE:
<221> NAME/KEY: misc_feature
<222> LOCATION: (7)..(7)
<223> OTHER INFORMATION: Xaa may be Asn
<220> FEATURE:
<221> NAME/KEY: misc_feature
<222> LOCATION: (8)..(8)
<223> OTHER INFORMATION: Xaa may be His

<400> SEQUENCE: 277

Xaa Xaa Xaa Xaa Xaa Xaa Xaa Xaa
1               5

<210> SEQ ID NO 278
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 12
<220> FEATURE:
<221> NAME/KEY: misc_feature
<222> LOCATION: (1)..(1)
<223> OTHER INFORMATION: Xaa may be Leu or Val
<220> FEATURE:
<221> NAME/KEY: misc_feature
<222> LOCATION: (2)..(2)
<223> OTHER INFORMATION: Xaa may be Ser
<220> FEATURE:
<221> NAME/KEY: misc_feature
<222> LOCATION: (3)..(3)
<223> OTHER INFORMATION: Xaa may be Gly
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Ala or Asp
<220> FEATURE:
<221> NAME/KEY: misc_feature
<222> LOCATION: (7)..(7)
<223> OTHER INFORMATION: Xaa may be Asn
<220> FEATURE:
<221> NAME/KEY: misc_feature
<222> LOCATION: (8)..(8)
<223> OTHER INFORMATION: Xaa may be His

<400> SEQUENCE: 278

Xaa Xaa Xaa Xaa Xaa Xaa Xaa Xaa
1               5

<210> SEQ ID NO 279
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 12
<220> FEATURE:
<221> NAME/KEY: misc_feature
<222> LOCATION: (1)..(1)
<223> OTHER INFORMATION: Xaa may be Leu
```

```
-continued

<220> FEATURE:
<221> NAME/KEY: misc_feature
<222> LOCATION: (2)..(2)
<223> OTHER INFORMATION: Xaa may be Asn or Ser
<220> FEATURE:
<221> NAME/KEY: misc_feature
<222> LOCATION: (3)..(3)
<223> OTHER INFORMATION: Xaa may be Gly
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Ala or Asp
<220> FEATURE:
<221> NAME/KEY: misc_feature
<222> LOCATION: (7)..(7)
<223> OTHER INFORMATION: Xaa may be Asn or Arg
<220> FEATURE:
<221> NAME/KEY: misc_feature
<222> LOCATION: (8)..(8)
<223> OTHER INFORMATION: Xaa may be His

<400> SEQUENCE: 279

Xaa Xaa Xaa Xaa Xaa Xaa Xaa Xaa
 1               5

<210> SEQ ID NO 280
<211> LENGTH: 8
<212> TYPE: PRT
<213> ORGANISM: Artificial Sequence
<220> FEATURE:
<223> OTHER INFORMATION: uPA and/or Matriptase Cleavable Core CM
      Consensus Sequence 13
<220> FEATURE:
<221> NAME/KEY: misc_feature
<222> LOCATION: (1)..(1)
<223> OTHER INFORMATION: Xaa may be Cys, Gly, His, Leu, Pro, Arg, Ser,
      Thr or Val
<220> FEATURE:
<221> NAME/KEY: misc_feature
<222> LOCATION: (2)..(2)
<223> OTHER INFORMATION: Xaa may be Ile, Leu, Met, Asn, Ser, Thr, Val
      or Tyr
<220> FEATURE:
<221> NAME/KEY: misc_feature
<222> LOCATION: (3)..(3)
<223> OTHER INFORMATION: Xaa may be Ala, Asp, Glu, Gly, Lys, Arg or Val
<220> FEATURE:
<221> NAME/KEY: misc_feature
<222> LOCATION: (4)..(4)
<223> OTHER INFORMATION: Xaa may be Ala, Cys, Gly, His, Leu, Arg, Ser,
      Thr or Val
<220> FEATURE:
<221> NAME/KEY: misc_feature
<222> LOCATION: (5)..(5)
<223> OTHER INFORMATION: Xaa may be Cys, Phe, Pro, Ser, Thr, Val or Tyr
<220> FEATURE:
<221> NAME/KEY: misc_feature
<222> LOCATION: (6)..(6)
<223> OTHER INFORMATION: Xaa may be Ala, Asp, Glu, Gly, His, Asn, Thr,
      Val or Tyr
<220> FEATURE:
<221> NAME/KEY: misc_feature
<222> LOCATION: (7)..(7)
<223> OTHER INFORMATION: Xaa may be Asp, Glu, His, Lys, Asn, Gln, Arg,
      Ser, Thr
<220> FEATURE:
<221> NAME/KEY: misc_feature
<222> LOCATION: (8)..(8)
<223> OTHER INFORMATION: Xaa may be His, Leu, Asn, Arg, Ser, Val or Tyr
```

<400> SEQUENCE: 280

Xaa Xaa Xaa Xaa Xaa Xaa Xaa Xaa
1               5

<210> SEQ ID NO 281
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 13
<220> FEATURE:
<221> NAME/KEY: misc_feature
<222> LOCATION: (1)..(1)
<223> OTHER INFORMATION: Xaa may be Cys or Arg
<220> FEATURE:
<221> NAME/KEY: misc_feature
<222> LOCATION: (2)..(2)
<223> OTHER INFORMATION: Xaa may be Ile, Ser or Tyr
<220> FEATURE:
<221> NAME/KEY: misc_feature
<222> LOCATION: (3)..(3)
<223> OTHER INFORMATION: Xaa may be Gly or Arg
<220> FEATURE:
<221> NAME/KEY: misc_feature
<222> LOCATION: (4)..(4)
<223> OTHER INFORMATION: Xaa may be Arg or Ser
<220> FEATURE:
<221> NAME/KEY: misc_feature
<222> LOCATION: (5)..(5)
<223> OTHER INFORMATION: Xaa may be Phe, Pro or Ser
<220> FEATURE:
<221> NAME/KEY: misc_feature
<222> LOCATION: (6)..(6)
<223> OTHER INFORMATION: Xaa may be Asp, Gly or His
<220> FEATURE:
<221> NAME/KEY: misc_feature
<222> LOCATION: (7)..(7)
<223> OTHER INFORMATION: Xaa may be His or Asn
<220> FEATURE:
<221> NAME/KEY: misc_feature
<222> LOCATION: (8)..(8)
<223> OTHER INFORMATION: Xaa may be His

<400> SEQUENCE: 281

Xaa Xaa Xaa Xaa Xaa Xaa Xaa Xaa
1               5

<210> SEQ ID NO 282
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 13
<220> FEATURE:
<221> NAME/KEY: misc_feature
<222> LOCATION: (1)..(1)
<223> OTHER INFORMATION: Xaa may be Arg
<220> FEATURE:
<221> NAME/KEY: misc_feature
<222> LOCATION: (2)..(2)
<223> OTHER INFORMATION: Xaa may be Ile
<220> FEATURE:
<221> NAME/KEY: misc_feature
<222> LOCATION: (3)..(3)
<223> OTHER INFORMATION: Xaa may be Gly
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)

```
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Asp or His
<220> FEATURE:
<221> NAME/KEY: misc_feature
<222> LOCATION: (7)..(7)
<223> OTHER INFORMATION: Xaa may be Asn
<220> FEATURE:
<221> NAME/KEY: misc_feature
<222> LOCATION: (8)..(8)
<223> OTHER INFORMATION: Xaa may be His

<400> SEQUENCE: 282

Xaa Xaa Xaa Xaa Xaa Xaa Xaa Xaa
1               5

<210> SEQ ID NO 283
<211> LENGTH: 8
<212> TYPE: PRT
<213> ORGANISM: Artificial Sequence
<220> FEATURE:
<223> OTHER INFORMATION: uPA and/or Matriptase Cleavable Core CM
      Consensus Sequence 14
<220> FEATURE:
<221> NAME/KEY: misc_feature
<222> LOCATION: (1)..(1)
<223> OTHER INFORMATION: Xaa may be Leu, Arg, Thr or Val
<220> FEATURE:
<221> NAME/KEY: misc_feature
<222> LOCATION: (2)..(2)
<223> OTHER INFORMATION: Xaa may be Glu, Gly, Ile, Asn, Arg or Ser
<220> FEATURE:
<221> NAME/KEY: misc_feature
<222> LOCATION: (3)..(3)
<223> OTHER INFORMATION: Xaa may be Gly
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Pro or Ser
<220> FEATURE:
<221> NAME/KEY: misc_feature
<222> LOCATION: (6)..(6)
<223> OTHER INFORMATION: Xaa may be Ala, Gly or Tyr
<220> FEATURE:
<221> NAME/KEY: misc_feature
<222> LOCATION: (7)..(7)
<223> OTHER INFORMATION: Xaa may be Glu, Lys, Asn or Tyr
<220> FEATURE:
<221> NAME/KEY: misc_feature
<222> LOCATION: (8)..(8)
<223> OTHER INFORMATION: Xaa may be Pro, Gln or Ser

<400> SEQUENCE: 283

Xaa Xaa Xaa Xaa Xaa Xaa Xaa Xaa
1               5

<210> SEQ ID NO 284
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 14
<220> FEATURE:
<221> NAME/KEY: misc_feature
<222> LOCATION: (1)..(1)
<223> OTHER INFORMATION: Xaa may be Leu or Thr
<220> FEATURE:
<221> NAME/KEY: misc_feature
```

```
<222> LOCATION: (2)..(2)
<223> OTHER INFORMATION: Xaa may be Glu, Arg or Ser
<220> FEATURE:
<221> NAME/KEY: misc_feature
<222> LOCATION: (3)..(3)
<223> OTHER INFORMATION: Xaa may be Gly
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Pro or Ser
<220> FEATURE:
<221> NAME/KEY: misc_feature
<222> LOCATION: (6)..(6)
<223> OTHER INFORMATION: Xaa may be Ala, Gly or Tyr
<220> FEATURE:
<221> NAME/KEY: misc_feature
<222> LOCATION: (7)..(7)
<223> OTHER INFORMATION: Xaa may be Glu or Asn
<220> FEATURE:
<221> NAME/KEY: misc_feature
<222> LOCATION: (8)..(8)
<223> OTHER INFORMATION: Xaa may be Pro, Gln or Ser

<400> SEQUENCE: 284

Xaa Xaa Xaa Xaa Xaa Xaa Xaa Xaa
1               5

<210> SEQ ID NO 285
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 14
<220> FEATURE:
<221> NAME/KEY: misc_feature
<222> LOCATION: (1)..(1)
<223> OTHER INFORMATION: Xaa may be Leu, Thr or Val
<220> FEATURE:
<221> NAME/KEY: misc_feature
<222> LOCATION: (2)..(2)
<223> OTHER INFORMATION: Xaa may be Arg or Ser
<220> FEATURE:
<221> NAME/KEY: misc_feature
<222> LOCATION: (3)..(3)
<223> OTHER INFORMATION: Xaa may be Gly
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Ala or Gly
<220> FEATURE:
<221> NAME/KEY: misc_feature
<222> LOCATION: (7)..(7)
<223> OTHER INFORMATION: Xaa may be Lys, Asn or Tyr
<220> FEATURE:
<221> NAME/KEY: misc_feature
<222> LOCATION: (8)..(8)
<223> OTHER INFORMATION: Xaa may be Pro

<400> SEQUENCE: 285

Xaa Xaa Xaa Xaa Xaa Xaa Xaa Xaa
1               5
```

```
<210> SEQ ID NO 286
<211> LENGTH: 8
<212> TYPE: PRT
<213> ORGANISM: Artificial Sequence
<220> FEATURE:
<223> OTHER INFORMATION: uPA and/or Matriptase Cleavable Subgenus of
      Core CM Consensus 14
<220> FEATURE:
<221> NAME/KEY: misc_feature
<222> LOCATION: (1)..(1)
<223> OTHER INFORMATION: Xaa may be Leu or Thr
<220> FEATURE:
<221> NAME/KEY: misc_feature
<222> LOCATION: (2)..(2)
<223> OTHER INFORMATION: Xaa may be Ser
<220> FEATURE:
<221> NAME/KEY: misc_feature
<222> LOCATION: (3)..(3)
<223> OTHER INFORMATION: Xaa may be Gly
<220> FEATURE:
<221> NAME/KEY: misc_feature
<222> LOCATION: (4)..(4)
<223> OTHER INFORMATION: Xaa may be Arg
<220> FEATURE:
<221> NAME/KEY: misc_feature
<222> LOCATION: (5)..(5)
<223> OTHER INFORMATION: Xaa may be Ser
<220> FEATURE:
<221> NAME/KEY: misc_feature
<222> LOCATION: (6)..(6)
<223> OTHER INFORMATION: Xaa may be Ala or Gly
<220> FEATURE:
<221> NAME/KEY: misc_feature
<222> LOCATION: (7)..(7)
<223> OTHER INFORMATION: Xaa may be Asn
<220> FEATURE:
<221> NAME/KEY: misc_feature
<222> LOCATION: (8)..(8)
<223> OTHER INFORMATION: Xaa may be Pro

<400> SEQUENCE: 286

Xaa Xaa Xaa Xaa Xaa Xaa Xaa Xaa
1               5

<210> SEQ ID NO 287
<211> LENGTH: 12
<212> TYPE: PRT
<213> ORGANISM: Artificial Sequence
<220> FEATURE:
<223> OTHER INFORMATION: uPA and/or Matriptase Cleavable Expanded Core
      CM Consensus Sequence 11
<220> FEATURE:
<221> NAME/KEY: misc_feature
<222> LOCATION: (1)..(1)
<223> OTHER INFORMATION: Xaa may be Ala, Asp, Gly, Lys, Leu, Asn, Arg,
      Ser, Thr or Val
<220> FEATURE:
<221> NAME/KEY: misc_feature
<222> LOCATION: (2)..(2)
<223> OTHER INFORMATION: Xaa may be Ala, Gly, Lys, Met, Pro, Gln, Arg,
      Ser or Thr
<220> FEATURE:
<221> NAME/KEY: misc_feature
<222> LOCATION: (3)..(3)
<223> OTHER INFORMATION: Xaa may be Asp, Ile, Leu, Arg, Ser or Val
<220> FEATURE:
<221> NAME/KEY: misc_feature
<222> LOCATION: (4)..(4)
<223> OTHER INFORMATION: Xaa may be Cys, Gly, His, Ile, Lys, Asn, Arg,
      Ser, Thr or Tyr
<220> FEATURE:
<221> NAME/KEY: misc_feature
<222> LOCATION: (5)..(5)
<223> OTHER INFORMATION: Xaa may be Asp, Gly or Ser
<220> FEATURE:
<221> NAME/KEY: misc_feature
<222> LOCATION: (6)..(6)
```

```
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Phe or Ser
<220> FEATURE:
<221> NAME/KEY: misc_feature
<222> LOCATION: (8)..(8)
<223> OTHER INFORMATION: Xaa may be Ala, Asp, Gly, His, Ile, Leu, Thr
      or Val
<220> FEATURE:
<221> NAME/KEY: misc_feature
<222> LOCATION: (9)..(9)
<223> OTHER INFORMATION: Xaa may be His, Ile, Asn, Arg, Ser or Thr
<220> FEATURE:
<221> NAME/KEY: misc_feature
<222> LOCATION: (10)..(10)
<223> OTHER INFORMATION: Xaa may be His, Leu, Met, Arg, Val or Tyr
<220> FEATURE:
<221> NAME/KEY: misc_feature
<222> LOCATION: (11)..(11)
<223> OTHER INFORMATION: Xaa may be Glu, Gly, Lys, Asn, Gln, Arg or Val
<220> FEATURE:
<221> NAME/KEY: misc_feature
<222> LOCATION: (12)..(12)
<223> OTHER INFORMATION: Xaa may be Ala, Gly, Lys, Leu, Gln, Arg or Ser

<400> SEQUENCE: 287

Xaa Xaa Xaa Xaa Xaa Xaa Xaa Xaa Xaa Xaa Xaa Xaa
1               5                   10

<210> SEQ ID NO 288
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 11
<220> FEATURE:
<221> NAME/KEY: misc_feature
<222> LOCATION: (1)..(1)
<223> OTHER INFORMATION: Xaa may be Ala, Asp, Gly, Lys, Asn, Ser or Val
<220> FEATURE:
<221> NAME/KEY: misc_feature
<222> LOCATION: (2)..(2)
<223> OTHER INFORMATION: Xaa may be Ala, Gly, Lys, Met, Arg, Ser or Thr
<220> FEATURE:
<221> NAME/KEY: misc_feature
<222> LOCATION: (3)..(3)
<223> OTHER INFORMATION: Xaa may be Asp, Leu, Ser or Val
<220> FEATURE:
<221> NAME/KEY: misc_feature
<222> LOCATION: (4)..(4)
<223> OTHER INFORMATION: Xaa may be Cys, Gly, Asn, Arg, Ser or Thr
<220> FEATURE:
<221> NAME/KEY: misc_feature
<222> LOCATION: (5)..(5)
<223> OTHER INFORMATION: Xaa may be Asp, Gly or Ser
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Phe or Ser
<220> FEATURE:
<221> NAME/KEY: misc_feature
<222> LOCATION: (8)..(8)
<223> OTHER INFORMATION: Xaa may be Ala, Gly, Ile, Leu, Thr or Val
<220> FEATURE:
<221> NAME/KEY: misc_feature
<222> LOCATION: (9)..(9)
<223> OTHER INFORMATION: Xaa may be His, Ile, Asn or Ser
<220> FEATURE:
<221> NAME/KEY: misc_feature
<222> LOCATION: (10)..(10)
```

```
<223> OTHER INFORMATION: Xaa may be His, Met, Arg or Tyr
<220> FEATURE:
<221> NAME/KEY: misc_feature
<222> LOCATION: (11)..(11)
<223> OTHER INFORMATION: Xaa may be Glu, Gly, Lys or Arg
<220> FEATURE:
<221> NAME/KEY: misc_feature
<222> LOCATION: (12)..(12)
<223> OTHER INFORMATION: Xaa may be Lys, Arg or Ser

<400> SEQUENCE: 288

Xaa Xaa Xaa Xaa Xaa Xaa Xaa Xaa Xaa Xaa Xaa Xaa
1               5                   10

<210> SEQ ID NO 289
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 11
<220> FEATURE:
<221> NAME/KEY: misc_feature
<222> LOCATION: (1)..(1)
<223> OTHER INFORMATION: Xaa may be Ala, Asp, Gly, Asn, Arg or Thr
<220> FEATURE:
<221> NAME/KEY: misc_feature
<222> LOCATION: (2)..(2)
<223> OTHER INFORMATION: Xaa may be Gly, Lys, Pro, Arg, Ser or Thr
<220> FEATURE:
<221> NAME/KEY: misc_feature
<222> LOCATION: (3)..(3)
<223> OTHER INFORMATION: Xaa may be Leu or Val
<220> FEATURE:
<221> NAME/KEY: misc_feature
<222> LOCATION: (4)..(4)
<223> OTHER INFORMATION: Xaa may be Gly, His, Lys, Asn, Ser or Thr
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
<222> LOCATION: (8)..(8)
<223> OTHER INFORMATION: Xaa may be Ala or Asp
<220> FEATURE:
<221> NAME/KEY: misc_feature
<222> LOCATION: (9)..(9)
<223> OTHER INFORMATION: Xaa may be Asn or Arg
<220> FEATURE:
<221> NAME/KEY: misc_feature
<222> LOCATION: (10)..(10)
<223> OTHER INFORMATION: Xaa may be His or Tyr
<220> FEATURE:
<221> NAME/KEY: misc_feature
<222> LOCATION: (11)..(11)
<223> OTHER INFORMATION: Xaa may be Glu, Lys, Asn, Gln or Arg
<220> FEATURE:
<221> NAME/KEY: misc_feature
<222> LOCATION: (12)..(12)
<223> OTHER INFORMATION: Xaa may be Ala, Lys or Arg

<400> SEQUENCE: 289

Xaa Xaa Xaa Xaa Xaa Xaa Xaa Xaa Xaa Xaa Xaa Xaa
1               5                   10

<210> SEQ ID NO 290
```

```
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 11
<220> FEATURE:
<221> NAME/KEY: misc_feature
<222> LOCATION: (1)..(1)
<223> OTHER INFORMATION: Xaa may be Ala, Asp, Gly or Arg
<220> FEATURE:
<221> NAME/KEY: misc_feature
<222> LOCATION: (2)..(2)
<223> OTHER INFORMATION: Xaa may be Lys, Pro, Arg or Thr
<220> FEATURE:
<221> NAME/KEY: misc_feature
<222> LOCATION: (3)..(3)
<223> OTHER INFORMATION: Xaa may be Leu or Val
<220> FEATURE:
<221> NAME/KEY: misc_feature
<222> LOCATION: (4)..(4)
<223> OTHER INFORMATION: Xaa may be Gly, His, Asn or Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
<222> LOCATION: (8)..(8)
<223> OTHER INFORMATION: Xaa may be Ala or Asp
<220> FEATURE:
<221> NAME/KEY: misc_feature
<222> LOCATION: (9)..(9)
<223> OTHER INFORMATION: Xaa may be Asn
<220> FEATURE:
<221> NAME/KEY: misc_feature
<222> LOCATION: (10)..(10)
<223> OTHER INFORMATION: Xaa may be His
<220> FEATURE:
<221> NAME/KEY: misc_feature
<222> LOCATION: (11)..(11)
<223> OTHER INFORMATION: Xaa may be Lys, Asn or Arg
<220> FEATURE:
<221> NAME/KEY: misc_feature
<222> LOCATION: (12)..(12)
<223> OTHER INFORMATION: Xaa may be Ala, Lys or Arg

<400> SEQUENCE: 290

Xaa Xaa Xaa Xaa Xaa Xaa Xaa Xaa Xaa Xaa Xaa Xaa
1               5                   10

<210> SEQ ID NO 291
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 11
<220> FEATURE:
<221> NAME/KEY: misc_feature
<222> LOCATION: (1)..(1)
<223> OTHER INFORMATION: Xaa may be Ala or Asp
<220> FEATURE:
<221> NAME/KEY: misc_feature
<222> LOCATION: (2)..(2)
<223> OTHER INFORMATION: Xaa may be Lys, Pro or Arg
<220> FEATURE:
<221> NAME/KEY: misc_feature
<222> LOCATION: (3)..(3)
```

```
<223> OTHER INFORMATION: Xaa may be Leu or Val
<220> FEATURE:
<221> NAME/KEY: misc_feature
<222> LOCATION: (4)..(4)
<223> OTHER INFORMATION: Xaa may be Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
<222> LOCATION: (8)..(8)
<223> OTHER INFORMATION: Xaa may be Ala or Asp
<220> FEATURE:
<221> NAME/KEY: misc_feature
<222> LOCATION: (9)..(9)
<223> OTHER INFORMATION: Xaa may be Asn
<220> FEATURE:
<221> NAME/KEY: misc_feature
<222> LOCATION: (10)..(10)
<223> OTHER INFORMATION: Xaa may be His
<220> FEATURE:
<221> NAME/KEY: misc_feature
<222> LOCATION: (11)..(11)
<223> OTHER INFORMATION: Xaa may be Lys or Arg
<220> FEATURE:
<221> NAME/KEY: misc_feature
<222> LOCATION: (12)..(12)
<223> OTHER INFORMATION: Xaa may be Lys or Arg

<400> SEQUENCE: 291

Xaa Xaa Xaa Xaa Xaa Xaa Xaa Xaa Xaa Xaa Xaa Xaa
1               5                   10

<210> SEQ ID NO 292
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 11
<220> FEATURE:
<221> NAME/KEY: misc_feature
<222> LOCATION: (1)..(1)
<223> OTHER INFORMATION: Xaa may be Asp, Gly or Asn
<220> FEATURE:
<221> NAME/KEY: misc_feature
<222> LOCATION: (2)..(2)
<223> OTHER INFORMATION: Xaa may be Lys, Arg or Ser
<220> FEATURE:
<221> NAME/KEY: misc_feature
<222> LOCATION: (3)..(3)
<223> OTHER INFORMATION: Xaa may be Leu or Val
<220> FEATURE:
<221> NAME/KEY: misc_feature
<222> LOCATION: (4)..(4)
<223> OTHER INFORMATION: Xaa may be Gly or Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
```

```
<220> FEATURE:
<221> NAME/KEY: misc_feature
<222> LOCATION: (8)..(8)
<223> OTHER INFORMATION: Xaa may be Ala
<220> FEATURE:
<221> NAME/KEY: misc_feature
<222> LOCATION: (9)..(9)
<223> OTHER INFORMATION: Xaa may be Asn
<220> FEATURE:
<221> NAME/KEY: misc_feature
<222> LOCATION: (10)..(10)
<223> OTHER INFORMATION: Xaa may be His
<220> FEATURE:
<221> NAME/KEY: misc_feature
<222> LOCATION: (11)..(11)
<223> OTHER INFORMATION: Xaa may be Lys
<220> FEATURE:
<221> NAME/KEY: misc_feature
<222> LOCATION: (12)..(12)
<223> OTHER INFORMATION: Xaa may be Lys

<400> SEQUENCE: 292

Xaa Xaa Xaa Xaa Xaa Xaa Xaa Xaa Xaa Xaa Xaa Xaa
1               5                   10

<210> SEQ ID NO 293
<211> LENGTH: 12
<212> TYPE: PRT
<213> ORGANISM: Artificial Sequence
<220> FEATURE:
<223> OTHER INFORMATION: uPA and/or Matriptase Cleavable Expanded Core
      CM Consensus Sequence 12
<220> FEATURE:
<221> NAME/KEY: misc_feature
<222> LOCATION: (1)..(1)
<223> OTHER INFORMATION: Xaa may be Ala, Asp, Gly, Lys, Leu, Asn, Arg,
      Ser, Thr or Val
<220> FEATURE:
<221> NAME/KEY: misc_feature
<222> LOCATION: (2)..(2)
<223> OTHER INFORMATION: Xaa may be Ala, Gly, Lys, Met, Pro, Gln, Arg,
      Ser or Thr
<220> FEATURE:
<221> NAME/KEY: misc_feature
<222> LOCATION: (3)..(3)
<223> OTHER INFORMATION: Xaa may be Asp, Ile, Leu, Arg, Ser or Val
<220> FEATURE:
<221> NAME/KEY: misc_feature
<222> LOCATION: (4)..(4)
<223> OTHER INFORMATION: Xaa may be Cys, Gly, His, Ile, Lys, Asn, Arg,
      Ser, Thr or Tyr
<220> FEATURE:
<221> NAME/KEY: misc_feature
<222> LOCATION: (5)..(5)
<223> OTHER INFORMATION: Xaa may be Asp, Gly or Ser
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Phe or Ser
<220> FEATURE:
<221> NAME/KEY: misc_feature
<222> LOCATION: (8)..(8)
<223> OTHER INFORMATION: Xaa may be Ala, Asp, Gly, His, Ile, Leu, Thr
      or Val
<220> FEATURE:
<221> NAME/KEY: misc_feature
<222> LOCATION: (9)..(9)
<223> OTHER INFORMATION: Xaa may be His, Ile, Asn, Arg, Ser or Thr
<220> FEATURE:
<221> NAME/KEY: misc_feature
<222> LOCATION: (10)..(10)
<223> OTHER INFORMATION: Xaa may be His, Leu, Met, Arg, Val or Tyr
<220> FEATURE:
```

```
<221> NAME/KEY: misc_feature
<222> LOCATION: (11)..(11)
<223> OTHER INFORMATION: Xaa may be Glu, Gly, Lys, Asn, Gln, Arg or Val
<220> FEATURE:
<221> NAME/KEY: misc_feature
<222> LOCATION: (12)..(12)
<223> OTHER INFORMATION: Xaa may be Ala, Gly, Lys, Leu, Gln, Arg or Ser

<400> SEQUENCE: 293

Xaa Xaa Xaa Xaa Xaa Xaa Xaa Xaa Xaa Xaa Xaa Xaa
1               5                   10

<210> SEQ ID NO 294
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 12
<220> FEATURE:
<221> NAME/KEY: misc_feature
<222> LOCATION: (1)..(1)
<223> OTHER INFORMATION: Xaa may be Asp, Gly, Lys or Arg
<220> FEATURE:
<221> NAME/KEY: misc_feature
<222> LOCATION: (2)..(2)
<223> OTHER INFORMATION: Xaa may be Gly, Pro or Arg
<220> FEATURE:
<221> NAME/KEY: misc_feature
<222> LOCATION: (3)..(3)
<223> OTHER INFORMATION: Xaa may be Leu
<220> FEATURE:
<221> NAME/KEY: misc_feature
<222> LOCATION: (4)..(4)
<223> OTHER INFORMATION: Xaa may be Asn, Ser or Thr
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
<222> LOCATION: (8)..(8)
<223> OTHER INFORMATION: Xaa may be Ala, Asp or His
<220> FEATURE:
<221> NAME/KEY: misc_feature
<222> LOCATION: (9)..(9)
<223> OTHER INFORMATION: Xaa may be Asn or Arg
<220> FEATURE:
<221> NAME/KEY: misc_feature
<222> LOCATION: (10)..(10)
<223> OTHER INFORMATION: Xaa may be His, Leu, Val or Tyr
<220> FEATURE:
<221> NAME/KEY: misc_feature
<222> LOCATION: (11)..(11)
<223> OTHER INFORMATION: Xaa may be Glu, Gly, Lys, Asn, Gln or Arg
<220> FEATURE:
<221> NAME/KEY: misc_feature
<222> LOCATION: (12)..(12)
<223> OTHER INFORMATION: Xaa may be Ala, Gly, Lys, Leu, Gln or Arg

<400> SEQUENCE: 294

Xaa Xaa Xaa Xaa Xaa Xaa Xaa Xaa Xaa Xaa Xaa Xaa
1               5                   10

<210> SEQ ID NO 295
<211> LENGTH: 12
<212> TYPE: PRT
```

```
<213> ORGANISM: Artificial Sequence
<220> FEATURE:
<223> OTHER INFORMATION: uPA and/or Matriptase Cleavable Subgenus of
      Expanded Core CM Consensus 12
<220> FEATURE:
<221> NAME/KEY: misc_feature
<222> LOCATION: (1)..(1)
<223> OTHER INFORMATION: Xaa may be Ala, Asp, Gly, Asn, Arg or Thr
<220> FEATURE:
<221> NAME/KEY: misc_feature
<222> LOCATION: (2)..(2)
<223> OTHER INFORMATION: Xaa may be Gly, Lys, Pro, Arg, Ser or Thr
<220> FEATURE:
<221> NAME/KEY: misc_feature
<222> LOCATION: (3)..(3)
<223> OTHER INFORMATION: Xaa may be Leu or Val
<220> FEATURE:
<221> NAME/KEY: misc_feature
<222> LOCATION: (4)..(4)
<223> OTHER INFORMATION: Xaa may be Gly, His, Lys, Asn, Ser or Thr
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
<222> LOCATION: (8)..(8)
<223> OTHER INFORMATION: Xaa may be Ala or Asp
<220> FEATURE:
<221> NAME/KEY: misc_feature
<222> LOCATION: (9)..(9)
<223> OTHER INFORMATION: Xaa may be Asn or Arg
<220> FEATURE:
<221> NAME/KEY: misc_feature
<222> LOCATION: (10)..(10)
<223> OTHER INFORMATION: Xaa may be His or Tyr
<220> FEATURE:
<221> NAME/KEY: misc_feature
<222> LOCATION: (11)..(11)
<223> OTHER INFORMATION: Xaa may be Glu, Lys, Asn, Gln or Arg
<220> FEATURE:
<221> NAME/KEY: misc_feature
<222> LOCATION: (12)..(12)
<223> OTHER INFORMATION: Xaa may be Ala, Lys or Arg

<400> SEQUENCE: 295

Xaa Xaa Xaa Xaa Xaa Xaa Xaa Xaa Xaa Xaa Xaa Xaa
1               5                   10

<210> SEQ ID NO 296
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 12
<220> FEATURE:
<221> NAME/KEY: misc_feature
<222> LOCATION: (1)..(1)
<223> OTHER INFORMATION: Xaa may be Ala, Asp, Gly or Arg
<220> FEATURE:
<221> NAME/KEY: misc_feature
<222> LOCATION: (2)..(2)
<223> OTHER INFORMATION: Xaa may be Lys, Pro, Arg or Thr
<220> FEATURE:
<221> NAME/KEY: misc_feature
<222> LOCATION: (3)..(3)
<223> OTHER INFORMATION: Xaa may be Leu or Val
<220> FEATURE:
```

```
<221> NAME/KEY: misc_feature
<222> LOCATION: (4)..(4)
<223> OTHER INFORMATION: Xaa may be Gly, His, Asn or Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
<222> LOCATION: (8)..(8)
<223> OTHER INFORMATION: Xaa may be Ala or Asp
<220> FEATURE:
<221> NAME/KEY: misc_feature
<222> LOCATION: (9)..(9)
<223> OTHER INFORMATION: Xaa may be Asn
<220> FEATURE:
<221> NAME/KEY: misc_feature
<222> LOCATION: (10)..(10)
<223> OTHER INFORMATION: Xaa may be His
<220> FEATURE:
<221> NAME/KEY: misc_feature
<222> LOCATION: (11)..(11)
<223> OTHER INFORMATION: Xaa may be Lys, Asn or Arg
<220> FEATURE:
<221> NAME/KEY: misc_feature
<222> LOCATION: (12)..(12)
<223> OTHER INFORMATION: Xaa may be Ala, Lys or Arg

<400> SEQUENCE: 296

Xaa Xaa Xaa Xaa Xaa Xaa Xaa Xaa Xaa Xaa Xaa Xaa
1               5                   10

<210> SEQ ID NO 297
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 12
<220> FEATURE:
<221> NAME/KEY: misc_feature
<222> LOCATION: (1)..(1)
<223> OTHER INFORMATION: Xaa may be Ala or Asp
<220> FEATURE:
<221> NAME/KEY: misc_feature
<222> LOCATION: (2)..(2)
<223> OTHER INFORMATION: Xaa may be Lys, Pro or Arg
<220> FEATURE:
<221> NAME/KEY: misc_feature
<222> LOCATION: (3)..(3)
<223> OTHER INFORMATION: Xaa may be Leu or Val
<220> FEATURE:
<221> NAME/KEY: misc_feature
<222> LOCATION: (4)..(4)
<223> OTHER INFORMATION: Xaa may be Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
```

-continued

```
<222> LOCATION: (8)..(8)
<223> OTHER INFORMATION: Xaa may be Ala or Asp
<220> FEATURE:
<221> NAME/KEY: misc_feature
<222> LOCATION: (9)..(9)
<223> OTHER INFORMATION: Xaa may be Asn
<220> FEATURE:
<221> NAME/KEY: misc_feature
<222> LOCATION: (10)..(10)
<223> OTHER INFORMATION: Xaa may be His
<220> FEATURE:
<221> NAME/KEY: misc_feature
<222> LOCATION: (11)..(11)
<223> OTHER INFORMATION: Xaa may be Lys or Arg
<220> FEATURE:
<221> NAME/KEY: misc_feature
<222> LOCATION: (12)..(12)
<223> OTHER INFORMATION: Xaa may be Lys or Arg

<400> SEQUENCE: 297

Xaa Xaa Xaa Xaa Xaa Xaa Xaa Xaa Xaa Xaa Xaa Xaa
1               5                   10

<210> SEQ ID NO 298
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 12
<220> FEATURE:
<221> NAME/KEY: misc_feature
<222> LOCATION: (1)..(1)
<223> OTHER INFORMATION: Xaa may be Gly or Arg
<220> FEATURE:
<221> NAME/KEY: misc_feature
<222> LOCATION: (2)..(2)
<223> OTHER INFORMATION: Xaa may be Pro
<220> FEATURE:
<221> NAME/KEY: misc_feature
<222> LOCATION: (3)..(3)
<223> OTHER INFORMATION: Xaa may be Leu
<220> FEATURE:
<221> NAME/KEY: misc_feature
<222> LOCATION: (4)..(4)
<223> OTHER INFORMATION: Xaa may be Asn or Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
<222> LOCATION: (8)..(8)
<223> OTHER INFORMATION: Xaa may be Ala or Asp
<220> FEATURE:
<221> NAME/KEY: misc_feature
<222> LOCATION: (9)..(9)
<223> OTHER INFORMATION: Xaa may be Asn or Arg
<220> FEATURE:
<221> NAME/KEY: misc_feature
<222> LOCATION: (10)..(10)
<223> OTHER INFORMATION: Xaa may be His
<220> FEATURE:
<221> NAME/KEY: misc_feature
<222> LOCATION: (11)..(11)
<223> OTHER INFORMATION: Xaa may be Lys, Gln or Arg
<220> FEATURE:
<221> NAME/KEY: misc_feature
<222> LOCATION: (12)..(12)
```

<223> OTHER INFORMATION: Xaa may be Ala, Lys or Arg

<400> SEQUENCE: 298

Xaa Xaa Xaa Xaa Xaa Xaa Xaa Xaa Xaa Xaa Xaa Xaa
1               5                   10

<210> SEQ ID NO 299
<211> LENGTH: 12
<212> TYPE: PRT
<213> ORGANISM: Artificial Sequence
<220> FEATURE:
<223> OTHER INFORMATION: uPA and/or Matriptase Cleavable Expanded Core
      CM Consensus Sequence 13
<220> FEATURE:
<221> NAME/KEY: misc_feature
<222> LOCATION: (1)..(1)
<223> OTHER INFORMATION: Xaa may be Ala, Asp, Gly, His, Ile, Lys, Asn,
      Arg, Ser, Thr,
      or Tyr
<220> FEATURE:
<221> NAME/KEY: misc_feature
<222> LOCATION: (2)..(2)
<223> OTHER INFORMATION: Xaa may be Asp, Gly, His, Leu, Asn, Gln, Arg
      or Tyr
<220> FEATURE:
<221> NAME/KEY: misc_feature
<222> LOCATION: (3)..(3)
<223> OTHER INFORMATION: Xaa may be Cys, Gly, His, Leu, Pro, Arg, Ser,
      Thr or Val
<220> FEATURE:
<221> NAME/KEY: misc_feature
<222> LOCATION: (4)..(4)
<223> OTHER INFORMATION: Xaa may be Ile, Leu, Met, Asn, Ser, Thr, Val
      or Tyr
<220> FEATURE:
<221> NAME/KEY: misc_feature
<222> LOCATION: (5)..(5)
<223> OTHER INFORMATION: Xaa may be Ala, Asp, Glu, Gly, Lys, Arg or Val
<220> FEATURE:
<221> NAME/KEY: misc_feature
<222> LOCATION: (6)..(6)
<223> OTHER INFORMATION: Xaa may be Ala, Cys, Gly, His, Leu, Arg, Ser,
      Thr or Val
<220> FEATURE:
<221> NAME/KEY: misc_feature
<222> LOCATION: (7)..(7)
<223> OTHER INFORMATION: Xaa may be Cys, Phe, Pro, Ser, Thr, Val or Tyr
<220> FEATURE:
<221> NAME/KEY: misc_feature
<222> LOCATION: (8)..(8)
<223> OTHER INFORMATION: Xaa may be Ala, Asp, Glu, Gly, His, Asn, Thr,
      Val or Tyr
<220> FEATURE:
<221> NAME/KEY: misc_feature
<222> LOCATION: (9)..(9)
<223> OTHER INFORMATION: Xaa may be Asp, Glu, His, Lys, Asn, Gln, Arg,
      Ser or Thr
<220> FEATURE:
<221> NAME/KEY: misc_feature
<222> LOCATION: (10)..(10)
<223> OTHER INFORMATION: Xaa may be His, Leu, Asn, Arg, Ser, Val or Tyr
<220> FEATURE:
<221> NAME/KEY: misc_feature
<222> LOCATION: (11)..(11)
<223> OTHER INFORMATION: Xaa may be Glu, Gly, Lys, Leu, Asn, Gln, Arg,
      Ser, Val or Trp
<220> FEATURE:
<221> NAME/KEY: misc_feature
<222> LOCATION: (12)..(12)
<223> OTHER INFORMATION: Xaa may be Ala, Glu, Gly, Lys, Leu, Asn, Pro,
      Gln, Arg or Trp

<400> SEQUENCE: 299

Xaa Xaa Xaa Xaa Xaa Xaa Xaa Xaa Xaa Xaa Xaa Xaa
1               5                   10

```
<210> SEQ ID NO 300
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 13
<220> FEATURE:
<221> NAME/KEY: misc_feature
<222> LOCATION: (1)..(1)
<223> OTHER INFORMATION: Xaa may be Asn
<220> FEATURE:
<221> NAME/KEY: misc_feature
<222> LOCATION: (2)..(2)
<223> OTHER INFORMATION: Xaa may be His or Arg
<220> FEATURE:
<221> NAME/KEY: misc_feature
<222> LOCATION: (3)..(3)
<223> OTHER INFORMATION: Xaa may be Cys or Arg
<220> FEATURE:
<221> NAME/KEY: misc_feature
<222> LOCATION: (4)..(4)
<223> OTHER INFORMATION: Xaa may be Ile, Ser or Tyr
<220> FEATURE:
<221> NAME/KEY: misc_feature
<222> LOCATION: (5)..(5)
<223> OTHER INFORMATION: Xaa may be Gly or Arg
<220> FEATURE:
<221> NAME/KEY: misc_feature
<222> LOCATION: (6)..(6)
<223> OTHER INFORMATION: Xaa may be Arg or Ser
<220> FEATURE:
<221> NAME/KEY: misc_feature
<222> LOCATION: (7)..(7)
<223> OTHER INFORMATION: Xaa may be Phe, Pro or Ser
<220> FEATURE:
<221> NAME/KEY: misc_feature
<222> LOCATION: (8)..(8)
<223> OTHER INFORMATION: Xaa may be Asp, Gly or His
<220> FEATURE:
<221> NAME/KEY: misc_feature
<222> LOCATION: (9)..(9)
<223> OTHER INFORMATION: Xaa may be His or Asn
<220> FEATURE:
<221> NAME/KEY: misc_feature
<222> LOCATION: (10)..(10)
<223> OTHER INFORMATION: Xaa may be His
<220> FEATURE:
<221> NAME/KEY: misc_feature
<222> LOCATION: (11)..(11)
<223> OTHER INFORMATION: Xaa may be Glu, Lys, Arg or Val
<220> FEATURE:
<221> NAME/KEY: misc_feature
<222> LOCATION: (12)..(12)
<223> OTHER INFORMATION: Xaa may be Ala, Gly, Gln, Arg or Trp

<400> SEQUENCE: 300

Xaa Xaa Xaa Xaa Xaa Xaa Xaa Xaa Xaa Xaa Xaa Xaa
1               5                   10

<210> SEQ ID NO 301
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 13
<220> FEATURE:
<221> NAME/KEY: misc_feature
<222> LOCATION: (1)..(1)
<223> OTHER INFORMATION: Xaa may be Asn
<220> FEATURE:
<221> NAME/KEY: misc_feature
<222> LOCATION: (2)..(2)
<223> OTHER INFORMATION: Xaa may be His
<220> FEATURE:
```

```
<221> NAME/KEY: misc_feature
<222> LOCATION: (3)..(3)
<223> OTHER INFORMATION: Xaa may be Arg
<220> FEATURE:
<221> NAME/KEY: misc_feature
<222> LOCATION: (4)..(4)
<223> OTHER INFORMATION: Xaa may be Ile
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
<222> LOCATION: (8)..(8)
<223> OTHER INFORMATION: Xaa may be Asp or His
<220> FEATURE:
<221> NAME/KEY: misc_feature
<222> LOCATION: (9)..(9)
<223> OTHER INFORMATION: Xaa may be Asn
<220> FEATURE:
<221> NAME/KEY: misc_feature
<222> LOCATION: (10)..(10)
<223> OTHER INFORMATION: Xaa may be His
<220> FEATURE:
<221> NAME/KEY: misc_feature
<222> LOCATION: (11)..(11)
<223> OTHER INFORMATION: Xaa may be Arg
<220> FEATURE:
<221> NAME/KEY: misc_feature
<222> LOCATION: (12)..(12)
<223> OTHER INFORMATION: Xaa may be Gly or Arg

<400> SEQUENCE: 301

Xaa Xaa Xaa Xaa Xaa Xaa Xaa Xaa Xaa Xaa Xaa Xaa
1               5                   10

<210> SEQ ID NO 302
<211> LENGTH: 12
<212> TYPE: PRT
<213> ORGANISM: Artificial Sequence
<220> FEATURE:
<223> OTHER INFORMATION: uPA and/or Matriptase Cleavable Expanded Core
      CM Consensus Sequence 14
<220> FEATURE:
<221> NAME/KEY: misc_feature
<222> LOCATION: (1)..(1)
<223> OTHER INFORMATION: Xaa may be Ala, Asp, Gly, Met, Asn, Pro, Arg
      or Thr
<220> FEATURE:
<221> NAME/KEY: misc_feature
<222> LOCATION: (2)..(2)
<223> OTHER INFORMATION: Xaa may be Ala, His, Lys, Pro, Arg or Ser
<220> FEATURE:
<221> NAME/KEY: misc_feature
<222> LOCATION: (3)..(3)
<223> OTHER INFORMATION: Xaa may be Leu, Arg, Thr or Val
<220> FEATURE:
<221> NAME/KEY: misc_feature
<222> LOCATION: (4)..(4)
<223> OTHER INFORMATION: Xaa may be Glu, Gly, Ile, Asn, Arg or Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
```

```
<221> NAME/KEY: misc_feature
<222> LOCATION: (7)..(7)
<223> OTHER INFORMATION: Xaa may be Pro or Ser
<220> FEATURE:
<221> NAME/KEY: misc_feature
<222> LOCATION: (8)..(8)
<223> OTHER INFORMATION: Xaa may be Ala, Gly or Tyr
<220> FEATURE:
<221> NAME/KEY: misc_feature
<222> LOCATION: (9)..(9)
<223> OTHER INFORMATION: Xaa may be Glu, Lys, Asn or Tyr
<220> FEATURE:
<221> NAME/KEY: misc_feature
<222> LOCATION: (10)..(10)
<223> OTHER INFORMATION: Xaa may be Pro, Gln or Ser
<220> FEATURE:
<221> NAME/KEY: misc_feature
<222> LOCATION: (11)..(11)
<223> OTHER INFORMATION: Xaa may be Glu, Lys or Arg
<220> FEATURE:
<221> NAME/KEY: misc_feature
<222> LOCATION: (12)..(12)
<223> OTHER INFORMATION: Xaa may be Asp, Glu, Gly, His or Arg

<400> SEQUENCE: 302

Xaa Xaa Xaa Xaa Xaa Xaa Xaa Xaa Xaa Xaa Xaa Xaa
1               5                   10

<210> SEQ ID NO 303
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 14
<220> FEATURE:
<221> NAME/KEY: misc_feature
<222> LOCATION: (1)..(1)
<223> OTHER INFORMATION: Xaa may be Met, Asn, Pro, Arg or Thr
<220> FEATURE:
<221> NAME/KEY: misc_feature
<222> LOCATION: (2)..(2)
<223> OTHER INFORMATION: Xaa may be Ala, Pro or Ser
<220> FEATURE:
<221> NAME/KEY: misc_feature
<222> LOCATION: (3)..(3)
<223> OTHER INFORMATION: Xaa may be Leu or Thr
<220> FEATURE:
<221> NAME/KEY: misc_feature
<222> LOCATION: (4)..(4)
<223> OTHER INFORMATION: Xaa may be Glu, Arg or Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Pro or Ser
<220> FEATURE:
<221> NAME/KEY: misc_feature
<222> LOCATION: (8)..(8)
<223> OTHER INFORMATION: Xaa may be Ala, Gly or Tyr
<220> FEATURE:
<221> NAME/KEY: misc_feature
<222> LOCATION: (9)..(9)
<223> OTHER INFORMATION: Xaa may be Glu or Asn
<220> FEATURE:
<221> NAME/KEY: misc_feature
<222> LOCATION: (10)..(10)
<223> OTHER INFORMATION: Xaa may be Pro, Gln or Ser
<220> FEATURE:
<221> NAME/KEY: misc_feature
```

<222> LOCATION: (11)..(11)
<223> OTHER INFORMATION: Xaa may be Glu, Lys, Arg
<220> FEATURE:
<221> NAME/KEY: misc_feature
<222> LOCATION: (12)..(12)
<223> OTHER INFORMATION: Xaa may be Glu, Gly or Arg

<400> SEQUENCE: 303

Xaa Xaa Xaa Xaa Xaa Xaa Xaa Xaa Xaa Xaa Xaa Xaa
1               5                   10

<210> SEQ ID NO 304
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 14
<220> FEATURE:
<221> NAME/KEY: misc_feature
<222> LOCATION: (1)..(1)
<223> OTHER INFORMATION: Xaa may be Gly, Asn or Thr
<220> FEATURE:
<221> NAME/KEY: misc_feature
<222> LOCATION: (2)..(2)
<223> OTHER INFORMATION: Xaa may be Ala, Pro or Ser
<220> FEATURE:
<221> NAME/KEY: misc_feature
<222> LOCATION: (3)..(3)
<223> OTHER INFORMATION: Xaa may be Leu, Thr or Val
<220> FEATURE:
<221> NAME/KEY: misc_feature
<222> LOCATION: (4)..(4)
<223> OTHER INFORMATION: Xaa may be Arg or Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
<222> LOCATION: (8)..(8)
<223> OTHER INFORMATION: Xaa may be Ala or Gly
<220> FEATURE:
<221> NAME/KEY: misc_feature
<222> LOCATION: (9)..(9)
<223> OTHER INFORMATION: Xaa may be Lys, Asn or Tyr
<220> FEATURE:
<221> NAME/KEY: misc_feature
<222> LOCATION: (10)..(10)
<223> OTHER INFORMATION: Xaa may be Pro
<220> FEATURE:
<221> NAME/KEY: misc_feature
<222> LOCATION: (11)..(11)
<223> OTHER INFORMATION: Xaa may be Lys or Arg
<220> FEATURE:
<221> NAME/KEY: misc_feature
<222> LOCATION: (12)..(12)
<223> OTHER INFORMATION: Xaa may be Asp, Gly or His

<400> SEQUENCE: 304

Xaa Xaa Xaa Xaa Xaa Xaa Xaa Xaa Xaa Xaa Xaa Xaa
1               5                   10

<210> SEQ ID NO 305
<211> LENGTH: 12
<212> TYPE: PRT
<213> ORGANISM: Artificial Sequence

```
<220> FEATURE:
<223> OTHER INFORMATION: uPA and/or Matriptase Cleavable Subgenus of
      Expanded Core CM Consensus 14
<220> FEATURE:
<221> NAME/KEY: misc_feature
<222> LOCATION: (1)..(1)
<223> OTHER INFORMATION: Xaa may be Thr
<220> FEATURE:
<221> NAME/KEY: misc_feature
<222> LOCATION: (2)..(2)
<223> OTHER INFORMATION: Xaa may be Pro or Ser
<220> FEATURE:
<221> NAME/KEY: misc_feature
<222> LOCATION: (3)..(3)
<223> OTHER INFORMATION: Xaa may be Leu or Thr
<220> FEATURE:
<221> NAME/KEY: misc_feature
<222> LOCATION: (4)..(4)
<223> OTHER INFORMATION: Xaa may be Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
<222> LOCATION: (8)..(8)
<223> OTHER INFORMATION: Xaa may be Ala or Gly
<220> FEATURE:
<221> NAME/KEY: misc_feature
<222> LOCATION: (9)..(9)
<223> OTHER INFORMATION: Xaa may be Asn
<220> FEATURE:
<221> NAME/KEY: misc_feature
<222> LOCATION: (10)..(10)
<223> OTHER INFORMATION: Xaa may be Pro
<220> FEATURE:
<221> NAME/KEY: misc_feature
<222> LOCATION: (11)..(11)
<223> OTHER INFORMATION: Xaa may be Lys or Arg
<220> FEATURE:
<221> NAME/KEY: misc_feature
<222> LOCATION: (12)..(12)
<223> OTHER INFORMATION: Xaa may be Gly or His

<400> SEQUENCE: 305

Xaa Xaa Xaa Xaa Xaa Xaa Xaa Xaa Xaa Xaa Xaa Xaa
1               5                   10

<210> SEQ ID NO 306
<211> LENGTH: 12
<212> TYPE: PRT
<213> ORGANISM: Artificial Sequence
<220> FEATURE:
<223> OTHER INFORMATION: uPA and/or Matriptase Cleavable Subgenus of
      Expanded Core CM Consensus 14
<220> FEATURE:
<221> NAME/KEY: misc_feature
<222> LOCATION: (1)..(1)
<223> OTHER INFORMATION: Xaa may be Thr
<220> FEATURE:
<221> NAME/KEY: misc_feature
<222> LOCATION: (2)..(2)
<223> OTHER INFORMATION: Xaa may be Ser
<220> FEATURE:
<221> NAME/KEY: misc_feature
<222> LOCATION: (3)..(3)
<223> OTHER INFORMATION: Xaa may be Leu or Thr
<220> FEATURE:
<221> NAME/KEY: misc_feature
```

```
<222> LOCATION: (4)..(4)
<223> OTHER INFORMATION: Xaa may be Ser
<220> FEATURE:
<221> NAME/KEY: misc_feature
<222> LOCATION: (5)..(5)
<223> OTHER INFORMATION: Xaa may be Gly
<220> FEATURE:
<221> NAME/KEY: misc_feature
<222> LOCATION: (6)..(6)
<223> OTHER INFORMATION: Xaa may be Arg
<220> FEATURE:
<221> NAME/KEY: misc_feature
<222> LOCATION: (7)..(7)
<223> OTHER INFORMATION: Xaa may be Ser
<220> FEATURE:
<221> NAME/KEY: misc_feature
<222> LOCATION: (8)..(8)
<223> OTHER INFORMATION: Xaa may be Ala or Gly
<220> FEATURE:
<221> NAME/KEY: misc_feature
<222> LOCATION: (9)..(9)
<223> OTHER INFORMATION: Xaa may be Asn
<220> FEATURE:
<221> NAME/KEY: misc_feature
<222> LOCATION: (10)..(10)
<223> OTHER INFORMATION: Xaa may be Pro
<220> FEATURE:
<221> NAME/KEY: misc_feature
<222> LOCATION: (11)..(11)
<223> OTHER INFORMATION: Xaa may be Arg
<220> FEATURE:
<221> NAME/KEY: misc_feature
<222> LOCATION: (12)..(12)
<223> OTHER INFORMATION: Xaa may be Gly

<400> SEQUENCE: 306

Xaa Xaa Xaa Xaa Xaa Xaa Xaa Xaa Xaa Xaa Xaa Xaa
1               5                   10

<210> SEQ ID NO 307
<211> LENGTH: 8
<212> TYPE: PRT
<213> ORGANISM: Artificial Sequence
<220> FEATURE:
<223> OTHER INFORMATION: Core CM consensus 11 sequence

<400> SEQUENCE: 307

Leu Ser Gly Arg Ser Ala Asn His
1               5

<210> SEQ ID NO 308
<211> LENGTH: 8
<212> TYPE: PRT
<213> ORGANISM: Artificial Sequence
<220> FEATURE:
<223> OTHER INFORMATION: Core CM consensus 11 sequence

<400> SEQUENCE: 308

Leu Ser Gly Arg Ser Gly Asn His
1               5

<210> SEQ ID NO 309
<211> LENGTH: 12
<212> TYPE: PRT
<213> ORGANISM: Artificial Sequence
<220> FEATURE:
<223> OTHER INFORMATION: Expanded core CM consensus 11 or 12 sequence

<400> SEQUENCE: 309

Asp Arg Leu Ser Gly Arg Ser Ala Asn His Lys Lys
1               5                   10
```

<210> SEQ ID NO 310
<211> LENGTH: 12
<212> TYPE: PRT
<213> ORGANISM: Artificial Sequence
<220> FEATURE:
<223> OTHER INFORMATION: Expanded core CM consensus 11 or 12 sequence

<400> SEQUENCE: 310

Asp Arg Leu Ser Gly Arg Ser Asp Asn His Lys Lys
1               5                   10

<210> SEQ ID NO 311
<211> LENGTH: 12
<212> TYPE: PRT
<213> ORGANISM: Artificial Sequence
<220> FEATURE:
<223> OTHER INFORMATION: Expanded core CM consensus 11 sequence

<400> SEQUENCE: 311

Asn Thr Leu Ser Gly Arg Ser Gly Asn His Gly Ser
1               5                   10

<210> SEQ ID NO 312
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 312

Gln Ala Leu Ala Met Ser Ala Ile
1               5

<210> SEQ ID NO 313
<211> LENGTH: 8
<212> TYPE: PRT
<213> ORGANISM: Artificial Sequence
<220> FEATURE:
<223> OTHER INFORMATION: Core CM consensus 12 sequence

<400> SEQUENCE: 313

Leu Asn Gly Arg Ser Asp Asn His
1               5

<210> SEQ ID NO 314
<211> LENGTH: 8
<212> TYPE: PRT
<213> ORGANISM: Artificial Sequence
<220> FEATURE:
<223> OTHER INFORMATION: Core CM consensus 12 sequence

<400> SEQUENCE: 314

Leu Thr Gly Arg Ser Asp Arg His
1               5

<210> SEQ ID NO 315
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 315

Ala Ala Tyr His Leu Val Ser Gln
1               5

```
<210> SEQ ID NO 316
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 316

Met Asp Ala Phe Leu Glu Ser Ser
1               5

<210> SEQ ID NO 317
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 317

Glu Ser Leu Pro Val Val Ala Val
1               5

<210> SEQ ID NO 318
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 318

Ser Ala Pro Ala Val Glu Ser Glu
1               5

<210> SEQ ID NO 319
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 319

Asp Val Ala Gln Phe Val Leu Thr
1               5

<210> SEQ ID NO 320
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 320

Gly Pro Leu Asn Gly Arg Ser Asp Asn His Lys Ala
1               5                   10

<210> SEQ ID NO 321
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 321

Gly Pro Leu Asn Gly Arg Ser Asp Asn His Lys Lys
1               5                   10

<210> SEQ ID NO 322
```

```
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 322

Gly Pro Leu Asn Gly Arg Ser Asp Asn His Lys Arg
1               5                   10

<210> SEQ ID NO 323
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 323

Gly Pro Leu Asn Gly Arg Ser Asp Asn His Gln Ala
1               5                   10

<210> SEQ ID NO 324
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 324

Gly Pro Leu Asn Gly Arg Ser Asp Asn His Gln Lys
1               5                   10

<210> SEQ ID NO 325
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 325

Gly Pro Leu Asn Gly Arg Ser Asp Asn His Gln Arg
1               5                   10

<210> SEQ ID NO 326
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 326

Gly Pro Leu Asn Gly Arg Ser Asp Asn His Arg Ala
1               5                   10

<210> SEQ ID NO 327
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 327

Gly Pro Leu Asn Gly Arg Ser Asp Asn His Arg Lys
1               5                   10

<210> SEQ ID NO 328
<211> LENGTH: 12
```

```
<212> TYPE: PRT
<213> ORGANISM: Artificial Sequence
<220> FEATURE:
<223> OTHER INFORMATION: Expanded core CM consensus 12 sequence

<400> SEQUENCE: 328

Gly Pro Leu Asn Gly Arg Ser Asp Asn His Arg Arg
1               5                   10

<210> SEQ ID NO 329
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 329

Arg Pro Leu Asn Gly Arg Ser Asp Asn His Lys Ala
1               5                   10

<210> SEQ ID NO 330
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 330

Arg Pro Leu Asn Gly Arg Ser Asp Asn His Lys Lys
1               5                   10

<210> SEQ ID NO 331
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 331

Arg Pro Leu Asn Gly Arg Ser Asp Asn His Lys Arg
1               5                   10

<210> SEQ ID NO 332
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 332

Arg Pro Leu Asn Gly Arg Ser Asp Asn His Gln Ala
1               5                   10

<210> SEQ ID NO 333
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 333

Arg Pro Leu Asn Gly Arg Ser Asp Asn His Gln Lys
1               5                   10

<210> SEQ ID NO 334
<211> LENGTH: 12
<212> TYPE: PRT
```

```
<213> ORGANISM: Artificial Sequence
<220> FEATURE:
<223> OTHER INFORMATION: Expanded core CM consensus 12 sequence

<400> SEQUENCE: 334

Arg Pro Leu Asn Gly Arg Ser Asp Asn His Gln Arg
1               5                   10

<210> SEQ ID NO 335
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 335

Arg Pro Leu Asn Gly Arg Ser Asp Asn His Arg Ala
1               5                   10

<210> SEQ ID NO 336
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 336

Arg Pro Leu Asn Gly Arg Ser Asp Asn His Arg Lys
1               5                   10

<210> SEQ ID NO 337
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 337

Arg Pro Leu Asn Gly Arg Ser Asp Asn His Arg Arg
1               5                   10

<210> SEQ ID NO 338
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 338

Gly Pro Leu Ser Gly Arg Ser Asp Asn His Lys Ala
1               5                   10

<210> SEQ ID NO 339
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 339

Gly Pro Leu Ser Gly Arg Ser Asp Asn His Lys Lys
1               5                   10

<210> SEQ ID NO 340
<211> LENGTH: 12
<212> TYPE: PRT
<213> ORGANISM: Artificial Sequence
```

```
<220> FEATURE:
<223> OTHER INFORMATION: Expanded core CM consensus 12 sequence

<400> SEQUENCE: 340

Gly Pro Leu Ser Gly Arg Ser Asp Asn His Lys Arg
1               5                   10

<210> SEQ ID NO 341
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 341

Gly Pro Leu Ser Gly Arg Ser Asp Asn His Gln Ala
1               5                   10

<210> SEQ ID NO 342
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 342

Gly Pro Leu Ser Gly Arg Ser Asp Asn His Gln Lys
1               5                   10

<210> SEQ ID NO 343
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 343

Gly Pro Leu Ser Gly Arg Ser Asp Asn His Gln Arg
1               5                   10

<210> SEQ ID NO 344
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 344

Gly Pro Leu Ser Gly Arg Ser Asp Asn His Arg Ala
1               5                   10

<210> SEQ ID NO 345
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 345

Gly Pro Leu Ser Gly Arg Ser Asp Asn His Arg Lys
1               5                   10

<210> SEQ ID NO 346
<211> LENGTH: 12
<212> TYPE: PRT
<213> ORGANISM: Artificial Sequence
<220> FEATURE:
```

<223> OTHER INFORMATION: Expanded core CM consensus 12 sequence

<400> SEQUENCE: 346

Gly Pro Leu Ser Gly Arg Ser Asp Asn His Arg Arg
1               5                   10

<210> SEQ ID NO 347
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 347

Arg Pro Leu Ser Gly Arg Ser Asp Asn His Lys Ala
1               5                   10

<210> SEQ ID NO 348
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 348

Arg Pro Leu Ser Gly Arg Ser Asp Asn His Lys Lys
1               5                   10

<210> SEQ ID NO 349
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 349

Arg Pro Leu Ser Gly Arg Ser Asp Asn His Lys Arg
1               5                   10

<210> SEQ ID NO 350
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 350

Arg Pro Leu Ser Gly Arg Ser Asp Asn His Gln Ala
1               5                   10

<210> SEQ ID NO 351
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 351

Arg Pro Leu Ser Gly Arg Ser Asp Asn His Gln Lys
1               5                   10

<210> SEQ ID NO 352
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 352

Arg Pro Leu Ser Gly Arg Ser Asp Asn His Gln Arg
1               5                   10

<210> SEQ ID NO 353
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 353

Arg Pro Leu Ser Gly Arg Ser Asp Asn His Arg Ala
1               5                   10

<210> SEQ ID NO 354
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 354

Arg Pro Leu Ser Gly Arg Ser Asp Asn His Arg Lys
1               5                   10

<210> SEQ ID NO 355
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 355

Arg Pro Leu Ser Gly Arg Ser Asp Asn His Arg Arg
1               5                   10

<210> SEQ ID NO 356
<211> LENGTH: 12
<212> TYPE: PRT
<213> ORGANISM: Artificial Sequence
<220> FEATURE:
<223> OTHER INFORMATION: Expanded core CM consensus 12 sequence

<400> SEQUENCE: 356

Lys Gly Leu Thr Gly Arg Ser Asp Arg His Gln Ala
1               5                   10

<210> SEQ ID NO 357
<211> LENGTH: 8
<212> TYPE: PRT
<213> ORGANISM: Artificial Sequence
<220> FEATURE:
<223> OTHER INFORMATION: Core CM consensus 13 sequence

<400> SEQUENCE: 357

Arg Ile Gly Arg Ser Asp Asn His
1               5

<210> SEQ ID NO 358
<211> LENGTH: 8
<212> TYPE: PRT
<213> ORGANISM: Artificial Sequence
<220> FEATURE:
<223> OTHER INFORMATION: Core CM consensus 13 sequence

```
<400> SEQUENCE: 358

Arg Leu Gly Arg Ser Asp Asn Asn
1               5

<210> SEQ ID NO 359
<211> LENGTH: 12
<212> TYPE: PRT
<213> ORGANISM: Artificial Sequence
<220> FEATURE:
<223> OTHER INFORMATION: Expanded core CM consensus 13 sequence

<400> SEQUENCE: 359

Asn His Arg Ile Gly Arg Ser Asp Asn His Arg Arg
1               5                   10

<210> SEQ ID NO 360
<211> LENGTH: 12
<212> TYPE: PRT
<213> ORGANISM: Artificial Sequence
<220> FEATURE:
<223> OTHER INFORMATION: Expanded core CM consensus 13 sequence

<400> SEQUENCE: 360

Thr Leu Arg Leu Gly Arg Ser Asp Asn Asn Lys Asn
1               5                   10

<210> SEQ ID NO 361
<211> LENGTH: 8
<212> TYPE: PRT
<213> ORGANISM: Artificial Sequence
<220> FEATURE:
<223> OTHER INFORMATION: Core CM consensus 14 sequence

<400> SEQUENCE: 361

Thr Ser Gly Arg Ser Ala Asn Pro
1               5

<210> SEQ ID NO 362
<211> LENGTH: 8
<212> TYPE: PRT
<213> ORGANISM: Artificial Sequence
<220> FEATURE:
<223> OTHER INFORMATION: Core CM consensus 14 sequence

<400> SEQUENCE: 362

Thr Ser Gly Arg Ser Gly Asn Pro
1               5

<210> SEQ ID NO 363
<211> LENGTH: 8
<212> TYPE: PRT
<213> ORGANISM: Artificial Sequence
<220> FEATURE:
<223> OTHER INFORMATION: Core CM consensus 14 sequence

<400> SEQUENCE: 363

Leu Ser Gly Arg Ser Ala Asn Pro
1               5

<210> SEQ ID NO 364
<211> LENGTH: 8
<212> TYPE: PRT
<213> ORGANISM: Artificial Sequence
<220> FEATURE:
<223> OTHER INFORMATION: Core CM consensus 14 sequence

<400> SEQUENCE: 364
```

Leu Ser Gly Arg Ser Gly Asn Pro
1               5

<210> SEQ ID NO 365
<211> LENGTH: 12
<212> TYPE: PRT
<213> ORGANISM: Artificial Sequence
<220> FEATURE:
<223> OTHER INFORMATION: Expanded core CM consensus 14 sequence

<400> SEQUENCE: 365

Thr Ser Thr Ser Gly Arg Ser Ala Asn Pro Arg Gly
1               5                   10

<210> SEQ ID NO 366
<211> LENGTH: 12
<212> TYPE: PRT
<213> ORGANISM: Artificial Sequence
<220> FEATURE:
<223> OTHER INFORMATION: Expanded core CM consensus 14 sequence

<400> SEQUENCE: 366

Thr Ser Thr Ser Gly Arg Ser Gly Asn Pro Arg Gly
1               5                   10

<210> SEQ ID NO 367
<211> LENGTH: 12
<212> TYPE: PRT
<213> ORGANISM: Artificial Sequence
<220> FEATURE:
<223> OTHER INFORMATION: Expanded core CM consensus 14 sequence

<400> SEQUENCE: 367

Thr Ser Leu Ser Gly Arg Ser Ala Asn Pro Arg Gly
1               5                   10

<210> SEQ ID NO 368
<211> LENGTH: 12
<212> TYPE: PRT
<213> ORGANISM: Artificial Sequence
<220> FEATURE:
<223> OTHER INFORMATION: Expanded core CM consensus 14 sequence

<400> SEQUENCE: 368

Thr Ser Leu Ser Gly Arg Ser Gly Asn Pro Arg Gly
1               5                   10

<210> SEQ ID NO 369
<211> LENGTH: 8
<212> TYPE: PRT
<213> ORGANISM: Artificial Sequence
<220> FEATURE:
<223> OTHER INFORMATION: Cleavable moiety

<400> SEQUENCE: 369

Leu Ser Gly Arg Ser Glu Asn His
1               5

<210> SEQ ID NO 370
<211> LENGTH: 8
<212> TYPE: PRT
<213> ORGANISM: Artificial Sequence
<220> FEATURE:
<223> OTHER INFORMATION: Cleavable moiety

<400> SEQUENCE: 370

```
Ser Ile Ala Arg Ser Asp Asn Leu
1               5

<210> SEQ ID NO 371
<211> LENGTH: 8
<212> TYPE: PRT
<213> ORGANISM: Artificial Sequence
<220> FEATURE:
<223> OTHER INFORMATION: Cleavable moiety

<400> SEQUENCE: 371

Leu Ser Gly Arg Ser Val Thr Gln
1               5

<210> SEQ ID NO 372
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 372

Val Ala Gln Phe Val Leu Thr Glu
1               5

<210> SEQ ID NO 373
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 373

Ala Gln Phe Val Leu Thr Glu Gly
1               5

<210> SEQ ID NO 374
<211> LENGTH: 8
<212> TYPE: PRT
<213> ORGANISM: Artificial Sequence
<220> FEATURE:
<223> OTHER INFORMATION: Cleavable moiety

<400> SEQUENCE: 374

Leu Tyr Gly Arg Ser Glu Asn Asn
1               5

<210> SEQ ID NO 375
<211> LENGTH: 8
<212> TYPE: PRT
<213> ORGANISM: Artificial Sequence
<220> FEATURE:
<223> OTHER INFORMATION: Cleavable moiety

<400> SEQUENCE: 375

Arg Leu Gly Arg Ser Asp Asn Asn
1               5

<210> SEQ ID NO 376
<211> LENGTH: 8
<212> TYPE: PRT
<213> ORGANISM: Artificial Sequence
<220> FEATURE:
<223> OTHER INFORMATION: Cleavable moiety

<400> SEQUENCE: 376

Thr Ser Gly Arg Ser Ala Asn Pro
```

```
1               5

<210> SEQ ID NO 377
<211> LENGTH: 12
<212> TYPE: PRT
<213> ORGANISM: Artificial Sequence
<220> FEATURE:
<223> OTHER INFORMATION: Cleavable moiety

<400> SEQUENCE: 377

Asn Thr Leu Ser Gly Arg Ser Glu Asn His Ser Gly
1               5                   10

<210> SEQ ID NO 378
<211> LENGTH: 12
<212> TYPE: PRT
<213> ORGANISM: Artificial Sequence
<220> FEATURE:
<223> OTHER INFORMATION: Cleavable moiety

<400> SEQUENCE: 378

Pro Pro Ser Ile Ala Arg Ser Asp Asn Leu Ala Asn
1               5                   10

<210> SEQ ID NO 379
<211> LENGTH: 12
<212> TYPE: PRT
<213> ORGANISM: Artificial Sequence
<220> FEATURE:
<223> OTHER INFORMATION: Cleavable moiety

<400> SEQUENCE: 379

Thr Gly Leu Ser Gly Arg Ser Val Thr Gln Thr Ser
1               5                   10

<210> SEQ ID NO 380
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 380

Pro Val Gln Pro Ile Gly Pro Gln
1               5

<210> SEQ ID NO 381
<211> LENGTH: 12
<212> TYPE: PRT
<213> ORGANISM: Artificial Sequence
<220> FEATURE:
<223> OTHER INFORMATION: Cleavable moiety

<400> SEQUENCE: 381

Lys Gly Leu Thr Gly Arg Ser Asp Arg His Gln Ala
1               5                   10

<210> SEQ ID NO 382
<211> LENGTH: 12
<212> TYPE: PRT
<213> ORGANISM: Artificial Sequence
<220> FEATURE:
<223> OTHER INFORMATION: Cleavable moiety

<400> SEQUENCE: 382

Lys Asn Leu Tyr Gly Arg Ser Glu Asn Asn Gly Asn
1               5                   10
```

```
<210> SEQ ID NO 383
<211> LENGTH: 12
<212> TYPE: PRT
<213> ORGANISM: Artificial Sequence
<220> FEATURE:
<223> OTHER INFORMATION: Cleavable moiety

<400> SEQUENCE: 383

Thr Leu Arg Leu Gly Arg Ser Asp Asn Asn Lys Asn
1               5                   10

<210> SEQ ID NO 384
<211> LENGTH: 12
<212> TYPE: PRT
<213> ORGANISM: Artificial Sequence
<220> FEATURE:
<223> OTHER INFORMATION: Cleavable moiety

<400> SEQUENCE: 384

Thr Ser Thr Ser Gly Arg Ser Ala Asn Pro Arg Gly
1               5                   10

<210> SEQ ID NO 385
<211> LENGTH: 5
<212> TYPE: PRT
<213> ORGANISM: Artificial Sequence
<220> FEATURE:
<223> OTHER INFORMATION: Linking peptide
<220> FEATURE:
<221> NAME/KEY: REPEAT
<222> LOCATION: (1)..(5)
<223> OTHER INFORMATION: May be repeated

<400> SEQUENCE: 385

Gly Ser Gly Gly Ser
1               5

<210> SEQ ID NO 386
<211> LENGTH: 4
<212> TYPE: PRT
<213> ORGANISM: Artificial Sequence
<220> FEATURE:
<223> OTHER INFORMATION: Linking peptide
<220> FEATURE:
<221> NAME/KEY: REPEAT
<222> LOCATION: (1)..(4)
<223> OTHER INFORMATION: May be repeated

<400> SEQUENCE: 386

Gly Gly Gly Ser
1

<210> SEQ ID NO 387
<211> LENGTH: 4
<212> TYPE: PRT
<213> ORGANISM: Artificial Sequence
<220> FEATURE:
<223> OTHER INFORMATION: Linking peptide

<400> SEQUENCE: 387

Gly Gly Ser Gly
1

<210> SEQ ID NO 388
<211> LENGTH: 5
<212> TYPE: PRT
<213> ORGANISM: Artificial Sequence
```

```
<220> FEATURE:
<223> OTHER INFORMATION: Linking peptide

<400> SEQUENCE: 388

Gly Gly Ser Gly Gly
1               5

<210> SEQ ID NO 389
<211> LENGTH: 5
<212> TYPE: PRT
<213> ORGANISM: Artificial Sequence
<220> FEATURE:
<223> OTHER INFORMATION: Linking peptide

<400> SEQUENCE: 389

Gly Ser Gly Ser Gly
1               5

<210> SEQ ID NO 390
<211> LENGTH: 5
<212> TYPE: PRT
<213> ORGANISM: Artificial Sequence
<220> FEATURE:
<223> OTHER INFORMATION: Linking peptide

<400> SEQUENCE: 390

Gly Ser Gly Gly Gly
1               5

<210> SEQ ID NO 391
<211> LENGTH: 5
<212> TYPE: PRT
<213> ORGANISM: Artificial Sequence
<220> FEATURE:
<223> OTHER INFORMATION: Linking peptide

<400> SEQUENCE: 391

Gly Gly Gly Ser Gly
1               5

<210> SEQ ID NO 392
<211> LENGTH: 5
<212> TYPE: PRT
<213> ORGANISM: Artificial Sequence
<220> FEATURE:
<223> OTHER INFORMATION: Linking peptide

<400> SEQUENCE: 392

Gly Ser Ser Ser Gly
1               5

<210> SEQ ID NO 393
<211> LENGTH: 13
<212> TYPE: PRT
<213> ORGANISM: Artificial Sequence
<220> FEATURE:
<223> OTHER INFORMATION: Linking peptide

<400> SEQUENCE: 393

Gly Ser Ser Gly Gly Ser Gly Gly Ser Gly Gly Ser Gly
1               5                   10

<210> SEQ ID NO 394
<211> LENGTH: 11
<212> TYPE: PRT
<213> ORGANISM: Artificial Sequence
<220> FEATURE:
```

```
<223> OTHER INFORMATION: Linking peptide

<400> SEQUENCE: 394

Gly Ser Ser Gly Gly Ser Gly Gly Ser Gly Gly
1               5                   10

<210> SEQ ID NO 395
<211> LENGTH: 12
<212> TYPE: PRT
<213> ORGANISM: Artificial Sequence
<220> FEATURE:
<223> OTHER INFORMATION: Linking peptide

<400> SEQUENCE: 395

Gly Ser Ser Gly Gly Ser Gly Gly Ser Gly Gly Ser
1               5                   10

<210> SEQ ID NO 396
<211> LENGTH: 16
<212> TYPE: PRT
<213> ORGANISM: Artificial Sequence
<220> FEATURE:
<223> OTHER INFORMATION: Linking peptide

<400> SEQUENCE: 396

Gly Ser Ser Gly Gly Ser Gly Gly Ser Gly Gly Ser Gly Gly Gly Ser
1               5                   10                  15

<210> SEQ ID NO 397
<211> LENGTH: 10
<212> TYPE: PRT
<213> ORGANISM: Artificial Sequence
<220> FEATURE:
<223> OTHER INFORMATION: Linking peptide

<400> SEQUENCE: 397

Gly Ser Ser Gly Gly Ser Gly Gly Ser Gly
1               5                   10

<210> SEQ ID NO 398
<211> LENGTH: 11
<212> TYPE: PRT
<213> ORGANISM: Artificial Sequence
<220> FEATURE:
<223> OTHER INFORMATION: Linking peptide

<400> SEQUENCE: 398

Gly Ser Ser Gly Gly Ser Gly Gly Ser Gly Ser
1               5                   10

<210> SEQ ID NO 399
<211> LENGTH: 4
<212> TYPE: PRT
<213> ORGANISM: Artificial Sequence
<220> FEATURE:
<223> OTHER INFORMATION: Linking peptide

<400> SEQUENCE: 399

Gly Gly Gly Ser
1

<210> SEQ ID NO 400
<211> LENGTH: 5
<212> TYPE: PRT
<213> ORGANISM: Artificial Sequence
<220> FEATURE:
<223> OTHER INFORMATION: Linking peptide
```

-continued

```
<400> SEQUENCE: 400

Gly Ser Ser Gly Thr
1               5

<210> SEQ ID NO 401
<211> LENGTH: 4
<212> TYPE: PRT
<213> ORGANISM: Artificial Sequence
<220> FEATURE:
<223> OTHER INFORMATION: Linking peptide

<400> SEQUENCE: 401

Gly Ser Ser Gly
1

<210> SEQ ID NO 402
<211> LENGTH: 8
<212> TYPE: PRT
<213> ORGANISM: Artificial Sequence
<220> FEATURE:
<223> OTHER INFORMATION: Cleavable moiety

<400> SEQUENCE: 402

Thr Gly Arg Gly Pro Ser Trp Val
1               5

<210> SEQ ID NO 403
<211> LENGTH: 8
<212> TYPE: PRT
<213> ORGANISM: Artificial Sequence
<220> FEATURE:
<223> OTHER INFORMATION: Cleavable moiety

<400> SEQUENCE: 403

Ser Ala Arg Gly Pro Ser Arg Trp
1               5

<210> SEQ ID NO 404
<211> LENGTH: 8
<212> TYPE: PRT
<213> ORGANISM: Artificial Sequence
<220> FEATURE:
<223> OTHER INFORMATION: Cleavable moiety

<400> SEQUENCE: 404

Thr Ala Arg Gly Pro Ser Phe Lys
1               5

<210> SEQ ID NO 405
<211> LENGTH: 7
<212> TYPE: PRT
<213> ORGANISM: Artificial Sequence
<220> FEATURE:
<223> OTHER INFORMATION: Cleavable moiety

<400> SEQUENCE: 405

Thr Ala Arg Gly Pro Ser Trp
1               5

<210> SEQ ID NO 406
<211> LENGTH: 8
<212> TYPE: PRT
<213> ORGANISM: Artificial Sequence
<220> FEATURE:
<223> OTHER INFORMATION: Cleavable moiety
```

```
<400> SEQUENCE: 406

Leu Ser Gly Arg Ser Asp Asn His
1               5

<210> SEQ ID NO 407
<211> LENGTH: 8
<212> TYPE: PRT
<213> ORGANISM: Artificial Sequence
<220> FEATURE:
<223> OTHER INFORMATION: Cleavable moiety

<400> SEQUENCE: 407

Gly Gly Trp His Thr Gly Arg Asn
1               5

<210> SEQ ID NO 408
<211> LENGTH: 8
<212> TYPE: PRT
<213> ORGANISM: Artificial Sequence
<220> FEATURE:
<223> OTHER INFORMATION: Cleavable moiety

<400> SEQUENCE: 408

His Thr Gly Arg Ser Gly Ala Leu
1               5

<210> SEQ ID NO 409
<211> LENGTH: 8
<212> TYPE: PRT
<213> ORGANISM: Artificial Sequence
<220> FEATURE:
<223> OTHER INFORMATION: Cleavable moiety

<400> SEQUENCE: 409

Pro Leu Thr Gly Arg Ser Gly Gly
1               5

<210> SEQ ID NO 410
<211> LENGTH: 7
<212> TYPE: PRT
<213> ORGANISM: Artificial Sequence
<220> FEATURE:
<223> OTHER INFORMATION: Cleavable moiety

<400> SEQUENCE: 410

Leu Thr Gly Arg Ser Gly Ala
1               5

<210> SEQ ID NO 411
<211> LENGTH: 8
<212> TYPE: PRT
<213> ORGANISM: Artificial Sequence
<220> FEATURE:
<223> OTHER INFORMATION: Cleavable moiety

<400> SEQUENCE: 411

Ala Ala Arg Gly Pro Ala Ile His
1               5

<210> SEQ ID NO 412
<211> LENGTH: 8
<212> TYPE: PRT
<213> ORGANISM: Artificial Sequence
<220> FEATURE:
<223> OTHER INFORMATION: Cleavable moiety

<400> SEQUENCE: 412
```

Arg Gly Pro Ala Phe Asn Pro Met
1               5

<210> SEQ ID NO 413
<211> LENGTH: 8
<212> TYPE: PRT
<213> ORGANISM: Artificial Sequence
<220> FEATURE:
<223> OTHER INFORMATION: Cleavable moiety

<400> SEQUENCE: 413

Ser Ser Arg Gly Pro Ala Tyr Leu
1               5

<210> SEQ ID NO 414
<211> LENGTH: 8
<212> TYPE: PRT
<213> ORGANISM: Artificial Sequence
<220> FEATURE:
<223> OTHER INFORMATION: Cleavable moiety

<400> SEQUENCE: 414

Arg Gly Pro Ala Thr Pro Ile Met
1               5

<210> SEQ ID NO 415
<211> LENGTH: 4
<212> TYPE: PRT
<213> ORGANISM: Artificial Sequence
<220> FEATURE:
<223> OTHER INFORMATION: Cleavable moiety

<400> SEQUENCE: 415

Arg Gly Pro Ala
1

<210> SEQ ID NO 416
<211> LENGTH: 10
<212> TYPE: PRT
<213> ORGANISM: Artificial Sequence
<220> FEATURE:
<223> OTHER INFORMATION: Cleavable moiety

<400> SEQUENCE: 416

Gly Gly Gln Pro Ser Gly Met Trp Gly Trp
1               5                   10

<210> SEQ ID NO 417
<211> LENGTH: 10
<212> TYPE: PRT
<213> ORGANISM: Artificial Sequence
<220> FEATURE:
<223> OTHER INFORMATION: Cleavable moiety

<400> SEQUENCE: 417

Phe Pro Arg Pro Leu Gly Ile Thr Gly Leu
1               5                   10

<210> SEQ ID NO 418
<211> LENGTH: 10
<212> TYPE: PRT
<213> ORGANISM: Artificial Sequence
<220> FEATURE:
<223> OTHER INFORMATION: Cleavable moiety

<400> SEQUENCE: 418

```
Val His Met Pro Leu Gly Phe Leu Gly Pro
1               5                   10

<210> SEQ ID NO 419
<211> LENGTH: 8
<212> TYPE: PRT
<213> ORGANISM: Artificial Sequence
<220> FEATURE:
<223> OTHER INFORMATION: Cleavable moiety

<400> SEQUENCE: 419

Ser Pro Leu Thr Gly Arg Ser Gly
1               5

<210> SEQ ID NO 420
<211> LENGTH: 9
<212> TYPE: PRT
<213> ORGANISM: Artificial Sequence
<220> FEATURE:
<223> OTHER INFORMATION: Cleavable moiety

<400> SEQUENCE: 420

Leu Ala Pro Leu Gly Leu Gln Arg Arg
1               5

<210> SEQ ID NO 421
<211> LENGTH: 8
<212> TYPE: PRT
<213> ORGANISM: Artificial Sequence
<220> FEATURE:
<223> OTHER INFORMATION: Cleavable moiety

<400> SEQUENCE: 421

Ser Gly Gly Pro Leu Gly Val Arg
1               5

<210> SEQ ID NO 422
<211> LENGTH: 4
<212> TYPE: PRT
<213> ORGANISM: Artificial Sequence
<220> FEATURE:
<223> OTHER INFORMATION: Cleavable moiety

<400> SEQUENCE: 422

Pro Leu Gly Leu
1

<210> SEQ ID NO 423
<211> LENGTH: 7
<212> TYPE: PRT
<213> ORGANISM: Artificial Sequence
<220> FEATURE:
<223> OTHER INFORMATION: Cleavable moiety

<400> SEQUENCE: 423

Gly Pro Arg Ser Phe Gly Leu
1               5

<210> SEQ ID NO 424
<211> LENGTH: 6
<212> TYPE: PRT
<213> ORGANISM: Artificial Sequence
<220> FEATURE:
<223> OTHER INFORMATION: Cleavable moiety

<400> SEQUENCE: 424

Gly Pro Arg Ser Phe Gly
```

```
1               5

<210> SEQ ID NO 425
<211> LENGTH: 8
<212> TYPE: PRT
<213> ORGANISM: Artificial Sequence
<220> FEATURE:
<223> OTHER INFORMATION: Cleavable moiety

<400> SEQUENCE: 425

Ile Ser Ser Gly Leu Leu Ser Ser
1               5

<210> SEQ ID NO 426
<211> LENGTH: 8
<212> TYPE: PRT
<213> ORGANISM: Artificial Sequence
<220> FEATURE:
<223> OTHER INFORMATION: Cleavable moiety

<400> SEQUENCE: 426

Gln Asn Gln Ala Leu Arg Met Ala
1               5

<210> SEQ ID NO 427
<211> LENGTH: 8
<212> TYPE: PRT
<213> ORGANISM: Artificial Sequence
<220> FEATURE:
<223> OTHER INFORMATION: Cleavable moiety

<400> SEQUENCE: 427

Ala Gln Asn Leu Leu Gly Met Val
1               5

<210> SEQ ID NO 428
<211> LENGTH: 8
<212> TYPE: PRT
<213> ORGANISM: Artificial Sequence
<220> FEATURE:
<223> OTHER INFORMATION: Cleavable moiety

<400> SEQUENCE: 428

Ser Thr Phe Pro Phe Gly Met Phe
1               5

<210> SEQ ID NO 429
<211> LENGTH: 8
<212> TYPE: PRT
<213> ORGANISM: Artificial Sequence
<220> FEATURE:
<223> OTHER INFORMATION: Cleavable moiety

<400> SEQUENCE: 429

Pro Val Gly Tyr Thr Ser Ser Leu
1               5

<210> SEQ ID NO 430
<211> LENGTH: 8
<212> TYPE: PRT
<213> ORGANISM: Artificial Sequence
<220> FEATURE:
<223> OTHER INFORMATION: Cleavable moiety

<400> SEQUENCE: 430

Asp Trp Leu Tyr Trp Pro Gly Ile
1               5
```

```
<210> SEQ ID NO 431
<211> LENGTH: 8
<212> TYPE: PRT
<213> ORGANISM: Artificial Sequence
<220> FEATURE:
<223> OTHER INFORMATION: Cleavable moiety

<400> SEQUENCE: 431

Met Ile Ala Pro Val Ala Tyr Arg
1               5

<210> SEQ ID NO 432
<211> LENGTH: 8
<212> TYPE: PRT
<213> ORGANISM: Artificial Sequence
<220> FEATURE:
<223> OTHER INFORMATION: Cleavable moiety

<400> SEQUENCE: 432

Arg Pro Ser Pro Met Trp Ala Tyr
1               5

<210> SEQ ID NO 433
<211> LENGTH: 8
<212> TYPE: PRT
<213> ORGANISM: Artificial Sequence
<220> FEATURE:
<223> OTHER INFORMATION: Cleavable moiety

<400> SEQUENCE: 433

Trp Ala Thr Pro Arg Pro Met Arg
1               5

<210> SEQ ID NO 434
<211> LENGTH: 8
<212> TYPE: PRT
<213> ORGANISM: Artificial Sequence
<220> FEATURE:
<223> OTHER INFORMATION: Cleavable moiety

<400> SEQUENCE: 434

Phe Arg Leu Leu Asp Trp Gln Trp
1               5

<210> SEQ ID NO 435
<211> LENGTH: 8
<212> TYPE: PRT
<213> ORGANISM: Artificial Sequence
<220> FEATURE:
<223> OTHER INFORMATION: Cleavable moiety

<400> SEQUENCE: 435

Leu Lys Ala Ala Pro Arg Trp Ala
1               5

<210> SEQ ID NO 436
<211> LENGTH: 8
<212> TYPE: PRT
<213> ORGANISM: Artificial Sequence
<220> FEATURE:
<223> OTHER INFORMATION: Cleavable moiety

<400> SEQUENCE: 436

Gly Pro Ser His Leu Val Leu Thr
1               5
```

```
<210> SEQ ID NO 437
<211> LENGTH: 8
<212> TYPE: PRT
<213> ORGANISM: Artificial Sequence
<220> FEATURE:
<223> OTHER INFORMATION: Cleavable moiety

<400> SEQUENCE: 437

Leu Pro Gly Gly Leu Ser Pro Trp
1               5

<210> SEQ ID NO 438
<211> LENGTH: 8
<212> TYPE: PRT
<213> ORGANISM: Artificial Sequence
<220> FEATURE:
<223> OTHER INFORMATION: Cleavable moiety

<400> SEQUENCE: 438

Met Gly Leu Phe Ser Glu Ala Gly
1               5

<210> SEQ ID NO 439
<211> LENGTH: 8
<212> TYPE: PRT
<213> ORGANISM: Artificial Sequence
<220> FEATURE:
<223> OTHER INFORMATION: Cleavable moiety

<400> SEQUENCE: 439

Ser Pro Leu Pro Leu Arg Val Pro
1               5

<210> SEQ ID NO 440
<211> LENGTH: 8
<212> TYPE: PRT
<213> ORGANISM: Artificial Sequence
<220> FEATURE:
<223> OTHER INFORMATION: Cleavable moiety

<400> SEQUENCE: 440

Arg Met His Leu Arg Ser Leu Gly
1               5

<210> SEQ ID NO 441
<211> LENGTH: 8
<212> TYPE: PRT
<213> ORGANISM: Artificial Sequence
<220> FEATURE:
<223> OTHER INFORMATION: Cleavable moiety

<400> SEQUENCE: 441

Leu Ala Ala Pro Leu Gly Leu Leu
1               5

<210> SEQ ID NO 442
<211> LENGTH: 8
<212> TYPE: PRT
<213> ORGANISM: Artificial Sequence
<220> FEATURE:
<223> OTHER INFORMATION: Cleavable moiety

<400> SEQUENCE: 442

Ala Val Gly Leu Leu Ala Pro Pro
1               5
```

-continued

```
<210> SEQ ID NO 443
<211> LENGTH: 8
<212> TYPE: PRT
<213> ORGANISM: Artificial Sequence
<220> FEATURE:
<223> OTHER INFORMATION: Cleavable moiety

<400> SEQUENCE: 443

Leu Leu Ala Pro Ser His Arg Ala
1               5

<210> SEQ ID NO 444
<211> LENGTH: 8
<212> TYPE: PRT
<213> ORGANISM: Artificial Sequence
<220> FEATURE:
<223> OTHER INFORMATION: Cleavable moiety

<400> SEQUENCE: 444

Pro Ala Gly Leu Trp Leu Asp Pro
1               5

<210> SEQ ID NO 445
<211> LENGTH: 7
<212> TYPE: PRT
<213> ORGANISM: Artificial Sequence
<220> FEATURE:
<223> OTHER INFORMATION: Cleavable moiety

<400> SEQUENCE: 445

Ile Ser Ser Gly Leu Ser Ser
1               5

<210> SEQ ID NO 446
<211> LENGTH: 6
<212> TYPE: PRT
<213> ORGANISM: Artificial Sequence
<220> FEATURE:
<223> OTHER INFORMATION: Spacer peptide

<400> SEQUENCE: 446

Gln Gly Gln Ser Gly Gln
1               5

<210> SEQ ID NO 447
<211> LENGTH: 449
<212> TYPE: PRT
<213> ORGANISM: Artificial Sequence
<220> FEATURE:
<223> OTHER INFORMATION: Av1 Antibody Heavy Chain

<400> SEQUENCE: 447

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
                20                  25                  30

His Ala Trp Ser Trp Val Arg Gln Pro Pro Gly Arg Gly Leu Glu Trp
            35                  40                  45

Ile Gly Tyr Ile Ser Tyr Ser Gly Ile Thr Thr Tyr Asn Pro Ser Leu
        50                  55                  60

Lys Ser Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 448
<211> LENGTH: 214
<212> TYPE: PRT
<213> ORGANISM: Artificial Sequence
<220> FEATURE:
<223> OTHER INFORMATION: Av1 Antibody Light Chain

<400> SEQUENCE: 448

Asp Ile Gln Met Thr Gln Ser Pro Ser Ser Leu Ser Ala Ser Val Gly
```

```
1               5                   10                  15
Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 449
<211> LENGTH: 15
<212> TYPE: PRT
<213> ORGANISM: Artificial Sequence
<220> FEATURE:
<223> OTHER INFORMATION: N-terminal sequence attached to AV1 light chain

<400> SEQUENCE: 449

Tyr Gly Ser Cys Ser Trp Asn Tyr Val His Ile Phe Met Asp Cys
1               5                   10                  15

<210> SEQ ID NO 450
<211> LENGTH: 16
<212> TYPE: PRT
<213> ORGANISM: Artificial Sequence
<220> FEATURE:
<223> OTHER INFORMATION: N-terminal sequence attached to AV1 light chain

<400> SEQUENCE: 450

Gln Gly Asp Phe Asp Ile Pro Phe Pro Ala His Trp Val Pro Ile Thr
1               5                   10                  15

<210> SEQ ID NO 451
<211> LENGTH: 18
<212> TYPE: PRT
<213> ORGANISM: Artificial Sequence
<220> FEATURE:
<223> OTHER INFORMATION: N-terminal sequence attached to AV1 light chain

<400> SEQUENCE: 451

Met Gly Val Pro Ala Gly Cys Val Trp Asn Tyr Ala His Ile Phe Met
1               5                   10                  15
```

Asp Cys

<210> SEQ ID NO 452
<211> LENGTH: 21
<212> TYPE: PRT
<213> ORGANISM: Artificial Sequence
<220> FEATURE:
<223> OTHER INFORMATION: N-terminal sequence attached to AV1 light chain

<400> SEQUENCE: 452

Gln Gly Gln Ser Gly Gln Tyr Gly Ser Cys Ser Trp Asn Tyr Val His
1               5                   10                  15

Ile Phe Met Asp Cys
            20

<210> SEQ ID NO 453
<211> LENGTH: 21
<212> TYPE: PRT
<213> ORGANISM: Artificial Sequence
<220> FEATURE:
<223> OTHER INFORMATION: N-terminal sequence attached to AV1 light chain

<400> SEQUENCE: 453

Gln Gly Gln Ser Gly Gln Gly Asp Phe Asp Ile Pro Phe Pro Ala His
1               5                   10                  15

Trp Val Pro Ile Thr
            20

<210> SEQ ID NO 454
<211> LENGTH: 24
<212> TYPE: PRT
<213> ORGANISM: Artificial Sequence
<220> FEATURE:
<223> OTHER INFORMATION: N-terminal sequence attached to AV1 light chain

<400> SEQUENCE: 454

Gln Gly Gln Ser Gly Gln Met Gly Val Pro Ala Gly Cys Val Trp Asn
1               5                   10                  15

Tyr Ala His Ile Phe Met Asp Cys
            20

<210> SEQ ID NO 455
<211> LENGTH: 449
<212> TYPE: PRT
<213> ORGANISM: Artificial Sequence
<220> FEATURE:
<223> OTHER INFORMATION: C225v5 Antibody Heavy Chain

<400> SEQUENCE: 455

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

-continued

```
Arg Ala Leu Thr Tyr Tyr Asp Tyr Glu Phe Ala Tyr Trp Gly Gln Gly
                100                 105                 110
Thr Leu Val Thr Val Ser Ala Ala Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys
```

<210> SEQ ID NO 456
<211> LENGTH: 449
<212> TYPE: PRT
<213> ORGANISM: Artificial Sequence
<220> FEATURE:
<223> OTHER INFORMATION: C225v4 Antibody Heavy Chain

<400> SEQUENCE: 456

Gln Val Gln Leu Lys Gln Ser Gly Pro Gly Leu Val Gln Pro Ser Gln

-continued

```
  1               5                  10                 15
Ser Leu Ser Ile Thr Cys Thr Val Ser Gly Phe Ser Leu Thr Asn Tyr
             20                  25                  30
Gly Val His Trp Val Arg Gln Ser Pro Gly Lys Gly Leu Glu Trp Leu
             35                  40                  45
Gly Val Ile Trp Ser Gly Gly Asn Thr Asp Tyr Asn Thr Pro Phe Thr
             50                  55                  60
Ser Arg Leu Ser Ile Asn Lys Asp Asn Ser Lys Ser Gln Val Phe Phe
 65              70                  75                  80
Lys Met Asn Ser Leu Gln Ser Asn Asp Thr Ala Ile Tyr Tyr Cys Ala
             85                  90                  95
Arg Ala Leu Thr Tyr Tyr Asp Tyr Glu Phe Ala Tyr Trp Gly Gln Gly
            100                 105                 110
Thr Leu Val Thr Val Ser Ala Ala Ser Thr Lys Gly Pro Ser Val Phe
            115                 120                 125
Pro Leu Ala Pro Ser Ser Lys Ser Thr Ser Gly Gly Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
            210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
            420                 425                 430
```

```
Ala Leu His Asn His Tyr Thr Gln Lys Ser Leu Ser Leu Ser Pro Gly
            435                 440                 445

Lys

<210> SEQ ID NO 457
<211> LENGTH: 449
<212> TYPE: PRT
<213> ORGANISM: Artificial Sequence
<220> FEATURE:
<223> OTHER INFORMATION: C225v6 Antibody Heavy Chain

<400> SEQUENCE: 457

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys

<210> SEQ ID NO 458
<211> LENGTH: 214
<212> TYPE: PRT
<213> ORGANISM: Artificial Sequence
<220> FEATURE:
<223> OTHER INFORMATION: C225 Antibody Light Chain

<400> SEQUENCE: 458

Gln Ile Leu Leu Thr Gln Ser Pro Val Ile Leu Ser Val Ser Pro Gly
1               5                   10                  15
Glu Arg Val Ser Phe Ser Cys Arg Ala Ser Gln Ser Ile Gly Thr Asn
            20                  25                  30
Ile His Trp Tyr Gln Gln Arg Thr Asn Gly Ser Pro Arg Leu Leu Ile
        35                  40                  45
Lys Tyr Ala Ser Glu Ser Ile Ser Gly Ile Pro Ser Arg Phe Ser Gly
    50                  55                  60
Ser Gly Ser Gly Thr Asp Phe Thr Leu Ser Ile Asn Ser Val Glu Ser
65                  70                  75                  80
Glu Asp Ile Ala Asp Tyr Tyr Cys Gln Gln Asn Asn Asn Trp Pro Thr
                85                  90                  95
Thr Phe Gly Ala Gly Thr Lys Leu Glu Leu Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 459
<211> LENGTH: 108
<212> TYPE: PRT
```

```
<213> ORGANISM: Artificial Sequence
<220> FEATURE:
<223> OTHER INFORMATION: Variable Light Chain Amino Sequence Lc4

<400> SEQUENCE: 459

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 460
<211> LENGTH: 119
<212> TYPE: PRT
<213> ORGANISM: Artificial Sequence
<220> FEATURE:
<223> OTHER INFORMATION: Variable Heavy Chain Amino Sequence Hc4

<400> SEQUENCE: 460

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115

<210> SEQ ID NO 461
<211> LENGTH: 108
<212> TYPE: PRT
<213> ORGANISM: Artificial Sequence
<220> FEATURE:
<223> OTHER INFORMATION: Variable Light Chain Amino Sequence Lc5

<400> SEQUENCE: 461

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 462
<211> LENGTH: 119
<212> TYPE: PRT
<213> ORGANISM: Artificial Sequence
<220> FEATURE:
<223> OTHER INFORMATION: Variable Heavy Chain Amino Sequence Hc5

<400> SEQUENCE: 462

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Tyr His Gly Gln Phe Asp Tyr Trp Gly Gln Gly
            100                 105                 110

Thr Leu Val Thr Val Ser Ser
        115

<210> SEQ ID NO 463
<211> LENGTH: 108
<212> TYPE: PRT
<213> ORGANISM: Artificial Sequence
<220> FEATURE:
<223> OTHER INFORMATION: Variable Light Chain Amino Sequence Lc7

<400> SEQUENCE: 463

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

```
<210> SEQ ID NO 464
<211> LENGTH: 119
<212> TYPE: PRT
<213> ORGANISM: Artificial Sequence
<220> FEATURE:
<223> OTHER INFORMATION: Variable Heavy Chain Amino Sequence Hc7

<400> SEQUENCE: 464
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly
            100                 105                 110

Thr Leu Val Thr Val Ser Ser
        115

```
<210> SEQ ID NO 465
<211> LENGTH: 108
<212> TYPE: PRT
<213> ORGANISM: Artificial Sequence
<220> FEATURE:
<223> OTHER INFORMATION: Variable Light Chain Amino Sequence Lc8

<400> SEQUENCE: 465
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

```
<210> SEQ ID NO 466
<211> LENGTH: 119
<212> TYPE: PRT
<213> ORGANISM: Artificial Sequence
<220> FEATURE:
<223> OTHER INFORMATION: Variable Heavy Chain Amino Sequence Hc8

<400> SEQUENCE: 466
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ala Met Ser Trp Val Arg Gln Ala Pro Gly Lys Gly Leu Glu Trp Val
            35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Ile Gly Arg Thr Asn Pro Phe Asp Tyr Trp Gly Gln Gly
            100                 105                 110

Thr Leu Val Thr Val Ser Ser
            115
```

<210> SEQ ID NO 467
<211> LENGTH: 108
<212> TYPE: PRT
<213> ORGANISM: Artificial Sequence
<220> FEATURE:
<223> OTHER INFORMATION: Variable Light Chain Amino Sequence Lc13

<400> SEQUENCE: 467

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 468
<211> LENGTH: 116
<212> TYPE: PRT
<213> ORGANISM: Artificial Sequence
<220> FEATURE:
<223> OTHER INFORMATION: Variable Heavy Chain Amino Sequence Hc13

<400> SEQUENCE: 468

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ser Ile Glu Gln Met Gly Trp Gln Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
```

```
                  100                 105                 110

Thr Val Ser Ser
        115

<210> SEQ ID NO 469
<211> LENGTH: 108
<212> TYPE: PRT
<213> ORGANISM: Artificial Sequence
<220> FEATURE:
<223> OTHER INFORMATION: Variable Light Chain Amino Sequence Lc16

<400> SEQUENCE: 469

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 470
<211> LENGTH: 119
<212> TYPE: PRT
<213> ORGANISM: Artificial Sequence
<220> FEATURE:
<223> OTHER INFORMATION: Variable Heavy Chain Amino Sequence Hc16

<400> SEQUENCE: 470

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Tyr Tyr Gly Gln Phe Asp Tyr Trp Gly Gln Gly
            100                 105                 110

Thr Leu Val Thr Val Ser Ser
        115

<210> SEQ ID NO 471
<211> LENGTH: 108
<212> TYPE: PRT
<213> ORGANISM: Artificial Sequence
<220> FEATURE:
<223> OTHER INFORMATION: Variable Light Chain Amino Sequence Lc19

<400> SEQUENCE: 471
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105
```

<210> SEQ ID NO 472
<211> LENGTH: 119
<212> TYPE: PRT
<213> ORGANISM: Artificial Sequence
<220> FEATURE:
<223> OTHER INFORMATION: Variable Heavy Chain Amino Sequence Hc19

<400> SEQUENCE: 472

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly
            100                 105                 110

Thr Leu Val Thr Val Ser Ser
        115
```

<210> SEQ ID NO 473
<211> LENGTH: 108
<212> TYPE: PRT
<213> ORGANISM: Artificial Sequence
<220> FEATURE:
<223> OTHER INFORMATION: Variable Light Chain Amino Sequence Lc21

<400> SEQUENCE: 473

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
```

```
65                  70                  75                  80
Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
                100                 105
```

<210> SEQ ID NO 474
<211> LENGTH: 119
<212> TYPE: PRT
<213> ORGANISM: Artificial Sequence
<220> FEATURE:
<223> OTHER INFORMATION: Variable Heavy Chain Amino Sequence Hc21

<400> SEQUENCE: 474

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ser Ile Glu Gln Met Gly Trp Gln Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
                100                 105                 110

Thr Leu Val Thr Val Ser Ser
        115
```

<210> SEQ ID NO 475
<211> LENGTH: 108
<212> TYPE: PRT
<213> ORGANISM: Artificial Sequence
<220> FEATURE:
<223> OTHER INFORMATION: Variable Light Chain Amino Sequence Lc24

<400> SEQUENCE: 475

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
                100                 105
```

<210> SEQ ID NO 476
<211> LENGTH: 116
<212> TYPE: PRT
<213> ORGANISM: Artificial Sequence
<220> FEATURE:

<223> OTHER INFORMATION: Variable Heavy Chain Amino Sequence Hc24

<400> SEQUENCE: 476

Glu Val Gln Leu Leu Glu Ser Gly Gly Gly Leu Val Gln Pro Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Glu Met Gly Trp Gln Thr Leu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
            115

<210> SEQ ID NO 477
<211> LENGTH: 108
<212> TYPE: PRT
<213> ORGANISM: Artificial Sequence
<220> FEATURE:
<223> OTHER INFORMATION: Variable Light Chain Amino Sequence Lc26

<400> SEQUENCE: 477

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 478
<211> LENGTH: 119
<212> TYPE: PRT
<213> ORGANISM: Artificial Sequence
<220> FEATURE:
<223> OTHER INFORMATION: Variable Heavy Chain Amino Sequence Hc26

<400> SEQUENCE: 478

Glu Val Gln Leu Leu Glu Ser Gly Gly Gly Leu Val Gln Pro Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ile Gly Gly Arg Ser Ala Phe Asp Tyr Trp Gly Gln Gly
                100                 105                 110

Thr Leu Val Thr Val Ser Ser
            115

<210> SEQ ID NO 479
<211> LENGTH: 108
<212> TYPE: PRT
<213> ORGANISM: Artificial Sequence
<220> FEATURE:
<223> OTHER INFORMATION: Variable Light Chain Amino Sequence Lc27

<400> SEQUENCE: 479

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Val Val Ala Pro Leu
                 85                  90                  95

Thr Phe Gly Gln Gly Thr Lys Val Glu Ile Lys Arg
                100                 105

<210> SEQ ID NO 480
<211> LENGTH: 119
<212> TYPE: PRT
<213> ORGANISM: Artificial Sequence
<220> FEATURE:
<223> OTHER INFORMATION: Variable Heavy Chain Amino Sequence Hc27

<400> SEQUENCE: 480

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Ser Ile Glu Gln Met Gly Trp Gln Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Pro Pro Phe Tyr Gly Gln Phe Asp Tyr Trp Gly Gln Gly
                100                 105                 110

Thr Leu Val Thr Val Ser Ser
            115
```

```
<210> SEQ ID NO 481
<211> LENGTH: 108
<212> TYPE: PRT
<213> ORGANISM: Artificial Sequence
<220> FEATURE:
<223> OTHER INFORMATION: Variable Light Chain Amino Sequence Lc28

<400> SEQUENCE: 481

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 482
<211> LENGTH: 119
<212> TYPE: PRT
<213> ORGANISM: Artificial Sequence
<220> FEATURE:
<223> OTHER INFORMATION: Variable Heavy Chain Amino Sequence Hc28

<400> SEQUENCE: 482

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly
            100                 105                 110

Thr Leu Val Thr Val Ser Ser
        115

<210> SEQ ID NO 483
<211> LENGTH: 108
<212> TYPE: PRT
<213> ORGANISM: Artificial Sequence
<220> FEATURE:
<223> OTHER INFORMATION: Variable Light Chain Amino Sequence Lc30

<400> SEQUENCE: 483

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
```

-continued

```
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                 85                  90                  95

Thr Phe Gly Gln Gly Thr Lys Val Glu Ile Lys Arg
             100                 105

<210> SEQ ID NO 484
<211> LENGTH: 115
<212> TYPE: PRT
<213> ORGANISM: Artificial Sequence
<220> FEATURE:
<223> OTHER INFORMATION: Variable Heavy Chain Amino Sequence Hc30

<400> SEQUENCE: 484

Glu Val Gln Leu Leu Glu Ser Gly Gly Gly Leu Val Gln Pro Gly Gly
1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ser Ile Glu Glu Met Gly Trp Gln Thr Leu Tyr Ala Asp Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Ala
                 85                  90                  95

Lys Ser Ala Ala Ala Phe Asp Tyr Trp Gly Gln Gly Thr Leu Val Thr
             100                 105                 110

Val Ser Ser
         115

<210> SEQ ID NO 485
<211> LENGTH: 108
<212> TYPE: PRT
<213> ORGANISM: Artificial Sequence
<220> FEATURE:
<223> OTHER INFORMATION: Variable Light Chain Amino Sequence Lc31

<400> SEQUENCE: 485

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                 85                  90                  95
```

Thr Phe Gly Gln Gly Thr Lys Val Glu Ile Lys Arg
           100                 105

<210> SEQ ID NO 486
<211> LENGTH: 119
<212> TYPE: PRT
<213> ORGANISM: Artificial Sequence
<220> FEATURE:
<223> OTHER INFORMATION: Variable Heavy Chain Amino Sequence Hc31

<400> SEQUENCE: 486

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115

<210> SEQ ID NO 487
<211> LENGTH: 108
<212> TYPE: PRT
<213> ORGANISM: Artificial Sequence
<220> FEATURE:
<223> OTHER INFORMATION: Variable Light Chain Amino Sequence Lc32

<400> SEQUENCE: 487

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 488
<211> LENGTH: 116
<212> TYPE: PRT
<213> ORGANISM: Artificial Sequence
<220> FEATURE:
<223> OTHER INFORMATION: Variable Heavy Chain Amino Sequence Hc32

<400> SEQUENCE: 488

Glu Val Gln Leu Leu Glu Ser Gly Gly Gly Leu Val Gln Pro Gly Gly

```
                1               5                   10                  15
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ser Ile Asp Pro Glu Gly Trp Gln Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
            85                  90                  95

Ala Lys Ser Ala Ala Ala Phe Asp Tyr Trp Gly Gln Gly Thr Leu Val
            100                 105                 110

Thr Val Ser Ser
            115

<210> SEQ ID NO 489
<211> LENGTH: 108
<212> TYPE: PRT
<213> ORGANISM: Artificial Sequence
<220> FEATURE:
<223> OTHER INFORMATION: Variable Light Chain Amino Sequence Lc37

<400> SEQUENCE: 489

Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Val Val Ala Pro Leu
            85                  90                  95

Thr Phe Gly Gln Gly Thr Lys Val Glu Ile Lys Arg
            100                 105

<210> SEQ ID NO 490
<211> LENGTH: 119
<212> TYPE: PRT
<213> ORGANISM: Artificial Sequence
<220> FEATURE:
<223> OTHER INFORMATION: Variable Heavy Chain Amino Sequence Hc37

<400> SEQUENCE: 490

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ser Ile Glu Gln Met Gly Trp Gln Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Lys Ser Pro Pro His Asn Gly Gln Phe Asp Tyr Trp Gly Gln Gly
            100                 105                 110

Thr Leu Val Thr Val Ser Ser
        115

<210> SEQ ID NO 491
<211> LENGTH: 108
<212> TYPE: PRT
<213> ORGANISM: Artificial Sequence
<220> FEATURE:
<223> OTHER INFORMATION: Variable Light Chain Amino Sequence Lc39

<400> SEQUENCE: 491

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 492
<211> LENGTH: 116
<212> TYPE: PRT
<213> ORGANISM: Artificial Sequence
<220> FEATURE:
<223> OTHER INFORMATION: Variable Heavy Chain Amino Sequence Hc39

<400> SEQUENCE: 492

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115

<210> SEQ ID NO 493
<211> LENGTH: 108
<212> TYPE: PRT
<213> ORGANISM: Artificial Sequence
```

```
<220> FEATURE:
<223> OTHER INFORMATION: Variable Light Chain Amino Sequence Lc40

<400> SEQUENCE: 493

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
            100                 105

<210> SEQ ID NO 494
<211> LENGTH: 119
<212> TYPE: PRT
<213> ORGANISM: Artificial Sequence
<220> FEATURE:
<223> OTHER INFORMATION: Heavy Chain Amino Sequence Hc40

<400> SEQUENCE: 494

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Pro Pro Phe Phe Gly Gln Phe Asp Tyr Trp Gly Gln Gly
            100                 105                 110

Thr Leu Val Thr Val Ser Ser
        115

<210> SEQ ID NO 495
<211> LENGTH: 108
<212> TYPE: PRT
<213> ORGANISM: Artificial Sequence
<220> FEATURE:
<223> OTHER INFORMATION: Variable Light Chain Amino Sequence Lc47

<400> SEQUENCE: 495

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Val Ala Pro Leu
                85                  90                  95

Thr Phe Gly Gln Gly Thr Lys Val Glu Ile Lys Arg
                100                 105

<210> SEQ ID NO 496
<211> LENGTH: 116
<212> TYPE: PRT
<213> ORGANISM: Artificial Sequence
<220> FEATURE:
<223> OTHER INFORMATION: Variable Heavy Chain Amino Sequence Hc47

<400> SEQUENCE: 496

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ser Ile Asp Glu Met Gly Trp Gln Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
                100                 105                 110

Thr Val Ser Ser
            115

<210> SEQ ID NO 497
<211> LENGTH: 108
<212> TYPE: PRT
<213> ORGANISM: Artificial Sequence
<220> FEATURE:
<223> OTHER INFORMATION: Variable 4B2 Light Chain

<400> SEQUENCE: 497

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Leu Asp Ala Pro Pro
                85                  90                  95

Gln Phe Gly Gln Gly Thr Lys Val Glu Ile Lys Arg
                100                 105

<210> SEQ ID NO 498
```

```
<211> LENGTH: 119
<212> TYPE: PRT
<213> ORGANISM: Artificial Sequence
<220> FEATURE:
<223> OTHER INFORMATION: Variable 4B2 Heavy Chain

<400> SEQUENCE: 498

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Gln Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115

<210> SEQ ID NO 499
<211> LENGTH: 108
<212> TYPE: PRT
<213> ORGANISM: Artificial Sequence
<220> FEATURE:
<223> OTHER INFORMATION: Variable 4D11 Light Chain

<400> SEQUENCE: 499

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Val Ala Pro Pro
                85                  90                  95

Leu Phe Gly Gln Gly Thr Lys Val Glu Ile Lys Arg
            100                 105

<210> SEQ ID NO 500
<211> LENGTH: 119
<212> TYPE: PRT
<213> ORGANISM: Artificial Sequence
<220> FEATURE:
<223> OTHER INFORMATION: Variable 4D11 Heavy Chain

<400> SEQUENCE: 500

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Ala Met Ser Trp Val Arg Gln Ala Pro Gly Lys Gly Leu Glu Trp Val
            35                  40                  45

Ser Ser Ile Asp Pro Glu Gly Arg Gln Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ile Gly Gly Arg Ser Ala Phe Asp Tyr Trp Gly Gln Gly
            100                 105                 110

Thr Leu Val Thr Val Ser Ser
            115

<210> SEQ ID NO 501
<211> LENGTH: 108
<212> TYPE: PRT
<213> ORGANISM: Artificial Sequence
<220> FEATURE:
<223> OTHER INFORMATION: Variable 4E7 Light Chain

<400> SEQUENCE: 501

Asp Ile Gln Met Thr Gln Ser Pro Ser Ser Leu Ser Ala Ser Val Gly
 1                   5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Leu Val Ala Pro Leu
                 85                  90                  95

Thr Phe Gly Gln Gly Thr Lys Val Glu Ile Lys Arg
            100                 105

<210> SEQ ID NO 502
<211> LENGTH: 116
<212> TYPE: PRT
<213> ORGANISM: Artificial Sequence
<220> FEATURE:
<223> OTHER INFORMATION: Variable 4E7 Heavy Chain

<400> SEQUENCE: 502

Glu Val Gln Leu Leu Glu Ser Gly Gly Gly Leu Val Gln Pro Gly Gly
 1                   5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
            35                  40                  45

Ser Ser Ile Glu Glu Met Gly Trp Gln Thr Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Ala Ala Ala Phe Asp Tyr Trp Gly Gln Gly Thr Leu Val
            100                 105                 110
```

Thr Val Ser Ser
        115

<210> SEQ ID NO 503
<211> LENGTH: 108
<212> TYPE: PRT
<213> ORGANISM: Artificial Sequence
<220> FEATURE:
<223> OTHER INFORMATION: Variable 4E11 Light Chain

<400> SEQUENCE: 503

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Asp Ala Pro Leu
                85                  90                  95

Met Phe Gly Gln Gly Thr Lys Val Glu Ile Lys Arg
            100                 105

<210> SEQ ID NO 504
<211> LENGTH: 119
<212> TYPE: PRT
<213> ORGANISM: Artificial Sequence
<220> FEATURE:
<223> OTHER INFORMATION: Variable 4E11 Heavy Chain

<400> SEQUENCE: 504

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Glu Pro Met Gly Gln Leu Thr Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser
        115

<210> SEQ ID NO 505
<211> LENGTH: 108
<212> TYPE: PRT
<213> ORGANISM: Artificial Sequence
<220> FEATURE:
<223> OTHER INFORMATION: Variable 6B7 Light Chain

<400> SEQUENCE: 505

-continued

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Leu Val Ala Pro Leu
            85                  90                  95

Thr Phe Gly Gln Gly Thr Lys Val Glu Ile Lys Arg
            100                 105

<210> SEQ ID NO 506
<211> LENGTH: 116
<212> TYPE: PRT
<213> ORGANISM: Artificial Sequence
<220> FEATURE:
<223> OTHER INFORMATION: Variable 6B7 Heavy Chain

<400> SEQUENCE: 506

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Glu Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Ser Ala Ala Ala Phe Asp Tyr Trp Gly Gln Gly Thr Leu Val
            100                 105                 110

Thr Val Ser Ser
        115

<210> SEQ ID NO 507
<211> LENGTH: 108
<212> TYPE: PRT
<213> ORGANISM: Artificial Sequence
<220> FEATURE:
<223> OTHER INFORMATION: Variable 6F8 Light Chain

<400> SEQUENCE: 507

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

-continued

Glu Asp Phe Ala Thr Tyr Tyr Cys Gln Gln Ala Leu Val Ala Pro Leu
                85                  90                  95

Thr Phe Gly Gln Gly Thr Lys Val Glu Ile Lys Arg
            100                 105

<210> SEQ ID NO 508
<211> LENGTH: 116
<212> TYPE: PRT
<213> ORGANISM: Artificial Sequence
<220> FEATURE:
<223> OTHER INFORMATION: Variable 6F8 Heavy Chain

<400> SEQUENCE: 508

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Glu Met Gly Trp Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Ala Ala Phe Asp Tyr Trp Gly Gln Gly Thr Leu Val
            100                 105                 110

Thr Val Ser Ser
        115

<210> SEQ ID NO 509
<211> LENGTH: 214
<212> TYPE: PRT
<213> ORGANISM: Artificial Sequence
<220> FEATURE:
<223> OTHER INFORMATION: 4D11 Light Chain

<400> SEQUENCE: 509

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Val Ala Pro Pro
                85                  90                  95

Leu Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln

```
            145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 510
<211> LENGTH: 449
<212> TYPE: PRT
<213> ORGANISM: Artificial Sequence
<220> FEATURE:
<223> OTHER INFORMATION: 4D11 Heavy Chain

<400> SEQUENCE: 510

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
```

```
                290                 295                 300
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 511
<211> LENGTH: 449
<212> TYPE: PRT
<213> ORGANISM: Artificial Sequence
<220> FEATURE:
<223> OTHER INFORMATION: 4D11v2 Heavy Chain

<400> SEQUENCE: 511

Glu Val His Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ser Ile Asp Pro Glu Gly Arg Gln Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205
```

```
Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 512
<211> LENGTH: 214
<212> TYPE: PRT
<213> ORGANISM: Artificial Sequence
<220> FEATURE:
<223> OTHER INFORMATION: 4D11v2 Light Chain
<220> FEATURE:
<221> NAME/KEY: misc_feature
<222> LOCATION: (182)..(182)
<223> OTHER INFORMATION: Xaa may be any amino acid

<400> SEQUENCE: 512

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Val Ala Pro Pro
                85                  90                  95
```

-continued

```
Leu Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Xaa Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 513
<211> LENGTH: 6
<212> TYPE: PRT
<213> ORGANISM: Artificial Sequence
<220> FEATURE:
<223> OTHER INFORMATION: masking moiety

<400> SEQUENCE: 513

Cys Ile Ser Pro Arg Gly
1               5

<210> SEQ ID NO 514
<211> LENGTH: 8
<212> TYPE: PRT
<213> ORGANISM: Artificial Sequence
<220> FEATURE:
<223> OTHER INFORMATION: masking moiety

<400> SEQUENCE: 514

Cys Ile Ser Pro Arg Gly Cys Gly
1               5

<210> SEQ ID NO 515
<211> LENGTH: 15
<212> TYPE: PRT
<213> ORGANISM: Artificial Sequence
<220> FEATURE:
<223> OTHER INFORMATION: masking moiety

<400> SEQUENCE: 515

Cys Ile Ser Pro Arg Gly Cys Pro Asp Gly Pro Tyr Val Met Tyr
1               5                   10                  15

<210> SEQ ID NO 516
<211> LENGTH: 14
<212> TYPE: PRT
<213> ORGANISM: Artificial Sequence
<220> FEATURE:
<223> OTHER INFORMATION: masking moiety

<400> SEQUENCE: 516

Cys Ile Ser Pro Arg Gly Cys Pro Asp Gly Pro Tyr Val Met
1               5                   10

<210> SEQ ID NO 517
```

<211> LENGTH: 15
<212> TYPE: PRT
<213> ORGANISM: Artificial Sequence
<220> FEATURE:
<223> OTHER INFORMATION: masking moiety

<400> SEQUENCE: 517

Cys Ile Ser Pro Arg Gly Cys Glu Pro Gly Thr Tyr Val Pro Thr
1 5 10 15

<210> SEQ ID NO 518
<211> LENGTH: 15
<212> TYPE: PRT
<213> ORGANISM: Artificial Sequence
<220> FEATURE:
<223> OTHER INFORMATION: masking moiety

<400> SEQUENCE: 518

Cys Ile Ser Pro Arg Gly Cys Pro Gly Gln Ile Trp His Pro Pro
1 5 10 15

<210> SEQ ID NO 519
<211> LENGTH: 15
<212> TYPE: PRT
<213> ORGANISM: Artificial Sequence
<220> FEATURE:
<223> OTHER INFORMATION: masking moiety

<400> SEQUENCE: 519

Gly Ser His Cys Leu Ile Pro Ile Asn Met Gly Ala Pro Ser Cys
1 5 10 15

<210> SEQ ID NO 520
<211> LENGTH: 32
<212> TYPE: PRT
<213> ORGANISM: Artificial Sequence
<220> FEATURE:
<223> OTHER INFORMATION: masking moiety

<400> SEQUENCE: 520

Cys Ile Ser Pro Arg Gly Cys Gly Gly Ser Ser Ala Ser Gln Ser Gly
1 5 10 15

Gln Gly Ser His Cys Leu Ile Pro Ile Asn Met Gly Ala Pro Ser Cys
20 25 30

<210> SEQ ID NO 521
<211> LENGTH: 19
<212> TYPE: PRT
<213> ORGANISM: Artificial Sequence
<220> FEATURE:
<223> OTHER INFORMATION: masking moiety

<400> SEQUENCE: 521

Cys Asn His His Tyr Phe Tyr Thr Cys Gly Cys Ile Ser Pro Arg Gly
1 5 10 15

Cys Pro Gly

<210> SEQ ID NO 522
<211> LENGTH: 19
<212> TYPE: PRT
<213> ORGANISM: Artificial Sequence
<220> FEATURE:
<223> OTHER INFORMATION: masking moiety

<400> SEQUENCE: 522

Ala Asp His Val Phe Trp Gly Ser Tyr Gly Cys Ile Ser Pro Arg Gly

```
1               5                   10                  15

Cys Pro Gly

<210> SEQ ID NO 523
<211> LENGTH: 19
<212> TYPE: PRT
<213> ORGANISM: Artificial Sequence
<220> FEATURE:
<223> OTHER INFORMATION: masking moiety

<400> SEQUENCE: 523

Cys His His Val Tyr Trp Gly His Cys Gly Cys Ile Ser Pro Arg Gly
1               5                   10                  15

Cys Pro Gly

<210> SEQ ID NO 524
<211> LENGTH: 19
<212> TYPE: PRT
<213> ORGANISM: Artificial Sequence
<220> FEATURE:
<223> OTHER INFORMATION: masking moiety

<400> SEQUENCE: 524

Cys Pro His Phe Thr Thr Thr Ser Cys Gly Cys Ile Ser Pro Arg Gly
1               5                   10                  15

Cys Pro Gly

<210> SEQ ID NO 525
<211> LENGTH: 19
<212> TYPE: PRT
<213> ORGANISM: Artificial Sequence
<220> FEATURE:
<223> OTHER INFORMATION: masking moiety

<400> SEQUENCE: 525

Cys Asn His His Tyr His Tyr Tyr Cys Gly Cys Ile Ser Pro Arg Gly
1               5                   10                  15

Cys Pro Gly

<210> SEQ ID NO 526
<211> LENGTH: 19
<212> TYPE: PRT
<213> ORGANISM: Artificial Sequence
<220> FEATURE:
<223> OTHER INFORMATION: masking moiety

<400> SEQUENCE: 526

Cys

<210> SEQ ID NO 528
<211> LENGTH: 19
<212> TYPE: PRT
<213> ORGANISM: Artificial Sequence
<220> FEATURE:
<223> OTHER INFORMATION: masking moiety

<400> SEQUENCE: 528

Cys Asn His Val Tyr Phe Gly Thr Cys Gly Cys Ile Ser Pro Arg Gly
1               5                   10                  15

Cys Pro Gly

<210> SEQ ID NO 529
<211> LENGTH: 19
<212> TYPE: PRT
<213> ORGANISM: Artificial Sequence
<220> FEATURE:
<223> OTHER INFORMATION: masking moiety

<400> SEQUENCE: 529

Cys Asn His Phe Thr Leu Thr Thr Cys Gly Cys Ile Ser Pro Arg Gly
1               5                   10                  15

Cys Pro Gly

<210> SEQ ID NO 530
<211> LENGTH: 19
<212> TYPE: PRT
<213> ORGANISM: Artificial Sequence
<220> FEATURE:
<223> OTHER INFORMATION: masking moiety

<400> SEQUENCE: 530

Cys His His Phe Thr Leu Thr Thr Cys Gly Cys Ile Ser Pro Arg Gly
1               5                   10                  15

Cys Pro Gly

<210> SEQ ID NO 531
<211> LENGTH: 18
<212> TYPE: PRT
<213> ORGANISM: Artificial Sequence
<220> FEATURE:
<223> OTHER INFORMATION: masking moiety

<400> SEQUENCE: 531

Tyr Asn Pro Cys Ala Thr Pro Met Cys Cys Ile Ser Pro Arg Gly Cys
1               5                   10                  15

Pro Gly

<210> SEQ ID NO 532
<211> LENGTH: 18
<212> TYPE: PRT
<213> ORGANISM: Artificial Sequence
<220> FEATURE:
<223> OTHER INFORMATION: masking moiety

<400> SEQUENCE: 532

Cys Asn His His Tyr Phe Tyr Thr Cys Gly Cys Ile Ser Pro Arg Gly
1               5                   10                  15

Cys Gly

<210> SEQ ID NO 533
<211> LENGTH: 18
<212> TYPE: PRT

<213> ORGANISM: Artificial Sequence
<220> FEATURE:
<223> OTHER INFORMATION: masking moiety

<400> SEQUENCE: 533

Cys Asn His His Tyr His Tyr Tyr Cys Gly Cys Ile Ser Pro Arg Gly
1               5                   10                  15

Cys Gly

<210> SEQ ID NO 534
<211> LENGTH: 18
<212> TYPE: PRT
<213> ORGANISM: Artificial Sequence
<220> FEATURE:
<223> OTHER INFORMATION: masking moiety

<400> SEQUENCE: 534

Cys Asn His Val Tyr Phe Gly Thr Cys Gly Cys Ile Ser Pro Arg Gly
1               5                   10                  15

Cys Gly

<210> SEQ ID NO 535
<211> LENGTH: 18
<212> TYPE: PRT
<213> ORGANISM: Artificial Sequence
<220> FEATURE:
<223> OTHER INFORMATION: masking moiety

<400> SEQUENCE: 535

Cys His His Val Tyr Trp Gly His Cys Gly Cys Ile Ser Pro Arg Gly
1               5                   10                  15

Cys Gly

<210> SEQ ID NO 536
<211> LENGTH: 18
<212> TYPE: PRT
<213> ORGANISM: Artificial Sequence
<220> FEATURE:
<223> OTHER INFORMATION: masking moiety

<400> SEQUENCE: 536

Cys Pro His Phe Thr Thr Thr Ser Cys Gly Cys Ile Ser Pro Arg Gly
1               5                   10                  15

Cys Gly

<210> SEQ ID NO 537
<211> LENGTH: 18
<212> TYPE: PRT
<213> ORGANISM: Artificial Sequence
<220> FEATURE:
<223> OTHER INFORMATION: masking moiety

<400> SEQUENCE: 537

Cys Asn His Phe Thr Leu Thr Thr Cys Gly Cys Ile Ser Pro Arg Gly
1               5                   10                  15

Cys Gly

<210> SEQ ID NO 538
<211> LENGTH: 18
<212> TYPE: PRT
<213> ORGANISM: Artificial Sequence
<220> FEATURE:
<223> OTHER INFORMATION: masking moiety

<400> SEQUENCE: 538

Cys His His Phe Thr Leu Thr Thr Cys Gly Cys Ile Ser Pro Arg Gly
1 5 10 15

Cys Gly

<210> SEQ ID NO 539
<211> LENGTH: 18
<212> TYPE: PRT
<213> ORGANISM: Artificial Sequence
<220> FEATURE:
<223> OTHER INFORMATION: masking moiety

<400> SEQUENCE: 539

Cys Pro Tyr Tyr Thr Leu Ser Tyr Cys Gly Cys Ile Ser Pro Arg Gly
1 5 10 15

Cys Gly

<210> SEQ ID NO 540
<211> LENGTH: 18
<212> TYPE: PRT
<213> ORGANISM: Artificial Sequence
<220> FEATURE:
<223> OTHER INFORMATION: masking moiety

<400> SEQUENCE: 540

Cys Pro His Val Ser Phe Gly Ser Cys Gly Cys Ile Ser Pro Arg Gly
1 5 10 15

Cys Gly

<210> SEQ ID NO 541
<211> LENGTH: 18
<212> TYPE: PRT
<213> ORGANISM: Artificial Sequence
<220> FEATURE:
<223> OTHER INFORMATION: masking moiety

<400> SEQUENCE: 541

Ala Asp His Val Phe Trp Gly Ser Tyr Gly Cys Ile Ser Pro Arg Gly
1 5 10 15

Cys Gly

<210> SEQ ID NO 542
<211> LENGTH: 17
<212> TYPE: PRT
<213> ORGANISM: Artificial Sequence
<220> FEATURE:
<223> OTHER INFORMATION: masking moiety

<400> SEQUENCE: 542

Tyr Asn Pro Cys Ala Thr Pro Met Cys Cys Ile Ser Pro Arg Gly Cys
1 5 10 15

Gly

<210> SEQ ID NO 543
<211> LENGTH: 18
<212> TYPE: PRT
<213> ORGANISM: Artificial Sequence
<220> FEATURE:
<223> OTHER INFORMATION: masking moiety

<400> SEQUENCE: 543

Cys His His Val Tyr Trp Gly His Cys Gly Cys Ile Ser Pro Arg Gly
1 5 10 15

Cys Gly

```
<210> SEQ ID NO 544
<211> LENGTH: 18
<212> TYPE: PRT
<213> ORGANISM: Artificial Sequence
<220> FEATURE:
<223> OTHER INFORMATION: masking moiety
<220> FEATURE:
<221> NAME/KEY: misc_feature
<222> LOCATION: (2)..(2)
<223> OTHER INFORMATION: Xaa may be Asn or Pro
<220> FEATURE:
<221> NAME/KEY: misc_feature
<222> LOCATION: (4)..(4)
<223> OTHER INFORMATION: Xaa may be His, Val or Phe
<220> FEATURE:
<221> NAME/KEY: misc_feature
<222> LOCATION: (5)..(5)
<223> OTHER INFORMATION: Xaa may be Tyr or Thr
<220> FEATURE:
<221> NAME/KEY: misc_feature
<222> LOCATION: (6)..(6)
<223> OTHER INFORMATION: Xaa may be Phe, Trp, Thr or Leu
<220> FEATURE:
<221> NAME/KEY: misc_feature
<222> LOCATION: (7)..(7)
<223> OTHER INFORMATION: Xaa may be Tyr, Gly, Thr or Ser
<220> FEATURE:
<221> NAME/KEY: misc_feature
<222> LOCATION: (8)..(8)
<223> OTHER INFORMATION: Xaa may be Thr, Ser, Tyr or His

<400> SEQUENCE: 544

Cys Xaa His Xaa Xaa Xaa Xaa Xaa Cys Gly Cys Ile Ser Pro Arg Gly
1               5                   10                  15

Cys Gly

<210> SEQ ID NO 545
<211> LENGTH: 15
<212> TYPE: PRT
<213> ORGANISM: Artificial Sequence
<220> FEATURE:
<223> OTHER INFORMATION: masking moiety

<400> SEQUENCE: 545

Cys Ile Ser Pro Arg Gly Cys Gly Gln Pro Ile Pro Ser Val Lys
1               5                   10                  15

<210> SEQ ID NO 546
<211> LENGTH: 15
<212> TYPE: PRT
<213> ORGANISM: Artificial Sequence
<220> FEATURE:
<223> OTHER INFORMATION: masking moiety

<400> SEQUENCE: 546

Cys Ile Ser Pro Arg Gly Cys Thr Gln Pro Tyr His Val Ser Arg
1               5                   10                  15

<210> SEQ ID NO 547
<211> LENGTH: 15
<212> TYPE: PRT
<213> ORGANISM: Artificial Sequence
<220> FEATURE:
<223> OTHER INFORMATION: masking moiety

<400> SEQUENCE: 547

Cys Ile Ser Pro Arg Gly Cys Asn Ala Val Ser Gly Leu Gly Ser
```

<210> SEQ ID NO 548
<211> LENGTH: 26
<212> TYPE: PRT
<213> ORGANISM: Artificial Sequence
<220> FEATURE:
<223> OTHER INFORMATION: masking moiety

<400> SEQUENCE: 548

```
Gln Gly Gln Ser Gly Gln Gly Gln Gln Gln Trp Cys Asn Ile Trp Ile
1               5                   10                  15
Asn Gly Gly Asp Cys Arg Gly Trp Asn Gly
            20                  25
```

<210> SEQ ID NO 549
<211> LENGTH: 15
<212> TYPE: PRT
<213> ORGANISM: Artificial Sequence
<220> FEATURE:
<223> OTHER INFORMATION: masking moiety

<400> SEQUENCE: 549

```
Pro Trp Cys Met Gln Arg Gln Asp Phe Leu Arg Cys Pro Gln Pro
1               5                   10                  15
```

<210> SEQ ID NO 550
<211> LENGTH: 15
<212> TYPE: PRT
<213> ORGANISM: Artificial Sequence
<220> FEATURE:
<223> OTHER INFORMATION: masking moiety

<400> SEQUENCE: 550

```
Gln Leu Gly Leu Pro Ala Tyr Met Cys Thr Phe Glu Cys Leu Arg
1               5                   10                  15
```

<210> SEQ ID NO 551
<211> LENGTH: 15
<212> TYPE: PRT
<213> ORGANISM: Artificial Sequence
<220> FEATURE:
<223> OTHER INFORMATION: masking moiety

<400> SEQUENCE: 551

```
Cys Asn Leu Trp Val Ser Gly Gly Asp Cys Gly Gly Leu Gln Gly
1               5                   10                  15
```

<210> SEQ ID NO 552
<211> LENGTH: 15
<212> TYPE: PRT
<213> ORGANISM: Artificial Sequence
<220> FEATURE:
<223> OTHER INFORMATION: masking moiety

<400> SEQUENCE: 552

```
Ser Cys Ser Leu Trp Thr Ser Gly Ser Cys Leu Pro His Ser Pro
1               5                   10                  15
```

<210> SEQ ID NO 553
<211> LENGTH: 15
<212> TYPE: PRT
<213> ORGANISM: Artificial Sequence
<220> FEATURE:
<223> OTHER INFORMATION: masking moiety

<400> SEQUENCE: 553

```
Tyr Cys Leu Gln Leu Pro His Tyr Met Gln Ala Met Cys Gly Arg
1               5                   10                  15

<210> SEQ ID NO 554
<211> LENGTH: 15
<212> TYPE: PRT
<213> ORGANISM: Artificial Sequence
<220> FEATURE:
<223> OTHER INFORMATION: masking moiety

<400> SEQUENCE: 554

Cys Phe Leu Tyr Ser Cys Thr Asp Val Ser Tyr Trp Asn Asn Thr
1               5                   10                  15

<210> SEQ ID NO 555
<211> LENGTH: 15
<212> TYPE: PRT
<213> ORGANISM: Artificial Sequence
<220> FEATURE:
<223> OTHER INFORMATION: masking moiety

<400> SEQUENCE: 555

Pro Trp Cys Met Gln Arg Gln Asp Tyr Leu Arg Cys Pro Gln Pro
1               5                   10                  15

<210> SEQ ID NO 556
<211> LENGTH: 15
<212> TYPE: PRT
<213> ORGANISM: Artificial Sequence
<220> FEATURE:
<223> OTHER INFORMATION: masking moiety

<400> SEQUENCE: 556

Cys Asn Leu Trp Ile Ser Gly Gly Asp Cys Arg Gly Leu Ala Gly
1               5                   10                  15

<210> SEQ ID NO 557
<211> LENGTH: 15
<212> TYPE: PRT
<213> ORGANISM: Artificial Sequence
<220> FEATURE:
<223> OTHER INFORMATION: masking moiety

<400> SEQUENCE: 557

Cys Asn Leu Trp Val Ser Gly Gly Asp Cys Arg Gly Val Gln Gly
1               5                   10                  15

<210> SEQ ID NO 558
<211> LENGTH: 15
<212> TYPE: PRT
<213> ORGANISM: Artificial Sequence
<220> FEATURE:
<223> OTHER INFORMATION: masking moiety

<400> SEQUENCE: 558

Cys Asn Leu Trp Val Ser Gly Gly Asp Cys Arg Gly Leu Arg Gly
1               5                   10                  15

<210> SEQ ID NO 559
<211> LENGTH: 15
<212> TYPE: PRT
<213> ORGANISM: Artificial Sequence
<220> FEATURE:
<223> OTHER INFORMATION: masking moiety

<400> SEQUENCE: 559
```

```
Cys Asn Leu Trp Ile Ser Gly Gly Asp Cys Arg Gly Leu Pro Gly
1               5                   10                  15

<210> SEQ ID NO 560
<211> LENGTH: 15
<212> TYPE: PRT
<213> ORGANISM: Artificial Sequence
<220> FEATURE:
<223> OTHER INFORMATION: masking moiety

<400> SEQUENCE: 560

Cys Asn Leu Trp Val Ser Gly Gly Asp Cys Arg Asp Ala Pro Trp
1               5                   10                  15

<210> SEQ ID NO 561
<211> LENGTH: 15
<212> TYPE: PRT
<213> ORGANISM: Artificial Sequence
<220> FEATURE:
<223> OTHER INFORMATION: masking moiety

<400> SEQUENCE: 561

Cys Asn Leu Trp Val Ser Gly Gly Asp Cys Arg Asp Leu Leu Gly
1               5                   10                  15

<210> SEQ ID NO 562
<211> LENGTH: 15
<212> TYPE: PRT
<213> ORGANISM: Artificial Sequence
<220> FEATURE:
<223> OTHER INFORMATION: masking moiety

<400> SEQUENCE: 562

Cys Asn Leu Trp Val Ser Gly Gly Asp Cys Arg Gly Leu Gln Gly
1               5                   10                  15

<210> SEQ ID NO 563
<211> LENGTH: 15
<212> TYPE: PRT
<213> ORGANISM: Artificial Sequence
<220> FEATURE:
<223> OTHER INFORMATION: masking moiety

<400> SEQUENCE: 563

Cys Asn Leu Trp Leu His Gly Gly Asp Cys Arg Gly Trp Gln Gly
1               5                   10                  15

<210> SEQ ID NO 564
<211> LENGTH: 15
<212> TYPE: PRT
<213> ORGANISM: Artificial Sequence
<220> FEATURE:
<223> OTHER INFORMATION: masking moiety

<400> SEQUENCE: 564

Cys Asn Ile Trp Leu Val Gly Gly Asp Cys Arg Gly Trp Gln Gly
1               5                   10                  15

<210> SEQ ID NO 565
<211> LENGTH: 15
<212> TYPE: PRT
<213> ORGANISM: Artificial Sequence
<220> FEATURE:
<223> OTHER INFORMATION: masking moiety

<400> SEQUENCE: 565

Cys Thr Thr Trp Phe Cys Gly Gly Asp Cys Gly Val Met Arg Gly
```

-continued

```
<210> SEQ ID NO 566
<211> LENGTH: 15
<212> TYPE: PRT
<213> ORGANISM: Artificial Sequence
<220> FEATURE:
<223> OTHER INFORMATION: masking moiety

<400> SEQUENCE: 566

Cys Asn Ile Trp Gly Pro Ser Val Asp Cys Gly Ala Leu Leu Gly
1               5                   10                  15

<210> SEQ ID NO 567
<211> LENGTH: 15
<212> TYPE: PRT
<213> ORGANISM: Artificial Sequence
<220> FEATURE:
<223> OTHER INFORMATION: masking moiety

<400> SEQUENCE: 567

Cys Asn Ile Trp Val Asn Gly Gly Asp Cys Arg Ser Phe Glu Gly
1               5                   10                  15

<210> SEQ ID NO 568
<211> LENGTH: 15
<212> TYPE: PRT
<213> ORGANISM: Artificial Sequence
<220> FEATURE:
<223> OTHER INFORMATION: masking moiety

<400> SEQUENCE: 568

Tyr Cys Leu Asn Leu Pro Arg Tyr Met Gln Asp Met Cys Trp Ala
1               5                   10                  15

<210> SEQ ID NO 569
<211> LENGTH: 15
<212> TYPE: PRT
<213> ORGANISM: Artificial Sequence
<220> FEATURE:
<223> OTHER INFORMATION: masking moiety

<400> SEQUENCE: 569

Tyr Cys Leu Ala Leu Pro His Tyr Met Gln Ala Asp Cys Ala Arg
1               5                   10                  15

<210> SEQ ID NO 570
<211> LENGTH: 15
<212> TYPE: PRT
<213> ORGANISM: Artificial Sequence
<220> FEATURE:
<223> OTHER INFORMATION: masking moiety

<400> SEQUENCE: 570

Cys Phe Leu Tyr Ser Cys Gly Asp Val Ser Tyr Trp Gly Ser Ala
1               5                   10                  15

<210> SEQ ID NO 571
<211> LENGTH: 15
<212> TYPE: PRT
<213> ORGANISM: Artificial Sequence
<220> FEATURE:
<223> OTHER INFORMATION: masking moiety

<400> SEQUENCE: 571

Cys Tyr Leu Tyr Ser Cys Thr Asp Ser Ala Phe Trp Asn Asn Arg
1               5                   10                  15
```

<210> SEQ ID NO 572
<211> LENGTH: 15
<212> TYPE: PRT
<213> ORGANISM: Artificial Sequence
<220> FEATURE:
<223> OTHER INFORMATION: masking moiety

<400> SEQUENCE: 572

Cys Tyr Leu Tyr Ser Cys Asn Asp Val Ser Tyr Trp Ser Asn Thr
1 5 10 15

<210> SEQ ID NO 573
<211> LENGTH: 12
<212> TYPE: PRT
<213> ORGANISM: Artificial Sequence
<220> FEATURE:
<223> OTHER INFORMATION: masking moiety

<400> SEQUENCE: 573

Cys Phe Leu Tyr Ser Cys Thr Asp Val Ser Tyr Trp
1 5 10

<210> SEQ ID NO 574
<211> LENGTH: 15
<212> TYPE: PRT
<213> ORGANISM: Artificial Sequence
<220> FEATURE:
<223> OTHER INFORMATION: masking moiety

<400> SEQUENCE: 574

Cys Phe Leu Tyr Ser Cys Thr Asp Val Ala Tyr Trp Asn Ser Ala
1 5 10 15

<210> SEQ ID NO 575
<211> LENGTH: 15
<212> TYPE: PRT
<213> ORGANISM: Artificial Sequence
<220> FEATURE:
<223> OTHER INFORMATION: masking moiety

<400> SEQUENCE: 575

Cys Phe Leu Tyr Ser Cys Thr Asp Val Ser Tyr Trp Gly Asp Thr
1 5 10 15

<210> SEQ ID NO 576
<211> LENGTH: 15
<212> TYPE: PRT
<213> ORGANISM: Artificial Sequence
<220> FEATURE:
<223> OTHER INFORMATION: masking moiety

<400> SEQUENCE: 576

Cys Phe Leu Tyr Ser Cys Thr Asp Val Ser Tyr Trp Gly Asn Ser
1 5 10 15

<210> SEQ ID NO 577
<211> LENGTH: 15
<212> TYPE: PRT
<213> ORGANISM: Artificial Sequence
<220> FEATURE:
<223> OTHER INFORMATION: masking moiety

<400> SEQUENCE: 577

Cys Phe Leu Tyr Ser Cys Thr Asp Val Ala Tyr Trp Asn Asn Thr
1 5 10 15

```
<210> SEQ ID NO 578
<211> LENGTH: 18
<212> TYPE: PRT
<213> ORGANISM: Artificial Sequence
<220> FEATURE:
<223> OTHER INFORMATION: masking moiety

<400> SEQUENCE: 578

Cys Phe Leu Tyr Ser Cys Gly Asp Val Ser Tyr Trp Gly Asn Pro Gly
1               5                   10                  15

Leu Ser

<210> SEQ ID NO 579
<211> LENGTH: 15
<212> TYPE: PRT
<213> ORGANISM: Artificial Sequence
<220> FEATURE:
<223> OTHER INFORMATION: masking moiety

<400> SEQUENCE: 579

Cys Phe Leu Tyr Ser Cys Thr Asp Val Ala Tyr Trp Ser Gly Leu
1               5                   10                  15

<210> SEQ ID NO 580
<211> LENGTH: 15
<212> TYPE: PRT
<213> ORGANISM: Artificial Sequence
<220> FEATURE:
<223> OTHER INFORMATION: masking moiety

<400> SEQUENCE: 580

Cys Tyr Leu Tyr Ser Cys Thr Asp Gly Ser Tyr Trp Asn Ser Thr
1               5                   10                  15

<210> SEQ ID NO 581
<211> LENGTH: 15
<212> TYPE: PRT
<213> ORGANISM: Artificial Sequence
<220> FEATURE:
<223> OTHER INFORMATION: masking moiety

<400> SEQUENCE: 581

Cys Phe Leu Tyr Ser Cys Ser Asp Val Ser Tyr Trp Gly Asn Ile
1               5                   10                  15

<210> SEQ ID NO 582
<211> LENGTH: 12
<212> TYPE: PRT
<213> ORGANISM: Artificial Sequence
<220> FEATURE:
<223> OTHER INFORMATION: masking moiety

<400> SEQUENCE: 582

Cys Phe Leu Tyr Ser Cys Thr Asp Val Ala Tyr Trp
1               5                   10

<210> SEQ ID NO 583
<211> LENGTH: 15
<212> TYPE: PRT
<213> ORGANISM: Artificial Sequence
<220> FEATURE:
<223> OTHER INFORMATION: masking moiety

<400> SEQUENCE: 583

Cys Phe Leu Tyr Ser Cys Thr Asp Val Ser Tyr Trp Gly Ser Thr
1               5                   10                  15
```

<210> SEQ ID NO 584
<211> LENGTH: 15
<212> TYPE: PRT
<213> ORGANISM: Artificial Sequence
<220> FEATURE:
<223> OTHER INFORMATION: masking moiety

<400> SEQUENCE: 584

Cys Phe Leu Tyr Ser Cys Thr Asp Val Ala Tyr Trp Gly Asp Thr
1               5                   10                  15

<210> SEQ ID NO 585
<211> LENGTH: 20
<212> TYPE: PRT
<213> ORGANISM: Artificial Sequence
<220> FEATURE:
<223> OTHER INFORMATION: masking moiety

<400> SEQUENCE: 585

Gly Cys Asn Ile Trp Leu Asn Gly Gly Asp Cys Arg Gly Trp Val Asp
1               5                   10                  15

Pro Leu Gln Gly
            20

<210> SEQ ID NO 586
<211> LENGTH: 20
<212> TYPE: PRT
<213> ORGANISM: Artificial Sequence
<220> FEATURE:
<223> OTHER INFORMATION: masking moiety

<400> SEQUENCE: 586

Gly Cys Asn Ile Trp Leu Val Gly Gly Asp Cys Arg Gly Trp Ile Gly
1               5                   10                  15

Asp Thr Asn Gly
            20

<210> SEQ ID NO 587
<211> LENGTH: 20
<212> TYPE: PRT
<213> ORGANISM: Artificial Sequence
<220> FEATURE:
<223> OTHER INFORMATION: masking moiety

<400> SEQUENCE: 587

Gly Cys Asn Ile Trp Leu Val Gly Gly Asp Cys Arg Gly Trp Ile Glu
1               5                   10                  15

Asp Ser Asn Gly
            20

<210> SEQ ID NO 588
<211> LENGTH: 20
<212> TYPE: PRT
<213> ORGANISM: Artificial Sequence
<220> FEATURE:
<223> OTHER INFORMATION: masking moiety

<400> SEQUENCE: 588

Gly Cys Asn Ile Trp Ala Asn Gly Gly Asp Cys Arg Gly Trp Ile Asp
1               5                   10                  15

Asn Ile Asp Gly
            20

-continued

```
<210> SEQ ID NO 589
<211> LENGTH: 20
<212> TYPE: PRT
<213> ORGANISM: Artificial Sequence
<220> FEATURE:
<223> OTHER INFORMATION: masking moiety

<400> SEQUENCE: 589

Gly Cys Asn Ile Trp Leu Val Gly Gly Asp Cys Arg Gly Trp Leu Gly
1               5                   10                  15

Glu Ala Val Gly
            20

<210> SEQ ID NO 590
<211> LENGTH: 20
<212> TYPE: PRT
<213> ORGANISM: Artificial Sequence
<220> FEATURE:
<223> OTHER INFORMATION: masking moiety

<400> SEQUENCE: 590

Gly Cys Asn Ile Trp Leu Val Gly Gly Asp Cys Arg Gly Trp Leu Glu
1               5                   10                  15

Glu Ala Val Gly
            20

<210> SEQ ID NO 591
<211> LENGTH: 20
<212> TYPE: PRT
<213> ORGANISM: Artificial Sequence
<220> FEATURE:
<223> OTHER INFORMATION: masking moiety

<400> SEQUENCE: 591

Gly Gly Pro Ala Leu Cys Asn Ile Trp Leu Asn Gly Gly Asp Cys Arg
1               5                   10                  15

Gly Trp Ser Gly
            20

<210> SEQ ID NO 592
<211> LENGTH: 20
<212> TYPE: PRT
<213> ORGANISM: Artificial Sequence
<220> FEATURE:
<223> OTHER INFORMATION: masking moiety

<400> SEQUENCE: 592

Gly Ala Pro Val Phe Cys Asn Ile Trp Leu Asn Gly Gly Asp Cys Arg
1               5                   10                  15

Gly Trp Met Gly
            20

<210> SEQ ID NO 593
<211> LENGTH: 20
<212> TYPE: PRT
<213> ORGANISM: Artificial Sequence
<220> FEATURE:
<223> OTHER INFORMATION: masking moiety

<400> SEQUENCE: 593

Gly Gln Gln Gln Trp Cys Asn Ile Trp Ile Asn Gly Gly Asp Cys Arg
1               5                   10                  15

Gly Trp Asn Gly
            20
```

<210> SEQ ID NO 594
<211> LENGTH: 20
<212> TYPE: PRT
<213> ORGANISM: Artificial Sequence
<220> FEATURE:
<223> OTHER INFORMATION: masking moiety

<400> SEQUENCE: 594

Gly Lys Ser Glu Phe Cys Asn Ile Trp Leu Asn Gly Gly Asp Cys Arg
1 5 10 15

Gly Trp Ile Gly
20

<210> SEQ ID NO 595
<211> LENGTH: 20
<212> TYPE: PRT
<213> ORGANISM: Artificial Sequence
<220> FEATURE:
<223> OTHER INFORMATION: masking moiety

<400> SEQUENCE: 595

Gly Thr Pro Gly Gly Cys Asn Ile Trp Ala Asn Gly Gly Asp Cys Arg
1 5 10 15

Gly Trp Glu Gly
20

<210> SEQ ID NO 596
<211> LENGTH: 20
<212> TYPE: PRT
<213> ORGANISM: Artificial Sequence
<220> FEATURE:
<223> OTHER INFORMATION: masking moiety

<400> SEQUENCE: 596

Gly Ala Ser Gln Tyr Cys Asn Leu Trp Ile Asn Gly Gly Asp Cys Arg
1 5 10 15

Gly Trp Arg Gly
20

<210> SEQ ID NO 597
<211> LENGTH: 18
<212> TYPE: PRT
<213> ORGANISM: Artificial Sequence
<220> FEATURE:
<223> OTHER INFORMATION: masking moiety

<400> SEQUENCE: 597

Gly Cys Asn Ile Trp Leu Val Gly Gly Asp Cys Arg Pro Trp Val Glu
1 5 10 15

Gly Gly

<210> SEQ ID NO 598
<211> LENGTH: 18
<212> TYPE: PRT
<213> ORGANISM: Artificial Sequence
<220> FEATURE:
<223> OTHER INFORMATION: masking moiety

<400> SEQUENCE: 598

Gly Cys Asn Ile Trp Ala Val Gly Gly Asp Cys Arg Pro Phe Val Asp
1 5 10 15

Gly Gly

```
<210> SEQ ID NO 599
<211> LENGTH: 18
<212> TYPE: PRT
<213> ORGANISM: Artificial Sequence
<220> FEATURE:
<223> OTHER INFORMATION: masking moiety

<400> SEQUENCE: 599

Gly Cys Asn Ile Trp Leu Asn Gly Gly Asp Cys Arg Ala Trp Val Asp
1               5                   10                  15

Thr Gly

<210> SEQ ID NO 600
<211> LENGTH: 18
<212> TYPE: PRT
<213> ORGANISM: Artificial Sequence
<220> FEATURE:
<223> OTHER INFORMATION: masking moiety

<400> SEQUENCE: 600

Gly Cys Asn Ile Trp Ile Val Gly Gly Asp Cys Arg Pro Phe Ile Asn
1               5                   10                  15

Asp Gly

<210> SEQ ID NO 601
<211> LENGTH: 18
<212> TYPE: PRT
<213> ORGANISM: Artificial Sequence
<220> FEATURE:
<223> OTHER INFORMATION: masking moiety

<400> SEQUENCE: 601

Gly Cys Asn Ile Trp Leu Asn Gly Gly Asp Cys Arg Pro Val Val Phe
1               5                   10                  15

Gly Gly

<210> SEQ ID NO 602
<211> LENGTH: 18
<212> TYPE: PRT
<213> ORGANISM: Artificial Sequence
<220> FEATURE:
<223> OTHER INFORMATION: masking moiety

<400> SEQUENCE: 602

Gly Cys Asn Ile Trp Leu Ser Gly Gly Asp Cys Arg Met Phe Met Asn
1               5                   10                  15

Glu Gly

<210> SEQ ID NO 603
<211> LENGTH: 18
<212> TYPE: PRT
<213> ORGANISM: Artificial Sequence
<220> FEATURE:
<223> OTHER INFORMATION: masking moiety

<400> SEQUENCE: 603

Gly Cys Asn Ile Trp Val Asn Gly Gly Asp Cys Arg Ser Phe Val Tyr
1               5                   10                  15

Ser Gly

<210> SEQ ID NO 604
<211> LENGTH: 18
<212> TYPE: PRT
<213> ORGANISM: Artificial Sequence
```

```
<220> FEATURE:
<223> OTHER INFORMATION: masking moiety

<400> SEQUENCE: 604

Gly Cys Asn Ile Trp Leu Asn Gly Gly Asp Cys Arg Gly Trp Glu Ala
1               5                   10                  15

Ser Gly

<210> SEQ ID NO 605
<211> LENGTH: 18
<212> TYPE: PRT
<213> ORGANISM: Artificial Sequence
<220> FEATURE:
<223> OTHER INFORMATION: masking moiety

<400> SEQUENCE: 605

Gly Cys Asn Ile Trp Ala His Gly Gly Asp Cys Arg Gly Phe Ile Glu
1               5                   10                  15

Pro Gly

<210> SEQ ID NO 606
<211> LENGTH: 18
<212> TYPE: PRT
<213> ORGANISM: Artificial Sequence
<220> FEATURE:
<223> OTHER INFORMATION: masking moiety

<400> SEQUENCE: 606

Gly Cys Asn Ile Trp Leu Asn Gly Gly Asp Cys Arg Thr Phe Val Ala
1               5                   10                  15

Ser Gly

<210> SEQ ID NO 607
<211> LENGTH: 18
<212> TYPE: PRT
<213> ORGANISM: Artificial Sequence
<220> FEATURE:
<223> OTHER INFORMATION: masking moiety

<400> SEQUENCE: 607

Gly Cys Asn Ile Trp Ala His Gly Gly Asp Cys Arg Gly Phe Ile Glu
1               5                   10                  15

Pro Gly

<210> SEQ ID NO 608
<211> LENGTH: 18
<212> TYPE: PRT
<213> ORGANISM: Artificial Sequence
<220> FEATURE:
<223> OTHER INFORMATION: masking moiety

<400> SEQUENCE: 608

Gly Phe Leu Glu Asn Cys Asn Ile Trp Leu Asn Gly Gly Asp Cys Arg
1               5                   10                  15

Thr Gly

<210> SEQ ID NO 609
<211> LENGTH: 18
<212> TYPE: PRT
<213> ORGANISM: Artificial Sequence
<220> FEATURE:
<223> OTHER INFORMATION: masking moiety

<400> SEQUENCE: 609
```

```
Gly Ile Tyr Glu Asn Cys Asn Ile Trp Leu Asn Gly Gly Asp Cys Arg
1               5                   10                  15

Met Gly

<210> SEQ ID NO 610
<211> LENGTH: 18
<212> TYPE: PRT
<213> ORGANISM: Artificial Sequence
<220> FEATURE:
<223> OTHER INFORMATION: masking moiety

<400> SEQUENCE: 610

Gly Ile Pro Asp Asn Cys Asn Ile Trp Ile Asn Gly Gly Asp Cys Arg
1               5                   10                  15

Tyr Gly

<210> SEQ ID NO 611
<211> LENGTH: 21
<212> TYPE: PRT
<213> ORGANISM: Artificial Sequence
<220> FEATURE:
<223> OTHER INFORMATION: masking moiety

<400> SEQUENCE: 611

Gln Gly Gln Ser Gly Gln Tyr Gly Ser Cys Ser Trp Asn Tyr Val His
1               5                   10                  15

Ile Phe Met Asp Cys
            20

<210> SEQ ID NO 612
<211> LENGTH: 21
<212> TYPE: PRT
<213> ORGANISM: Artificial Sequence
<220> FEATURE:
<223> OTHER INFORMATION: masking moiety

<400> SEQUENCE: 612

Gln Gly Gln Ser Gly Gln Gly Asp Phe Asp Ile Pro Phe Pro Ala His
1               5                   10                  15

Trp Val Pro Ile Thr
            20

<210> SEQ ID NO 613
<211> LENGTH: 24
<212> TYPE: PRT
<213> ORGANISM: Artificial Sequence
<220> FEATURE:
<223> OTHER INFORMATION: masking moiety

<400> SEQUENCE: 613

Gln Gly Gln Ser Gly Gln Met Gly Val Pro Ala Gly Cys Val Trp Asn
1               5                   10                  15

Tyr Ala His Ile Phe Met Asp Cys
            20

<210> SEQ ID NO 614
<211> LENGTH: 15
<212> TYPE: PRT
<213> ORGANISM: Artificial Sequence
<220> FEATURE:
<223> OTHER INFORMATION: masking moiety

<400> SEQUENCE: 614
```

Tyr Arg Ser Cys Asn Trp Asn Tyr Val Ser Ile Phe Leu Asp Cys
1 5 10 15

<210> SEQ ID NO 615
<211> LENGTH: 16
<212> TYPE: PRT
<213> ORGANISM: Artificial Sequence
<220> FEATURE:
<223> OTHER INFORMATION: masking moiety

<400> SEQUENCE: 615

Pro Gly Ala Phe Asp Ile Pro Phe Pro Ala His Trp Val Pro Asn Thr
1 5 10 15

<210> SEQ ID NO 616
<211> LENGTH: 15
<212> TYPE: PRT
<213> ORGANISM: Artificial Sequence
<220> FEATURE:
<223> OTHER INFORMATION: masking moiety

<400> SEQUENCE: 616

Glu Ser Ser Cys Val Trp Asn Tyr Val His Ile Tyr Met Asp Cys
1 5 10 15

<210> SEQ ID NO 617
<211> LENGTH: 15
<212> TYPE: PRT
<213> ORGANISM: Artificial Sequence
<220> FEATURE:
<223> OTHER INFORMATION: masking moiety

<400> SEQUENCE: 617

Tyr Pro Gly Cys Lys Trp Asn Tyr Asp Arg Ile Phe Leu Asp Cys
1 5 10 15

<210> SEQ ID NO 618
<211> LENGTH: 15
<212> TYPE: PRT
<213> ORGANISM: Artificial Sequence
<220> FEATURE:
<223> OTHER INFORMATION: masking moiety

<400> SEQUENCE: 618

Tyr Arg Thr Cys Ser Trp Asn Tyr Val Gly Ile Phe Leu Asp Cys
1 5 10 15

<210> SEQ ID NO 619
<211> LENGTH: 15
<212> TYPE: PRT
<213> ORGANISM: Artificial Sequence
<220> FEATURE:
<223> OTHER INFORMATION: masking moiety

<400> SEQUENCE: 619

Tyr Gly Ser Cys Ser Trp Asn Tyr Val His Ile Phe Met Asp Cys
1 5 10 15

<210> SEQ ID NO 620
<211> LENGTH: 15
<212> TYPE: PRT
<213> ORGANISM: Artificial Sequence
<220> FEATURE:
<223> OTHER INFORMATION: masking moiety

<400> SEQUENCE: 620

Tyr Gly Ser Cys Ser Trp Asn Tyr Val His Ile Phe Leu Asp Cys 1 5 10 15

<210> SEQ ID NO 621
<211> LENGTH: 15
<212> TYPE: PRT
<213> ORGANISM: Artificial Sequence
<220> FEATURE:
<223> OTHER INFORMATION: masking moiety

<400> SEQUENCE: 621

Tyr Gly Ser Cys Asn Trp Asn Tyr Val His Ile Phe Leu Asp Cys
1 5 10 15

<210> SEQ ID NO 622
<211> LENGTH: 15
<212> TYPE: PRT
<213> ORGANISM: Artificial Sequence
<220> FEATURE:
<223> OTHER INFORMATION: masking moiety

<400> SEQUENCE: 622

Tyr Thr Ser Cys Asn Trp Asn Tyr Val His Ile Phe Met Asp Cys
1 5 10 15

<210> SEQ ID NO 623
<211> LENGTH: 15
<212> TYPE: PRT
<213> ORGANISM: Artificial Sequence
<220> FEATURE:
<223> OTHER INFORMATION: masking moiety

<400> SEQUENCE: 623

Tyr Pro Gly Cys Lys Trp Asn Tyr Asp Arg Ile Phe Leu Asp Cys
1 5 10 15

<210> SEQ ID NO 624
<211> LENGTH: 15
<212> TYPE: PRT
<213> ORGANISM: Artificial Sequence
<220> FEATURE:
<223> OTHER INFORMATION: masking moiety

<400> SEQUENCE: 624

Trp Arg Ser Cys Asn Trp Asn Tyr Ala His Ile Phe Leu Asp Cys
1 5 10 15

<210> SEQ ID NO 625
<211> LENGTH: 15
<212> TYPE: PRT
<213> ORGANISM: Artificial Sequence
<220> FEATURE:
<223> OTHER INFORMATION: masking moiety

<400> SEQUENCE: 625

Trp Ser Asn Cys His Trp Asn Tyr Val His Ile Phe Leu Asp Cys
1 5 10 15

<210> SEQ ID NO 626
<211> LENGTH: 15
<212> TYPE: PRT
<213> ORGANISM: Artificial Sequence
<220> FEATURE:
<223> OTHER INFORMATION: masking moiety

<400> SEQUENCE: 626

Asp Arg Ser Cys Thr Trp Asn Tyr Val Arg Ile Ser Tyr Asp Cys
1 5 10 15

```
<210> SEQ ID NO 627
<211> LENGTH: 15
<212> TYPE: PRT
<213> ORGANISM: Artificial Sequence
<220> FEATURE:
<223> OTHER INFORMATION: masking moiety

<400> SEQUENCE: 627

Ser Gly Ser Cys Lys Trp Asp Tyr Val His Ile Phe Leu Asp Cys
1               5                   10                  15

<210> SEQ ID NO 628
<211> LENGTH: 15
<212> TYPE: PRT
<213> ORGANISM: Artificial Sequence
<220> FEATURE:
<223> OTHER INFORMATION: masking moiety

<400> SEQUENCE: 628

Ser Arg Ser Cys Ile Trp Asn Tyr Ala His Ile His Leu Asp Cys
1               5                   10                  15

<210> SEQ ID NO 629
<211> LENGTH: 15
<212> TYPE: PRT
<213> ORGANISM: Artificial Sequence
<220> FEATURE:
<223> OTHER INFORMATION: masking moiety

<400> SEQUENCE: 629

Ser Met Ser Cys Tyr Trp Gln Tyr Glu Arg Ile Phe Leu Asp Cys
1               5                   10                  15

<210> SEQ ID NO 630
<211> LENGTH: 15
<212> TYPE: PRT
<213> ORGANISM: Artificial Sequence
<220> FEATURE:
<223> OTHER INFORMATION: masking moiety

<400> SEQUENCE: 630

Tyr Arg Ser Cys Asn Trp Asn Tyr Val Ser Ile Phe Leu Asp Cys
1               5                   10                  15

<210> SEQ ID NO 631
<211> LENGTH: 15
<212> TYPE: PRT
<213> ORGANISM: Artificial Sequence
<220> FEATURE:
<223> OTHER INFORMATION: masking moiety

<400> SEQUENCE: 631

Ser Gly Ser Cys Lys Trp Asp Tyr Val His Ile Phe Leu Asp Cys
1               5                   10                  15

<210> SEQ ID NO 632
<211> LENGTH: 15
<212> TYPE: PRT
<213> ORGANISM: Artificial Sequence
<220> FEATURE:
<223> OTHER INFORMATION: masking moiety

<400> SEQUENCE: 632

Tyr Lys Ser Cys His Trp Asp Tyr Val His Ile Phe Leu Asp Cys
1               5                   10                  15
```

<210> SEQ ID NO 633
<211> LENGTH: 15
<212> TYPE: PRT
<213> ORGANISM: Artificial Sequence
<220> FEATURE:
<223> OTHER INFORMATION: masking moiety

<400> SEQUENCE: 633

Tyr Gly Ser Cys Thr Trp Asn Tyr Val His Ile Phe Met Glu Cys
1               5                   10                  15

<210> SEQ ID NO 634
<211> LENGTH: 15
<212> TYPE: PRT
<213> ORGANISM: Artificial Sequence
<220> FEATURE:
<223> OTHER INFORMATION: masking moiety

<400> SEQUENCE: 634

Phe Ser Ser Cys Asn Trp Asn Tyr Val His Ile Phe Leu Asp Cys
1               5                   10                  15

<210> SEQ ID NO 635
<211> LENGTH: 15
<212> TYPE: PRT
<213> ORGANISM: Artificial Sequence
<220> FEATURE:
<223> OTHER INFORMATION: masking moiety

<400> SEQUENCE: 635

Trp Arg Ser Cys Asn Trp Asn Tyr Ala His Ile Phe Leu Asp Cys
1               5                   10                  15

<210> SEQ ID NO 636
<211> LENGTH: 15
<212> TYPE: PRT
<213> ORGANISM: Artificial Sequence
<220> FEATURE:
<223> OTHER INFORMATION: masking moiety

<400> SEQUENCE: 636

Tyr Gly Ser Cys Gln Trp Asn Tyr Val His Ile Phe Leu Asp Cys
1               5                   10                  15

<210> SEQ ID NO 637
<211> LENGTH: 15
<212> TYPE: PRT
<213> ORGANISM: Artificial Sequence
<220> FEATURE:
<223> OTHER INFORMATION: masking moiety

<400> SEQUENCE: 637

Tyr Arg Ser Cys Asn Trp Asn Tyr Val His Ile Phe Leu Asp Cys
1               5                   10                  15

<210> SEQ ID NO 638
<211> LENGTH: 15
<212> TYPE: PRT
<213> ORGANISM: Artificial Sequence
<220> FEATURE:
<223> OTHER INFORMATION: masking moiety

<400> SEQUENCE: 638

Asn Met Ser Cys His Trp Asp Tyr Val His Ile Phe Leu Asp Cys
1               5                   10                  15

-continued

<210> SEQ ID NO 639
<211> LENGTH: 15
<212> TYPE: PRT
<213> ORGANISM: Artificial Sequence
<220> FEATURE:
<223> OTHER INFORMATION: masking moiety

<400> SEQUENCE: 639

Phe Gly Pro Cys Thr Trp Asn Tyr Ala Arg Ile Ser Trp Asp Cys
1 5 10 15

<210> SEQ ID NO 640
<211> LENGTH: 15
<212> TYPE: PRT
<213> ORGANISM: Artificial Sequence
<220> FEATURE:
<223> OTHER INFORMATION: masking moiety
<220> FEATURE:
<221> NAME/KEY: misc_feature
<222> LOCATION: (1)..(2)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (7)..(7)
<223> OTHER INFORMATION: Xaa may be any amino acid
<220> FEATURE:
<221> NAME/KEY: misc_feature
<222> LOCATION: (13)..(13)
<223> OTHER INFORMATION: Xaa may be any amino acid

<400> SEQUENCE: 640

Xaa Xaa Ser Cys Xaa Trp Xaa Tyr Val His Ile Phe Xaa Asp Cys
1 5 10 15

<210> SEQ ID NO 641
<211> LENGTH: 18
<212> TYPE: PRT
<213> ORGANISM: Artificial Sequence
<220> FEATURE:
<223> OTHER INFORMATION: masking moiety

<400> SEQUENCE: 641

Met Gly Val Pro Ala Gly Cys Val Trp Asn Tyr Ala His Ile Phe Met
1 5 10 15

Asp Cys

<210> SEQ ID NO 642
<211> LENGTH: 18
<212> TYPE: PRT
<213> ORGANISM: Artificial Sequence
<220> FEATURE:
<223> OTHER INFORMATION: masking moiety

<400> SEQUENCE: 642

Arg Asp Thr Gly Gly Gln Cys Arg Trp Asp Tyr Val His Ile Phe Met
1 5 10 15

Asp Cys

<210> SEQ ID NO 643
<211> LENGTH: 18
<212> TYPE: PRT
<213> ORGANISM: Artificial Sequence
<220> FEATURE:
<223> OTHER INFORMATION: masking moiety

<400> SEQUENCE: 643

Ala Gly Val Pro Ala Gly Cys Thr Trp Asn Tyr Val His Ile Phe Met
1 5 10 15

Glu Cys

<210> SEQ ID NO 644
<211> LENGTH: 18
<212> TYPE: PRT
<213> ORGANISM: Artificial Sequence
<220> FEATURE:
<223> OTHER INFORMATION: masking moiety

<400> SEQUENCE: 644

Val Gly Val Pro Asn Gly Cys Val Trp Asn Tyr Ala His Ile Phe Met
1 5 10 15

Glu Cys

<210> SEQ ID NO 645
<211> LENGTH: 18
<212> TYPE: PRT
<213> ORGANISM: Artificial Sequence
<220> FEATURE:
<223> OTHER INFORMATION: masking moiety

<400> SEQUENCE: 645

Asp Gly Gly Pro Ala Gly Cys Ser Trp Asn Tyr Val His Ile Phe Met
1 5 10 15

Glu Cys

<210> SEQ ID NO 646
<211> LENGTH: 18
<212> TYPE: PRT
<213> ORGANISM: Artificial Sequence
<220> FEATURE:
<223> OTHER INFORMATION: masking moiety

<400> SEQUENCE: 646

Ala Val Gly Pro Ala Gly Cys Trp Trp Asn Tyr Val His Ile Phe Met
1 5 10 15

Glu Cys

<210> SEQ ID NO 647
<211> LENGTH: 18
<212> TYPE: PRT
<213> ORGANISM: Artificial Sequence
<220> FEATURE:
<223> OTHER INFORMATION: masking moiety

<400> SEQUENCE: 647

Cys Thr Trp Asn Tyr Val His Ile Phe Met Asp Cys Gly Glu Gly Glu
1 5 10 15

Gly Pro

<210> SEQ ID NO 648
<211> LENGTH: 18
<212> TYPE: PRT
<213> ORGANISM: Artificial Sequence
<220> FEATURE:
<223> OTHER INFORMATION: masking moiety

<400> SEQUENCE: 648

Gly Gly Val Pro Glu Gly Cys Thr Trp Asn Tyr Ala His Ile Phe Met
1 5 10 15

Glu Cys

<210> SEQ ID NO 649
<211> LENGTH: 18
<212> TYPE: PRT
<213> ORGANISM: Artificial Sequence
<220> FEATURE:
<223> OTHER INFORMATION: masking moiety

<400> SEQUENCE: 649

Ala Glu Val Pro Ala Gly Cys Trp Trp Asn Tyr Val His Ile Phe Met
1               5                   10                  15

Glu Cys

<210> SEQ ID NO 650
<211> LENGTH: 18
<212> TYPE: PRT
<213> ORGANISM: Artificial Sequence
<220> FEATURE:
<223> OTHER INFORMATION: masking moiety

<400> SEQUENCE: 650

Ala Gly Val Pro Ala Gly Cys Thr Trp Asn Tyr Val His Ile Phe Met
1               5                   10                  15

Glu Cys

<210> SEQ ID NO 651
<211> LENGTH: 18
<212> TYPE: PRT
<213> ORGANISM: Artificial Sequence
<220> FEATURE:
<223> OTHER INFORMATION: masking moiety

<400> SEQUENCE: 651

Ser Gly Ala Ser Gly Gly Cys Lys Trp Asn Tyr Val His Ile Phe Met
1               5                   10                  15

Asp Cys

<210> SEQ ID NO 652
<211> LENGTH: 18
<212> TYPE: PRT
<213> ORGANISM: Artificial Sequence
<220> FEATURE:
<223> OTHER INFORMATION: masking moiety

<400> SEQUENCE: 652

Thr Pro Gly Cys Arg Trp Asn Tyr Val His Ile Phe Met Glu Cys Glu
1 5 10 15

Ala Leu

<210> SEQ ID NO 653
<211> LENGTH: 18
<212> TYPE: PRT
<213> ORGANISM: Artificial Sequence
<220> FEATURE:
<223> OTHER INFORMATION: masking moiety

<400> SEQUENCE: 653

Val Gly Val Pro Asn Gly Cys Val Trp Asn Tyr Ala His Ile Phe Met
1 5 10 15

Glu Cys

```
<210> SEQ ID NO 654
<211> LENGTH: 16
<212> TYPE: PRT
<213> ORGANISM: Artificial Sequence
<220> FEATURE:
<223> OTHER INFORMATION: masking moiety

<400> SEQUENCE: 654

Pro Gly Ala Phe Asp Ile Pro Phe Pro Ala His Trp Val Pro Asn Thr
1               5                   10                  15

<210> SEQ ID NO 655
<211> LENGTH: 16
<212> TYPE: PRT
<213> ORGANISM: Artificial Sequence
<220> FEATURE:
<223> OTHER INFORMATION: masking moiety

<400> SEQUENCE: 655

Arg Gly Ala Cys Asp Ile Pro Phe Pro Ala His Trp Ile Pro Asn Thr
1               5                   10                  15

<210> SEQ ID NO 656
<211> LENGTH: 16
<212> TYPE: PRT
<213> ORGANISM: Artificial Sequence
<220> FEATURE:
<223> OTHER INFORMATION: masking moiety

<400> SEQUENCE: 656

Gln Gly Asp Phe Asp Ile Pro Phe Pro Ala His Trp Val Pro Ile Thr
1               5                   10                  15

<210> SEQ ID NO 657
<211> LENGTH: 16
<212> TYPE: PRT
<213> ORGANISM: Artificial Sequence
<220> FEATURE:
<223> OTHER INFORMATION: masking moiety
<220> FEATURE:
<221> NAME/KEY: misc_feature
<222> LOCATION: (1)..(1)
<223> OTHER INFORMATION: Xaa may be any amino acid

<400> SEQUENCE: 657

Xaa Gly Ala Phe Asp Ile Pro Phe Pro Ala His Trp Val Pro Asn Thr
1               5                   10                  15

<210> SEQ ID NO 658
<211> LENGTH: 19
<212> TYPE: PRT
<213> ORGANISM: Artificial Sequence
<220> FEATURE:
<223> OTHER INFORMATION: masking moiety

<400> SEQUENCE: 658

Arg Gly Asp Gly Asn Asp Ser Asp Ile Pro Phe Pro Ala His Trp Val
1               5                   10                  15

Pro Arg Thr

<210> SEQ ID NO 659
<211> LENGTH: 19
<212> TYPE: PRT
<213> ORGANISM: Artificial Sequence
<220> FEATURE:
<223> OTHER INFORMATION: masking moiety

<400> SEQUENCE: 659
```

```
Ser Gly Val Gly Arg Asp Arg Asp Ile Pro Phe Pro Ala His Trp Val
1               5                   10                  15

Pro Arg Thr

<210> SEQ ID NO 660
<211> LENGTH: 19
<212> TYPE: PRT
<213> ORGANISM: Artificial Sequence
<220> FEATURE:
<223> OTHER INFORMATION: masking moiety

<400> SEQUENCE: 660

Trp Ala Gly Gly Asn Asp Cys Asp Ile Pro Phe Pro Ala His Trp Ile
1               5                   10                  15

Pro Asn Thr

<210> SEQ ID NO 661
<211> LENGTH: 19
<212> TYPE: PRT
<213> ORGANISM: Artificial Sequence
<220> FEATURE:
<223> OTHER INFORMATION: masking moiety

<400> SEQUENCE: 661

Trp Gly Asp Gly Met Asp Val Asp Ile Pro Phe Pro Ala His Trp Val
1               5                   10                  15

Pro Val Thr

<210> SEQ ID NO 662
<211> LENGTH: 19
<212> TYPE: PRT
<213> ORGANISM: Artificial Sequence
<220> FEATURE:
<223> OTHER INFORMATION: masking moiety

<400> SEQUENCE: 662

Ala Gly Ser Gly Asn Asp Ser Asp Ile Pro Phe Pro Ala His Trp Val
1               5                   10                  15

Pro Arg Thr

<210> SEQ ID NO 663
<211> LENGTH: 19
<212> TYPE: PRT
<213> ORGANISM: Artificial Sequence
<220> FEATURE:
<223> OTHER INFORMATION: masking moiety

<400> SEQUENCE: 663

Glu Ser Arg Ser Gly Tyr Ala Asp Ile Pro Phe Pro Ala His Trp Val
1               5                   10                  15

Pro Arg Thr

<210> SEQ ID NO 664
<211> LENGTH: 19
<212> TYPE: PRT
<213> ORGANISM: Artificial Sequence
<220> FEATURE:
<223> OTHER INFORMATION: masking moiety

<400> SEQUENCE: 664

Arg Glu Cys Gly Arg Cys Gly Asp Ile Pro Phe Pro Ala His Trp Val
1               5                   10                  15
```

Pro Arg Thr

<210> SEQ ID NO 665
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 665

Pro Arg Phe Lys Ile Ile Gly Gly
1               5

<210> SEQ ID NO 666
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 666

Pro Arg Phe Arg Ile Ile Gly Gly
1               5

<210> SEQ ID NO 667
<211> LENGTH: 9
<212> TYPE: PRT
<213> ORGANISM: Artificial Sequence
<220> FEATURE:
<223> OTHER INFORMATION: cleavable linker sequence

<400> SEQUENCE: 667

Ser Ser Arg His Arg Arg Ala Leu Asp
1               5

<210> SEQ ID NO 668
<211> LENGTH: 14
<212> TYPE: PRT
<213> ORGANISM: Artificial Sequence
<220> FEATURE:
<223> OTHER INFORMATION: cleavable linker sequence

<400> SEQUENCE: 668

Arg Lys Ser Ser Ile Ile Ile Arg Met Arg Asp Val Val Leu
1               5                   10

<210> SEQ ID NO 669
<211> LENGTH: 15
<212> TYPE: PRT
<213> ORGANISM: Artificial Sequence
<220> FEATURE:
<223> OTHER INFORMATION: cleavable linker sequence

<400> SEQUENCE: 669

Ser Ser Ser Phe Asp Lys Gly Lys Tyr Lys Lys Gly Asp Asp Ala
1               5                   10                  15

<210> SEQ ID NO 670
<211> LENGTH: 15
<212> TYPE: PRT
<213> ORGANISM: Artificial Sequence
<220> FEATURE:
<223> OTHER INFORMATION: cleavable linker sequence

<400> SEQUENCE: 670

Ser Ser Ser Phe Asp Lys Gly Lys Tyr Lys Arg Gly Asp Asp Ala
1               5                   10                  15

```
<210> SEQ ID NO 671
<211> LENGTH: 4
<212> TYPE: PRT
<213> ORGANISM: Artificial Sequence
<220> FEATURE:
<223> OTHER INFORMATION: cleavable linker sequence

<400> SEQUENCE: 671

Ile Glu Gly Arg
1

<210> SEQ ID NO 672
<211> LENGTH: 4
<212> TYPE: PRT
<213> ORGANISM: Artificial Sequence
<220> FEATURE:
<223> OTHER INFORMATION: cleavable linker sequence

<400> SEQUENCE: 672

Ile Asp Gly Arg
1

<210> SEQ ID NO 673
<211> LENGTH: 7
<212> TYPE: PRT
<213> ORGANISM: Artificial Sequence
<220> FEATURE:
<223> OTHER INFORMATION: cleavable linker sequence

<400> SEQUENCE: 673

Gly Gly Ser Ile Asp Gly Arg
1               5

<210> SEQ ID NO 674
<211> LENGTH: 6
<212> TYPE: PRT
<213> ORGANISM: Artificial Sequence
<220> FEATURE:
<223> OTHER INFORMATION: cleavable linker sequence

<400> SEQUENCE: 674

Pro Leu Gly Leu Trp Ala
1               5

<210> SEQ ID NO 675
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 675

Gly Pro Gln Gly Ile Ala Gly Gln
1               5

<210> SEQ ID NO 676
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 676

Gly Pro Gln Gly Leu Leu Gly Ala
1               5
```

```
<210> SEQ ID NO 677
<211> LENGTH: 5
<212> TYPE: PRT
<213> ORGANISM: Artificial Sequence
<220> FEATURE:
<223> OTHER INFORMATION: cleavable linker sequence

<400> SEQUENCE: 677

Gly Ile Ala Gly Gln
1               5

<210> SEQ ID NO 678
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 678

Gly Pro Leu Gly Ile Ala Gly Ile
1               5

<210> SEQ ID NO 679
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 679

Gly Pro Glu Gly Leu Arg Val Gly
1               5

<210> SEQ ID NO 680
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 680

Tyr Gly Ala Gly Leu Gly Val Val
1               5

<210> SEQ ID NO 681
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 681

Ala Gly Leu Gly Val Val Glu Arg
1               5

<210> SEQ ID NO 682
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 682

Ala Gly Leu Gly Ile Ser Ser Thr
1               5
```

<210> SEQ ID NO 683
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 683

Glu Pro Gln Ala Leu Ala Met Ser
1               5

<210> SEQ ID NO 684
<211> LENGTH: 1410
<212> TYPE: DNA
<213> ORGANISM: Artificial Sequence
<220> FEATURE:
<223> OTHER INFORMATION: C225v5 Antibody Heavy Chain with Signal Peptide

<400> SEQUENCE: 684

```
atgtacagga tgcaactcct gtcttgcatt gcactaagtc ttgcacttgt cacgaattcg      60
caggtgcagc tgaaacagag cggcccgggc ctggtgcagc cgagccagag cctgagcatt     120
acctgcaccg tgagcggctt tagcctgacc aactatggcg tgcattgggt gcgccagagc     180
ccgggcaaag cctggaatg gctgggcgtg atttggagcg gcggcaacac cgattataac     240
accccgttta ccagccgcct gagcattaac aaagataaca gcaaaagcca ggtgtttttt     300
aaaatgaaca gcctgcaaag ccaggatacc gcgatttatt attgcgcgcg cgcgctgacc     360
tattatgatt atgaatttgc gtattggggc cagggcaccc tggtgaccgt gagcgcggct     420
agcaccaagg gcccatcggt cttccccctg gcaccctcct ccaagagcac ctctgggggc     480
acagcggccc tgggctgcct ggtcaaggac tacttccccg aaccggtgac ggtgtcgtgg     540
aactcaggcg ccctgaccag cggcgtgcac accttcccgg ctgtcctaca gtcctcagga     600
ctctactccc tcagcagcgt ggtgaccgtg ccctccagca gcttgggcac ccagacctac     660
atctgcaacg tgaatcacaa gcccagcaac accaaggtgg acaagaaagt tgagcccaaa     720
tcttgtgaca aaactcacac atgcccaccg tgcccagcac ctgaactcct ggggggaccg     780
tcagtcttcc tcttcccccc aaaacccaag gacaccctca tgatctcccg gacccctgag     840
gtcacatgcg tggtggtgga cgtgagccac gaagaccctg aggtcaagtt caactggtac     900
gtggacggcg tggaggtgca taatgccaag acaaagccgc gggaggagca gtacaacagc     960
acgtaccgtg tggtcagcgt cctcaccgtc ctgcaccagg actggctgaa tggcaaggag    1020
tacaagtgca aggtctccaa caaagccctc ccagccccca tcgagaaaac catctccaaa    1080
gccaaagggc agccccgaga accacaggtg tacaccctgc cccatcccg ggaggagatg     1140 accaagaacc aggtcagcct gacctgcctg gtcaaaggct tctatcccag cgacatcgcc    1200
gtggagtggg agagcaatgg gcagccggag aacaactaca agaccacgcc tcccgtgctg    1260
gactccgacg gctccttctt cctctacagc aagctcaccg tggacaagag caggtggcag    1320
caggggaacg tcttctcatg ctccgtgatg catgaggctc tgcacaacca ctacacgcag    1380
aagagcctct ccctgtctcc gggtaaatga                                     1410
```

<210> SEQ ID NO 685
<211> LENGTH: 469
<212> TYPE: PRT
<213> ORGANISM: Artificial Sequence
<220> FEATURE:
<223> OTHER INFORMATION: C225v5 Antibody Heavy Chain with Signal Peptide

<400> SEQUENCE: 685

```
Met Tyr Arg Met Gln Leu Leu Ser Cys Ile Ala Leu Ser Leu Ala Leu
1               5                   10                  15

Val Thr Asn Ser Gln Val Gln Leu Lys Gln Ser Gly Pro Gly Leu Val
            20                  25                  30

Gln Pro Ser Gln Ser Leu Ser Ile Thr Cys Thr Val Ser Gly Phe Ser
            35                  40                  45

Leu Thr Asn Tyr Gly Val His Trp Val Arg Gln Ser Pro Gly Lys Gly
50                  55                  60

Leu Glu Trp Leu Gly Val Ile Trp Ser Gly Gly Asn Thr Asp Tyr Asn
65                  70                  75                  80

Thr Pro Phe Thr Ser Arg Leu Ser Ile Asn Lys Asp Asn Ser Lys Ser
                85                  90                  95

Gln Val Phe Phe Lys Met Asn Ser Leu Gln Ser Gln Asp Thr Ala Ile
            100                 105                 110

Tyr Tyr Cys Ala Arg Ala Leu Thr Tyr Tyr Asp Tyr Glu Phe Ala Tyr
            115                 120                 125

Trp Gly Gln Gly Thr Leu Val Thr Val Ser Ala Ala Ser Thr Lys Gly
            130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
            290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Glu Glu Met Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415
```

```
Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys
465

<210> SEQ ID NO 686
<211> LENGTH: 858
<212> TYPE: DNA
<213> ORGANISM: Artificial Sequence
<220> FEATURE:
<223> OTHER INFORMATION: 3954-2787-c225 Light Chain with Signal Peptide

<400> SEQUENCE: 686
atgtacagga tgcaactcct gtcttgcatt gcactaagtc ttgcacttgt cacgaattcg     60
caaggccagt ctggccagtg catctcacct cgtggttgtc cggacggccc atacgtcatg    120
tacggctcga gcggtggcag cggtggctct ggtggatccg gtacctccac ctccggccgt    180
tccgcgaacc cgcgtggtgg cagtagcggt acccagatct tgctgaccca gagcccggtg    240
attctgagcg tgagcccggg cgaacgtgtg agctttagct ccgcgcgag ccagagcatt     300 ggcaccaaca ttcattggta tcagcagcgc accaacggca gccgcgcct gctgattaaa     360 tatgcgagcg aaagcattag cggcattccg agccgcttta gcggcagcgg cagcggcacc    420
gattttaccc tgagcattaa cagcgtggaa agcgaagata ttgcggatta ttattgccag    480
cagaacaaca actggccgac cacctttggc gcgggcacca aactggaact gaaacgtacg    540
gtggctgcac catctgtctt catcttcccg ccatctgatg agcagttgaa atctggaact    600
gcctctgttg tgtgcctgct gaataacttc tatcccagag aggccaaagt acagtggaag    660
gtggataacg ccctccaatc gggtaactcc caggagagtg tcacagagca ggacagcaag    720
gacagcacct acagcctcag cagcaccctg acgctgagca agcagactac gagaaacac     780 aaagtctacg cctgcgaagt cacccatcag ggcctgagct cgcccgtcac aaagagcttc    840
aacaggggag agtgttag                                                   858

<210> SEQ ID NO 687
<211> LENGTH: 285
<212> TYPE: PRT
<213> ORGANISM: Artificial Sequence
<220> FEATURE:
<223> OTHER INFORMATION: 3954-2787-c225 Light Chain with Signal Peptide

<400> SEQUENCE: 687

Met Tyr Arg Met Gln Leu Leu Ser Cys Ile Ala Leu Ser Leu Ala Leu
1               5                   10                  15

Val Thr Asn Ser Gln Gly Gln Ser Gly Gln Cys Ile Ser Pro Arg Gly
            20                  25                  30

Cys Pro Asp Gly Pro Tyr Val Met Tyr Gly Ser Ser Gly Gly Ser Gly
            35                  40                  45

Gly Ser Gly Gly Ser Gly Thr Ser Thr Ser Gly Arg Ser Ala Asn Pro
        50                  55                  60

Arg Gly Gly Ser Ser Gly Thr Gln Ile Leu Leu Thr Gln Ser Pro Val
65                  70                  75                  80

Ile Leu Ser Val Ser Pro Gly Glu Arg Val Ser Phe Ser Cys Arg Ala
                85                  90                  95
```

```
Ser Gln Ser Ile Gly Thr Asn Ile His Trp Tyr Gln Gln Arg Thr Asn
                100                 105                 110
Gly Ser Pro Arg Leu Leu Ile Lys Tyr Ala Ser Glu Ser Ile Ser Gly
            115                 120                 125
Ile Pro Ser Arg Phe Ser Gly Ser Gly Ser Gly Thr Asp Phe Thr Leu
130                 135                 140
Ser Ile Asn Ser Val Glu Ser Glu Asp Ile Ala Asp Tyr Tyr Cys Gln
145                 150                 155                 160
Gln Asn Asn Asn Trp Pro Thr Thr Phe Gly Ala Gly Thr Lys Leu Glu
                165                 170                 175
Leu Lys Arg Thr Val Ala Ala Pro Ser Val Phe Ile Phe Pro Pro Ser
            180                 185                 190
Asp Glu Gln Leu Lys Ser Gly Thr Ala Ser Val Val Cys Leu Leu Asn
        195                 200                 205
Asn Phe Tyr Pro Arg Glu Ala Lys Val Gln Trp Lys Val Asp Asn Ala
210                 215                 220
Leu Gln Ser Gly Asn Ser Gln Glu Ser Val Thr Glu Gln Asp Ser Lys
225                 230                 235                 240
Asp Ser Thr Tyr Ser Leu Ser Ser Thr Leu Thr Leu Ser Lys Ala Asp
                245                 250                 255
Tyr Glu Lys His Lys Val Tyr Ala Cys Glu Val Thr His Gln Gly Leu
            260                 265                 270
Ser Ser Pro Val Thr Lys Ser Phe Asn Arg Gly Glu Cys
        275                 280                 285

<210> SEQ ID NO 688
<211> LENGTH: 798
<212> TYPE: DNA
<213> ORGANISM: Artificial Sequence
<220> FEATURE:
<223> OTHER INFORMATION: 3954-2787-c225 Light Chain

<400> SEQUENCE: 688
caaggccagt ctggccagtg catctcacct cgtggttgtc cggacggccc atacgtcatg      60
tacggctcga gcggtggcag cggtggctct ggtggatccg gtacctccac ctccggccgt     120
tccgcgaacc cgcgtggtgg cagtagcggt acccagatct tgctgaccca gagcccggtg     180
attctgagcg tgagcccggg cgaacgtgtg agctttagct gccgcgcgag ccagagcatt     240
ggcaccaaca ttcattggta tcagcagcgc accaacggca gcccgcgcct gctgattaaa     300
tatgcgagcg aaagcattag cggcattccg agccgcttta gcggcagcgg cagcggcacc     360
gattttaccc tgagcattaa cagcgtggaa agcgaagata ttgcggatta ttattgccag     420
cagaacaaca actggccgac cacctttggc gcgggcacca aactggaact gaaacgtacg     480
gtggctgcac catctgtctt catcttcccg ccatctgatg agcagttgaa atctggaact     540
gcctctgttg tgtgcctgct gaataacttc tatcccagag aggccaaagt acagtggaag     600
gtggataacg ccctccaatc gggtaactcc caggagagtg tcacagagca ggacagcaag     660
gacagcacct acagcctcag cagcaccctg acgctgagca agcagactac gagaaacac      720 aaagtctacg cctgcgaagt cacccatcag ggcctgagct cgcccgtcac aaagagcttc     780
aacaggggag agtgttag                                                   798

<210> SEQ ID NO 689
<211> LENGTH: 265
<212> TYPE: PRT
```

<213> ORGANISM: Artificial Sequence
<220> FEATURE:
<223> OTHER INFORMATION: 3954-2787-c225 Light Chain

<400> SEQUENCE: 689

Gln Gly Gln Ser Gly Gln Cys Ile Ser Pro Arg Gly Cys Pro Asp Gly
1               5                   10                  15

Pro Tyr Val Met Tyr Gly Ser Ser Gly Ser Gly Gly Ser Gly Gly
            20                  25                  30

Ser Gly Thr Ser Thr Ser Gly Arg Ser Ala Asn Pro Arg Gly Gly Ser
        35                  40                  45

Ser Gly Thr Gln Ile Leu Leu Thr Gln Ser Pro Val Ile Leu Ser Val
    50                  55                  60

Ser Pro Gly Glu Arg Val Ser Phe Ser Cys Arg Ala Ser Gln Ser Ile
65                  70                  75                  80

Gly Thr Asn Ile His Trp Tyr Gln Gln Arg Thr Asn Gly Ser Pro Arg
                85                  90                  95

Leu Leu Ile Lys Tyr Ala Ser Glu Ser Ile Ser Gly Ile Pro Ser Arg
            100                 105                 110

Phe Ser Gly Ser Gly Ser Gly Thr Asp Phe Thr Leu Ser Ile Asn Ser
        115                 120                 125

Val Glu Ser Glu Asp Ile Ala Asp Tyr Tyr Cys Gln Gln Asn Asn Asn
    130                 135                 140

Trp Pro Thr Thr Phe Gly Ala Gly Thr Lys Leu Glu Leu Lys Arg Thr
145                 150                 155                 160

Val Ala Ala Pro Ser Val Phe Ile Phe Pro Pro Ser Asp Glu Gln Leu
                165                 170                 175

Lys Ser Gly Thr Ala Ser Val Val Cys Leu Leu Asn Asn Phe Tyr Pro
            180                 185                 190

Arg Glu Ala Lys Val Gln Trp Lys Val Asp Asn Ala Leu Gln Ser Gly
        195                 200                 205

Asn Ser Gln Glu Ser Val Thr Glu Gln Asp Ser Lys Asp Ser Thr Tyr
    210                 215                 220

Ser Leu Ser Ser Thr Leu Thr Leu Ser Lys Ala Asp Tyr Glu Lys His
225                 230                 235                 240

Lys Val Tyr Ala Cys Glu Val Thr His Gln Gly Leu Ser Ser Pro Val
                245                 250                 255

Thr Lys Ser Phe Asn Arg Gly Glu Cys
            260                 265

<210> SEQ ID NO 690
<211> LENGTH: 7
<212> TYPE: PRT
<213> ORGANISM: Artificial Sequence
<220> FEATURE:
<223> OTHER INFORMATION: masking moiety

<400> SEQUENCE: 690

Cys Ile Ser Pro Arg Gly Cys
1               5

<210> SEQ ID NO 691
<211> LENGTH: 21
<212> TYPE: PRT
<213> ORGANISM: Artificial Sequence
<220> FEATURE:
<223> OTHER INFORMATION: masking moiety

<400> SEQUENCE: 691

Gln Gly Gln Ser Gly Gln Cys Asn Ile Trp Leu Val Gly Gly Asp Cys
1               5                   10                  15

Arg Gly Trp Gln Gly
            20

<210> SEQ ID NO 692
<211> LENGTH: 273
<212> TYPE: PRT
<213> ORGANISM: Artificial Sequence
<220> FEATURE:
<223> OTHER INFORMATION: anti-CTLA-4 scFv

<400> SEQUENCE: 692

Gly Gly Gly Ser Gly Gly Gly Ser Gly Ser Gly Gly Ser Gly
1               5                   10                  15

Gly Gly Gly Ser Gly Gly Gly Glu Ile Val Leu Thr Gln Ser Pro Gly
                20                  25                  30

Thr Leu Ser Leu Ser Pro Gly Glu Arg Ala Thr Leu Ser Cys Arg Ala
            35                  40                  45

Ser Gln Ser Val Ser Ser Tyr Leu Ala Trp Tyr Gln Gln Lys Pro
    50                  55                  60

Gly Gln Ala Pro Arg Leu Leu Ile Tyr Gly Ala Ser Ser Arg Ala Thr
65                  70                  75                  80

Gly Ile Pro Asp Arg Phe Ser Gly Ser Gly Ser Gly Thr Asp Phe Thr
                85                  90                  95

Leu Thr Ile Ser Arg Leu Glu Pro Glu Asp Phe Ala Val Tyr Tyr Cys
            100                 105                 110

Gln Gln Tyr Gly Ser Ser Pro Leu Thr Phe Gly Gly Gly Thr Lys Val
        115                 120                 125

Glu Ile Lys Arg Ser Gly Gly Ser Thr Ile Thr Ser Tyr Asn Val Tyr
130                 135                 140

Tyr Thr Lys Leu Ser Ser Ser Gly Thr Gln Val Gln Leu Val Gln Thr
145                 150                 155                 160

Gly Gly Gly Val Val Gln Pro Gly Arg Ser Leu Arg Leu Ser Cys Ala
                165                 170                 175

Ala Ser Gly Ser Thr Phe Ser Ser Tyr Ala Met Ser Trp Val Arg Gln
            180                 185                 190

Ala Pro Gly Lys Gly Leu Glu Trp Val Ser Ala Ile Ser Gly Ser Gly
        195                 200                 205

Gly Ser Thr Tyr Tyr Ala Asp Ser Val Lys Gly Arg Phe Thr Ile Ser
    210                 215                 220

Arg Asp Asn Ser Lys Asn Thr Leu Tyr Leu Gln Met Asn Ser Leu Arg
225                 230                 235                 240

Ala Glu Asp Thr Ala Val Tyr Tyr Cys Ala Thr Asn Ser Leu Tyr Trp
                245                 250                 255

Tyr Phe Asp Leu Trp Gly Arg Gly Thr Leu Val Thr Val Ser Ser Ala
            260                 265                 270

Ser

<210> SEQ ID NO 693
<211> LENGTH: 264
<212> TYPE: PRT
<213> ORGANISM: Artificial Sequence
<220> FEATURE:
<223> OTHER INFORMATION: anti-CTLA-4 scFv

<400> SEQUENCE: 693

-continued

```
Gly Gly Gly Ser Gly Gly Gly Ser Gly Gly Gly Ser Gly
1               5                   10                  15

Gly Gly Gly Ser Gly Gly Gly Gln Val Gln Leu Gln Ser Gly Ala
            20                  25                  30

Glu Leu Ala Arg Pro Gly Ala Ser Val Lys Met Ser Cys Lys Ala Ser
            35                  40                  45

Gly Tyr Thr Phe Thr Arg Tyr Thr Met His Trp Val Lys Gln Arg Pro
        50                  55                  60

Gly Gln Gly Leu Glu Trp Ile Gly Tyr Ile Asn Pro Ser Arg Gly Tyr
65              70                  75                  80

Thr Asn Tyr Asn Gln Lys Phe Lys Asp Lys Ala Thr Leu Thr Thr Asp
                85                  90                  95

Lys Ser Ser Ser Thr Ala Tyr Met Gln Leu Ser Ser Leu Thr Ser Glu
            100                 105                 110

Asp Ser Ala Val Tyr Tyr Cys Ala Arg Tyr Tyr Asp Asp His Tyr Cys
            115                 120                 125

Leu Asp Tyr Trp Gly Gln Gly Thr Thr Leu Thr Val Ser Ser Gly Gly
        130                 135                 140

Gly Gly Ser Gly Gly Gly Gly Ser Gly Gly Gly Gly Ser Gln Ile Val
145                 150                 155                 160

Leu Thr Gln Ser Pro Ala Ile Met Ser Ala Ser Pro Gly Glu Lys Val
                165                 170                 175

Thr Met Thr Cys Ser Ala Ser Ser Ser Val Ser Tyr Met Asn Trp Tyr
            180                 185                 190

Gln Gln Lys Ser Gly Thr Ser Pro Lys Arg Trp Ile Tyr Asp Thr Ser
            195                 200                 205

Lys Leu Ala Ser Gly Val Pro Ala His Phe Arg Gly Ser Gly Ser Gly
        210                 215                 220

Thr Ser Tyr Ser Leu Thr Ile Ser Gly Met Glu Ala Glu Asp Ala Ala
225                 230                 235                 240

Thr Tyr Tyr Cys Gln Gln Trp Ser Ser Asn Pro Phe Thr Phe Gly Ser
                245                 250                 255

Gly Thr Lys Leu Glu Ile Asn Arg
                260

<210> SEQ ID NO 694
<211> LENGTH: 194
<212> TYPE: PRT
<213> ORGANISM: Artificial Sequence
<220> FEATURE:
<223> OTHER INFORMATION: Display Platform CYTX-DP-XXXXXXXX
<220> FEATURE:
<221> NAME/KEY: misc_feature
<222> LOCATION: (17)..(24)
<223> OTHER INFORMATION: Xaa may be any amino acid

<400> SEQUENCE: 694

Gly Gln Ser Gly Gln Glu Tyr Met Pro Met Glu Gly Gly Ser Gly Gln
1               5                   10                  15

Xaa Xaa Xaa Xaa Xaa Xaa Xaa Xaa Ser Gly Gly Gln Gly Gly Ser Gly
            20                  25                  30

Gly Ser Gly Gly Ser Gly Gly Ser Gly Gly Ser Ala Tyr Gly Ile
            35                  40                  45

Thr Ala Gly Pro Ala Tyr Arg Ile Asn Asp Trp Ala Ser Ile Tyr Gly
        50                  55                  60

Val Val Gly Val Gly Tyr Gly Ser Gly Pro Gly Gly Ser Tyr Gly Phe
```

```
                65                  70                  75                  80
        Ser Tyr Gly Ala Gly Leu Gln Phe Asn Pro Met Glu Asn Val Ala Leu
                        85                  90                  95

Asp Phe Ser Tyr Glu Gln Ser Arg Ile Arg Ser Val Asp Val Gly Thr
                       100                 105                 110

Trp Ile Leu Ser Val Gly Tyr Arg Phe Gly Ser Lys Ser Arg Arg Ala
                       115                 120                 125

Thr Ser Thr Val Thr Gly Gly Tyr Ala Gln Ser Asp Ala Gln Gly Gln
                       130                 135                 140

Met Asn Lys Met Gly Gly Phe Asn Leu Lys Tyr Arg Tyr Glu Glu Asp
        145                 150                 155                 160

Asn Ser Pro Leu Gly Val Ile Gly Ser Phe Thr Tyr Thr Gly Gly Ser
                           165                 170                 175

Gly Gly Ser Ser Gly Gln Ala Ala Ala Gly His His His His His His
                       180                 185                 190

His His

<210> SEQ ID NO 695
<211> LENGTH: 217
<212> TYPE: PRT
<213> ORGANISM: Artificial Sequence
<220> FEATURE:
<223> OTHER INFORMATION: Display Platform SP-CYTX-DP-XXXXXXXX
<220> FEATURE:
<221> NAME/KEY: misc_feature
<222> LOCATION: (40)..(47)
<223> OTHER INFORMATION: Xaa may be any amino acid

<400> SEQUENCE: 695

Met Lys Lys Ile Ala Cys Leu Ser Ala Leu Ala Ala Val Leu Ala Phe
        1               5                  10                  15

Thr Ala Gly Thr Ser Val Ala Gly Gln Ser Gly Gln Glu Tyr Met Pro
                        20                  25                  30

Met Glu Gly Gly Ser Gly Gln Xaa Xaa Xaa Xaa Xaa Xaa Xaa Xaa Ser
                        35                  40                  45

Gly Gly Gln Gly Gly Ser Gly Gly Ser Gly Gly Ser Gly Gly Ser Gly
                        50                  55                  60

Gly Ser Ala Tyr Tyr Gly Ile Thr Ala Gly Pro Ala Tyr Arg Ile Asn
        65                  70                  75                  80

Asp Trp Ala Ser Ile Tyr Gly Val Val Gly Val Gly Tyr Gly Ser Gly
                        85                  90                  95

Pro Gly Gly Ser Tyr Gly Phe Ser Tyr Gly Ala Gly Leu Gln Phe Asn
                       100                 105                 110

Pro Met Glu Asn Val Ala Leu Asp Phe Ser Tyr Glu Gln Ser Arg Ile
                       115                 120                 125

Arg Ser Val Asp Val Gly Thr Trp Ile Leu Ser Val Gly Tyr Arg Phe
                       130                 135                 140

Gly Ser Lys Ser Arg Arg Ala Thr Ser Thr Val Thr Gly Gly Tyr Ala
        145                 150                 155                 160

Gln Ser Asp Ala Gln Gly Gln Met Asn Lys Met Gly Gly Phe Asn Leu
                           165                 170                 175

Lys Tyr Arg Tyr Glu Glu Asp Asn Ser Pro Leu Gly Val Ile Gly Ser
                           180                 185                 190

Phe Thr Tyr Thr Gly Gly Ser Gly Gly Ser Ser Gly Gln Ala Ala Ala
                           195                 200                 205

Gly His His His His His His His His
```

```
<210> SEQ ID NO 696
<211> LENGTH: 8
<212> TYPE: PRT
<213> ORGANISM: Artificial Sequence
<220> FEATURE:
<223> OTHER INFORMATION: linker sequence

<400> SEQUENCE: 696

Gly Gly Gly Ser Gly Gly Gly Ser
1               5
```

MATRIPTASE AND U-PLASMINOGEN ACTIVATOR SUBSTRATES AND OTHER CLEAVABLE MOIETIES AND METHODS OF USE THEREOF

RELATED APPLICATIONS

This application is a divisional of U.S. Ser. No. 16/160,846 filed Oct. 15, 2018, which is a continuation of U.S. patent application Ser. No. 15/390,975, filed Dec. 27, 2016, now U.S. Pat. No. 10,138,272, issued Nov. 27, 2018; which is a divisional of U.S. patent application Ser. No. 14/610,468, filed Jan. 30, 2015, now U.S. Pat. No. 9,562,073, issued Feb. 7, 2017, which claims the benefit of U.S. Provisional Application No. 61/934,619, filed Jan. 31, 2014 and U.S. Provisional Application No. 61/971,009, filed Mar. 27, 2014, the contents of each of which are incorporated herein by reference in their entireties.

INCORPORATION OF SEQUENCE LISTING

The contents of the text file named "CYTM-034C01USSeqList.txt," which was created on Oct. 15, 2018 and is 360 KB in size, are hereby incorporated by reference in their entirety.

FIELD OF THE INVENTION

The invention relates generally to polypeptides that include a cleavable moiety that is a substrate for at least one protease selected from matriptase and u-plasminogen activator (uPA), to activatable antibodies and other larger molecules that include the cleavable moiety that is a substrate for at least one protease selected from matriptase and uPA, and to methods of making and using these polypeptides that include a cleavable moiety that is a substrate for at least one protease selected from matriptase and uPA in a variety of therapeutic, diagnostic and prophylactic indications.

BACKGROUND OF THE INVENTION

Proteases are enzymes that cleave the peptide bonds between amino acid residues. Some proteases are known to break specific peptide bonds based on the presence of a particular amino acid sequence within a protein. Proteases occur naturally in all organisms and are involved in a variety of physiological reactions from simple degradation to highly regulated pathways. However, many pathological conditions are associated with deregulated expression and/or activity of proteases. As such, inappropriate proteolysis can have a major role in development and progression of cancer as well as cardiovascular, inflammatory, neurodegenerative, eukaryotic, bacterial and viral and parasitic diseases.

Accordingly, there exists a need to identify new substrates for proteases and to use these substrates in a variety of therapeutic, diagnostic and prophylactic indications.

SUMMARY OF THE INVENTION

The disclosure provides amino acid sequences that include a cleavable moiety (CM) that is a substrate for at least one protease selected from matriptase (also referred to herein as MT-SP1, matriptase-1, and similar terms denoting matriptase) and u-plasminogen activator (also referred to herein as uPA, urokinase, urokinase-type plasminogen activator, and similar terms denoting uPA). These CMs are useful in a variety of therapeutic, diagnostic and prophylactic indications.

In some embodiments, the CM is linked or otherwise attached to an antibody. For example, the CM is used to link one or more agents to the antibody or antigen binding fragment thereof that binds a given target, such that the CM is cleaved when exposed to the protease, i.e., matriptase and/or uPA, and the agent is released from the antibody or antigen-binding fragment. Exemplary targets include, but are not limited to the targets shown in Table 1. Exemplary antibodies or antigen-binding fragments thereof include, but are not limited to, the targets shown in Table 2. In some embodiments, the antibody in the uncleaved state has the structural arrangement from N-terminus to C-terminus as follows: Agent-CM-(Antibody or Antigen-Binding Fragment) or (Antibody or Antigen-Binding Fragment)-CM-Agent. In some embodiments, the antibody comprises a linking peptide between the antibody or antigen-binding fragment and the CM. In some embodiments, the antibody or antigen-binding fragment comprises a linking peptide between the CM and the conjugated agent.

In some embodiments, the antibody comprises a first linking peptide (LP1) and a second linking peptide (LP2), wherein the antibody in the uncleaved state has the structural arrangement from N-terminus to C-terminus as follows: Agent-LP1-CM-LP2—(Antibody or Antigen-Binding Fragment) or (Antibody or Antigen-Binding Fragment)-LP2-CM-LP1-Agent. In some embodiments, the two linking peptides need not be identical to each other.

In some embodiments, at least one of LP1 or LP2 comprises an amino acid sequence selected from the group consisting of $(GS)_n$, $(GGS)_n$, $(GSGGS)_n$ (SEQ ID NO: 385) and $(GGGS)_n$ (SEQ ID NO: 386), where n is an integer of at least one.

In some embodiments, at least one of LP1 or LP2 comprises an amino acid sequence selected from the group consisting of GGSG (SEQ ID NO: 387), GGSGG (SEQ ID NO: 388), GSGSG (SEQ ID NO: 389), GSGGG (SEQ ID NO: 390), GGGSG (SEQ ID NO: 391), and GSSSG (SEQ ID NO: 392).

In some embodiments, LP1 comprises the amino acid sequence GSSGGSGGSGGSG (SEQ ID NO: 393), GSSGGSGGSGG (SEQ ID NO: 394), GSSGGSGGSGGS (SEQ ID NO: 395), GSSGGSGGSGGSGGS (SEQ ID NO: 396), GSSGGSGGSG (SEQ ID NO: 397), or GSSGGSGGSGS (SEQ ID NO: 398).

In some embodiments, LP2 comprises the amino acid sequence GSS, GGS, GGGS (SEQ ID NO: 399), GSSGT (SEQ ID NO: 400) or GSSG (SEQ ID NO: 401).

In some embodiments, the antibody or antigen-binding fragment has an equilibrium dissociation constant of about 100 nM or less for binding to the target.

In some embodiments, the antibody or antigen-binding fragment thereof specifically binds a target. In some embodiments, the antibody or immunologically active fragment thereof that binds the target is a monoclonal antibody, domain antibody, single chain, Fab fragment, a F(ab')$_2$ fragment, a scFv, a scab, a dAb, a single domain heavy chain antibody, or a single domain light chain antibody. In some embodiments, such an antibody or immunologically active fragment thereof that binds the target is a mouse, other rodent, chimeric, humanized or fully human monoclonal antibody.

In some embodiments, the protease, i.e., matriptase and/or uPA is co-localized with the target in a tissue, and the protease cleaves the CM in the antibody when the antibody is exposed to the protease.

In some embodiments, the CM is a polypeptide of up to 15 amino acids in length.

In some embodiments, the CM is a substrate for at least matriptase. In some embodiments, the CM is a substrate for at least uPA. In some embodiments, the CM is a substrate for at least matriptase and uPA.

In some embodiments, the CM is a substrate for matriptase and/or uPA, and is resistant to cleavage by at least one other protease. In some embodiments, the CM is a substrate for matriptase and/or uPA, and is resistant to cleavage by at least plasmin. In some embodiments, the CM is a substrate for matriptase and/or uPA, and is resistant to cleavage by at least tissue plasminogen activator (tPA).

In some embodiments, the CM is a substrate for matriptase and/or uPA and includes a motif sequence that is recognized by matriptase and/or uPA, provided that for any given motif sequence of the disclosure:

(i) the CM does not comprise any of the following amino acid sequences TGRGPSWV (SEQ ID NO: 402), SARGPSRW (SEQ ID NO: 403), or TARGPSFK (SEQ ID NO: 404); and the CM does not comprise a consensus amino acid sequence based on these amino acid sequences, such as for example, TARGPSW (SEQ ID NO: 405);

(ii) the CM does not comprise any of the following amino acid sequences LSGRSDNH (SEQ ID NO: 406), GGWHTGRN (SEQ ID NO: 407), HTGRSGAL (SEQ ID NO: 408), or PLTGRSGG (SEQ ID NO: 409); and the CM does not comprise a consensus amino acid sequence based on these amino acid sequences, such as for example, LTGRSGA (SEQ ID NO: 410); and/or (iii) the CM does not comprise any of the following amino acid sequences AARGPAIH (SEQ ID NO: 411), RGPAFNPM (SEQ ID NO: 412), SSRGPAYL (SEQ ID NO: 413), or RGPATPIM (SEQ ID NO: 414); and the CM does not comprise a consensus amino acid sequence based on these amino acid sequences, such as for example, RGPA (SEQ ID NO: 415).

In some embodiments, the motif sequence is a substrate for at least matriptase and includes a core CM consensus sequence shown in Tables 8A-8J below. In some embodiments, the motif sequence includes a subgenus, i.e., a subset, of the core CM consensus sequence shown in Tables 8A-8J below.

TABLE 8A

Matriptase Cleavable Core CM Consensus Sequence 1

| Core CM Consensus 1 | Subgenus of Core CM Consensus 1 |
|---|---|
| $X_1X_2X_3X_4X_5$ (SEQ ID NO: 1), wherein: <br> $X_1$ is A, G, H, K, L, N, P, R, S, or V; <br> $X_2$ is A, H, L, M, P, Q, R, S, or V; <br> $X_3$ is A, E, F, G, I, L, P, R, S, T, or V; <br> $X_4$ is A, I, K, N, R, T, or W; and <br> $X_5$ is A, G, I, L, M, Q, R, S, or V | $X_1X_2X_3X_4X_5$ (SEQ ID NO: 2), wherein $X_1$ is A, G, P, R, S, or V; $X_2$ is A, L, M, P, S, or V; $X_3$ is G, L, or P; $X_4$ is R; and $X_5$ is A, G, R, S, or V <br> $X_1X_2X_3X_4X_5$ (SEQ ID NO: 3), wherein $X_1$ is A, P, R, S, or V; $X_2$ is A, L, M, S, or V; $X_3$ is P; $X_4$ is R; and $X_5$ is A, G, S, or V <br> $X_1X_2X_3X_4X_5$ (SEQ ID NO: 4), wherein: $X_1$ is A, P, or R; $X_2$ is A, S, or V; $X_3$ is P; $X_4$ is R; and $X_5$ is S or V <br> $X_1X_2X_3X_4X_5$ (SEQ ID NO: 5), wherein: $X_1$ is A, P, or R; $X_2$ is A or S; $X_3$ is P; $X_4$ iS R; and $X_5$ is S |

TABLE 8B

Matriptase Cleavable Core CM Consensus Sequence 2

| Core CM Consensus 2 | Subgenus of Core CM Consensus 2 |
|---|---|
| $X_{10}X_{11}X_{12}X_{13}X_{14}$ (SEQ ID NO: 6), wherein: <br> $X_{10}$ is A, L, P, R, S, T, or V; <br> $X_{11}$ is K or R; <br> $X_{12}$ iS D or R; <br> $X_{13}$ is A, G, L, M, S, T, V, or W; and <br> $X_{14}$ is F, G, M, P, or V | $X_{10}X_{11}X_{12}X_{13}X_{14}$ (SEQ ID NO: 7), wherein: $X_{10}$ is A, R, S, or T; $X_{11}$ is K or R; $X_{12}$ is D or R; $X_{13}$ is L or V; and $X_{14}$ is F or P <br> $X_{10}X_{11}X_{12}X_{13}X_{14}$ (SEQ ID NO: 8), wherein: $X_{10}$ is A, S, or T; $X_{11}$ is K or R; $X_{12}$ is R; $X_{13}$ is L or V; and $X_{14}$ is F or P <br> $X_{10}X_{11}X_{12}X_{13}X_{14}$ (SEQ ID NO: 9), wherein: $X_{10}$ is S or T; $X_{11}$ is R; $X_{12}$ is R; $X_{13}$ is L or V; and $X_{14}$ is P |

TABLE 8C

Matriptase Cleavable Core CM Consensus Sequence 3

| Core CM Consensus 3 | Subgenus of Core CM Consensus 3 |
|---|---|
| $X_{20}X_{21}X_{22}X_{23}X_{24}$ (SEQ ID NO: 10), wherein: <br> $X_{20}$ is E, G, P, R, S, V, or W; <br> $X_{21}$ is A, G, L, M, P, S, or V; <br> $X_{22}$ is A, I, L, or R; <br> $X_{23}$ is A, G, I, or P; and <br> $X_{24}$ is G or R | $X_{20}X_{21}X_{22}X_{23}X_{24}$ (SEQ ID NO: 11), wherein: $X_{20}$ is G, P, R, S, or V; $X_{21}$ is P or V; $X_{22}$ is L or R; $X_{23}$ is G; and $X_{24}$ is G or R <br> $X_{20}X_{21}X_{22}X_{23}X_{24}$ (SEQ ID NO: 12), wherein: $X_{20}$ is P or R; $X_{21}$ is P; $X_{22}$ is L; $X_{23}$ is G; and $X_{24}$ is R |

TABLE 8D

Matriptase Cleavable Core CM Consensus Sequence 4

| Core CM Consensus 4 | Subgenus of Core CM Consensus 4 |
|---|---|
| $X_{26}X_{27}X_{28}X_{29}X_{30}$ (SEQ ID NO: 13), wherein: $X_{26}$ is A, G, H, L, R, or S; $X_{27}$ is D, H, N, R, S, T, or W; $X_{28}$ is A, N, P, R, S, T, or V; $X_{29}$ is F, G, L, M, P, Q, R, S, or Y; and $X_{30}$ is I, G, L, P, S, V, or W | $X_{26}X_{27}X_{28}X_{29}X_{30}$ (SEQ ID NO: 14), wherein: $X_{26}$ is A, G, H, L, R, or S; $X_{27}$ is D, H, R, or T; $X_{28}$ is A, P, R, S, T, or V; $X_{29}$ is F, G, L, M, P, or S; and $X_{30}$ is G, L, P, S, V, or W<br>$X_{26}X_{27}X_{28}X_{29}X_{30}$ (SEQ ID NO: 15), wherein: $X_{26}$ is G, L, or S; $X_{27}$ is R or T; $X_{28}$ is A, P, or S; $X_{29}$ is F, G, M, or S; and $X_{30}$ is G, P, S, V, or W<br>$X_{26}X_{27}X_{28}X_{29}X_{30}$ (SEQ ID NO: 16), wherein: $X_{26}$ is G, L, or S; $X_{27}$ is R; $X_{28}$ is A or S; $X_{29}$ is G or M; and $X_{30}$ is G, P, S, or W<br>$X_{26}X_{27}X_{28}X_{29}X_{30}$ (SEQ ID NO: 17), wherein: $X_{26}$ is L; $X_{27}$ is R; $X_{28}$ is A or S; $X_{29}$ is G; and $X_{30}$ is W |

TABLE 8E

Matriptase Cleavable Core CM Consensus Sequence 5

| Core CM Consensus 5 | Subgenus of Core CM Consensus 5 |
|---|---|
| $X_{36}X_{37}X_{38}X_{39}X_{40}$ (SEQ ID NO: 18), wherein: $X_{36}$ is G, K, L, S, V, or W; $X_{37}$ is G, I, P, Q, R, or S; $X_{38}$ is R; $X_{39}$ is G, K, R, S, or V; and $X_{40}$ is A, C, G, L, M, P, S, V, or Y | $X_{36}X_{37}X_{38}X_{39}X_{40}$ (SEQ ID NO: 19), wherein: $X_{36}$ is G, L, S, V, or W; $X_{37}$ is G, Q, R, or S; $X_{38}$ is R; $X_{39}$ is G, S, or V; and $X_{40}$ is A, G, L, S, and V<br>$X_{36}X_{37}X_{38}X_{39}X_{40}$ (SEQ ID NO: 20), wherein: $X_{36}$ is V; $X_{37}$ is S; $X_{38}$ is R; $X_{39}$ is S; and $X_{40}$ is A and V |

TABLE 8F

Matriptase Cleavable Core CM Consensus Sequence 6

| Core CM Consensus 6 | Subgenus of Core CM Consensus 6 |
|---|---|
| $X_{42}X_{43}X_{44}X_{45}X_{46}$ (SEQ ID NO: 21), wherein: $X_{42}$ is A, E, G, I, L, M, R, or S; $X_{43}$ is A, G, K, L, N, R, S, or V; $X_{44}$ is F, H, L, R, or Y; $X_{45}$ is A, F, G, H, P, or S; and $X_{46}$ is F, G, M, N, P, R, S, or V | $X_{42}X_{43}X_{44}X_{45}X_{46}$ (SEQ ID NO: 22), wherein: $X_{42}$ is A, E, G, L, M, R, or S; $X_{43}$ is G, K, L, N, R, S, or V; $X_{44}$ is R or Y; $X_{45}$ is A, F, G, P, or S; and $X_{46}$ is F, G, M, P, R, S, or V<br>$X_{42}X_{43}X_{44}X_{45}X_{46}$ (SEQ ID NO: 23), wherein: $X_{42}$ is A, E, G, M, or S; $X_{43}$ is G, L, S, or V; $X_{44}$ is R or Y; $X_{45}$ is A, G, P, or S; and $X_{46}$ is F, G, M, P, R, S, or V<br>$X_{42}X_{43}X_{44}X_{45}X_{46}$ (SEQ ID NO: 24), wherein: $X_{42}$ is A, G, or S; $X_{43}$ is L, S, or V; $X_{44}$ is R; $X_{45}$ is A; and $X46$ is M or P<br>$X_{42}X_{43}X_{44}X_{45}X_{46}$ (SEQ ID NO: 25), wherein: $X_{42}$ is A; $X_{43}$ is L, S or V; $X_{44}$ is R; $X_{45}$ is A; and $X_{46}$ is M or P |

TABLE 8G

Matriptase Cleavable Core CM Consensus Sequence 7

| Core CM Consensus 7 | Subgenus of Core CM Consensus 7 |
|---|---|
| $X_{50}X_{51}X_{52}X_{53}X_{54}$ (SEQ ID NO: 26), wherein: $X_{50}$ is A, E, K, L, P, S, T, V, W, or Y; $X_{51}$ is A, I, L, P, R, S, V, or Y; $X_{52}$ is E, G, H, L, P, or V; $X_{53}$ is G, K, L, or R; and $X_{54}$ is Q or R | $X_{50}X_{51}X_{52}X_{53}X_{54}$ (SEQ ID NO: 27), wherein: $X_{50}$ is E, P, S, V, or W; $X_{51}$ is A, P, R, S, V, or Y; $X_{52}$ is E, G, H, L, P, or V; $X_{53}$ is G, K, L, or R; and $X_{54}$ is Q or R<br>$X_{50}X_{51}X_{52}X_{53}X_{54}$ (SEQ ID NO: 28), wherein: $X_{50}$ is P or V; $X_{51}$ is A, P, or R; $X_{52}$ is E, G, P, or |

TABLE 8G-continued

Matriptase Cleavable Core CM Consensus Sequence 7

| Core CM Consensus 7 | Subgenus of Core CM Consensus 7 |
|---|---|
| | V; $X_{53}$ is G or R; and $X_{54}$ is R<br>$X_{50}X_{51}X_{52}X_{53}X_{54}$ (SEQ ID NO: 29), wherein:<br>$X_{50}$ is P or V; $X_{51}$ is A or R; $X_{52}$ is G or V; $X_{53}$ is G or R; and $X_{54}$ is R<br>$X_{50}X_{51}X_{52}X_{53}X_{54}$ (SEQ ID NO: 30), wherein:<br>$X_{50}$ is P or V; $X_{51}$ is A; $X_{52}$ is G or V; $X_{53}$ is R; and $X_{54}$ is R |

TABLE 8H

Matriptase Cleavable Core CM Consensus Sequence 8

| Core CM Consensus 8 | Subgenus of Core CM Consensus 8 |
|---|---|
| $X_{57}X_{58}X_{59}X_{60}X_{61}$ (SEQ ID NO: 31), wherein:<br>$X_{57}$ is A, G, I, K, P, S, or T;<br>$X_{58}$ is R or T;<br>$X_{59}$ is H, M, or S;<br>$X_{60}$ is F, M, or R; and<br>$X_{61}$ is A, G, I, L, P, Q, R, S, V, or W | $X_{57}X_{58}X_{59}X_{60}X_{61}$ (SEQ ID NO: 32), wherein:<br>$X_{57}$ is A, G, I, K, S, or T; $X_{58}$ is R; $X_{59}$ is 5; $X_{60}$ is F, M, or R; and $X_{61}$ is A, I, L, R, or W<br>$X_{57}X_{58}X_{59}X_{60}X_{61}$ (SEQ ID NO: 33), wherein:<br>$X_{57}$ is G or K; $X_{58}$ is R; $X_{59}$ is 5; $X_{60}$ is M; and $X_{61}$ is A, L, R, or W<br>$X_{57}X_{58}X_{59}X_{60}X_{61}$ (SEQ ID NO: 34), wherein:<br>$X_{57}$ is G; $X_{58}$ is R; $X_{59}$ is 5; $X_{60}$ is M; and $X_{61}$ is A or L |

TABLE 8I

Matriptase Cleavable Core CM Consensus Sequence 9

| Core CM Consensus 9 | Subgenus of Core CM Consensus 9 |
|---|---|
| $X_{67}X_{68}X_{69}X_{70}X_{71}$ (SEQ ID NO: 35), wherein:<br>$X_{67}$ is I, L, or S;<br>$X_{68}$ is A, G, K, P, R, or V;<br>$X_{69}$ is L, R or S;<br>$X_{70}$ is A, K, M, P, R, S, or T; and<br>$X_{71}$ is F, G, H, I, K, L, M, P, R, S, or V | $X_{67}X_{68}X_{69}X_{70}X_{71}$ (SEQ ID NO: 36), wherein:<br>$X_{67}$ is I or L; $X_{68}$ is A, G, P, or V; $X_{69}$ is R; $X_{70}$ is A, M, P, R, S, or T; and $X_{71}$ is G, K, L, R, S, or V<br>$X_{67}X_{68}X_{69}X_{70}X_{71}$ (SEQ ID NO: 37), wherein:<br>X67 is L; $X_{68}$ is A, G, P, or V; $X_{69}$ is R; $X_{70}$ is A, M, P, R, or S; and $X_{71}$ is G, K, L, S, or V<br>$X_{67}X_{68}X_{69}X_{70}X_{71}$ (SEQ ID NO: 38), wherein:<br>$X_{67}$ is L; $X_{68}$ is A, G, or P; $X_{69}$ is R; $X_{70}$ is A or S; and $X_{71}$ is G or L<br>$X_{67}X_{68}X_{69}X_{70}X_{71}$ (SEQ ID NO: 39), wherein:<br>$X_{67}$ is L; $X_{68}$ is A or P; $X_{69}$ is R; $X_{70}$ is A; and $X_{71}$ is G or L |

TABLE 8J

Matriptase Cleavable Core CM Consensus Sequence 10

| Core CM Consensus 10 | Subgenus of Core CM Consensus 10 |
|---|---|
| $X_{74}X_{75}X_{76}X_{77}X_{78}$ (SEQ ID NO: 40), wherein:<br>$X_{74}$ is E, L, Q, S, T or V;<br>$X_{75}$ is L, R, or S;<br>$X_{76}$ is H, K, or R;<br>$X_{77}$ is A, M, R, or S; and<br>$X_{78}$ is G, L, M, R, S, or W | $X_{74}X_{75}X_{76}X_{77}X_{78}$ (SEQ ID NO: 41), wherein:<br>$X_{74}$ is E, L, T or V; $X_{75}$ is R or S; $X_{76}$ is K or R; $X_{77}$ is M, R, or S; and $X_{78}$ is G, L, M, S, or W<br>$X_{74}X_{75}X_{76}X_{77}X_{78}$ (SEQ ID NO: 42), wherein:<br>$X_{74}$ is E, T or V; $X_{75}$ is R or S; $X_{76}$ is K or R; $X_{77}$ is M or R; and $X_{78}$ is G, L, M, S, or W<br>$X_{74}X_{75}X_{76}X_{77}X_{78}$ (SEQ ID NO: 43), wherein:<br>$X_{74}$ is E or V; $X_{75}$ is 5; $X_{76}$ is K or R; $X_{77}$ is R; and $X_{78}$ is L, S, or W<br>$X_{74}X_{75}X_{76}X_{77}X_{78}$ (SEQ ID NO: 44), wherein:<br>$X_{74}$ is E; $X_{75}$ is 5; $X_{76}$ is K or R; $X_{77}$ is R; and $X_{78}$ is L or W |

In some embodiments, the motif sequence is a substrate for at least matriptase and includes an expanded consensus sequence based on one of the core CM consensus sequence shown in Tables 8A-8J. In some embodiments, the expanded consensus sequence is a consensus sequence shown in Tables 9A-9J-3 below.

TABLE 9A

Matriptase Cleavable Expanded Core CM Consensus Sequence 1

| Expanded Core CM Consensus 1 | Subgenus of Expanded Core CM Consensus 1 |
|---|---|
| $X_1X_2X_3X_4X_5X_6$ (SEQ ID NO: 45) wherein: $X_1$ is A, G, H, K, L, N, P, R, S, or V; $X_2$ is A, H, L, M, P, Q, R, S, or V; $X_3$ is A, E, F, G, I, L, P, R, S, T, or V; $X_4$ is A, I, K, N, R, T, or W; $X_5$ is A, G, I, L, M, Q, R, S, or V; and $X_6$ is F, G, H, L, M, R, S, or W | $X_1X_2X_3X_4X_5X_6$ (SEQ ID NO: 46), wherein: X1 is A, G, P, R, S, or V; $X_2$ is A, L, M, P, S, or V; $X_3$ is G, L, or P; $X_4$ is R; $X_5$ is A, G, R, S, or V; and $X_6$ is F, G, H, L, M, S, or W, $X_1X_2X_3X_4X_5X_6$ (SEQ ID NO: 47), wherein: $X_1$ is A, P, R, S, or V; $X_2$ is A, L, M, S, or V; $X_3$ is P; $X_4$ is R; $X_5$ is A, G, S, or V; and $X_6$ is F, G, H, M, S, or W $X_1X_2X_3X_4X_5X_6$ (SEQ ID NO: 48), wherein: $X_1$ is A, P, or R; $X_2$ is A, S, or V; $X_3$ is P; $X_4$ is R; $X_5$ is S or V; and $X_6$ is F, G, H, M, or S $X_1X_2X_3X_4X_5X_6$ (SEQ ID NO: 49), wherein: $X_1$ is A, P, or R; $X_2$ is A or S; $X_3$ is P; $X_4$ is R; $X_5$ is S; and $X_6$ is F, G, H, or S |

TABLE 9B-1

Matriptase Cleavable Expanded Core CM Consensus Sequence 2A

| Expanded Core CM Consensus 2A | Subgenus of Expanded Core CM Consensus 2A |
|---|---|
| $X_9X_{10}X_{11}X_{12}X_{13}X_{14}$ (SEQ ID NO: 50), wherein: $X_9$ is A, E, G, L, P, Q, 5, T or V; $X_{10}$ is A, L, P, R, S, T, or V; $X_{11}$ is K or R; $X_{12}$ is D or R; $X_{13}$ is A, G, L, M, S, T, V, or W; and $X_{14}$ is F, G, M, P, or V | $X_9X_{10}X_{11}X_{12}X_{13}X_{14}$ (SEQ ID NO: 51), wherein: $X_9$ is E, G, L, P, Q or S; $X_{10}$ is A, R, S, or T; $X_{11}$ is K or R; $X_{12}$ is D or R; $X_{13}$ is L or V; and $X_{14}$ is F or P $X_9X_{10}X_{11}X_{12}X_{13}X_{14}$ (SEQ ID NO: 52), wherein: $X_9$ is E, L, P or Q; $X_{10}$ is A, S, or T; $X_{11}$ is K or R; $X_{12}$ is R; $X_{13}$ is L or V; and $X_{14}$ is F or P $X_9X_{10}X_{11}X_{12}X_{13}X_{14}$ (SEQ ID NO: 53), wherein: $X_9$ is E, P or Q; $X_{10}$ is S or T; $X_{11}$ is R; $X_{12}$ is R; $X_{13}$ is L or V; and $X_{14}$ is P |

TABLE 9B-2

Matriptase Cleavable Expanded Core CM Consensus Sequence 2B

| Expanded Core CM Consensus 2B | Subgenus of Expanded Core CM Consensus 2B |
|---|---|
| $X_{10}X_{11}X_{12}X_{13}X_{14}X_{15}$ (SEQ ID NO: 54), wherein: $X_{10}$ is A, L, P, R, S, T, or V; $X_{11}$ is K or R; $X_{12}$ is D or R; $X_{13}$ is A, G, L, M, S, T, V, or W; $X_{14}$ is F, G, M, P, or V; and $X_{15}$ is G, L, M, N, P, S, V, or Y | $X_{10}X_{11}X_{12}X_{13}X_{14}X_{15}$ (SEQ ID NO: 55), wherein: $X_{10}$ is A, R, S, or T; $X_{11}$ is K or R; $X_{12}$ is D or R; $X_{13}$ is L or V; $X_{14}$ is F or P; and $X_{15}$ is G, L, S or V $X_{10}X_{11}X_{12}X_{13}X_{14}X_{15}$ (SEQ ID NO: 56), wherein: $X_{10}$ is A, S, or T; $X_{11}$ is K or R; $X_{12}$ is R; $X_{13}$ is L or V; $X_{14}$ is F or P; and $X_{15}$ is G, L, S or V $X_{10}X_{11}X_{12}X_{13}X_{14}X_{15}$ (SEQ ID NO: 57), wherein: $X_{10}$ is S or T; $X_{11}$ is R; $X_{12}$ is R; $X_{13}$ is L or V; $X_{14}$ is P; and $X_{15}$ is L or V |

TABLE 9B-3

Matriptase Cleavable Expanded Core CM Consensus Sequence 2C

| Expanded Core CM Consensus 2C | Subgenus of Expanded Core CM Consensus 2C |
|---|---|
| $X_9X_{10}X_{11}X_{12}X_{13}X_{14}X_{15}$ (SEQ ID NO: 58), wherein: $X_9$ is A, E, G, L, P, Q, 5, T or V; $X_{10}$ is A, L, P, R, S, T, or V; $X_{11}$ is K or R; $X_{12}$ is D or R; | $X_9X_{10}X_{11}X_{12}X_{13}X_{14}X_{15}$ (SEQ ID NO: 59), wherein: $X_9$ is E, G, L, P, Q or S; $X_{10}$ is A, R, S, or T; $X_{11}$ is K or R; $X_{12}$ is D or R; $X_{13}$ is L or V; $X_{14}$ is F or P; and $X_{14}$ is G, L, S or V $X_9X_{10}X_{11}X_{12}X_{13}X_{14}X_{15}$ (SEQ ID NO: 60), wherein: $X_9$ is E, L, P or Q; $X_{10}$ is A, S, or T; $X_{11}$ is K or R; |

TABLE 9B-3-continued

Matriptase Cleavable Expanded Core CM Consensus Sequence 2C

| Expanded Core CM Consensus 2C | Subgenus of Expanded Core CM Consensus 2C |
|---|---|
| $X_{13}$ is A, G, L, M, S, T, V, or W; $X_{14}$ is F, G, M, P, or V; and $X_{15}$ is G, L, M, N, P, S, V, or Y | $X_{12}$ is R; $X_{13}$ is L or V; $X_{14}$ is F or P; and $X_{14}$ is G, L, S or V<br>$X_9X_{10}X_{11}X_{12}X_{13}X_{14}X_{15}$ (SEQ ID NO: 61), wherein: $X_9$ is E, P or Q; $X_{10}$ is S or T; $X_{11}$ is R; $X_{12}$ is R; $X_{13}$ is L or V; $X_{14}$ is P; and $X_{14}$ is L or V |

TABLE 9C-1

Matriptase Cleavable Expanded Core CM Consensus Sequence 3A

| Expanded Core CM Consensus 3A | Subgenus of Expanded Core CM Consensus 3A |
|---|---|
| $X_{19}X_{20}X_{21}X_{22}X_{23}X_{24}$ (SEQ ID NO: 62), wherein:<br>$X_{19}$ is D, G, K, S, T, or V;<br>$X_{20}$ is E, G, P, R, S, V, or W;<br>$X_{21}$ is A, G, L, M, P, S, or V;<br>$X_{22}$ is A, I, L, or R;<br>$X_{23}$ is A, G, I, or P; and<br>$X_{24}$ is G or R | $X_{19}X_{20}X_{21}X_{22}X_{23}X_{24}$ (SEQ ID NO: 63), wherein: $X_{19}$ is G, K, or S; $X_{20}$ is G, P, R, S, or V; $X_{21}$ is P or V; $X_{22}$ is L or R; $X_{23}$ is G; and $X_{24}$ is G or R<br>$X_{19}X_{20}X_{21}X_{22}X_{23}X_{24}$ (SEQ ID NO: 64), wherein: $X_{19}$ is G or S; $X_{20}$ is P or R; $X_{21}$ is P; $X_{22}$ is L; $X_{23}$ is G; $X_{24}$ is R |

TABLE 9C-2

Matriptase Cleavable Expanded Core CM Consensus Sequence 3B

| Expanded Core CM Consensus 3B | Subgenus of Expanded Core CM Consensus 3B |
|---|---|
| $X_{18}X_{19}X_{20}X_{21}X_{22}X_{23}X_{24}$ (SEQ ID NO: 65), wherein:<br>$X_{18}$ is C, G, I, L or S;<br>$X_{19}$ is D, G, K, S, T, or V;<br>$X_{20}$ is E, G, P, R, S, V, or W;<br>$X_{21}$ is A, G, L, M, P, S, or V;<br>$X_{22}$ is A, I, L, or R;<br>$X_{23}$ is A, G, I, or P; and<br>$X_{24}$ is G or R | $X_{18}X_{19}X_{20}X_{21}X_{22}X_{23}X_{24}$ (SEQ ID NO: 66), wherein: $X_{18}$ is C, G, or S; $X_{19}$ is G, K, or S; $X_{20}$ is G, P, R, S, or V; $X_{21}$ is P or V; $X_{22}$ is L or R; $X_{23}$ is G; and $X_{24}$ is G or R<br>$X_{18}X_{19}X_{20}X_{21}X_{22}X_{23}X_{24}$ (SEQ ID NO: 67), wherein: $X_{18}$ is C, G, or S; $X_{19}$ is G or S; $X_{20}$ is P or R; $X_{21}$ is P; $X_{22}$ is L; $X_{23}$ is G; $X_{24}$ is R |

TABLE 9C-3

Matriptase Cleavable Expanded Core CM Consensus Sequence 3C

| Expanded Core CM Consensus 3C | Subgenus of Expanded Core CM Consensus 3C |
|---|---|
| $X_{17}X_{18}X_{19}X_{20}X_{21}X_{22}X_{23}X_{24}$ (SEQ ID NO: 68), wherein:<br>$X_{17}$ is G or S;<br>$X_{18}$ is C, G, I, L or S;<br>$X_{19}$ is D, G, K, S, T, or V;<br>$X_{20}$ is E, G, P, R, S, V, or W;<br>$X_{21}$ is A, G, L, M, P, S, or V;<br>$X_{22}$ is A, I, L, or R;<br>$X_{23}$ is A, G, I, or P; and<br>$X_{24}$ is G or R | $X_{17}X_{18}X_{19}X_{20}X_{21}X_{22}X_{23}X_{24}$ (SEQ ID NO: 69), wherein: $X_{17}$ is G or S; $X_{18}$ is C, G, or S; $X_{19}$ is G, K, or S; $X_{20}$ is G, P, R, S, or V; $X_{21}$ is P or V; $X_{22}$ is L or R; $X_{23}$ is G; and $X_{24}$ is G or R<br>$X_{17}X_{18}X_{19}X_{20}X_{21}X_{22}X_{23}X_{24}$ (SEQ ID NO: 70), wherein: $X_{17}$ is G or S; $X_{18}$ is C, G, or S; $X_{19}$ is G or S; $X_{20}$ is P or R; $X_{21}$ is P; $X_{22}$ is L; $X_{23}$ is G; $X_{24}$ is R |

TABLE 9D-1

Matriptase Cleavable Expanded Core CM Consensus Sequence 4A

| Expanded Core CM Consensus 4A | Subgenus of Expanded Core CM Consensus 4A |
|---|---|
| $X_{25}X_{26}X_{27}X_{28}X_{29}X_{30}$ (SEQ ID NO: 71), wherein:<br>$X_{25}$ is G, M, R, or S;<br>$X_{26}$ is A, G, H, L, R, or S;<br>$X_{27}$ is D, H, N, R, S, T, or W;<br>$X_{28}$ is A, N, P, R, S, T, or V; | $X_{25}X_{26}X_{27}X_{28}X_{29}X_{30}$ (SEQ ID NO: 72), wherein: $X_{25}$ is G, M, R, or S; $X_{26}$ is A, G, H, L, R, or S; $X_{27}$ is D, H, R, or T; $X_{28}$ is A, P, R, S, T, or V; $X_{29}$ is F, G, L, M, P, or S; and $X_{30}$ is G, L, P, S, V, or W<br>$X_{25}X_{26}X_{27}X_{28}X_{29}X_{30}$ (SEQ ID NO: 73), wherein: $X_{25}$ is G, M, R, or S; $X_{26}$ is G, L, or S; $X_{27}$ is R or T; |

TABLE 9D-1-continued

Matriptase Cleavable Expanded Core CM Consensus Sequence 4A

| Expanded Core CM Consensus 4A | Subgenus of Expanded Core CM Consensus 4A |
|---|---|
| $X_{29}$ is F, G, L, M, P, Q, R, S, or Y; and $X_{30}$ is I, G, L, P, S, V, or W | $X_{28}$ is A, P, or S; $X_{29}$ is F, G, M, or S; and $X_{30}$ is G, P, S, V, or W<br>$X_{25}X_{26}X_{27}X_{28}X_{29}X_{30}$ (SEQ ID NO: 74), wherein:<br>$X_{25}$ is G, M, R, or S; $X_{26}$ is G, L, or S; $X_{27}$ is R; $X_{28}$ is A or S; $X_{29}$ is G or M; and $X_{30}$ is G, P, S, or W<br>$X_{25}X_{26}X_{27}X_{28}X_{29}X_{30}$ (SEQ ID NO: 75), wherein:<br>$X_{25}$ is M; $X_{26}$ is L; $X_{27}$ is R; $X_{28}$ is A or S; $X_{29}$ is G; and $X_{30}$ is W |

TABLE 9D-2

Matriptase Cleavable Expanded Core CM Consensus Sequence 4B

| Expanded Core CM Consensus 4B | Subgenus of Expanded Core CM Consensus 4B |
|---|---|
| $X_{25}X_{26}X_{27}X_{28}X_{29}X_{30}X_{31}$ (SEQ ID NO: 76), wherein:<br>$X_{25}$ is G, M, R, or S;<br>$X_{26}$ is A, G, H, L, R, or S;<br>$X_{27}$ is D, H, N, R, S, T, or W;<br>$X_{28}$ is A, N, P, R, S, T, or V;<br>$X_{29}$ is F, G, L, M, P, Q, R, S, or Y;<br>$X_{30}$ is I, G, L, P, S, V, or W; and<br>$X_{31}$ is G, P, R, or S<br>$X_{31}$ is G, R, or S | $X_{25}X_{26}X_{27}X_{28}X_{29}X_{30}X_{31}$ (SEQ ID NO: 77), wherein:<br>$X_{25}$ is G, M, R, or S; $X_{26}$ is A, G, H, L, R, or S; $X_{27}$ is D, H, R, or T; $X_{28}$ is A, P, R, S, T, or V; $X_{29}$ is F, G, L, M, P, or S; $X_{30}$ is G, L, P, S, V, or W; and $X_{31}$ is G, P, R, or S<br>$X_{25}X_{26}X_{27}X_{28}X_{29}X_{30}X_{31}$ (SEQ ID NO: 78), wherein:<br>$X_{25}$ is G, M, R, or S; $X_{26}$ is G, L, or S; $X_{27}$ is R or T; $X_{28}$ is A, P, or S; $X_{29}$ is F, G, M, or S; $X_{30}$ is G, P, S, V, or W; and $X_{31}$ is G, R, or S<br>$X_{25}X_{26}X_{27}X_{28}X_{29}X_{30}X_{31}$ (SEQ ID NO: 79), wherein:<br>$X_{25}$ is G, M, R, or S; $X_{26}$ is G, L, or S; $X_{27}$ is R; $X_{28}$ is A or S; $X_{29}$ is G or M; $X_{30}$ is G, P, S, or W; and<br>$X_{25}X_{26}X_{27}X_{28}X_{29}X_{30}X_{31}$ (SEQ ID NO: 80), wherein:<br>$X_{25}$ is M; $X_{26}$ is L; $X_{27}$ is R; $X_{28}$ is A or S; $X_{29}$ is G; $X_{30}$ is W; and $X_{31}$ is R |

TABLE 9D-3

Matriptase Cleavable Expanded Core CM Consensus Sequence 4C

| Expanded Core CM Consensus 4C | Subgenus of Expanded Core CM Consensus 4C |
|---|---|
| $X_{25}X_{26}X_{27}X_{28}X_{29}X_{30}X_{31}X_{32}$ (SEQ ID NO: 81), wherein:<br>$X_{25}$ is G, M, R, or S;<br>$X_{26}$ is A, G, H, L, R, or S;<br>$X_{27}$ is D, H, N, R, S, T, or W;<br>$X_{28}$ is A, N, P, R, S, T, or V;<br>$X_{29}$ is F, G, L, M, P, Q, R, S, or Y;<br>$X_{30}$ is I, G, L, P, S, V, or W;<br>$X_{31}$ is G, P, R, or S; and<br>$X_{32}$ is G, L, R, S, or V | $X_{25}X_{26}X_{27}X_{28}X_{29}X_{30}X_{31}X_{32}$ (SEQ ID NO: 82), wherein: $X_{25}$ is G, M, R, or S; $X_{26}$ is A, G, H, L, R, or S; $X_{27}$ is D, H, R, or T; $X_{28}$ is A, P, R, S, T, or V; $X_{29}$ is F, G, L, M, P, or S; $X_{30}$ is G, L, P, S, V, or W; $X_{31}$ is G, P, R, or S; and $X_{32}$ is G, L, R, S, or V<br>$X_{25}X_{26}X_{27}X_{28}X_{29}X_{30}X_{31}X_{32}$ (SEQ ID NO: 83), wherein: $X_{25}$ is G, M, R, or S; $X_{26}$ is G, L, or S; $X_{27}$ is R or T; $X_{28}$ is A, P, or S; $X_{29}$ is F, G, M, or S; $X_{30}$ is G, P, S, V, or W; $X_{31}$ is G, R, or S; and $X_{32}$ is G, L, S, or V<br>$X_{25}X_{26}X_{27}X_{28}X_{29}X_{30}X_{31}X_{32}$ (SEQ ID NO: 84), wherein: $X_{25}$ is G, M, R, or S; $X_{26}$ is G, L, or S; $X_{27}$ is R; $X_{28}$ is A or S; $X_{29}$ is G or M; $X_{30}$ is G, P, S, or W; $X_{31}$ is G, R, or S; and $X_{32}$ is G, L, S, or V<br>$X_{25}X_{26}X_{27}X_{28}X_{29}X_{30}X_{31}X_{32}$ (SEQ ID NO: 85), wherein: $X_{25}$ is M; $X_{26}$ is L; $X_{27}$ is R; $X_{28}$ is A or S; $X_{29}$ is G; $X_{30}$ is W; $X_{31}$ is R; and $X_{32}$ is G, L, or S |

TABLE 9E-1

Matriptase Cleavable Expanded Core CM Consensus Sequence 5A

| Expanded Core CM Consensus 5A | Subgenus of Expanded Core CM Consensus 5A |
|---|---|
| $X_{35}X_{36}X_{37}X_{38}X_{39}X_{40}$ (SEQ ID NO: 86), wherein:<br>$X_{35}$ is A, E, G, H, I, L, N, P, S, or V;<br>$X_{36}$ is G, K, L, S, V, or W;<br>$X_{37}$ is G, I, P, Q, R, or S;<br>$X_{38}$ is R;<br>$X_{39}$ is G, K, R, S, or V; and | $X_{35}X_{36}X_{37}X_{38}X_{39}X_{40}$ (SEQ ID NO: 87), wherein:<br>$X_{35}$ is G, I, S, or V $X_{36}$ is G, L, S, V, or W; $X_{37}$ is G, Q, R, or S; $X_{38}$ is R; $X_{39}$ is G, S, or V; and $X_{40}$ is A, G, L, S, or V<br>$X_{35}X_{36}X_{37}X_{38}X_{39}X_{40}$ (SEQ ID NO: 88), wherein:<br>$X_{35}$ is G, I, S, or V $X_{36}$ is V; $X_{37}$ is S; $X_{38}$ is R; $X_{39}$ is S; and $X_{40}$ is A or V |

TABLE 9E-1-continued

Matriptase Cleavable Expanded Core CM Consensus Sequence 5A

| Expanded Core CM Consensus 5A | Subgenus of Expanded Core CM Consensus 5A |
|---|---|
| $X_{40}$ is A, C, G, L, M, P, S, V, or Y | $X_{35}X_{36}X_{37}X_{38}X_{39}X_{40}$ (SEQ ID NO: 89), wherein: $X_{35}$ is I; $X_{36}$ is V; $X_{37}$ is S; $X_{38}$ is R; $X_{39}$ is S; and $X_{40}$ is A or V |

TABLE 9E-2

Matriptase Cleavable Expanded Core CM Consensus Sequence 5B

| Expanded Core CM Consensus 5B | Subgenus of Expanded Core CM Consensus 5B |
|---|---|
| $X_{34}X_{35}X_{36}X_{37}X_{38}X_{39}X_{40}$ (SEQ ID NO: 90), wherein: $X_{34}$ is A, G, K, M, P, Q, S, V, or Y; $X_{35}$ is A, E, G, H, I, L, N, P, S, or V; $X_{36}$ is G, K, L, S, V, or W; $X_{37}$ is G, I, P, Q, R, or S; $X_{38}$ is R; $X_{39}$ is G, K, R, S, or V; and $X_{40}$ is A, C, G, L, M, P, S, V, or Y | $X_{34}X_{35}X_{36}X_{37}X_{38}X_{39}X_{40}$ (SEQ ID NO: 91), wherein: $X_{34}$ is A, G, K, S, V, or Y; and $X_{35}$ is G, I, S, or V $X_{36}$ is G, L, S, V, or W; $X_{37}$ is G, Q, R, or S; $X_{38}$ is R; $X_{39}$ is G, S, or V; and $X_{40}$ is A, G, L, S, or V $X_{34}X_{35}X_{36}X_{37}X_{38}X_{39}X_{40}$ (SEQ ID NO: 92), wherein: $X_{34}$ is G, S, V, or Y; $X_{35}$ is G, I, S, or V $X_{36}$ is V; $X_{37}$ is S; $X_{38}$ is R; $X_{39}$ is S; and $X_{40}$ is A or V $X_{34}X_{35}X_{36}X_{37}X_{38}X_{39}X_{40}$ (SEQ ID NO: 93), wherein: $X_{34}$ is Y; $X_{35}$ is I; $X_{36}$ is V; $X_{37}$ is S; $X_{38}$ is R; $X_{39}$ is S; and $X_{40}$ is A or V |

TABLE 9E-3

Matriptase Cleavable Expanded Core CM Consensus Sequence 5C

| Expanded Core CM Consensus 5C | Subgenus of Expanded Core CM Consensus 5C |
|---|---|
| $X_{33}X_{34}X_{35}X_{36}X_{37}X_{38}X_{39}X_{40}$ (SEQ ID NO: 94), wherein: $X_{33}$ is G, K, P, Q, S, or T; $X_{34}$ is A, G, K, M, P, Q, S, V, or Y; $X_{35}$ is A, E, G, H, I, L, N, P, S, or V; $X_{36}$ is G, K, L, S, V, or W; $X_{37}$ is G, I, P, Q, R, or S; $X_{38}$ is R; $X_{39}$ is G, K, R, S, or V; and $X_{40}$ is A, C, G, L, M, P, S, V, or Y | $X_{33}X_{34}X_{35}X_{36}X_{37}X_{38}X_{39}X_{40}$ (SEQ ID NO: 95), wherein: $X_{33}$ is G, P, Q, S, or T; $X_{34}$ is A, G, K, S, V, or Y; and $X_{35}$ is G, I, S, or V $X_{36}$ is G, L, S, V, or W; $X_{37}$ is G, Q, R, or S; $X_{38}$ is R; $X_{39}$ is G, S, or V; and $X_{40}$ is A, G, L, S, or V $X_{33}X_{34}X_{35}X_{36}X_{37}X_{38}X_{39}X_{40}$ (SEQ ID NO: 96), wherein: $X_{33}$ is G, Q, or S; $X_{34}$ is G, S, V, or Y; $X_{35}$ is G, I, S, or V $X_{36}$ is V; $X_{37}$ is S; $X_{38}$ is R; $X_{39}$ is S; and $X_{40}$ is A or V $X_{33}X_{34}X_{35}X_{36}X_{37}X_{38}X_{39}X_{40}$ (SEQ ID NO: 97), wherein: $X_{33}$ is G, Q, or S; $X_{34}$ is Y; $X_{35}$ is I; $X_{36}$ is V; $X_{37}$ is S; $X_{38}$ is R; $X_{39}$ is S; and $X_{40}$ is A or V |

TABLE 9F

Matriptase Cleavable Expanded Core CM Consensus Sequence 6

| Expanded Core CM Consensus 6 | Subgenus of Expanded Core CM Consensus 6 |
|---|---|
| $X_{41}X_{42}X_{43}X_{44}X_{45}X_{46}$ (SEQ ID NO: 98), wherein: $X_{41}$ is G, K, P, R, S, or T; $X_{42}$ is A, E, G, I, L, M, R, or S; $X_{43}$ is A, G, K, L, N, R, S, or V; $X_{44}$ is F, H, L, R, or Y; $X_{45}$ is A, F, G, H, P, or S; and $X_{46}$ is F, G, M, N, P, R, S, or V | $X_{41}X_{42}X_{43}X_{44}X_{45}X_{46}$ (SEQ ID NO: 99), wherein: $X_{41}$ is G, K, R, S, or T; $X_{42}$ is A, E, G, L, M, R, or S; $X_{43}$ is G, K, L, N, R, S, or V; $X_{44}$ is R or Y; $X_{45}$ is A, F, G, P, or S; and $X_{46}$ is F, G, M, P, R, S, or V $X_{41}X_{42}X_{43}X_{44}X_{45}X_{46}$ (SEQ ID NO: 100), wherein: $X_{41}$ is G, R, S, or T; $X_{42}$ is A, E, G, M, or S; $X_{43}$ is G, L, S, or V; $X_{44}$ is R or Y; $X_{45}$ is A, G, P, or S; and $X_{46}$ is F, G, M, P, R, S, or V $X_{41}X_{42}X_{43}X_{44}X_{45}X_{46}$ (SEQ ID NO: 101), wherein: $X_{41}$ is G, R, or S; $X_{42}$ is A, G, or S; $X_{43}$ is L, S, or V; $X_{44}$ is R; $X_{45}$ is A; and $X_{46}$ is M or P $X_{41}X_{42}X_{43}X_{44}X_{45}X_{46}$ (SEQ ID NO: 102), wherein: $X_{41}$ is G, R, or S; $X_{42}$ is A; $X_{43}$ is L, S or V; $X_{44}$ is R; $X_{45}$ is A; and $X_{46}$ is M or P |

TABLE 9G-1

Matriptase Cleavable Expanded Core CM Consensus Sequence 7A

| Expanded Core CM Consensus 7A | Subgenus of Expanded Core CM Consensus 7A |
|---|---|
| $X_{50}X_{51}X_{52}X_{53}X_{54}X_{55}$ (SEQ ID NO: 103), wherein:<br>$X_{50}$ is A, E, K, L, P, S, T, V, W, or Y;<br>$X_{51}$ is A, I, L, P, R, S, V, or Y;<br>$X_{52}$ is E, G, H, L, P, or V;<br>$X_{53}$ is G, K, L, or R;<br>$X_{54}$ is Q or R; and<br>$X_{55}$ is A, G, H, M, R, or S | $X_{50}X_{51}X_{52}X_{53}X_{54}X_{55}$ (SEQ ID NO: 104), wherein: $X_{50}$ is E, P, S, V, or W; $X_{51}$ is A, P, R, S, V, or Y; $X_{52}$ is E, G, H, L, P, or V; $X_{53}$ is G, K, L, or R; $X_{54}$ is Q or R; and $X_{55}$ is A, G, H, M, R, or S<br>$X_{50}X_{51}X_{52}X_{53}X_{54}X_{55}$ (SEQ ID NO: 105), wherein: $X_{50}$ is P or V; $X_{51}$ is A, P, or R; $X_{52}$ is E, G, P, or V; and $X_{53}$ is G or R; $X_{54}$ is R; $X_{55}$ is G, M, or S<br>$X_{50}X_{51}X_{52}X_{53}X_{54}X_{55}$ (SEQ ID NO: 106), wherein: $X_{50}$ is P or V; $X_{51}$ is A or R; $X_{52}$ is G or V; $X_{53}$ is G or R; $X_{54}$ is R; and $X_{55}$ is M or S<br>$X_{50}X_{51}X_{52}X_{53}X_{54}X_{55}$ (SEQ ID NO: 107), wherein: $X_{50}$ is P or V; $X_{51}$ is A; $X_{52}$ is G or V; $X_{53}$ is R; $X_{54}$ is R; and $X_{55}$ is M or S |

TABLE 9G-2

Matriptase Cleavable Expanded Core CM Consensus Sequence 7B

| Expanded Core CM Consensus 7B | Subgenus of Expanded Core CM Consensus 7B |
|---|---|
| $X_{49}X_{50}X_{51}X_{52}X_{53}X_{54}X_{55}$ (SEQ ID NO: 108), wherein:<br>$X_{49}$ is E, G, K, P, Q, S, T, or V;<br>$X_{50}$ is A, E, K, L, P, S, T, V, W, or Y;<br>$X_{51}$ is A, I, L, P, R, S, V, or Y;<br>$X_{52}$ is E, G, H, L, P, or V;<br>$X_{53}$ is G, K, L, or R;<br>$X_{54}$ is Q or R; and<br>$X_{55}$ is A, G, H, M, R, or S | $X_{49}X_{50}X_{51}X_{52}X_{53}X_{54}X_{55}$ (SEQ ID NO: 109), wherein: $X_{49}$ is G, K, P, Q, S, or V; $X_{50}$ is E, P, S, V, or W; $X_{51}$ is A, P, R, S, V, or Y; $X_{52}$ is E, G, H, L, P, or V; $X_{53}$ is G, K, L, or R; $X_{54}$ is Q or R; and $X_{55}$ is A, G, H, M, R, or S<br>$X_{49}X_{50}X_{51}X_{52}X_{53}X_{54}X_{55}$ (SEQ ID NO:: 110), wherein: $X_{49}$ is G, P, S, or V; $X_{50}$ is P or V; $X_{51}$ is A, P, or R; $X_{52}$ is E, G, P, or V; $X_{53}$ is G or R; $X_{54}$ is R; and $X_{55}$ is G, M, or S<br>$X_{49}X_{50}X_{51}X_{52}X_{53}X_{54}X_{55}$ (SEQ ID NO: 111), wherein: $X_{49}$ is G, P, S, or V; $X_{50}$ is P or V; $X_{51}$ is A or R; $X_{52}$ is G or V; $X_{53}$ is G or R; $X_{54}$ is R; and $X_{55}$ is M or S<br>$X_{49}X_{50}X_{51}X_{52}X_{53}X_{54}X_{55}$ (SEQ ID NO: 112), wherein: $X_{49}$ is G, S, or V; $X_{50}$ is P or V; $X_{51}$ is A; $X_{52}$ is G or V; $X_{53}$ is R; $X_{54}$ is R; and $X_{55}$ is M or S |

TABLE 9G-3

Matriptase Cleavable Expanded Core CM Consensus Sequence 7C

| Expanded Core CM Consensus 7C | Subgenus of Expanded Core CM Consensus 7C |
|---|---|
| $X_{49}X_{50}X_{51}X_{52}X_{53}X_{54}X_{55}X_{56}$ (SEQ ID NO: 113), wherein:<br>$X_{49}$ is E, G, K, P, Q, S, T, or V;<br>$X_{50}$ is A, E, K, L, P, S, T, V, W, or Y;<br>$X_{51}$ is A, I, L, P, R, S, V, or Y;<br>$X_{52}$ is E, G, H, L, P, or V;<br>$X_{53}$ is G, K, L, or R;<br>$X_{54}$ is Q or R;<br>$X_{55}$ is A, G, H, M, R, or S; and<br>$X_{56}$ is F, G, L, M, P, S, or W | $X_{49}X_{50}X_{51}X_{52}X_{53}X_{54}X_{55}X_{56}$ (SEQ ID NO: 114), wherein: $X_{49}$ is G, K, P, Q, S, or V; $X_{50}$ is E, P, S, V, or W; $X_{51}$ is A, P, R, S, V, or Y; $X_{52}$ is E, G, H, L, P, or V; $X_{53}$ is G, K, L, or R; $X_{54}$ is Q or R; $X_{55}$ is A, G, H, M, R, or S; and $X_{56}$ is G, L, M, P, S, or W<br>$X_{49}X_{50}X_{51}X_{52}X_{53}X_{54}X_{55}X_{56}$ (SEQ ID NO: 115), wherein: $X_{49}$ is G, P, S, or V; $X_{50}$ is P or V; $X_{51}$ is A, P, or R; $X_{52}$ is E, G, P, or V; $X_{53}$ is G or R; $X_{54}$ is R; $X_{55}$ is G, M, or S; and $X_{56}$ is G, L, M, P, S, or W<br>$X_{49}X_{50}X_{51}X_{52}X_{53}X_{54}X_{55}X_{56}$ (SEQ ID NO: 116), wherein: $X_{49}$ is G, P, S, or V; $X_{50}$ is P or V; $X_{51}$ is A or R; $X_{52}$ is G or V; $X_{53}$ is G or R; $X_{54}$ is R; $X_{55}$ is M or S; and $X_{56}$ is G, L, P, S, or W<br>$X_{49}X_{50}X_{51}X_{52}X_{53}X_{54}X_{55}X_{56}$ (SEQ ID NO: 117), wherein: $X_{49}$ is G, S, or V; $X_{50}$ is P or V; $X_{51}$ is A; $X_{52}$ is G or V; $X_{53}$ is R; $X_{54}$ is R; $X_{55}$ is M or S; and $X_{56}$ is G, L, or S |

TABLE 9H-1

Matriptase Cleavable Expanded Core CM Consensus Sequence 8A

| Expanded Core CM Consensus 8A | Subgenus of Expanded Core CM Consensus 8A |
|---|---|
| $X_{57}X_{58}X_{59}X_{60}X_{61}X_{62}$ (SEQ ID NO: 118), wherein: <br> $X_{57}$ is A, G, I, K, P, S, or T; <br> $X_{58}$ is R or T; <br> $X_{59}$ is H, M, or S; <br> $X_{60}$ is F, M, or R; <br> $X_{61}$ is A, G, I, L, P, Q, R, S, V, or W; and <br> $X_{62}$ is A, G, L, M, P, Q, R, S, T, V, or W | $X_{57}X_{58}X_{59}X_{60}X_{61}X_{62}$ (SEQ ID NO: 119), wherein: $X_{57}$ is A, G, I, K, S, or T; $X_{58}$ is R; $X_{59}$ is S; $X_{60}$ is F, M, or R; $X_{61}$ is A, I, L, R, or W; and $X_{62}$ is G, L, M, P, Q, R, S, or V <br> $X_{57}X_{58}X_{59}X_{60}X_{61}X_{62}$ (SEQ ID NO: 120), wherein: $X_{57}$ is G or K; $X_{58}$ is R; $X_{59}$ is S; $X_{60}$ is M; $X_{61}$ is A, L, R, or W; and $X_{62}$ is G, L, M, P, R, or S <br> $X_{57}X_{58}X_{59}X_{60}X_{61}X_{62}$ (SEQ ID NO: 121), wherein: $X_{57}$ is G; $X_{58}$ is R; $X_{59}$ is S; $X_{60}$ is M; $X_{61}$ is A or L; and $X_{62}$ is G, L, M, R, or S <br> $X_{57}X_{58}X_{59}X_{60}X_{61}X_{62}$ (SEQ ID NO: 122), wherein: $X_{57}$ is G; $X_{58}$ is R; $X_{59}$ is S; $X_{60}$ is M; $X_{61}$ is A or L; and $X_{62}$ is L or M |

TABLE 9H-2

Matriptase Cleavable Expanded Core CM Consensus Sequence 8B

| Expanded Core CM Consensus 8B | Subgenus of Expanded Core CM Consensus 8B |
|---|---|
| $X_{57}X_{58}X_{59}X_{60}X_{61}X_{62}X_{63}$ (SEQ ID NO: 123), wherein: <br> $X_{57}$ is A, G, I, K, P, S, or T; <br> $X_{58}$ is R or T; <br> $X_{59}$ is H, M, or S; <br> $X_{60}$ is F, M, or R; <br> $X_{61}$ is A, G, I, L, P, Q, R, S, V, or W; <br> $X_{62}$ is A, G, L, M, P, Q, R, S, T, V, or W; and <br> $X_{63}$ is A, G, K, M, P, R, S, W, or Y | $X_{57}X_{58}X_{59}X_{60}X_{61}X_{62}X_{63}$ (SEQ ID NO: 124), wherein: $X_{57}$ is A, G, I, K, S, or T; $X_{58}$ is R; $X_{59}$ is S; $X_{60}$ is F, M, or R; $X_{61}$ is A, I, L, R, or W; $X_{62}$ is G, L, M, P, Q, R, S, or V; and $X_{63}$ is A, G, P, R, S, W, or Y <br> $X_{57}X_{58}X_{59}X_{60}X_{61}X_{62}X_{63}$ (SEQ ID NO: 125), wherein: $X_{57}$ is G or K; $X_{58}$ is R; $X_{59}$ is S; $X_{60}$ is M; $X_{61}$ is A, L, R, or W; $X_{62}$ is G, L, M, P, R, or S; and $X_{63}$ is A, G, P, R, S, or W <br> $X_{57}X_{58}X_{59}X_{60}X_{61}X_{62}X_{63}$ (SEQ ID NO: 126), wherein: $X_{57}$ is G; $X_{58}$ is R; $X_{59}$ is S; $X_{60}$ is M; $X_{61}$ is A or L; $X_{62}$ is G, L, M, R, or S; and $X_{63}$ is A, G, P, R, or S <br> $X_{57}X_{58}X_{59}X_{60}X_{61}X_{62}X_{63}$ (SEQ ID NO: 127), wherein: $X_{57}$ is G; $X_{58}$ is R; $X_{59}$ is S; $X_{60}$ is M; $X_{61}$ is A or L; $X_{62}$ is L or M; and $X_{63}$ is G, P, or S |

TABLE 9H-3

Matriptase Cleavable Expanded Core CM Consensus Sequence 8C

| Expanded Core CM Consensus 8C | Subgenus of Expanded Core CM Consensus 8C |
|---|---|
| $X_{57}X_{58}X_{59}X_{60}X_{61}X_{62}X_{63}X_{64}$ (SEQ ID NO: 128), wherein: <br> $X_{57}$ is A, G, I, K, P, S, or T; <br> $X_{58}$ is R or T; <br> $X_{59}$ is H, M, or S; <br> $X_{60}$ is F, M, or R; <br> $X_{61}$ is A, G, I, L, P, Q, R, S, V, or W; <br> $X_{62}$ is A, G, L, M, P, Q, R, S, T, V, or W; <br> $X_{63}$ is A, G, K, M, P, R, S, W, or Y; and <br> $X_{64}$ is F, G, I, L, P, Q, S, or Y | $X_{57}X_{58}X_{59}X_{60}X_{61}X_{62}X_{63}X_{64}$ (SEQ ID NO: 129), wherein: $X_{57}$ is A, G, I, K, S, or T; $X_{58}$ is R; $X_{59}$ is S; $X_{60}$ is F, M, or R; $X_{61}$ is A, I, L, R, or W; $X_{62}$ is G, L, M, P, Q, R, S, or V; $X_{63}$ is A, G, P, R, S, W, or Y; and $X_{64}$ is F, G, L, P, or S <br> $X_{57}X_{58}X_{59}X_{60}X_{61}X_{62}X_{63}X_{64}$ (SEQ ID NO: 130), wherein: $X_{57}$ is G or K; $X_{58}$ is R; $X_{59}$ is S; $X_{60}$ is M; $X_{61}$ is A, L, R, or W; $X_{62}$ is G, L, M, P, R, or S; $X_{63}$ is A, G, P, R, S, or W; and $X_{64}$ is F, G, L, P, or S <br> $X_{57}X_{58}X_{59}X_{60}X_{61}X_{62}X_{63}X_{64}$ (SEQ ID NO: 131), wherein: $X_{57}$ is G; $X_{58}$ is R; $X_{59}$ is S; $X_{60}$ is M; $X_{61}$ is A or L; $X_{62}$ is G, L, M, R, or S; $X_{63}$ is A, G, P, R, or S; and $X_{64}$ is F, G, P, or S <br> $X_{57}X_{58}X_{59}X_{60}X_{61}X_{62}X_{63}X_{64}$ (SEQ ID NO: 132), wherein: $X_{57}$ is G; $X_{58}$ is R; $X_{59}$ is S; $X_{60}$ is M; $X_{61}$ is A or L; $X_{62}$ is L or M; $X_{63}$ is G, P, or S; and $X_{64}$ is G, P, or S |

TABLE 9I-1

Matriptase Cleavable Expanded Core CM Consensus Sequence 9A

| Expanded Core CM Consensus 9A | Subgenus of Expanded Core CM Consensus 9A |
|---|---|
| $X_{67}X_{68}X_{69}X_{70}X_{71}X_{72}$ (SEQ ID NO: 133), wherein: | $X_{67}X_{68}X_{69}X_{70}X_{71}X_{72}$ (SEQ ID NO: 134), wherein: $X_{67}$ is I or L; $X_{68}$ is A, G, P, or V; $X_{69}$ is R; $X_{70}$ is A, |

TABLE 9I-1-continued

Matriptase Cleavable Expanded Core CM Consensus Sequence 9A

| Expanded Core CM Consensus 9A | Subgenus of Expanded Core CM Consensus 9A |
|---|---|
| $X_{67}$ is I, L, or S;<br>$X_{68}$ is A, G, K, P, R, or V;<br>$X_{69}$ is L, R or S;<br>$X_{70}$ is A, K, M, P, R, S, or T;<br>$X_{71}$ is F, G, H, I, K, L, M, P, R, S, or V; and<br>$X_{72}$ is F, G, I, L, M, P, R, S, T, V, W, or Y | M, P, R, S, or T; $X_{71}$ is G, K, L, R, S, or V; and $X_{72}$ is F, G, I, L, M, S, or V<br>$X_{67}X_{68}X_{69}X_{70}X_{71}X_{72}$ (SEQ ID NO: 135), wherein:<br>$X_{67}$ is L; $X_{68}$ is A, G, P, or V; $X_{69}$ is R; $X_{70}$ is A, M, P, R, or S; $X_{71}$ is G, K, L, S, or V; and $X_{72}$ is F, G, I, L, S, or V<br>$X_{67}X_{68}X_{69}X_{70}X_{71}X_{72}$ (SEQ ID NO: 136), wherein:<br>$X_{67}$ is L; $X_{68}$ is A, G, or P; $X_{69}$ is R; $X_{70}$ is A or S; $X_{71}$ is G or L; and $X_{72}$ is I or L<br>$X_{67}X_{68}X_{69}X_{70}X_{71}X_{72}$ (SEQ ID NO: 137), wherein:<br>$X_{67}$ is L; $X_{68}$ is A or P; $X_{69}$ is R; $X_{70}$ is A; $X_{71}$ is G or L; and $X_{72}$ is I or L |

TABLE 9I-2

Matriptase Cleavable Expanded Core CM Consensus Sequence 9B

| Expanded Core CM Consensus 9B | Subgenus of Expanded Core CM Consensus 9B |
|---|---|
| $X_{66}X_{67}X_{68}X_{69}X_{70}X_{71}X_{72}$ (SEQ ID NO: 138), wherein:<br>$X_{66}$ is G, K, P, Q, R, S, or T;<br>$X_{67}$ is I, L, or S;<br>$X_{68}$ is A, G, K, P, R, or V;<br>$X_{69}$ is L, R or S;<br>$X_{70}$ is A, K, M, P, R, S, or T;<br>$X_{71}$ is F, G, H, I, K, L, M, P, R, S, or V; and<br>$X_{72}$ is F, G, I, L, M, P, R, S, T, V, W, or Y | $X_{66}X_{67}X_{68}X_{69}X_{70}X_{71}X_{72}$ (SEQ ID NO: 139), wherein: $X_{66}$ is G, P, R, S, or T; $X_{67}$ is I or L; $X_{68}$ is A, G, P, or V; $X_{69}$ is R; $X_{70}$ is A, M, P, R, S, or T; $X_{71}$ is G, K, L, R, S, or V; and $X_{72}$ is F, G, I, L, M, S, or V<br>$X_{66}X_{67}X_{68}X_{69}X_{70}X_{71}X_{72}$ (SEQ ID NO: 140), wherein: $X_{66}$ is G, P, R, or S; $X_{67}$ is L; $X_{68}$ is A, G, P, or V; $X_{69}$ is R; $X_{70}$ is A, M, P, R, or S; $X_{71}$ is G, K, L, S, or V; and $X_{72}$ is F, G, I, L, S, or V<br>$X_{66}X_{67}X_{68}X_{69}X_{70}X_{71}X_{72}$ (SEQ ID NO: 141), wherein: $X_{66}$ is P; $X_{67}$ is L; $X_{68}$ is A, G, or P; $X_{69}$ is R; $X_{70}$ is A or S; $X_{71}$ is G or L; and $X_{72}$ is I or L<br>$X_{66}X_{67}X_{68}X_{69}X_{70}X_{71}X_{72}$ (SEQ ID NO: 142), wherein: $X_{66}$ is P; $X_{67}$ is L; $X_{68}$ is A or P; $X_{69}$ is R; $X_{70}$ is A; $X_{71}$ is G or L; and $X_{72}$ is I or L |

TABLE 9I-3

Matriptase Cleavable Expanded Core CM Consensus Sequence 9C

| Expanded Core CM Consensus 9C | Subgenus of Expanded Core CM Consensus 9C |
|---|---|
| $X_{65}X_{66}X_{67}X_{68}X_{69}X_{70}X_{71}X_{72}$ (SEQ ID NO: 143), wherein:<br>$X_{65}$ is A, G, I, K, P, R, S, or V;<br>$X_{66}$ is G, K, P, Q, R, S, or T;<br>$X_{67}$ is I, L, or S;<br>$X_{68}$ is A, G, K, P, R, or V;<br>$X_{69}$ is L, R or S;<br>$X_{70}$ is A, K, M, P, R, S, or T;<br>$X_{71}$ is F, G, H, I, K, L, M, P, R, S, or V; and<br>$X_{72}$ is F, G, I, L, M, P, R, S, T, V, W, or Y | $X_{65}X_{66}X_{67}X_{68}X_{69}X_{70}X_{71}X_{72}$ (SEQ ID NO: 144), wherein: $X_{65}$ is G, K, P, R, S, or V; $X_{66}$ is G, P, R, S, or T; $X_{67}$ is I or L; $X_{68}$ is A, G, P, or V; $X_{69}$ is R; $X_{70}$ is A, M, P, R, S, or T; $X_{71}$ is G, K, L, R, S, or V; and $X_{72}$ is F, G, I, L, M, S, or V<br>$X_{65}X_{66}X_{67}X_{68}X_{69}X_{70}X_{71}X_{72}$ (SEQ ID NO: 145), wherein: $X_{65}$ is G, P, R, or S; $X_{66}$ is G, P, R, or S; $X_{67}$ is L; $X_{68}$ is A, G, P, or V; $X_{69}$ is R; $X_{70}$ is A, M, P, R, or S; $X_{71}$ is G, K, L, S, or V; and $X_{72}$ is F, G, I, L, S, or V<br>$X_{65}X_{66}X_{67}X_{68}X_{69}X_{70}X_{71}X_{72}$ (SEQ ID NO: 146), wherein: $X_{65}$ is G, P, R, or S; $X_{66}$ is P; $X_{67}$ is L; $X_{68}$ is A, G, or P; $X_{69}$ is R; $X_{70}$ is A or S; $X_{71}$ is G or L; and $X_{72}$ is I or L<br>$X_{65}X_{66}X_{67}X_{68}X_{69}X_{70}X_{71}X_{72}$ (SEQ ID NO: 147), wherein: $X_{65}$ is R; $X_{66}$ is P; $X_{67}$ is L; $X_{68}$ is A or P; $X_{69}$ is R; $X_{70}$ is A; $X_{71}$ is G or L; and $X_{72}$ is I or L |

TABLE 9J-1

Matriptase Cleavable Expanded Core CM Consensus Sequence 10A

| Expanded Core CM Consensus 10A | Subgenus of Expanded Core CM Consensus 10A |
|---|---|
| $X_{73}X_{74}X_{75}X_{76}X_{77}X_{78}X_{79}$ (SEQ ID NO: 148), wherein:<br>$X_{73}$ is G, H, N, P, R, S, T, or V;<br>$X_{74}$ is E, L, Q, S, T or V; | $X_{73}X_{74}X_{75}X_{76}X_{77}X_{78}X_{79}$ (SEQ ID NO: 149), wherein: $X_{73}$ is G, N, P, S, T, or V; $X_{74}$ is E, L, T or V; $X_{75}$ is R or S; $X_{76}$ is K or R; $X_{77}$ is M, R, or S; $X_{78}$ is G, L, M, S, or W; and $X_{79}$ is A, G, I, M, P, S, |

TABLE 9J-1-continued

Matriptase Cleavable Expanded Core CM Consensus Sequence 10A

| Expanded Core CM Consensus 10A | Subgenus of Expanded Core CM Consensus 10A |
|---|---|
| $X_{75}$ is L, R, or S; <br> $X_{76}$ is H, K, or R; <br> $X_{77}$ is A, M, R, or S; <br> $X_{78}$ is G, L, M, R, S, or W; and <br> $X_{79}$ is A, G, I, M, N, P, S, V, or Y | or V <br> $X_{73}X_{74}X_{75}X_{76}X_{77}X_{78}X_{79}$ (SEQ ID NO: 150), <br> wherein: $X_{73}$ is G, N, P, S, or V; $X_{74}$ is E, T or V; $X_{75}$ is R or S; $X_{76}$ is K or R; $X_{77}$ is M or R; $X_{78}$ is G, L, M, S, or W; and $X_{79}$ is A, G, I, M, P, S, or V <br> $X_{73}X_{74}X_{75}X_{76}X_{77}X_{78}X_{79}$ (SEQ ID NO: 151), <br> wherein: $X_{73}$ is G, P, S, or V; $X_{74}$ is E or V; $X_{75}$ is S; $X_{76}$ is K or R; $X_{77}$ is R; $X_{78}$ is L, S, or W; and $X_{79}$ is G, I, M, P, S, or V <br> $X_{73}X_{74}X_{75}X_{76}X_{77}X_{78}X_{79}$ (SEQ ID NO: 152), <br> wherein: $X_{73}$ is G, P, or S; $X_{74}$ is E; $X_{75}$ is S; $X_{76}$ is K or R; $X_{77}$ is R; $X_{78}$ is L or W; and $X_{79}$ is M |

TABLE 9J-2

Matriptase Cleavable Expanded Core CM Consensus Sequence 10B

| Expanded Core CM Consensus 10B | Subgenus of Expanded Core CM Consensus 10B |
|---|---|
| $X_{74}X_{75}X_{76}X_{77}X_{78}X_{79}X_{80}$ (SEQ ID NO: 153), wherein: <br> $X_{74}$ is E, L, Q, S, T or V; <br> $X_{75}$ is L, R, or S; <br> $X_{76}$ is H, K, or R; <br> $X_{77}$ is A, M, R, or S; <br> $X_{78}$ is G, L, M, R, S, or W; <br> $X_{79}$ is A, G, I, M, N, P, S, V, or Y; and <br> $X_{80}$ is G, I, L, N, P, S, V, or W | $X_{74}X_{75}X_{76}X_{77}X_{78}X_{79}X_{80}$ (SEQ ID NO: 154), <br> wherein: $X_{74}$ is E, L, T or V; $X_{75}$ is R or S; $X_{76}$ is K or R; $X_{77}$ is M, R, or S; $X_{78}$ is G, L, M, S, or W; $X_{79}$ is A, G, I, M, P, S, or V; and $X_{80}$ is G, I, L, N, P, S, or V <br> $X_{74}X_{75}X_{76}X_{77}X_{78}X_{79}X_{80}$ (SEQ ID NO: 155), <br> wherein: $X_{74}$ is E, T or V; $X_{75}$ is R or S; $X_{76}$ is K or R; $X_{77}$ is M or R; $X_{78}$ is G, L, M, S, or W; $X_{79}$ is A, G, I, M, P, S, or V; and $X_{80}$ is G, I, L, N, P, S, or V <br> $X_{74}X_{75}X_{76}X_{77}X_{78}X_{79}X_{80}$ (SEQ ID NO: 156), <br> wherein: $X_{74}$ is E or V; $X_{75}$ is S; $X_{76}$ is K or R; $X_{77}$ is R; $X_{78}$ is L, S, or W; $X_{79}$ is G, I, M, P, S, or V; and $X_{80}$ is G, L, N, P, S, or V <br> $X_{74}X_{75}X_{76}X_{77}X_{78}X_{79}X_{80}$ (SEQ ID NO: 157), <br> wherein: $X_{74}$ is E; $X_{75}$ is S; $X_{76}$ is K or R; $X_{77}$ is R; $X_{78}$ is L or W; $X_{79}$ is M; and $X_{80}$ is G, P, or S |

TABLE 9J-3

Matriptase Cleavable Expanded Core CM Consensus Sequence 10C

| Expanded Core CM Consensus 10C | Subgenus of Expanded Core CM Consensus 10C |
|---|---|
| $X_{73}X_{74}X_{75}X_{76}X_{77}X_{78}X_{79}X_{80}$ (SEQ ID NO: 158), wherein: <br> $X_{73}$ is G, H, N, P, R, S, T, or V; <br> $X_{74}$ is E, L, Q, S, T or V; <br> $X_{75}$ is L, R, or S; <br> $X_{76}$ is H, K, or R; <br> $X_{77}$ is A, M, R, or S; <br> $X_{78}$ is G, L, M, R, S, or W; <br> $X_{79}$ is A, G, I, M, N, P, S, V, or Y; and <br> $X_{80}$ is G, I, L, N, P, S, V, or W | $X_{73}X_{74}X_{75}X_{76}X_{77}X_{78}X_{79}X_{80}$ (SEQ ID NO: 159), <br> wherein: $X_{73}$ is G, N, P, S, T, or V; $X_{74}$ is E, L, T or V; $X_{75}$ is R or S; $X_{76}$ is K or R; $X_{77}$ is M, R, or S; $X_{78}$ is G, L, M, S, or W; $X_{79}$ is A, G, I, M, P, S, or V; and $X_{80}$ is G, I, L, N, P, S, or V <br> $X_{73}X_{74}X_{75}X_{76}X_{77}X_{78}X_{79}X_{80}$ (SEQ ID NO: 160), <br> wherein: $X_{73}$ is G, N, P, S, or V; $X_{74}$ is E, T or V; $X_{75}$ is R or S; $X_{76}$ is K or R; $X_{77}$ is M or R; $X_{78}$ is G, L, M, S, or W; $X_{79}$ is A, G, I, M, P, S, or V; and $X_{80}$ is G, I, L, N, P, S, or V <br> $X_{73}X_{74}X_{75}X_{76}X_{77}X_{78}X_{79}X_{80}$ (SEQ ID NO: 161), <br> wherein: $X_{73}$ is G, P, S, or V; $X_{74}$ is E or V; $X_{75}$ is S; $X_{76}$ is K or R; $X_{77}$ is R; $X_{78}$ is L, S, or W; $X_{79}$ is G, I, M, P, S, or V; and $X_{80}$ is G, L, N, P, S, or V <br> $X_{73}X_{74}X_{75}X_{76}X_{77}X_{78}X_{79}X_{80}$ (SEQ ID NO: 162), <br> wherein: $X_{73}$ is G, P, or S; $X_{74}$ is E; $X_{75}$ is S; $X_{76}$ is K or R; $X_{77}$ is R; $X_{78}$ is L or W; $X_{79}$ is M; and $X_{80}$ is G, P, or S |

In some embodiments, the CM comprises a core CM consensus 1 sequence comprising the amino acid sequence AAPRS (SEQ ID NO: 163). In some embodiments, the CM comprises an expanded core CM consensus 1 sequence comprising the amino acid sequence AAPRSF (SEQ ID NO: 164).

In some embodiments, the CM comprises a core CM consensus 2 sequence comprising the amino acid sequence SRRVP (SEQ ID NO: 165). In some embodiments, the CM comprises an expanded core CM consensus 2 sequence comprising an amino acid sequence selected from the group consisting of QSRRVP (SEQ ID NO: 166), QTRRVP (SEQ ID NO: 167), SRRVPL (SEQ ID NO: 168), SRRVPV (SEQ ID NO: 169), QSRRVPL (SEQ ID NO: 170), QSRRVPV (SEQ ID NO: 171), QTRRVPL (SEQ ID NO: 172), and QTRRVPV (SEQ ID NO: 173).

In some embodiments, the CM comprises the amino acid sequence QSRRVP (SEQ ID NO: 166). In some embodiments, the CM comprises the amino acid sequence QTRRVP (SEQ ID NO: 167). In some embodiments, the CM comprises the amino acid sequence SRRVPL (SEQ ID NO: 168). In some embodiments, the CM comprises the amino acid sequence SRRVPV (SEQ ID NO: 169). In some embodiments, the CM comprises the amino acid sequence QSRRVPL (SEQ ID NO: 170). In some embodiments, the CM comprises the amino acid sequence QSRRVPV (SEQ ID NO: 171). In some embodiments, the CM comprises the amino acid sequence QTRRVPL (SEQ ID NO: 172). In some embodiments, the CM comprises the amino acid sequence QTRRVPV (SEQ ID NO: 173).

In some embodiments, the CM comprises a core CM consensus 3 sequence comprising the amino acid sequence PPLGR (SEQ ID NO: 174). In some embodiments, the CM comprises an expanded core CM consensus 3 sequence comprising an amino acid sequence selected from the group consisting of GPPLGR (SEQ ID NO: 175), SPPLGR (SEQ ID NO: 176), CGPPLGR (SEQ ID NO: 177), CSPPLGR (SEQ ID NO: 178), GGPPLGR (SEQ ID NO: 179), GSPPLGR (SEQ ID NO: 180), SGPPLGR (SEQ ID NO: 181), SSPPLGR (SEQ ID NO: 182), GCGPPLGR (SEQ ID NO: 183), GCSPPLGR (SEQ ID NO: 184), GGGPPLGR (SEQ ID NO: 185), GGSPPLGR (SEQ ID NO: 186), GSGPPLGR (SEQ ID NO: 187), GSSPPLGR (SEQ ID NO: 188), SCGPPLGR (SEQ ID NO: 189), SCSPPLGR (SEQ ID NO: 190), SGGPPLGR (SEQ ID NO: 191), SGSPPLGR (SEQ ID NO: 192), SSGPPLGR (SEQ ID NO: 193), and SSSPPLGR (SEQ ID NO: 194).

In some embodiments, the CM comprises the amino acid sequence GPPLGR (SEQ ID NO: 175). In some embodiments, the CM comprises the amino acid sequence SPPLGR (SEQ ID NO: 176). In some embodiments, the CM comprises the amino acid sequence CGPPLGR (SEQ ID NO: 177). In some embodiments, the CM comprises the amino acid sequence CSPPLGR (SEQ ID NO: 178). In some embodiments, the CM comprises the amino acid sequence GGPPLGR (SEQ ID NO: 179). In some embodiments, the CM comprises the amino acid sequence GSPPLGR (SEQ ID NO: 180). In some embodiments, the CM comprises the amino acid sequence SGPPLGR (SEQ ID NO: 181). In some embodiments, the CM comprises the amino acid sequence SSPPLGR (SEQ ID NO: 182). In some embodiments, the CM comprises the amino acid sequence GCGPPLGR (SEQ ID NO: 183). In some embodiments, the CM comprises the amino acid sequence GCSPPLGR (SEQ ID NO: 184). In some embodiments, the CM comprises the amino acid sequence GGGPPLGR (SEQ ID NO: 185). In some embodiments, the CM comprises the amino acid sequence GGSPPLGR (SEQ ID NO: 186). In some embodiments, the CM comprises the amino acid sequence GSGPPLGR (SEQ ID NO: 187). In some embodiments, the CM comprises the amino acid sequence GSSPPLGR (SEQ ID NO: 188). In some embodiments, the CM comprises the amino acid sequence SCGPPLGR (SEQ ID NO: 189). In some embodiments, the CM comprises the amino acid sequence SCSPPLGR (SEQ ID NO: 190). In some embodiments, the CM comprises the amino acid sequence SGGPPLGR (SEQ ID NO: 191). In some embodiments, the CM comprises the amino acid sequence SGSPPLGR (SEQ ID NO: 192). In some embodiments, the CM comprises the amino acid sequence SSGPPLGR (SEQ ID NO: 193). In some embodiments, the CM comprises the amino acid sequence SSSPPLGR (SEQ ID NO: 194).

In some embodiments, the CM comprises a core CM consensus 4 sequence comprising the amino acid sequence LRSGW (SEQ ID NO: 195). In some embodiments, the CM comprises an expanded core CM consensus 4 sequence comprising an amino acid sequence selected from the group consisting of MLRSGW (SEQ ID NO: 196), MLRSGWR (SEQ ID NO: 197), MLRSGWRG (SEQ ID NO: 198), MLRSGWRL (SEQ ID NO: 199), and MLRSGWRS (SEQ ID NO: 200).

In some embodiments, the CM comprises the amino acid sequence MLRSGW, (SEQ ID NO: 196). In some embodiments, the CM comprises the amino acid sequence MLRSGWR (SEQ ID NO: 197). In some embodiments, the CM comprises the amino acid sequence MLRSGWRG (SEQ ID NO: 198). In some embodiments, the CM comprises the amino acid sequence MLRSGWRL (SEQ ID NO: 199). In some embodiments, the CM comprises the amino acid sequence MLRSGWRS (SEQ ID NO: 200).

In some embodiments, the CM comprises a core CM consensus 5 sequence comprising the amino acid sequence VSRSA (SEQ ID NO: 201). In some embodiments, the CM comprises an expanded core CM consensus 5 sequence comprising an amino acid sequence selected from the group consisting of IVSRSA (SEQ ID NO: 202), YIVSRSA (SEQ ID NO: 203), and QYIVSRSA (SEQ ID NO: 204).

In some embodiments, the CM comprises the amino acid sequence IVSRSA (SEQ ID NO: 202). In some embodiments, the CM comprises the amino acid sequence YIVSRSA (SEQ ID NO: 203). In some embodiments, the CM comprises the amino acid sequence QYIVSRSA (SEQ ID NO: 204).

In some embodiments, the CM comprises a core CM consensus 6 sequence comprising the amino acid sequence ALRAP (SEQ ID NO: 205). In some embodiments, the CM comprises an expanded core CM consensus 6 sequence comprising the amino acid sequence RALRAP (SEQ ID NO: 206).

In some embodiments, the CM comprises a core CM consensus 7 sequence comprising the amino acid sequence PAGRR (SEQ ID NO: 207). In some embodiments, the CM comprises an expanded core CM consensus 7 sequence comprising an amino acid sequence selected from the group consisting of PAGRRS (SEQ ID NO: 208), PAGRRSL (SEQ ID NO: 209), VPAGRRS (SEQ ID NO: 210), and VPAGRRSL (SEQ ID NO: 211).

In some embodiments, the CM comprises the amino acid sequence PAGRRS (SEQ ID NO: 208). In some embodiments, the CM comprises the amino acid sequence PAGRRSL (SEQ ID NO: 209). In some embodiments, the CM comprises the amino acid sequence VPAGRRS (SEQ ID NO: 210). In some embodiments, the CM comprises the amino acid sequence VPAGRRSL (SEQ ID NO: 211).

In some embodiments, the CM comprises a core CM consensus 8 sequence comprising the amino acid sequence GRSML (SEQ ID NO: 212). In some embodiments, the CM comprises an expanded core CM consensus 8 sequence comprising an amino acid sequence selected from the group consisting of GRSMLL (SEQ ID NO: 213), GRSMLM (SEQ ID NO: 214), GRSMLLG (SEQ ID NO: 215), GRSMLLP (SEQ ID NO: 216), GRSMLLS (SEQ ID NO: 217), GRSMLMG (SEQ ID NO: 218), GRSMLMP (SEQ ID NO: 219), GRSMLMS (SEQ ID NO: 220), GRSMLLGG (SEQ ID NO: 221), GRSMLLPG (SEQ ID NO: 222), GRSMLLSG (SEQ ID NO: 223), GRSMLMGG (SEQ ID NO: 224), GRSMLMPG (SEQ ID NO: 225), GRSMLMSG (SEQ ID NO: 226), GRSMLLGP (SEQ ID NO: 227), GRSMLLPP (SEQ ID NO: 228), GRSMLLSP (SEQ ID NO:

229), GRSMLMGP (SEQ ID NO: 230), GRSMLPP (SEQ ID NO: 231), GRSMLMSP (SEQ ID NO: 232), GRSMLLGS (SEQ ID NO: 233), GRSMLLPS (SEQ ID NO: 234), GRSMLLSS (SEQ ID NO: 235), GRSMLMGS (SEQ ID NO: 236), GRSMLMPS (SEQ ID NO: 237), and GRSMLMSS (SEQ ID NO: 238).

In some embodiments, the CM comprises the amino acid sequence GRSMLL (SEQ ID NO: 213). In some embodiments, the CM comprises the amino acid sequence GRSMLM (SEQ ID NO: 214). In some embodiments, the CM comprises the amino acid sequence GRSMLLG (SEQ ID NO: 215). In some embodiments, the CM comprises the amino acid sequence GRSMLLP (SEQ ID NO: 216). In some embodiments, the CM comprises the amino acid sequence GRSMLLS (SEQ ID NO: 217). In some embodiments, the CM comprises the amino acid sequence GRSMLMG (SEQ ID NO: 218). In some embodiments, the CM comprises the amino acid sequence GRSMLMP (SEQ ID NO: 219). In some embodiments, the CM comprises the amino acid sequence GRSMLMS (SEQ ID NO: 220). In some embodiments, the CM comprises the amino acid sequence GRSMLLGG (SEQ ID NO: 221). In some embodiments, the CM comprises the amino acid sequence GRSMLLPG (SEQ ID NO: 222). In some embodiments, the CM comprises the amino acid sequence GRSMLLSG (SEQ ID NO: 223). In some embodiments, the CM comprises the amino acid sequence GRSMLMGG (SEQ ID NO: 224). In some embodiments, the CM comprises the amino acid sequence GRSMLMPG (SEQ ID NO: 225). In some embodiments, the CM comprises the amino acid sequence GRSMLMSG (SEQ ID NO: 226). In some embodiments, the CM comprises the amino acid sequence GRSMLLGP (SEQ ID NO: 227). In some embodiments, the CM comprises the amino acid sequence GRSMLLPP (SEQ ID NO: 228). In some embodiments, the CM comprises the amino acid sequence GRSMLLSP (SEQ ID NO: 229). In some embodiments, the CM comprises the amino acid sequence GRSMLMGP (SEQ ID NO: 230). In some embodiments, the CM comprises the amino acid sequence GRSMLMPP (SEQ ID NO: 231). In some embodiments, the CM comprises the amino acid sequence GRSMLMSP (SEQ ID NO: 232). In some embodiments, the CM comprises the amino acid sequence GRSMLLGS (SEQ ID NO: 233). In some embodiments, the CM comprises the amino acid sequence GRSMLLPS (SEQ ID NO: 234). In some embodiments, the CM comprises the amino acid sequence GRSMLLSS (SEQ ID NO: 235). In some embodiments, the CM comprises the amino acid sequence GRSMLMGS (SEQ ID NO: 236). In some embodiments, the CM comprises the amino acid sequence GRSMLMPS (SEQ ID NO: 237). In some embodiments, the CM comprises the amino acid sequence GRSMLMSS (SEQ ID NO: 238).

In some embodiments, the CM comprises a core CM consensus 9 sequence comprising the amino acid sequence LARAG (SEQ ID NO: 239). In some embodiments, the CM comprises an expanded core CM consensus 9 sequence comprising an amino acid sequence selected from the group consisting of LARAGI (SEQ ID NO: 240), LARAGL (SEQ ID NO: 241), PLARAGI (SEQ ID NO: 242), PLARAGL (SEQ ID NO: 243), RPLARAGI (SEQ ID NO: 244), and RPLARAGL (SEQ ID NO: 245).

In some embodiments, the CM comprises the amino acid sequence LARAGI (SEQ ID NO: 240). In some embodiments, the CM comprises the amino acid sequence LARAGL (SEQ ID NO: 241). In some embodiments, the CM comprises the amino acid sequence PLARAGI (SEQ ID NO: 242). In some embodiments, the CM comprises the amino acid sequence PLARAGL (SEQ ID NO: 243). In some embodiments, the CM comprises the amino acid sequence RPLARAGI (SEQ ID NO: 244). In some embodiments, the CM comprises the amino acid sequence RPLARAGL (SEQ ID NO: 245).

In some embodiments, the CM comprises a core CM consensus 10 sequence comprising the amino acid sequence ESRRW (SEQ ID NO: 246). In some embodiments, the CM comprises an expanded core CM consensus 10 sequence comprising an amino acid sequence selected from the group consisting of ESRRWM (SEQ ID NO: 247), ESRRWMP (SEQ ID NO: 248), and PESRRWMP (SEQ ID NO: 249).

In some embodiments, the CM comprises the amino acid sequence ESRRWM (SEQ ID NO: 247). In some embodiments, the CM comprises the amino acid sequence ESRRWMP (SEQ ID NO: 248). In some embodiments, the CM comprises the amino acid sequence PESRRWMP (SEQ ID NO: 249).

In some embodiments, the CM comprises an amino acid sequence selected from the group consisting of ILPRSPAF (SEQ ID NO: 250), VAGRSMRP (SEQ ID NO: 251), VVPEGRRS (SEQ ID NO: 252), QGRAITFI (SEQ ID NO: 253), VLSKQMSF (SEQ ID NO: 254), LKGRSYYY (SEQ ID NO: 255), KRMPVQFL (SEQ ID NO: 256), PQHRIVSF (SEQ ID NO: 257), YKKFVGSL (SEQ ID NO: 258), HMMQYARH (SEQ ID NO: 259), IPFSWSRF (SEQ ID NO: 260), LSQARWRK (SEQ ID NO: 261), DISHWRRS (SEQ ID NO: 262), RKTVQHWW (SEQ ID NO: 263), RFYRNQFF (SEQ ID NO: 264), RSLVFAPI (SEQ ID NO: 265), RSPSRLKC (SEQ ID NO: 266), and RKMPNITV (SEQ ID NO: 267).

In some embodiments, the CM comprises the amino acid sequence ILPRSPAF (SEQ ID NO: 250). In some embodiments, the CM comprises the amino acid sequence VAGRSMRP (SEQ ID NO: 251). In some embodiments, the CM comprises the amino acid sequence VVPEGRRS (SEQ ID NO: 252). In some embodiments, the CM comprises the amino acid sequence QGRAITFI (SEQ ID NO: 253). In some embodiments, the CM comprises the amino acid sequence VLSKQMSF (SEQ ID NO: 254). In some embodiments, the CM comprises the amino acid sequence LKGRSYYY (SEQ ID NO: 255). In some embodiments, the CM comprises the amino acid sequence KRMPVQFL (SEQ ID NO: 256). In some embodiments, the CM comprises the amino acid sequence PQHRIVSF (SEQ ID NO: 257). In some embodiments, the CM comprises the amino acid sequence YKKFVGSL (SEQ ID NO: 258). In some embodiments, the CM comprises the amino acid sequence HMMQYARH (SEQ ID NO: 259). In some embodiments, the CM comprises the amino acid sequence IPFSWSRF (SEQ ID NO: 260). In some embodiments, the CM comprises the amino acid sequence LSQARWRK (SEQ ID NO: 261). In some embodiments, the CM comprises the amino acid sequence DISHWRRS (SEQ ID NO: 262). In some embodiments, the CM comprises the amino acid sequence RKTVQHWW (SEQ ID NO: 263J. In some embodiments, the CM comprises the amino acid sequence RFYRNQFF (SEQ ID NO: 264). In some embodiments, the CM comprises the amino acid sequence RSLVFAPI (SEQ ID NO: 265). In some embodiments, the CM comprises the amino acid sequence RSPSRLKC (SEQ ID NO: 266). In some embodiments, the CM comprises the amino acid sequence RKMPNITV (SEQ ID NO: 267).

In some embodiments, the CM includes a motif sequence that is a substrate for at least uPA and/or matriptase and includes a core CM consensus sequence shown in Tables 10A-10J below. In some embodiments, the motif sequence includes a subgenus, i.e., a subset, of the core CM consensus sequence shown in Tables 10A-10D below.

TABLE 10A

| uPA and/or Matriptase Cleavable Core CM Consensus Sequence 11 | |
|---|---|
| Core CM Consensus 11 | Subgenus of Core CM Consensus 11 |
| $X_{87}X_{88}X_{89}X_{90}X_{91}X_{92}X_{93}X_{94}$ (SEQ ID NO: 268), wherein: $X_{87}$ is D, I, L, R, S, or V; $X_{88}$ is C, G, H, I, K, N, R, S, T, or Y; $X_{89}$ is D, G, or S; $X_{90}$ is R; $X_{91}$ is F or S; $X_{92}$ is A, D, G, H, I, L, T, or V; $X_{93}$ is H, I, N, R, S, or T; and $X_{94}$ is H, L, M, R, V or Y | $X_{87}X_{88}X_{89}X_{90}X_{91}X_{92}X_{93}X_{94}$ (SEQ ID NO: 269), wherein: $X_{87}$ is D, L, S, or V; $X_{88}$ is C, G, N, R, S, or T; $X_{89}$ is D, G, or S; $X_{90}$ is R; $X_{91}$ is F or S; $X_{92}$ is A, G, I, L, T, or V; $X_{93}$ is H, I, N, or S; and $X_{94}$ is H, M, R, or Y<br>$X_{87}X_{88}X_{89}X_{90}X_{91}X_{92}X_{93}X_{94}$ (SEQ ID NO: 270), wherein: $X_{87}$ is L or V; $X_{88}$ is G, H, K, N, S, or T; $X_{89}$ is G; $X_{90}$ is R; $X_{91}$ is S; $X_{92}$ is A or D; $X_{93}$ is N or R; and $X_{94}$ is H or Y<br>$X_{87}X_{88}X_{89}X_{90}X_{91}X_{92}X_{93}X_{94}$ (SEQ ID NO: 271), wherein: $X_{87}$ is L or V; $X_{88}$ is G, H, N or S; $X_{89}$ is G; $X_{90}$ is R; $X_{91}$ is S; $X_{92}$ is A or D; $X_{93}$ is N; and $X_{94}$ is H<br>$X_{87}X_{88}X_{89}X_{90}X_{91}X_{92}X_{93}X_{94}$ (SEQ ID NO: 272), wherein: $X_{87}$ is L or V; $X_{88}$ is S; $X_{89}$ is G; $X_{90}$ is R; $X_{91}$ is S; $X_{92}$ is A or D; $X_{93}$ is N; and $X_{94}$ is H<br>$X_{87}X_{88}X_{89}X_{90}X_{91}X_{92}X_{93}X_{94}$ (SEQ ID NO: 273), wherein: $X_{87}$ is L or V; $X_{88}$ is G or S; $X_{89}$ is G; $X_{90}$ is R; $X_{91}$ is S; $X_{92}$ is A; $X_{93}$ is N; and $X_{94}$ is H |

TABLE 10B

| uPA and/or Matriptase Cleavable Core CM Consensus Sequence 12 | |
|---|---|
| Core CM Consensus 12 | Subgenus of Core CM Consensus 12 |
| $X_{99}X_{100}X_{101}X_{102}X_{103}X_{104}X_{105}X_{106}$ (SEQ ID NO: 274), wherein: $X_{99}$ is D, I, L, R, S, or V; $X_{100}$ is C, G, H, I, K, N, R, S, T or Y; $X_{101}$ is D, G, or S; $X_{102}$ is R; $X_{103}$ is F or S; $X_{104}$ is A, D, G, H, I, L, T, or V; $X_{105}$ is H, I, N, R, S, or T; and $X_{106}$ is H, L, M, R, V, or Y | $X_{99}X_{100}X_{101}X_{102}X_{103}X_{104}X_{105}X_{106}$ (SEQ ID NO: 275), wherein: $X_{99}$ is L; $X_{100}$ is N, S, or T; $X_{101}$ is G; $X_{102}$ is R; $X_{103}$ is S; $X_{104}$ is A, D, or H; $X_{105}$ is N or R; and $X_{106}$ is H, L, V, or Y<br>$X_{99}X_{100}X_{101}X_{102}X_{103}X_{104}X_{105}X_{106}$ (SEQ ID NO: 276), wherein: $X_{99}$ is L or V; $X_{100}$ is G, H, K, N, S, or T; $X_{101}$ is G; $X_{102}$ is R; $X_{103}$ is S; $X_{104}$ is A or D; $X_{105}$ is N or R; and $X_{106}$ is H or Y<br>$X_{99}X_{100}X_{101}X_{102}X_{103}X_{104}X_{105}X_{106}$ (SEQ ID NO: 277), wherein: $X_{99}$ is L or V; $X_{100}$ is G, H, N, or S; $X_{101}$ is G; $X_{102}$ is R; $X_{103}$ is S; $X_{104}$ is A or D; $X_{105}$ is N; and $X_{106}$ is H<br>$X_{99}X_{100}X_{101}X_{102}X_{103}X_{104}X_{105}X_{106}$ (SEQ ID NO: 278), wherein: $X_{99}$ is L or V; $X_{100}$ is S; $X_{101}$ is G; $X_{102}$ is R; $X_{103}$ is S; $X_{104}$ is A or D; $X_{105}$ is N; and $X_{106}$ is H<br>$X_{99}X_{100}X_{101}X_{102}X_{103}X_{104}X_{105}X_{106}$ (SEQ ID NO: 279), wherein: $X_{99}$ is L; $X_{100}$ is N or S; $X_{101}$ is G; $X_{102}$ is R; $X_{103}$ is S; $X_{104}$ is A or D; $X_{105}$ is N or R; and $X_{106}$ is H |

TABLE 10C

| uPA and/or Matriptase Cleavable Core CM Consensus Sequence 13 | |
|---|---|
| Core CM Consensus 13 | Subgenus of Core CM Consensus 13 |
| $X_{111}X_{112}X_{113}X_{114}X_{115}X_{116}X_{117}X_{118}$ (SEQ ID NO: 280), wherein: $X_{111}$ is C, G, H, L, P, R, S, T, or V; $X_{112}$ is I, L, M, N, S, T, V, or Y; $X_{113}$ is A, D, E, G, K, R, or V; $X_{114}$ is A, C, G, H, L, R, S, T, or V; $X_{115}$ is C, F, P, S, T, V, or Y; $X_{116}$ is A, D, E, G, H, N, T, V, or Y; $X_{117}$ is D, E, H, K, N, Q, R, S, T; and $X_{118}$ is H, L, N, R, S, V, or Y | $X_{111}X_{112}X_{113}X_{114}X_{115}X_{116}X_{117}X_{118}$ (SEQ ID NO: 281), wherein: $X_{111}$ is C or R; $X_{112}$ is I, S, or Y; $X_{113}$ is G or R; $X_{114}$ is R or S; $X_{115}$ is F, P, or S; $X_{116}$ is D, G, or H; $X_{117}$ is H or N; and $X_{118}$ is H<br>$X_{111}X_{112}X_{113}X_{114}X_{115}X_{116}X_{117}X_{118}$ (SEQ ID NO: 282), wherein: $X_{111}$ is R; $X_{112}$ is I; $X_{113}$ is G; $X_{114}$ is R; $X_{115}$ is S; $X_{116}$ is D or H; $X_{117}$ is N; and $X_{118}$ is H |

TABLE 10D

| uPA and/or Matriptase Cleavable Core CM Consensus Sequence 14 | |
|---|---|
| Core CM Consensus 14 | Subgenus of Core CM Consensus 14 |
| $X_{123}X_{124}X_{125}X_{126}X_{127}X_{128}X_{129}X_{130}$ (SEQ ID NO: 283), wherein: | $X_{123}X_{124}X_{125}X_{126}X_{127}X_{128}X_{129}X_{130}$ (SEQ ID NO: 284), wherein: $X_{123}$ is L or T; $X_{124}$ is E, R, or S; $X_{125}$ is G; |

TABLE 10D-continued uPA and/or Matriptase Cleavable Core CM Consensus Sequence 14

| Core CM Consensus 14 | Subgenus of Core CM Consensus 14 |
|---|---|
| $X_{123}$ is L, R, T, or V;<br>$X_{124}$ is E, G, I, N, R, or S;<br>$X_{125}$ is G;<br>$X_{126}$ is R;<br>$X_{127}$ is P or S;<br>$X_{128}$ is A, G, or Y;<br>$X_{129}$ is E, K, N, or Y; and<br>$X_{130}$ is P, Q, or S | $X_{126}$ is R; $X_{127}$ is P or S; $X_{128}$ is A, G, or Y; $X_{129}$ is E or N; and $X_{130}$ is P, Q, or S<br>$X_{123}X_{124}X_{125}X_{126}X_{127}X_{128}X_{129}X_{130}$ (SEQ ID NO: 285),<br>wherein: $X_{123}$ is L, T, or V; $X_{124}$ is R or S; $X_{125}$ is G; $X_{126}$ is R; $X_{127}$ is S; $X_{128}$ is A or G; $X_{129}$ is K, N or Y; and $X_{130}$ is P<br>$X_{123}X_{124}X_{125}X_{126}X_{127}X_{128}X_{129}X_{130}$ (SEQ ID NO: 286),<br>wherein: $X_{123}$ is L or T; $X_{124}$ is S; $X_{125}$ is G; $X_{126}$ is R; $X_{127}$ is S; $X_{128}$ is A or G; $X_{129}$ is N; and $X_{130}$ is P |

In some embodiments, the motif sequence is a substrate for at least uPA and/or matriptase and includes an expanded consensus sequence based on one of the core CM consensus sequence shown in Tables 10A-10D. In some embodiments, the expanded consensus sequence is a consensus sequence shown in Tables 11A-11D below.

TABLE 11A uPA and/or Matriptase Cleavable Expanded Core CM Consensus Sequence 11

| Expanded Core CM Consensus 11 | Subgenus of Expanded Core CM Consensus 11 |
|---|---|
| $X_{85}X_{86}X_{87}X_{88}X_{89}X_{90}X_{91}X_{92}X_{93}X_{94}$<br>$X_{95}X_{96}$ (SEQ ID NO: 287), wherein:<br>$X_{85}$ is A, D, G, K, L, N, R, S, T, or V;<br>$X_{86}$ is A, G, K, M, P, Q, R, S, or T;<br>$X_{87}$ is D, I, L, R, S, or V;<br>$X_{88}$ is C, G, H, I, K, N, R, S, T, or Y;<br>$X_{89}$ is D, G, or S;<br>$X_{90}$ is R;<br>$X_{91}$ is F or S;<br>$X_{92}$ is A, D, G, H, I, L, T, or V;<br>$X_{93}$ is H, I, N, R, S, or T;<br>$X_{94}$ is H, L, M, R, V or Y;<br>$X_{95}$ is E, G, K, N, Q, R, or V; and<br>$X_{96}$ is A, G, K, L, Q, R, or S | $X_{85}X_{86}X_{87}X_{88}X_{89}X_{90}X_{91}X_{92}X_{93}X_{94}X_{95}X_{96}$ (SEQ ID NO: 288), wherein:<br>$X_{85}$ is A, D, G, K, N, S, or V; $X_{86}$ is A, G, K, M, R, S, or T; $X_{87}$ is D, L, S, or V; $X_{88}$ is C, G, N, R, S, or T; $X_{89}$ is D, G, or S; $X_{90}$ is R; $X_{91}$ is F or S; $X_{92}$ is A, G, I, L, T, or V; $X_{93}$ is H, I, N, or S; $X_{94}$ is H, M, R, or Y; $X_{95}$ is E, G, K, or R; and $X_{96}$ is K, R, or S<br>$X_{85}X_{86}X_{87}X_{88}X_{89}X_{90}X_{91}X_{92}X_{93}X_{94}X_{95}X_{96}$ (SEQ ID NO: 289), wherein:<br>$X_{85}$ is A, D, G, N, R, or T; $X_{86}$ is G, K, P, R, S, or T; $X_{87}$ is L or V; $X_{88}$ is G, H, K, N, S, or T; $X_{89}$ is G; $X_{90}$ is R; $X_{91}$ is S; $X_{92}$ is A or D; $X_{93}$ is N or R; $X_{94}$ is H or Y; $X_{95}$ is E, K, N, Q, or R; and $X_{96}$ is A, K, or R<br>$X_{85}X_{86}X_{87}X_{88}X_{89}X_{90}X_{91}X_{92}X_{93}X_{94}X_{95}X_{96}$ (SEQ ID NO: 290), wherein:<br>$X_{85}$ is A, D, G, or R; $X_{86}$ is K, P, R or T; $X_{87}$ is L or V; $X_{88}$ is G, H, N or S; $X_{89}$ is G; $X_{90}$ is R; $X_{91}$ is S; $X_{92}$ is A or D; $X_{93}$ is N; $X_{94}$ is H; $X_{95}$ is K, N, or R; and $X_{96}$ is A, K, or R<br>$X_{85}X_{86}X_{87}X_{88}X_{89}X_{90}X_{91}X_{92}X_{93}X_{94}X_{95}X_{96}$ (SEQ ID NO: 291), wherein:<br>$X_{85}$ is A or D; $X_{86}$ is K, P, or R; $X_{87}$ is L or V; $X_{88}$ is S; $X_{89}$ is G; $X_{90}$ is R; $X_{91}$ is S; $X_{92}$ is A or D; $X_{93}$ is N; $X_{94}$ is H; $X_{95}$ is K or R; and $X_{96}$ is K or R<br>$X_{85}X_{86}X_{87}X_{88}X_{89}X_{90}X_{91}X_{92}X_{93}X_{94}X_{95}X_{96}$ (SEQ ID NO: 292), wherein:<br>$X_{85}$ is D, G, or N; $X_{86}$ is K, R, or S; $X_{87}$ is L or V; $X_{88}$ is G or S; $X_{89}$ is G; $X_{90}$ is R; $X_{91}$ is S; $X_{92}$ is A; $X_{93}$ is N; $X_{94}$ is H; $X_{95}$ is K; and $X_{96}$ is K |

TABLE 11B uPA and/or Matriptase Cleavable Expanded Core CM Consensus Sequence 12

| Expanded Core CM Consensus 12 | Subgenus of Expanded Core CM Consensus 12 |
|---|---|
| $X_{97}X_{98}X_{99}X_{100}X_{101}X_{102}X_{103}X_{104}X_{105}X_{106}$<br>$X_{107}X_{108}$ (SEQ ID NO: 293),<br>wherein:<br>$X_{97}$ is A, D, G, K, L, N, R, S, T, or V;<br>$X_{98}$ is A, G, K, M, P, Q, R, S, or T;<br>$X_{99}$ is D, I, L, R, S, or V;<br>$X_{100}$ is C, G, H, I, K, N, R, S, T or Y;<br>$X_{101}$ is D, G, or S;<br>$X_{102}$ is R;<br>$X_{103}$ is F or S;<br>$X_{104}$ is A, D, G, H, I, L, T, or V;<br>$X_{105}$ is H, I, N, R, S, or T;<br>$X_{106}$ is H, L, M, R, V, or Y;<br>$X_{107}$ is E, G, K, N, Q, R, or V; and<br>$X_{108}$ is A, G, K, L, Q, R, or S | $X_{97}X_{98}X_{99}X_{100}X_{101}X_{102}X_{103}X_{104}X_{105}X_{106}X_{107}X_{108}$ (SEQ ID NO: 294), wherein: $X_{97}$ is D, G, K, or R; $X_{98}$ is G, P, or R; $X_{99}$ is L; $X_{100}$ is N, S, or T; $X_{101}$ is G; $X_{102}$ is R; $X_{103}$ is S; $X_{104}$ is A, D, or H; $X_{105}$ is N or R; $X_{106}$ is H, L, V, or Y; $X_{107}$ is E, G, K, N, Q, or R; and $X_{108}$ is A, G, K, L, Q, or R<br>$X_{97}X_{98}X_{99}X_{100}X_{101}X_{102}X_{103}X_{104}X_{105}X_{106}X_{107}X_{108}$ (SEQ ID NO: 295), wherein: $X_{97}$ is A, D, G, N, R, or T; $X_{98}$ is G, K, P, R, S, or T; $X_{99}$ is L or V; $X_{100}$ is G, H, K, N, S, or T; $X_{101}$ is G; $X_{102}$ is R; $X_{103}$ is S; $X_{104}$ is A or D; $X_{105}$ is N or R; $X_{106}$ is H or Y; $X_{107}$ is E, K, N, Q, or R; and $X_{108}$ is A, K, or R<br>$X_{97}X_{98}X_{99}X_{100}X_{101}X_{102}X_{103}X_{104}X_{105}X_{106}X_{107}X_{108}$ (SEQ ID NO: 296), wherein: $X_{97}$ is A, D, G, or R; $X_{98}$ is K, P, R, or T; $X_{99}$ is L or V; $X_{100}$ is G, H, N, or S; |

TABLE 11B-continued uPA and/or Matriptase Cleavable Expanded Core CM Consensus Sequence 12

| Expanded Core CM Consensus 12 | Subgenus of Expanded Core CM Consensus 12 |
|---|---|
| | $X_{101}$ is G; $X_{102}$ is R; $X_{103}$ is S; $X_{104}$ is A or D; $X_{105}$ is N; $X_{106}$ is H; $X_{107}$ is K, N, or R; and $X_{108}$ is A, K, or R $X_{97}X_{98}X_{99}X_{100}X_{101}X_{102}X_{103}X_{104}X_{105}X_{106}X_{107}X_{108}$ (SEQ ID NO: 297), wherein: $X_{97}$ is A or D; $X_{98}$ is K, P, or R; $X_{99}$ is L or V; $X_{100}$ is S; $X_{101}$ is G; $X_{102}$ is R; $X_{103}$ is S; $X_{104}$ is A or D; $X_{105}$ is N; $X_{106}$ is H; $X_{107}$ is K or R; and $X_{108}$ is K or R $X_{97}X_{98}X_{99}X_{100}X_{101}X_{102}X_{103}X_{104}X_{105}X_{106}X_{107}X_{108}$ (SEQ ID NO: 298), wherein: $X_{97}$ is G or R; $X_{98}$ is P; $X_{99}$ is L; $X_{100}$ is N or S; $X_{101}$ is G; $X_{102}$ is R; $X_{103}$ is S; $X_{104}$ is A or D; $X_{105}$ is N or R; $X_{106}$ is H; $X_{107}$ is K, Q, or R; and $X_{108}$ is A, K, or R |

TABLE 11C uPA and/or Matriptase Cleavable Expanded Core CM Consensus Sequence 13

| Expanded Core CM Consensus 13 | Subgenus of Expanded Core CM Consensus 13 |
|---|---|
| $X_{109}X_{110}X_{111}X_{112}X_{113}X_{114}X_{115}X_{116}X_{117}X_{118}X_{119}X_{120}$ (SEQ ID NO: 299), wherein: $X_{109}$ is A, D, G, H, I, K, N, R, S, T, or Y; $X_{110}$ is D, G, H, L, N, Q, R, or Y; $X_{111}$ is C, G, H, L, P, R, S, T, or V; $X_{112}$ is I, L, M, N, S, T, V, or Y; $X_{113}$ is A, D, E, G, K, R, or V; $X_{114}$ is A, C, G, H, L, R, S, T, or V; $X_{115}$ is C, F, P, S, T, V, or Y; $X_{116}$ is A, D, E, G, H, N, T, V, or Y; $X_{117}$ is D, E, H, K, N, Q, R, S, T; $X_{118}$ is H, L, N, R, S, V, or Y; $X_{119}$ is E, G, K, L, N, Q, R, S, V, or W; and $X_{120}$ is A, E, G, K, L, N, P, Q, R, or W | $X_{109}X_{110}X_{111}X_{112}X_{113}X_{114}X_{115}X_{116}X_{117}X_{118}X_{119}X_{120}$ (SEQ ID NO: 300), wherein: $X_{109}$ is N; $X_{110}$ is H or R; $X_{111}$ is C or R; $X_{112}$ is I, S, or Y; $X_{113}$ is G or R; $X_{114}$ is R or S; $X_{115}$ is F, P, or S; $X_{116}$ is D, G, or H; $X_{117}$ is H or N; $X_{118}$ is H; $X_{119}$ is E, K, R, or V; and $X_{120}$ is A, G, Q, R, or W $X_{109}X_{110}X_{111}X_{112}X_{113}X_{114}X_{115}X_{116}X_{117}X_{118}X_{119}X_{120}$ (SEQ ID NO: 301), wherein: $X_{109}$ is N; $X_{110}$ is H; $X_{111}$ is R; $X_{112}$ is I; $X_{113}$ is G; $X_{114}$ is R; $X_{115}$ is S; $X_{116}$ is D or H; $X_{117}$ is N; $X_{118}$ is H; $X_{119}$ is R; and $X_{120}$ is G or R |

TABLE 11D uPA and/or Matriptase Cleavable Expanded Core CM Consensus Sequence 14

| Expanded Core CM Consensus 14 | Subgenus of Expanded Core CM Consensus 14 |
|---|---|
| $X_{121}X_{122}X_{123}X_{124}X_{125}X_{126}X_{127}X_{128}X_{129}X_{130}X_{131}X_{132}$ (SEQ ID NO: 302), wherein: $X_{121}$ is A, D, G, M, N, P, R, or T; $X_{122}$ is A, H, K, P, R, or S; $X_{123}$ is L, R, T, or V; $X_{124}$ is E, G, I, N, R, or S; $X_{125}$ is G; $X_{126}$ is R; $X_{127}$ is P or S; $X_{128}$ is A, G, or Y; $X_{129}$ is E, K, N, or Y; $X_{130}$ is P, Q, or S; $X_{131}$ is E, K, or R; and $X_{132}$ is D, E, G, H, or R | $X_{121}X_{122}X_{123}X_{124}X_{125}X_{126}X_{127}X_{128}X_{129}X_{130}X_{131}X_{132}$ (SEQ ID NO: 303), wherein: $X_{121}$ is M, N, P, R, or T; $X_{122}$ is A, P, or S; $X_{123}$ is L or T; $X_{124}$ is E, R, or S; $X_{125}$ is G; $X_{126}$ is R; $X_{127}$ is P or S; $X_{128}$ is A, G, or Y; $X_{129}$ is E or N; $X_{130}$ is P, Q, or S; $X_{131}$ is E, K, R; and $X_{132}$ is E, G, or R $X_{121}X_{122}X_{123}X_{124}X_{125}X_{126}X_{127}X_{128}X_{129}X_{130}X_{131}X_{132}$ (SEQ ID NO: 304), wherein: $X_{121}$ is G, N, or T; $X_{122}$ is A, P, or S; $X_{123}$ is L, T, or V; $X_{124}$ is R or S; $X_{125}$ is G; $X_{126}$ is R; $X_{127}$ is S; $X_{128}$ is A or G; $X_{129}$ is K, N or Y; $X_{130}$ is P; $X_{131}$ is K or R; and $X_{132}$ is D, G or H $X_{121}X_{122}X_{123}X_{124}X_{125}X_{126}X_{127}X_{128}X_{129}X_{130}X_{131}X_{132}$ (SEQ ID NO: 305), wherein: $X_{121}$ is T; $X_{122}$ is P or S; $X_{123}$ is L or T; $X_{124}$ is S; $X_{125}$ is G; $X_{126}$ is R; $X_{127}$ is S; $X_{128}$ is A or G; $X_{129}$ is N; $X_{130}$ is P; $X_{131}$ is K or R; and $X_{132}$ is G or H $X_{121}X_{122}X_{123}X_{124}X_{125}X_{126}X_{127}X_{128}X_{129}X_{130}X_{131}X_{132}$ (SEQ ID NO: 306), wherein: $X_{121}$ is T; $X_{122}$ is S; $X_{123}$ is L or T; $X_{124}$ is S; $X_{125}$ is G; $X_{126}$ is R; $X_{127}$ is S; $X_{128}$ is A or G; $X_{129}$ is N; $X_{130}$ is P; $X_{131}$ is R; and $X_{132}$ is G |

In some embodiments, the CM comprises a core CM consensus 11 sequence comprising the amino acid sequence LSGRSANH (SEQ ID NO: 307) or LSGRSGNH (SEQ ID NO: 308). In some embodiments, the CM comprises an expanded core CM consensus 11 sequence comprising the amino acid sequence DRLSGRSANHKK (SEQ ID NO: 309), DRLSGRSDNHKK (SEQ ID NO: 310), or NTLSGRSGNHGS (SEQ ID NO: 311).

In some embodiments, the CM comprises the amino acid sequence LSGRSANH (SEQ ID NO: 307). In some embodiments, the CM comprises the amino acid sequence LSGRSGNH (SEQ ID NO: 308). In some embodiments, the CM comprises the amino acid sequence DRLSGRSANHKK (SEQ ID NO: 309). In some embodiments, the CM comprises the amino acid sequence DRLSGRSDNHKK (SEQ ID NO: 310). In some embodiments, the CM comprises the amino acid sequence NTLSGRSGNHGS (SEQ ID NO: 311).

In some embodiments, the CM comprises the amino acid sequence LSGRSANH (SEQ ID NO: 307). In some embodiments, the CM comprises the amino acid sequence LNGRSDNH (SEQ ID NO: 313). In some embodiments, the CM comprises the amino acid sequence LTGRSDRH (SEQ ID NO: 314). In some embodiments, the CM comprises a core CM consensus 12 sequence comprising the amino acid sequence LSGRSANH (SEQ ID NO: 307), LNGRSDNH (SEQ ID NO: 313), and LTGRSDRH (SEQ ID NO: 314). In some embodiments, the CM an expanded core CM consensus 12 sequence comprising an amino acid sequence selected from the group consisting of DRLSGRSANHKK (SEQ ID NO: 309), DRLSGRSDNHKK (SEQ ID NO: 310), GPLNGRSDNHKA (SEQ ID NO: 320), GPLNGRSDNHKK (SEQ ID NO: 321), GPLNGRSDNHKR (SEQ ID NO: 322), GPLNGRSDNHQA (SEQ ID NO: 323), GPLNGRSDNHQK (SEQ ID NO: 324), GPLNGRSDNHQR (SEQ ID NO: 325), GPLNGRSDNHRA (SEQ ID NO: 326), GPLNGRSDNHRK (SEQ ID NO: 327), GPLNGRSDNHRR (SEQ ID NO: 328), RPLNGRSDNHKA (SEQ ID NO: 329), RPLNGRSDNHKK (SEQ ID NO: 330), RPLNGRSDNHKR (SEQ ID NO: 331), RPLNGRSDNHQA (SEQ ID NO: 332), RPLNGRSDNHQK (SEQ ID NO: 333), RPLNGRSDNHQR (SEQ ID NO: 334), RPLNGRSDNHRA (SEQ ID NO: 335), RPLNGRSDNHRK (SEQ ID NO: 336), RPLNGRSDNHRR (SEQ ID NO: 337), GPLSGRSDNHKA (SEQ ID NO: 338), GPLSGRSDNHKK (SEQ ID NO: 339), GPLSGRSDNHKR (SEQ ID NO: 340), GPLSGRSDNHQA (SEQ ID NO: 341), GPLSGRSDNHQK (SEQ ID NO: 342), GPLSGRSDNHQR (SEQ ID NO: 343), GPLSGRSDNHRA (SEQ ID NO: 344), GPLSGRSDNHRK (SEQ ID NO: 345), GPLSGRSDNHRR (SEQ ID NO: 346), RPLSGRSDNHKA (SEQ ID NO: 347), RPLSGRSDNHKK (SEQ ID NO: 348), RPLSGRSDNHKR (SEQ ID NO: 349), RPLSGRSDNHQA (SEQ ID NO: 350), RPLSGRSDNHQK (SEQ ID NO: 351), RPLSGRSDNHQR (SEQ ID NO: 352), RPLSGRSDNHRA (SEQ ID NO: 353), RPLSGRSDNHRK (SEQ ID NO: 354), RPLSGRSDNHRR (SEQ ID NO: 355), and KGLTGRSDRHQA (SEQ ID NO: 356).

In some embodiments, the CM comprises the amino acid sequence DRLSGRSANHKK (SEQ ID NO: 309). In some embodiments, the CM comprises the amino acid sequence DRLSGRSDNHKK (SEQ ID NO: 310). In some embodiments, the CM comprises the amino acid sequence GPLNGRSDNHKA (SEQ ID NO: 320). In some embodiments, the CM comprises the amino acid sequence GPLNGRSDNHKK (SEQ ID NO: 321). In some embodiments, the CM comprises the amino acid sequence GPLNGRSDNHKR (SEQ ID NO: 322). In some embodiments, the CM comprises the amino acid sequence GPLNGRSDNHQA (SEQ ID NO: 323). In some embodiments, the CM comprises the amino acid sequence GPLNGRSDNHQK (SEQ ID NO: 324). In some embodiments, the CM comprises the amino acid sequence GPLNGRSDNHQR (SEQ ID NO: 325). In some embodiments, the CM comprises the amino acid sequence GPLNGRSDNHRA (SEQ ID NO: 326). In some embodiments, the CM comprises the amino acid sequence GPLNGRSDNHRK (SEQ ID NO: 327). In some embodiments, the CM comprises the amino acid sequence GPLNGRSDNHRR (SEQ ID NO: 328). In some embodiments, the CM comprises the amino acid sequence RPLNGRSDNHKA (SEQ ID NO: 329). In some embodiments, the CM comprises the amino acid sequence RPLNGRSDNHKK (SEQ ID NO: 330). In some embodiments, the CM comprises the amino acid sequence RPLNGRSDNHKR (SEQ ID NO: 331). In some embodiments, the CM comprises the amino acid sequence RPLNGRSDNHQA (SEQ ID NO: 332). In some embodiments, the CM comprises the amino acid sequence RPLNGRSDNHQK (SEQ ID NO: 333). In some embodiments, the CM comprises the amino acid sequence RPLNGRSDNHQR (SEQ ID NO: 334). In some embodiments, the CM comprises the amino acid sequence RPLNGRSDNHRA (SEQ ID NO: 335). In some embodiments, the CM comprises the amino acid sequence RPLNGRSDNHRK (SEQ ID NO: 336). In some embodiments, the CM comprises the amino acid sequence RPLNGRSDNHRR (SEQ ID NO: 337). In some embodiments, the CM comprises the amino acid sequence GPLSGRSDNHKA (SEQ ID NO: 338). In some embodiments, the CM comprises the amino acid sequence GPLSGRSDNHKK (SEQ ID NO: 339). In some embodiments, the CM comprises the amino acid sequence GPLSGRSDNHKR (SEQ ID NO: 340). In some embodiments, the CM comprises the amino acid sequence GPLSGRSDNHKA (SEQ ID NO: 341). In some embodiments, the CM comprises the amino acid sequence GPLSGRSDNHKK (SEQ ID NO: 342). In some embodiments, the CM comprises the amino acid sequence GPLSGRSDNHQR (SEQ ID NO: 343). In some embodiments, the CM comprises the amino acid sequence GPLSGRSDNHKA (SEQ ID NO: 344). In some embodiments, the CM comprises the amino acid sequence GPLSGRSDNHKK (SEQ ID NO: 345). In some embodiments, the CM comprises the amino acid sequence GPLSGRSDNHKR (SEQ ID NO: 346). In some embodiments, the CM comprises the amino acid sequence RPLSGRSDNHKA (SEQ ID NO: 347). In some embodiments, the CM comprises the amino acid sequence RPLSGRSDNHKK (SEQ ID NO: 348). In some embodiments, the CM comprises the amino acid sequence RPLSGRSDNHKR (SEQ ID NO: 349). In some embodiments, the CM comprises the amino acid sequence RPLSGRSDNHKA (SEQ ID NO: 350). In some embodiments, the CM comprises the amino acid sequence RPLSGRSDNHKK (SEQ ID NO: 351). In some embodiments, the CM comprises the amino acid sequence RPLSGRSDNHQR (SEQ ID NO: 352). In some embodiments, the CM comprises the amino acid sequence RPLSGRSDNHKA (SEQ ID NO: 353). In some embodiments, the CM comprises the amino acid sequence RPLSGRSDNHRK (SEQ ID NO: 354). In some embodiments, the CM comprises the amino acid sequence RPLSGRSDNHRR (SEQ ID NO: 355). In some embodiments, the CM comprises the amino acid sequence KGLTGRSDRHQA (SEQ ID NO: 356).

In some embodiments, the CM comprises a core CM consensus 13 sequence comprising the amino acid sequence RIGRSDNH (SEQ ID NO: 357) or RLGRSDNN (SEQ ID NO: 358). In some embodiments, the CM comprises an expanded core CM consensus 13 sequence comprising the amino acid sequence NHRIGRSDNHRR (SEQ ID NO: 359) or TLRLGRSDNNKN (SEQ ID NO: 360).

In some embodiments, the CM comprises the amino acid sequence RIGRSDNH (SEQ ID NO: 357). In some embodiments, the CM comprises the amino acid sequence RLGRSDNN (SEQ ID NO: 358). In some embodiments, the CM comprises the amino acid sequence NHRIGRSDNHRR (SEQ ID NO: 359). In some embodiments, the CM comprises the amino acid sequence TLRLGRSDNNKN (SEQ ID NO: 360).

In some embodiments, the CM comprises a core CM consensus 14 sequence comprising an amino acid sequence selected from the group consisting of TSGRSANP (SEQ ID NO: 361), TSGRSGNP (SEQ ID NO: 362), LSGRSANP (SEQ ID NO: 363), and LSGRSGNP (SEQ ID NO: 364). In some embodiments, the CM comprises an expanded core CM consensus 14 sequence comprising an amino acid sequence selected from the group consisting of TSTSGRSANPRG (SEQ ID NO: 365), TSTSGRSGNPRG (SEQ ID NO: 366), TSLSGRSANPRG (SEQ ID NO: 367), and TSLSGRSGNPRG (SEQ ID NO: 368).

In some embodiments, the CM comprises the amino acid sequence TSGRSANP (SEQ ID NO: 361). In some embodiments, the CM comprises the amino acid sequence TSGRSGNP (SEQ ID NO: 362). In some embodiments, the CM comprises the amino acid sequence LSGRSANP (SEQ ID NO: 363). In some embodiments, the CM comprises the amino acid sequence LSGRSGNP (SEQ ID NO: 364). In some embodiments. In some embodiments, the CM comprises the amino acid sequence the CM comprises the amino acid sequence TSTSGRSANPRG (SEQ ID NO: 365). In some embodiments, the CM comprises the amino acid sequence TSTSGRSGNPRG (SEQ ID NO: 366). In some embodiments, the CM comprises the amino acid sequence TSLSGRSANPRG (SEQ ID NO: 367). In some embodiments, the CM comprises the amino acid sequence and TSLSGRSGNPRG (SEQ ID NO: 368).

In some embodiments, the CM comprises an amino acid sequence selected from the group consisting of LSGRSENH (SEQ ID NO: 369), SIARSDNL (SEQ ID NO: 370), LSGRSVTQ (SEQ ID NO: 371), LSGRSGNH (SEQ ID NO: 308), LTGRSDRH (SEQ ID NO: 314), LYGRSENN (SEQ ID NO: 374), RLGRSDNN (SEQ ID NO: 375), TSGRSANP (SEQ ID NO: 376), NTLSGRSENHSG (SEQ ID NO: 377), PPSIARSDNLAN (SEQ ID NO: 378), TGLSGRSVTQTS (SEQ ID NO: 379), NTLSGRSGNHGS (SEQ ID NO: 311), KGLTGRSDRHQA (SEQ ID NO: 381), KNLYGRSENNGN (SEQ ID NO: 382), TLRLGRSDNNKN (SEQ ID NO: 383), and TSTSGRSANPRG (SEQ ID NO: 384).

In some embodiments, the CM comprises the amino acid sequence LSGRSENH (SEQ ID NO: 369). In some embodiments, the CM comprises the amino acid sequence SIARSDNL (SEQ ID NO: 370). In some embodiments, the CM comprises the amino acid sequence LSGRSVTQ (SEQ ID NO: 371). In some embodiments, the CM comprises the amino acid sequence LSGRSGNH (SEQ ID NO: 308). In some embodiments, the CM comprises the amino acid sequence LTGRSDRH (SEQ ID NO: 314). In some embodiments, the CM comprises the amino acid sequence LYGRSENN (SEQ ID NO: 374). In some embodiments, the CM comprises the amino acid sequence RLGRSDNN (SEQ ID NO: 375). In some embodiments, the CM comprises the amino acid sequence TSGRSANP (SEQ ID NO: 376). In some embodiments, the CM comprises the amino acid sequence NTLSGRSENHSG (SEQ ID NO: 377). In some embodiments, the CM comprises the amino acid sequence PPSIARSDNLAN (SEQ ID NO: 378). In some embodiments, the CM comprises the amino acid sequence TGLSGRSVTQTS (SEQ ID NO: 379). In some embodiments, the CM comprises the amino acid sequence NTLSGRSGNHGS (SEQ ID NO: 311). In some embodiments, the CM comprises the amino acid sequence KGLTGRSDRHQA (SEQ ID NO: 381). In some embodiments, the CM comprises the amino acid sequence KNLYGRSENNGN (SEQ ID NO: 382). In some embodiments, the CM comprises the amino acid sequence TLRLGRSDNNKN (SEQ ID NO: 383). In some embodiments, the CM comprises the amino acid sequence TSTSGRSANPRG (SEQ ID NO: 384).

In some embodiments, the CM is a substrate for at least two proteases. In some embodiments, at least one protease is matriptase or uPA and at least one protease is selected from the group consisting of those shown in Table 7.

TABLE 7

| Exemplary Proteases and/or Enzymes |
|---|
| ADAMS, ADAMTS, e.g. |
| ADAM8 |
| ADAM9 |
| ADAM10 |
| ADAM12 |
| ADAM15 |
| ADAM17/TACE |
| ADAMDEC1 |
| ADAMTS1 |
| ADAMTS4 |
| ADAMTS5 |
| Aspartate proteases, e.g., |
| BACE |
| Renin |
| Aspartic cathepsins, e.g., |
| Cathepsin D |
| Cathepsin E |
| Caspases, e.g., |
| Caspase 1 |
| Caspase 2 |
| Caspase 3 |
| Caspase 4 |
| Caspase 5 |
| Caspase 6 |
| Caspase 7 |
| Caspase 8 |
| Caspase 9 |
| Caspase 10 |
| Caspase 14 |
| Cysteine cathepsins, e.g., |
| Cathepsin B |
| Cathepsin C |
| Cathepsin K |
| Cathepsin L |
| Cathepsin S |
| Cathepsin V/L2 |
| Cathepsin X/Z/P |
| Cysteine proteinases, e.g., |
| Cruzipain |
| Legumain |
| Otubain-2 |
| KLKs, e.g., |
| KLK4 |
| KLK5 |
| KLK6 |
| KLK7 |
| KLK8 |
| KLK10 |
| KLK11 |
| KLK13 |
| KLK14 |
| Metallo proteinases, e.g., |
| Meprin |

TABLE 7-continued

Exemplary Proteases and/or Enzymes

Neprilysin
PSMA
BMP-1
MMPs, e.g.,
MMP1
MMP2
MMP3
MMP7
MMP8
MMP9
MMP10
MMP11
MMP12
MMP13
MMP14
MMP15
MMP16
MMP17
MMP19
MMP20
MMP23
MMP24
MMP26
MMP27
Serine proteases, e.g.,
activated protein C
Cathepsin A
Cathepsin G
Chymase
coagulation factor proteases
(e.g., FVIIa, FIXa, FXa, FXIa, FXIIa)
Elastase
Granzyme B
Guanidinobenzoatase
HtrA1
Human Neutrophil Elastase
Lactoferrin
Marapsin
NS3/4A
PACE4
Plasmin
PSA
tPA
Thrombin
Tryptase
uPA
Type II Transmembrane
Serine Proteases (TTSPs), e.g.,
DESC1
DPP-4
FAP
Hepsin
Matriptase-2
MT-SP1/Matriptase
TMPRSS2
TMPRSS3
TMPRSS4

In some embodiments, the antibody is attached to at least a first CM and a second CM. In some embodiments, the first CM and the second CM are each polypeptides of no more than 15 amino acids long. In some embodiments, the first CM and the second CM in the antibody in the uncleaved state have the structural arrangement from N-terminus to C-terminus as follows: Agent-CM1-CM2-(Antibody or Antigen-Binding Fragment), (Antibody or Antigen-Binding Fragment)-CM2-CM1-Agent, Agent-CM2-CM1-(Antibody or Antigen-Binding Fragment), or (Antibody or Antigen-Binding Fragment)-CM1-CM2-Agent. In some embodiments, the antibody includes a linking peptide between the agent and CM1. In some embodiments, the antibody includes a linking peptide between CM1 and CM2. In some embodiments, the antibody includes a linking peptide between CM2 and antibody or antigen-binding fragment. In some embodiments, the antibody includes a linking peptide between the agent and CM1 and a linking peptide between CM2 and antibody or antigen-binding fragment. In some embodiments, the antibody includes a linking peptide between agent and CM1 and a linking peptide between CM1 and CM2. In some embodiments, the antibody includes a linking peptide between CM1 and CM2 and a linking peptide between CM2 and antibody or antigen-binding fragment. In some embodiments, the antibody includes a linking peptide between agent and CM1, a linking peptide between CM1 and CM2, and a linking peptide between CM2 and antibody or antigen-binding fragment.

In some embodiments, the antibody includes at least a first CM that includes a substrate for at least one protease selected from matriptase and uPA and a second CM that includes a substrate sequence. Exemplary substrates for the second CM (CM2) include but are not limited to substrates cleavable by one or more of the following enzymes or proteases listed in Table 7.

In some embodiments, the CM2 is selected for use with a specific protease. In some embodiments, the CM2 is a substrate for at least one protease selected from the group consisting of a matrix metalloprotease (MMP), a neutrophil elastase, uPA (also referred to as u-plasminogen activator), legumain, matriptase, thrombin, a cysteine protease such as a cathepsin, ADAM17, BMP-1, HtrA1, and a TMPRSS such as TMPRSS3 or TMPRSS4.

In some embodiments, the CM2 is a substrate for a neutrophil elastase. In some embodiments, the CM2 is a substrate for uPA. In some embodiments, the CM2 is a substrate for legumain. In some embodiments, the CM2 is a substrate for matriptase. In some embodiments, the CM2 is a substrate for thrombin. In some embodiments, the CM2 is a substrate for a cysteine protease. In some embodiments, the CM2 is a substrate for a cathepsin. In some embodiments, the CM2 is a substrate for ADAM17. In some embodiments, the CM2 is a substrate for BMP-1. In some embodiments, the CM2 is a substrate for HtrA1. In some embodiments, the CM2 is a substrate for a TMPRSS. In some embodiments, the CM2 is a substrate for TMPRSS3. In some embodiments, the CM2 is a substrate for TMPRSS4.

For example, suitable CM2 are cleaved by at least one protease and include the sequence TGRGPSWV (SEQ ID NO: 402); SARGPSRW (SEQ ID NO: 403); TARGPSFK (SEQ ID NO: 404); TARGPSW (SEQ ID NO: 405); LSGRSDNH (SEQ ID NO: 406); GGWHTGRN (SEQ ID NO: 407); HTGRSGAL (SEQ ID NO: 408); PLTGRSGG (SEQ ID NO: 409); AARGPAIH (SEQ ID NO: 411); RGPAFNPM (SEQ ID NO: 412); SSRGPAYL (SEQ ID NO: 413); RGPATPIM (SEQ ID NO: 414); RGPA (SEQ ID NO: 415); GGQPSGMWGW (SEQ ID NO: 416); FPRPLGITGL (SEQ ID NO: 417); VHMPLGFLGP (SEQ ID NO: 418); SPLTGRSG (SEQ ID NO: 419); SAGFSLPA (SEQ ID NO: 126); LAPLGLQRR (SEQ ID NO: 420); SGGPLGVR (SEQ ID NO: 421); PLGL (SEQ ID NO: 422); GPRSFGL (SEQ ID NO: 423) and/or GPRSFG (SEQ ID NO: 424).

In some embodiments, the CM2 comprises the amino acid sequence TGRGPSWV (SEQ ID NO: 402). In some embodiments, the CM2 comprises the amino acid sequence SARGPSRW (SEQ ID NO: 403). In some embodiments, the CM2 comprises the amino acid sequence TARGPSFK (SEQ ID NO: 404). In some embodiments, the CM2 comprises the amino acid sequence TARGPSW (SEQ ID NO: 405). In some embodiments, the CM2 comprises the amino acid sequence LSGRSDNH (SEQ ID NO: 406). In some embodiments, the CM2 comprises the amino acid sequence GGWHTGRN (SEQ ID NO: 407). In some embodiments, the CM2 comprises the amino acid sequence HTGRSGAL (SEQ ID NO: 408). In some embodiments, the CM2 comprises the amino acid sequence PLTGRSGG (SEQ ID NO: 409). In some embodiments, the CM2 comprises the amino acid sequence AARGPAIH (SEQ ID NO: 411). In some embodiments, the CM2 comprises the amino acid sequence RGPAFNPM (SEQ ID NO: 412). In some embodiments, the CM2 comprises the amino acid sequence SSRGPAYL (SEQ ID NO: 413). In some embodiments, the CM2 comprises the amino acid sequence RGPATPIM (SEQ ID NO: 414). In some embodiments, the CM2 comprises the amino acid sequence RGPA (SEQ ID NO: 415). In some embodiments, the CM2 comprises the amino acid sequence GGQPSGMWGW (SEQ ID NO: 416). In some embodiments, the CM2 comprises the amino acid sequence FPRPLGITGL (SEQ ID NO: 417). In some embodiments, the CM2 comprises the amino acid sequence VHMPLGFLGP (SEQ ID NO: 418). In some embodiments, the CM2 comprises the amino acid sequence SPLTGRSG (SEQ ID NO: 419). In some embodiments, the CM2 comprises the amino acid sequence LAPLGLQRR (SEQ ID NO: 420). In some embodiments, the CM2 comprises the amino acid sequence SGGPLGVR (SEQ ID NO: 421). In some embodiments, the CM2 comprises the amino acid sequence PLGL (SEQ ID NO: 422). In some embodiments, the CM2 comprises the amino acid sequence GPRSFGL (SEQ ID NO: 423). In some embodiments, the CM2 comprises the amino acid sequence GPRSFG (SEQ ID NO: 424).

In some embodiments, the CM2 is a substrate for at least one MMP. In some embodiments, the CM2 is a substrate for at least one MMP listed in the Table 7. In some embodiments, the CM2 is a substrate for MMP9. In some embodiments, the CM2 is a substrate for MMP14. In some embodiments, the CM2 is a substrate for two or more MMPs. In some embodiments, the CM2 is a substrate for at least MMP9 or MMP14. In some embodiments, the CM2 is a substrate for two or more MMPs. In some embodiments, the CM2 is a substrate for at least MMP9 and MMP14.

In some embodiments, CM2 is a substrate for an MMP and includes the sequence ISSGLLSS (SEQ ID NO: 425); QNQALRMA (SEQ ID NO: 426); AQNLLGMV (SEQ ID NO: 427); STFPFGMF (SEQ ID NO: 428); PVGYTSSL (SEQ ID NO: 429); DWLYWPGI (SEQ ID NO: 430); MIAPVAYR (SEQ ID NO: 431); RPSPMWAY (SEQ ID NO: 432); WATPRPMR (SEQ ID NO: 433); FRLLDWQW (SEQ ID NO: 434); LKAAPRWA (SEQ ID NO: 435); GPSHLVLT (SEQ ID NO: 436); LPGGLSPW (SEQ ID NO: 437); MGLFSEAG (SEQ ID NO: 438); SPLPLRVP (SEQ ID NO: 439); RMHLRSLG (SEQ ID NO: 440); LAAPLGLL (SEQ ID NO: 441); AVGLLAPP (SEQ ID NO: 442); LLAPSHRA (SEQ ID NO: 443), PAGLWLDP (SEQ ID NO: 444); and/or ISSGLSS (SEQ ID NO: 445).

In some embodiments, the first cleaving agent and the second cleaving agent are the same protease, and the first CM and the second CM are different substrates for the enzyme. In some embodiments, the first cleaving agent and the second cleaving agent are different proteases. In some embodiments, the first cleaving agent and the second cleaving agent are co-localized in the target tissue. In some embodiments, the first CM and the second CM are cleaved by at least one cleaving agent in the target tissue.

In some embodiments, the CM comprises the non-prime side of the protease cleavage site; that is, the CM comprises at least the P1 and P2 amino acids, and in some embodiments comprises the P1, P2 and P3 amino acids and in some embodiments comprises the P1, P2, P3, and P4 amino acids. In some embodiments, the CM comprises the non-prime side and the prime side of the protease cleavage site. In some embodiments, the CM comprises the non-prime side but lacks at least part of the prime side of the protease cleavage site. In some embodiments, the CM comprises the non-prime side but lacks the prime side of the protease cleavage site. Such a CM can be linked directly or through a linker to an antibody or other molecule as disclosed herein, such as, but not limited to, a detection moiety.

In some embodiments, the agent conjugated to the antibody or antigen-binding fragment is a therapeutic agent. In some embodiments, the agent is an antineoplastic agent. In some embodiments, the agent is a toxin or fragment thereof. As used herein, a fragment of a toxin is a fragment that retains toxic activity. In some embodiments, the agent is conjugated to the AB via a cleavable linker. In some embodiments, the agent is conjugated to the AB via a linker that includes at least one cleavable substrate sequence described herein. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the agent is an anti-inflammatory agent.

In some embodiments, the antibody also includes a detectable moiety. In some embodiments, the detectable moiety is a diagnostic agent.

In some embodiments, the conjugated antibody and/or conjugated activatable antibody includes a detectable label. In some embodiments, the detectable label includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or β-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label comprises an N-methylacrydium derivative. In some embodiments, the label comprises an Alexa Fluor® label, such as Alex Fluor® 680 or Alexa Fluor® 750. In some embodiments, the ligand-based label comprises biotin, avidin, streptavidin or one or more haptens.

In some embodiments, the antibody naturally contains one or more disulfide bonds. In some embodiments, the antibody or antigen-binding fragment can be engineered to include one or more disulfide bonds.

In some embodiments, the antibody and/or conjugated antibody is monospecific. In some embodiments, the antibody and/or conjugated antibody is multispecific, e.g., by way of non-limiting example, bispecific or trifunctional. In some embodiments, the antibody and/or conjugated antibody is formulated as part of a pro-Bispecific T Cell Engager (pro-BITE) molecule. In some embodiments, the antibody and/or conjugated antibody is formulated as part of a pro-Chimeric Antigen Receptor (pro-CAR) modified T cell or other engineered receptor.

In some embodiments, the activatable antibody and/or conjugated activatable antibody is monospecific. In some embodiments, the activatable antibody and/or conjugated activatable antibody is multispecific, referred to herein as multispecific activatable antibodies and/or conjugated multispecific activatable antibodies. As used herein, terms such as "activatable antibody" and all grammatical variations thereof, unless otherwise noted, are intended to encompass, but are not limited to embodiments where the activatable antibody is a multispecific activatable antibody of the disclosure. As used herein, terms such as "conjugated activatable antibody" and all grammatical variations thereof, unless otherwise noted, are intended to encompass, but are not limited to embodiments where the conjugated activatable antibody is a conjugated multispecific activatable antibody of the disclosure. In some embodiments, the multispecific activatable antibody and/or conjugated multispecific activatable antibody is bispecific or trifunctional.

In some embodiments, the conjugated antibodies described herein are used in conjunction with one or more additional agents or a combination of additional agents. Suitable additional agents include current pharmaceutical and/or surgical therapies for an intended application, such as, for example, cancer. For example, the conjugated antibodies can be used in conjunction with an additional chemotherapeutic or anti-neoplastic agent.

The matriptase and/or uPA substrates of the disclosure are also useful in activatable antibodies. The activatable antibodies described herein in an activated state bind a given target and include (i) an antibody or an antigen binding fragment thereof (AB) that specifically binds to the target; (ii) a masking moiety (MM) that inhibits the binding of the AB to the target in an uncleaved state; and (c) a cleavable moiety (CM) coupled to the AB, wherein the CM is a polypeptide that functions as a substrate for at least one protease selected from matriptase and/or uPA.

In some embodiments, the activatable antibody in the uncleaved state has the structural arrangement from N-terminus to C-terminus as follows: MM-CM-AB or AB-CM-MM.

In some embodiments, the activatable antibody comprises a linking peptide between the MM and the CM.

In some embodiments, the activatable antibody comprises a linking peptide between the CM and the AB.

In some embodiments, the activatable antibody comprises a first linking peptide (LP1) and a second linking peptide (LP2), wherein the activatable antibody in the uncleaved state has the structural arrangement from N-terminus to C-terminus as follows: MM-LP1-CM-LP2-AB or AB-LP2-CM-LP1-MM.

In some embodiments, the two linking peptides need not be identical to each other.

In some embodiments, at least one of LP1 or LP2 comprises an amino acid sequence selected from the group consisting of $(GS)_n$, $(GGS)_n$, $(GSGGS)_n$ (SEQ ID NO: 385) and $(GGGS)_n$ (SEQ ID NO: 386), where n is an integer of at least one.

In some embodiments, at least one of LP1 or LP2 comprises an amino acid sequence selected from the group consisting of GGSG (SEQ ID NO: 387), GGSGG (SEQ ID NO: 388), GSGSG (SEQ ID NO: 389), GSGGG (SEQ ID NO: 390), GGGSG (SEQ ID NO: 391), and GSSSG (SEQ ID NO: 392).

In some embodiments, LP1 comprises the amino acid sequence GSSGGSGGSGGSG (SEQ ID NO: 393), GSSGGSGGSGG (SEQ ID NO: 394), GSSGGSGGSGGS (SEQ ID NO: 395), GSSGGSGGSGGSGGGS (SEQ ID NO: 396), GSSGGSGGSG (SEQ ID NO: 397), or GSSGGSGGSGS (SEQ ID NO: 398).

In some embodiments, LP2 comprises the amino acid sequence GSS, GGS, GGGS (SEQ ID NO: 399), GSSGT (SEQ ID NO: 400) or GSSG (SEQ ID NO: 401).

In some embodiments, the AB has an equilibrium dissociation constant of about 100 nM or less for binding to the target.

In some embodiments, the activatable antibody includes an antibody or antigen-binding fragment thereof that specifically binds a target. In some embodiments, the antibody or immunologically active fragment thereof that binds the target is a monoclonal antibody, domain antibody, single chain, Fab fragment, a $F(ab')_2$ fragment, a scFv, a scab, a dAb, a single domain heavy chain antibody, or a single domain light chain antibody. In some embodiments, such an antibody or immunologically active fragment thereof that binds the target is a mouse, other rodent, chimeric, humanized or fully human monoclonal antibody.

In some embodiments, the MM has an equilibrium dissociation constant for binding to the AB that is greater than the equilibrium dissociation constant of the AB to the target.

In some embodiments, the MM has an equilibrium dissociation constant for binding to the AB that is no more than the equilibrium dissociation constant of the AB to the target.

In some embodiments, the MM does not interfere or compete with the AB for binding to the target in a cleaved state.

In some embodiments, the MM is a polypeptide of about 2 to 40 amino acids in length. For example, the MM is a polypeptide of up to about 40 amino acids in length.

In some embodiments, the MM polypeptide sequence is different from that of any natural binding partner of the AB. In some embodiments, the MM polypeptide sequence is no more than 50% identical to any natural binding partner of the AB. In some embodiments, the MM polypeptide sequence is no more than 40%, 30%, 25%, 20%, 15%, or 10% identical to any natural binding partner of the AB.

In some embodiments, the coupling of the MM to the AB reduces the ability of the AB to bind its target such that the dissociation constant ($K_d$) of the AB when coupled to the MM towards the target is at least two times greater than the $K_d$ of the AB when not coupled to the MM towards the target.

In some embodiments, the coupling of the MM to the AB reduces the ability of the AB to bind its target such that the dissociation constant ($K_d$) of the AB when coupled to the MM towards the target is at least three times greater than the $K_d$ of the AB when not coupled to the MM towards the target.

In some embodiments, the coupling of the MM to the AB reduces the ability of the AB to bind its target such that the dissociation constant ($K_d$) of the AB when coupled to the MM towards the target is at least five times greater than the $K_d$ of the AB when not coupled to the MM towards the target.

In some embodiments, the coupling of the MM to the AB reduces the ability of the AB to bind its target such that the dissociation constant ($K_d$) of the AB when coupled to the MM towards the target is at least 10 times greater than the $K_d$ of the AB when not coupled to the MM towards the target.

In some embodiments, the coupling of the MM to the AB reduces the ability of the AB to bind its target such that the dissociation constant ($K_d$) of the AB when coupled to the MM towards the target is at least 20 times greater than the $K_d$ of the AB when not coupled to the MM towards the target.

In some embodiments, the coupling of the MM to the AB reduces the ability of the AB to bind the target such that the dissociation constant ($K_d$) of the AB when coupled to the MM towards the target is at least 40 times greater than the $K_d$ of the AB when not coupled to the MM towards the target.

In some embodiments, the coupling of the MM to the AB reduces the ability of the AB to bind the target such that the dissociation constant ($K_d$) of the AB when coupled to the MM towards the target is at least 100 times greater than the $K_d$ of the AB when not coupled to the MM towards the target.

In some embodiments, the coupling of the MM to the AB reduces the ability of the AB to bind the target such that the dissociation constant ($K_d$) of the AB when coupled to the MM towards the target is at least 1000 times greater than the $K_d$ of the AB when not coupled to the MM towards the target.

In some embodiments, the coupling of the MM to the AB reduces the ability of the AB to bind the target such that the dissociation constant ($K_d$) of the AB when coupled to the MM towards the target is at least 10,000 times greater than the $K_d$ of the AB when not coupled to the MM towards the target.

In some embodiments, the protease, i.e., matriptase and/or uPA, is co-localized with the target in a tissue, and the protease cleaves the CM in the activatable antibody when the activatable antibody is exposed to the protease.

In some embodiments, in the presence of the target, the MM reduces the ability of the AB to bind the target by at least 90% when the CM is uncleaved, as compared to when the CM is cleaved when assayed in vitro using a target displacement assay such as, for example, the assay described in PCT Publication Nos. WO 2009/025846 and WO 2010/081173.

In some embodiments, the CM is positioned in the activatable antibody such that in the uncleaved state, binding of the activatable antibody to the target is reduced to occur with an equilibrium dissociation constant that is at least twofold greater than the equilibrium dissociation constant of an unmodified AB binding to the target, whereas in the cleaved state (i.e., when the activatable antibody is in the cleaved state), the AB binds the target.

In some embodiments, the CM is positioned in the activatable antibody such that in the uncleaved state, binding of the activatable antibody to the target is reduced to occur with an equilibrium dissociation constant that is at least five-fold greater than the equilibrium dissociation constant of an unmodified AB binding to the target, whereas in the cleaved state (i.e., when the activatable antibody is in the cleaved state), the AB binds the target.

In some embodiments, the CM is positioned in the activatable antibody such that in the uncleaved state, binding of the activatable antibody to the target is reduced to occur with an equilibrium dissociation constant that is at least ten-fold greater than the equilibrium dissociation constant of an unmodified AB binding to the target, whereas in the cleaved state (i.e., when the activatable antibody is in the cleaved state), the AB binds the target.

In some embodiments, the CM is positioned in the activatable antibody such that in the uncleaved state, binding of the activatable antibody to the target is reduced to occur with an equilibrium dissociation constant that is at least 20-fold greater than the equilibrium dissociation constant of an unmodified AB binding to the target, whereas in the cleaved state (i.e., when the activatable antibody is in the cleaved state), the AB binds the target.

In some embodiments, the CM is positioned in the activatable antibody such that in the uncleaved state, binding of the activatable antibody to the target is reduced to occur with an equilibrium dissociation constant that is at least 40-fold greater than the equilibrium dissociation constant of an unmodified AB binding to the target, whereas in the cleaved state, the AB binds the target.

In some embodiments, the CM is positioned in the activatable antibody such that in the uncleaved state, binding of the activatable antibody to the target is reduced to occur with an equilibrium dissociation constant that is at least 50-fold greater than the equilibrium dissociation constant of an unmodified AB binding to the target, whereas in the cleaved state, the AB binds the target.

In some embodiments, the CM is positioned in the activatable antibody such that in the uncleaved state, binding of the activatable antibody to the target is reduced to occur with an equilibrium dissociation constant that is at least 100-fold greater than the equilibrium dissociation constant of an unmodified AB binding to the target, whereas in the cleaved state, the AB binds the target.

In some embodiments, the CM is positioned in the activatable antibody such that in the uncleaved state, binding of the activatable antibody to the target is reduced to occur with an equilibrium dissociation constant that is at least 200-fold greater than the equilibrium dissociation constant of an unmodified AB binding to the target, whereas in the cleaved state, the AB binds the target.

In some embodiments, the CM is a polypeptide of up to 15 amino acids in length.

In some embodiments, the CM is a substrate for at least matriptase. In some embodiments, the CM is a substrate for at least uPA. In some embodiments, the CM is a substrate for at least matriptase and uPA.

In some embodiments, the CM is a substrate for matriptase and/or uPA, and is resistant to cleavage by at least one other protease. In some embodiments, the CM is a substrate for matriptase and/or uPA, and is resistant to cleavage by at least plasmin. In some embodiments, the CM is a substrate for matriptase and/or uPA, and is resistant to cleavage by at least tissue plasminogen activator (tPA).

In some embodiments, the CM is a substrate for matriptase and/or uPA and includes a motif sequence that is recognized by matriptase and/or uPA, provided that for any given motif sequence of the disclosure:
    (i) the CM does not comprise any of the following amino acid sequences TGRGPSWV (SEQ ID NO: 402), SARGPSRW (SEQ ID NO: 403), or TARGPSFK (SEQ ID NO: 404); and the CM does not comprise a consensus amino acid sequence based on these amino acid sequences, such as for example, TARGPSW (SEQ ID NO: 405);

(ii) the CM does not comprise any of the following amino acid sequences LSGRSDNH (SEQ ID NO: 406), GGWHTGRN (SEQ ID NO: 407), HTGRSGAL (SEQ ID NO: 408), or PLTGRSGG (SEQ ID NO: 409); and the CM does not comprise a consensus amino acid sequence based on these amino acid sequences, such as for example, LTGRSGA (SEQ ID NO: 410); and/or (iii) the CM does not comprise any of the following amino acid sequences AARGPAIH (SEQ ID NO: 411), RGPAFNPM (SEQ ID NO: 412), SSRGPAYL (SEQ ID NO: 413), or RGPATPIM (SEQ ID NO: 414); and the CM does not comprise a consensus amino acid sequence based on these amino acid sequences, such as for example, RGPA (SEQ ID NO: 415).

In some embodiments, the motif sequence includes a core CM consensus sequence shown in Tables 8A-8J. In some embodiments, the motif sequence includes a subgenus, i.e., a subset, of the core CM consensus sequence shown in Tables 8A-8J.

In some embodiments, the motif sequence includes an expanded consensus sequence based on one of the core CM consensus sequence shown in Tables 8A-8J. In some embodiments, the expanded consensus sequence is a consensus sequence shown in Tables 9A-9J-3.

In some embodiments, the CM comprises a core CM consensus 1 sequence comprising the amino acid sequence AAPRS (SEQ ID NO: 163). In some embodiments, the CM comprises an expanded core CM consensus 1 sequence comprising the amino acid sequence AAPRSF (SEQ ID NO: 164).

In some embodiments, the CM comprises a core CM consensus 2 sequence comprising the amino acid sequence SRRVP (SEQ ID NO: 165). In some embodiments, the CM comprises an expanded core CM consensus 2 sequence comprising an amino acid sequence selected from the group consisting of QSRRVP (SEQ ID NO: 166), QTRRVP (SEQ ID NO: 167), SRRVPL (SEQ ID NO: 168), SRRVPV (SEQ ID NO: 169), QSRRVPL (SEQ ID NO: 170), QSRRVPV (SEQ ID NO: 171), QTRRVPL (SEQ ID NO: 172), and QTRRVPV (SEQ ID NO: 173).

In some embodiments, the CM comprises the amino acid sequence QSRRVP (SEQ ID NO: 166). In some embodiments, the CM comprises the amino acid sequence QTRRVP (SEQ ID NO: 167). In some embodiments, the CM comprises the amino acid sequence SRRVPL (SEQ ID NO: 168). In some embodiments, the CM comprises the amino acid sequence SRRVPV (SEQ ID NO: 169). In some embodiments, the CM comprises the amino acid sequence QSRRVPL (SEQ ID NO: 170). In some embodiments, the CM comprises the amino acid sequence QSRRVPV (SEQ ID NO: 171). In some embodiments, the CM comprises the amino acid sequence QTRRVPL (SEQ ID NO: 172). In some embodiments, the CM comprises the amino acid sequence QTRRVPV (SEQ ID NO: 173).

In some embodiments, the CM comprises a core CM consensus 3 sequence comprising the amino acid sequence PPLGR (SEQ ID NO: 174). In some embodiments, the CM comprises an expanded core CM consensus 3 sequence comprising an amino acid sequence selected from the group consisting of GPPLGR (SEQ ID NO: 175), SPPLGR (SEQ ID NO: 176), CGPPLGR (SEQ ID NO: 177), CSPPLGR (SEQ ID NO: 178), GGPPLGR (SEQ ID NO: 179), GSPPLGR (SEQ ID NO: 180), SGPPLGR (SEQ ID NO: 181), SSPPLGR (SEQ ID NO: 182), GCGPPLGR (SEQ ID NO: 183), GCSPPLGR (SEQ ID NO: 184), GGGPPLGR (SEQ ID NO: 185), GGSPPLGR (SEQ ID NO: 186), GSGPPLGR (SEQ ID NO: 187), GSSPPLGR (SEQ ID NO: 188), SCGPPLGR (SEQ ID NO: 189), SCSPPLGR (SEQ ID NO: 190), SGGPPLGR (SEQ ID NO: 191), SGSPPLGR (SEQ ID NO: 192), SSGPPLGR (SEQ ID NO: 193), and SSSPPLGR (SEQ ID NO: 194).

In some embodiments, the CM comprises the amino acid sequence GPPLGR (SEQ ID NO: 175). In some embodiments, the CM comprises the amino acid sequence SPPLGR (SEQ ID NO: 176). In some embodiments, the CM comprises the amino acid sequence CGPPLGR (SEQ ID NO: 177). In some embodiments, the CM comprises the amino acid sequence CSPPLGR (SEQ ID NO: 178). In some embodiments, the CM comprises the amino acid sequence GGPPLGR (SEQ ID NO: 179). In some embodiments, the CM comprises the amino acid sequence GSPPLGR (SEQ ID NO: 180). In some embodiments, the CM comprises the amino acid sequence SGPPLGR (SEQ ID NO: 181). In some embodiments, the CM comprises the amino acid sequence SSPPLGR (SEQ ID NO: 182). In some embodiments, the CM comprises the amino acid sequence GCGPPLGR (SEQ ID NO: 183). In some embodiments, the CM comprises the amino acid sequence GCSPPLGR (SEQ ID NO: 184). In some embodiments, the CM comprises the amino acid sequence GGGPPLGR (SEQ ID NO: 185). In some embodiments, the CM comprises the amino acid sequence GGSPPLGR (SEQ ID NO: 186). In some embodiments, the CM comprises the amino acid sequence GSGPPLGR (SEQ ID NO: 187). In some embodiments, the CM comprises the amino acid sequence GSSPPLGR (SEQ ID NO: 188). In some embodiments, the CM comprises the amino acid sequence SCGPPLGR (SEQ ID NO: 189). In some embodiments, the CM comprises the amino acid sequence SCSPPLGR (SEQ ID NO: 190). In some embodiments, the CM comprises the amino acid sequence SGGPPLGR (SEQ ID NO: 191). In some embodiments, the CM comprises the amino acid sequence SGSPPLGR (SEQ ID NO: 192). In some embodiments, the CM comprises the amino acid sequence SSGPPLGR (SEQ ID NO: 193). In some embodiments, the CM comprises the amino acid sequence SSSPPLGR (SEQ ID NO: 194).

In some embodiments, the CM comprises a core CM consensus 4 sequence comprising the amino acid sequence LRSGW (SEQ ID NO: 195). In some embodiments, the CM comprises an expanded core CM consensus 4 sequence comprising an amino acid sequence selected from the group consisting of MLRSGW, (SEQ ID NO: 196), MLRSGWR, (SEQ ID NO: 197), MLRSGWRG, (SEQ ID NO: 198), MLRSGWRL, (SEQ ID NO: 199), and MLRSGWRS (SEQ ID NO: 200).

In some embodiments, the CM comprises the amino acid sequence MLRSGW, (SEQ ID NO: 196). In some embodiments, the CM comprises the amino acid sequence MLRSGWR (SEQ ID NO: 197). In some embodiments, the CM comprises the amino acid sequence MLRSGWRG (SEQ ID NO: 198). In some embodiments, the CM comprises the amino acid sequence MLRSGWRL (SEQ ID NO: 199). In some embodiments, the CM comprises the amino acid sequence MLRSGWRS (SEQ ID NO: 200).

In some embodiments, the CM comprises a core CM consensus 5 sequence comprising the amino acid sequence VSRSA (SEQ ID NO: 201). In some embodiments, the CM comprises an expanded core CM consensus 5 sequence comprising an amino acid sequence selected from the group consisting of IVSRSA (SEQ ID NO: 202), YIVSRSA (SEQ ID NO: 203), and QYIVSRSA (SEQ ID NO: 204).

In some embodiments, the CM comprises the amino acid sequence IVSRSA (SEQ ID NO: 202). In some embodiments, the CM comprises the amino acid sequence YIVSRSA (SEQ ID NO: 203). In some embodiments, the CM comprises the amino acid sequence QYIVSRSA (SEQ ID NO: 204).

In some embodiments, the CM comprises a core CM consensus 6 sequence comprising the amino acid sequence ALRAP (SEQ ID NO: 205). In some embodiments, the CM comprises an expanded core CM consensus 6 sequence comprising the amino acid sequence RALRAP (SEQ ID NO: 206).

In some embodiments, the CM comprises a core CM consensus 7 sequence comprising the amino acid sequence PAGRR (SEQ ID NO: 207). In some embodiments, the CM comprises an expanded core CM consensus 7 sequence comprising an amino acid sequence selected from the group consisting of PAGRRS (SEQ ID NO: 208), PAGRRSL (SEQ ID NO: 209), VPAGRRS (SEQ ID NO: 210), and VPAGRRSL (SEQ ID NO: 211).

In some embodiments, the CM comprises the amino acid sequence PAGRRS (SEQ ID NO: 208). In some embodiments, the CM comprises the amino acid sequence PAGRRSL (SEQ ID NO: 209). In some embodiments, the CM comprises the amino acid sequence VPAGRRS (SEQ ID NO: 210). In some embodiments, the CM comprises the amino acid sequence VPAGRRSL (SEQ ID NO: 211).

In some embodiments, the CM comprises a core CM consensus 8 sequence comprising the amino acid sequence GRSML (SEQ ID NO: 212). In some embodiments, the CM comprises an expanded core CM consensus 8 sequence comprising an amino acid sequence selected from the group consisting of GRSMLL (SEQ ID NO: 213), GRSMLM (SEQ ID NO: 214), GRSMLLG (SEQ ID NO: 215), GRSMLLP (SEQ ID NO: 216), GRSMLLS (SEQ ID NO: 217), GRSMLMG (SEQ ID NO: 218), GRSMLMP (SEQ ID NO: 219), GRSMLMS (SEQ ID NO: 220), GRSMLLGG (SEQ ID NO: 221), GRSMLLPG (SEQ ID NO: 222), GRSMLLSG (SEQ ID NO: 223), GRSMLMGG (SEQ ID NO: 224), GRSMLMPG (SEQ ID NO: 225), GRSMLMSG (SEQ ID NO: 226), GRSMLLGP (SEQ ID NO: 227), GRSMLLPP (SEQ ID NO: 228), GRSMLLSP (SEQ ID NO: 229), GRSMLMGP (SEQ ID NO: 230), GRSMLMPP (SEQ ID NO: 231), GRSMLMSP (SEQ ID NO: 232), GRSMLLGS (SEQ ID NO: 233), GRSMLLPS (SEQ ID NO: 234), GRSMLLSS (SEQ ID NO: 235), GRSMLMGS (SEQ ID NO: 236), GRSMLMPS (SEQ ID NO: 237), and GRSMLMSS (SEQ ID NO: 238).

In some embodiments, the CM comprises the amino acid sequence GRSMLL (SEQ ID NO: 213). In some embodiments, the CM comprises the amino acid sequence GRSMLM (SEQ ID NO: 214). In some embodiments, the CM comprises the amino acid sequence GRSMLLG (SEQ ID NO: 215). In some embodiments, the CM comprises the amino acid sequence GRSMLLP (SEQ ID NO: 216). In some embodiments, the CM comprises the amino acid sequence GRSMLLS (SEQ ID NO: 217). In some embodiments, the CM comprises the amino acid sequence GRSMLMG (SEQ ID NO: 218). In some embodiments, the CM comprises the amino acid sequence GRSMLMP (SEQ ID NO: 219). In some embodiments, the CM comprises the amino acid sequence GRSMLMS (SEQ ID NO: 220). In some embodiments, the CM comprises the amino acid sequence GRSMLLGG (SEQ ID NO: 221). In some embodiments, the CM comprises the amino acid sequence GRSMLLPG (SEQ ID NO: 222). In some embodiments, the CM comprises the amino acid sequence GRSMLLSG (SEQ ID NO: 223). In some embodiments, the CM comprises the amino acid sequence GRSMLMGG (SEQ ID NO: 224). In some embodiments, the CM comprises the amino acid sequence GRSMLMPG (SEQ ID NO: 225). In some embodiments, the CM comprises the amino acid sequence GRSMLMSG (SEQ ID NO: 226). In some embodiments, the CM comprises the amino acid sequence GRSMLLGP (SEQ ID NO: 227). In some embodiments, the CM comprises the amino acid sequence GRSMLLPP (SEQ ID NO: 228). In some embodiments, the CM comprises the amino acid sequence GRSMLLSP (SEQ ID NO: 229). In some embodiments, the CM comprises the amino acid sequence GRSMLMGP (SEQ ID NO: 230). In some embodiments, the CM comprises the amino acid sequence GRSMLMPP (SEQ ID NO: 231). In some embodiments, the CM comprises the amino acid sequence GRSMLMSP (SEQ ID NO: 232). In some embodiments, the CM comprises the amino acid sequence GRSMLLGS (SEQ ID NO: 233). In some embodiments, the CM comprises the amino acid sequence GRSMLLPS (SEQ ID NO: 234). In some embodiments, the CM comprises the amino acid sequence GRSMLLSS (SEQ ID NO: 235). In some embodiments, the CM comprises the amino acid sequence GRSMLMGS (SEQ ID NO: 236). In some embodiments, the CM comprises the amino acid sequence GRSMLMPS (SEQ ID NO: 237). In some embodiments, the CM comprises the amino acid sequence GRSMLMSS (SEQ ID NO: 238).

In some embodiments, the CM comprises a core CM consensus 9 sequence comprising the amino acid sequence LARAG (SEQ ID NO: 239). In some embodiments, the CM comprises an expanded core CM consensus 9 sequence comprising an amino acid sequence selected from the group consisting of LARAGI (SEQ ID NO: 240), LARAGL (SEQ ID NO: 241), PLARAGI (SEQ ID NO: 242), PLARAGL (SEQ ID NO: 243), RPLARAGI (SEQ ID NO: 244), and RPLARAGL (SEQ ID NO: 245).

In some embodiments, the CM comprises the amino acid sequence LARAGI (SEQ ID NO: 240). In some embodiments, the CM comprises the amino acid sequence LARAGL (SEQ ID NO: 241). In some embodiments, the CM comprises the amino acid sequence PLARAGI (SEQ ID NO: 242). In some embodiments, the CM comprises the amino acid sequence PLARAGL (SEQ ID NO: 243). In some embodiments, the CM comprises the amino acid sequence RPLARAGI (SEQ ID NO: 244). In some embodiments, the CM comprises the amino acid sequence RPLARAGL (SEQ ID NO: 245).

In some embodiments, the CM comprises a core CM consensus 10 sequence comprising the amino acid sequence ESRRW (SEQ ID NO: 246). In some embodiments, the CM comprises an expanded core CM consensus 10 sequence comprising an amino acid sequence selected from the group consisting of ESRRWM (SEQ ID NO: 247), ESRRWMP (SEQ ID NO: 248), and PESRRWMP (SEQ ID NO: 249).

In some embodiments, the CM comprises the amino acid sequence ESRRWM (SEQ ID NO: 247). In some embodiments, the CM comprises the amino acid sequence ESRRWMP (SEQ ID NO: 248). In some embodiments, the CM comprises the amino acid sequence PESRRWMP (SEQ ID NO: 249).

In some embodiments, the CM comprises an amino acid sequence selected from the group consisting of ILPRSPAF (SEQ ID NO: 250), VAGRSMRP (SEQ ID NO: 251), VVPEGRRS (SEQ ID NO: 252), QGRAITFI (SEQ ID NO: 253), VLSKQMSF (SEQ ID NO: 254), LKGRSYYY (SEQ ID NO: 255), KRMPVQFL (SEQ ID NO: 256), PQHRIVSF (SEQ ID NO: 257), YKKFVGSL (SEQ ID NO: 258), HMMQYARH (SEQ ID NO: 259), IPFSWSRF (SEQ ID NO: 260), LSQARWRK (SEQ ID NO: 261), DISHWRRS (SEQ ID NO: 262), RKTVQHWW (SEQ ID NO: 263), RFYRNQFF (SEQ ID NO: 264), RSLVFAPI (SEQ ID NO: 265), RSPSRLKC (SEQ ID NO: 266), and RKMPNITV (SEQ ID NO: 267).

In some embodiments, the CM comprises the amino acid sequence ILPRSPAF (SEQ ID NO: 250). In some embodiments, the CM comprises the amino acid sequence VAGRSMRP (SEQ ID NO: 251). In some embodiments, the CM comprises the amino acid sequence VVPEGRRS (SEQ ID NO: 252). In some embodiments, the CM comprises the amino acid sequence QGRAITFI (SEQ ID NO: 253). In some embodiments, the CM comprises the amino acid sequence VLSKQMSF (SEQ ID NO: 254). In some embodiments, the CM comprises the amino acid sequence LKGRSYYY (SEQ ID NO: 255). In some embodiments, the CM comprises the amino acid sequence KRMPVQFL (SEQ ID NO: 256). In some embodiments, the CM comprises the amino acid sequence PQHRIVSF (SEQ ID NO: 257). In some embodiments, the CM comprises the amino acid sequence YKKFVGSL (SEQ ID NO: 258). In some embodiments, the CM comprises the amino acid sequence HMMQYARH (SEQ ID NO: 259). In some embodiments, the CM comprises the amino acid sequence IPFSWSRF (SEQ ID NO: 260). In some embodiments, the CM comprises the amino acid sequence LSQARWRK (SEQ ID NO: 261). In some embodiments, the CM comprises the amino acid sequence DISHWRRS (SEQ ID NO: 262). In some embodiments, the CM comprises the amino acid sequence RKTVQHWW (SEQ ID NO: 263J. In some embodiments, the CM comprises the amino acid sequence RFYRNQFF (SEQ ID NO: 264). In some embodiments, the CM comprises the amino acid sequence RSLVFAPI (SEQ ID NO: 265). In some embodiments, the CM comprises the amino acid sequence RSPSRLKC (SEQ ID NO: 266). In some embodiments, the CM comprises the amino acid sequence RKMPNITV (SEQ ID NO: 267).

In some embodiments, the motif sequence includes a core CM consensus sequence shown in Tables 10A-10D. In some embodiments, the motif sequence includes a subgenus, i.e., a subset, of the core CM consensus sequence shown in Tables 10A-10D.

In some embodiments, the motif sequence includes an expanded consensus sequence based on one of the core CM consensus sequence shown in Tables 10A-10D. In some embodiments, the expanded consensus sequence is a consensus sequence shown in Tables 11A-11D.

In some embodiments, the CM comprises a core CM consensus 11 sequence comprising the amino acid sequence LSGRSANH (SEQ ID NO: 307) or LSGRSGNH (SEQ ID NO: 308). In some embodiments, the CM comprises an expanded core CM consensus 11 sequence comprising the amino acid sequence DRLSGRSANHKK (SEQ ID NO: 309), DRLSGRSDNHKK (SEQ ID NO: 310), or NTLSGRSGNHGS (SEQ ID NO: 311).

In some embodiments, the CM comprises the amino acid sequence LSGRSANH (SEQ ID NO: 307). In some embodiments, the CM comprises the amino acid sequence LSGRSGNH (SEQ ID NO: 308). In some embodiments, the CM comprises the amino acid sequence DRLSGRSANHKK (SEQ ID NO: 309). In some embodiments, the CM comprises the amino acid sequence DRLSGRSDNHKK (SEQ ID NO: 310). In some embodiments, the CM comprises the amino acid sequence NTLSGRSGNHGS (SEQ ID NO: 311).

In some embodiments, the CM comprises the amino acid sequence LSGRSANH (SEQ ID NO: 307). In some embodiments, the CM comprises the amino acid sequence LNGRSDNH (SEQ ID NO: 313). In some embodiments, the CM comprises the amino acid sequence LTGRSDRH (SEQ ID NO: 314). In some embodiments, the CM comprises a core CM consensus 12 sequence comprising the amino acid sequence LSGRSANH (SEQ ID NO: 307), LNGRSDNH (SEQ ID NO: 313), and LTGRSDRH (SEQ ID NO: 314). In some embodiments, the CM an expanded core CM consensus 12 sequence comprising an amino acid sequence selected from the group consisting of DRLSGRSANHKK (SEQ ID NO: 309), DRLSGRSDNHKK (SEQ ID NO: 310), GPLNGRSDNHKA (SEQ ID NO: 320), GPLNGRSDNHKK (SEQ ID NO: 321), GPLNGRSDNHKR (SEQ ID NO: 322), GPLNGRSDNHQA (SEQ ID NO: 323), GPLNGRSDNHQK (SEQ ID NO: 324), GPLNGRSDNHQR (SEQ ID NO: 325), GPLNGRSDNHRA (SEQ ID NO: 326), GPLNGRSDNHRK (SEQ ID NO: 327), GPLNGRSDNHRR (SEQ ID NO: 328), RPLNGRSDNHKA (SEQ ID NO: 329), RPLNGRSDNHKK (SEQ ID NO: 330), RPLNGRSDNHKR (SEQ ID NO: 331), RPLNGRSDNHQA (SEQ ID NO: 332), RPLNGRSDNHQK (SEQ ID NO: 333), RPLNGRSDNHQR (SEQ ID NO: 334), RPLNGRSDNHRA (SEQ ID NO: 335), RPLNGRSDNHRK (SEQ ID NO: 336), RPLNGRSDNHRR (SEQ ID NO: 337), GPLSGRSDNHKA (SEQ ID NO: 338), GPLSGRSDNHKK (SEQ ID NO: 339), GPLSGRSDNHKR (SEQ ID NO: 340), GPLSGRSDNHQA (SEQ ID NO: 341), GPLSGRSDNHQK (SEQ ID NO: 342), GPLSGRSDNHQR (SEQ ID NO: 343), GPLSGRSDNHRA (SEQ ID NO: 344), GPLSGRSDNHRK (SEQ ID NO: 345), GPLSGRSDNHRR (SEQ ID NO: 346), RPLSGRSDNHKA (SEQ ID NO: 347), RPLSGRSDNHKK (SEQ ID NO: 348), RPLSGRSDNHKR (SEQ ID NO: 349), RPLSGRSDNHQA (SEQ ID NO: 350), RPLSGRSDNHQK (SEQ ID NO: 351), RPLSGRSDNHQR (SEQ ID NO: 352), RPLSGRSDNHRA (SEQ ID NO: 353), RPLSGRSDNHRK (SEQ ID NO: 354), RPLSGRSDNHRR (SEQ ID NO: 355), and KGLTGRSDRHQA (SEQ ID NO: 356).

In some embodiments, the CM comprises the amino acid sequence DRLSGRSANHKK (SEQ ID NO: 309). In some embodiments, the CM comprises the amino acid sequence DRLSGRSDNHKK (SEQ ID NO: 310). In some embodiments, the CM comprises the amino acid sequence GPLNGRSDNHKA (SEQ ID NO: 320). In some embodiments, the CM comprises the amino acid sequence GPLNGRSDNHKK (SEQ ID NO: 321). In some embodiments, the CM comprises the amino acid sequence GPLNGRSDNHKR (SEQ ID NO: 322). In some embodiments, the CM comprises the amino acid sequence GPLNGRSDNHQA (SEQ ID NO: 323). In some embodiments, the CM comprises the amino acid sequence GPLNGRSDNHQK (SEQ ID NO: 324). In some embodiments, the CM comprises the amino acid sequence GPLNGRSDNHQR (SEQ ID NO: 325). In some embodiments, the CM comprises the amino acid sequence GPLNGRSDNHRA (SEQ ID NO: 326). In some embodiments, the CM comprises the amino acid sequence GPLNGRSDNHRK (SEQ ID NO: 327). In some embodiments, the CM comprises the amino acid sequence GPLNGRSDNHRR (SEQ ID NO: 328). In some embodiments, the CM comprises the amino acid sequence RPLNGRSDNHKA (SEQ ID NO: 329). In some embodiments, the CM comprises the amino acid sequence RPLNGRSDNHKK (SEQ ID NO: 330). In some embodiments, the CM comprises the amino acid sequence RPLNGRSDNHKR (SEQ ID NO: 331). In some embodiments, the CM comprises the amino acid sequence RPLNGRSDNHRA (SEQ ID NO: 332). In some embodiments, the CM comprises the amino acid sequence RPLNGRSDNHRK (SEQ ID NO: 333). In some embodiments, the CM comprises the amino acid sequence RPLNGRSDNHQR (SEQ ID NO: 334). In some embodiments, the CM comprises the amino acid sequence RPLNGRSDNHRA (SEQ ID NO: 335). In some embodiments, the CM comprises the amino acid sequence RPLNGRSDNHRK (SEQ ID NO: 336). In some embodiments, the CM comprises the amino acid sequence RPLNGRSDNHQR (SEQ ID NO: 337). In some embodiments, the CM comprises the amino acid sequence GPLSGRSDNHKA (SEQ ID NO: 338). In some embodiments, the CM comprises the amino acid sequence GPLSGRSDNHKK (SEQ ID NO: 339). In some embodiments, the CM comprises the amino acid sequence GPLSGRSDNHKR (SEQ ID NO: 340). In some embodiments, the CM comprises the amino acid sequence GPLSGRSDNHKA (SEQ ID NO: 341). In some embodiments, the CM comprises the amino acid sequence GPLSGRSDNHKK (SEQ ID NO: 342). In some embodiments, the CM comprises the amino acid sequence GPLSGRSDNHQR (SEQ ID NO: 343). In some embodiments, the CM comprises the amino acid sequence GPLSGRSDNHKA (SEQ ID NO: 344). In some embodiments, the CM comprises the amino acid sequence GPLSGRSDNHKK (SEQ ID NO: 345). In some embodiments, the CM comprises the amino acid sequence GPLSGRSDNHKR (SEQ ID NO: 346). In some embodiments, the CM comprises the amino acid sequence RPLSGRSDNHKA (SEQ ID NO: 347). In some embodiments, the CM comprises the amino acid sequence RPLSGRSDNHKK (SEQ ID NO: 348). In some embodiments, the CM comprises the amino acid sequence RPLSGRSDNHKR (SEQ ID NO: 349). In some embodiments, the CM comprises the amino acid sequence RPLSGRSDNHKA (SEQ ID NO: 350). In some embodiments, the CM comprises the amino acid sequence RPLSGRSDNHKK (SEQ ID NO: 351). In some embodiments, the CM comprises the amino acid sequence RPLSGRSDNHQR (SEQ ID NO: 352). In some embodiments, the CM comprises the amino acid sequence RPLSGRSDNHKA (SEQ ID NO: 353). In some embodiments, the CM comprises the amino acid sequence RPLSGRSDNHKK (SEQ ID NO: 354). In some embodiments, the CM comprises the amino acid sequence RPLSGRSDNHKR (SEQ ID NO: 355). In some embodiments, the CM comprises the amino acid sequence KGLTGRSDRHQA (SEQ ID NO: 356).

In some embodiments, the CM comprises a core CM consensus 13 sequence comprising the amino acid sequence RIGRSDNH (SEQ ID NO: 357) or RLGRSDNN (SEQ ID NO: 358). In some embodiments, the CM comprises an expanded core CM consensus 13 sequence comprising the amino acid sequence NHRIGRSDNHRR (SEQ ID NO: 359) or TLRLGRSDNNKN (SEQ ID NO: 360).

In some embodiments, the CM comprises the amino acid sequence RIGRSDNH (SEQ ID NO: 357). In some embodiments, the CM comprises the amino acid sequence RLGRSDNN (SEQ ID NO: 358). In some embodiments, the CM comprises the amino acid sequence NHRIGRSDNHRR (SEQ ID NO: 359). In some embodiments, the CM comprises the amino acid sequence TLRLGRSDNNKN (SEQ ID NO: 360).

In some embodiments, the CM comprises a core CM consensus 14 sequence comprising an amino acid sequence selected from the group consisting of TSGRSANP (SEQ ID NO: 361), TSGRSGNP (SEQ ID NO: 362), LSGRSANP (SEQ ID NO: 363), and LSGRSGNP (SEQ ID NO: 364). In some embodiments, the CM comprises an expanded core CM consensus 14 sequence comprising an amino acid sequence selected from the group consisting of TSTSGRSANPRG (SEQ ID NO: 365), TSTSGRSGNPRG (SEQ ID NO: 366), TSLSGRSANPRG (SEQ ID NO: 367), and TSLSGRSGNPRG (SEQ ID NO: 368).

In some embodiments, the CM comprises the amino acid sequence TSGRSANP (SEQ ID NO: 361). In some embodiments, the CM comprises the amino acid sequence TSGRSGNP (SEQ ID NO: 362). In some embodiments, the CM comprises the amino acid sequence LSGRSANP (SEQ ID NO: 363). In some embodiments, the CM comprises the amino acid sequence LSGRSGNP (SEQ ID NO: 364). In some embodiments. In some embodiments, the CM comprises the amino acid sequence the CM comprises the amino acid sequence TSTSGRSANPRG (SEQ ID NO: 365). In some embodiments, the CM comprises the amino acid sequence TSTSGRSGNPRG (SEQ ID NO: 366). In some embodiments, the CM comprises the amino acid sequence TSLSGRSANPRG (SEQ ID NO: 367). In some embodiments, the CM comprises the amino acid sequence and TSLSGRSGNPRG (SEQ ID NO: 368).

In some embodiments, the CM comprises an amino acid sequence selected from the group consisting of LSGRSENH (SEQ ID NO: 369), SIARSDNL (SEQ ID NO: 370), LSGRSVTQ (SEQ ID NO: 371), LSGRSGNH (SEQ ID NO: 308), LTGRSDRH (SEQ ID NO: 314), LYGRSENN (SEQ ID NO: 374), RLGRSDNN (SEQ ID NO: 375), TSGRSANP (SEQ ID NO: 376), NTLSGRSENHSG (SEQ ID NO: 377), PPSIARSDNLAN (SEQ ID NO: 378), TGLSGRSVTQTS (SEQ ID NO: 379), NTLSGRSGNHGS (SEQ ID NO: 311), KGLTGRSDRHQA (SEQ ID NO: 381), KNLYGRSENNGN (SEQ ID NO: 382), TLRLGRSDNNKN (SEQ ID NO: 383), and TSTSGRSANPRG (SEQ ID NO: 384).

In some embodiments, the CM comprises the amino acid sequence LSGRSENH (SEQ ID NO: 369). In some embodiments, the CM comprises the amino acid sequence SIARSDNL (SEQ ID NO: 370). In some embodiments, the CM comprises the amino acid sequence LSGRSVTQ (SEQ ID NO: 371). In some embodiments, the CM comprises the amino acid sequence LSGRSGNH (SEQ ID NO: 308). In some embodiments, the CM comprises the amino acid sequence LTGRSDRH (SEQ ID NO: 314). In some embodiments, the CM comprises the amino acid sequence LYGRSENN (SEQ ID NO: 374). In some embodiments, the CM comprises the amino acid sequence RLGRSDNN (SEQ ID NO: 375). In some embodiments, the CM comprises the amino acid sequence TSGRSANP (SEQ ID NO: 376). In some embodiments, the CM comprises the amino acid sequence NTLSGRSENHSG (SEQ ID NO: 377). In some embodiments, the CM comprises the amino acid sequence PPSIARSDNLAN (SEQ ID NO: 378). In some embodiments, the CM comprises the amino acid sequence TGLSGRSVTQTS (SEQ ID NO: 379). In some embodiments, the CM comprises the amino acid sequence NTLSGRSGNHGS (SEQ ID NO: 311). In some embodiments, the CM comprises the amino acid sequence KGLTGRSDRHQA (SEQ ID NO: 381). In some embodiments, the CM comprises the amino acid sequence KNLYGRSENNGN (SEQ ID NO: 382). In some embodiments, the CM comprises the amino acid sequence TLRLGRSDNNKN (SEQ ID NO: 383). In some embodiments, the CM comprises the amino acid sequence TSTSGRSANPRG (SEQ ID NO: 384).

In some embodiments, the CM is a substrate for at least two proteases. In some embodiments, at least one protease is selected from matriptase and uPA, and at least one protease is selected from the group consisting of those shown in Table 7.

In some embodiments, the activatable antibody includes at least a first CM and a second CM. In some embodiments, the first CM and the second CM are each polypeptides of no more than 15 amino acids long. In some embodiments, the first CM and the second CM in the activatable antibody have the structural arrangement from N-terminus to C-terminus as follows in the uncleaved state: MM-CM1-CM2-AB, AB-CM2-CM1-MM, MM-CM2-CM1-AB, or AB-CM1-CM2-MM. In some embodiments, the activatable antibody includes a linking peptide between MM and CM1. In some embodiments, the activatable antibody includes a linking peptide between CM1 and CM2. In some embodiments, the activatable antibody includes a linking peptide between CM2 and AB. In some embodiments, the activatable antibody includes a linking peptide between MM and CM1 and a linking peptide between CM2 and AB. In some embodiments, the activatable antibody includes a linking peptide between MM and CM1 and a linking peptide between CM1 and CM2. In some embodiments, the activatable antibody includes a linking peptide between CM1 and CM2 and a linking peptide between CM2 and AB. In some embodiments, the activatable antibody includes a linking peptide between MM and CM1, a linking peptide between CM1 and CM2, and a linking peptide between CM2 and AB.

In some embodiments, the CM2 is selected for use with a specific protease. In some embodiments, the CM2 is a substrate for at least one protease selected from the group consisting of a matrix metalloprotease (MMP), a neutrophil elastase, uPA, legumain, matriptase, thrombin, a cysteine protease such as a cathepsin, ADAM17, BMP-1, HtrA1, and a TMPRSS such as TMPRSS3 or TMPRSS4.

In some embodiments, the CM2 is a substrate for a neutrophil elastase. In some embodiments, the CM2 is a substrate for uPA. In some embodiments, the CM2 is a substrate for legumain. In some embodiments, the CM2 is a substrate for matriptase. In some embodiments, the CM2 is a substrate for thrombin. In some embodiments, the CM2 is a substrate for a cysteine protease. In some embodiments, the CM2 is a substrate for a cathepsin. In some embodiments, the CM2 is a substrate for ADAM17. In some embodiments, the CM2 is a substrate for BMP-1. In some embodiments, the CM2 is a substrate for HtrA1. In some embodiments, the CM2 is a substrate for a TMPRSS. In some embodiments, the CM2 is a substrate for TMPRSS3. In some embodiments, the CM2 is a substrate for TMPRSS4.

For example, suitable CM2 are cleaved by at least one protease and include the sequence TGRGPSWV (SEQ ID NO: 402); SARGPSRW (SEQ ID NO: 403); TARGPSFK (SEQ ID NO: 404); TARGPSW (SEQ ID NO: 405); LSGRSDNH (SEQ ID NO: 406); GGWHTGRN (SEQ ID NO: 407); HTGRSGAL (SEQ ID NO: 408); PLTGRSGG (SEQ ID NO: 409); AARGPAIH (SEQ ID NO: 411); RGPAFNPM (SEQ ID NO: 412); SSRGPAYL (SEQ ID NO: 413); RGPATPIM (SEQ ID NO: 414); RGPA (SEQ ID NO: 415); GGQPSGMWGW (SEQ ID NO: 416); FPRPLGITGL (SEQ ID NO: 417); VHMPLGFLGP (SEQ ID NO: 418); SPLTGRSG (SEQ ID NO: 419); SAGFSLPA (SEQ ID NO: 126); LAPLGLQRR (SEQ ID NO: 420); SGGPLGVR (SEQ ID NO: 421); PLGL (SEQ ID NO: 422); GPRSFGL (SEQ ID NO: 423) and/or GPRSFG (SEQ ID NO: 424).

In some embodiments, the CM2 comprises the amino acid sequence TGRGPSWV (SEQ ID NO: 402). In some embodiments, the CM2 comprises the amino acid sequence SARGPSRW (SEQ ID NO: 403). In some embodiments, the CM2 comprises the amino acid sequence TARGPSFK (SEQ ID NO: 404). In some embodiments, the CM2 comprises the amino acid sequence TARGPSW (SEQ ID NO: 405). In some embodiments, the CM2 comprises the amino acid sequence LSGRSDNH (SEQ ID NO: 406). In some embodiments, the CM2 comprises the amino acid sequence GGWHTGRN (SEQ ID NO: 407). In some embodiments, the CM2 comprises the amino acid sequence HTGRSGAL (SEQ ID NO: 408). In some embodiments, the CM2 comprises the amino acid sequence PLTGRSGG (SEQ ID NO: 409). In some embodiments, the CM2 comprises the amino acid sequence AARGPAIH (SEQ ID NO: 411). In some embodiments, the CM2 comprises the amino acid sequence RGPAFNPM (SEQ ID NO: 412). In some embodiments, the CM2 comprises the amino acid sequence SSRGPAYL (SEQ ID NO: 413). In some embodiments, the CM2 comprises the amino acid sequence RGPATPIM (SEQ ID NO: 414). In some embodiments, the CM2 comprises the amino acid sequence RGPA (SEQ ID NO: 415). In some embodiments, the CM2 comprises the amino acid sequence GGQPSGMWGW (SEQ ID NO: 416). In some embodiments, the CM2 comprises the amino acid sequence FPRPLGITGL (SEQ ID NO: 417). In some embodiments, the CM2 comprises the amino acid sequence VHMPLGFLGP (SEQ ID NO: 418). In some embodiments, the CM2 comprises the amino acid sequence SPLTGRSG (SEQ ID NO: 419). In some embodiments, the CM2 comprises the amino acid sequence LAPLGLQRR (SEQ ID NO: 420). In some embodiments, the CM2 comprises the amino acid sequence SGGPLGVR (SEQ ID NO: 421). In some embodiments, the CM2 comprises the amino acid sequence PLGL (SEQ ID NO: 422). In some embodiments, the CM2 comprises the amino acid sequence GPRSFGL (SEQ ID NO: 423). In some embodiments, the CM2 comprises the amino acid sequence GPRSFG (SEQ ID NO: 424).

In some embodiments, the CM2 is a substrate for at least one MMP. In some embodiments, the CM2 is a substrate for at least one MMP listed in the Table 7. In some embodiments, the CM2 is a substrate for MMP9. In some embodiments, the CM2 is a substrate for MMP14. In some embodiments, the CM2 is a substrate for two or more MMPs. In some embodiments, the CM2 is a substrate for at least MMP9 or MMP14. In some embodiments, the CM2 is a substrate for two or more MMPs. In some embodiments, the CM2 is a substrate for at least MMP9 and MMP14.

In some embodiments, CM2 is a substrate for an MMP and includes the sequence ISSGLLSS (SEQ ID NO: 425); QNQALRMA (SEQ ID NO: 426); AQNLLGMV (SEQ ID NO: 427); STFPFGMF (SEQ ID NO: 428); PVGYTSSL (SEQ ID NO: 429); DWLYWPGI (SEQ ID NO: 430); MIAPVAYR (SEQ ID NO: 431); RPSPMWAY (SEQ ID NO: 432); WATPRPMR (SEQ ID NO: 433); FRLLDWQW (SEQ ID NO: 434); LKAAPRWA (SEQ ID NO: 435); GPSHLVLT (SEQ ID NO: 436); LPGGLSPW (SEQ ID NO: 437); MGLFSEAG (SEQ ID NO: 438); SPLPLRVP (SEQ ID NO: 439); RMHLRSLG (SEQ ID NO: 440); LAAPLGLL (SEQ ID NO: 441); AVGLLAPP (SEQ ID NO: 442); LLAPSHRA (SEQ ID NO: 443), PAGLWLDP (SEQ ID NO: 444); and/or ISSGLSS (SEQ ID NO: 445).

In some embodiments, the first cleaving agent and the second cleaving agent are the protease selected from matriptase and uPA, and the first CM and the second CM are different substrates for the enzyme. In some embodiments, the first cleaving agent and the second cleaving agent are different proteases, where at least one protease is selected from matriptase and uPA. In some embodiments, the first cleaving agent and the second cleaving agent are co-localized in the target tissue. In some embodiments, the first CM and the second CM are cleaved by at least one cleaving agent selected from matriptase and uPA in the target tissue.

In some embodiments, the activatable antibody is exposed to and cleaved by a protease selected from matriptase and uPA such that, in the activated or cleaved state, the activated antibody includes a light chain amino acid sequence that includes at least a portion of LP2 and/or CM sequence after the protease has cleaved the CM.

In some embodiments, the CM comprises the non-prime side of the protease cleavage site; that is, the CM comprises at least the P1 and P2 amino acids, and in some embodiments comprises the P1, P2 and P3 amino acids and in some embodiments comprises the P1, P2, P3, and P4 amino acids. In some embodiments, the CM comprises the non-prime side and the prime side of the protease cleavage site. In some embodiments, the CM comprises the non-prime side but lacks at least part of the prime side of the protease cleavage site. In some embodiments, the CM comprises the non-prime side but lacks the prime side of the protease cleavage site. Such a CM can be linked directly or through a linker to an antibody or other molecule as disclosed herein, such as, but not limited to, a detection moiety.

In some embodiments, the activatable antibody also includes an agent conjugated to the AB. In some embodiments, the agent is a therapeutic agent. In some embodiments, the agent is an antineoplastic agent. In some embodiments, the agent is a toxin or a fragment thereof. In some embodiments, the agent is conjugated to the AB via a linker. In some embodiments, the linker is a cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is conjugated to the AB via a linker that includes at least one MMP-cleavable substrate sequence. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the agent is an anti-inflammatory agent.

In some embodiments, the activatable antibody also includes a detectable moiety. In some embodiments, the detectable moiety is a diagnostic agent.

In some embodiments, the conjugated antibody includes a detectable label. In some embodiments, the detectable label includes an imaging agent, a contrasting agent, an enzyme, a fluorescent label, a chromophore, a dye, one or more metal ions, or a ligand-based label. In some embodiments, the imaging agent comprises a radioisotope. In some embodiments, the radioisotope is indium or technetium. In some embodiments, the contrasting agent comprises iodine, gadolinium or iron oxide. In some embodiments, the enzyme comprises horseradish peroxidase, alkaline phosphatase, or β-galactosidase. In some embodiments, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments, the luminescent label comprises an N-methylacrydium derivative. In some embodiments, the label comprises an Alexa Fluor® label, such as Alex Fluor® 680 or Alexa Fluor® 750. In some embodiments, the ligand-based label comprises biotin, avidin, streptavidin or one or more haptens.

In some embodiments, the activatable antibody also includes a signal peptide. In some embodiments, the signal peptide is conjugated to the activatable antibody via a spacer. In some embodiments, the spacer is conjugated to the activatable antibody in the absence of a signal peptide. In some embodiments, the spacer is joined directly to the MM of the activatable antibody. In some embodiments, the spacer is joined directly to the MM of the activatable antibody in the structural arrangement from N-terminus to C-terminus of spacer-MM-CM-AB. An example of a spacer joined directly to the N-terminus of MM of the activatable antibody is QGQSGQ (SEQ ID NO: 446). In some embodiments, the spacer includes at least the amino acid sequence QGQSGQ (SEQ ID NO: 446).

In some embodiments, the AB of the activatable antibody naturally contains one or more disulfide bonds. In some embodiments, the AB can be engineered to include one or more disulfide bonds.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

In some embodiments, the activatable antibody and/or conjugated activatable antibody is monospecific. In some embodiments, the activatable antibody and/or conjugated activatable antibody is multispecific, e.g., by way of non-limiting example, bispecific or trifunctional. In some embodiments, the activatable antibody and/or conjugated activatable antibody is formulated as part of a pro-Bispecific T Cell Engager (BITE) molecule. In some embodiments, the activatable antibody and/or conjugated activatable antibody is formulated as part of a pro-Chimeric Antigen Receptor (CAR) modified T cell or other engineered receptor.

The disclosure also provides compositions and methods that include an activatable antibody that includes an antibody or antibody fragment (AB) that specifically binds a given target, where the AB is coupled to a masking moiety (MM) that decreases the ability of the AB to bind its target. In some embodiments, the activatable antibody further includes a cleavable moiety (CM) that is a substrate for at least one protease selected from matriptase and uPA. The compositions and methods provided herein enable the attachment of one or more agents to one or more cysteine residues in the AB without compromising the activity (e.g., the masking, activating or binding activity) of the activatable antibody. In some embodiments, the compositions and methods provided herein enable the attachment of one or more agents to one or more cysteine residues in the AB without reducing or otherwise disturbing one or more disulfide bonds within the MM. The compositions and methods provided herein produce an activatable antibody that is conjugated to one or more agents, e.g., any of a variety of therapeutic, diagnostic and/or prophylactic agents, for example, in some embodiments, without any of the agent(s) being conjugated to the MM of the activatable antibody. The compositions and methods provided herein produce conjugated activatable antibodies in which the MM retains the ability to effectively and efficiently mask the AB of the activatable antibody in an uncleaved state. The compositions and methods provided herein produce conjugated activatable antibodies in which the activatable antibody is still activated, i.e., cleaved, in the presence of a protease, i.e., matriptase and/or uPA, that can cleave the CM.

The activatable antibodies have at least one point of conjugation for an agent, but in the methods and compositions provided herein less than all possible points of conjugation are available for conjugation to an agent. In some embodiments, the one or more points of conjugation are sulfur atoms involved in disulfide bonds. In some embodiments, the one or more points of conjugation are sulfur atoms involved in interchain disulfide bonds. In some embodiments, the one or more points of conjugation are sulfur atoms involved in interchain sulfide bonds, but not sulfur atoms involved in intrachain disulfide bonds. In some embodiments, the one or more points of conjugation are sulfur atoms of cysteine or other amino acid residues containing a sulfur atom. Such residues may occur naturally in the antibody structure or may be incorporated into the antibody by site-directed mutagenesis, chemical conversion, or mis-incorporation of non-natural amino acids.

Also provided are methods of preparing a conjugate of an activatable antibody having one or more interchain disulfide bonds in the AB and one or more intrachain disulfide bonds in the MM, and a drug reactive with free thiols is provided. The method generally includes partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where an activatable antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In some embodiments, a method of reducing and conjugating an agent, e.g., a drug, to an activatable antibody resulting in selectivity in the placement of the agent is provided. The method generally includes partially reducing the activatable antibody with a reducing agent such that any conjugation sites in the masking moiety or other non-AB portion of the activatable antibody are not reduced, and conjugating the agent to interchain thiols in the AB. The conjugation site(s) are selected so as to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the MM retains the ability to effectively and efficiently mask the AB of the activatable antibody in an uncleaved state. The ratio of reduction agent to activatable antibody will vary depending on the activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

In some embodiments, a method of reducing interchain disulfide bonds in the AB of an activatable antibody and conjugating an agent, e.g., a thiol-containing agent such as a drug, to the resulting interchain thiols to selectively locate agent(s) on the AB is provided. The method generally includes partially reducing the AB with a reducing agent to form at least two interchain thiols without forming all possible interchain thiols in the activatable antibody; and conjugating the agent to the interchain thiols of the partially reduced AB. For example, the AB of the activatable antibody is partially reduced for about 1 hour at about 37° C. at a desired ratio of reducing agent:activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration. In some embodiments, the reduced antibody is not purified after partial reduction and prior to conjugation.

The disclosure also provides partially reduced activatable antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to the target, a masking moiety (MM) that inhibits the binding of the AB of the activatable antibody in an uncleaved state to the target, and a cleavable moiety (CM) coupled to the AB, wherein the CM is a polypeptide that functions as a substrate for at least one protease selected from matriptase and uPA. In some embodiments, the MM is coupled to the AB via the CM. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM-AB or AB-CM-MM. In some embodiments, reducing agent is TCEP.

The disclosure also provides conjugated activatable antibodies that include an activatable antibody linked to monomethyl auristatin D (MMAD) payload, wherein the activatable antibody includes an antibody or an antigen binding fragment thereof (AB) that specifically binds to a target, a masking moiety (MM) that inhibits the binding of the AB of the activatable antibody in an uncleaved state to the target, and cleavable moiety (CM) coupled to the AB, and the CM is a polypeptide that functions as a substrate for at least one MMP protease.

In some embodiments, the MMAD-conjugated activatable antibody can be conjugated using any of several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB.

In some embodiments, the MMAD payload is conjugated to the AB via a linker. In some embodiments, the MMAD payload is conjugated to a cysteine in the AB via a linker. In some embodiments, the MMAD payload is conjugated to a lysine in the AB via a linker. In some embodiments, the MMAD payload is conjugated to another residue of the AB via a linker, such as those residues disclosed herein. In some embodiments, the linker is a thiol-containing linker. In some embodiments, the linker is a cleavable linker. In some embodiments, the linker is a non-cleavable linker. In some embodiments, the linker is selected from the group consisting of the linkers shown in Tables 5 and 6. In some embodiments, the activatable antibody and the MMAD payload are linked via a maleimide caproyl-valine-citrulline linker. In some embodiments, the activatable antibody and the MMAD payload are linked via a maleimide PEG-valine-citrulline linker. In some embodiments, the activatable antibody and the MMAD payload are linked via a maleimide caproyl-valine-citrulline-para-aminobenzyloxycarbonyl linker. In some embodiments, the activatable antibody and the MMAD payload are linked via a maleimide PEG-valine-citrulline-para-aminobenzyloxycarbonyl linker. In some embodiments, the MMAD payload is conjugated to the AB using the partial reduction and conjugation technology disclosed herein.

The disclosure also provides polypeptides and other larger molecules that include one or more of the matriptase-cleavable substrate sequences presented herein and/or uPA-cleavable substrate sequences presented herein. By way of non-limiting example, matriptase-cleavable substrate sequences presented herein and/or uPA-cleavable substrate sequences presented herein are useful in prodrug compositions and methods of use thereof. These matriptase-cleavable substrate sequences presented herein and/or uPA-cleavable substrate sequences presented herein are also useful in probes and other detection agents and methods of use thereof. For example, the matriptase-cleavable substrate sequences presented herein and/or uPA-cleavable substrate sequences presented herein can be used in conjunction with fluors and other quenchers to produce detection agents, such as imaging agents and/or other diagnostic agents. Those of ordinary skill in the art will appreciate that the matriptase-cleavable substrate sequences presented herein and/or uPA-cleavable substrate sequences presented herein are useful in any composition and/or method in the art that would use a substrate that is cleavable by matriptase and/or uPA.

In some embodiments, the matriptase and/or uPA substrates of the disclosure are used in larger molecules, for example, isolated polypeptides that include at least one additional moiety (M) selected from the group consisting of (i) at least one moiety that is located amino (N) terminally to the CM ($M_N$), i.e., at a location within the larger molecule that is situated closer to the N-terminus of the larger molecule than the CM; (ii) at least one moiety that is located carboxyl (C) terminally to the CM ($M_C$), i.e., at a location within the larger molecule that is situated closer to the C-terminus of the larger molecule than the CM; and (iii) combinations thereof. In some embodiments, the larger molecule includes at least one $M_N$ and at least one $M_C$.

By way of non-limiting examples, suitable $M_N$ for use in the larger molecules of the disclosure include at least one of the following: a masking moiety, an antibody, a protein, a therapeutic agent, an antineoplastic agent, a toxic agent, a drug, a detectable moiety, a diagnostic agent, an affinity tag, and combinations thereof.

By way of non-limiting examples, suitable $M_C$ for use in the larger molecules of the disclosure include at least one of the following: a masking moiety, an antibody, a protein, a therapeutic agent, an antineoplastic agent, a toxic agent, a drug, a detectable moiety, a diagnostic agent, an affinity tag, and combinations thereof.

The disclosure also provides an isolated nucleic acid molecule encoding a CM-containing molecule of the disclosure, e.g., a CM-containing polypeptide such as, e.g., a CM-containing probe, an antibody and/or an activatable antibody described herein, as well as vectors that include these isolated nucleic acid sequences. The disclosure provides methods of producing CM-containing polypeptide by culturing a cell under conditions that lead to expression of the CM-containing polypeptide, wherein the cell comprises such a vector. The disclosure provides methods of producing an antibody and/or activatable antibody by culturing a cell under conditions that lead to expression of the antibody and/or activatable antibody, wherein the cell comprises such a vector.

The disclosure provides a method of manufacturing a CM-containing polypeptide of the disclosure that binds a given target by (a) culturing a cell comprising a nucleic acid construct that encodes the CM-containing polypeptide under conditions that lead to expression of the polypeptide, (i) wherein the polypeptide includes a cleavable moiety (CM), and (ii) wherein the CM is a polypeptide that functions as a substrate for at least one protease selected from matriptase and uPA; and (b) recovering the polypeptide. These methods can also include the further step of (c) conjugating the recovered polypeptide to one or more additional agents.

The disclosure provides a method of manufacturing a conjugated antibody of the disclosure that binds a given target by (a) culturing a cell comprising a nucleic acid construct that encodes the antibody under conditions that lead to expression of the antibody, (i) wherein the antibody includes a cleavable moiety (CM), and (ii) wherein the CM is a polypeptide that functions as a substrate for at least one protease selected from matriptase and uPA; (b) recovering the antibody; and (c) conjugating the recovered antibody to one or more additional agents.

The disclosure also provides a method of manufacturing the activatable antibodies of the disclosure that bind in an activated state a given target by (a) culturing a cell comprising a nucleic acid construct that encodes the activatable antibody under conditions that lead to expression of the activatable antibody, wherein the activatable antibody comprises a masking moiety (MM), a cleavable moiety (CM), and an antibody or an antigen binding fragment thereof (AB) that specifically binds the target, (i) wherein the CM is a polypeptide that functions as a substrate for a protease selected from matriptase and uPA; and (ii) wherein the CM is positioned in the activatable antibody such that, in an uncleaved state, the MM interferes with specific binding of the AB to the target and in a cleaved state the MM does not interfere or compete with specific binding of the AB to the target; and (b) recovering the activatable antibody.

The disclosure also provides methods of producing non-polypeptide CM-containing molecules, including by way of non-limiting examples, prodrugs, non-peptide probes, etc. These non-polypeptide CM-containing molecules can be made using any of a variety of art-recognized techniques, including standard chemical synthesis and/or conjugation methods.

The disclosure provides methods of preventing, delaying the progression of, treating, alleviating a symptom of, or otherwise ameliorating a target-related disease in a subject by administering a therapeutically effective amount of a conjugated antibody, an activatable antibody and/or a conjugated activatable antibody described herein to a subject in need thereof.

The disclosure provides methods of preventing, delaying the progression of, treating, alleviating a symptom of, or otherwise ameliorating inflammation and/or an inflammatory disorder in a subject by administering a therapeutically effective amount of a conjugated antibody, an activatable antibody and/or a conjugated activatable antibody described herein to a subject in need thereof. The disclosure also provides methods of preventing, delaying the progression of, treating, alleviating a symptom of, or otherwise ameliorating cancer in a subject by administering a therapeutically effective amount of a conjugated antibody, an activatable antibody and/or a conjugated activatable antibody described herein to a subject in need thereof. The disclosure also provides methods of preventing, delaying the progression of, treating, alleviating a symptom of, or otherwise ameliorating an autoimmune disease in a subject by administering a therapeutically effective amount a conjugated antibody, an activatable antibody and/or a conjugated activatable antibody described herein to a subject in need thereof.

A conjugated antibody, an activatable antibody and/or a conjugated activatable antibody used in any of the embodiments of these methods and uses can be administered at any stage of the disease. For example, such a conjugated antibody, activatable antibody and/or conjugated activatable antibody can be administered to a patient suffering cancer of any stage, from early to metastatic. The terms subject and patient are used interchangeably herein.

In some embodiments, the subject is a mammal, such as a human, non-human primate, companion animal (e.g., cat, dog, horse), farm animal, work animal, or zoo animal. In some embodiments, the subject is a human. In some embodiments, the subject is a companion animal. In some embodiments, the subject is an animal in the care of a veterinarian.

The conjugated antibody, activatable antibody and/or conjugated activatable antibody and therapeutic formulations thereof are administered to a subject suffering from or susceptible to a disease or disorder associated with aberrant target expression and/or activity. A subject suffering from or susceptible to a disease or disorder associated with aberrant target expression and/or activity is identified using any of a variety of methods known in the art. For example, subjects suffering from cancer or other neoplastic condition are identified using any of a variety of clinical and/or laboratory tests such as, physical examination and blood, urine and/or stool analysis to evaluate health status. For example, subjects suffering from inflammation and/or an inflammatory disorder are identified using any of a variety of clinical and/or laboratory tests such as physical examination and/or bodily fluid analysis, e.g., blood, urine and/or stool analysis, to evaluate health status.

Administration of a conjugated antibody, an activatable antibody and/or a conjugated activatable antibody to a patient suffering from a disease or disorder associated with aberrant target expression and/or activity is considered successful if any of a variety of laboratory or clinical objectives is achieved. For example, administration of a conjugated antibody, an activatable antibody and/or a conjugated activatable antibody to a patient suffering from a disease or disorder associated with aberrant target expression and/or activity is considered successful if one or more of the symptoms associated with the disease or disorder is alleviated, reduced, inhibited or does not progress to a further, i.e., worse, state. Administration of a conjugated antibody, an activatable antibody and/or a conjugated activatable antibody to a patient suffering from a disease or disorder associated with aberrant target expression and/or activity is considered successful if the disease or disorder enters remission or does not progress to a further, i.e., worse, state.

In some embodiments, the conjugated antibody, activatable antibody and/or conjugated activatable antibody is administered during and/or after treatment in combination with one or more additional agents such as, for example, an anti-inflammatory agent, an immunosuppressive agent, and/or a chemotherapeutic agent. In some embodiments, the conjugated antibody, activatable antibody and/or conjugated activatable antibody and the additional agent(s) are administered simultaneously. For example, the conjugated antibody, activatable antibody and/or conjugated activatable antibody and the additional agent(s) can be formulated in a single composition or administered as two or more separate compositions. In some embodiments, the conjugated antibody, activatable antibody and/or conjugated activatable antibody and the additional agent(s) are administered sequentially, or the antibody and/or conjugated antibodies and the additional agent are administered at different times during a treatment regimen. For example, the antibody and/or conjugated antibodies is administered prior to the administration of the additional agent, the antibody and/or conjugated antibodies is administered subsequent to the administration of the additional agent, or the antibody and/or conjugated antibodies and the additional agent are administered in an alternating fashion. As described herein, the antibody and/or conjugated antibodies and additional agent are administered in single doses or in multiple doses.

In some embodiments, the conjugated antibody, activatable antibody and/or conjugated activatable antibody is administered during and/or after treatment in combination with one or more additional agents such as, by way of non-limiting example, an anti-inflammatory agent, an immunosuppressive agent, a chemotherapeutic agent, such as an alkylating agent, an anti-metabolite, an anti-microtubule agent, a topoisomerase inhibitor, a cytotoxic antibiotic, and/or any other nucleic acid damaging agent. In some embodiments, the additional agent is a taxane, such as paclitaxel (e.g., Abraxane®). In some embodiments, the additional agent is an anti-metabolite, such as gemcitabine. In some embodiments, the additional agent is an alkylating agent, such as platinum-based chemotherapy, such as carboplatin or cisplatin. In some embodiments, the additional agent is a targeted agent, such as a kinase inhibitor, e.g., sorafenib or erlotinib. In some embodiments, the additional agent is a targeted agent, such as another antibody, e.g., a monoclonal antibody (e.g., bevacizumab), a bispecific antibody, or a multispecific antibody. In some embodiments, the additional agent is a proteosome inhibitor, such as bortezomib or carfilzomib. In some embodiments, the additional agent is an immune modulating agent, such as lenolidominde or IL-2. In some embodiments, the additional agent is radiation. In some embodiments, the additional agent is an agent considered standard of care by those skilled in the art. In some embodiments, the additional agent is a chemotherapeutic agent well known to those skilled in the art.

In some embodiments, the additional agent is an antibody, another conjugated antibody, another activatable antibody and/or another conjugated activatable antibody. In some embodiments the additional agent is an antibody, another conjugated antibody, another activatable antibody and/or another conjugated activatable antibody against the same target as the first conjugated antibody, activatable antibody and/or a conjugated activatable antibody. In some embodiments the additional agent is an antibody, another conjugated antibody, another activatable antibody and/or another conjugated activatable antibody against a target different than the target of the first conjugated antibody, activatable antibody and/or a conjugated activatable antibody.

In some embodiments, the conjugated antibody, activatable antibody and/or conjugated activatable antibody and the additional agent(s) are administered simultaneously. For example, the conjugated antibody, activatable antibody and/or conjugated activatable antibody and the additional agent(s) can be formulated in a single composition or administered as two or more separate compositions. In some embodiments, the conjugated antibody, activatable antibody and/or conjugated activatable antibody and the additional agent(s) are administered sequentially, or the antibody and/or conjugated antibodies and the additional agent are administered at different times during a treatment regimen. For example, the antibody and/or conjugated antibodies is administered prior to the administration of the additional agent, the antibody and/or conjugated antibodies is administered subsequent to the administration of the additional agent, or the antibody and/or conjugated antibodies and the additional agent are administered in an alternating fashion. As described herein, the antibody and/or conjugated antibodies and additional agent are in single doses or in multiple doses.

In some embodiments, the CM is linked or otherwise attached to an activatable antibody that includes an antibody or antigen-binding fragment thereof that specifically binds a given target coupled to a masking moiety (MM), such that coupling of the MM to the AB reduces the ability of the antibody or antigen-binding fragment thereof to bind the target. In some embodiments, the MM is coupled via the CM. Exemplary targets include, but are not limited to the targets shown in Table 1. Exemplary ABs include, but are not limited to, the targets shown in Table 2. The activatable antibodies provided herein are stable in circulation, activated at intended sites of therapy and/or diagnosis but not in normal, e.g., healthy tissue or other tissue not targeted for treatment and/or diagnosis, and, when activated, exhibit binding to the target that is at least comparable to the corresponding, unmodified antibody.

The disclosure also provides methods and kits for using the conjugated antibodies, activatable antibodies and/or conjugated activatable antibodies in a variety of diagnostic and/or prophylactic indications.

In some embodiments, the disclosure provides methods and kits for detecting presence or absence of a cleaving agent and a target of interest in a subject or a sample by (i) contacting a subject or sample with an activatable antibody, wherein the activatable antibody comprises a masking moiety (MM), a cleavable moiety (CM) that is cleaved by the cleaving agent, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent and the target are present in the subject or sample and wherein no detectable level of activated activatable antibody in the subject or sample indicates that the cleaving agent, the target or both the cleaving agent and the target are absent in the subject or sample.

In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

In some embodiments of these methods and kits, the activatable antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods and kits, the method is an in vivo method. In some embodiments of these methods, the method is an in situ method. In some embodiments of these methods, the method is an ex vivo method. In some embodiments of these methods, the method is an in vitro method.

The disclosure also provides methods of detecting presence or absence of a cleaving agent in a subject or a sample by (i) contacting a subject or biological sample with a probe comprising a cleavable moiety (CM) and a detectable label that is released or activated following cleavage of the CM; and (ii) measuring a level of detectable label in the subject or biological sample. When such release or activation increases detection of the label (e.g., stimulates a detectable signal), a detectable level of the detectable label in the subject or biological sample indicates that the cleaving agent is present in the subject or biological sample, and wherein a reduced detectable level of the detectable label in the subject or biological sample indicates that the cleaving agent is absent and/or not sufficiently present in the subject or biological sample at a detectable level, such that protease cleavage of the CM cannot be detected in the subject or biological sample. When such release or activation reduces detection of the label, a detectable level of the detectable label in the subject or biological sample indicates that the cleaving agent is absent and/or not sufficiently present in the subject or biological sample at a detectable level, such that protease cleavage of the CM cannot be detected in the subject or biological sample, and wherein a reduced detectable level of the detectable label in the subject or biological sample indicates that the cleaving agent is present in the subject or biological sample.

In some embodiments of these methods and kits, the probes comprising CM includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments of the methods and kits, the method is used to identify or otherwise refine a patient population suitable for treatment with an activatable antibody of the disclosure, followed by treatment by administering that activatable antibody and/or conjugated activatable antibody to a subject in need thereof. For example, patients that test positive for both the target and at least one protease selected from matriptase and uPA that cleaves the substrate in the cleavable moiety (CM) of the activatable antibody being tested in these methods are identified as suitable candidates for treatment with such an activatable antibody comprising such a CM, and the patient is then administered a therapeutically effective amount of the activatable antibody and/or conjugated activatable antibody that was tested. Likewise, patients that test negative for either or both of the target and the protease, i.e., matriptase and/or uPA that cleaves the substrate in the CM in the activatable antibody being tested using these methods might be identified as suitable candidates for another form of therapy. In some embodiments, such patients can be tested with other activatable antibodies until a suitable activatable antibody for treatment is identified (e.g., an activatable antibody comprising a CM that is cleaved by the patient at the site of disease). In some embodiments, the patient is then administered a therapeutically effective amount of the activatable antibody and/or conjugated for which the patient tested positive.

The disclosure also provides polypeptides and other larger molecules that include one or more of the matriptase-cleavable substrate sequences presented herein and/or uPA-cleavable substrate sequences presented herein. By way of non-limiting example, matriptase-cleavable substrate sequences presented herein and/or uPA-cleavable substrate sequences presented herein are useful in prodrug compositions and methods of use thereof. In some embodiments, the polypeptide comprises a CM joined to a drug, such as a small molecule. Examples of drugs are well known in the art. These matriptase-cleavable substrate sequences presented herein and/or uPA-cleavable substrate sequences presented herein are also useful in probes and other detection agents and methods of use thereof. For example, the matriptase-cleavable substrate sequences presented herein and/or uPA-cleavable substrate sequences presented herein can be used in conjunction with fluors and other quenchers to produce detection agents, such as imaging agents and/or other diagnostic agents. Those of ordinary skill in the art will appreciate that the matriptase-cleavable substrate sequences presented herein and/or uPA-cleavable substrate sequences presented herein are useful in any composition and/or method in the art that would use a substrate that is cleavable by matriptase and/or uPA.

In some embodiments, the matriptase and/or uPA substrates of the disclosure are used in larger molecules, for example, isolated polypeptides that include at least one additional moiety (M) selected from the group consisting of (i) at least one moiety that is located amino (N) terminally to the CM ($M_N$), i.e., at a location within the larger molecule that is situated closer to the N-terminus of the larger molecule than the CM; (ii) at least one moiety that is located carboxyl (C) terminally to the CM ($M_C$), i.e., at a location within the larger molecule that is situated closer to the C-terminus of the larger molecule than the CM; and (iii) combinations thereof. In some embodiments, the larger molecule includes at least one $M_N$ and at least one $M_C$.

By way of non-limiting examples, suitable $M_N$ for use in the larger molecules of the disclosure include at least one of the following: a masking moiety, an antibody, a protein, a therapeutic agent, an antineoplastic agent, a toxic agent, a drug, a detectable moiety, a diagnostic agent, an affinity tag, and combinations thereof.

By way of non-limiting examples, suitable $M_C$ for use in the larger molecules of the disclosure include at least one of the following: a masking moiety, an antibody, a protein, a therapeutic agent, an antineoplastic agent, a toxic agent, a drug, a detectable moiety, a diagnostic agent, an affinity tag, and combinations thereof.

Pharmaceutical compositions according to the disclosure can include an antibody of the disclosure and a carrier. These pharmaceutical compositions can be included in kits, such as, for example, diagnostic kits.

BRIEF DESCRIPTION OF THE DRAWINGS

FIG. 4A is a schematic representation of the sequence of the display platform referred to herein as "Display Platform CYTX-DP-XXXXXXXX" or "CYTX-DP-XXXXXXXX" (SEQ ID NO: 694). FIG. 4B is a schematic representation of the sequence of the display platform referred to herein as "Display Platform SP-CYTX-DP-XXXXXXXX" or "SP-CYTX-DP-XXXXXXXX" (SEQ ID NO: 695), where SP-CYTX-DP-XXXXXXXX is the CYTX-DP-XXXXXXXX platform with a signal peptide.

DETAILED DESCRIPTION OF THE INVENTION

Figure 1:
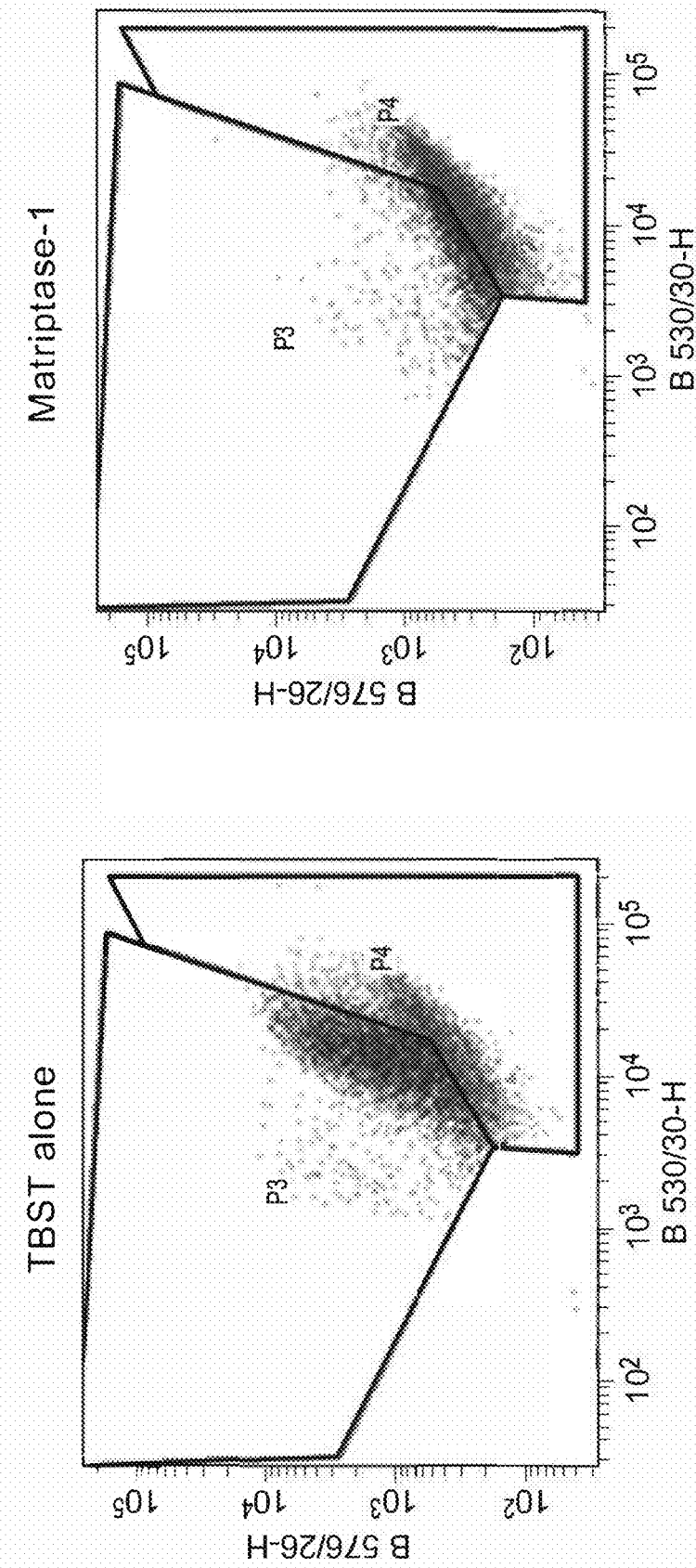
FIG. 1 is a series of graphs depicting cleavage of pool SMP30 by matriptase-1.

The disclosure provides amino acid sequences that include a cleavable moiety (CM) that is a substrate for at least one protease selected from matriptase and u-plasminogen activator (uPA). These CMs are useful in a variety of therapeutic, diagnostic and prophylactic indications.

The disclosure provides antibodies that include one or more of these matriptase-cleavable substrates and/or uPA-cleavable substrates. For example, these matriptase-cleavable substrates and/or uPA-cleavable substrates are useful when conjugating antibodies to one or more additional agents to produce conjugated antibodies. These matriptase-cleavable substrates and/or uPA-cleavable substrates are useful in activatable antibody constructs.

The conjugated antibodies include an antibody or antigen-binding fragment thereof that specifically binds a target, and the activatable antibodies include an antibody or antigen-binding fragment thereof (AB) that specifically binds a target. Exemplary classes of targets of an antibody or antigen-binding fragment thereof include, but are not necessarily limited to, cell surface receptors and secreted binding proteins (e.g., growth factors), soluble enzymes, structural proteins (e.g. collagen, fibronectin) and the like. In some embodiments, conjugated antibodies and/or activatable antibodies have an antibody or antigen-binding fragment thereof that binds an extracellular target, usually an extracellular protein target. In some embodiments, conjugated antibodies and/or activatable antibodies are designed for cellular uptake and are switchable inside a cell.

As a non-limiting example, the antibody or antigen-binding fragment and/or the AB of an activatable antibody is a binding partner for any target listed in Table 1.

TABLE 1

| Exemplary Targets | | | | | |
|---|---|---|---|---|---|
| 1-92-LFA-3 | CD52 | DL44 | HVEM | LIF-R | STEAP1 |
| Alpha-4 integrin | CD56 | DLK1 | Hyaluronidase | Lewis X | STEAP2 |

TABLE 1-continued

| Exemplary Targets | | | | | |
|---|---|---|---|---|---|
| Alpha-V integrin | CD64 | DLL4 | ICOS | LIGHT | TAG-72 |
| alpha4beta1 integrin | CD70 | DPP-4 | IFNalpha | LRP4 | TAPA1 |
| alpha4beta7 integrin | CD71 | DSG1 | IFNbeta | LRRC26 | TGFbeta |
| AGR2 | CD74 | EGFR | IFNgamma | MCSP | TIGIT |
| Anti-Lewis-Y | | EGFRviii | IgE | Mesothelin | TIM-3 |
| Apelin J receptor | CD80 | Endothelin B receptor (ETBR) | IgE Receptor (FceRI) | MRP4 | TLR2 |
| APRIL | CD81 | ENPP3 | IGF | MUC1 | TLR4 |
| B7-H4 | CD86 | EpCAM | IGF1R | Mucin-16 (MUC16, CA-125) | TLR6 |
| BAFF | CD95 | EPHA2 | IL1B | Na/K ATPase | TLR7 |
| BTLA | CD117 | EPHB2 | IL1R | Neutrophil elastase | TLR8 |
| C5 complement | CD125 | ERBB3 | IL2 | NGF | TLR9 |
| C-242 | CD132 (IL-2RG) | F protein of RSV | IL11 | Nicastrin | TMEM31 |
| CA9 | CD133 | FAP | IL12 | Notch Receptors | TNFalpha |
| CA19-9 (Lewis a) | CD137 | FGF-2 | IL12p40 | Notch 1 | TNFR |
| Carbonic anhydrase 9 | CD138 | FGF8 | IL-12R, IL-12Rbeta1 | Notch 2 | TNFRS12A |
| CD2 | CD166 | FGFR1 | IL13 | Notch 3 | TRAIL-R1 |
| CD3 | CD172A | FGFR2 | IL13R | Notch 4 | TRAIL-R2 |
| CD6 | CD248 | FGFR3 | IL15 | NOV | Transferrin |
| CD9 | CDH6 | FGFR4 | IL17 | OSM-R | Transferrin receptor |
| CD11a | CEACAM5 (CEA) | Folate receptor | IL18 | OX-40 | TRK-A |
| CD19 | CEACAM6 (NCA-90) | GAL3ST1 | IL21 | PAR2 | TRK-B |
| CD20 | CLAUDIN-3 | G-CSF | IL23 | PDGF-AA | uPAR |
| CD22 | CLAUDIN-4 | G-CSFR | IL23R | PDGF-BB | VAP1 |
| CD24 | cMet | GD2 | IL27/IL27R (wsx1) | PDGFRalpha | VCAM-1 |
| CD25 | Collagen | GITR | IL29 | PDGFRbeta | VEGF |
| CD27 | Cripto | GLUT1 | IL-31R | PD-1 | VEGF-A |
| CD28 | CSFR | GLUT4 | IL31/IL31R | PD-L1 | VEGF-B |
| CD30 | CSFR-1 | GM-CSF | IL2R | PD-L2 | VEGF-C |
| CD33 | CTLA-4 | GM-CSFR | IL4 | Phosphatidyl-serine | VEGF-D |
| CD38 | CTGF | GP IIb/IIIa receptors | IL4R | P1GF | VEGFR1 |
| CD40 | CXCL10 | Gp130 | IL6, IL6R | PSCA | VEGFR2 |
| CD40L | CXCL13 | GPIIB/IIIA | Insulin Receptor | PSMA | VEGFR3 |
| CD41 | CXCR1 | GPNMB | Jagged Ligands | RAAG12 | VISTA |
| CD44 | CXCR2 | GRP78 | Jagged 1 | RAGE | WISP-1 |
| CD44v6 | | HER2/neu | Jagged 2 | SLC44A4 | WISP-2 |
| CD47 | CXCR4 | HGF | LAG-3 | Sphingosine 1 Phosphate | WISP-3 |
| CD51 | CYR61 | hGH | | | |

As a non-limiting example, the antibody or antigen-binding fragment and/or the AB of an activatable antibody is or is derived from an antibody listed in Table 2.

TABLE 2

| Exemplary sources for Abs | |
|---|---|
| Antibody Trade Name (antibody name) | Target |
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |

TABLE 2-continued

| Exemplary sources for Abs | |
|---|---|
| Antibody Trade Name (antibody name) | Target |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Ocrelizumab | CD20 |

TABLE 2-continued

Exemplary sources for Abs

| Antibody Trade Name (antibody name) | Target |
| --- | --- |
| Arzerra ™ (ofatumumab) | CD20 |
| Obinutuzumab | CD20 |
| Zenapax ™ (daclizumab) | CD25 |
| Adcetris ™ (brentuximab vedotin) | CD30 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Kadcyla ™ (trastuzumab emtansine) | Her2 |
| Synagis ™ (palivizumab) | F protein of RSV |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |
| ICR62 | EGFR |
| mAb 528 | EGFR |
| CH806 | EGFR |
| MDX-447 | EGFR/CD64 |
| (edrecolomab) | EpCAM |
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
|  | Notch, e.g., Notch 1 |
|  | Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |

Exemplary conjugated antibodies and/or activatable antibodies of the disclosure include, for example, antibodies that bind interleukin 6 receptor (IL-6R) and that include a heavy chain and a light chain that are, or are derived from, the antibody referred to herein as the "Av1" antibody, which binds interleukin-6 receptor (IL-6R). The amino acid sequences for the Av1 heavy chain and the Av1 light chain are shown below in SEQ ID NO: 54 and SEQ ID NO: 55, respectively.

Av1 Antibody Heavy Chain Amino Acid Sequence:
(SEQ ID NO: 447)
QVQLQESGPGLVRPSQTLSLTCTVSGYSITSDHAWSWVRQPPGRGLEWIG

YISYSGITTYNPSLKSRVTISRDNSKNTLYLQMNSLRAEDTAVYYCARSL

ARTTAMDYWGQGSLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

Av1 Antibody Light Chain Amino Acid Sequence:
(SEQ ID NO: 448)
DIQMTQSPSSLSASVGDRVTITCRASQDISSYLNWYQQKPGKAPKLLIYY

TSRLHSGVPSRFSGSGSGTDFTFTISSLQPEDIATYYCQQGNTLPYTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Exemplary conjugated antibodies and/or activatable antibodies of the disclosure include, for example, antibodies that bind interleukin 6 receptor (IL-6R) and that include a heavy chain and a light chain that are, or are derived from, the Av1 antibody and a masking moiety. Exemplary conjugated antibodies and/or activatable antibodies of the disclosure include an amino acid sequence attached to the N-terminus of the AV1 light chain. These N-terminal amino acid sequences include, for example, YGSCSWNYVHIFMDC (SEQ ID NO: 449); QGDFDIPFPAHWVPIT (SEQ ID NO: 450); MGVPAGCVWNYAHIFMDC (SEQ ID NO: 451); QGQSGQYGSCSWNYVHIFMDC (SEQ ID NO: 452); QGQSGQGDFDIPFPAHWVPIT (SEQ ID NO: 453); or QGQSGQMGVPAGCVWNYAHIFMDC (SEQ ID NO: 454). It is also to be appreciated that such amino acid sequences can be attached to the N-terminus of the AV1 heavy chain or to the C-terminus of the AV1 heavy or light chain.

Exemplary activatable antibodies of the disclosure include, for example, antibodies that bind Epidermal Growth Factor Receptor (EGFR) and that include a heavy chain and a light chain that are, or are derived from, an antibody selected from the group consisting of the antibody referred to herein as the "c225v5" antibody, the antibody referred to herein as the "c225v4" antibody, and the antibody referred to herein as the "c225v6" antibody, each of which binds EGFR. The c225v5 antibody, the c225v4 antibody, and the c225v6 antibody share the same light chain sequence, referred to herein as "c225 light chain." The amino acid sequences for the c225v5 heavy chain, the c225v4 antibody, the c225v6 antibody, and the c225 light chain are shown below.

C225v5 Antibody Heavy Chain Amino Acid Sequence:
(SEQ ID NO: 455)
QVQLKQSGPGLVQPSQSLSITCTVSGFSLTNYGVHWVRQSPGKGLEWLGV

IWSGGNTDYNTPFTSRLSINKDNSKSQVFFKMNSLQSQDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK*

C225v4 Antibody Heavy Chain Amino Acid Sequence:
(SEQ ID NO: 456)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK*

C225v6 Antibody Heavy Chain Amino Acid Sequence:
(SEQ ID NO: 457)
QVQLKQSGPGLVQPSQSLSITCTVSGFSLTNYGVHWVRQSPGKGLEWLGV

IWSGGNTDYNTPFTSRLSINKDNSKSQVFFKMNSLQSQDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYAS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK*

C225 Antibody Light Chain Amino Acid Sequence:
(SEQ ID NO: 458)
QILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC*

Exemplary activatable antibodies of the disclosure include, for example, antibodies that bind EGFR, that include a heavy chain and a light chain that are, or are derived from, the c225v5 antibody, and that include a masking moiety, a first linking peptide, a cleavable moiety, and a second linking peptide. In some embodiments, the heavy chain and/or the light chain includes a signal peptide. The heavy chain and light chain amino acid sequences for c225v5 without the signal peptide are shown above in SEQ ID NO: 455 (heavy chain without signal peptide) and SEQ ID NO: 458 (light chain without signal peptide). In some embodiments, the activatable anti-EGFR antibody includes a combination of the amino acid sequences shown in SEQ ID NO: 455, SEQ ID NO: 458 and/or the nucleic acid and amino acid sequences shown below:

C225v5 Antibody Heavy Chain Nucleic Acid Sequence with Signal Peptide:
(SEQ ID NO: 684)
ATGTACAGGATGCAACTCCTGTCTTGCATTGCACTAAGTCTTGCACTTGTCACGAATTCGCAGG

TGCAGCTGAAACAGAGCGGCCCGGGCCTGGTGCAGCCGAGCCAGAGCCTGAGCATTACCTGCAC

CGTGAGCGGCTTTAGCCTGACCAACTATGGCGTGCATTGGGTGCGCCAGAGCCCGGGCAAAGGC

CTGGAATGGCTGGGCGTGATTTGGAGCGGCGGCAACACCGATTATAACACCCCGTTTACCAGCC

GCCTGAGCATTAACAAAGATAACAGCAAAAGCCAGGTGTTTTTTAAAATGAACAGCCTGCAAAG

CCAGGATACCGCGATTTATTATTGCGCGCGCGCGCTGACCTATTATGATTATGAATTTGCGTAT

TGGGGCCAGGGCACCCTGGTGACCGTGAGCGCGGCTAGCACCAAGGGCCCATCGGTCTTCCCCC

TGGCACCCTCCTCCAAGAGCACCTCTGGGGGCACAGCGGCCCTGGGCTGCCTGGTCAAGGACTA

CTTCCCCGAACCGGTGACGGTGTCGTGGAACTCAGGCGCCCTGACCAGCGGCGTGCACACCTTC

CCGGCTGTCCTACAGTCCTCAGGACTCTACTCCCTCAGCAGCGTGGTGACCGTGCCCTCCAGCA

GCTTGGGCACCCAGACCTACATCTGCAACGTGAATCACAAGCCCAGCAACACCAAGGTGGACAA

GAAAGTTGAGCCCAAATCTTGTGACAAAACTCACACATGCCCACCGTGCCCAGCACCTGAACTC

CTGGGGGGACCGTCAGTCTTCCTCTTCCCCCCAAAACCCAAGGACACCCTCATGATCTCCCGGA

CCCCTGAGGTCACATGCGTGGTGGTGGACGTGAGCCACGAAGACCCTGAGGTCAAGTTCAACTG

GTACGTGGACGGCGTGGAGGTGCATAATGCCAAGACAAAGCCGCGGGAGGAGCAGTACAACAGC

ACGTACCGTGTGGTCAGCGTCCTCACCGTCCTGCACCAGGACTGGCTGAATGGCAAGGAGTACA

AGTGCAAGGTCTCCAACAAAGCCCTCCCAGCCCCCATCGAGAAAACCATCTCCAAAGCCAAAGG

GCAGCCCCGAGAACCACAGGTGTACACCCTGCCCCCATCCCGGGAGGAGATGACCAAGAACCAG

GTCAGCCTGACCTGCCTGGTCAAAGGCTTCTATCCCAGCGACATCGCCGTGGAGTGGGAGAGCA

ATGGGCAGCCGGAGAACAACTACAAGACCACGCCTCCCGTGCTGGACTCCGACGGCTCCTTCTT

```
CCTCTACAGCAAGCTCACCGTGGACAAGAGCAGGTGGCAGCAGGGGAACGTCTTCTCATGCTCC

GTGATGCATGAGGCTCTGCACAACCACTACACGCAGAAGAGCCTCTCCCTGTCTCCGGGTAAAT

GA
```
Underlined: Signal peptide

C225v5 Antibody Heavy Chain Amino Acid Sequence with Signal
Peptide:
(SEQ ID NO: 685)

```
MYRMQLLSCIALSLALVTNSQVQLKQSGPGLVQPSQSLSITCTVSGFSLTNYGVHWVRQSPGKG

LEWLGVIWSGGNIDYNTPFTSRLSINKDNSKSQVFFKMNSLQSDTAIYYCARALTYYDYEFAY

WGQGTLVTVSAASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKTHTCPPCPAPEL

LGGPSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLTVDKSRWQQGNVFSCS

VMHEALHNHYTQKSLSLSPGK*
```
Underlined: Signal peptide 3954-2787-c225 Light Chain Nucleic Acid Sequence with Signal
Peptide:
(SEQ ID NO: 686)

```
ATGTACAGGATGCAACTCCTGTCTTGCATTGCACTAAGTCTTGCACTTGTCACGAATTCGCAAG

GCCAGTCTGGCCAGTGCATCTCACCTCGTGGTTGTCCGGACGGCCCATACGTCATGTACGGCTC

GAGCGGTGGCAGCGGTGGCTCTGGTGGATCCGGTACCTCCACCTCCGGCCGTTCCGCGAACCCG

CGTGGTGGCAGTAGCGGTACCCAGATCTTGCTGACCCAGAGCCCGGTGATTCTGAGCGTGAGCC

CGGGCGAACGTGTGAGCTTTAGCTGCCGCGCGAGCCAGAGCATTGGCACCAACATTCATTGGTA

TCAGCAGCGCACCAACGGCAGCCCGCGCCTGCTGATTAAATATGCGAGCGAAAGCATTAGCGGC

ATTCCGAGCCGCTTTAGCGGCAGCGGCAGCGGCACCGATTTTACCCTGAGCATTAACAGCGTGG

AAAGCGAAGATATTGCGGATTATTATTGCCAGCAGAACAACAACTGGCCGACCACCTTTGGCGC

GGGCACCAAACTGGAACTGAAACGTACGGTGGCTGCACCATCTGTCTTCATCTTCCCGCCATCT

GATGAGCAGTTGAAATCTGGAACTGCCTCTGTTGTGTGCCTGCTGAATAACTTCTATCCCAGAG

AGGCCAAAGTACAGTGGAAGGTGGATAACGCCCTCCAATCGGGTAACTCCCAGGAGAGTGTCAC

AGAGCAGGACAGCAAGGACAGCACCTACAGCCTCAGCAGCACCCTGACGCTGAGCAAAGCAGAC

TACGAGAAACACAAAGTCTACGCCTGCGAAGTCACCCATCAGGGCCTGAGCTCGCCCGTCACAA

AGAGCTTCAACAGGGGAGAGTGTTAG
```
Underlined: Signal Peptide 3954-2787-c225 Light Chain Amino Acid Sequence with Signal
Peptide:
(SEQ ID NO: 687)

```
MYRMQLLSCIALSLALVTNSQGQSGQCISPRGCPDGPYVMYGSSGGSGGSGGSGTSTSGRSANP

RGGSSGTQILLTQSPVILSVSPGERVSFSCRASQSIGTNIHWYQQRTNGSPRLLIKYASESISG

IPSRFSGSGSGTDFTLSINSVESEDIADYYCQQNNNWPTTFGAGTKLELKRTVAAPSVFIFPPS

DEQLKSGTASVVCLLNNFYPREAKVQWKVDNALQSGNSQESVTEQDSKDSTYSLSSTLTLSKAD

YEKHKVYACEVTHQGLSSPVTKSFNRGEC*
```
Underlined: Signal Peptide 3954-2787-c225 Light Chain Nucleic Acid Sequence
(without Signal Peptide):
(SEQ ID NO: 688)

```
CAAGGCCAGTCTGGCCAGTGCATCTCACCTCGTGGTTGTCCGGACGGCCCATACGTCATGTACG

GCTCGAGCGGTGGCAGCGGTGGCTCTGGTGGATCCGGTACCTCCACCTCCGGCCGTTCCGCGAA
```

-continued

```
CCCGCGTGGTGGCAGTAGCGGTACCCAGATCTTGCTGACCCAGAGCCCGGTGATTCTGAGCGTG

AGCCCGGGCGAACGTGTGAGCTTTAGCTGCCGCGCGAGCCAGAGCATTGGCACCAACATTCATT

GGTATCAGCAGCGCACCAACGGCAGCCCGCGCCTGCTGATTAAATATGCGAGCGAAAGCATTAG

CGGCATTCCGAGCCGCTTTAGCGGCAGCGGCAGCGGCACCGATTTTACCCTGAGCATTAACAGC

GTGGAAAGCGAAGATATTGCGGATTATTATTGCCAGCAGAACAACAACTGGCCGACCACCTTTG

GCGCGGGCACCAAACTGGAACTGAAACGTACGGTGGCTGCACCATCTGTCTTCATCTTCCCGCC

ATCTGATGAGCAGTTGAAATCTGGAACTGCCTCTGTTGTGTGCCTGCTGAATAACTTCTATCCC

AGAGAGGCCAAAGTACAGTGGAAGGTGGATAACGCCCTCCAATCGGGTAACTCCCAGGAGAGTG

TCACAGAGCAGGACAGCAAGGACAGCACCTACAGCCTCAGCAGCACCCTGACGCTGAGCAAAGC

AGACTACGAGAAACACAAAGTCTACGCCTGCGAAGTCACCCATCAGGGCCTGAGCTCGCCCGTC

ACAAAGAGCTTCAACAGGGGAGAGTGTTAG
```

```
3954-2787-c225 Light Chain Amino Acid Sequence
(without Signal Peptide):
                                             (SEQ ID NO: 689)
QGQSGQCISPRGCPDGPYVMYGSSGGSGGSGGSGTSTSGRSANPRGGSSGTQILLTQSPVILSV

SPGERVSFSCRASQSIGTNIHWYQQRTNGSPRLLIKYASESISGIPSRFSGSGSGTDFTLSINS

VESEDIADYYCQQNNNWPTTFGAGTKLELKRTVAAPSVFIFPPSDEQLKSGTASVVCLLNNFYP

REAKVQWKVDNALQSGNSQESVTEQDSKDSTYSLSSTLTLSKADYEKHKVYACEVTHQGLSSPV

TKSFNRGEC*
```

Exemplary conjugated antibodies and/or activatable antibodies of the disclosure include, for example, antibodies that bind a Jagged target, e.g., Jagged-1, Jagged-2 and/or both Jagged-1 and Jagged-2, and that include a combination of a variable heavy chain region and a variable light chain region that are, or are derived from, the variable heavy chain and variable light chain sequences shown below.

```
Variable Light Chain Amino Sequence Lc4
                                             (SEQ ID NO: 459)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc4
                                             (SEQ ID NO: 460)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc5
                                             (SEQ ID NO: 461)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc5
                                             (SEQ ID NO: 462)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPYHGQFDYWGQGTLVTVSS

Variable Light Chain Amino Sequence Lc7
                                             (SEQ ID NO: 463)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc7
                                             (SEQ ID NO: 464)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS
```

-continued

Variable Light Chain Amino Sequence Lc8
(SEQ ID NO: 465)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc8
(SEQ ID NO: 466)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKHIGRTNPFDYWGQGTLVTVSS

Variable Light Chain Amino Sequence Lc13
(SEQ ID NO: 467)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc13
(SEQ ID NO: 468)
EVQLLESGGGLVQPGGSLRLSCAASGFTFSSYAMSWVRQAPGKGLEWVSSIEQMGWQTEYADSV

KGRFTISRDNSKNTLYLQMNSLRAEDTAVYYCAKSAAAFDYWGQGTLVTVSS

Variable Light Chain Amino Sequence Lc16
(SEQ ID NO: 469)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc16
(SEQ ID NO: 470)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPYYGQFDYWGQGTLVTVSS

Variable Light Chain Amino Sequence Lc19
(SEQ ID NO: 471)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc19
(SEQ ID NO: 472)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc21
(SEQ ID NO: 473)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc21
(SEQ ID NO: 474)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable Light Chain Amino Sequence Lc24
(SEQ ID NO: 475)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc24
(SEQ ID NO: 476)
EVQLLESGGGLVQPGGSLRLSCAASGFTFSSYAMSWVRQAPGKGLEWVSSIEEMGWQTLYADSV

KGRFTISRDNSKNTLYLQMNSLRAEDTAVYYCAKSAAAFDYWGQGTLVTVSS

Variable Light Chain Amino Sequence Lc26
(SEQ ID NO: 477)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

```
Variable Heavy Chain Amino Sequence Hc26
                                                    (SEQ ID NO: 478)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKDIGGRSAFDYWGQGTLVTVSS Variable Light Chain Amino Sequence Lc27
                                                    (SEQ ID NO: 479)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc27
                                                    (SEQ ID NO: 480)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKSPPFYGQFDYWGQGTLVTVSS Variable Light Chain Amino Sequence Lc28
                                                    (SEQ ID NO: 481)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc28
                                                    (SEQ ID NO: 482)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKSPPFFGQFDYWGQGTLVTVSS Variable Light Chain Amino Sequence Lc30
                                                    (SEQ ID NO: 483)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc30
                                                    (SEQ ID NO: 484)
EVQLLESGGGLVQPGGSLRLSCAASGFTFSSYAMSWVRQAPGKGLEWVSSIEEMGWQTLYADSV
KGRFTISRDNSKNTLYLQMNSLRAEDTAVYYAKSAAAFDYWGQGTLVTVSS Variable Light Chain Amino Sequence Lc31
                                                    (SEQ ID NO: 485)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc31
                                                    (SEQ ID NO: 486)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKDIGGRSAFDYWGQGTLVTVSS Variable Light Chain Amino Sequence Lc32
                                                    (SEQ ID NO: 487)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc32
                                                    (SEQ ID NO: 488)
EVQLLESGGGLVQPGGSLRLSCAASGFTFSSYAMSWVRQAPGKGLEWVSSIDPEGWQTYYADSV
KGRFTISRDNSKNTLYLQMNSLRAEDTAVYYCAKSAAAFDYWGQGTLVTVSS Variable Light Chain Amino Sequence Lc37
                                                    (SEQ ID NO: 489)
DIQMTQSPSSLSASVGDRVTITCRASQSISSYLNWYQQKPGKAPKLLIYAASSLQSGVPSRFSG
SGSGTDFTLTISSLQPEDFATYYCQQSVVAPLTFGQGTKVEIKR Variable Heavy Chain Amino Sequence Hc37
                                                    (SEQ ID NO: 490)
EVQLLESGGGLVQPGGSLRLSCAASGFTFSSYAMSWVRQAPGKGLEWVSSIEQMGWQTYYADSV
KGRFTISRDNSKNTLYLQMNSLRAEDTAVYYCAKSPPHNGQFDYWGQGTLVTVSS
```

```
Variable Light Chain Amino Sequence Lc39
                                                  (SEQ ID NO: 491)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc39
                                                  (SEQ ID NO: 492)
EVQLLESGGGLVQPGGSLRLSCAASGFTFSSYAMSWVRQAPGKGLEWVSSIEQMGWQTEYADSV

KGRFTISRDNSKNTLYLQMNSLRAEDTAVYYCAKSAAAFDYWGQGTLVTVSS

Variable Light Chain Amino Sequence Lc40
                                                  (SEQ ID NO: 493)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Heavy Chain Amino Sequence Hc40
                                                  (SEQ ID NO: 494)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKSPPFFGQFDYWGQGTLVTVSS

Variable Light Chain Amino Sequence Lc47
                                                  (SEQ ID NO: 495)
DIQMTQSPSSLSASVGDRVTITCRASQSISSYLNWYQQKPGKAPKLLIYAASSLQSGVPSRFSG

SGSGTDFTLTISSLQPEDFATYYCQQSVVAPLTFGQGTKVEIKR

Variable Heavy Chain Amino Sequence Hc47
                                                  (SEQ ID NO: 496)
EVQLLESGGGLVQPGGSLRLSCAASGFTFSSYAMSWVRQAPGKGLEWVSSIDEMGWQTEYADSV

KGRFTISRDNSKNTLYLQMNSLRAEDTAVYYCAKSAAAFDYWGQGTLVTVSS

Variable 4B2 Light Chain
                                                  (SEQ ID NO: 497)
DIQMTQSPSSLSASVGDRVTITCRASQSISSYLNWYQQKPGKAPKLLIYAASSLQSGVPSRFSG

SGSGTDFTLTISSLQPEDFATYYCQQTLDAPPQFGQGTKVEIKR

Variable 4B2 Heavy Chain
                                                  (SEQ ID NO: 498)
EVQLLESGGGLVQPGGSLRLSCAASGFTFSSYAMSWVRQAPGKGLEWVSSIEQMGWQTYYADSV

KGRFTISRDNSKNTLYLQMNSLRAEDTAVYYCAKDIGGRSAFDYWGQGTLVTVSS

Variable 4D11 Light Chain
                                                  (SEQ ID NO: 499)
DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKR

Variable 4D11 Heavy Chain
                                                  (SEQ ID NO: 500)
EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSS

Variable 4E7 Light Chain
                                                  (SEQ ID NO: 501)
DIQMTQSPSSLSASVGDRVTITCRASQSISSYLNWYQQKPGKAPKLLIYAASSLQSGVPSRFSG

SGSGTDFTLTISSLQPEDFATYYCQQSLVAPLTFGQGTKVEIKR

Variable 4E7 Heavy Chain
                                                  (SEQ ID NO: 502)
EVQLLESGGGLVQPGGSLRLSCAASGFTFSSYAMSWVRQAPGKGLEWVSSIEEMGWQTKYADSV

KGRFTISRDNSKNTLYLQMNSLRAEDTAVYYCAKSAAAFDYWGQGTLVTVSS

Variable 4E11 Light Chain
                                                  (SEQ ID NO: 503)
DIQMTQSPSSLSASVGDRVTITCRASQSISSYLNWYQQKPGKAPKLLIYAASSLQSGVPSRFSG

SGSGTDFTLTISSLQPEDFATYYCQQALDAPLMFGQGTKVEIKR
```

```
Variable 4E11 Heavy Chain
                                                (SEQ ID NO: 504)
EVQLLESGGGLVQPGGSLRLSCAASGFTFSSYAMSWVRQAPGKGLEWVSSIEPMGQLTEYADSV

KGRFTISRDNSKNTLYLQMNSLRAEDTAVYYCAKDIGGRSAFDYWGQGTLVTVSS

Variable 6B7 Light Chain
                                                (SEQ ID NO: 505)
DIQMTQSPSSLSASVGDRVTITCRASQSISSYLNWYQQKPGKAPKLLIYAASSLQSGVPSRFSG

SGSGTDFTLTISSLQPEDFATYYCQQALVAPLTFGQGTKVEIKR

Variable 6B7 Heavy Chain
                                                (SEQ ID NO: 506)
EVQLLESGGGLVQPGGSLRLSCAASGFTFSSYAMSWVRQAPGKGLEWVSSIDEMGWQTYYADSV

KGRFTISRDNSKNTLYLQMNSLRAEDTAVYYCAKSAAAFDYWGQGTLVTVSS

Variable 6F8 Light Chain
                                                (SEQ ID NO: 507)
DIQMTQSPSSLSASVGDRVTITCRASQSISSYLNWYQQKPGKAPKLLIYAASSLQSGVPSRFSG

SGSGTDFTLTISSLQPEDFATYYCQQALVAPLTFGQGTKVEIKR

Variable 6F8 Heavy Chain
                                                (SEQ ID NO: 508)
EVQLLESGGGLVQPGGSLRLSCAASGFTFSSYAMSWVRQAPGKGLEWVSSIDEMGWQTYYADSV

KGRFTISRDNSKNTLYLQMNSLRAEDTAVYYCAKSAAAFDYWGQGTLVTVSS
```

Exemplary conjugated antibodies and/or activatable antibodies of the disclosure include, for example, antibodies that bind a Jagged target, e.g., Jagged-1, Jagged-2 and/or both Jagged-1 and Jagged-2, and that include a combination of a heavy chain region and a light chain region that are, or are derived from, the heavy chain and light chain sequences shown below.

```
4D11 Light Chain sequence:
                                                (SEQ ID NO: 509)
DIQMTQSPSSLSASVGDRVTITCRASQSISSYLNWYQQKPGKAPKLLIYA

ASSLQSGVPSRFSGSGSGTDFTLTISSLQPEDFATYYCQQTVVAPPLFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

4D11 Heavy Chain sequence:
                                                (SEQ ID NO: 510)
EVQLLESGGGLVQPGGSLRLSCAASGFTFSSYAMSWVRQAPGKGLEWVSS

IDPEGRQTYYADSVKGRFTISRDNSKNTLYLQMNSLRAEDTAVYYCAKDI

GGRSAFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

4D11v2 Heavy Chain sequence
                                                (SEQ ID NO: 511)
EVHLLESGGGLVQPGGSLRLSCAASGFTFSSYAMSWVRQAPGKGLEWVSS

IDPEGRQTYYADSVKGRFTISRDNSKNTLYLQMNSLRAEDTAVYYCAKDI

GGRSAFDYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

4D11v2 Light Chain Sequence
                                                (SEQ ID NO: 512)
DIQMTQSPSSLSASVGDRVTITCRASQSISSYLNWYQQKPGKAPKLLIYA

ASSLQSGVPSRFSGSGSGTDFTLTISSLQPEDFATYYCQQTVVAPPLFGQ

GTKVEIKRTVAAPSVFIFPPSDEQLKSGTASVVCLLNNFYPREAKVQWKV

DNALQSGNSQESVTEQDSKDSTYSLSSTLTLXKADYEKHKVYACEVTHQG

LSSPVTKSFNRGEC
```

The activatable antibodies provided herein contain at least an antibody or antibody fragment thereof (collectively referred to as AB throughout the disclosure) that specifically binds a target, e.g., a human target, wherein the AB is modified by a masking moiety (MM).

In some embodiments, the masking moiety is selected for use with a specific antibody or antibody fragment. For example, suitable masking moieties for use with antibodies that bind EGFR include MMs that include the sequence CISPRG (SEQ ID NO: 513). By way of non-limiting examples, the MM can include a sequence such as CISPRGC (SEQ ID NO: 690) CISPRGCG (SEQ ID NO: 514); CISPRGCPDGPYVMY (SEQ ID NO: 515); CISPRGCPDGPYVM (SEQ ID NO: 516), CISPRGCEPGTYVPT (SEQ ID NO: 517) and CISPRGCPGQIWHPP (SEQ ID NO: 518). Other suitable masking moieties include any of the EGFR-specific masks disclosed in PCT Publication No. WO 2010/081173, such as, by way of non-limiting example, GSHCLIPINMGAPSC (SEQ ID NO: 519); CISPRGCGGSSASQSGQGSHCLIPINMGAPSC (SEQ ID NO: 520); CNHHYFYTCGCISPRGCPG (SEQ ID NO: 521); ADHVFWGSYGCISPRGCPG (SEQ ID NO: 522); CHHVYWGHCGCISPRGCPG (SEQ ID NO: 523); CPHFTTTSCGCISPRGCPG (SEQ ID NO: 524); CNHHYHYYCGCISPRGCPG (SEQ ID NO: 525); CPHVSFGSCGCISPRGCPG (SEQ ID NO: 526); CPYYTLSYCGCISPRGCPG (SEQ ID NO: 527); CNHVYFGTCGCISPRGCPG (SEQ ID NO: 528); CNHFTLTTCGCISPRGCPG (SEQ ID NO: 529); CHHFTLTTCGCISPRGCPG (SEQ ID NO: 530); YNPCATPMCCISPRGCPG (SEQ ID NO: 531); CNHHYFYTCGCISPRGCG (SEQ ID NO: 532); CNHHYHYYCGCISPRGCG (SEQ ID NO: 533); CNHVYFGTCGCISPRGCG (SEQ ID NO: 534); CHHVYWGHCGCISPRGCG (SEQ ID NO: 535); CPHFTTTSCGCISPRGCG (SEQ ID NO: 536); CNHFTLTTCGCISPRGCG (SEQ ID NO: 537); CHHFTLTTCGCISPRGCG (SEQ ID NO: 538); CPYYTLSYCGCISPRGCG (SEQ ID NO: 539); CPHVSFGSCGCISPRGCG (SEQ ID NO: 540); ADHVFWGSYGCISPRGCG (SEQ ID NO: 541); YNPCATPMCCISPRGCG (SEQ ID NO: 542); CHHVYWGHCGCISPRGCG (SEQ ID NO: 543); C(N/P)H(H/V/F)(Y/T)(F/W/T/L)(Y/G/T/S)(T/S/Y/H)CGCISPRGCG (SEQ ID NO: 544); CISPRGCGQPIPSVK (SEQ ID NO: 545); CISPRGCTQPYHVSR (SEQ ID NO: 546); and/or CISPRGCNAVSGLGS (SEQ ID NO: 547).

Suitable masking moieties for use with antibodies that bind a Jagged target, e.g., Jagged 1 and/or Jagged 2, include, by way of non-limiting example, masking moieties that include a sequence such as QGQSGQCNIWLVGGDCRGWQG (SEQ ID NO: 691); QGQSGQGQQWCNIWINGGDCRGWNG (SEQ ID NO: 548); PWCMQRQDFLRCPQP (SEQ ID NO: 549); QLGLPAYMCTFECLR (SEQ ID NO: 550); CNLWVSGGDCGGLQG (SEQ ID NO: 551); SCSLWTSGSCLPHSP (SEQ ID NO: 552); YCLQLPHYMQAMCGR (SEQ ID NO: 553); CFLYSCTDVSYWNNT (SEQ ID NO: 554); PWCMQRQDYLRCPQP (SEQ ID NO: 555); CNLWISGGDCRGLAG (SEQ ID NO: 556); CNLWVSGGDCRGVQG (SEQ ID NO: 557); CNLWVSGGDCRGLRG (SEQ ID NO: 558); CNLWISGGDCRGLPG (SEQ ID NO: 559); CNLWVSGGDCRDAPW (SEQ ID NO: 560); CNLWVSGGDCRDLLG (SEQ ID NO: 561); CNLWVSGGDCRGLQG (SEQ ID NO: 562); CNLWLHGGDCRGWQG (SEQ ID NO: 563); CNIWLVGGDCRGWQG (SEQ ID NO: 564); CTTWFCGGDCGVMRG (SEQ ID NO: 565); CNIWGPSVDCGALLG (SEQ ID NO: 566); CNIWVNGGDCRSFEG (SEQ ID NO: 567); YCLNLPRYMQDMCWA (SEQ ID NO: 568); YCLALPHYMQADCAR (SEQ ID NO: 569); CFLYSCGDVSYWGSA (SEQ ID NO: 570); CYLYSCTDSAFWNNR (SEQ ID NO: 571); CYLYSCNDVSYWSNT (SEQ ID NO: 572); CFLYSCTDVSYW (SEQ ID NO: 573); CFLYSCTDVAYWNSA (SEQ ID NO: 574); CFLYSCTDVSYWGDT (SEQ ID NO: 575); CFLYSCTDVSYWGNS (SEQ ID NO: 576); CFLYSCTDVAYWNNT (SEQ ID NO: 577); CFLYSCGDVSYWGNPGLS (SEQ ID NO: 578); CFLYSCTDVAYWSGL (SEQ ID NO: 579); CYLYSCTDGSYWNST (SEQ ID NO: 580); CFLYSCSDVSYWGNI (SEQ ID NO: 581); CFLYSCTDVAYW (SEQ ID NO: 582); CFLYSCTDVSYWGST (SEQ ID NO: 583); CFLYSCTDVAYWGDT (SEQ ID NO: 584); GCNIWLNGGDCRGWVDPLQG (SEQ ID NO: 585); GCNIWLVGGDCRGWIGDTNG (SEQ ID NO: 586); GCNIWLVGGDCRGWIEDSNG (SEQ ID NO: 587); GCNIWANGGDCRGWIDNIDG (SEQ ID NO: 588); GCNIWLVGGDCRGWLGEAVG (SEQ ID NO: 589); GCNIWLVGGDCRGWLEEAVG (SEQ ID NO: 590); GGPALCNIWLNGGDCRGWSG (SEQ ID NO: 591); GAPVFCNIWLNGGDCRGWMG (SEQ ID NO: 592); GQQQWCNIWINGGDCRGWNG (SEQ ID NO: 593); GKSEFCNIWLNGGDCRGWIG (SEQ ID NO: 594); GTPGGCNIWANGGDCRGWEG (SEQ ID NO: 595); GASQYCNLWINGGDCRGWRG (SEQ ID NO: 596); GCNIWLVGGDCRPWVEGG (SEQ ID NO: 597); GCNIWAVGGDCRPFVDGG (SEQ ID NO: 598); GCNIWLNGGDCRAWVDTG (SEQ ID NO: 599); GCNIWIVGGDCRPFINDG (SEQ ID NO: 600); GCNIWLNGGDCRPVVFGG (SEQ ID NO: 601); GCNIWLSGGDCRMFMNEG (SEQ ID NO: 602); GCNIWVNGGDCRSFVYSG (SEQ ID NO: 603); GCNIWLNGGDCRGWEASG (SEQ ID NO: 604); GCNIWAHGGDCRGFIEPG (SEQ ID NO: 605); GCNIWLNGGDCRTFVASG (SEQ ID NO: 606); GCNIWAHGGDCRGFIEPG (SEQ ID NO: 607); GFLENCNIWLNGGDCRTG (SEQ ID NO: 608); GIYENCNIWLNGGDCRMG (SEQ ID NO: 609); and/or GIPDNCNIWINGGDCRYG (SEQ ID NO: 610).

Suitable masking moieties for use with antibodies that bind an interleukin 6 target, e.g., interleukin 6 receptor (IL-6R), include, by way of non-limiting example, masking moieties that include a sequence such as QGQSGQYGSCSWNYVHIFMDC (SEQ ID NO: 611); QGQSGQGDFDIPFPAHWVPIT (SEQ ID NO: 612); QGQSGQMGVPAGCVWNYAHIFMDC (SEQ ID NO: 613); YRSCNWNYVSIFLDC (SEQ ID NO: 614); PGAFDIPFPAHWVPNT (SEQ ID NO: 615); ESSCVWNYVHIYMDC (SEQ ID NO: 616); YPGCKWNYDRIFLDC (SEQ ID NO: 617); YRTCSWNYVGIFLDC (SEQ ID NO: 618); YGSCSWNYVHIFMDC (SEQ ID NO: 619); YGSCSWNYVHIFLDC (SEQ ID NO: 620); YGSCNWNYVHIFLDC (SEQ ID NO: 621); YTSCNWNYVHIFMDC (SEQ ID NO: 622); YPGCKWNYDRIFLDC (SEQ ID NO: 623); WRSCNWNYAHIFLDC (SEQ ID NO: 624); WSNCHWNYVHIFLDC (SEQ ID NO: 625); DRSCTWNYVRISYDC (SEQ ID NO: 626); SGSCKWDYVHIFLDC (SEQ ID NO: 627); SRSCIWNYAHIHLDC (SEQ ID NO: 628); SMSCYWQYERIFLDC (SEQ ID NO: 629); YRSCNWNYVSIFLDC (SEQ ID NO: 630); SGSCKWDYVHIFLDC (SEQ ID NO: 631); YKSCHWDYVHIFLDC (SEQ ID NO: 632); YGSCTWNYVHIFMEC (SEQ ID NO: 633); FSSCNWNYVHIFLDC (SEQ ID NO: 634); WRSCNWNYAHIFLDC (SEQ ID NO: 635); YGSCQWNYVHIFLDC (SEQ ID NO: 636); YRSCNWNYVHIFLDC (SEQ ID NO: 637); NMSCHWDYVHIFLDC (SEQ ID NO: 638); FGPCTWNYARISWDC (SEQ ID NO: 639); XXsCXWXYvhIfXdC (SEQ ID NO: 640); MGVPAGCVWNYAHIFMDC (SEQ ID NO: 641); RDTGGQCRWDYVHIFMDC (SEQ ID NO: 642); AGVPAGCTWNYVHIFMEC (SEQ ID NO: 643); VGVPNGCVWNYAHIFMEC (SEQ ID NO: 644); DGGPAGCSWNYVHIFMEC (SEQ ID NO: 645); AVGPAGCWWNYVHIFMEC (SEQ ID NO: 646); CTWNYVHIFMDCGEGEGP (SEQ ID NO: 647); GGVPEGCTWNYAHIFMEC (SEQ ID NO: 648); AEVPAGCWWNYVHIFMEC (SEQ ID NO: 649); AGVPAGCTWNYVHIFMEC (SEQ ID NO: 650);

SGASGGCKWNYVHIFMDC (SEQ ID NO: 651); TPGCRWNYVHIFMECEAL (SEQ ID NO: 652); VGVPNGCVWNYAHIFMEC (SEQ ID NO: 653); PGAFDIPFPAHWVPNT (SEQ ID NO: 654); RGACDIPFPAHWIPNT (SEQ ID NO: 655); QGDFDIPFPAHWVPIT (SEQ ID NO: 656); XGafDIPFPAHWvPnT (SEQ ID NO: 657); RGDGNDSDIPFPAHWVPRT (SEQ ID NO: 658); SGVGRDRDIPFPAHWVPRT (SEQ ID NO: 659); WAGGNDCDIPFPAHWIPNT (SEQ ID NO: 660); WGDGMDVDIPFPAHWVPVT (SEQ ID NO: 661); AGSGNDSDIPFPAHWVPRT (SEQ ID NO: 662); ESRSGYADIPFPAHWVPRT (SEQ ID NO: 663); and/or RECGRCGDIPFPAHWVPRT (SEQ ID NO: 664).

When the AB is modified with a MM and is in the presence of the target, specific binding of the AB to its target is reduced or inhibited, as compared to the specific binding of the AB not modified with an MM or the specific binding of the parental AB to the target.

The $K_d$ of the AB modified with a MM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000, 000, 100-1,000, 100-10,000, 100-100,000, 100-1,000,000, 100-10,000,000, 1,000-10,000, 1,000-100,000, 1,000-1,000, 000, 1000-10,000,000, 10,000-100,000, 10,000-1,000,000, 10,000-10,000,000, 100,000-1,000,000, or 100,000-10,000, 000 times greater than the $K_d$ of the AB not modified with an MM or of the parental AB towards the target. Conversely, the binding affinity of the AB modified with a MM towards the target is at least 2, 3, 4, 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000, 000,000, or 100,000-10,000,000 times lower than the binding affinity of the AB not modified with an MM or of the parental AB towards the target.

The dissociation constant ($K_d$) of the MM towards the AB is generally greater than the $K_d$ of the AB towards the target. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target. Conversely, the binding affinity of the MM towards the AB is generally lower than the binding affinity of the AB towards the target. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target.

When the AB is modified with a MM and is in the presence of the target specific binding of the AB to its target is reduced or inhibited, as compared to the specific binding of the AB not modified with an MM or the specific binding of the parental AB to the target. When compared to the binding of the AB not modified with an MM or the binding of the parental AB to the target the AB's ability to bind the target when modified with a MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

The MM inhibits the binding of the AB to the target. The MM binds the antigen binding domain of the AB and inhibits binding of the AB to the target. The MM can sterically inhibit the binding of the AB to the target. The MM can allosterically inhibit the binding of the AB to its target. In these embodiments when the AB is modified or coupled to a MM and in the presence of target there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When an AB is coupled to or modified by a MM, the MM 'masks' or reduces or otherwise inhibits the specific binding of the AB to the target. When an AB is coupled to or modified by a MM, such coupling or modification can effect a structural change that reduces or inhibits the ability of the AB to specifically bind its target.

An AB coupled to or modified with an MM can be represented by the following formulae (in order from an amino (N) terminal region to carboxyl (C) terminal region:

(MM)-(AB)

(AB)-(MM)

(MM)-L-(AB)

(AB)-L-(MM)

where MM is a masking moiety, the AB is an antibody or antibody fragment thereof, and the L is a linker. In many embodiments, it may be desirable to insert one or more linkers, e.g., flexible linkers, into the composition so as to provide for flexibility.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 25% identical to any natural binding partner of the AB. In some embodiments, the MM is no more than 50% identical to any natural binding partner of the AB. In some embodiments, the MM is no more than 20% identical to any natural binding partner of the AB. In some embodiments, the MM is no more than 10% identical to any natural binding partner of the AB.

In some embodiments, the activatable antibodies include an AB that is modified by an MM and also includes one or more cleavable moieties (CM). Such activatable antibodies exhibit activatable/switchable binding, to the AB's target. Activatable antibodies generally include an antibody or antibody fragment (AB), modified by or coupled to a masking moiety (MM) and a modifiable or cleavable moiety (CM). In some embodiments, the CM contains an amino acid sequence that serves as a substrate for at least one protease selected from matriptase and uPA.

The elements of the activatable antibodies are arranged so that the MM and CM are positioned such that in a cleaved (or relatively active) state and in the presence of a target, the AB binds a target while in an uncleaved (or relatively inactive) state in the presence of the target, specific binding of the AB to its target is reduced or inhibited. The specific binding of the AB to its target can be reduced due to the inhibition or masking of the AB's ability to specifically bind its target by the MM.

The $K_d$ of the AB modified with a MM and a CM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM and a CM or of the parental AB towards the target. Conversely, the binding affinity of the AB modified with a MM and a CM towards the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM and a CM or of the parental AB towards the target.

When the AB is modified with a MM and a CM and is in the presence of the target but not in the presence of a modifying agent (for example at least one protease selected from matriptase and uPA), specific binding of the AB to its target is reduced or inhibited, as compared to the specific binding of the AB not modified with an MM and a CM or of the parental AB to the target. When compared to the binding of the parental AB or the binding of an AB not modified with an MM and a CM to its target, the AB's ability to bind the target when modified with an MM and a CM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

As used herein, the term cleaved state refers to the condition of the activatable antibodies following modification of the CM by at least one protease selected from matriptase and uPA. The term uncleaved state, as used herein, refers to the condition of the activatable antibodies in the absence of cleavage of the CM by a protease selected from matriptase and uPA. As discussed above, the term "activatable antibodies" is used herein to refer to an activatable antibody in both its uncleaved (native) state, as well as in its cleaved state. It will be apparent to the ordinarily skilled artisan that in some embodiments a cleaved activatable antibody may lack an MM due to cleavage of the CM by protease, resulting in release of at least the MM (e.g., where the MM is not joined to the activatable antibodies by a covalent bond (e.g., a disulfide bond between cysteine residues).

By activatable or switchable is meant that the activatable antibody exhibits a first level of binding to a target when in a inhibited, masked or uncleaved state (i.e., a first conformation), and a second level of binding to the target in the uninhibited, unmasked and/or cleaved state (i.e., a second conformation), where the second level of target binding is greater than the first level of binding. In general, the access of target to the AB of the activatable antibody is greater in the presence of a cleaving agent capable of cleaving the CM, i.e., a protease selected from matriptase and uPA, than in the absence of such a cleaving agent. Thus, when the activatable antibody is in the uncleaved state, the AB is inhibited from target binding and can be masked from target binding (i.e., the first conformation is such the AB cannot bind the target), and in the cleaved state the AB is not inhibited or is unmasked to target binding.

The CM and AB of the activatable antibodies are selected so that the AB represents a binding moiety for a given target, and the CM represents a substrate for a protease selected from matriptase and uPA. In some embodiments, the protease is co-localized with the target at a treatment site or diagnostic site in a subject. As used herein, co-localized refers to being at the same site or relatively close nearby. In some embodiments, a protease cleaves a CM yielding an activated antibody that binds to a target located nearby the cleavage site. The activatable antibodies disclosed herein find particular use where, for example, a protease capable of cleaving a site in the CM, i.e., a protease selected from matriptase and uPA, is present at relatively higher levels in target-containing tissue of a treatment site or diagnostic site than in tissue of non-treatment sites (for example in healthy tissue). In some embodiments, a CM of the disclosure is also cleaved by one or more other proteases. In some embodiments, it is the one or more other proteases that is co-localized with the target and that is responsible for cleavage of the CM in vivo.

In some embodiments activatable antibodies provide for reduced toxicity and/or adverse side effects that could otherwise result from binding of the AB at non-treatment sites if the AB were not masked or otherwise inhibited from binding to the target.

In general, an activatable antibody can be designed by selecting an AB of interest and constructing the remainder of the activatable antibody so that, when conformationally constrained, the MM provides for masking of the AB or reduction of binding of the AB to its target. Structural design criteria can be to be taken into account to provide for this functional feature.

Activatable antibodies exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of an activatable antibody, the dynamic range refers to the ratio of (a) a maximum detected level of target protein binding to an activatable antibody in the presence of at least one protease selected from matriptase and uPA capable of cleaving the CM of the activatable antibodies to (b) a minimum detected level of target protein binding to an activatable antibody in the absence of the protease. The dynamic range of an activatable antibody can be calculated as the ratio of the equilibrium dissociation constant of an activatable antibody cleaving agent (e.g., enzyme) treatment to the equilibrium dissociation constant of the activatable antibodies cleaving agent treatment. The greater the dynamic range of an activatable antibody, the better the switchable phenotype of the activatable antibody. Activatable antibodies having relatively higher dynamic range values (e.g., greater than 1) exhibit more desirable switching phenotypes such that target protein binding by the activatable antibodies occurs to a greater extent (e.g., predominantly occurs) in the presence of a cleaving agent (e.g., enzyme) capable of cleaving the CM of the activatable antibodies than in the absence of a cleaving agent.

Activatable antibodies can be provided in a variety of structural configurations. Exemplary formulae for activatable antibodies are provided below. It is specifically contemplated that the N- to C-terminal order of the AB, MM and CM may be reversed within an activatable antibody. It is also specifically contemplated that the CM and MM may overlap in amino acid sequence, e.g., such that the CM is contained within the MM.

For example, activatable antibodies can be represented by the following formula (in order from an amino (N) terminal region to carboxyl (C) terminal region:

(MM)-(CM)-(AB)

(AB)-(CM)-(MM)

where MM is a masking moiety, CM is a cleavable moiety, and AB is an antibody or fragment thereof. It should be noted that although MM and CM are indicated as distinct components in the formulae above, in all exemplary embodiments (including formulae) disclosed herein it is contemplated that the amino acid sequences of the MM and the CM could overlap, e.g., such that the CM is completely or partially contained within the MM. In addition, the formulae above provide for additional amino acid sequences that may be positioned N-terminal or C-terminal to the activatable antibodies elements.

In certain embodiments, the MM is not a natural binding partner of the AB. In some embodiments, the MM contains no or substantially no homology to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

In many embodiments it may be desirable to insert one or more linkers, e.g., flexible linkers, into the activatable antibody construct so as to provide for flexibility at one or more of the MM-CM junction, the CM-AB junction, or both. For example, the AB, MM, and/or CM may not contain a sufficient number of residues (e.g., Gly, Ser, Asp, Asn, especially Gly and Ser, particularly Gly) to provide the desired flexibility. As such, the switchable phenotype of such activatable antibody constructs may benefit from introduction of one or more amino acids to provide for a flexible linker. In addition, as described below, where the activatable antibody is provided as a conformationally constrained construct, a flexible linker can be operably inserted to facilitate formation and maintenance of a cyclic structure in the uncleaved activatable antibody.

For example, in certain embodiments an activatable antibody comprises one of the following formulae (where the formula below represent an amino acid sequence in either N- to C-terminal direction or C- to N-terminal direction):

(MM)-L1-(CM)-(AB)

(MM)-(CM)-L2-(AB)

(MM)-L1-(CM)-L2-(AB)

wherein MM, CM, and AB are as defined above; wherein L1 and L2 are each independently and optionally present or absent, are the same or different flexible linkers that include at least 1 flexible amino acid (e.g., Gly). In addition, the formulae above provide for additional amino acid sequences that may be positioned N-terminal or C-terminal to the activatable antibodies elements. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HAS)).

The CM is specifically cleaved by at least one protease selected from matriptase and uPA at a rate of about 0.001-1500×10$^4$ M$^{-1}$ S$^{-1}$ or at least 0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250, or 1500×10$^4$ M$^{-1}$ S$^{-1}$. In some embodiments, the CM is specifically cleaved at a rate of about 100,000 M$^{-1}$ S$^{-1}$. In some embodiments, the CM is specifically cleaved at a rate from about 1×10E2 to about 1×10E6 M$^{-1}$ S$^{-1}$ (i.e., from about 1×10$^2$ to about 1×10$^6$ M$^{-1}$ S$^{-1}$).

For specific cleavage by an enzyme, contact between the enzyme and CM is made. When the activatable antibody comprising an AB coupled to a MM and a CM is in the presence of target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but unable to cleave because of other cellular factors or protein modification of the enzyme.

Linkers suitable for use in compositions described herein are generally ones that provide flexibility of the modified AB or the activatable antibodies to facilitate the inhibition of the binding of the AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, or 20 amino acids in length.

Exemplary flexible linkers include glycine polymers (G)n, glycine-serine polymers (including, for example, (GS)n, (GSGGS)n (SEQ ID NO: 385) and (GGGS)n (SEQ ID NO: 386), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 387), Gly-Gly-Ser-Gly-Gly (SEQ ID NO: 388), Gly-Ser-Gly-Ser-Gly (SEQ ID NO: 389), Gly-Ser-Gly-Gly-Gly (SEQ ID NO: 390), Gly-Gly-Gly-Ser-Gly (SEQ ID NO: 391), Gly-Ser-Ser-Gly-Gly (SEQ ID NO: 392), and the like. The ordinarily skilled artisan will recognize that design of an activatable antibodies can include linkers that are all or partially flexible, such that the linker can include a flexible linker as well as one or more portions that confer less flexible structure to provide for a desired activatable antibodies structure.

In some embodiments, the activatable antibodies described herein also include an agent conjugated to the activatable antibody. In some embodiments, the conjugated agent is a therapeutic agent, such as an anti-inflammatory and/or an antineoplastic agent. In such embodiments, the agent is conjugated to a carbohydrate moiety of the activatable antibody, for example, in some embodiments, where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate).

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

The disclosure also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, dolastatins and derivatives thereof (e.g. auristatin E, AFP, MMAF, MMAE, MMAD, DMAF, DMAE). For example, the agent is monomethyl auristatin E (MMAE) or monomethyl auristatin D (MMAD). In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the agent is linked to the AB using a maleimide caproyl-valine-citrulline linker or a maleimide PEG-valine-citrulline linker. In some embodiments, the agent is linked to the AB using a maleimide caproyl-valine-citrulline linker. In some embodiments, the agent is linked to the AB using a maleimide PEG-valine-citrulline linker In some embodiments, the agent is monomethyl auristatin D (MMAD) linked to the AB using a maleimide PEG-valine-citrulline-para-aminobenzyloxycarbonyl linker, and this linker payload construct is referred to herein as "vc-MMAD." In some embodiments, the agent is monomethyl auristatin E (MMAE) linked to the AB using a maleimide PEG-valine-citrulline-para-aminobenzyloxycarbonyl linker, and this linker payload construct is referred to herein as "vc-MMAE." The structures of vc-MMAD and vc-MMAE are shown below:

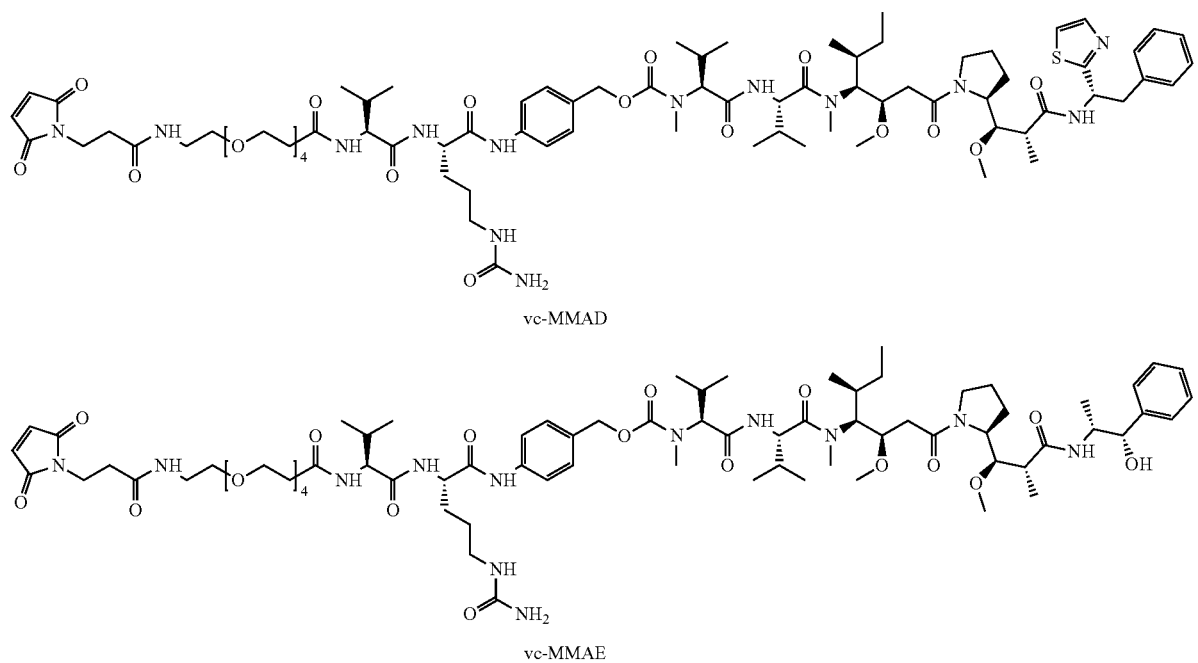

vc-MMAD vc-MMAE

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Table 3 lists some of the exemplary pharmaceutical agents that may be employed in the herein described disclosure but in no way is meant to be an exhaustive list.

TABLE 3

Exemplary Pharmaceutical Agents for Conjugation

CYTOTOXIC AGENTS

Auristatins
Auristatin E
Monomethyl auristatin D (MMAD)
Monomethyl auristatin E (MMAE)
Desmethyl auristatin E (DMAE)
Auristatin F
Monomethyl auristatin F (MMAF)
Desmethyl auristatin F (DMAF)
Auristatin derivatives, e.g., amides thereof
Auristatin tyramine
Auristatin quinoline
Dolastatins
Dolastatin derivatives
Dolastatin 16 DmJ
Dolastatin 16 Dpv
Maytansinoids, e.g. DM-1; DM-4
Maytansinoid derivatives
Duocarmycin
Duocarmycin derivatives
Alpha-amanitin
Anthracyclines
Doxorubicin
Daunorubicin
Bryostatins
Camptothecin
Camptothecin derivatives
7-substituted Camptothecin
10,11-Difluoromethylenedioxycamptothecin
Combretastatins
Debromoaplysiatoxin
Kahalalide-F
Discodermolide
Ecteinascidins

TABLE 3-continued

Exemplary Pharmaceutical Agents for Conjugation

ANTIVIRALS

Acyclovir
Vira A
Symmetrel

ANTIFUNGALS

Nystatin

ADDITIONAL ANTI-NEOPLASTICS

Adriamycin
Cerubidine
Bleomycin
Alkeran
Velban
Oncovin
Fluorouracil
Methotrexate
Thiotepa
Bisantrene
Novantrone
Thioguanine
Procarabizine
Cytarabine

ANTI-BACTERIALS

Aminoglycosides
Streptomycin
Neomycin
Kanamycin
Amikacin
Gentamicin
Tobramycin
Streptomycin B
Spectinomycin
Ampicillin
Sulfanilamide
Polymyxin
Chloramphenicol
Turbostatin
Phenstatins
Hydroxyphenstatin
Spongistatin 5
Spongistatin 7
Halistatin 1
Halistatin 2
Halistatin 3
Modified Bryostatins
Halocomstatins
Pyrrolobenzimidazoles (PBI)
Cibrostatin6
Doxaliform
Anthracyclins analogues
Cemadotin analogue (CemCH2-SH)
Pseudomonas toxin A (PE38) variant
Pseudomonas toxin A (ZZ-PE38) variant
ZJ-101
OSW-1
4-Nitrobenzyloxycarbonyl Derivatives of
O6-Benzylguanine
Topoisomerase inhibitors
Hemiasterlin
Cephalotaxine
Homoharringtonine
Pyrrolobenzodiazepine dimers (PBDs)
Functionalized pyrrolobenzodiazepenes
Calicheamicins
Podophyllotoxins
Taxanes
Vinca alkaloids

CONJUGATABLE DETECTION REAGENTS

Fluorescein and derivatives thereof
Fluorescein isothiocyanate (FITC)

TABLE 3-continued

Exemplary Pharmaceutical Agents for Conjugation

RADIOPHARMACEUTICALS $^{125}$I
$^{131}$I
$^{89}$Zr
$^{111}$In
$^{123}$I
$^{131}$I
$^{99}$mTc
$^{201}$Tl
$^{133}$Xe
$^{11}$C
$^{62}$Cu
$^{18}$F
$^{68}$Ga
$^{13}$N
$^{15}$O
$^{38}$K
$^{82}$Rb
$^{99}$mTc (Technetium)
HEAVY METALS Barium
Gold
Platinum
ANTI-MYCOPLASMALS Tylosine
Spectinomycin Those of ordinary skill in the art will recognize that a large variety of possible moieties can be coupled to the resultant antibodies of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present disclosure, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

In some embodiments, in addition to the compositions and methods provided herein, the conjugated activatable antibody can also be modified for site-specific conjugation through modified amino acid sequences inserted or otherwise included in the activatable antibody sequence. These modified amino acid sequences are designed to allow for controlled placement and/or dosage of the conjugated agent within a conjugated activatable antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. In some embodiments, suitable linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC. Additional linkers include, but are not limited to, SMCC, sulfo-SMCC, SPDB, or sulfo-SPDB.

The linkers described above contain components that have different attributes, thus leading to conjugates with differing physio-chemical properties. For example, sulfo-NHS esters of alkyl carboxylates are more stable than sulfo-NHS esters of aromatic carboxylates. NETS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

In some embodiments, the linkers are cleavable. In some embodiments, the linkers are non-cleavable. In some embodiments, two or more linkers are present. The two or more linkers are all the same, i.e., cleavable or non-cleavable, or the two or more linkers are different, i.e., at least one cleavable and at least one non-cleavable.

The present disclosure utilizes several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the disclosure, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present disclosure, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

According to the present disclosure, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present disclosure, suitable linkers for attachment to neither oxidized nor reduced Abs include those having certain functional groups capable of reaction with the carboxylic acid groups present in aspartate or glutamate residues in the Ab, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In some embodiments, the AB is first attached to the MM, CM and associated linkers and then attached to the linker for conjugation purposes.

Branched Linkers:

In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

In some embodiments, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers:

Peptide linkers that are susceptible to cleavage by enzymes of the complement system, such as but not limited to u-plasminogen activator, tissue plasminogen activator, trypsin, plasmin, or another enzyme having proteolytic activity may be used in one embodiment of the present disclosure. According to one method of the present disclosure, an agent is attached via a linker susceptible to cleavage by complement. The antibody is selected from a class that can activate complement. The antibody-agent conjugate, thus, activates the complement cascade and releases the agent at the target site. According to another method of the present disclosure, an agent is attached via a linker susceptible to cleavage by enzymes having a proteolytic activity such as a u-plasminogen activator, a tissue plasminogen activator, plasmin, or trypsin. These cleavable linkers are useful in conjugated activatable antibodies that include an extracellular toxin, e.g., by way of non-limiting example, any of the extracellular toxins shown in Table 3.

Non-limiting examples of cleavable linker sequences are provided in Table 4.

TABLE 4

Exemplary Linker Sequences for Conjugation

| Types of Cleavable Sequences | Amino Acid Sequence |
|---|---|
| Plasmin cleavable sequences | |
| Pro-urokinase | PRFKIIGG (SEQ ID NO: 665) |
|  | PRFRIIGG (SEQ ID NO: 666) |
| TGFβ | SSRHRRALD (SEQ ID NO: 667) |
| Plasminogen | RKSSIIIRMRDVVL (SEQ ID NO: 668) |
| Staphylokinase | SSSFDKGKYKKGDDA (SEQ ID NO: 669) |
|  | SSSFDKGKYKRGDDA (SEQ ID NO: 670) |
| Factor Xa cleavable sequences | IEGR (SEQ ID NO: 671) |
|  | IDGR (SEQ ID NO: 672) |
|  | GGSIDGR (SEQ ID NO: 673) |

TABLE 4-continued

Exemplary Linker Sequences for Conjugation

| Types of Cleavable Sequences | Amino Acid Sequence |
|---|---|
| MMP cleavable sequences | |
| Gelatinase A | PLGLWA (SEQ ID NO: 674) |
| Collagenase cleavable sequences | |
| Calf skin collagen (α1(I) chain) | GPQGIAGQ (SEQ ID NO: 675) |
| Calf skin collagen (α2(I) chain) | GPQGLLGA (SEQ ID NO: 676) |
| Bovine cartilage collagen (α1(II) chain) | GIAGQ (SEQ ID NO: 677) |
| Human liver collagen (α1(III) chain) | GPLGIAGI (SEQ ID NO: 678) |
| Human α$_2$M | GPEGLRVG (SEQ ID NO: 679) |
| Human PZP | YGAGLGVV (SEQ ID NO: 680)<br>AGLGVVER (SEQ ID NO: 681)<br>AGLGISST (SEQ ID NO: 682) |
| Rat α$_1$M | EPQALAMS (SEQ ID NO: 683)<br>QALAMSAI (SEQ ID NO: 312) |
| Rat α$_2$M | AAYHLVSQ (SEQ ID NO: 315)<br>MDAFLESS (SEQ ID NO: 316) |
| Rat α$_1$I$_3$(2J) | ESLPVVAV (SEQ ID NO: 317) |
| Rat α$_1$I$_3$(27J) | SAPAVESE (SEQ ID NO: 318) |
| Human fibroblast collagenase (autolytic cleavages) | DVAQFVLT (SEQ ID NO: 319)<br>VAQFVLTE (SEQ ID NO: 372)<br>AQFVLTEG (SEQ ID NO: 373)<br>PVQPIGPQ (SEQ ID NO: 380) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In some embodiments, the reducing agent that would modify a CM would also modify the linker of the conjugated activatable antibody.

Spacers and Cleavable Elements:

In some embodiments, it may be necessary to construct the linker in such a way as to optimize the spacing between the agent and the AB of the activatable antibody. This may be accomplished by use of a linker of the general structure:

wherein
W is either —NH—CH$_2$— or —CH$_2$—;
Q is an amino acid, peptide; and
n is an integer from 0 to 20.

In some embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers:

According to one method of the present disclosure, when release of an agent is desired, an AB that is an antibody of a class that can activate complement is used. The resulting conjugate retains both the ability to bind antigen and activate the complement cascade. Thus, according to this embodiment of the present disclosure, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 3.

Linkers for Release without Complement Activation:

In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers:

In some embodiments, the activatable antibody may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH.

Exemplary hetero-bifunctional cross-linkers are referenced in Table 5.

TABLE 5

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
| --- | --- | --- | --- |
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extender spacer arm Water-soluble | 15.6 Å |
| SMCC | Primary amines | Stable maleimide reactive group | 11.6 Å |
|  | Sulfhydryls | Enzyme-antibody conjugation Hapten-carrier protein conjugation |  |
| Sulfo-SMCC | Primary amines | Stable maleimide reactive group | 11.6 Å |
|  | Sulfhydryls | Water-soluble Enzyme-antibody conjugation |  |
| MBS | Primary amines Sulfhydryls | Enzyme-antibody conjugation Hapten-carrier protein conjugation | 9.9 Å |
| Sulfo-MBS | Primary amines Sulfhydryls | Water-soluble | 9.9 Å |

TABLE 5-continued

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
| --- | --- | --- | --- |
| SIAB | Primary amines Sulfhydryls | Enzyme-antibody conjugation | 10.6 Å |
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å |

Non-Cleavable Linkers or Direct Attachment:

In some embodiments of the disclosure, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A general formula for such an organic linker could be

W—(CH$_2$)$n$-Q wherein

W is either —NH—CH$_2$— or —CH$_2$—;

Q is an amino acid, peptide; and n is an integer from 0 to 20.

Non-Cleavable Conjugates:

In some embodiments, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al., J. Biol. Chem., 257: 286-288 (1982) via a disulfide-interchange reaction.

Definitions

Unless otherwise defined, scientific and technical terms used in connection with the present disclosure shall have the meanings that are commonly understood by those of ordinary skill in the art. The term "a" entity or "an" entity refers to one or more of that entity. For example, a compound refers to one or more compounds. As such, the terms "a", "an", "one or more" and "at least one" can be used interchangeably. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, domain antibody, single chain, Fab, and F(ab')$_2$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 µM; in some embodiments, ≤100 nM and in some embodiments, ≤10 nM.

As used herein, the terms "specific binding," "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to the target, when the equilibrium binding constant ($K_d$) is ≤1 µM, in some embodiments ≤100 nM, in some embodiments ≤10 nM, and in some embodiments ≤100 µM to about 1 µM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the disclosure include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Green, Eds., Sinauer Associates, Sunderland, Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present disclosure, providing that the variations in the amino acid sequence maintain at least 75%, in some embodiments, at least 80%, 90%, 95%, and in some embodiments, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Suitable amino acid substitutions are those that: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to the target, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3$H, $^{14}$C, $^{15}$N, $^{35}$S, $^{90}$Y, $^{99}$Tc, $^{111}$In, $^{125}$I, $^{131}$I) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Activatable antibodies of the disclosure specifically bind a given target, e.g., a human target protein. Also included in the disclosure are activatable antibodies that bind to the same epitope as the activatable antibodies described herein.

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to the target. If the monoclonal antibody being tested competes with the monoclonal antibody of the disclosure, as shown by a decrease in binding by the monoclonal antibody of the disclosure, then the two monoclonal antibodies bind to the same, or a closely related, epitope. An alternative method for determining whether a monoclonal antibody has the specificity of a monoclonal antibody of the disclosure is to pre-incubate the monoclonal antibody of the disclosure with the target and then add the monoclonal antibody being tested to determine if the monoclonal antibody being tested is inhibited in its ability to bind the target. If the monoclonal antibody being tested is inhibited then, in all likelihood, it has the same, or functionally equivalent, epitopic specificity as the monoclonal antibody of the disclosure.

Multispecific Activatable Antibodies

The disclosure also provides multispecific activatable antibodies. The multispecific activatable antibodies provided herein are multispecific antibodies that recognize two or more different antigens or epitopes and that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a cleavable moiety (CM) that functions as a substrate for at least one protease selected from uPA and matriptase. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the multispecific activatable antibodies are designed to engage immune effector cells, also referred to herein as immune-effector cell engaging multispecific activatable antibodies. In some embodiments, the multispecific activatable antibodies are designed to engage leukocytes, also referred to herein as leukocyte engaging multispecific activatable antibodies. In some embodiments, the multispecific activatable antibodies are designed to engage T cells, also referred to herein as T-cell engaging multispecific activatable antibodies. In some embodiments, the multispecific activatable antibodies engage a surface antigen on a leukocyte, such as on a T cell, on a natural killer (NK) cell, on a myeloid mononuclear cell, on a macrophage, and/or on another immune effector cell. In some embodiments, the immune effector cell is a leukocyte. In some embodiments, the immune effector cell is a T cell. In some embodiments, the immune effector cell is a NK cell. In some embodiments, the immune effector cell is a mononuclear cell, such as a myeloid mononuclear cell. In some embodiments, the multispecific activatable antibodies are designed to bind or otherwise interact with more than one target and/or more than one epitope, also referred to herein as multi-antigen targeting activatable antibodies. As used herein, the terms "target" and "antigen" are used interchangeably.

In some embodiments, immune effector cell engaging multispecific activatable antibodies of the disclosure include a targeting antibody or antigen-binding fragment thereof and an immune effector cell engaging antibody or antigen-binding portion thereof, where at least one of the targeting antibody or antigen-binding fragment thereof and/or the immune effector cell engaging antibody or antigen-binding portion thereof is masked. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the non-immune effector cell engaging antibody is a cancer targeting antibody. In some embodiments the non-immune cell effector antibody is an IgG. In some embodiments the immune effector cell engaging antibody is a scFv. In some embodiments the targeting antibody (e.g., non-immune cell effector antibody) is an IgG and the immune effector cell engaging antibody is a scFv. In some embodiments, the immune effector cell is a leukocyte. In some embodiments, the immune effector cell is a T cell. In some embodiments, the immune effector cell is a NK cell. In some embodiments, the immune effector cell is a myeloid mononuclear cell.

In some embodiments, T-cell engaging multispecific activatable antibodies of the disclosure include a targeting antibody or antigen-binding fragment thereof and a T-cell engaging antibody or antigen-binding portion thereof, where at least one of the targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibodies include a cancer targeting antibody or antigen-binding fragment thereof and a T-cell engaging antibody or antigen-binding portion thereof, where at least one of the cancer targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibodies include a cancer targeting IgG antibody or antigen-binding fragment thereof and a T-cell engaging scFv, where at least one of the cancer targeting IgG antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MIND reduces the ability of the AB1 to bind the first target. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MIM1 reduces the ability of the AB1 to bind the first target, and the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments of an immune effector cell engaging multi specific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA. In some embodiments, the antigen is a stimulatory receptor present on the surface of a T cell or NK cell; examples of such stimulatory receptors include, but are not limited to, CD3, CD27, CD28, CD137 (also referred to as 4-1BB), GITR, HVEM, ICOS, NKG2D, and OX40. In some embodiments, the antigen is an inhibitory receptor present on the surface of a T-cell; examples of such inhibitory receptors include, but are not limited to, BTLA, CTLA-4, LAG3, PD-1, TIGIT, TIM3, and NK-expressed KIRs. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9.

One embodiment of the disclosure is a multispecific activatable antibody that is activatable in a cancer microenvironment and that includes an antibody, for example a IgG or scFv, directed to a tumor target and an agonist antibody, for example an IgG or scFv, directed to a co-stimulatory receptor expressed on the surface of an activated T cell or NK cell, wherein at least one of the cancer target antibody and/or agonist antibody is masked. Examples of co-stimulatory receptors include, but are not limited to, CD27, CD137, GITR, HVEM, NKG2D, and OX40. In this embodiment, the multispecific activatable antibody, once activated by tumor-associated proteases, would effectively crosslink and activate the T cell or NK cell expressed co-stimulatory receptors in a tumor-dependent manner to enhance the activity of T cells that are responding to any tumor antigen via their endogenous T cell antigen or NK-activating receptors. The activation-dependent nature of these T cell or NK cell costimulatory receptors would focus the activity of the activated multispecific activatable antibody to tumor-specific T cells, without activating all T cells independent of their antigen specificity. In one embodiment, at least the co-stimulatory receptor antibody of the multispecific activatable antibody is masked to prevent activation of autoreactive T cells that may be present in tissues that also express the antigen recognized by the tumor target-directed antibody in the multispecific activatable antibody, but whose activity is restricted by lack of co-receptor engagement.

One embodiment of the disclosure is a multispecific activatable antibody that is activatable in a disease characterized by T cell overstimulation, such as, but not limited to, an autoimmune disease or inflammatory disease microenvironment. Such a multispecific activatable antibody includes an antibody, for example a IgG or scFv, directed to a target comprising a surface antigen expressed in a tissue targeted by a T cell in autoimmune or inflammatory disease and an antibody, for example a IgG or scFv, directed to an inhibitory receptor expressed on the surface of a T cell or NK cell, wherein at least one of the disease tissue target antibody and/or T cell inhibitory receptor antibody is masked. Examples of inhibitory receptors include, but are not limited to, BTLA, CTLA-4, LAG3, PD-1, TIGIT, TIM3, and NK-expressed KIRs. Examples of a tissue antigen targeted by T cells in autoimmune disease include, but are not limited to, a surface antigen expressed on myelin or nerve cells in multiple sclerosis or a surface antigen expressed on pancreatic islet cells in Type 1 diabetes. In this embodiment, the multispecific activatable antibody when localized in the tissue under autoimmune attack or inflammation is activated and co-engages the T cell or NK cell inhibitory receptor to suppress the activity of autoreactive T cells responding to any disease tissue-targeted antigens via their endogenous TCR or activating receptors. In one embodiment, at least one or multiple antibodies are masked to prevent suppression of T cell responses in non-disease tissues where the target antigen may also be expressed.

In some embodiments, the T-cell engaging multispecific activatable antibody includes an anti-CD3 epsilon (CD3ε, also referred to herein as CD3e and CD3) scFv and a targeting antibody or antigen-binding fragment thereof, where at least one of the anti-CD3ε scFv and/or the targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CD3ε scFv and a cancer targeting antibody or antigen-binding fragment thereof, where at least one of the anti-CD3ε scFv and/or the cancer targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3ε scFv and a cancer targeting IgG antibody or antigen-binding fragment thereof, where at least one of the anti-CD3ε scFv and/or the cancer targeting IgG antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3 epsilon (CD3ε) scFv that is derived from OKT3, where at least one of the targeting antibody or antigen-binding fragment thereof and/ or the OKT3 scFv or OKT3-derived scFv is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an OKT3 scFv or OKT3-derived scFv and a cancer targeting antibody or antigen-binding fragment thereof, where at least one of the OKT3 scFv or OKT3-derived scFv and/or the cancer targeting antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3 ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an OKT3 scFv or OKT3-derived scFv and a cancer targeting IgG antibody or antigen-binding fragment thereof, where at least one of the OKT3 scFv or OKT3-derived scFv and/or the cancer targeting IgG antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CTLA-4 scFv, where at least one of the targeting antibody or antigen-binding fragment thereof and/or the anti-CTLA-4 scFv is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CTLA-4 scFv and a targeting IgG antibody or antigen-binding fragment thereof, where at least one of the anti-CTLA-4 scFv and/or the targeting IgG antibody or antigen-binding portion thereof is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4. In some embodiments, the targeting IgG antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody IgG or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the multi-antigen targeting antibodies and/or multi-antigen targeting activatable antibodies include at least a first antibody or antigen-binding fragment thereof that binds a first target and/or first epitope and a second antibody or antigen-binding fragment thereof that binds a second target and/or a second epitope. In some embodiments, the multi-antigen targeting antibodies and/or multi-antigen targeting activatable antibodies bind two or more different targets. In some embodiments, the multi-antigen targeting antibodies and/or multi-antigen targeting activatable antibodies bind two or more different epitopes on the same target. In some embodiments, the multi-antigen targeting antibodies and/or multi-antigen targeting activatable antibodies bind a combination of two or more different targets and two or more different epitopes on the same target.

In some embodiments, a multispecific activatable antibody comprising an IgG has the IgG variable domains masked. In some embodiments, a multispecific activatable antibody comprising a scFv has the scFv domains masked. In some embodiments, a multispecific activatable antibody has both IgG variable domains and scFv domains, where at least one of the IgG variable domains is coupled to a masking moiety. In some embodiments, a multispecific activatable antibody has both IgG variable domains and scFv domains, where at least one of the scFv domains is coupled to a masking moiety. In some embodiments, a multispecific activatable antibody has both IgG variable domains and scFv domains, where at least one of the IgG variable domains is coupled to a masking moiety and at least one of the scFv domains is coupled to a masking moiety. In some embodiments, a multispecific activatable antibody has both IgG variable domains and scFv domains, where each of the IgG variable domains and the scFv domains is coupled to its own masking moiety. In some embodiments, one antibody domain of a multispecific activatable antibody has specificity for a target antigen and another antibody domain has specificity for a T-cell surface antigen. In some embodiments, one antibody domain of a multispecific activatable antibody has specificity for a target antigen and another antibody domain has specificity for another target antigen. In some embodiments, one antibody domain of a multispecific activatable antibody has specificity for an epitope of a target antigen and another antibody domain has specificity for another epitope of the target antigen.

In a multispecific activatable antibody, a scFv can be fused to the carboxyl terminus of the heavy chain of an IgG activatable antibody, to the carboxyl terminus of the light chain of an IgG activatable antibody, or to the carboxyl termini of both the heavy and light chains of an IgG activatable antibody. In a multispecific activatable antibody, a scFv can be fused to the amino terminus of the heavy chain of an IgG activatable antibody, to the amino terminus of the light chain of an IgG activatable antibody, or to the amino termini of both the heavy and light chains of an IgG activatable antibody. In a multispecific activatable antibody, a scFv can be fused to any combination of one or more carboxyl termini and one or more amino termini of an IgG activatable antibody. In some embodiments, a masking moiety (MM) linked to a cleavable moiety (CM) is attached to and masks an antigen binding domain of the IgG. In some embodiments, a masking moiety (MM) linked to a cleavable moiety (CM) is attached to and masks an antigen binding domain of at least one scFv. In some embodiments, a masking moiety (MM) linked to a cleavable moiety (CM) is attached to and masks an antigen binding domain of an IgG and a masking moiety (MM) linked to a cleavable moiety (CM) is attached to and masks an antigen binding domain of at least one scFv.

The disclosure provides examples of multispecific activatable antibody structures which include, but are not limited to, the following: $(VL\text{-}CL)_2\text{:}(VH\text{-}CH1\text{-}CH2\text{-}CH3\text{-}L4\text{-}VH^*\text{-}L3\text{-}VL^*\text{-}L2\text{-}CM\text{-}L1\text{-}MM)_2$; $(VL\text{-}CL)_2\text{:}(VH\text{-}CH1\text{-}CH2\text{-}CH3\text{-}L4\text{-}VL^*\text{-}L3\text{-}VH^*\text{-}L2\text{-}CM\text{-}L1\text{-}MM)_2$; $(MM\text{-}L1\text{-}CM\text{-}L2\text{-}VL\text{-}CL)_2\text{:}(VH\text{-}CH1\text{-}CH2\text{-}CH3\text{-}L4\text{-}VH^*\text{-}L3\text{-}VL^*)_2$; $(MM\text{-}L1\text{-}CM\text{-}L2\text{-}VL\text{-}CL)_2\text{:}(VH\text{-}CH1\text{-}CH2\text{-}CH3\text{-}L4\text{-}VL^*\text{-}L3\text{-}VH^*)_2$; $(VL\text{-}CL)_2\text{:}(MM\text{-}L1\text{-}CM\text{-}L2\text{-}VL^*\text{-}L3\text{-}VH^*\text{-}L4\text{-}VH\text{-}CH1\text{-}CH2\text{-}CH3)_2$; $(VL\text{-}CL)_2\text{:}(MM\text{-}L1\text{-}CM\text{-}L2\text{-}VH^*\text{-}L3\text{-}VL^*\text{-}L4\text{-}VH\text{-}CH1\text{-}CH2\text{-}CH3)_2$; $(MM\text{-}L1\text{-}CM\text{-}L2\text{-}VL\text{-}CL)_2\text{:}(VL^*\text{-}L3\text{-}VH^*\text{-}L4\text{-}VH\text{-}CH1\text{-}CH2\text{-}CH3)_2$; $(MM\text{-}L1\text{-}CM\text{-}L2\text{-}VL\text{-}CL)_2\text{:}(VH^*\text{-}L3\text{-}VL^*\text{-}L4\text{-}VH\text{-}CH1\text{-}CH2\text{-}CH3)_2$; $(VL\text{-}CL\text{-}L4\text{-}VH^*\text{-}L3\text{-}VL^*\text{-}L2\text{-}CM\text{-}L1\text{-}MM)_2\text{:}(VH\text{-}CH1\text{-}CH2\text{-}CH3)_2$; $(VL\text{-}CL\text{-}L4\text{-}VL^*\text{-}L3\text{-}VH^*\text{-}L2\text{-}CM\text{-}L1\text{-}MM)_2\text{:}(VH\text{-}CH1\text{-}CH2\text{-}CH3)_2$; $(MM\text{-}L1\text{-}CM\text{-}L2\text{-}VL^*\text{-}L3\text{-}VH^*\text{-}L4\text{-}VL\text{-}CL)_2\text{:}(VH\text{-}CH1\text{-}CH2\text{-}CH3)_2$; $(MM\text{-}L1\text{-}CM\text{-}L2\text{-}VH^*\text{-}L3\text{-}VL^*\text{-}L4\text{-}VL\text{-}CL)_2\text{:}(VH\text{-}CH1\text{-}CH2\text{-}CH3)_2$; $(VL\text{-}CL\text{-}L4\text{-}VH^*\text{-}L3\text{-}VL^*\text{-}L2\text{-}CM\text{-}L1\text{-}MM)_2\text{:}(MM\text{-}L1\text{-}CM\text{-}L2\text{-}VL^*\text{-}L3\text{-}VH^*\text{-}L4\text{-}VH\text{-}CH1\text{-}CH2\text{-}CH3)_2$; $(VL\text{-}CL\text{-}L4\text{-}VH^*\text{-}L3\text{-}VL^*\text{-}L2\text{-}CM\text{-}L1\text{-}MM)_2\text{:}(MM\text{-}L1\text{-}CM\text{-}L2\text{-}VH^*\text{-}L3\text{-}VL^*\text{-}L4\text{-}VH\text{-}CH1\text{-}CH2\text{-}CH3)_2$; $(VL\text{-}CL\text{-}L4\text{-}VL^*\text{-}L3\text{-}VH^*\text{-}L2\text{-}CM\text{-}L1\text{-}MM)_2\text{:}(MM\text{-}L1\text{-}CM\text{-}L2\text{-}VL^*\text{-}L3\text{-}VH^*\text{-}L4\text{-}VH\text{-}CH1\text{-}CH2\text{-}CH3)_2$; $(VL\text{-}CL\text{-}L4\text{-}VL^*\text{-}L3\text{-}VH^*\text{-}L2\text{-}CM\text{-}L1\text{-}MM)_2\text{:}(MM\text{-}L1\text{-}CM\text{-}L2\text{-}VH^*\text{-}L3\text{-}VL^*\text{-}L4\text{-}VH\text{-}CH1\text{-}CH2\text{-}CH3)_2$; $(VL\text{-}CL\text{-}L4\text{-}VH^*\text{-}L3\text{-}VL^*)_2\text{:}(MM\text{-}L1\text{-}CM\text{-}L2\text{-}VL^*\text{-}L3\text{-}VH^*\text{-}L4\text{-}VH\text{-}CH1\text{-}CH2\text{-}CH3)_2$; $(VL\text{-}CL\text{-}L4\text{-}VH^*\text{-}L3\text{-}VL^*)_2\text{:}(MM\text{-}L1\text{-}CM\text{-}L2\text{-}VH^*\text{-}L3\text{-}VL^*\text{-}L4\text{-}VH\text{-}CH1\text{-}CH2\text{-}CH3)_2$; $(VL\text{-}CL\text{-}L4\text{-}VL^*\text{-}L3\text{-}VH^*)_2\text{:}(MM\text{-}L1\text{-}CM\text{-}L2\text{-}VL^*\text{-}L3\text{-}VH^*\text{-}L4\text{-}VH\text{-}CH1\text{-}CH2\text{-}CH3)_2$; $(VL\text{-}CL\text{-}L4\text{-}VL^*\text{-}L3\text{-}VH^*)_2\text{:}(MM\text{-}L1\text{-}CM\text{-}L2\text{-}VH^*\text{-}L3\text{-}VL^*\text{-}L4\text{-}VH\text{-}CH1\text{-}CH2\text{-}CH3)_2$; $(VL\text{-}CL\text{-}L4\text{-}VH^*\text{-}L3\text{-}VL^*\text{-}L2\text{-}CM\text{-}L1\text{-}MM)_2\text{:}(VL^*\text{-}L3\text{-}VH^*\text{-}L4\text{-}VH\text{-}CH1\text{-}CH2\text{-}CH3)_2$; $(VL\text{-}CL\text{-}L4\text{-}VH^*\text{-}L3\text{-}VL^*\text{-}L2\text{-}CM\text{-}L1\text{-}MM)_2\text{:}(VH^*\text{-}L3\text{-}VL^*\text{-}L4\text{-}VH\text{-}CH1\text{-}CH2\text{-}CH3)_2$; $(VL\text{-}CL\text{-}L4\text{-}VL^*\text{-}L3\text{-}VH^*\text{-}L2\text{-}CM\text{-}L1\text{-}MM)_2\text{:}(VL^*\text{-}L3\text{-}VH^*\text{-}L4\text{-}VH\text{-}CH1\text{-}CH2\text{-}CH3)_2$; or $(VL\text{-}CL\text{-}L4\text{-}VL^*\text{-}L3\text{-}VH^*\text{-}L2\text{-}CM\text{-}L1\text{-}MM)_2\text{:}(VH^*\text{-}L3\text{-}VL^*\text{-}L4\text{-}VH\text{-}CH1\text{-}CH2\text{-}CH3)_2$, wherein: VL and VH represent the light and heavy variable domains of the first specificity, contained in the IgG; VL* and VH* represent the variable domains of the second specificity, contained in the scFv; L1 is a linker peptide connecting the masking moiety (MM) and the cleavable moiety (CM); L2 is a linker peptide connecting the cleavable moiety (CM), and the antibody; L3 is a linker peptide connecting the variable domains of the scFv; L4 is a linker peptide connecting the antibody of the first specificity to the antibody of the second specificity; CL is the light-chain constant domain; and CH1, CH2, CH3 are the heavy chain constant domains. The first and second specificities may be toward any antigen or epitope.

In some embodiments of a T-cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory (also referred to herein as activating) or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137 (also referred to as TNFRSF9), CTLA-4, GITR, HVEM, ICOS, LAG3, NKG2D, OX40, PD-1, TIGIT, TIM3, or VISTA. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9. In some embodiments of a multi-antigen targeting activatable antibody, one antigen is selected from the group of targets listed in Table 1, and another antigen is selected from the group of targets listed in Table 1.

In some embodiments, the targeting antibody is an anti-EGFR antibody. In some embodiments, the targeting antibody is C225v5, which is specific for binding to EGFR. In some embodiments, the targeting antibody is C225, which is specific for binding to EGFR. In some embodiments, the targeting antibody is C225v4, which is specific for binding to EGFR. In some embodiments, the targeting antibody is C225v6, which is specific for binding to EGFR. In some embodiments, the targeting antibody is an anti-Jagged antibody. In some embodiments, the targeting antibody is 4D11, which is specific for binding to human and mouse Jagged 1 and Jagged 2. In some embodiments, the targeting antibody is 4D11v2, which is specific for binding to human and mouse Jagged 1 and Jagged 2.

In some embodiments, the targeting antibody can be in the form an activatable antibody. In some embodiments, the scFv(s) can be in the form of a Pro-scFv (see, e.g., WO 2009/025846, WO 2010/081173).

In some embodiments, the scFv is specific for binding CDR, and is or is derived from an antibody or fragment thereof that binds CDR, e.g., CH2527, FN18, H2C, OKT3, 2C11, UCHT1, or V9. In some embodiments, the scFv is specific for binding CTLA-4 (also referred to herein as CTLA and CTLA4).

In some embodiments, the anti-CTLA-4 scFv includes the amino acid sequence:

(SEQ ID NO: 692)
GGGSGGGGSGSGGGSGGGGSGGGEIVLTQSPGTLSLSPGERATLSCRASQ

SVSSSYLAWYQQKPGQAPRLLIYGASSRATGIPDRFSGSGSGTDFTLTIS

RLEPEDFAVYYCQQYGSSPLTFGGGTKVEIKRSGGSTITSYNVYYTKLSS

SGTQVQLVQTGGGVVQPGRSLRLSCAASGSTFSSYAMSWVRQAPGKGLEW

VSAISGSGGSTYYADSVKGRFTISRDNSKNTLYLQMNSLRAEDTAVYYCA

TNSLYWYFDLWGRGTLVTVSSAS

In some embodiments, the anti-CTLA-4 scFv includes the amino acid sequence that is at least 90%, 91%, 92%, 93%, 94%, 95%, 96%, 97%, 98%, 99% or more identical to the amino acid sequence of SEQ ID NO: 692.

In some embodiments, the anti-CDR scFv includes the amino acid sequence:

(SEQ ID NO: 693)
GGGSGGGGSGSGGGSGGGGSGGGQVQLQQSGAELARPGASVKMSCKASGY

TFTRYTMHWVKQRPGQGLEWIGYINPSRGYTNYNQKFKDKATLTTDKSSS

TAYMQLSSLTSEDSAVYYCARYYDDHYCLDYWGQGTTLTVSSGGGGSGGG

GSGGGGSQIVLTQSPAIMSASPGEKVTMTCSASSSVSYMNWYQQKSGTSP

KRWIYDTSKLASGVPAHFRGSGSGTSYSLTISGMEAEDAATYYCQQWSSN

PFTFGSGTKLEINR

In some embodiments, the anti-CDR scFv includes the amino acid sequence that is at least 90%, 91%, 92%, 93%, 94%, 95%, 96%, 97%, 98%, 99% or more identical to the amino acid sequence of SEQ ID NO: 693.

In some embodiments, the scFv is specific for binding one or more T-cells, one or more NK-cells and/or one or more macrophages. In some embodiments, the scFv is specific for binding a target selected from the group consisting of B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA.

In some embodiments, the multispecific activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the multispecific activatable antibody via a linker. In some embodiments, the agent is conjugated to the AB via a cleavable linker. In some embodiments, the agent is conjugated to the AB via a linker that includes at least one uPA-cleavable substrate sequence or at least one matriptase-cleavable substrate sequence. In some embodiments, the linker is a non-cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is an agent selected from the group listed in Table 4. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the multispecific activatable antibody also includes a detectable moiety. In some embodiments, the detectable moiety is a diagnostic agent.

In some embodiments, the multispecific activatable antibody naturally contains one or more disulfide bonds. In some embodiments, the multispecific activatable antibody can be engineered to include one or more disulfide bonds.

The disclosure also provides an isolated nucleic acid molecule encoding a multispecific activatable antibody described herein, as well as vectors that include these isolated nucleic acid sequences. The disclosure provides methods of producing a multispecific activatable antibody by culturing a cell under conditions that lead to expression of the activatable antibody, wherein the cell comprises such a nucleic acid molecule. In some embodiments, the cell comprises such a vector.

The disclosure also provides a method of manufacturing multispecific activatable antibodies of the disclosure by (a) culturing a cell comprising a nucleic acid construct that encodes the multispecific activatable antibody under conditions that lead to expression of the multispecific activatable, and (b) recovering the multispecific activatable antibody.

The disclosure also provides multispecific activatable antibodies and/or multispecific activatable antibody compositions that include at least a first antibody or antigen-binding fragment thereof (AB1) that specifically binds a first target or first epitope and a second antibody or antigen-biding fragment thereof (AB2) that binds a second target or a second epitope, where at least AB1 is coupled or otherwise attached to a masking moiety (MM1), such that coupling of the MM1 reduces the ability of AB1 to bind its target. In some embodiments, the MM1 is coupled to AB1 via a first cleavable moiety (CM1) sequence that includes a substrate for a protease, for example, a protease that is co-localized with the target of AB1 at a treatment site or a diagnostic site in a subject. The multispecific activatable antibodies provided herein are stable in circulation, activated at intended sites of therapy and/or diagnosis but not in normal, i.e., healthy tissue, and, when activated, exhibit binding to the target of AB1 that is at least comparable to the corresponding, unmodified multispecific antibody.

In some embodiments, the multispecific activatable antibody comprises a linking peptide between the MM1 and the CM1.

In some embodiments, the multispecific activatable antibody comprises a linking peptide between the CM1 and the AB1.

In some embodiments, the activatable antibody comprises a first linking peptide (LP1) and a second linking peptide (LP2), and at least a portion of the multispecific activatable antibody has the structural arrangement from N-terminus to C-terminus as follows in the uncleaved state: MM1-LP1-CM1-LP2-AB1 or AB1-LP2-CM1-LP1-MM1. In some embodiments, the two linking peptides need not be identical to each other.

In some embodiments, at least one of LP1 or LP2 includes an amino acid sequence selected from the group consisting of $(GS)_n$, $(GGS)_n$, $(GSGGS)_n$ (SEQ ID NO: 385) and $(GGGS)_n$ (SEQ ID NO: 386), where n is an integer of at least one. In some embodiments, at least one of LP1 or LP2 includes an amino acid sequence selected from the group consisting of GGSG (SEQ ID NO: 387), GGSGG (SEQ ID NO: 388), GSGSG (SEQ ID NO: 389), GSGGG (SEQ ID NO: 390), GGGSG (SEQ ID NO: 391), and GSSSG (SEQ ID NO: 392).

In some embodiments, the multispecific activatable antibody includes at least a first antibody or antigen-binding fragment thereof (AB1) that specifically binds a first target or first epitope and a second antibody or antigen-binding fragment thereof (AB2) that specifically binds a second target or second epitope. In some embodiments, each of the AB in the multispecific activatable antibody is independently selected from the group consisting of a monoclonal antibody, domain antibody, single chain, Fab fragment, a F(ab')$_2$ fragment, a scFv, a scAb, a dAb, a single domain heavy chain antibody, and a single domain light chain antibody. In some embodiments, each of the AB in the multispecific activatable antibody is a rodent (e.g., mouse or rat), chimeric, humanized or fully human monoclonal antibody.

In some embodiments, each of the AB in the multispecific activatable antibody has an equilibrium dissociation constant of about 100 nM or less for binding to its corresponding target or epitope.

In some embodiments, MM1 has an equilibrium dissociation constant for binding to its corresponding AB that is greater than the equilibrium dissociation constant of the AB to its corresponding target or epitope.

In some embodiments, MM1 has an equilibrium dissociation constant for binding to its corresponding AB that is no more than the equilibrium dissociation constant of the AB to its corresponding target or epitope.

In some embodiments, MM1 does not interfere or compete with its corresponding AB for binding to the corresponding target or epitope when the multispecific activatable antibody is in a cleaved state.

In some embodiments, MM1 is a polypeptide of about 2 to 40 amino acids in length. In some embodiments, each of the MM in the multispecific activatable antibody is a polypeptide of no more than 40 amino acids in length.

In some embodiments, MM1 has a polypeptide sequence that is different from that of target of the corresponding AB.

In some embodiments, MM1 has a polypeptide sequence that is no more than 50% identical to any natural binding partner of the corresponding AB. In some embodiments, MM1 has a polypeptide sequence that is no more than 25% identical to any natural binding partner of the corresponding AB. In some embodiments, MM1 has a polypeptide sequence that is no more than 10% identical to any natural binding partner of the corresponding AB.

In some embodiments, the coupling of MM1 reduces the ability of the corresponding AB to bind its target or epitope such that the dissociation constant ($K_d$) of the AB when coupled to the MM1 towards its corresponding target or epitope is at least 20 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 40 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 100 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 1000 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 10,000 times greater than the $K_d$ of the AB when not coupled to the MM1 towards its corresponding target or epitope.

In some embodiments, MM1 is an amino acid sequence selected from a MM disclosed herein.

In some embodiments, the multispecific activatable antibody includes at least a second masking moiety (MM2) that inhibits the binding of the AB2 to its target when the multispecific activatable antibody is in an uncleaved state, and a second cleavable moiety (CM2) coupled to the AB2, wherein the CM2 is a polypeptide that functions as a substrate for a second protease. In some embodiments, CM2 is a polypeptide of no more than 15 amino acids long. In some embodiments, the second protease is co-localized with the second target or epitope in a tissue, and wherein the second protease cleaves the CM2 in the multispecific activatable antibody when the multispecific activatable antibody is exposed to the second protease. In some embodiments, the first protease and the second protease are co-localized with the first target or epitope and the second target or epitope in a tissue. In some embodiments, the first protease and the second protease are the same protease. In some embodiments, CM1 and CM2 are different substrates for the same protease. In some embodiments, the protease is selected from the group consisting of those shown in Table 7. In some embodiments, the first protease and the second protease are different proteases. In some embodiments, the first protease and the second protease are different proteases selected from the group consisting of those shown in Table 7.

In some embodiments, each of the MM in the multispecific activatable antibody, e.g., MM1 and at least MM2, has an equilibrium dissociation constant for binding to its corresponding AB that is greater than the equilibrium dissociation constant of the AB to its corresponding target or epitope.

In some embodiments, each of the MM in the multispecific activatable antibody has an equilibrium dissociation constant for binding to its corresponding AB that is no more than the equilibrium dissociation constant of the AB to its corresponding target or epitope.

In some embodiments, each of the MM in the multispecific activatable antibody does not interfere or compete with its corresponding AB for binding to the corresponding target or epitope when the multispecific activatable antibody is in a cleaved state.

In some embodiments, each of the MM in the multispecific activatable antibody is a polypeptide of about 2 to 40 amino acids in length. In some embodiments, each of the MM in the multispecific activatable antibody is a polypeptide of no more than 40 amino acids in length.

In some embodiments, each of the MM in the multispecific activatable antibody has a polypeptide sequence that is different from that of target of the corresponding AB.

In some embodiments, each of the MM in the multispecific activatable antibody has a polypeptide sequence that is no more than 50% identical to any natural binding partner of the corresponding AB. In some embodiments, each of the MM in the multispecific activatable antibody has a polypeptide sequence that is no more than 25% identical to any natural binding partner of the corresponding AB. In some embodiments, each of the MM in the multispecific activatable antibody has a polypeptide sequence that is no more than 10% identical to any natural binding partner of the corresponding AB.

In some embodiments, the coupling of each of the MM reduces the ability of the corresponding AB to bind its target or epitope such that the dissociation constant ($K_d$) of the AB when coupled to the MM towards its corresponding target or epitope is at least 20 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 40 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 100 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 1000 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 10,000 times greater than the $K_d$ of the AB when not coupled to the MM towards its corresponding target or epitope.

In some embodiments, each of the MM is an amino acid sequence selected from a MM disclosed herein.

In some embodiments, at least one of CM1 and/or CM2 is cleaved by at least one protease selected from uPA and matriptase. In some embodiments, at least one of CM1 and/or CM2 includes an amino acid sequence selected from the group consisting of a core CM consensus sequence shown in Tables 8A-8J, a subgenus of a core CM consensus sequence shown in Tables 8A-8J, an expanded consensus sequence based on one of the core CM consensus sequence shown in Tables 8A-8J, an. In some embodiments, the expanded consensus sequence is a consensus sequence shown in Tables 9A-9J-3, a core CM consensus sequence shown in Tables 10A-10D, a subgenus of a core CM consensus sequence shown in Tables 10A-10D, and a consensus sequence shown in Tables 11A-11D.

In some embodiments, at least one of CM1 and/or CM2 includes an amino acid sequence selected from the group consisting of SEQ ID NOs: 163-267.

In some embodiments, the protease that cleaves the first cleavable moiety (CM1) sequence is co-localized with the target of the AB1 in the multispecific activatable antibody in a tissue, and the protease cleaves the CM1 in the multispecific activatable antibody when the multispecific activatable antibody is exposed to the protease.

In some embodiments, the multispecific activatable antibody includes more than one cleavable moiety sequence, and the protease that cleaves at least one cleavable moiety sequence is co-localized with the target of at least one of the AB regions in the multispecific activatable antibody in a tissue, and the protease cleaves the CM in the multispecific activatable antibody when the multispecific activatable antibody is exposed to the protease.

In some embodiments, each CM, e.g., CM1 and at least CM2, is positioned in the multispecific activatable antibody such that in the uncleaved state, binding of the multispecific activatable antibody to a target of one of the AB regions is reduced to occur with an equilibrium dissociation constant that is at least twofold greater than the equilibrium dissociation constant of an unmodified AB binding to its target, and whereas in the cleaved state, the AB binds its target.

In some embodiments, each CM, e.g., CM1 and at least CM2, is positioned in the multispecific activatable antibody such that in the uncleaved state, binding of the multispecific activatable antibody to a target of one of the AB regions is reduced to occur with an equilibrium dissociation constant that is at least threefold greater than the equilibrium dissociation constant of an unmodified AB binding to its target, and whereas in the cleaved state, the AB binds its target.

In some embodiments, each CM, e.g., CM1 and at least CM2, is positioned in the multispecific activatable antibody such that in the uncleaved state, binding of the multispecific activatable antibody to a target of one of the AB regions is reduced to occur with an equilibrium dissociation constant that is at least fourfold greater than the equilibrium dissociation constant of an unmodified AB binding to its target, and whereas in the cleaved state, the AB binds its target.

In some embodiments, each CM, e.g., CM1 and at least CM2, is positioned in the multispecific activatable antibody such that in the uncleaved state, binding of the multispecific activatable antibody to a target of one of the AB regions is reduced to occur with an equilibrium dissociation constant that is at least fivefold greater than the equilibrium dissociation constant of an unmodified AB binding to its target, and whereas in the cleaved state, the AB binds its target.

In some embodiments, each CM, e.g., CM1 and at least CM2, is positioned in the multispecific activatable antibody such that in the uncleaved state, binding of the multispecific activatable antibody to a target of one of the AB regions is reduced to occur with an equilibrium dissociation constant that is at least tenfold greater than the equilibrium dissociation constant of an unmodified AB binding to its target, and whereas in the cleaved state, the AB binds its target.

In some embodiments, each CM, e.g., CM1 and at least CM2, is positioned in the multispecific activatable antibody such that in the uncleaved state, binding of the multispecific activatable antibody to a target of one of the AB regions is reduced to occur with an equilibrium dissociation constant that is at least 20-fold greater than the equilibrium dissociation constant of an unmodified AB binding to its target, and whereas in the cleaved state, the AB binds its target.

In some embodiments, each CM is positioned in the multispecific activatable antibody such that in the uncleaved state, binding of the multispecific activatable antibody to a target of one of the AB regions is reduced to occur with an equilibrium dissociation constant that is at least 40-fold greater than the equilibrium dissociation constant of an unmodified AB binding to its target, and whereas in the cleaved state, the AB binds its target.

In some embodiments, each CM is positioned in the multispecific activatable antibody such that in the uncleaved state, binding of the multispecific activatable antibody to a target of one of the AB regions is reduced to occur with an equilibrium dissociation constant that is at least 50-fold greater than the equilibrium dissociation constant of an unmodified AB binding to its target, and whereas in the cleaved state, the AB binds its target.

In some embodiments, each CM is positioned in the multispecific activatable antibody such that in the uncleaved state, binding of the multispecific activatable antibody to a target of one of the AB regions is reduced to occur with an equilibrium dissociation constant that is at least 100-fold greater than the equilibrium dissociation constant of an unmodified AB binding to its target, and whereas in the cleaved state, the AB binds its target.

In some embodiments, each CM is positioned in the multispecific activatable antibody such that in the uncleaved state, binding of the multispecific activatable antibody to a target of one of the AB regions is reduced to occur with an equilibrium dissociation constant that is at least 200-fold greater than the equilibrium dissociation constant of an unmodified AB binding to its target, and whereas in the cleaved state, the AB binds its target.

In some embodiments, each CM in the multispecific activatable antibody is a polypeptide of up to 15 amino acids in length.

In some embodiments, at least one CM in the multispecific activatable antibody includes an amino acid sequence selected from the group consisting of SEQ ID NOs: 163-267 and the other CM includes the amino acid sequence LSGRSDNH (SEQ ID NO: 406). In some embodiments, at least one CM includes the amino acid sequence LSGRSDNH (SEQ ID NO: 406). In some embodiments, at least one cleavable moiety is selected for use with a specific protease, for example a protease that is known to be co-localized with at least one target of the multispecific activatable antibody. For example, suitable cleavable moieties for use in the multispecific activatable antibodies of the disclosure are cleaved by at least a protease such as urokinase, legumain, and/or matriptase (also referred to herein as MT-SP1 or MTSP1). In some embodiments, a suitable cleavable moiety includes at least one amino acid sequence selected from the group consisting of SEQ ID NO: 163-267.

In some embodiments, one CM is a substrate for at least one protease selected from uPA and matriptase, and the other CM in the multispecific activatable antibody is a substrate for a protease selected from the group consisting of those shown in Table 7. In some embodiments, the protease is selected from the group consisting of uPA, legumain, matriptase, ADAM17, BMP-1, TMPRSS3, TMPRSS4, neutrophil elastase, MMP-7, MMP-9, MMP-12, MMP-13, and MMP-14. In some embodiments, the protease is a cathepsin, such as, but not limited to, cathepsin S. In some embodiments, each CM in the multispecific activatable antibody is a substrate for a protease selected from the group consisting of uPA (urokinase plasminogen activator), legumain and matriptase. In some embodiments, the protease comprises uPA. In some embodiments, the protease comprises legumain. In some embodiments, the protease comprises matriptase.

In some embodiments, at least one CM in the multispecific activatable antibody is a substrate for at least two proteases. In some embodiments, at least one CM in the multispecific activatable antibody is a substrate for at least two proteases, wherein one of the proteases is selected from the group consisting of uPA and matriptase and the other protease is selected from the group consisting of those shown in Table 7. In some embodiments, at least one CM in the multispecific activatable antibody is a substrate for at least two proteases selected from the group consisting of uPA, legumain and matriptase.

In some embodiments, the multispecific activatable antibody includes at least a first CM (CM1) and a second CM (CM2). In some embodiments, CM1 and CM2 are part of a single cleavable linker that joins an MM to an AB. In some embodiments, CM1 is part of a cleavable linker that joins MIM1 to AB1, and CM2 is part of a separate cleavable linker that joins an MM2 to AB2. In some embodiments, a multispecific activatable antibody comprises more than two CMs. In some embodiments, such a multispecific activatable antibody comprises more than two CMs and more than two MMs. In some embodiments, CM1 and CM2 are each polypeptides of no more than 15 amino acids long. In some embodiments, at least one of the first CM and the second CM is a polypeptide that functions as a substrate for a protease selected from the group consisting of those listed in Table 7. In some embodiments, at least one of the first CM and the second CM is a polypeptide that functions as a substrate for a protease selected from the group consisting of uPA, legumain, and matriptase. In some embodiments, the first CM is cleaved by a first cleaving agent selected from the group consisting of uPA, legumain, and matriptase in a target tissue and the second CM is cleaved by a second cleaving agent in a target tissue. In some embodiments, the other protease is selected from the group consisting of those shown in Table 7. In some embodiments, the first cleaving agent and the second cleaving agent are the same protease selected from the group consisting of those listed in Table 7, and the first CM and the second CM are different substrates for the enzyme. In some embodiments, the first cleaving agent and the second cleaving agent are the same protease selected from the group consisting of uPA, legumain, and matriptase, and the first CM and the second CM are different substrates for the enzyme. In some embodiments, the first cleaving agent and the second cleaving agent are the same protease selected from the group listed in Table 7, and the first CM and the second CM are the same substrate. In some embodiments, the first cleaving agent and the second cleaving agent are different proteases. In some embodiments, the first cleaving agent and the second cleaving agent are different proteases selected from the group consisting of those shown in Table 7. In some embodiments, the first cleaving agent and the second cleaving agent are co-localized in the target tissue. In some embodiments, the first CM and the second CM are cleaved by at least one cleaving agent in the target tissue.

In some embodiments, the multispecific activatable antibody is exposed to and cleaved by a protease such that, in the activated or cleaved state, the activated multispecific activatable antibody includes a light chain amino acid sequence that includes at least a portion of LP2 and/or CM sequence after the protease has cleaved the CM.

The disclosure also provides compositions and methods that include a multispecific activatable antibody that includes at least a first antibody or antibody fragment (AB1) that specifically binds a target and a second antibody or antibody fragment (AB2), where at least the first AB in the multispecific activatable antibody is coupled to a masking moiety (MM1) that decreases the ability of AB1 to bind its target. In some embodiments, each AB is coupled to a MM that decreases the ability of its corresponding AB to each target. For example, in bispecific activatable antibody embodiments, AB1 is coupled to a first masking moiety (MM1) that decreases the ability of AB1 to bind its target, and AB2 is coupled to a second masking moiety (MM2) that decreases the ability of AB2 to bind its target. In some embodiments, the multispecific activatable antibody comprises more than two AB regions; in such embodiments, AB1 is coupled to a first masking moiety (MM1) that decreases the ability of AB1 to bind its target, AB2 is coupled to a second masking moiety (MM2) that decreases the ability of AB2 to bind its target, AB3 is coupled to a third masking moiety (MM3) that decreases the ability of AB3 to bind its target, and so on for each AB in the multispecific activatable antibody.

In some embodiments, the multispecific activatable antibody further includes at least one cleavable moiety (CM) that is a substrate for a protease, where the CM links a MM to an AB. For example, in some embodiments, the multispecific activatable antibody includes at least a first antibody or antibody fragment (AB1) that specifically binds a target and a second antibody or antibody fragment (AB2), where at least the first AB in the multispecific activatable antibody is coupled via a first cleavable moiety (CM1) to a masking moiety (MM1) that decreases the ability of AB1 to bind its target. In some bispecific activatable antibody embodiments, AB1 is coupled via CM1 to MM1, and AB2 is coupled via a second cleavable moiety (CM2) to a second masking moiety (MM2) that decreases the ability of AB2 to bind its target. In some embodiments, the multispecific activatable antibody comprises more than two AB regions; in some of these embodiments, AB1 is coupled via CM1 to MM1, AB2 is coupled via CM2 to MM2, and AB3 is coupled via a third cleavable moiety (CM3) to a third masking moiety (MM3) that decreases the ability of AB3 to bind its target, and so on for each AB in the multispecific activatable antibody.

Activatable Antibodies Having Non-Binding Steric Moieties or Binding Partners for Non-Binding Steric Moieties The disclosure also provides activatable antibodies that include non-binding steric moieties (NB) or binding partners (BP) for non-binding steric moieties, where the BP recruits or otherwise attracts the NB to the activatable antibody. The activatable antibodies provided herein include, for example, an activatable antibody that includes a non-binding steric moiety (NB), a cleavable linker (CL) and antibody or antibody fragment (AB) that binds a target; an activatable antibody that includes a binding partner for a non-binding steric moiety (BP), a CL and an AB; and an activatable antibody that includes a BP to which an NB has been recruited, a CL and an AB that binds the target. Activatable antibodies in which the NB is covalently linked to the CL and AB of the activatable antibody or is associated by interaction with a BP that is covalently linked to the CL and AB of the activatable antibody are referred to herein as "NB-containing activatable antibodies." By activatable or switchable is meant that the activatable antibody exhibits a first level of binding to a target when the activatable antibody is in an inhibited, masked or uncleaved state (i.e., a first conformation), and a second level of binding to the target when the activatable antibody is in an uninhibited, unmasked and/or cleaved state (i.e., a second conformation, i.e., activated antibody), where the second level of target binding is greater than the first level of target binding. The activatable antibody compositions can exhibit increased bioavailability and more favorable biodistribution compared to conventional antibody therapeutics.

In some embodiments, activatable antibodies provide for reduced toxicity and/or adverse side effects that could otherwise result from binding of the at non-treatment sites and/or non-diagnostic sites if the AB were not masked or otherwise inhibited from binding to such a site.

In one embodiment, the activatable antibody includes a non-binding steric moiety (NB); a cleavable linker (CL); and an antibody or antibody fragment (AB) that binds specifically to the target, wherein the NB is a polypeptide that does not bind specifically to the AB; the CL is a polypeptide that includes a substrate (S) for an enzyme; the CL is positioned such that in an uncleaved state, the NB interferes with binding of the AB to the target and in a cleaved state, the NB does not interfere with binding of the AB to the target; and the NB does not inhibit cleavage of the CL by the enzyme. As used herein and throughout, the term polypeptide refers to any polypeptide that includes at least two amino acid residues, including larger polypeptides, full-length proteins and fragments thereof, and the term polypeptide is not limited to single-chain polypeptides and can include multi-unit, e.g., multi-chain, polypeptides. In cases where the polypeptide is of a shorter length, for example, less than 50 amino acids total, the terms peptide and polypeptide are used interchangeably herein, and in cases where the polypeptide is of a longer length, e.g., 50 amino acids or greater, the terms polypeptide and protein are used interchangeably herein.

In one embodiment, the activatable antibody includes a non-binding steric moiety (NB); a cleavable linker (CL); and an antibody or antibody fragment (AB) that binds specifically to the target, wherein (i) the NB includes a polypeptide that does not bind specifically to the AB; (ii) CL is a polypeptide of up to 50 amino acids in length that includes a substrate (S) for an enzyme, e.g., a protease selected from matriptase and uPA; (iii) the CL is positioned such that in an uncleaved state, the NB interferes with binding of the AB to the target and in a cleaved state, the NB does not interfere with binding of the AB to the target; and (iv) the NB does not inhibit cleavage of the CL by the enzyme. For example, the CL has a length of up to 15 amino acids, a length of up to 20 amino acids, a length of up to 25 amino acids, a length of up to 30 amino acids, a length of up to 35 amino acids, a length of up to 40 amino acids, a length of up to 45 amino acids, a length of up to 50 amino acids, a length in the range of 10-50 amino acids, a length in the range of 15-50 amino acids, a length in the range of 20-50 amino acids, a length in the range of 25-50 amino acids, a length in the range of 30-50 amino acids, a length in the range of 35-50 amino acids, a length in the range of 40-50 amino acids, a length in the range of 45-50 amino acids, a length in the range of 10-40 amino acids, a length in the range of 15-40 amino acids, a length in the range of 20-40 amino acids, a length in the range of 25-40 amino acids, a length in the range of 30-40 amino acids, a length in the range of 35-40 amino acids, a length in the range of 10-30 amino acids, a length in the range of 15-30 amino acids, a length in the range of 20-30 amino acids, a length in the range of 25-30 amino acids, a length in the range of 10-20 amino acids, or a length in the range of 10-15 amino acids.

In one embodiment, the activatable antibody includes a non-binding steric moiety (NB); a cleavable linker (CL); and an antibody or antibody fragment (AB) that binds specifically to the target, wherein (i) the NB includes a polypeptide that does not bind specifically to the AB; (ii) the CL is a polypeptide that includes a substrate (S) for an enzyme, e.g., a protease selected from matriptase and uPA; (iii) the CL is positioned such that in an uncleaved state, the NB interferes with binding of the AB to the target and in a cleaved state, the NB does not interfere with binding of the AB to the target; (iv) the NB does not inhibit cleavage of the CL by the enzyme; and (v) the activatable antibody has the structural arrangement from N-terminus to C-terminus as follows in the uncleaved state: NB-CL-AB or AB-CL-NB.

In one embodiment, the activatable antibody includes a non-binding steric moiety (NB); a cleavable linker (CL); and an antibody or antibody fragment (AB) that binds specifically to the target, wherein (i) the NB includes a polypeptide that does not bind specifically to the AB; (ii) the CL is a polypeptide that includes a substrate (S) for an enzyme, e.g., a protease selected from matriptase and uPA; (iii) the CL is positioned such that in an uncleaved state, the NB interferes with binding of the AB to the target and in a cleaved state, the NB does not interfere with binding of the AB to the target, and wherein the NB in the uncleaved activatable antibody reduces the ability of the AB to bind the target by at least 50%, for example, by at least 60%, by at least 70%, by at least 75%, by at least 80%, by at least 85%, by at least 90%, by at least 95%, by at least 96%, by at least 97%, by at least 98%, by at least 99%, by at least 100% as compared to the ability of the cleaved AB to bind the target; and (iv) the NB does not inhibit cleavage of the CL by the enzyme. The reduction in the ability of the AB to bind the target is determined, e.g., using an assay as described herein or an in vitro target displacement assay such as, for example, the assay described in PCT Publication Nos. WO 2009/025846 and WO 2010/081173.

In one embodiment, the activatable antibody includes a binding partner (BP) for a non-binding steric moiety (NB); a cleavable linker (CL); and an antibody or antibody fragment (AB) that binds specifically to the target, wherein the BP is a polypeptide that binds to the NB when exposed thereto; the NB does not bind specifically to the AB; the CL is a polypeptide that includes a substrate (S) for an enzyme, e.g., a protease selected from matriptase and uPA; the CL is positioned such that in an uncleaved state in the presence of the NB, the NB interferes with binding of the AB to the target and in a cleaved state, the NB does not interfere with binding of the AB to the target and the BP does not interfere with binding of the AB to the target; and the NB and the BP do not inhibit cleavage of the CL by the enzyme. In some examples of this embodiment, the BP of the activatable antibody is optionally bound to the NB. In one embodiment, the NB is recruited by the BP of the activatable antibody in vivo.

In some examples of any of these activatable antibody embodiments, the activatable antibody is formulated as a composition. In some of these embodiments, the composition also includes the NB, where the NB is co-formulated with the activatable antibody that includes the BP, the CL, and the AB. In some examples of this embodiment, the BP is selected from the group consisting of an albumin binding peptide, a fibrinogen binding peptide, a fibronectin binding peptide, a hemoglobin binding peptide, a transferrin binding peptide, an immunoglobulin domain binding peptide, and other serum protein binding peptides.

In some examples of any of these activatable antibody embodiments, the NB is a soluble, globular protein. In some examples of any of these activatable antibody embodiments, the NB is a protein that circulates in the bloodstream. In some examples of any of these activatable antibody embodiments, the NB is selected from the group consisting of albumin, fibrinogen, fibronectin, hemoglobin, transferrin, an immunoglobulin domain, and other serum proteins.

In some examples of any of these activatable antibody embodiments, the CL is a polypeptide that includes a substrate (S) for a protease selected from matriptase and uPA. In some examples of any of these activatable antibody embodiments, the protease is co-localized with the in a tissue, and the protease cleaves the CL in the activatable antibody when the activatable antibody is exposed to the protease. In some examples of any of these activatable antibody embodiments, the CL is a polypeptide of up to 50 amino acids in length. In some examples of any of these activatable antibody embodiments, the CL is a polypeptide that includes a substrate (S) having a length of up to 15 amino acids, e.g., 3 amino acids long, 4 amino acids long, 5 amino acids long, 6 amino acids long, 7 amino acids long, 8 amino acids long, 9 amino acids long, 10 amino acids long, 11 amino acids long, 12 amino acids long, 13 amino acids long, 14 amino acids long, or 15 amino acids long.

In some examples of any of these activatable antibody embodiments, the activatable antibody has the structural arrangement from N-terminus to C-terminus as follows in the uncleaved state: NB-CL-AB, AB-CL-NB, BP-CL-AB or AB-CL-BP. In embodiments where the activatable antibody includes a BP and the activatable antibody is in the presence of the corresponding NB, the activatable antibody has a structural arrangement from N-terminus to C-terminus as follows in the uncleaved state: NB:BP-CM-AB or AB-CM-BP:NB, where ":" represents an interaction, e.g., binding, between the NB and BP.

In some examples of any of these activatable antibody embodiments, the activatable antibody includes an antibody or antigen-binding fragment thereof that specifically binds a given target and is a monoclonal antibody, domain antibody, single chain, Fab fragment, a F(ab')$_2$ fragment, a scFv, a scab, a dAb, a single domain heavy chain antibody, or a single domain light chain antibody. In some embodiments, such an antibody or immunologically active fragment thereof that binds the target a mouse, other rodent, chimeric, humanized or fully human monoclonal antibody.

In some examples of any of these activatable antibody embodiments, the activatable antibody includes a combination of a variable heavy chain region comprising an amino acid sequence presented herein and a variable light chain region comprising an amino acid sequence presented herein. In some embodiments, the activatable antibody includes a combination of a variable heavy chain region comprising an amino acid sequence that is at least 90%, 91%, 92%, 93%, 94%, 95%, 96%, 97%, 98%, 99% or more identical to an amino acid sequence presented herein, and a variable light chain region comprising an amino acid sequence that is at least 90%, 91%, 92%, 93%, 94%, 95%, 96%, 97%, 98%, 99% or more identical to an amino acid sequence presented herein.

In some examples of any of these activatable antibody embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker. In some embodiments, the agent is conjugated to the AB via a noncleavable linker. In some embodiments, the agent is an agent selected from the group listed in Table 3. In some embodiments, the agent is a microtubule inhibitor. In some embodiments, the agent is a nucleic acid damaging agent, such as a DNA alkylator or DNA intercalator, or other DNA damaging agent. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some examples of any of these activatable antibody embodiments, the activatable antibody also includes a detectable moiety. In some embodiments, the detectable moiety is a diagnostic agent.

In some examples of any of these activatable antibody embodiments, the activatable antibody also includes a spacer. In some examples of any of these activatable antibody embodiments, the activatable antibody also includes a signal peptide. In some embodiments, the signal peptide is conjugated to the activatable antibody via a spacer. In some examples of any of these activatable antibody embodiments, the spacer is joined directly to the MM of the activatable antibody.

In some embodiments, the serum half-life of the activatable antibody is longer than that of the corresponding antibody; e.g., the pK of the activatable antibody is longer than that of the corresponding antibody. In some embodiments, the serum half-life of the activatable antibody is similar to that of the corresponding antibody. In some embodiments, the serum half-life of the activatable antibody is at least 15 days when administered to an organism. In some embodiments, the serum half-life of the activatable antibody is at least 12 days when administered to an organism. In some embodiments, the serum half-life of the activatable antibody is at least 11 days when administered to an organism. In some embodiments, the serum half-life of the activatable antibody is at least 10 days when administered to an organism. In some embodiments, the serum half-life of the activatable antibody is at least 9 days when administered to an organism. In some embodiments, the serum half-life of the activatable antibody is at least 8 days when administered to an organism. In some embodiments, the serum half-life of the activatable antibody is at least 7 days when administered to an organism. In some embodiments, the serum half-life of the activatable antibody is at least 6 days when administered to an organism. In some examples of any of these activatable antibody embodiments, the serum half-life of the activatable antibody is at least 5 days when administered to an organism. In some embodiments, the serum half-life of the activatable antibody is at least 4 days when administered to an organism. In some embodiments, the serum half-life of the activatable antibody is at least 3 days when administered to an organism. In some embodiments, the serum half-life of the activatable antibody is at least 2 days when administered to an organism. In some embodiments, the serum half-life of the activatable antibody is at least 24 hours when administered to an organism. In some embodiments, the serum half-life of the activatable antibody is at least 20 hours when administered to an organism. In some embodiments, the serum half-life of the activatable antibody is at least 18 hours when administered to an organism. In some embodiments, the serum half-life of the activatable antibody is at least 16 hours when administered to an organism. In some embodiments, the serum half-life of the activatable antibody is at least 14 hours when administered to an organism. In some embodiments, the serum half-life of the activatable antibody is at least 12 hours when administered to an organism. In some embodiments, the serum half-life of the activatable antibody is at least 10 hours when administered to an organism. In some embodiments, the serum half-life of the activatable antibody is at least 8 hours when administered to an organism. In some embodiments, the serum half-life of the activatable antibody is at least 6 hours when administered to an organism. In some embodiments, the serum half-life of the activatable antibody is at least 4 hours when administered to an organism. In some embodiments, the serum half-life of the activatable antibody is at least 3 hours when administered to an organism.

The disclosure also provides an isolated nucleic acid molecule encoding any of these activatable antibodies, as well as vectors that include these isolated nucleic acid sequences. The disclosure provides methods of producing an activatable antibody by culturing a cell under conditions that lead to expression of the activatable antibody, wherein the cell comprises such a nucleic acid sequence. In some embodiments, the cell comprises such a vector.

The dissociation constant ($K_d$) of the NB-containing activatable antibody toward the target is greater than the $K_d$ of the AB towards the target when it is not associated with the NB or NB:BP. The dissociation constant ($K_d$) of the NB-containing activatable antibody toward the target is greater than the $K_d$ of the parental AB towards the target. For example, the $K_d$ of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB when it is not associated with the NB or NB:BP or the $K_d$ of the parental AB towards the target. Conversely, the binding affinity of the NB-containing activatable antibody towards the target is lower than the binding affinity of the AB when it is not associated with the NB or NB:BP or lower than the binding affinity of the parental AB towards the target. For example, the binding affinity of the NB-containing activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB when it is not associated with the NB or NB:BP or lower than the binding affinity of the parental AB towards the target.

When the NB-containing activatable antibody is in the presence of the target, specific binding of the AB to the target is reduced or inhibited, as compared to the specific binding of the AB when it is not associated with the NB or NB:BP. When the NB-containing activatable antibody is in the presence of the target, specific binding of the AB to the target is reduced or inhibited, as compared to the specific binding of the parental AB to the target. When compared to the binding of the AB not associated with an NB or NB:BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

When the NB-containing activatable antibody is in the presence of the target but not in the presence of a modifying agent (for example a protease or other enzyme), specific binding of the AB to the target is reduced or inhibited, as compared to the specific binding of the AB when it is not associated with the NB or NB:BP. When the NB-containing activatable antibody is in the presence of the target but not in the presence of a modifying agent (for example a protease, other enzyme, reduction agent, or light), specific binding of the AB to the target is reduced or inhibited, as compared to the specific binding of the parental AB to the target. When compared to the binding of the AB not associated with an NB or NB:BP or the binding of the parental AB to the target, the ability of the NB-containing activatable antibody to bind the target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

In some examples of any of these activatable antibody embodiments, the activatable antibody includes an agent conjugated to the AB to produce an activatable antibody conjugate. In some embodiments of the activatable antibody conjugate, the agent is a therapeutic agent. In some embodiments, the agent is a diagnostic agent. In some embodiments, the agent is a detectable marker. In some embodiments of the activatable antibody conjugate, the agent is an antineoplastic agent. In some embodiments of the activatable antibody conjugate, the agent is a toxin or fragment thereof. In some embodiments of the activatable antibody conjugate, the agent is conjugated to the AB via a linker. In some embodiments of the activatable antibody conjugate, the linker is a cleavable linker. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 3. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some examples of any of these activatable antibody embodiments, the activatable antibodies are dual-target binding activatable antibodies. Such dual target binding activatable antibodies contain two Abs that may bind the same or different targets. In specific embodiments, dual-targeting activatable antibodies contain bispecific antibodies or antibody fragments.

Dual target binding activatable antibodies are designed so as to have a CL cleavable by a cleaving agent, e.g., a protease selected from matriptase and uPA, that is co-localized in a target tissue with one or both of the targets capable of binding to the ABs of the activatable antibodies. Dual target binding activatable antibodies with more than one AB to the same or different targets can be designed so as to have more than one CL, wherein the first CL is cleavable by a cleaving agent in a first target tissue and wherein the second CL is cleavable by a cleaving agent in a second target tissue, with one or more of the targets binding to the ABs of the activatable antibodies. In one embodiment, the first and second target tissues are spatially separated, for example, at different sites in the organism. In one embodiment, the first and second target tissues are the same tissue temporally separated, for example the same tissue at two different points in time, for example the first time point is when the tissue is an early stage tumor, and the second time point is when the tissue is a late stage tumor.

The disclosure also provides nucleic acid molecules encoding the activatable antibodies described herein. The disclosure also provides vectors that include these nucleic acids. The activatable antibodies described herein are produced by culturing a cell under conditions that lead to expression of the activatable antibody, wherein the cell includes these nucleic acid molecules or vectors.

The disclosure also provides methods of manufacturing activatable antibodies. In one embodiment, the method includes the steps of (a) culturing a cell that includes a nucleic acid construct that encodes the activatable antibody under conditions that lead to expression of the activatable antibody, wherein the activatable antibody includes (i) a non-binding steric moiety (NB); (ii) a cleavable linker (CL);

and (iii) an antibody or an antigen binding fragment thereof (AB) that specifically binds a target, wherein (1) the NB does not bind specifically to the AB; (2) the CL is a polypeptide that includes a substrate (S) for an enzyme, e.g., a protease selected from matriptase and uPA; (3) the CL is positioned such that in an uncleaved state, the NB interferes with binding of the AB to the target and in a cleaved state, the NB does not interfere with binding of the AB to the target; and (4) the NB does not inhibit cleavage of the CL by the enzyme; and (b) recovering the activatable antibody.

In some embodiments, the method includes the steps of (a) culturing a cell that includes a nucleic acid construct that encodes the activatable antibody under conditions that lead to expression of the activatable antibody, wherein the activatable antibody includes (i) a binding partner (BP) for a non-binding steric moiety (NB); (ii) a cleavable linker (CL); and (iii) an antibody or an antigen binding fragment thereof (AB) that specifically binds a target, wherein (1) the NB does not bind specifically to the AB; (2) the CL is a polypeptide that includes a substrate (S) for an enzyme, e.g., a protease selected from matriptase and uPA; (3) the CL is positioned such that in an uncleaved state in the presence of the NB, the NB interferes with binding of the AB to the target and in a cleaved state, the NB does not interfere with binding of the AB to the target and the BP does not interfere with binding of the AB to the target; and (4) the NB and the BP do not inhibit cleavage of the CL by the enzyme; and (b) recovering the activatable antibody. In some examples of this embodiment, the BP of the activatable antibody is bound to the NB.

Use of CM-Containing Molecules Including Conjugated Antibodies and Activatable Antibodies It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the disclosure, which include a CM-containing molecule, such as by way of non-limiting example, a conjugated antibody, an activatable antibody and/or a conjugated activatable antibody, are used to prevent, treat or otherwise ameliorate a disease or disorder associated with aberrant target expression and/or activity. For example, therapeutic formulations of the disclosure, which include a CM-containing molecule, e.g., a conjugated antibody, an activatable antibody and/or a conjugated activatable antibody, are used to treat or otherwise ameliorate inflammation, an inflammatory disorder, an autoimmune disease and/or a cancer or other neoplastic condition. In some embodiments, the cancer is a solid tumor or a hematologic malignancy where the target is expressed. In some embodiments, the cancer is a solid tumor where the target is expressed. In some embodiments, the cancer is a hematologic malignancy where the target is expressed. In some embodiments, the target is expressed on parenchyma (e.g., in cancer, the portion of an organ or tissue that often carries out function(s) of the organ or tissue). In some embodiments, the target is expressed on a cell, tissue, or organ. In some embodiments, the target is expressed on stroma (i.e., the connective supportive framework of a cell, tissue, or organ). In some embodiments, the target is expressed on an osteoblast. In some embodiments, the target is expressed on the endothelium (vasculature). In some embodiments, the target is expressed on a cancer stem cell. In some embodiments, the agent to which the activatable antibody is conjugated is a microtubule inhibitor. In some embodiments, the agent to which the activatable antibody is conjugated is a nucleic acid damaging agent.

Efficaciousness of prevention, amelioration or treatment is determined in association with any known method for diagnosing or treating the disease or disorder associated with target expression and/or activity, such as, for example, aberrant target expression and/or activity. Prolonging the survival of a subject or otherwise delaying the progression of the disease or disorder associated with target expression and/or activity, e.g., aberrant target expression and/or activity, in a subject indicates that the conjugated antibody, activatable antibody and/or conjugated activatable antibody confers a clinical benefit.

A CM-containing molecule, e.g., a conjugated antibody, an activatable antibody and/or a conjugated activatable antibody can be administered in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

In some embodiments where antibody fragments are used, the smallest fragment that specifically binds to the binding domain of the target protein is selected. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compounds as necessary for the particular indication being treated, for example, in some embodiments, those with complementary activities that do not adversely affect each other. In some embodiments, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

In some embodiments, the CM-containing molecule, e.g., the conjugated antibody, activatable antibody and/or conjugated activatable antibody contains a detectable label. An intact antibody, or a fragment thereof (e.g., Fab, scFv, or $F(ab)_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the disclosure can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, immunochemical staining, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, NJ, 1995; "Immunoassay", E. Diamandis and T. Christopoulus, Academic Press, Inc., San Diego, CA, 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The conjugated antibodies, activatable antibodies and/or conjugated activatable antibodies of the disclosure are also useful in a variety of diagnostic and prophylactic formulations. In one embodiment, a conjugated antibody, an activatable antibody and/or a conjugated activatable antibody is administered to patients that are at risk of developing one or more of the aforementioned disorders. A patient's or organ's predisposition to one or more of the aforementioned disorders can be determined using genotypic, serological or biochemical markers.

In some embodiments of the disclosure, a conjugated antibody, an activatable antibody and/or a conjugated activatable antibody is administered to human individuals diagnosed with a clinical indication associated with one or more of the aforementioned disorders. Upon diagnosis, a conjugated antibody, an activatable antibody and/or a conjugated activatable antibody is administered to mitigate or reverse the effects of the clinical indication.

A conjugated antibody, an activatable antibody and/or a conjugated activatable antibody of the disclosure is also useful in the detection of a target in patient samples and accordingly are useful as diagnostics. For example, the antibodies and/or activatable antibodies, and conjugated versions thereof, of the disclosure are used in in vitro assays, e.g., ELISA, to detect target levels in a patient sample.

In one embodiment, a conjugated antibody, an activatable antibody and/or a conjugated activatable antibody of the disclosure is immobilized on a solid support (e.g., the well(s) of a microtiter plate). The immobilized conjugated antibody, activatable antibody and/or conjugated activatable antibody serves as a capture antibody for any target that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies of the disclosure, and conjugated versions thereof, in an in vitro diagnostic assay, it is possible to stage a disease in a subject based on expression levels of the target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

A conjugated antibody, an activatable antibody and/or a conjugated activatable antibody can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM can be used to detect the presence or absence of an enzyme that is capable of cleaving the CM. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM) but also that the tissue expresses target to which the activated antibody binds.

For example, the CM can be selected to be substrate for at least one protease selected from matriptase and uPA found at the site of a tumor, at the site of a viral or bacterial infection at a biologically confined site (e.g., such as in an abscess, in an organ, and the like), and the like. The AB can be one that binds a target antigen. Using methods as disclosed herein, or when appropriate, methods familiar to one skilled in the art, a detectable label (e.g., a fluorescent label or radioactive label or radiotracer) can be conjugated to an AB or other region of an antibody and/or activatable antibody. Suitable detectable labels are discussed in the context of the above screening methods and additional specific examples are provided below. Using an AB specific to a protein or peptide of the disease state, along with at least one protease selected from matriptase and uPA whose activity is elevated in the disease tissue of interest, activatable antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM susceptible to cleavage by an enzyme, the activatable antibodies can be used to detect (either qualitatively or quantitatively) the presence of an enzyme in the sample. In another example, where the activatable antibodies contain a CM susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a protease selected from matriptase and uPA that is specific for the CM of the activatable antibody. In some embodiments, the presence of the protease selected from matriptase and uPA can be confirmed using broad spectrum protease inhibitors such as those described herein, and/or by using an agent that is specific for the protease, for example, an antibody such as A11, which is specific for the protease matriptase and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a protease selected from matriptase and uPA that is specific for the CM of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease selected from matriptase and uPA that is specific for the CM of the activatable antibody.

These techniques are also useful in kits and/or as reagents for the detection, identification or characterization of protease activity in a variety of cells, tissues, and organisms based on the protease-specific CM in the activatable antibody.

The disclosure provides methods of using the antibodies and/or activatable antibodies in a variety of diagnostic and/or prophylactic indications. For example, the disclosure provides methods of detecting presence or absence of a cleaving agent and a target of interest in a subject or a sample by (i) contacting a subject or sample with an activatable antibody, wherein the activatable antibody comprises a masking moiety (MM), a cleavable moiety (CM) that is cleaved by the cleaving agent, e.g., a protease selected from matriptase and uPA, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent and the target are present in the subject or sample and wherein no detectable level of activated activatable antibody in the subject or sample indicates that the cleaving agent, the target or both the cleaving agent and the target are absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody in the presence of a target of interest, e.g., the target, wherein the activatable antibody comprises a masking moiety (MM), a cleavable moiety (CM) that is cleaved by the cleaving agent, e.g., a protease selected from matriptase and uPA, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody comprises a masking moiety (MM), a cleavable moiety (CM) that is cleaved by the cleaving agent, e.g., a protease selected from matriptase and uPA, and an antigen binding domain or fragment thereof (AB) that specifically binds the target of interest, wherein the activatable antibody in an uncleaved, non-activated state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB and is not a modified form of a natural binding partner of the AB; and (b) wherein, in an uncleaved, non-activated state, the MM interferes with specific binding of the AB to the target, and in a cleaved, activated state the MM does not interfere or compete with specific binding of the AB to the target; and (ii) measuring a level of activated activatable antibody in the subject or sample, wherein a detectable level of activated activatable antibody in the subject or sample indicates that the cleaving agent is present in the subject or sample and wherein no detectable level of activated activatable antibody in the subject or sample indicates that the cleaving agent is absent and/or not sufficiently present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides methods of detecting presence or absence of a cleaving agent in a subject or a sample by (i) contacting a subject or sample with an activatable antibody, wherein the activatable antibody comprises a masking moiety (MM), a cleavable moiety (CM) that is cleaved by the cleaving agent, e.g., a protease selected from matriptase and uPA, an antigen binding domain (AB) that specifically binds the target, and a detectable label, wherein the activatable antibody in an uncleaved, non-activated state comprises a structural arrangement from N-terminus to C-terminus as follows: MM-CM-AB or AB-CM-MM; wherein the MM is a peptide that inhibits binding of the AB to the target, and wherein the MM does not have an amino acid sequence of a naturally occurring binding partner of the AB and is not a modified form of a natural binding partner of the AB; wherein, in an uncleaved, non-activated state, the MM interferes with specific binding of the AB to the target, and in a cleaved, activated state the MM does not interfere or compete with specific binding of the AB to the target; and wherein the detectable label is positioned on a portion of the activatable antibody that is released following cleavage of the CM; and (ii) measuring a level of detectable label in the subject or sample, wherein a detectable level of the detectable label in the subject or sample indicates that the cleaving agent is absent and/or not sufficiently present in the subject or sample and wherein no detectable level of the detectable label in the subject or sample indicates that the cleaving agent is present in the subject or sample. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody (e.g., an activatable antibody to which a therapeutic agent is conjugated) described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent and the target are present in the subject or biological sample and wherein no detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample.

The disclosure also provides methods of detecting presence or absence of a cleaving agent in a subject or a sample by (i) contacting a subject or biological sample with an activatable antibody in the presence of the target, and (ii) measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a cleavable moiety (CM) that is cleaved by the cleaving agent, e.g., a protease selected from matriptase and uPA, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments all antigen binding sites are masked. In some embodiments, the measuring step includes use of a secondary reagent comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample with an activatable antibody in the presence of the target, and measuring a level of activated activatable antibody in the subject or biological sample, wherein a detectable level of activated activatable antibody in the subject or biological sample indicates that the cleaving agent is present in the subject or biological sample and wherein no detectable level of activated activatable antibody in the subject or biological sample indicates that the cleaving agent is absent and/or not sufficiently present in the subject or biological sample at a detectable level, such that protease cleavage of the activatable antibody cannot be detected in the subject or biological sample. Such an activatable antibody includes a masking moiety (MM), a cleavable moiety (CM) that is cleaved by the cleaving agent, e.g., a protease selected from matriptase and uPA, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the detectable label is attached to the masking moiety. In some embodiments, the detectable label is attached to the cleavable moiety N-terminal to the protease cleavage site. In some embodiments, a single antigen binding site of the AB is masked. In some embodiments wherein an antibody of the disclosure has at least two antigen binding sites, at least one antigen binding site is masked and at least one antigen binding site is not masked. In some embodiments all antigen binding sites are masked. In some embodiments, the measuring step includes use of a secondary reagent comprising a detectable label.

The disclosure also provides kits for use in methods of detecting presence or absence of a cleaving agent in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM, wherein a detectable level of activated activatable antibody in the subject or biological sample indicates that the cleaving agent is absent and/or not sufficiently present in the subject or biological sample such that the target binding and/or protease cleavage of the activatable antibody cannot be detected in the subject or biological sample, and wherein no detectable level of activated activatable antibody in the subject or biological sample indicates that the cleaving agent is present in the subject or biological sample at a detectable level.

The disclosure provides methods of detecting presence or absence of a cleaving agent and the target in a subject or a sample by (i) contacting a subject or biological sample with an activatable antibody, wherein the activatable antibody includes a detectable label that is positioned on a portion of the activatable antibody that is released following cleavage of the CM and (ii) measuring a level of activated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a cleavable moiety (CM) that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent and the target in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein a detectable level of activated activatable antibody in the subject or biological sample indicates that the cleaving agent, the target or both the cleaving agent and the target are absent and/or not sufficiently present in the subject or biological sample, such that the target binding and/or protease cleavage of the activatable antibody cannot be detected in the subject or biological sample, and wherein a reduced detectable level of activated activatable antibody in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

The disclosure also provides methods of detecting presence or absence of a cleaving agent in a subject or a sample by (i) contacting a subject or biological sample with an activatable antibody, wherein the activatable antibody includes a detectable label that is positioned on a portion of the activatable antibody that is released following cleavage of the CM; and (ii) measuring a level of detectable label in the subject or biological sample, wherein a detectable level of the detectable label in the subject or biological sample indicates that the cleaving agent is absent and/or not sufficiently present in the subject or biological sample at a detectable level, such that protease cleavage of the activatable antibody cannot be detected in the subject or biological sample, and wherein a reduced detectable level of the detectable label in the subject or biological sample indicates that the cleaving agent is present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%. Such an activatable antibody includes a masking moiety (MM), a cleavable moiety (CM) that is cleaved by the cleaving agent, and an antigen binding domain or fragment thereof (AB) that specifically binds the target, wherein the activatable antibody in an uncleaved (i.e., non-activated) state comprises a structural arrangement from N-terminus to C-terminus as follows: MM-CM-AB or AB-CM-MM; (a) wherein the MM is a peptide that inhibits binding of the AB to the target, and wherein the MM does not have an amino acid sequence of a naturally occurring binding partner of the AB; and (b) wherein the MM of the activatable antibody in an uncleaved state interferes with specific binding of the AB to the target, and wherein the MM of an activatable antibody in a cleaved (i.e., activated) state does not interfere or compete with specific binding of the AB to the target. In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

The disclosure also provides kits for use in methods of detecting presence or absence of a cleaving agent of interest in a subject or a sample, where the kits include at least an activatable antibody and/or conjugated activatable antibody described herein for use in contacting a subject or biological sample and means for detecting the level of activated activatable antibody and/or conjugated activatable antibody in the subject or biological sample, wherein the activatable antibody includes a detectable label that is positioned on a portion of the activatable antibody that is released following cleavage of the CM, wherein a detectable level of the detectable label in the subject or biological sample indicates that the cleaving agent, the target, or both the cleaving agent and the target are absent and/or not sufficiently present in the subject or biological sample, such that the target binding and/or protease cleavage of the activatable antibody cannot be detected in the subject or biological sample, and wherein a reduced detectable level of the detectable label in the subject or biological sample indicates that the cleaving agent and the target are present in the subject or biological sample. A reduced level of detectable label is, for example, a reduction of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% and/or about 100%.

In some embodiments of these methods and kits, the activatable antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods and kits, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments in situ imaging is used to identify or otherwise refine a patient population suitable for treatment with an activatable antibody of the disclosure. For example, patients that test positive for both the target (e.g., the target) and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative for either or both of the target (e.g., the target) and the protease that cleaves the substrate in the CM in the activatable antibody being tested using these methods might be identified as suitable candidates for another form of therapy. In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease). In some embodiments, the patient is then administered a therapeutically effective amount of the conjugated activatable antibody for which the patient tested positive.

In some embodiments in vivo imaging is used to identify or otherwise refine a patient population suitable for treatment with an activatable antibody of the disclosure. For example, patients that test positive for both the target (e.g., the target) and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative might be identified as suitable candidates for another form of therapy. In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease). In some embodiments, the patient is then administered a therapeutically effective amount of the conjugated activatable antibody for which the patient tested positive.

In some embodiments of the methods and kits, the method or kit is used to identify or otherwise refine a patient population suitable for treatment with an activatable antibody of the disclosure. For example, patients that test positive for both the target (e.g., the target) and a protease that cleaves the substrate in the cleavable moiety (CM) of the activatable antibody being tested in these methods are identified as suitable candidates for treatment with such an activatable antibody comprising such a CM. Likewise, patients that test negative for both of the targets (e.g., the target) and the protease that cleaves the substrate in the CM in the activatable antibody being tested using these methods might be identified as suitable candidates for another form of therapy. In some embodiments, such patients can be tested with other activatable antibodies until a suitable activatable antibody for treatment is identified (e.g., an activatable antibody comprising a CM that is cleaved by the patient at the site of disease). In some embodiments, patients that test negative for either of the target (e.g., the target) are identified as suitable candidates for treatment with such an activatable antibody comprising such a CM. In some embodiments, patients that test negative for either of the target (e.g., the target) are identified as not being suitable candidates for treatment with such an activatable antibody comprising such a CM. In some embodiments, such patients can be tested with other activatable antibodies until a suitable activatable antibody for treatment is identified (e.g., an activatable antibody comprising a CM that is cleaved by the patient at the site of disease). In some embodiments, the activatable antibody is an activatable antibody to which a therapeutic agent is conjugated. In some embodiments, the activatable antibody is not conjugated to an agent. In some embodiments, the activatable antibody comprises a detectable label. In some embodiments, the detectable label is positioned on the AB. In some embodiments, measuring the level of activatable antibody in the subject or sample is accomplished using a secondary reagent that specifically binds to the activated antibody, wherein the reagent comprises a detectable label. In some embodiments, the secondary reagent is an antibody comprising a detectable label.

In some embodiments, a method or kit is used to identify or otherwise refine a patient population suitable for treatment with an anti-the target activatable antibody and/or conjugated activatable antibody (e.g., activatable antibody to which a therapeutic agent is conjugated) of the disclosure, followed by treatment by administering that activatable antibody and/or conjugated activatable antibody to a subject in need thereof. For example, patients that test positive for both the targets (e.g., the target) and a protease that cleaves the substrate in the cleavable moiety (CM) of the activatable antibody and/or conjugated activatable antibody being tested in these methods are identified as suitable candidates for treatment with such antibody and/or such a conjugated activatable antibody comprising such a CM, and the patient is then administered a therapeutically effective amount of the activatable antibody and/or conjugated activatable antibody that was tested. Likewise, patients that test negative for either or both of the target (e.g., the target) and the protease that cleaves the substrate in the CM in the activatable antibody being tested using these methods might be identified as suitable candidates for another form of therapy. In some embodiments, such patients can be tested with other antibody and/or conjugated activatable antibody until a suitable antibody and/or conjugated activatable antibody for treatment is identified (e.g., an activatable antibody and/or conjugated activatable antibody comprising a CM that is cleaved by the patient at the site of disease). In some embodiments, the patient is then administered a therapeutically effective amount of the activatable antibody and/or conjugated for which the patient tested positive.

In some embodiments of these methods and kits, the MM is a peptide having a length from about 4 to 40 amino acids. In some embodiments of these methods and kits, the activatable antibody comprises a linker peptide, wherein the linker peptide is positioned between the MM and the CM. In some embodiments of these methods and kits, the activatable antibody comprises a linker peptide, where the linker peptide is positioned between the AB and the CM. In some embodiments of these methods and kits, the activatable antibody comprises a first linker peptide (L1) and a second linker peptide (L2), wherein the first linker peptide is positioned between the MM and the CM and the second linker peptide is positioned between the AB and the CM. In some embodiments of these methods and kits, each of L1 and L2 is a peptide of about 1 to 20 amino acids in length, and wherein each of L1 and L2 need not be the same linker. In some embodiments of these methods and kits, one or both of L1 and L2 comprises a glycine-serine polymer. In some embodiments of these methods and kits, at least one of L1 and L2 comprises an amino acid sequence selected from the group consisting of (GS)n, (GSGGS)n (SEQ ID NO: 385) and (GGGS)n (SEQ ID NO: 386), where n is an integer of at least one. In some embodiments of these methods and kits, at least one of L1 and L2 comprises an amino acid sequence having the formula (GGS)n, where n is an integer of at least one. In some embodiments of these methods and kits, at least one of L1 and L2 comprises an amino acid sequence selected from the group consisting of Gly-Gly-Ser-Gly (SEQ ID NO: 387), Gly-Gly-Ser-Gly-Gly (SEQ ID NO: 388), Gly-Ser-Gly-Ser-Gly (SEQ ID NO: 389), Gly-Ser-Gly-Gly-Gly (SEQ ID NO: 390), Gly-Gly-Gly-Ser-Gly (SEQ ID NO: 391), and Gly-Ser-Ser-Ser-Gly (SEQ ID NO: 392).

In some embodiments of these methods and kits, the AB comprises an antibody or antibody fragment sequence selected from the cross-reactive antibody sequences presented herein. In some embodiments of these methods and kits, the AB comprises a Fab fragment, a scFv or a single chain antibody (scAb).

In some embodiments of these methods and kits, the cleaving agent is a protease that is co-localized in the subject or sample with the target and the CM is a polypeptide that functions as a substrate for the protease, wherein the protease cleaves the CM in the activatable antibody when the activatable antibody is exposed to the protease. In some embodiments of these methods and kits, the CM is a polypeptide of up to 15 amino acids in length. In some embodiments of these methods and kits, the CM is coupled to the N-terminus of the AB. In some embodiments of these methods and kits, the CM is coupled to the C-terminus of the AB. In some embodiments of these methods and kits, the CM is coupled to the N-terminus of a VL chain of the AB.

The activatable antibodies and/or conjugated activatable antibodies of the disclosure are used in diagnostic and prophylactic formulations. In one embodiment, an activatable antibody is administered to patients that are at risk of developing one or more of the aforementioned inflammation, inflammatory disorders, cancer or other disorders.

A patient's or organ's predisposition to one or more of the aforementioned disorders can be determined using genotypic, serological or biochemical markers.

In some embodiments of the disclosure, an activatable antibody and/or conjugated activatable antibodies is administered to human individuals diagnosed with a clinical indication associated with one or more of the aforementioned disorders. Upon diagnosis, an activatable antibody and/or conjugated activatable antibodies is administered to mitigate or reverse the effects of the clinical indication.

Activatable antibodies and/or conjugated activatable antibodies of the disclosure are also useful in the detection of the target in patient samples and accordingly are useful as diagnostics. For example, the activatable antibodies and/or conjugated activatable antibodies of the disclosure are used in in vitro assays, e.g., ELISA, to detect target levels in a patient sample.

In one embodiment, an activatable antibody of the disclosure is immobilized on a solid support (e.g., the well(s) of a microtiter plate). The immobilized activatable antibody serves as a capture antibody for any target that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen in the test sample is determined by comparison with a standard curve developed from the standard samples.

It will be appreciated that based on the results obtained using the antibodies of the disclosure in an in vitro diagnostic assay, it is possible to stage a disease in a subject based on expression levels of the Target antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Activatable antibodies and/or conjugated activatable antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable antibodies having an enzymatically cleavable CM can be used to detect the presence or absence of an enzyme that is capable of cleaving the CM. Such activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated antibodies (i.e., antibodies resulting from cleavage of an activatable antibody) in a given cell or tissue of a given host organism. Such accumulation of activated antibodies indicates not only that the tissue expresses enzymatic activity (or an increased reduction potential depending on the nature of the CM) but also that the tissue expresses target to which the activated antibody binds.

For example, the CM can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an activatable antibody. Suitable detectable labels are discussed in the context of the above screening methods and additional specific examples are provided below. Using an AB specific to a protein or peptide of the disease state, along with a protease whose activity is elevated in the disease tissue of interest, activatable antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated antibodies in the disease tissue is enhanced relative to non-disease tissues.

In another example, activatable antibodies can be used to detect the presence or absence of a cleaving agent in a sample. For example, where the activatable antibodies contain a CM susceptible to cleavage by an enzyme, the activatable antibodies can be used to detect (either qualitatively or quantitatively) the presence of an enzyme in the sample. In another example, where the activatable antibodies contain a CM susceptible to cleavage by reducing agent, the activatable antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the activatable antibodies as described above, and the presence or absence of the target can be detected by detection of a target-AB complex e.g., by use of a detectably labeled anti-target antibody.

Activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. Fluorescein Isothiocyanate (FITC), Rhodamine Isothiocyanate (TRITC), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, activatable antibody indicates that the sample contains the target and contains a protease that is specific for the CM of the activatable antibody. In some embodiments, the presence of the protease can be confirmed using broad spectrum protease inhibitors such as those described herein, and/or by using an agent that is specific for the protease, for example, an antibody such as A11, which is specific for the protease matriptase and inhibits the proteolytic activity of matriptase; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM of the activatable antibody. In some embodiments, the presence of the target can be confirmed using an agent that is specific for the target, e.g., another antibody, or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the CM of the activatable antibody.

These techniques are also useful in kits and/or as reagents for the detection, identification or characterization of protease activity in a variety of cells, tissues, and organisms based on the protease-specific CM in the activatable antibody.

In some embodiments, in situ imaging and/or in vivo imaging are useful in methods to identify which patients to treat. For example, in in situ imaging, the activatable antibodies are used to screen patient samples to identify those patients having the appropriate protease(s) and target(s) at the appropriate location, e.g., at a tumor site.

In some embodiments in situ imaging is used to identify or otherwise refine a patient population suitable for treatment with an activatable antibody of the disclosure. For example, patients that test positive for both the target and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative for either or both of the target and the protease that cleaves the substrate in the CM in the activatable antibody being tested using these methods are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease).

In some embodiments in vivo imaging is used to identify or otherwise refine a patient population suitable for treatment with an activatable antibody of the disclosure. For example, patients that test positive for both the target and a protease that cleaves the substrate in the cleavable moiety (CM) of the activatable antibody being tested (e.g., accumulate activated antibodies at the disease site) are identified as suitable candidates for treatment with such an activatable antibody comprising such a CM. Likewise, patients that test negative are identified as suitable candidates for another form of therapy (i.e., not suitable for treatment with the activatable antibody being tested). In some embodiments, such patients that test negative with respect to a first activatable antibody can be tested with other activatable antibodies comprising different CMs until a suitable activatable antibody for treatment is identified (e.g., an activatable antibody comprising a CM that is cleaved by the patient at the site of disease).

Pharmaceutical Compositions

The conjugated antibodies, activatable antibodies and/or conjugated activatable antibodies of the disclosure (also referred to herein as "active compounds"), and derivatives, fragments, analogs and homologs thereof, can be incorporated into pharmaceutical compositions suitable for administration. Such compositions typically comprise the conjugated antibody, activatable antibody and/or conjugated activatable antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL' (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some embodiments, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1. Materials and Methods

Reagents and Strains:
Streptavidin-conjugated phycoerythrin (SA-PE) (Invitrogen, Life Technologies) was used without modifications. Human matriptase-1 (Research & Diagnostics Systems, Inc.) was used without modifications. Human plasmin (Haematologic Technologies Inc.) was used without modifications. Human tPA (Molecular Innovations) was used without modifications. YPet fused to the SH3 domain of Mona (monocytic adaptor) was used without modifications. TBST, 50 mM Tris-HCl, 150 mM NaCl, 0.05% Tween20, pH 7.4, was used. *E. coli* MC1061 (Casadaban et al., JMB 138(2): 179-207 (1980)) was used. All bacterial growth was performed at 37° C. with vigorous shaking in Luria-Bertani broth (LB) supplemented with 34 μg/mL chloramphenicol, unless another antibiotic is specified.

Substrate Cleavage and Scaffold Stability Analysis:

For screening and clone analysis, overnight cultures were subcultured by dilution into fresh medium (1:50) and grown for 1.5-2 hours. Each subculture was then induced with 0.04% arabinose and incubated with shaking at 37° C. for 1 hour. To stop further growth, cells were incubated on ice for 15-30 minutes. Cell aliquots were harvested and washed with PBS (pH 7.4). Cells were pelleted by centrifugation, the supernatant removed, and the cells resuspended in reaction buffer containing the enzyme; the reaction mixture was incubated at 37° C. static. To stop the reaction cells, were removed and diluted 10-fold in PBS, pelleted by centrifugation, and resuspended in PBS containing either SA-PE (20 μg/mL) or YPet-MONA (50 nM). After incubation on ice (30 min), cells were washed with PBS and analyzed using a FACSAria™ cell sorter.

For protease cleavage assays, cultures were induced for 1 hour. The reaction buffer for matriptase-1 was TBST. Assays for matriptase-1 hydrolysis, were performed after reactions with 200 pM-200 nM matriptase-1 for 1 hr. Background hydrolysis of the regions flanking the substrate site (using platform eCLiPS3.0-NSUB_SP described in PCT patent application PCT/US13/54378, filed Aug. 9, 2013 and published as WO 2014/026136 on Feb. 13, 2014), was measured under each reaction condition to ensure that hydrolysis occurred in the designated substrate region.

For human plasmin stability assays, platform eCLiPS3.0-NSUB_SP was used; cultures were induced for 1 hr. The reaction buffer for plasmin was 50 mM Tris-HCl pH 7.5 supplemented with 100 mM NaCl, 0.01% Tween20 and 1 mM EDTA. Assays for plasmin hydrolysis were performed after reactions with plasmin for 1 hr.

For human tPA stability assays, platform eCLiPS3.0-NSUB_SP was used; cultures were induced for 1 hr. The reaction buffer for tPA was TBST. Assays for tPA hydrolysis were performed after reactions with tPA for 1 hr.

Amino and Carboxy Terminus Labeling Conditions:

Streptavidin conjugated phycoerythrin (SAPE) was used for labeling streptavidin binding affinity ligand on the N-termini of CPX. Fluorescent protein YPet fused to the SH3 domain of Mona was used for labeling the MONA binding affinity ligand on the C-termini of CPX. For optimum labeling of cells without protease reaction, the cells were incubated for 30 min at 4° C. with SAPE (20 μg/mL) or YPet-MONA (50 nM).

Kinetic Data Analysis:

The extent of conversion of cell surface displayed peptide substrates was measured directly, using flow cytometry to measure changes in mean fluorescence of clonal cell populations upon protease treatment. Specifically, for each sample, conversion was determined by flow cytometry analyses using the relationship $$\text{Conversion} = \frac{FL_- - FL_+}{FL_- - FL_0} \quad [1]$$

where $(FL-)$ is the fluorescence after incubating without enzyme, $(FL+)$ is fluorescence after incubation with enzyme, and $(FL_0)$ is fluorescence of unlabeled cells. Given that the expected substrate concentrations that were used are significantly below the expected $K_M$ of the substrate for the target protease, the Michaelis-Menton model simplifies to:

$$\frac{d[S]}{dt} \approx -\frac{k_{cat}}{k_M}[S][E] \quad [2]$$

allowing substrate conversion to be expressed as $$\text{Conversion} = 1 - \exp\left(-\frac{k_{cat}}{k_M} \cdot [E] \cdot t\right) \quad [3]$$

where [S] is the substrate concentration, [E] is enzyme concentration and t is time. To determine the second order rate constant ($k_{cat}/K_M$), equation [3] was simplified to:

$$\frac{kcat}{Km} = -\ln(1 - \text{product conversion})/(\text{time} * [\text{protease}])$$

Sequence Data Analysis—Meta Motifs:

Substrates were submitted to Ion Torrent™ sequencing (see, e.g., Rothenberg, J M, Nature 475, 348-352). Raw Ion Torrent reads were cropped by invariant vector sequences to obtain just the variable peptide insert. Insert sequences were translated, and sequences with stop codons were excluded from further analysis. The frequency of each sequence was obtained by number of times observed out of all viable peptide reads observed. Enrichment of sequences was obtained by comparison of observed frequency of each sequence post selection to the frequency of each sequence pre-selection. Motif analysis was performed by extracting all possible 2mers, 3mers, 4mers and non-consecutive 1n2mers 2n1mers 2n2mers and 2nn2mers (where the first number represents the first set of invariant positions, the second number represents the second set of invariant positions, and the number of n's between represents the number of variable positions allowed between the two invariant positions). The frequency of each motif was established across all normalized sequences in both the pre-selected and post selected libraries to establish significance of enrichment of each motif. To generate meta-motifs, all sequences containing each motif were aligned, and a Positional Weight Matrix (PWM) was created representing the amino acid propensity at each position in the motif carriers. Profile-profile alignments and scoring were conducted across all motifs, using a Minimum Mutual Information Content (MMIC) scoring function to score each profile-profile aligned register. Registers aligning above a background of incorrect registers of unique formed PWMs were extracted as significant; the individual PWMs were then added to create an average metamotif Sequence Data Analysis—Directed Families:

Final substrate pools were sequenced using Ion Torrent™ sequencing. Individual sequences were identified and isolated from these data, and sequences were aligned in CLC main lab (CLC Main Workbench 6.6.2, available online). The alignment file was imported to Jalview (see, e.g., Waterhouse, A. M., et al., 2009, Bioinformatics 9, 1189-1191), and an average distance tree was assembled using the BLOSUM62 algorithm (S Henikoff S et al., 1992, Proc Natl Acad Sci USA. 89, 10915-10919). The restricted group of sequences includes members of the cluster closest to the sequence of interest. The extended group of sequences includes the restricted group of sequences those plus of the branch that shares the closest common ancestor (where applicable).

Figure 2:
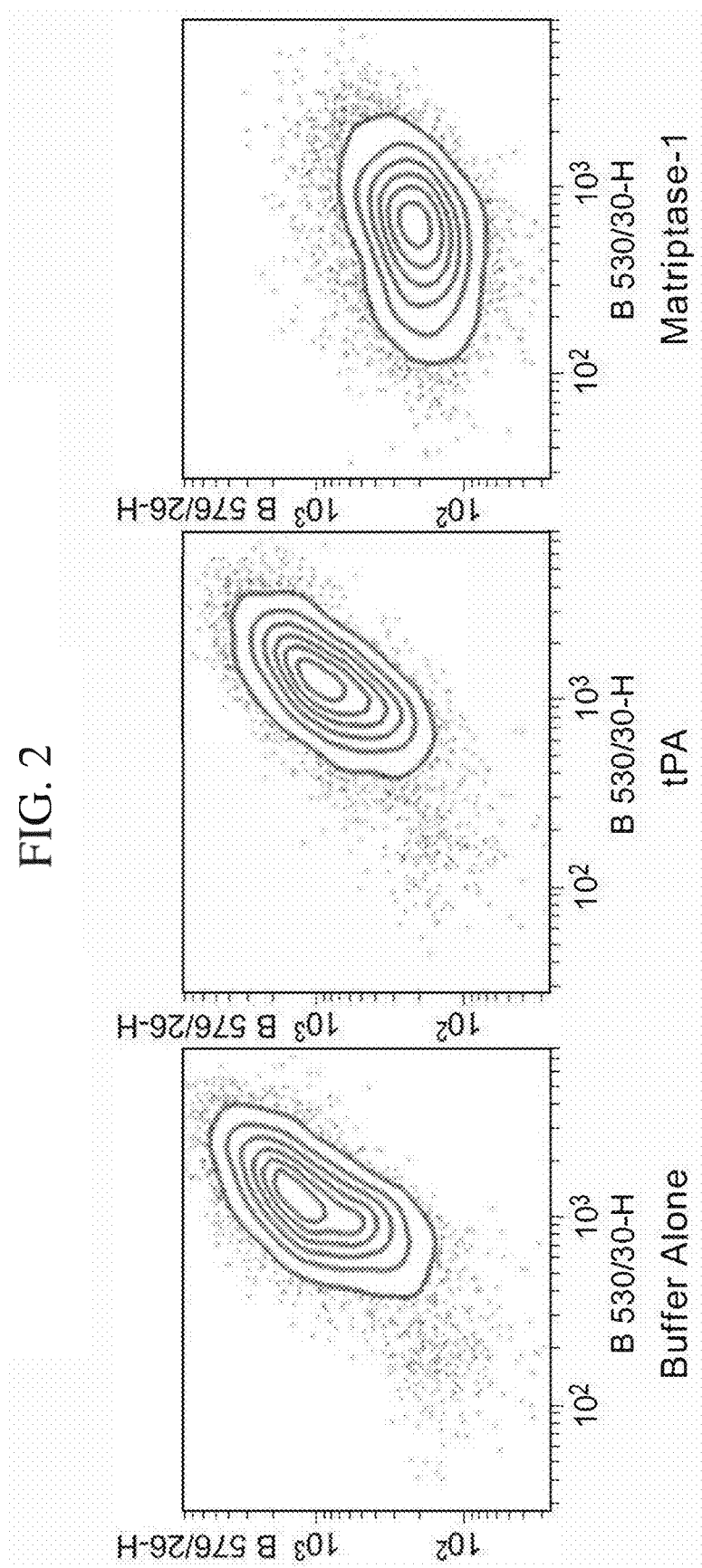
FIG. 2 is a series of graphs depicting cleavage of pool SMP17 by matriptase-1 and resistance to cleavage by tPA.

Example 2. Selection and Characterization of Substrate Pools in a Platform Scaffold The use of multi-copy substrate display on whole cells enabled selection of populations of substrates cleaved by matriptase-1. Selections were performed as described in U.S. Pat. No. 7,666,817 B, issued Feb. 23, 2010, using recombinant human matriptase-1. Background hydrolysis of the regions flanking the substrate site (using platform eCLiPS3.0-NSUB_SP) was measured under each reaction condition to ensure that hydrolysis occurred in the designated substrate region. Final pools were tested against matriptase-1, plasmin and tPA. The pools were cleaved by matriptase-1 but not by tPA or plasmin. FIG. 1 shows cleavage of pool SMP30 by matriptase-1 in TBST, FIG. 2 shows cleavage of pool SMP17 by matriptase-1 at 50 nM and resistance to tPA, both in TBST. Using similar techniques, a separate library was screened to select substrates cleaved by both matriptase-1 and u-plasminogen activator but not by tPA or plasmin.

Figure 3:
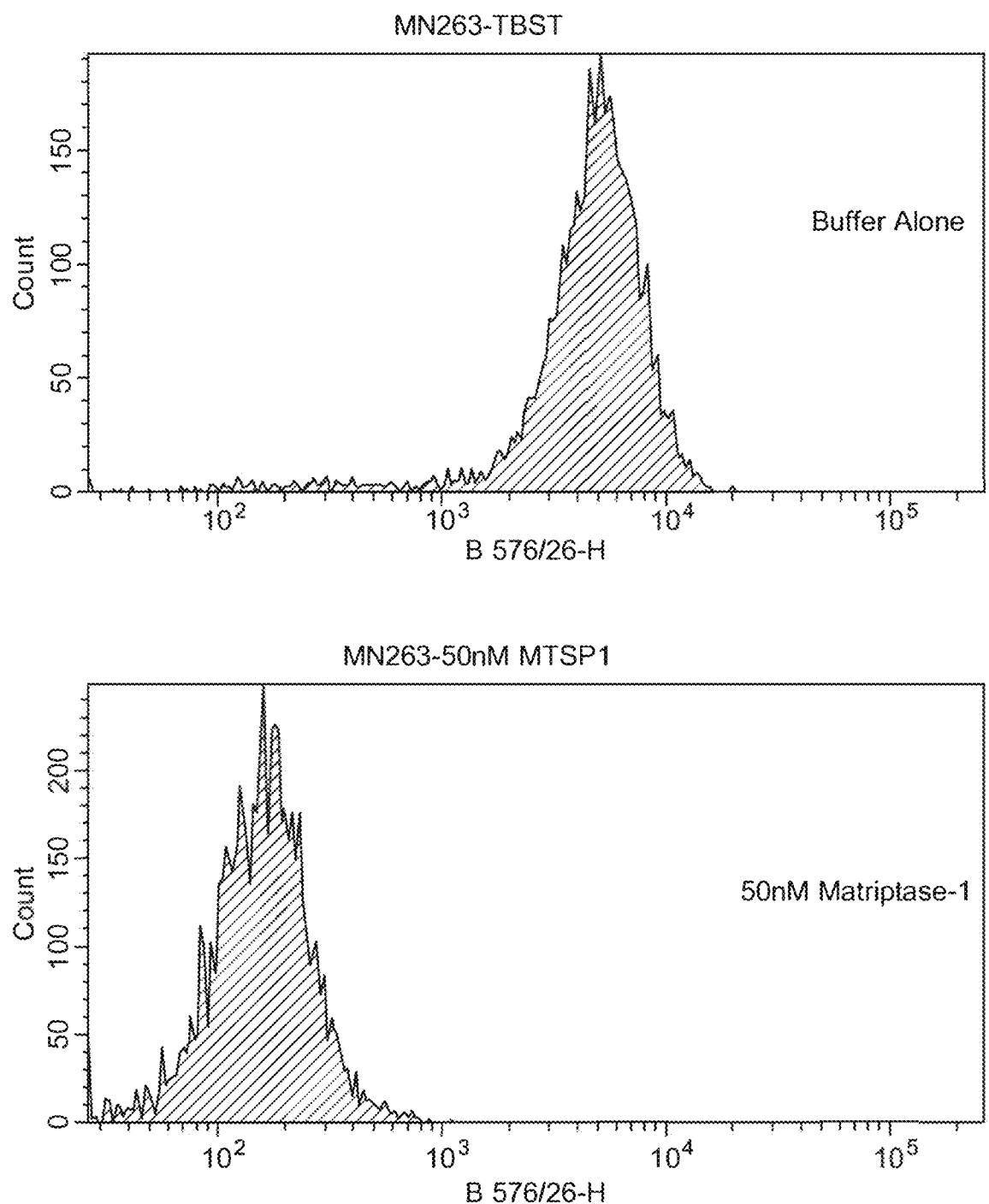
FIG. 3 is a series of graphs depicting cleavage of the substrate sequence VAGRSMRP (SEQ ID NO: 251) by matriptase-1.

Example 3. Characterization of Substrate Cleavage Kinetics in the Platform Scaffold The use of multi-copy substrate display on whole cells enabled simple and direct quantitative characterization of cleavage kinetics. Consequently, flow cytometry was used to rank individual isolated clones on the basis of substrate conversion, and clones were identified by DNA sequencing. In this way, the extent of conversion for each clone could be determined at several different protease concentrations and fit to a Michaelis-Menten model (Kinetic Data Analysis Section). The observed second order rate constant ($k_{cat}/K_M$) was determined for each substrate versus matriptase-1. Background hydrolysis of the regions flanking the substrate site (using platform eCLiPS3.0-NSUB_SP), was measured under each reaction condition to ensure that hydrolysis occurred in the designated substrate region. For example, FIG. 3 shows cleavage of a substrate comprising amino acid sequence VAGRSMRP (SEQ ID NO: 251) by matriptase-1 in TBST.

Example 4. In Vitro Substrate Activity in Activatable Antibodies

This Example demonstrates the in vitro activity of substrates of the disclosure when they are incorporated into activatable antibodies.

Several substrates identified in these studies were inserted into Probodies having the 3954 mask and C225v5 variant of cetuximab, which is described in PCT Publication No. WO 2013/163631), which is incorporated herein by reference in its entirety.

The ability of substrates in the resultant activatable antibodies to be cleaved by matriptase-1 or uPA was determined as follows. All protease digests were performed in 50 mM Tris-HCl, 150 mM NaCl, 0.05% Tween-20 pH=7.4. Varying concentrations of active site titrated uPA or matriptase was combined with a fixed activatable antibody concentration to maintain a substrate to protease ratio of at least 50. Samples were incubated at 37° C. for up to 20 h. To stop the reaction, 5 µl of the digest was added to 7 µl of HT Protein Express Sample Buffer (Caliper LifeSciences) containing 20 mM 2-Mercaptoethanol for 10 minutes at 95° C. After heat denaturation, 32 µl of ddH$_2$O was added and samples analyzed on a LabChip GXII per manufacturer's instructions. The LabChip GXII software was used to quantify light chain peak area. Product conversion was calculated by plugging the light chain peak areas into the following equation: cleaved LC/(cleaved LC+uncleaved LC), LC=light chain. kcat/Km values were determined with the following equation $$\frac{k_{cat}}{K_M} = -\ln(1 - C)/(t * p)$$

where C is product conversion, t is time (s), and p is protease concentration (M), which assumes that the substrate concentration is below the $K_m$ and in excess of the protease concentration.

Resultant activatable antibodies comprising substrates selected for cleavage by uPA and matriptase had $k_{cat}/K_M$ values ranging from about 400 to 5,000 M$^{-1}$ s$^{-1}$ for uPA and from about 3,000 to 100,000 M$^{-1}$ s$^{-1}$ for matriptase (7 substrates tested). Resultant activatable antibodies comprising substrates selected for cleavage by matriptase had $k_{cat}/K_M$ values ranging from about 6,500 to 100,000 M$^{-1}$ s$^{-1}$ for matriptase (5 substrates tested).

Example 5. Substrate Stability of Activatable Antibodies In Vivo

This Example demonstrates the in vivo stability of substrates of the disclosure when they are incorporated into activatable antibodies and injected into mice.

Activatable antibodies comprising several substrates of the disclosure, produced as described above, were labeled with either AlexaFluor 680 or DyLight 680 using standard NHS ester chemistry. Unreacted dye was removed by purification with a Zeba spin desalting column (40 kDa MWCO, ThermoFisher). Protein concentration was determined by A$_{280}$ using an extinction coefficient calculated from protein sequence and a correction factor that accounted for dye absorbance.

Three nude mice (Crl:NU-Foxn1nu) received a single IP dose of each activatable antibody at 10 mg/kg or 12.5 mg/kg on Day 0. Mice were euthanized on day 4 (about 96 h post-dose) by CO2 asphyxiation and blood was collected immediately as plasma-EDTA and stored at −80° C.

Plasma samples were prepared for analysis by capillary electrophoresis as described in the $k_{cat}/K_m$ section. Briefly, 5 µl of plasma was added to 7 µl Protein Express Sample Buffer with 2-mercaptoethanol. Quantification of circulating stability was identical to quantification of product conversion.

Of 14 activatable antibodies comprising substrates of the disclosure selected for cleavage by uPA or by matriptase, 13 exhibited less than 20% cleavage in the collected plasma samples.

Example 6. Materials and Methods

Reagents and Strains:

Human uPA (catalog no. 1310-SE, Research & Diagnostics Systems, Inc.) was used without modifications. Human matriptase-1 (catalog no. 3946-SE, Research & Diagnostics Systems, Inc.) was used without modifications. Human tPA (catalog no. HTPA-TC, Molecular Innovations) was used without modifications. Human plasmin (catalog no. HCPM-0140, Haematologic Technologies Inc.) was used without modifications. Anti-EE monoclonal antibody (Covance, Princeton, NJ) was labeled with Alexa 647 (Life Sciences) and used with no other modifications (named EE647). *E. coli* MC1061 or MC1061 derived strains (DH10β) were used for all experiments (Casadaban et al., JMB 138(2):179-207 (1980)). All bacterial growth was performed at 37° C. with vigorous shaking in Luria-Bertani broth (LB) supplemented with 34 µg/mL chloramphenicol (cm), unless another antibiotic is specified.

Figure 4A:
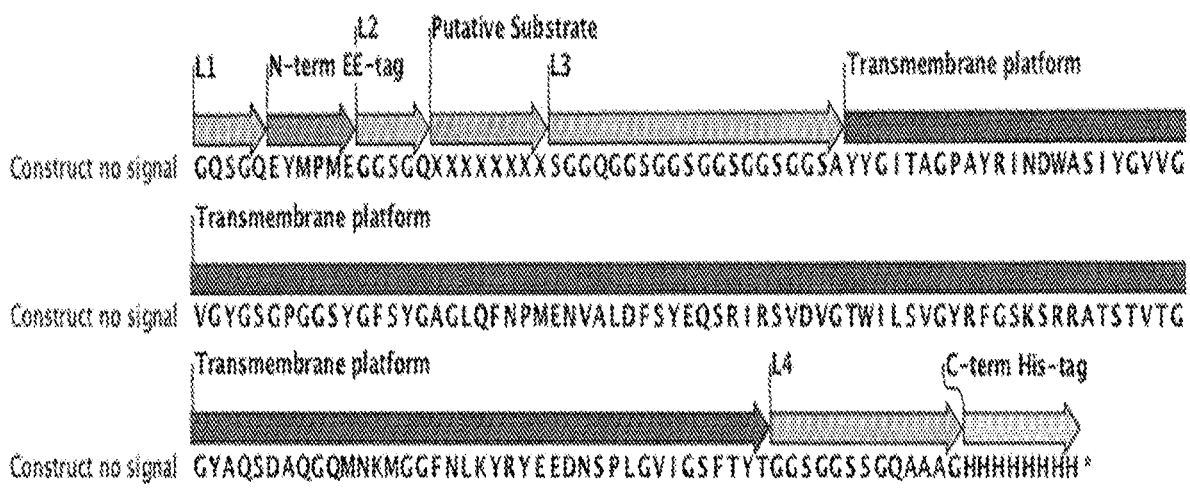
FIGS. 4A and 4B are a series of schematic representations of the peptide display platforms used in the working examples provided herein.
Figure 4B:
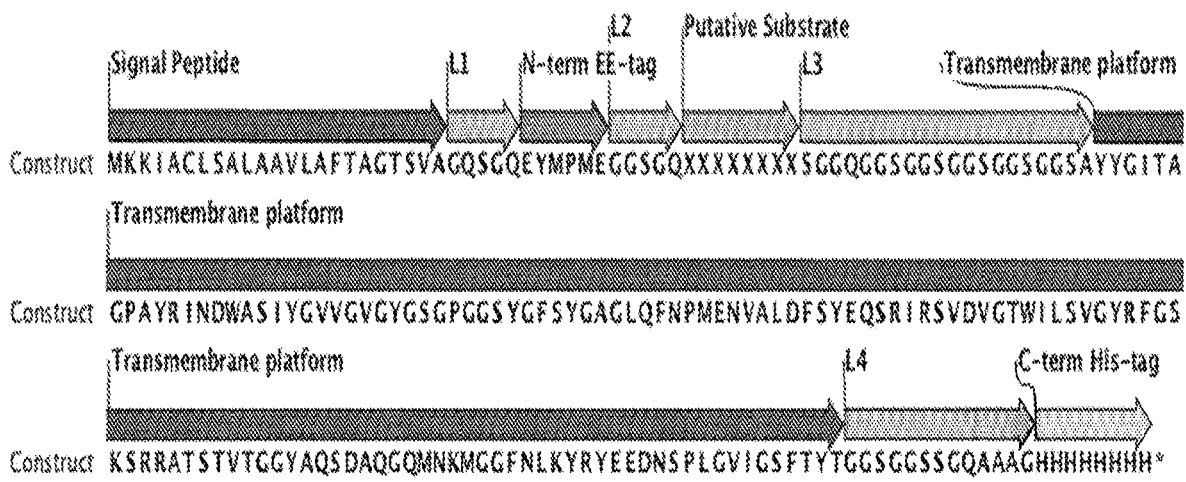

Display Platforms:

Display platforms, each engineered to contain an 8-to-12-amino acid substrate of the embodiments, were produced and used as described in International Publication No. WO 2014/026136, published 13 Feb. 2014, the contents of which are hereby incorporated by reference in their entirety. The amino acid sequence of the mature (i.e., without a signal peptide) CYTX-DP-XXXXXXXX display platform (SEQ ID NO: 694) is shown in FIG. 4A. XXXXXXXX indicates the location into which each substrate is inserted. The amino acid sequence of CYTX-DP-XXXXXXXX display platform also including its signal peptide, i.e., SP-CYTX-DP-XXXXXXXX display platform (SEQ ID NO: 695) is shown in FIG. 4B.

CYTX-DP-XXXXXXXX Display Platform:
(SEQ ID NO: 694)
GQSGQEYMPMEGGSGQXXXXXXXXSGGQGSGGSGGSGGSGGSAYYGITA

GPAYRINDWASIYGVVGVGYGSGPGGSYGFSYGAGLQFNPMENVALDFSY

EQSRIRSVDVGTWILSVGYRFGSKSRRATSTVTGGYAQSDAQGQMNKMGG

FNLKYRYEEDNSPLGVIGSFTYTGGSGGSSGQAAAGHHHHHHHH

SP-CYTX-DP-XXXXXXXX Display Platform:
(SEQ ID NO: 695)
MKKIACLSALAAVLAFTAGTSVAGQSGQEYMPMEGGSGQXXXXXXXXSGG

QGGSGGSGGSGGSGGSAYYGITAGPAYRINDWASIYGVVGVGYGSGPGGS

YGFSYGAGLQFNPMENVALDFSYEQSRIRSVDVGTWILSVGYRFGSKSRR

ATSTVTGGYAQSDAQGQMNKMGGFNLKYRYEEDNSPLGVIGSFTYTGGSG

GSSGQAAAGHHHHHHHH

Substrate Cleavage and Cleavage Kinetics Analysis:

For clone analysis, overnight cultures were subcultured by dilution into fresh medium (1:40) and grown for 1.5-2 hours. The subculture was then induced with 0.04% arabinose and incubated with shaking at 37° C. for 40 minutes to 1 hour. To stop further growth, cells were then incubated on ice for 15 minutes to 1 hour. Cell aliquots were harvested and washed with reaction buffer. Cells were pelleted by centrifugation, the supernatant removed and the cells resuspended in reaction buffer containing the enzyme; the reaction mixture was incubated at 37° C. with shaking. To stop the reaction, cells were removed and diluted 10-fold in PBS, pelleted by centrifugation, and resuspended in PBS containing anti-EE647 (20 micrograms per milliliter (also referred to herein as ug/ml or µg/ml)). After incubation on ice (up to 1 hour), cells were washed with PBS and analyzed using an Accuri C6 cell sorter.

For uPA protease cleavage assays, cultures were induced for 40 minutes to 1 hour. The reaction buffer for uPA was 50 mM Tris-HCl, 150 mM NaCl, 0.05% Tween20, pH 7.4 (TBST). Assays for uPA hydrolysis were performed after cleavage with 2 nM-50 nM uPA for 1 hour. Background hydrolysis of the regions flanking the substrate site (using, e.g., CYTX-DP-NSUB, a display platform in which the "Substrate" is non-cleavable linker GGGSGGGS (SEQ ID NO: 696)) was measured under each reaction condition to ensure that hydrolysis occurred in the designated substrate region.

For matriptase-1 protease cleavage assays, cultures were induced for 40 minutes to 1 hour. The reaction buffer for matriptase-1 was 50 mM Tris-HCl, 150 mM NaCl, 0.05% Tween20, pH 7.4 (TBST). Assays for matriptase-1 hydrolysis were performed after cleavage with 2 nM-50 nM matriptase-1 for 1 hr. Background hydrolysis of the regions flanking the substrate site (using, e.g., CYTX-DP-NSUB) was measured under each reaction condition to ensure that hydrolysis occurred in the designated substrate region.

For human plasmin cleavage assays, cultures were induced for 40 minutes to 1 hour. The reaction buffer for plasmin was 50 mM Tris-HCl pH 7.5 supplemented with 100 mM NaCl, 0.01% Tween20 and 1 mM EDTA. Assays for plasmin hydrolysis were performed after cleavage with 20-500 pM plasmin for 1 hr. Background hydrolysis of the regions flanking the substrate site (using, e.g., CYTX-DP-NSUB) was measured under each reaction condition to ensure that hydrolysis occurred in the designated substrate region.

For tPA protease cleavage assays, cultures were induced for 40 minutes to 1 hour. The reaction buffer for tPA was 50 mM Tris-HCl, 150 mM NaCl, 0.05% Tween20, pH 7.4 (TBST). Assays for tPA hydrolysis were performed after cleavage with 2 nM-50 nM tPA for 1 hour. Background hydrolysis of the regions flanking the substrate site (using, e.g., CYTX-DP-NSUB) was measured under each reaction condition to ensure that hydrolysis occurred in the designated substrate region.

Amino and Carboxyl Terminus Labeling Conditions:

Alexa-647 conjugated anti-EE antibody (EE647) was used for labeling the EE binding affinity ligand on the N-termini of the CYTX-DP-XXXXXXXX display platform. Alexa-647 conjugated anti-His antibody (His647) was used for labeling the 8His binding affinity ligand on the C-termini of the CYTX-DP-XXXXXXXX display platform. For optimum labeling of cells without protease reaction, the cells were incubated for 1 hour at 4° C. with EE647 (1 µg/mL) or His647 (2 µg/ml). For the example described below, a 1-hour incubation was used.

Kinetic Data Analysis:

The extent of conversion of cell surface displayed peptide substrates was measured directly, using flow cytometry to measure changes in mean fluorescence of clonal cell populations upon protease treatment. Specifically, for each sample, conversion was determined by flow cytometry analyses using the relationship $$Conversion_{CLiPS} = \frac{FL_- - FL_+}{FL_- - FL_0} \quad [1]$$

where ($FL_-$) is the fluorescence after incubating without enzyme, ($FL_+$) is fluorescence after incubation with enzyme, and ($FL_0$) is fluorescence of unlabeled cells. Given that the expected substrate concentrations that were used are significantly below the expected $K_M$ of the substrate for the target protease, the Michaelis-Menten model simplifies to $$\frac{d[S]}{dt} \approx -\frac{k_{cat}}{k_M}[S][E] \quad [2]$$

allowing substrate conversion to be expressed as $$Conversion_{MM} = 1 - \exp\left(-\frac{k_{cat}}{k_M}[E] \cdot t\right) \quad [3]$$

where [S] is the substrate concentration, [E] is enzyme concentration and t is time. To determine the second order rate constant ($k_{cat}/K_M$), the time dependent conversion for each substrate was fit to equation [3].

Example 7. Characterization of Substrate Cleavability in the CYTX-DP Display Platform This Example demonstrates the ability of substrates of the embodiments to be cleaved by matriptase and/or uPA, but not by plasmin and/or tPA.

The use of multi-copy substrate display on whole cells enabled simple and direct quantitative characterization of cleavage kinetics. Clones encoding substrates were identified by DNA sequencing and subcloned into the CYTX-DP-XXXXXXXX display platform such that the expressed display platform contained the substrate (typically 8 or 12 amino acids) in place of XXXXXXXX. Individual substrate-displaying clones (148 independent substrate-containing display platforms in total) were assessed for cleavage by matriptase and/or uPA (target proteases, i.e., the proteases used to select the substrate) and plasmin and/or tPA (off-target protease); turnover was determined by flow cytometry. Fifty-one of the substrates were selected for cleavage by both matriptase and uPA (i.e., Matriptase- and uPA-selected Substrates). The twenty-eight Matriptase- and uPA-selected Substrates from Pools were selected from the same pools as substrates comprising amino acid sequences SEQ ID NOs: 308, 314, and 361 as well as from substrates comprising amino acid sequences 369-371, 374-379, and 381-384. The twenty-three Matriptase- and uPA-selected Consensus Substrates were selected from substrates comprising amino acid sequences SEQ ID NOs: 307-311, 313-314, and 320-368. Ninety-seven of the substrates were selected for cleavage by matriptase (i.e., Matriptase-selected Substrates). The fifty-two Matriptase-selected Substrates from Pools were selected from substrates in Tables 8A through 8J and in Tables 9A through 9J-3 as well as from substrates comprising amino acid sequences SEQ ID NOs: 250-267. The forty-five Matriptase-selected Consensus Substrates were selected from substrates comprising amino acid sequences SEQ ID NOs: 163-249.

In this way, the extent of cleavage for each clone could be determined and the data aggregated to determine a percent of clones that were cleaved by the target protease and not the off-target protease. Background hydrolysis of the regions flanking the substrate site (using, e.g., the CYTX-DP-NSUB display platform) was measured under each reaction condition to ensure that hydrolysis occurred in the designated substrate region. Results are presented in Table 12.

TABLE 12

Summary statistics of substrate cleavability

| Discovery effort | Substrate Group | >20% Cleavage with 50 nM Matriptase-1 or 50 nM uPA | >20% Cleavage with 50 nM uPA | >20% Cleavage with 50 nM Matriptase-1 | <20% Cleavage with 500 pM Plasmin or 50 nM tPA | <20% Cleavage with 500 pM Plasmin | <20% Cleavage with 50 nM tPA |
|---|---|---|---|---|---|---|---|
| Matriptase- and uPA-selected Substrates | All Matriptase- and uPA-selected Substrates tested | 100% (51 of 51) | 78% (40 of 51) | 75% (38 of 51) | 76% (39 of 51) | 76% (39 of 51) | 96% (49 of 51) |
| | Substrates from Pools | 100% (28 of 28) | 64% (18 of 28) | 89% (25 of 28) | 89% (25 of 28) | 89% (25 of 28) | 93% (26 of 28) |
| | Consensus Substrates | 100% (23 of 23) | 96% (22 of 23) | 57% (13 of 23) | 61% (14 of 23) | 61% (14 of 23) | 100% (23 of 23) |
| Matriptase-selected Substrates | All Matriptase-selected Substrates | 86% (83 of 97) | 41% (40 of 97) | 67% (65 of 97) | 70% (68 of 97) | 82% (80 of 97) | 85% (82 of 97) |
| | Substrates from Pools | 81% (42 of 52) | 35% (18 of 52) | 62% (32 of 52) | 81% (42 of 52) | 94% (49 of 52) | 87% (45 of 52) |
| | Consensus Substrates | 91% (41 of 45) | 49% (22 of 45) | 73% (33 of 45) | 58 (26 of 45) | 69% (31 of 45) | 82% (37 of 45) |
| Combined substrates selected for cleavage by Matriptase and/or uPA | Total | 91% (134 of 148) | 54% (80 of 148) | 70% (103 of 148) | 72% (107 of 148) | 80% (119 of 148) | 89% (131 of 148) |

Table 12 depicts the percentage of Matriptase- and uPA-selected Substrates or Matriptase-selected Substrates tested in the CYTX-DP display platform (a) that exhibited greater than 20% cleavage when incubated with 50 nM human uPA (catalog no. 1310-SE, Research & Diagnostics Systems, Inc.) used without modifications for 1 hour at 37° C. in 50 mM Tris-HCl, 150 mM NaCl, 0.05% Tween20, pH 7.4 (TBST) (>20% cleavage with 50 nM uPA); (b) that exhibited greater than 20% cleavage when incubated with 50 nM human matriptase-1 (catalog no. 3946-SE, Research & Diagnostics Systems, Inc.) used without modifications for 1 hour at 37° C. in 50 mM Tris-HCl, 150 mM NaCl, 0.05% Tween20, pH 7.4 (TBST) (>20% cleavage with 50 nM matriptase-1); (c) that exhibited less than 20% cleavage when incubated with 500 pM human plasmin (catalog no. HCPM-0140, Haematologic Technologies, Inc.) used without modifications for 1 hour at 37° C. in 50 mM Tris-HCl pH 7.5 supplemented with 100 mM NaCl, 0.01% Tween20 and 1 mM EDTA (<20% cleavage with 500 pM plasmin); and (d) that exhibited less than 20% cleavage when incubated with 50 nM human tPA (catalog no. HTPA-TC, Molecular Innovations) used without modifications for 1 hour at 37° C. in 50 mM Tris-HCl, 150 mM NaCl, 0.05% Tween20, pH 7.4 (TBST) (<20% cleavage with 50 nM tPA).

Example 8. Characterization of Substrate Cleavage Kinetics in the CYTX-DP Display Platform This Example demonstrates the cleavage kinetics of various substrates of the embodiments.

The use of multi-copy substrate display on whole cells enabled simple and direct quantitative characterization of cleavage kinetics. Clones were identified by DNA sequencing and subcloned into the CYTX-DP-XXXXXXXX display platform as described herein. Ninety individual substrate-displaying clones were assessed for cleavage, and a subset was chosen to assess cleavage kinetics by the clone's target protease. The extent of conversion for each clone could be determined at several different protease concentrations and fit to the Michaelis-Menten model described herein. Background hydrolysis of the regions flanking the substrate site (using, e.g., CYTX-DP-NSUB) was measured under each reaction condition to ensure that hydrolysis occurred in the designated substrate region. Results are presented in Table 13 & Table 14.

TABLE 13

Summary statistics of uPA substrate kinetics

| Discovery effort | uPA kcat/Km > 1 × 10E2 | uPA kcat/Km > 1 × 10E3 | uPA kcat/Km > 1 × 10E4 |
|---|---|---|---|
| Matriptase- and uPA-selected Substrates | 100% (18 of 18) | 100% (18 of 18) | 50% (9 of 18) |
| Matriptase-selected Substrates | 100% (16 of 16) | 100% (16 of 16) | 6% (1 of 16) |
| Combined Substrates Cleaved by Matriptase and/or uPA | 100% (34 of 34) | 100% (34 of 34) | 29% (10 of 34) |

TABLE 14

Summary statistics of Matriptase-1 substrate kinetics

| Discovery effort | Matriptase-1 kcat/Km > 1 × 10E2 | Matriptase-1 kcat/Km > 1 × 10E3 | Matriptase-1 kcat/Km > 1 × 10E4 |
|---|---|---|---|
| Matriptase- and uPA-selected Substrates | 100% (25 of 25) | 100% (25 of 25) | 16% (4 of 25) |
| Matriptase-selected Substrates | 100% (31 of 31) | 100% (31 of 31) | 3% (1 of 31) |

TABLE 14-continued

Summary statistics of Matriptase-1 substrate kinetics

| Discovery effort | Matriptase-1 kcat/Km > 1 × 10E2 | Matriptase-1 kcat/Km > 1 × 10E3 | Matriptase-1 kcat/Km > 1 × 10E4 |
|---|---|---|---|
| Combined Substrates Cleaved by Matriptase and/or uPA | 100% (56 of 56) | 100% (56 of 56) | 9% (5 of 56) |

Example 9. In Vivo Efficacy and In Situ Activation of Activatable Antibodies Comprising a Substrate Cleavable by Matriptase and/or uPA This Example demonstrates that activatable antibodies comprising substrates of the embodiments cleavable by matriptase and/or uPA are efficacious in vivo. This Example also demonstrates that such activatable antibodies are activatable in an in situ imaging assay, such as that described in International Publication No. WO 2014/107559, published 10 Jul. 2014, the contents of which are hereby incorporated by reference in their entirety.

Three activatable antibodies, each comprising a different substrate of the embodiments that are cleaved by matriptase and/or uPA, were administered at 10 mg/kg to H292 xenograft tumor-bearing (lung cancer) mice on day 0. All three activatable antibodies also comprised the masking moiety comprising the amino acid sequence CISPRGCPDGPYVMY (SEQ ID NO: 515) and anti-EGFR antibody C225v5 antibody comprising a light chain (SEQ ID NO: 458) and a heavy chain (SEQ ID NO: 455). The configuration of the light chain of the activatable antibody was masking moiety-substrate-light chain of C225v5.

Mice were retro-orbitally bled on day 4 (about 96 hours post-dose). Blood was collected immediately as plasma-EDTA and stored at −80° C. The three activatable antibodies were purified from plasma by anti-human IgG immunoprecipitation using magnetic beads. To analyze by capillary electrophoresis, 5 μl of eluted IgG was added to 7 μl Protein Express Sample Buffer (Caliper LifeSciences) containing 20 mM 2-Mercaptoethanol for 10 minutes at 95° C. After heat denaturation, 32 μl of ddH$_2$O was added and samples analyzed on a LabChip GXII per manufacturer's instructions. The LabChip GXII software was used to quantify light chain peak area. Product conversion was calculated by plugging the light chain peak areas into the following equation: cleaved LC/(cleaved LC+uncleaved LC), LC=light chain peak area. At day 4, the three activatable antibodies demonstrated mean % activation values ranging from 13% to 30%. Mean % activation is calculated as ((product conversion sum of the test group)*100%)/(number of animals in the test group).

The three activatable antibodies demonstrated tumor growth inhibition ranging from 32% to 59% as measured by mean % Δ inhibition. Mean % Δ inhibition is calculated as (mean(C)−mean(C0))−(mean(T)−mean(T0))/(mean(C)−mean(C0))*100%, wherein T is the current test group value, T0 is the current test group initial value, C is the control group value, and C0 is the control group initial value. The EGFR antibody cetuximab demonstrated 96% inhibition in this study.

The same three activatable antibodies were submitted to in situ imaging assays of mouse xenograft tumor tissues, using the conditions described in the examples of WO 2014/107559, ibid. The three activatable antibodies were activated, demonstrating that substrates were cleaved and the released antibodies bound to EGFR on the tumor tissue. The staining signals ranged from 15% to 85% of the IHC signal intensity of cetuximab.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed is:

1. A method of manufacturing an activatable molecule that contains a cleavable moiety (CM) that is a substrate for a matriptase, the method comprising expressing and recovering an isolated polypeptide comprising a CM amino acid sequence of LSGRSANH (SEQ ID NO: 307), wherein said CM amino acid sequence is the substrate for the matriptase.

2. The method of claim 1, wherein the isolated polypeptide comprises at least one additional moiety (M) selected from the group consisting of a moiety that is located amino (N) terminally to the CM ($M_N$), a moiety that is located carboxyl (C) terminally to the CM ($M_C$), and combinations thereof.

3. The method of claim 2, wherein the isolated polypeptide comprises at least one $M_N$ and at least one $M_C$.

4. The method of claim 2, wherein $M_N$ is selected from the group consisting of a masking moiety, an antibody, a protein, a therapeutic agent, an antineoplastic agent, a toxic agent, a drug, a detectable moiety, a diagnostic agent, and an affinity tag.

5. The method of claim 2, wherein $M_C$ is selected from the group consisting of a masking moiety, an antibody, a protein, a therapeutic agent, an antineoplastic agent, a toxic agent, a drug, a detectable moiety, a diagnostic agent, and an affinity tag.

6. The method of claim 1, wherein the isolated polypeptide comprises a CM amino acid sequence of DRLSGRSANHKK (SEQ ID NO: 309).

* * * * *